US010501803B2

(12) United States Patent
Barreto et al.

(10) Patent No.: US 10,501,803 B2
(45) Date of Patent: *Dec. 10, 2019

(54) ISOFORMS OF GATA6 AND NKX2-1 AS MARKERS FOR DIAGNOSIS AND THERAPY OF CANCER AND AS TARGETS FOR ANTI-CANCER THERAPY

(71) Applicants: Max-Planck Gesellschaft zur Förderung der Wissenschaften e.V., Munich (DE); Justus-Liebig-Universität Giessen, Giessen (DE)

(72) Inventors: Guillermo Barreto, Karben (DE); Aditi Mehta, Bad Nauheim (DE); Indrabahadur Singh, Friedberg (DE); Marten Szibor, Espoo (FI); Rajkumar Savai, Bad Nauheim (DE); Werner Seeger, Biebertal (DE); Thomas Braun, Bad Nauheim (DE); Andreas Günther, Polheim Watzenborn-Steinberg (DE); Marcus Krüger, Bad Nauheim (DE)

(73) Assignees: MAX-PLANCK GESELLSCHAFT ZUR FÖRDERUNG DER WISSENSCHAFTEN E.V., Munich (DE); JUSTUS-LIEBIG-UNIVERSITÄT GIESSEN, Giessen (DE)

( * ) Notice: Subject to any disclaimer, the term of this patent is extended or adjusted under 35 U.S.C. 154(b) by 119 days.

This patent is subject to a terminal disclaimer.

(21) Appl. No.: 14/892,492

(22) PCT Filed: May 21, 2014

(86) PCT No.: PCT/EP2014/060489

§ 371 (c)(1),
(2) Date: Nov. 19, 2015

(87) PCT Pub. No.: WO2014/187881

PCT Pub. Date: Nov. 27, 2014

(65) Prior Publication Data

US 2016/0244842 A1 Aug. 25, 2016

(30) Foreign Application Priority Data

May 21, 2013 (EP) .................................... 13168629
May 21, 2013 (EP) .................................... 13168636

(51) Int. Cl.

| | |
|---|---|
| ***C12Q 1/68*** | (2018.01) |
| ***C12Q 1/6886*** | (2018.01) |
| ***G01N 33/574*** | (2006.01) |

(52) U.S. Cl.

CPC ..... *C12Q 1/6886* (2013.01); *G01N 33/57423* (2013.01); *C12Q 2600/112* (2013.01); *C12Q 2600/156* (2013.01); *C12Q 2600/158* (2013.01); *G01N 2333/47* (2013.01)

(58) Field of Classification Search

None

See application file for complete search history.

(56) References Cited

U.S. PATENT DOCUMENTS

| | | | | |
|---|---|---|---|---|
| 3,773,919 | A | 11/1973 | Boswell et al. | |
| 4,485,045 | A | 11/1984 | Regen et al. | |
| 4,544,545 | A | 10/1985 | Ryan et al. | |
| 4,683,195 | A * | 7/1987 | Mullis | C12Q 1/6827 435/6.1 |
| 6,582,908 | B2 * | 6/2003 | Fodor | B01J 19/0046 435/288.3 |
| 2006/0008468 | A1 * | 1/2006 | Chiang | A61K 39/0011 424/193.1 |
| 2008/0227663 | A1 * | 9/2008 | Tisone | B01J 19/0046 506/39 |
| 2010/0120627 | A1 * | 5/2010 | Belouchi | C12Q 1/6883 506/9 |
| 2012/0101002 | A1 * | 4/2012 | Riel-Mehan | C12Q 1/6886 506/9 |
| 2014/0322696 | A1 * | 10/2014 | Vunjak-Novakovic | A01N 1/0226 435/1.2 |

(Continued)

FOREIGN PATENT DOCUMENTS

| | | | |
|---|---|---|---|
| DE | 3218121 | A1 | 11/1983 |
| EP | 0036676 | A1 | 9/1981 |

(Continued)

OTHER PUBLICATIONS

Free Dictionary definition for "measuring." Available via url: < thefreedictionary.com/measuring>, printed on Sep. 20, 2017.*

(Continued)

*Primary Examiner* — Carla J Myers

(74) *Attorney, Agent, or Firm* — Steinfl + Bruno LLP

(57) ABSTRACT

The present invention relates to a method of assessing whether a subject suffers from cancer or is prone to suffering from cancer, in particular lung cancer, comprising the measurement of the amounts of specific isoforms of GATA6 and/or NKX2-1 in a sample of said subject. Furthermore, the present invention relates to a composition for use in medicine comprising (an) inhibitor(s) of specific isoforms of GATA6 and/or NKX2-1. Additionally, the present invention relates to a kit for use in a method of assessing whether a subject suffers from cancer or is prone to suffering from cancer, in particular lung cancer.

22 Claims, 51 Drawing Sheets

Specification includes a Sequence Listing.

(56) References Cited

U.S. PATENT DOCUMENTS

| | | | |
|---|---|---|---|
| 2016/0244842 | A1 | 8/2016 | Barreto et al. |
| 2018/0051344 | A1 | 2/2018 | Barreto et al. |

FOREIGN PATENT DOCUMENTS

| | | | |
|---|---|---|---|
| EP | 0052322 A2 | 5/1982 |
| EP | 0058481 A1 | 8/1982 |
| EP | 0088046 A2 | 9/1983 |
| EP | 0102324 A2 | 3/1984 |
| EP | 0133988 A2 | 3/1985 |
| EP | 0142641 A2 | 5/1985 |
| EP | 0143949 A1 | 6/1985 |
| EP | 2999797 A1 | 3/2016 |
| EP | 3215635 A1 | 9/2017 |
| EP | 3461909 A1 | 4/2019 |
| JP | S607934 A | 1/1985 |
| WO | WO 2004/060302 | 7/2004 |
| WO | WO 2014/187881 | 11/2014 |
| WO | 2016/071350 A1 | 5/2016 |

OTHER PUBLICATIONS

Palmer et al. BMC Genomics. 2006. 7:115.*
Min et al BMC Genomics. 2010. 11:96.*
Zhuo et al J Histochem Cytochem. 1996. 44(10): 1183-1193.*
Sanchez-Palencia et al International J Cancer. Nov. 28, 2010. 129(2): 355-364.*
Affymetrix NetAffxTM Analysis Center for U133 Plus 2.0 Array GATA6, available via url: < affymetrix.com/analysis/netaffx/fullrecord.affx?pk=HG-U133_PLUS_2:210002_AT> , printed on Nov. 2, 2017.*
Affymetrix NetAffxTM Analysis Center for U133 Plus 2.0 Array TTF-1 / NKX2-1, available via url: <affymetrix.com/analysis/netaffx/fullrecord.affx?pk=HG-U133_PLUS_2:210673_X_AT>, printed on Nov. 2, 2017.*
Nguyen, "Converging effectors of airway lineage specification and metastasis in lung cancer," *Cancer Research*, 74(19):3012, 2014.
PCT International Preliminary Report on Patentability issued in International Application No. PCT/EP2015/075615, dated May 18, 2017.
PCT International Search Report and Written Opinion issued in International Application No. PCT/EP2015/075615, dated Feb. 17, 2015.
Yamaguchi et al., "NKX2-1/TTF-1: an enigmatic oncogene that functions as a double-edged sword for cancer cell survival and progression," *Cancer Cell*, 23(6):718-723, 2013.
Coulson et al., "A splice variant of the neuron-restrictive silencer factor repressor is expressed in small cell lung cancer: a potential role in depression of neuroendocrine genes and a useful clinical marker," *Cancer Research*, 60:1840-1844, 2000.
Extended European Search Report issued in European Application No. 13168629.7, dated Oct. 10, 2013.
Guo, "Hypermethylation of the GATA genes in lung cancer," *Clinical Cancer Research*, 10(23):7917-7924, 2004.
Kendall et al., "Oncogenic cooperation and coamplification of developmental transcription factor genes in lung cancer," *Proceedings of the National Academy of Sciences*, 104(42):16663-16668, 2007.
Matsumoto et al., "Short alternative splice transcripts of the MDM2 oncogene correlate to malignancy in human astrocytic neoplasms," *Cancer Research*, 58:609-613, 1998.
PCT International Preliminary Report on Patentability issued in International Application No. PCT/EP2014/060489, dated Dec. 3, 2015.
PCT International Search Report and Written Opinion issued in International Application No. PCT/EP2014/060489, dated Oct. 7, 2014.
Winslow et al., "Suppression of lung adenocarcinoma progression by Nkx2-1," *Nature*, 473(7345):101-104, 2011.
Addgene "Integrin beta 2—mYFP—Plasmid #: 8638" *Addgene*. Sep. 2003. 4 pages.
"Safety Data Sheet—Cat #: 31330038" *Life Technologies*.Jul. 21, 2015. 8 pages.
Asnaghi et al. "E-cadherin negatively regulates neoplastic growth in non-small cell lung cancer: role of Rho GTPases" *Oncogene, Macmillan Publishers Ltd*. 2010. vol. 29. pp. 2760-2771. 12 pages.
BD Heidelberg "Product Specification Sheet—Dispase—Category #: 354235—Lot #: 47180" *BD Biosciences—Discovery Labware*. No Date. 2 pages.
Beadsmoore et al. "Classification, staging, and prognosis of lung cancer" *European Journal of Radiology, Elsevier*.2003. vol. 45. pp. 8-17. 10 pages.
Beer et al. "Gene-expression profiles predict survival of patients with lung adenocarcinoma" *Nature Medicine, Nature Publishing Group*.Aug. 2002. vol. 8, No. 8. pp. 816-824. 9 pages.
Bhattacharjee et al. "Classification of human lung carcinomas by mRNA expression profiling reveals distinct adenocarcinoma subclasses" *Proceedings of the National Academy of Sciences of the United States of America, National Academy of Sciences*.Nov. 20, 2001. vol. 98, No. 24. pp. 13790-13795. 6 pages.
Bishop et al. "Napsin A and thyroid transcription factor-1 expression in carcinomas of the lung, breast, pancreas, colon, kidney, thyroid, and malignant mesothelioma" *Human Pathology, Elsevier*. 2010. vol. 41. pp. 20-25. 6 pages.
Brodowicz et al. "Cisplatin and gemcitabine first-line chemotherapy followed by maintenance gemcitabine or best supportive care in advanced non-small cell lung cancer: A phase III trial" *Lung Cancer, Elsevier*.2006. vol. 52. pp. 155-163. 9 pages.
Bruno et al. "Lung Cell-specific Expression of the Murine Surfactant Protein A (SP-A) Gene is Mediated by Interactions between the SP-A Promoter and Thyroid Transcription Factor-1" *The Journal of Biological Chemistry, The American Society for Biochemistry and Molecular Biology Inc*. Mar. 24, 1995. vol. 270, No. 12. pp. 6531-6536. 6 pages.
Burdett et al. "Chemotherapy and surgery versus surgery alone in non-small cell lung cancer (Review)" *The Cochrane Collaboration—The Cochrane Library, John Wiley & Sons Ltd*.2007. No. 3. 3 pages.
Cagle et al. "Advances in Treatment of Lung Cancer with Targeted Therapy" *Archives of Pathology & Laboratory Medicine, College of American Pathologists*.May 2012.vol. 136. pp. 504-509. 6 pages.
Carpagnano et al. "Cigarette smoke and increased COX-2 and survivin levels in exhaled breath condensate of lung cancer patients: How hot is the link?" *Lung Cancer, Elsevier*.2010. vol. 67. pp. 108-113. 6 pages.
Chen HY et al. "A Five-Gene Signature and Clinical Outcome in Non-Small-Cell Lung Cancer" *The New England Journal of Medicine, Massachusetts Medical Society*.Jan. 4, 2007. vol. 356, No. 1. pp. 11-20. 10 pages.
Chen PM et al. "Activation of NF-kB by SOD2 promotes the aggressiveness of lung adenocarcinoma by modulating NKX2-1-mediated IKKβ expression" *Carcinogenesis, Oxford University Press*.2013. vol. 34, No. 11. pp. 2655-2663. 9 pages.
Cheung et al. "Control of Alveolar Differentiation by the Lineage Transcription Factors GATA6 and HOPX Inhibits Lung Adenocarcinoma Metastasis" *Cancer Cell, Cell Press*.Jun. 10, 2013. vol. 23. pp. 725-738. 14 pages.
Chevalier et al. "Significant Effect of Adjuvant Chemotherapy on Survival in Locally Advanced Non-Small-Cell Lung Carcinoma" *Journal of the National Cancer Institute, Oxford University Press*. Jan. 1, 1992. vol. 84, No. 1. pp. 58. 1 page.
Cox et al. "A practical guide to the MaxQuant computational platform for SILAC-based quantitative proteomics" *Nature Protocols, Nature Publishing Group*.2009. vol. 4, No. 5. pp. 698-705. 8 pages.
Davis et al. "Exhaled Breath Condensate—an overview" *Immunology and Allergy Clinics of North America, Elsevier*.Aug. 2012.vol. 32, No. 3. pp. 363-375. 14 pages.
Hughes et al. "The cellular delivery of antisense oligonucleotides and ribozymes" *Drug Discovery Today, Elsevier*.Mar. 2001. vol. 6, No. 6. pp. 303-315. 13 pages.
Dosoretz et al. "Radiation Therapy in the Management of Medically Inoperable Carcinoma of the Lung: Results and Implications for

(56) References Cited

OTHER PUBLICATIONS

Future Treatment Strategies" *International Journal of Radiation—Oncology—Biology—Physics, Pergamon Press Ltd.*1992.vol. 24, No. 1. pp. 3-9. 7 pages.
Dou et al. "Anti-Her2 single-chain antibody mediated DNMTs-siRNA delivery for targeted breast cancer therapy" *Journal of Controlled Release, Elsevier.*2012. vol. 161. pp. 875-883. 9 pages.
D'Urso et al. "Sputum Analysis: Non-Invasive Early Lung Cancer Detection" *Journal of Cellular Physiology, Wiley Periodicals Inc.* 2013. vol. 228. pp. 945-951. 7 pages.
Eden et al. "GOrilla: a tool for discovery and visualization of enriched GO terms in ranked gene lists" *BMC Bioinformatics, BioMed Central Ltd.*Feb. 3, 2009.vol. 10, No. 48. 7 pages.
Effros et al. "Dilution of Respiratory Solutes in Exhaled Condensates" *American Journal of Respiratory and Critical Care Medicine,American Thoracic Society.*2002.vol. 165. pp. 663-669. 7 pages.
Effros et al. "Exhaled Breath Condensates: Analyzing the Expiratory Plume" *American Journal of Respiratory and Critical Care Medicine, American Thoracic Society.*Apr. 15, 2012.vol. 185, No. 8. pp. 803-804. 2 pages.
Elkin et al. "Ch. 19, Unit 19.2: Tail Vein Assay of Cancer Metastasis" *Current Protocols in Cell Biology—Whole Organism and Tissue Analyses, John Wiley & Sons Inc.*2001. pp. 19.2.1-19.2.7. 7 pages.
Eng, John M.D. "ROC Analysis: Web-Based Calculator for ROC Curves." *John Hopkins—University School of Medicine.*Mar. 19, 2014. 2 pages.
Eppstein et al. "Biological activity of liposome-encapsulated murine interferon y is mediated by a cell membrane receptor" *Proceedings of the National Academy of Sciences of the United States of America, National Academy of Sciences.*Jun. 1985. vol. 82. pp. 3688-3692. 5 pages.
Eramo et al. "Review—Lung cancer stem cells: tools and targets to fight lung cancer" *Oncogene, Macmillan Publishers Ltd.*2010. vol. 29. pp. 4625-4635. 11 pages.
European Society for Medical Oncology (ESMO) "Early Detection of Lung Cancer" *ScienceDaily.*May 9, 2009. 2 pages.
Garber et al. "Diversity of gene expression in adenocarcinoma of the lung" *Proceedings of the National Academy of Sciences for the United States of America, National Academy of Sciences.*Nov. 20, 2001. vol. 98, No. 24. pp. 13784-13789. 6 pages.
Gauden et al. "The Curative Treatment by Radiotherapy Alone of Stage I Non-Small Cell Carcinoma of the Lung" *Chest, American College of Chest Physicians*. Nov. 1995. vol. 108, No. 5. pp. 1278-1282. 5 pages.
Gessner et al. "Detection of p53 gene mutations in exhaled breath condensate of non-small cell lung cancer patients" *Lung Cancer, Elsevier.*2004. vol. 43. pp. 215-222. 8 pages.
Giangreco et al. "Pulmonary Perspective: Lung Cancer and Lung Stem Cells" *American Journal of Respiratory and Critical Care Medicine, American Thoracic Society.*2007. vol. 175. pp. 547-553. 7 pages.
Goldstraw et al. "The IASLC Lung Cancer Staging Project: Proposals for the Revision of the TNM Stage Groupings in the Forthcoming (Seventh) edition of the TNM Classification of Malignant Tumours" *Journal of Thoracic Oncology, International Association for the Study of Lung Cancer.*Aug. 2007. vol. 2, No. 8. pp. 706-714. 9 pages.
Gorshkova et al. "Codon 12 Region of Mouse K-ras Gene Is the Site for in vitro Binding of Transcription Factors GATA-6 and NF-Y" *Biochemistry* (*Moscow*), *Pleiades Publishing Inc.*2005. vol. 70, No. 10. pp. 1180-1184. 5 pages.
Han et al. "Vascular Endothelial Growth Factor Expression in Stage I Non-Small Cell Lung Cancer Correlates With Neoangiogenesis and a Poor Prognosis" *Annals of Surgical Oncology, Lippincott Williams & Wilkins.*2001. vol. 8, No. 1. pp. 72-79. 2 pages.
Hanna et al. "Randomized Phase III Trial of Pemetrexed Versus Docetaxel in Patients With Non-Small-Cell Lung Cancer Previously Treated With Chemotherapy" *Journal of Clinical Oncology, American Society of Clinical Oncology.*May 1, 2004. vol. 22, No. 9. pp. 1589-1597. 9 pages.
Harlow et al. "Antibodies—A Laboratory Manual 2nd Edition" *Cold Spring Harbor Laboratory Press.*2014. 22 pages.
Henschke et al. "Early Lung Cancer Action Project: overall design and findings from baseline screening" *The Lancet, Elsevier.*Jul. 10, 1999. vol. 354. pp. 99-105. 7 pages.
Herbst et al. "Molecular Origins of Cancer: Lung Cancer" *The New England Journal of Medicine, Massachusetts Medical Society.*Sep. 25, 2008. vol. 359, No. 13. pp. 1367-1380. 14 pages.
Hillion et al. "Upregulation of MMP-2 by HMGA1 Promotes Transformation in Undifferentiated, Large-Cell Lung Cancer" *Molecular Cancer Research, American Association for Cancer Research.* 2009. vol. 7, No. 11. pp. 1803-1812. 11 pages.
Ho et al. "Nitrite levels in breath condensate of patients with cystic fibrosis is elevated in contrast to exhaled nitric oxide" *Thorax, BMJ Publishing Group Ltd.*1998. vol. 53. pp. 680-684. 5 pages.
Hoffman et al. "Lung Cancer" *The Lancet, Elsevier.*Feb. 5, 2000. vol. 355. pp. 479-485. 7 pages.
Horvath et al. "Exhaled breath condensate: methodological recommendations and unresolved questions" *European Respiratory Journal, European Respiratory Society Journals Ltd.*2005. vol. 26. pp. 523-548. 26 pages.
Howington et al. "Treatment of Stage 1 and II Non-small Cell Lung Cancer" *Chest, American College of Chest Physicians.*May 2013. vol. 143, No. 5. pp. e278S-e313S. 36 pages.
Hughes et al. "The cellular delivery of antisense oligonucleotides and ribozymes" *Drug Discovery Today, Elsevier.*Mar. 6, 2001. vol. 6, No. 6. pp. 303-315. 13 pages.
Huszar et al. "Adenosine in exhaled breath condensate in healthy volunteers and in patients with asthma" *European Respiratory Journal, European Respiratory Society Journals Ltd.*2002. vol. 20. pp. 1393-1398. 6 pages.
Hwang et al. "Hepatic uptake and degradation of unilamellar sphingomyelin / Cholesterol liposomes: A kinetic study" *Proceedings of the National Academy of Sciences for the United States of America, National Academy of Sciences.*Jul. 1980. vol. 77, No. 7. pp. 4030-4034. 5 pages.
Hyde et al. "Critical Review: Clinical Manifestations of Lung Cancer" *Chest, American College of Chest Physicians.*Mar. 1974. vol. 65, No. 3. pp. 299-306. 8 pages.
"IARC Monographs on the Evaluation of the Carcinogenic Risk of Chemicals to Humans—Tobacco Smoking" World Health Organization—International Agency for Research on Cancer. 1986. vol. 38. 432 pages.
Jett, James R. "Limitations of Screening for Lung Cancer with Low-Dose Spiral Computed Tomography" *Clinical Cancer Research, American Association for Cancer Research.*Jul. 1, 2005. vol. 11, No. 13. pp. 4988s-4992s. 6 pages.
Kalhor et al. "TTF-1 and p63 for distinguishing pulmonary small-cell carcinoma from poorly differentiated squamous cell carcinoma in previously pap-stained cytologic material" *Modern Pathology, United States and Canadian Academy of Pathology Inc.*2006. vol. 19. pp. 1117-1123. 7 pages.
Kase et al. "Expression of E-cadherin and B-Catenin in Human Non-Small Cell Lung Cancer and the Clinical Significance" *Clinical Cancer Research, American Association for Cancer Research.* Dec. 2000. vol. 6. pp. 4789-4796. 9 pages.
Keijzer et al. "The transcription factor GATA6 is essential for branching morphogenesis and epithelial cell differentiation during fetal pulmonary development" *Development, The Company of Biologists Ltd.*2001. vol. 128. pp. 503-511. 9 pages.
Kim et al. "Gefitinib versus docetaxel in previously treated non-small-cell lung cancer (INTEREST): A randomised phase III trial" *The Lancet, Elsevier.*Nov. 22, 2008. vol. 372. pp. 1809-1818. 10 pages.
Kishimoto et al. "Aberrations of the p53 Tumor Suppressor Gene in Human Non-Small Cell Carcinomas of the Lung" *Cancer Research,American Association for Cancer Research.*Sep. 1, 1992. vol. 52. pp. 4799-4804. 7 pages.
Kolla et al. "Thyroid Transcription Factor in Differentiating Type II Cells—Regulation, Isoforms, and Target Genes" *American Journal*

(56) References Cited

OTHER PUBLICATIONS

*of Respiratory Cell and Molecular Biology, American Thoracic Society*.2007. vol. 36. pp. 213-225. 13 pages.
Kostikas et al. "Prostaglandin E2 in the expired breath condensate of patients with asthma" *European Respiratory Journal, European Respiratory Society Journals Ltd*.2003. vol. 22. pp. 743-747. 5 pages.
Kullmann et al. "Differential Cytokine Pattern in the Exhaled Breath of Patients with Lung Cancer" *Pathology & Oncology Research, Springer Netherlands*.2008. vol. 14. pp. 481-483. 3 pages.
Kumar et al. "HMGA2 functions as a competing endogenous RNA to promote lung cancer progression" *Nature*,Macmillan Publishers Ltd. Jan. 9, 2014. vol. 505, No. 7482. pp. 212-217. 20 pages.
Kwak et al. "Anaplastic Lymphoma Kinase Inhibition in Non-Small-Cell Lung Cancer" *The New England Journal of Medicine, Massachusetts Medical Society*.Oct. 28, 2010. vol. 363, No. 18. pp. 1693-1703. 11 pages.
Lang et al. "Gain of Function of a P53 Hot Spot Mutation in a Mouse Model of Li-Fraumeni Syndrome" *Cell, Cell Press*.Dec. 17, 2004. vol. 119. pp. 861-872. 12 pages.
Langer et al. "Biocompatibility of polymeric delivery systems for macromolecules" *Journal of Biomedical Materials Research, John Wiley & Sons Inc*.1981. vol. 15. pp. 267-277. 11 pages.
Lee et al. "The tumor suppressor microRNA let-7 represses the HMGA2 oncogene" *Genes & Development, Cold Spring Harbor Laboratory Press*.2007. vol. 21. pp. 1025-1030. 7 pages.
Li et al. "Expressions of MUC1 and vascular andothelial growth factor mRNA in blood are biomarkers for predicting efficacy of gefitnib treatment in non-small cell lung cancer" *BMC Cancer, BioMed Central Ltd*.2014. vol. 14, No. 848. 11 pages.
Liang CC et al. "In vitro scratch assay: a convenient and inexpensive method for analysis of cell migration in vitro" *Nature Protocols, Nature Publishing Group*.2007. vol. 2, No. 2. pp. 329-333. 5 pages.
Liang et al. "Optimizing the delivery systems of chimeric RNA-DNA oligonucleotides" *European Journal of Biochemistry, Federation of European Biochemical Societies Press*.Dec. 2002. vol. 269, No. 23. pp. 5753-5758. 12 pages.
Lindholm et al. "Expression of GATA-6 transcription factor in pleural malignant mesothelioma and metastatic pulmonary adenocarcinoma" *Journal of Clinical Pathology, BMJ Publishing Group Ltd*.2009. vol. 62. pp. 339-344. 7 pages.
Mani et al. "The Epithelial-Mesenchymal Transition Generates Cells with Properties of Stem Cells" *Cell, Elsevier*.May 16, 2008. vol. 133. pp. 704-715. 12 pages.
Margana et al. "Functional Analysis of Surfactant Protein B (SP-B) Promoter" *The Journal of Biological Chemistry, The American Society for Biochemistry and Molecular Biology Inc*.Jan. 31, 1997. vol. 272, No. 5. pp. 3083-3090. 9 pages.
Martini et al. "Incidence of local recurrence and second primary tumors in resected stage I lung cancer" *Journal of Thoracic and Cardiovascular Surgery, Mosby-Year Book Inc*.1995.vol. 109, No. 1. pp. 120-129. 10 pages.
Martini N. et al. "Survival After Resection of Stage II Non-Small Cell Lung Cancer" *The Annals of Thoracic Surgery, The Society of Thoracic Surgeons*.1992. vol. 54. pp. 460-466. 7 pages.
Meyerson et al. "Genomic and Proteomic Profiling of Lung Cancers: Lung Cancer Classification in the Age of Targeted Therapy" *Journal of Clinical Oncology, American Society of Clinical Oncology*. May 10, 2005. vol. 23, No. 14. pp. 3219-3226. 8 pages.
Minoo et al. "Defects in Tracheoesophageal and Lung Morphogenesis in Nkx2.1( − / − ) Mouse Embryos" *Developmental Biology, Academic Press*.1999. vol. 209. pp. 60-71. 12 pages.
Mok et al. "Gefitinib or Carboplatin-Paclitaxel in Pulmonary Adenocarcinoma" *The New England Journal of Medicine, Massachusetts Medical Society*.Sep. 3, 2009. vol. 361, No. 10. pp. 947-957. 11 pages.
Molina et al. "Non-Small Cell Lung Cancer: Epidemiology, Risk Factors, Treatment, and Survivorship" *Mayo Clinic Proceedings, Mayo Foundation for Medical Education and Research*.May 2008. vol. 83, No. 5. pp. 584-594. 11 pages.
Montuschi P et al. "Exhaled leukotrienes and prostaglandins in COPD" *Thorax, BMJ Publishing Group Ltd*.2003. vol. 58. pp. 585-588. 4 pages.
Montuschi, Paolo "Review: Analysis of exhaled breath condensate in respiratory medicine: methodological aspects and potential clinical applications" *Therapeutic Advances in Respiratory Disease, SAGE Publications*.2007. vol. 1, No. 1. pp. 5-23. 20 pages.
Mountain, Clifton F. "Revisions in the International System for Staging Lung Cancer" *Chest, American College of Chest Physicians*. 1997. vol. 111. pp. 1710-1717. 8 pages.
National Lung Screening Trial Research Team "Reduced Lung-Cancer Mortality with Low-Dose Computed Tomographic Screening" *The New England Journal of Medicine, Massachusetts Medical Society*.Aug. 4, 2011. vol. 365, No. 5. pp. 395-409. 15 pages.
Okamoto et al. "Randomised phase III trial of carboplatin plus etoposide vs split doses of cisplatin plus etoposide in elderly or poor-risk patients with extensive disease small-cell lung cancer: JCOG 9702" *British Journal of Cancer, Cancer Research UK*.2007. vol. 97. pp. 162-169. 8 pages.
Osterlind et al. "Treatment policy of surgery in small cell carcinoma of the lung: retrospective analysis of a series of 874 consecutive patients" *Thorax, BMJ Publishing Group Ltd*.1985. vol. 40. pp. 272-277. 6 pages.
Pao et al. "Acquired Resistance of Lung Adenocarcinomas to Gefitinib or Erlotinib Is Associated with a Second Mutation in the EGFR Kinase Domain" *PLOS Medicine, Public Library of Science*. Mar. 2005. vol. 2, No. 3. pp. 0225-0235. 11 pages.
Park et al. "Phase III Trial of Two Versus Four Additional Cycles in Patients Who Are Nonprogressive After Two Cycles of Platinum-Based Chemotherapy in Non-Small-Cell Lung Cancer" *Journal of Clinical Oncology, American Society of Clinical Oncology*.Nov. 20, 2007. vol. 25, No. 33. pp. 5233-5239. 7 pages.
Paz Ares et al. "Maintenance therapy with pemetrexed plus best supportive care versus placebo plus best supportive care after induction therapy with pemetrexed plus cisplatin for advancednon-squamous non-small-cell lung cancer (PARAMOUNT): a double-blind, phase 3, randomised controlled trial" *The Lancet, Elsevier*. Mar. 2012. vol. 13. pp. 247-255. 9 pages.
Pelosi et al. "p63 immunoreactivity in lung cancer: yet another player in the development of squamous cell carcinomas?" *Journal of Pathology, John Wiley & Sons Ltd*.2002. vol. 198. pp. 100-109. 10 pages.
"Penicillin-Streptomycin (5,000 U/mL)" *Gibco—ThermoFisher Scientific*. No Date. 4 pages.
Pignon et al. "A Meta-Analysis of Thoracic Radiotherapy for Small-Cell Lung Cancer" *The New England Journal of Medicine, Massachusetts Medical Society*.Dec. 3, 1992. vol. 327, No. 23. pp. 1618-1624. 7 pages.
Pignon JP et al. "Lung Adjuvant Cisplatin Evaluation: A Pooled Analysis by the LACE Collaborative Group" *Journal of Clinical Oncology, American Society of Clinical Oncology*.Jul. 20, 2008. vol. 26, No. 21. pp. 3552-3559. 8 pages.
Prasad et al. "Long term survival after pulmonary resection for small cell carcinoma of the lung" *Thorax, BMJ Publishing Group Ltd*.1989. vol. 44. pp. 784-787. 4 pages.
Prestridge, Dan S. "Predicting Pol II Promoter Sequences using Transcription Factor Binding Sites" *Journal of Molecular Biology, Academic Press Ltd*.1995. vol. 249. pp. 923-932. 10 pages.
Promega "MagneSphere Magnetic Separation Products—Cat #: Z5410 & Z5481" *Promega Corporation*.Jun. 2009. 13 pages.
Qi et al. "Retinoblastoma Binding Protein 2 (RBP2) Promotes HIF-1a-VEGF-Induced Angiogenesis of Non-Small Cell Lung Cancer via the Akt Pathway" *PLOS ONE, Public Library of Science*. Aug. 2014. vol. 9, No. 8. pp. 1-12. 12 pages.
Rawlins et al. "Epithelial stem cells of the lung: privileged few or opportunities for many?" *Development, The Company of Biologists Ltd*.2006. vol. 133. pp. 2455-2465. 11 pages.
Rekhtman et al. "Immunohistochemical algorithm for differentiation of lung adenocarcinoma and squamous cell carcinoma based on

(56) References Cited

OTHER PUBLICATIONS large series of whole-tissue sections with validation in small specimens" *Modern Pathology, Nature Publishing Group*.2011. vol. 24, pp. 1348-1359. 12 pages.
Riely et al. "Frequency and Distinctive Spectrum of KRAS Mutations in Never Smokers with Lung Adenocarcinoma" *Clinical Cancer Research, American Association for Cancer Research*.2008. vol. 14. pp. 5731-5734. 5 pages.
Rollin et al. "The Intracellular Localization of ID2 Expression Has a Predictive Value in Non Small Cell Lung Cancer" *PLOS ONE, Public Library of Science*.Jan. 2009. vol. 4, No. 1. 7 pages.
Scagliotti et al. "Phase III Study Comparing Cisplatin Plus Gemcitabine With Cisplatin Plus Pemetrexed in Chemotherapy-Naive Patients With Advanced-Stage Non-Small-Cell Lung Cancer" *Journal of Clinical Oncology, American Society of Clinical Oncology*.Jul. 20, 2008. vol. 26, No. 21. pp. 3543-3551. 9 pages.
Schneider et al. "Targeted siRNA Delivery and mRNA Knockdown Mediated by Bispecific Digoxigenin-binding Antibodies" *Molecular Therapy-Nucleic Acids, Nature Publishing Group*.2012. vol. 1. 11 pages.
Schuchert et al. "Sublobar Resection for Early-Stage Lung Cancer" *Seminars in Thoracic and Cardiovascular Surgery, Elsevier*.2010. vol. 22, No. 1. pp. 22-31. 10 pages.
Shahid et al. "Increased Interleukin-4 and Dcreased Interferon-y in Exhaled Breath Condensate of Children with Asthma" *American Journal of Respiratory and Critical Care Medicine, American Thoracic Society*.2002. vol. 165. pp. 1290-1293. 4 pages.
Shaw et al. "Effect of crizotinib on overall survival in patients with advanced non-small-cell lung cancer harbouring ALK gene rearrangement: a retrospective analysis" *The Lancet Oncology, Elsevier*. Oct. 2011. vol. 12, No. 11. pp. 1004-1012. 20 pages.
Shijubo et al. "Vascular Endothelial Growth Factor and Osteopontin in Stage I Lung Adenocarcinoma" *American Journal of Respiratory and Critical Care Medicine, American Thoracic Society*.1999. vol. 160. pp. 1269-1273. 5 pages.
Sidman et al. "Controlled Release of Macromolecules and Pharmaceuticals from Synthetic Polypeptides Based on Glumatic Acid" *Biopolymers, John Wiley & Sons Inc*.1983. vol. 22. pp. 547-556. 10 pages.
Sing et al. "ROCR: visualizing classifier performance in R" *Bioinformatics, Oxford University Press*. 2005. vol. 21, No. 20. pp. 3940-3941. 2 pages.
Slotman et al. "Prophylactic Cranial Irradiation in Extensive Small-Cell Lung Cancer" *The New England Journal of Medicine, Massachusetts Medical Society*.Aug. 16, 2007. vol. 357, No. 7. pp. 664-672. 9 pages.
Smit et al. "Surgical resection for small cell carcinoma of the lung: a retrospective study" *Thorax, BMJ Publishing Group Ltd*.1994. vol. 49. pp. 20-22. 3 pages.
Song et al. "Antibody mediated in vivo delivery of small interfering RNAs via cell-surface receptors" *Nature Biotechnology, Nature Publishing Group*.Jun. 2005. vol. 23, No. 6. pp. 709-717. 9 pages.
Stacker et al. "VEGF-D promotes the metastatic spread of tumor cells via the lymphatics" *Nature Medicine, Nature Publishing Group*.Feb. 2001. vol. 7, No. 2. pp. 186-191. 6 pages.
Strauss et al. "Chest X-Ray Screening for Lung Cancer:Overdiagnosis, Endpoints, and Randomized Population Trials" *Journal of Surgical Oncology, Wiley Periodicals Inc*.2013. vol. 108. pp. 294-300. 7 pages.
Su et al. "The VEGF-C/Flt-4 axis promotes invasion and metastasis of cancer cells" *Cancer Cell, Cell Press*.Mar. 2006. vol. 9. pp. 209-223. 15 pages.
Sundstrom et al. "Hypofractionated Palliative Radiotherapy (17 Gy per two fractions) in Advanced Non-Small-Cell Lung Carcinoma Is Comparable to Standard Fractionation for Symptom Control and Survival: A National Phase III Trial" *Journal of Clinical Oncology, American Society of Clinical Oncology*.2004. vol. 22. pp. 801-810. 10 pages.
Sutherland et al. "Cell of Origin of Small Cell Lung Cancer: Inactivation of Trp53 and Rb1 in Distinct Cell Types of Adult Mouse Lung" *Cancer Cell, Cell Press*.Jun. 14, 2011. vol. 19. pp. 754-764. 11 pages.
Taguchi et al. "Circulating pro-surfactant protein B as a risk biomarker for lung cancer" *Cancer Epidemiology, Biomarkers, & Prevention, American Association for Cancer Research*.Jul. 29, 2013. 22 pages.
Tang et al. "FOXA2 functions as a suppressor of tumor metastasis by inhibition of epithelial-to-mesenchymal transition in human lung cancers" *Cell Research, Nature Publishing Group*.2011. vol. 21. pp. 316-326. 11 pages.
"Technical Data Sheet—Cat. #: 553078—Biotin Rat Anti-Mouse CD45" *BD Biosciences*.2017. 1 page.
"Technical Data Sheet—Cat. #: 553143—Biotin Rat Anti-Mouse CD16/CD323" *BD Biosciences*. 2017. 2 pages.
"The diagnosis and treatment of lung cancer (update)" *National Collaborating Centre for Cancer*.Apr. 2011. 198 pages.
Thierry-Mieg et al. "AceView: a comprehensive cDNA-supported gene and transcripts annotation" *Genome Biology, BioMed Central Ltd*.Aug. 7, 2006. vol. 7. pp. s12.1-s12.14. 14 pages.
Tian et al. "Regulation of lung endoderm progenitor cell behavior by miR302/367" *Development, The Company of Biologists Ltd*. 2011. vol. 138. pp. 1235-1245. 11 pages.
Travis et al. "Diagnosis of Lung Cancer in Small Biopsies and Cytology" *Archives of Pathology & Laboratory Medicine, College of American Pathologists*.May 2013. vol. 137. pp. 668-684. 17 pages.
Turner et al. "Napsin A, a New Marker for Lung Adenocarcinoma, Is Complementary and More Sensitive and Specific Than Thyroid Transcription Factor 1 in the Differential Diagnosis of Primary Pulmonary Carcinoma" *Archives of Pathology & Laboratory Medicine, College of American Pathologists*.Feb. 2012.vol. 136. pp. 163-171. 9 pages.
Wan et al. "Compensatory Roles of Foxa1 annd Foxa2 during Lung Morphogenesis" *The Journal of Biological Chemistry, The American Society for Biochemistry and Molecular Biology Inc*.Apr. 8, 2005. vol. 280, No. 14. pp. 13809-13816. 9 pages.
Wan et al. "Foxa2 is required for transition to air breathing at birth" *Proceedings of the National Academy of Sciences of the United States of America, National Academy of Sciences*.Oct. 5, 2004. vol. 101, No. 40. pp. 14449-14454. 6 pages.
Warde et al. "Does Thoracic Irradiation Improve Survival and Local Control in Limited-Stage Small-Cell Carcinoma of the Lung? A Meta-Analysis" *Journal of Clinical Oncology, American Society of Clinical Oncology*.1992. vol. 10. pp. 890-895. 6 pages.
White et al. "Epithelial stem cell mutations that promote squamous cell carcinoma metastasis" *The Journal of Clinical Investigation, The American Society for Clinical Investigation*.2013. vol. 123, No. 10. pp. 4390-4404. 16 pages.
Whithaus et al. "Evaluation of Napsin A, Cytokeratin 5/6, p63, and Thyroid Transcription Factor 1 in Adenocarcinoma Versus Squamous Cell Carcinoma of the Lung" *Archives of Pathology &Laboratory Medicine, College of American Pathologists*.Feb. 2012.vol. 136. pp. 155-162. 8 pages.
Wozniak et al. "Randomized Trial Comparing Cisplatin With Cisplatin Plus Vinorelbine in the Treatment of Advanced Non-Small-Cell Lung Cancer: A Southwest Oncology Group Study" *Journal of Clinical Oncology, American Society of Clinical Oncology*.Jul. 1998. vol. 16, No. 7. pp. 2459-2465. 7 pages.
Xiao et al. "Methylation of P16 in exhaled breath condensate for diagnosis of non-small cell lung cancer" *Lung Cancer, Elsevier*. 2014. vol. 83. pp. 56-60. 5 pages.
Xu et al. "Evidence for type II cells as cells of origin of K-Ras-induced distal lung adenocarcinoma" *Proceedings of the National Academy of Sciences of the United States of America, National Academy of Sciences*.Mar. 27, 2012. vol. 109, No. 13. pp. 4910-4915. 6 pages.
Xu et al. "Molecular and Microscopic Analysis of Bacteria and Viruses in Exhaled Breath Collected Using a Simple Impaction and Condensing Method" *PLOS ONE, Public Library of Science*.Jul. 2012. vol. 7, No. 7. 8 pages.

(56) References Cited

OTHER PUBLICATIONS

Xu ZY et al. "Smoking, Air Pollution, and the High Rates of Lung Cancer in Shenyang, China" *Journal of the National Cancer Institute, Oxford University Press*.1989. vol. 81. pp. 1800-1806. 7 pages.
Ye et al. "Combination of Napsin A and TTF-1 Immunohistochemistry Helps in Differentiating Primary Lung Adenocarcinoma From Metastatic Carcinoma in the Lung" *Applied Immunohistochemistry &Molecular Morphology, Lippincott Williams & Wilkins*.Jul. 2011.vol. 19, No. 4. pp. 313-317. 5 pages.
Zakharkina et al. "Detection of microorganisms in exhaled breath condensate during acute exacerbations of COPD" *Respirology, Asian Pacific Society of Respirology*.2011. vol. 16. pp. 932-938. 7 pages.
Zhang et al. "GATA and Nkx factors synergistically regulate tissue-specific gene expression and development in vivo" *Development, The Company of Biologists Ltd*.2007. vol. 134. pp. 189-198. 10 pages.
Affymetrix Expression Probeset Details https://www.affymetrix.com/analysis/netaffx/fullrecord.affx?pk=HG-U133. Nov. 2, 2017. 4 pages.
Affymetrix NetAffx™ Analysis Center for U133 Plus 2.0 Array GATA6 and TTF-1/NKX2-1 probe setshttp://www.affymetrix.com/support/technical/byproduct.affx?product=hg-u133-plus. Captured: Jun. 15, 2012. 4 pages.
Extended European Search Report for European Application No. 18181398.1, filed on Jul. 3, 2018, on behalf of Max-Planck-Gesellschaft Zur Forderung Der Wissensc, dated Jan. 2, 2019. 6 pages.
Sanchez-Palencia et al. "Gene expression profiling reveals novel biomarkers in nonsmall cell lung cancer" *International Journal of Cancer, Union of International Cancer Control*.2011. vol. 129. pp. 355-364. 10 pages.
EMBL online tool, CpG Plot http://www.ebi.ac.uk/Tools/emboss/cpgplot/. No Date. 2 pages.
Fan W. et al., "A statistical method for predicting splice variants between two groups of samples using GeneChip expression array data" BioMed Central pp. 1-9 (2006) 9 pages.
Integrin-deficient, B6.129S7-Itgb2tm2Bay /J, stock # 003329, [8700894]. No Date. 13 pages.
Pedraza V et al., "Gene Expression Signatures in Breast Cancer Distinguish Phenotype Characteristics, Histologic Subtypes, and Tumor Invasiveness" Cancer pp. 486-496 (2010) 11 pages.
Xiang et al., 1990, stock# 002644, Jackson Laboratories. 8 pages.
Zhou et al. "Thyroid Transcription Factor-1, Hepatocyte Nuclear Factor-3B, Surfactant Protein B, C, and Clara Cell Secretory Protein in Developing Mouse Lung" *The Journal of Histochemistry and Cytochemistry, The Histochemical Society Inc*.1996. vol. 44, No. 10. pp. 1183-1193. 12 pages.

* cited by examiner

A.

B.

A.

B.

C

Figure 4
A.
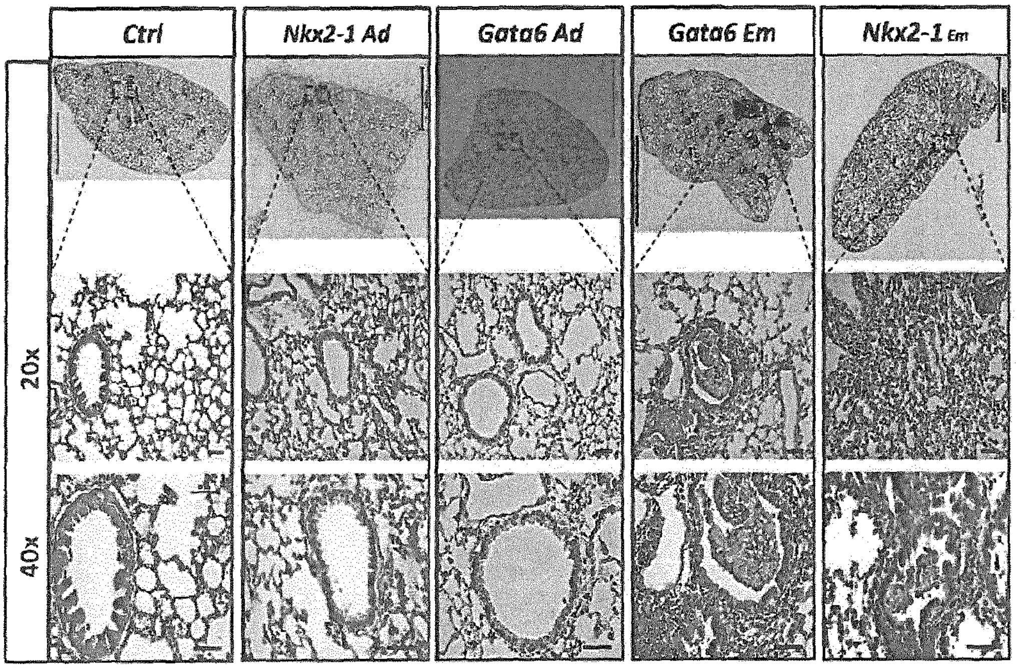
B.
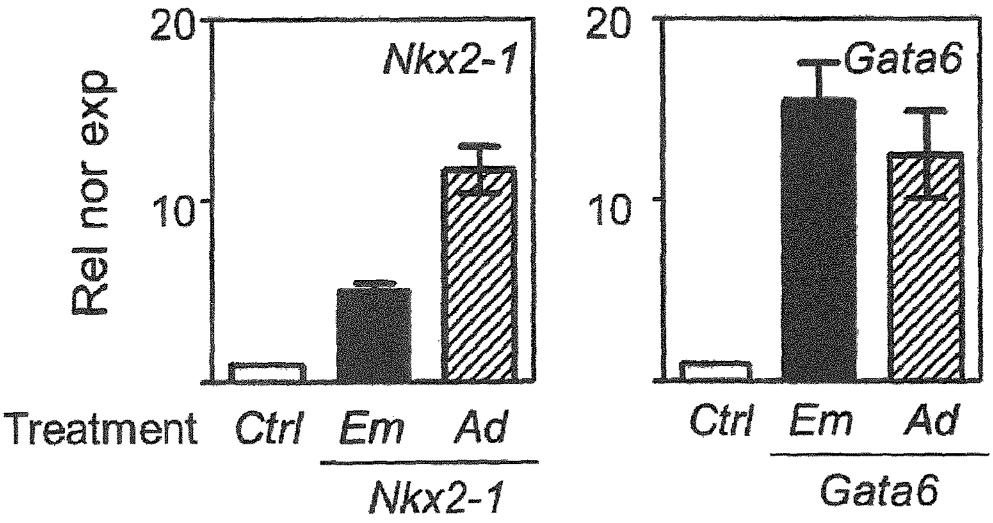

| *Gata6* | | |
|---|---|---|
| **Target Sequence** | **Sense strand siRNA** | **Antisense strand siRNA** |
| AATCAGGAGCGCAGGCTGCAG | UCAGGAGCGCAGGCUGCAGtt | CUGCAGCCUGCGCUCCUGAtt |
| AAGAGGCGCCTCCTCTCTCCT | GAGGCGCCUCCUCUCUCCUtt | AGGAGAGAGGAGGCGCCUCtt |

| *Nkx2-1* |
|---|
| **shHairpin sequence (5'-3')** |
| CCGGCCCATGAAGAAGAAAGCAATTCTCGAGAATTGCTTTCTTCTTCATGGGTTTTTG |
| GTACCGGGGGATCATCCTTGTAGATAAACTCGAGTTTATCTACAAGGATGATCCCTTTTTG |
| CCGGATTCGGAATCAGCTAGCAATTCTCGAGAATTGCTAGCTGATTCCGAATTTTTG |

A

B.

Scale bar: 1mm

*Gata6 Mus musculus*
*Gata6 Ad* : Aceview
***Gata6 Em* : NM_010258.3 (NCBI)**

Score = 7891.0, Identities = 1805/3476 (51%), Positives = 1805/3476 (51%), Gaps = 1587/3476 (45%)

```
Gata6 Em       1 ------TTCACCTCCGCACCCAGCAGCTTGTAGAGAGCAGTT----CCGACCCACAGCC
                       TT A                 TT TAG G G  GTT    CCGA
Gata6 Ad       1 TGGGCATTAA-----------------TTTTAGTGTG--GTTATCTCCGA---------

Gata6 Em      51 GGCACCCTTCGGCTAGCGCTGTTTGTTTAGGGCTCGGTGAGTCCAATC----------A
                                                      TGAG C AA C           A
Gata6 Ad      32 -------------------------------------TGAGCCTAAGCGATTTGGAAAA

Gata6 Em     101 GAGCGCAGGCTGCAGTTTTCCGGCAGAGCAGTAAGAGGCGCCT----------------
                  AGC               CCGG  GAG           GCCT
Gata6 Ad      55 CAGC---------------CCGGTGGAG-----------GCCTGCCTGGTTCCCCACCC

Gata6 Em     145 CTC----TCTCCTTTTTATTCACCAGCAGCGACTAGCAGACCCCGGACTCTCGCTCTCC
                 CTC    TCTCC T T ATTC                            TC  GCTCTCC
Gata6 Ad      89 CTCCAAGTCTCCCTGTCATTC----------------------------TTCCTGCTCTCC

Gata6 Em     201 ----------GCC----------GGCG---------CCCTCCGCCTC------------
                           GCC          GGCG         CCCTCC CCTC
Gata6 Ad     123 CTTTGGGGTGGCCTCGGCTCTGGGGCGGTCTCACCCCCCTCC-CCTCCTGCGTTTTCCC

Gata6 Em     219 ------TCTCCGCGCCCCGGAGCACCCT--------------------CGGTCGCGGCCG
                       TCTC GCGC C G   CACCCT                    CG TC  GGCC
Gata6 Ad     182 TCCTTTTCTCTGCGCTCTGCTCCACCCTACTATGACCAATTCCAGAACGATCT-GGCCT

Gata6 Em     254 TCTTCT---------------------------------------------------CGC
                 TC  CT                                                   CGC
Gata6 Ad     241 TCCCCTGCTGGGGTTGACCATGGGGTGGGCCAGGGGTGGCCCGGCCCGCCTGAGTACGC

Gata6 Em     264 CATCGCTCG------------------------AGGAATCAAAAGTCAGGTTGGAGTAG
                    CGCT G                        AGGAATCAAAAGTCAGGTTGGAGTAG
Gata6 Ad     301 ---CGCTGGTGGTTGTAAGGCGGTTTGTGTTTAAGGAATCAAAAGTCAGGTTGGAGTAG

Gata6 Em     300 GCCGGACAGTGGATGGCCTTGACTGACGGCGGCTGGTGCCTGCCAAAGCGTTTCGGGGC
                 GCCGGACAGTGGATGGCCTTGACTGACGGCGGCTGGTGCCTGCCAAAGCGTTTCGGGGC
Gata6 Ad     358 GCCGGACAGTGGATGGCCTTGACTGACGGCGGCTGGTGCCTGCCAAAGCGTTTCGGGGC

Gata6 Em     360 GCTGCTGCGGACGCCGGCGACTCCGGGCCCTTTCCAGCGCGGGAGCCCTCCTCGCCGCT
                 GCTGCTGCGGACGCCGGCGACTCCGGGCCCTTTCCAGCGCGGGAGCCCTCCTCGCCGCT
Gata6 Ad     418 GCTGCTGCGGACGCCGGCGACTCCGGGCCCTTTCCAGCGCGGGAGCCCTCCTCGCCGCT

Gata6 Em     420 TCCCCCATCTCGTCTTCGTCCTCCTCCTGCTCCCGGGGCGGGGATCGCGGTCCCTGCGG
                 TCCCCCATCTCGTCTTCGTCCTCCTCCTGCTCCCGGGGCGGGGATCGCGGTCCCTGCGG
Gata6 Ad     478 TCCCCCATCTCGTCTTCGTCCTCCTCCTGCTCCCGGGGCGGGGATCGCGGTCCCTGCGG
```

Figure 11 B

Gata6 Mus musculus
Gata6 Ad : Q61169-2 (Uniprot)
Gata6 Em : NP_034388.2 (NCBI), Q61169-1 (Uniprot)

Score = 2368.0, Identities = 443/589 (75%), Positives = 443/589 (75%), Gaps = 146/589 (24%)

```
Gata6 Em     1 MALTDGGWCLPKRFGAAAADAGDSGPFPAREPSSPLSPISSSSSSCSRGGDRGPCGASNC

Gata6 Ad       ------------------------------------------------------------

Gata6 Em    61 RTPQLDAEAVAGPPGRSLLLSPYASHPFAAAHGAAAPGVAGPGSALSTWEDLLLFTDLDQ

Gata6 Ad       ------------------------------------------------------------

Gata6 Em   121 AATASKLLWSSRGAKLSPFAAEQPEEMYQTLAALSSQGPAAYDGAPGGFVHSAAAAAAAA
                                         MYQTLAALSSQGPAAYDGAPGGFVHSAAAAAAAA
Gata6 Ad     1 --------------------------MYQTLAALSSQGPAAYDGAPGGFVHSAAAAAAAA

Gata6 Em   181 AAASSPVYVPTTRVGSMLSGLPYLQGAGSGPSNHAGGAGAHPGWSQASADSPPYGGGGAA
               AAASSPVYVPTTRVGSMLSGLPYLQGAGSGPSNHAGGAGAHPGWSQASADSPPYGGGGAA
Gata6 Ad    35 AAASSPVYVPTTRVGSMLSGLPYLQGAGSGPSNHAGGAGAHPGWSQASADSPPYGGGGAA

Gata6 Em   241 GGGAAGPGGAGSATAHASARFPYSPSPPMANGAARDPGGYVAAGGTGAGSVSGGGGSLAA
               GGGAAGPGGAGSATAHASARFPYSPSPPMANGAARDPGGYVAAGGTGAGSVSGGGGSLAA
Gata6 Ad    95 GGGAAGPGGAGSATAHASARFPYSPSPPMANGAARDPGGYVAAGGTGAGSVSGGGGSLAA

Gata6 Em   301 MGGREHQYSSLSAARPLNGTYHHHHHHHPTYSPYMAAPLTPAWPAGPFETPVLHSLQGRA
               MGGREHQYSSLSAARPLNGTYHHHHHHHPTYSPYMAAPLTPAWPAGPFETPVLHSLQGRA
Gata6 Ad   155 MGGREHQYSSLSAARPLNGTYHHHHHHHPTYSPYMAAPLTPAWPAGPFETPVLHSLQGRA

Gata6 Em   361 GAPLPVPRGPSTDLLEDLSESRECVNCGSIQTPLWRRDGTGHYLCNACGLYSKMNGLSRP
               GAPLPVPRGPSTDLLEDLSESRECVNCGSIQTPLWRRDGTGHYLCNACGLYSKMNGLSRP
Gata6 Ad   215 GAPLPVPRGPSTDLLEDLSESRECVNCGSIQTPLWRRDGTGHYLCNACGLYSKMNGLSRP

Gata6 Em   421 LIKPQKRVPSSRRLGLSCANCHTTTTTLWRRNAEGEPVCNACGLYMKLHGVPRPLAMKKE
               LIKPQKRVPSSRRLGLSCANCHTTTTTLWRRNAEGEPVCNACGLYMKLHGVPRPLAMKKE
Gata6 Ad   275 LIKPQKRVPSSRRLGLSCANCHTTTTTLWRRNAEGEPVCNACGLYMKLHGVPRPLAMKKE

Gata6 Em   481 GIQTRKRKPKNINKSKACSGNSSGSVPMTPTSSSSNSDDCTKNTSPSTQATTSGVGASVM
               GIQTRKRKPKNINKSKACSGNSSGSVPMTPTSSSSNSDDCTKNTSPSTQATTSGVGASVM
Gata6 Ad   335 GIQTRKRKPKNINKSKACSGNSSGSVPMTPTSSSSNSDDCTKNTSPSTQATTSGVGASVM

Gata6 Em   541 SAVGENANPENSDLKYSGQDGLYIGVSLSSPAEVTSSVRQDSWCALALA 589
               SAVGENANPENSDLKYSGQDGLYIGVSLSSPAEVTSSVRQDSWCALALA
Gata6 Ad   395 SAVGENANPENSDLKYSGQDGLYIGVSLSSPAEVTSSVRQDSWCALALA 443
```

Figure 11 C

*GATA6 Homo sapiens*

*GATA6 Ad* : Aceview

*GATA6 Em :* NM_005257.4 (NCBI)

Score = 15043.0, Identities = 3071/3828 (80%), Positives = 3071/3828 (80%), Gaps = 728/3828 (19%)

```
Gata6 Em      1 ---GA--CCCACAGCCTGGCACCCTTCGGCGAGC--------GCTGTTTGTTTAG-----
                   GA   CCAC  CC GG             GC        G T TTTG   AG
Gata6 Ad      1 ATTGATCTCCACGCCCGGG-------------GCAGAAATAGGATCTTTGAGAAGTCTC

Gata6 Em     43 ----GGCTCGGTGAG--------TCC-------------AATCAGGAGCCCAGGC-----
                    GG TC  TGAG        TCC             AA  AGGAG   AGGC
Gata6 Ad     48 AATGGGATCTTTGAGAAGTCAGATCCCATTTGAACTAGAAAAAGGAGTGGAGGCGAGGT

Gata6 Em     73 ---TGCAGTTTTCCGGCAGAGCAGTAAGAGGCGCCTCCTCTCTCCTTTTTATTCACCAG
                   TGCA                          GCCT C CTCT  TT
Gata6 Ad    108 GCGTGCA--------------------------GCCTACGCTCTTGTT------------

Gata6 Em    130 AGCGCGGCGCAGACCCCGGACTCGCGCTCG-------CCCGCTGGCGCCCTCGGCTTCT
                            A CCCG   TCG  CTC        CCCG                  T
Gata6 Ad    130 ------------AACCCG---TCGATCTCCTACCATACCCG------------------T

Gata6 Em    183 TCCGCGCCTGGGAGCACCCTCCGCCGCGGCCGTTCTCCATGCGCAGCGCCCGCCCGAGG
                TCC             CCC C                            CCC CC  AGG
Gata6 Ad    158 TCC-------------CCCAC----------------------------CCCACCTCAGG

Gata6 Em    243 GCTAGACGTCAGCTTGGAGCGGCGCCGGACCGTGGATGGCCTTGACTGACGGCGGCTGG
                GCTAGACGTCAGCTTGGAGCGGCGCCGGACCGTGGATGGCCTTGACTGACGGCGGCTGG
Gata6 Ad    178 GCTAGACGTCAGCTTGGAGCGGCGCCGGACCGTGGATGGCCTTGACTGACGGCGGCTGG

Gata6 Em    303 GCTTGCCGAAGCGCTTCGGGGCCGCGGGTGCGGACGCCAGCGACTCCAGAGCCTTTCCA
                GCTTGCCGAAGCGCTTCGGGGCCGCGGGTGCGGACGCCAGCGACTCCAGAGCCTTTCCA
Gata6 Ad    238 GCTTGCCGAAGCGCTTCGGGGCCGCGGGTGCGGACGCCAGCGACTCCAGAGCCTTTCCA

Gata6 Em    363 CGCGGGAGCCCTCCACGCCGCCTTCCCCCATCTCTTCCTCGTCCTCCTCCTGCTCCCGG
                CGCGGGAGCCCTCCACGCCGCCTTCCCCCATCTCTTCCTCGTCCTCCTCCTGCTCCCGG
Gata6 Ad    298 CGCGGGAGCCCTCCACGCCGCCTTCCCCCATCTCTTCCTCGTCCTCCTCCTGCTCCCGG

Gata6 Em    423 GCGGAGAGCGGGGCCCCGGCGGCGCCAGCAACTGCGGGACGCCTCAGCTCGACACGGAG
                GCGGAGAGCGGGGCCCCGGCGGCGCCAGCAACTGCGGGACGCCTCAGCTCGACACGGAG
Gata6 Ad    358 GCGGAGAGCGGGGCCCCGGCGGCGCCAGCAACTGCGGGACGCCTCAGCTCGACACGGAG

Gata6 Em    483 CGGCGGCCGGACCCCCGGCCCGCTCGCTGCTGCTCAGTTCCTACGCTTCGCATCCCTTC
                CGGCGGCCGGACCCCCGGCCCGCTCGCTGCTGCTCAGTTCCTACGCTTCGCATCCCTTC
Gata6 Ad    418 CGGCGGCCGGACCCCCGGCCCGCTCGCTGCTGCTCAGTTCCTACGCTTCGCATCCCTTC

Gata6 Em    543 GGGCTCCCCACGGACCTTCGGCGCCTGGGGTCGCGGGCCCCGGGGGCAACCTGTCGAGC
                GGGCTCCCCACGGACCTTCGGCGCCTGGGGTCGCGGGCCCCGGGGGCAACCTGTCGAGC
Gata6 Ad    478 GGGCTCCCCACGGACCTTCGGCGCCTGGGGTCGCGGGCCCCGGGGGCAACCTGTCGAGC

Gata6 Em    603 GGGAGGACTTGCTGCTGTTCACTGACCTCGACCAAGCCGCGACCGCCAGCAAGCTGCTG
                GGGAGGACTTGCTGCTGTTCACTGACCTCGACCAAGCCGCGACCGCCAGCAAGCTGCTG
Gata6 Ad    538 GGGAGGACTTGCTGCTGTTCACTGACCTCGACCAAGCCGCGACCGCCAGCAAGCTGCTG

Gata6 Em    663 GGTCCAGCCGCGGCGCCAAGCTGAGCCCCTTCGCACCCGAGCAGCCGGAGGAGATGTAC
                GGTCCAGCCGCGGCGCCAAGCTGAGCCCCTTCGCACCCGAGCAGCCGGAGGAGATGTAC
Gata6 Ad    598 GGTCCAGCCGCGGCGCCAAGCTGAGCCCCTTCGCACCCGAGCAGCCGGAGGAGATGTAC

Gata6 Em    723 AGACCCTCGCCGCTCTCTCCAGCCAGGGTCCGGCCGCCTACGACGGCGCGCCCGGCGGC
                AGACCCTCGCCGCTCTCTCCAGCCAGGGTCCGGCCGCCTACGACGGCGCGCCCGGCGGC
Gata6 Ad    658 AGACCCTCGCCGCTCTCTCCAGCCAGGGTCCGGCCGCCTACGACGGCGCGCCCGGCGGC

Gata6 Em    783 TCGTGCACTCTGCGGCCGCGGCGGCAGCAGCCGCGGCGGCGGCCAGCTCCCCGGTCTAC
                TCGTGCACTCTGCGGCCGCGGCGGCAGCAGCCGCGGCGGCGGCCAGCTCCCCGGTCTAC
Gata6 Ad    718 TCGTGCACTCTGCGGCCGCGGCGGCAGCAGCCGCGGCGGCGGCCAGCTCCCCGGTCTAC

Gata6 Em    843 TGCCCACCACCCGCGTGGGTTCCATGCTGCCCGGCCTACCGTACCACCTGCAGGGGTCG
                TGCCCACCACCCGCGTGGGTTCCATGCTGCCCGGCCTACCGTACCACCTGCAGGGGTCG
Gata6 Ad    778 TGCCCACCACCCGCGTGGGTTCCATGCTGCCCGGCCTACCGTACCACCTGCAGGGGTCG
```

Figure 11 D

GATA6 Homo sapiens

GATA6 Ad : Q92908-2 (Uniprot)

GATA6 Em : NP_005248.2 (NCBI), Q92908-1 (Uniprot)

Score = 2422.0, Identities = 449/595 (75%), Positives = 449/595 (75%), Gaps = 146/595 (24%)

```
Gata6 Em     1 MALTDGGWCLPKRFGAAGADASDSRAFPAREPSTPPSPISSSSSSCSRGGERGPGGASNC

Gata6 Ad       ------------------------------------------------------------

Gata6 Em    61 GTPQLDTEAAAGPPARSLLLSSYASHPFGAPHGPSAPGVAGPGGNLSSWEDLLLFTDLDQ

Gata6 Ad       ------------------------------------------------------------

Gata6 Em   121 AATASKLLWSSRGAKLSPFAPEQPEEMYQTLAALSSQGPAAYDGAPGGFVHSAAAAAAAA
                                         MYQTLAALSSQGPAAYDGAPGGFVHSAAAAAAAA
Gata6 Ad     1 --------------------------MYQTLAALSSQGPAAYDGAPGGFVHSAAAAAAAA

Gata6 Em   181 AAASSPVYVPTTRVGSMLPGLPYHLQGSGSGPANHAGGAGAHPGWPQASADSPPYGSGGG
               AAASSPVYVPTTRVGSMLPGLPYHLQGSGSGPANHAGGAGAHPGWPQASADSPPYGSGGG
Gata6 Ad    35 AAASSPVYVPTTRVGSMLPGLPYHLQGSGSGPANHAGGAGAHPGWPQASADSPPYGSGGG

Gata6 Em   241 AAGGGAAGPGGAGSAAAHVSARFPYSPSPPMANGAAREPGGYAAAGSGGAGGVSGGGSSL
               AAGGGAAGPGGAGSAAAHVSARFPYSPSPPMANGAAREPGGYAAAGSGGAGGVSGGGSSL
Gata6 Ad    95 AAGGGAAGPGGAGSAAAHVSARFPYSPSPPMANGAAREPGGYAAAGSGGAGGVSGGGSSL

Gata6 Em   301 AAMGGREPQYSSLSAARPLNGTYHHHHHHHHHHPSPYSPYVGAPLTPAWPAGPFETPVLH
               AAMGGREPQYSSLSAARPLNGTYHHHHHHHHHHPSPYSPYVGAPLTPAWPAGPFETPVLH
Gata6 Ad   155 AAMGGREPQYSSLSAARPLNGTYHHHHHHHHHHPSPYSPYVGAPLTPAWPAGPFETPVLH

Gata6 Em   361 SLQSRAGAPLPVPRGPSADLLEDLSESRECVNCGSIQTPLWRRDGTGHYLCNACGLYSKM
               SLQSRAGAPLPVPRGPSADLLEDLSESRECVNCGSIQTPLWRRDGTGHYLCNACGLYSKM
Gata6 Ad   215 SLQSRAGAPLPVPRGPSADLLEDLSESRECVNCGSIQTPLWRRDGTGHYLCNACGLYSKM

Gata6 Em   421 NGLSRPLIKPQKRVPSSRRLGLSCANCHTTTTTLWRRNAEGEPVCNACGLYMKLHGVPRP
               NGLSRPLIKPQKRVPSSRRLGLSCANCHTTTTTLWRRNAEGEPVCNACGLYMKLHGVPRP
Gata6 Ad   275 NGLSRPLIKPQKRVPSSRRLGLSCANCHTTTTTLWRRNAEGEPVCNACGLYMKLHGVPRP

Gata6 Em   481 LAMKKEGIQTRKRKPKNINKSKTCSGNSNNSIPMTPTSTSSNSDDCSKNTSPTTQPTASG
               LAMKKEGIQTRKRKPKNINKSKTCSGNSNNSIPMTPTSTSSNSDDCSKNTSPTTQPTASG
Gata6 Ad   335 LAMKKEGIQTRKRKPKNINKSKTCSGNSNNSIPMTPTSTSSNSDDCSKNTSPTTQPTASG

Gata6 Em   541 AGAPVMTGAGESTNPENSELKYSGQDGLYIGVSLASPAEVTSSVRPDSWCALALA 595
               AGAPVMTGAGESTNPENSELKYSGQDGLYIGVSLASPAEVTSSVRPDSWCALALA
Gata6 Ad   395 AGAPVMTGAGESTNPENSELKYSGQDGLYIGVSLASPAEVTSSVRPDSWCALALA 449
```

Figure 11 E

*Nkx2-1 Mus musculus*
*Nkx2-1 Ad* : NM_009385 (NCBI)
*Nkx2-1 Em* : NM_001146198 (NCBI)

Score = 11232.0, Identities = 2264/2832 (79%), Positives = 2264/2832 (79%), Gaps = 567/2832 (20%)

```
Nkx2.1 Ad      1 CTGGTAACAGCAATGAGGCTGACGCCCCCGGGCCCGCTAGGGAGCACAGCCCACAGCT

Nkx2.1 Em        ------------------------------------------------------------

Nkx2.1 Ad     61 CCCTTGCCAGGCGCCCAAGGACCCTCAAGGCGCGGGGCTCACACTTGAAGCCTGGGAA

Nkx2.1 Em        ------------------------------------------------------------

Nkx2.1 Ad    121 CTCAGACAGGAAACCCACTTCCTCCTAAGCAGTTTCTTCCTAGCCGGATGAGAGGCGC
                                                 TTT TT
Nkx2.1 Em      1 --------------------------------TTTTTT----------------------

Nkx2.1 Ad    181 AATTGAAGCAGAATGATCCTCATCTACTAATATCCAGCGTGGCCACAAAGCGACCGGC

Nkx2.1 Em        ------------------------------------------------------------

Nkx2.1 Ad    241 TTTACGCCGCCACTTTAGACAAAGATATTTGGTTATTCCCGGGGAAGCAAGTGCACTT
                                                                           TT
Nkx2.1 Em      7 ----------------------------------------------------------TT

Nkx2.1 Ad    301 GCATGGCTGAGCTCCGGGAGGAGGCGAGCCTCAGCCCAGCCTCCCGCCCGCTGGGCTG

Nkx2.1 Em        ------------------------------------------------------------

Nkx2.1 Ad    361 GGCGTCGAGATATTCGCCTCCTCCCGGACAACGAGTTCCACCCGGGTTCAGACTCAGT
                                 CCTCCTC            TTCC                    T
Nkx2.1 Em     11 ----------------CCTCCTC------------TTCC--------------------T

Nkx2.1 Ad    421 CACTCTGCAACGGATCTGCGGGCGCTCACGCGGCTCCCCGCCCGGGCTTTCACTGAAG
                 C
Nkx2.1 Em     25 C-----------------------------------------------------------

Nkx2.1 Ad    481 TCGGAAGGGAAAACTGCGGGGATCTGAGCTGGGGTGCTGGGACTGGGATGTCCTCGGA
                                                                     TCCT
Nkx2.1 Em     26 ----------------------------------------------------TCCT----

Nkx2.1 Ad    541 GACAGCATCAGCTTCTGAAGCCGAAGTATCCAGGCCATGGGCAAGGGTCAGGGGCACC
                                                                           CC
Nkx2.1 Em     30 ----------------------------------------------------------CC

Nkx2.1 Ad    601 CCGACGCCGAATCATGTCGATGAGTCCAAAGCACACGACTCCGTTCTCAGTGTCTGAC
                 CCGACGCCGAATCATGTCGATGAGTCCAAAGCACACGACTCCGTTCTCAGTGTCTGAC
Nkx2.1 Em     34 CCGACGCCGAATCATGTCGATGAGTCCAAAGCACACGACTCCGTTCTCAGTGTCTGAC

Nkx2.1 Ad    661 CTTGAGTCCCCTGGAGGAAAGCTACAAGAAAGTGGGCATGGAGGGCGGCGGCCTCGGG
                 CTTGAGTCCCCTGGAGGAAAGCTACAAGAAAGTGGGCATGGAGGGCGGCGGCCTCGGG
Nkx2.1 Em     94 CTTGAGTCCCCTGGAGGAAAGCTACAAGAAAGTGGGCATGGAGGGCGGCGGCCTCGGG

Nkx2.1 Ad    721 TCCGCTCGCAGCGTACAGACAGGGCCAGGCGGCCCCACCGGCCGCGGCCATGCAGCAG
                 TCCGCTCGCAGCGTACAGACAGGGCCAGGCGGCCCCACCGGCCGCGGCCATGCAGCAG
Nkx2.1 Em    154 TCCGCTCGCAGCGTACAGACAGGGCCAGGCGGCCCCACCGGCCGCGGCCATGCAGCAG

Nkx2.1 Ad    781 CGCCGTGGGGCACCACGGCGCCGTCACCGCCGCCTACCACATGACGGCGGCGGGGGTG
                 CGCCGTGGGGCACCACGGCGCCGTCACCGCCGCCTACCACATGACGGCGGCGGGGGTG
Nkx2.1 Em    214 CGCCGTGGGGCACCACGGCGCCGTCACCGCCGCCTACCACATGACGGCGGCGGGGGTG

Nkx2.1 Ad    841 CCAGCTCTCGCACTCCGCCGTGGGGGGCTACTGCAACGGCAACCTGGGCAACATGAGC
                 CCAGCTCTCGCACTCCGCCGTGGGGGGCTACTGCAACGGCAACCTGGGCAACATGAGC
Nkx2.1 Em    274 CCAGCTCTCGCACTCCGCCGTGGGGGGCTACTGCAACGGCAACCTGGGCAACATGAGC

Nkx2.1 Ad    901 GCTGCCGCCTTACCAGGACACCATGCGGAACAGCGCTTCGGGCCCCGGATGGTACGGC
                 GCTGCCGCCTTACCAGGACACCATGCGGAACAGCGCTTCGGGCCCCGGATGGTACGGC
Nkx2.1 Em    334 GCTGCCGCCTTACCAGGACACCATGCGGAACAGCGCTTCGGGCCCCGGATGGTACGGC
```

Figure 11 F

Nkx2-1 Mus musculus

Protein

Nkx2-1 Ad : no protein product

Nkx2-1 Em : NP_033411 (NCBI)

```
1       10        20        30        40        50
|       |         |         |         |         |
MSMSPKHTTPFSVSDILSPLEESYKKVGMEGGGLGAPLAAYRQGQAAPPA
AAMQQHAVGHHGAVTAAYHMTAAGVPQLSHSAVGGYCNGNLGNMSELPPY
QDTMRNSASGPGWYGANPDPRFPAISRFMGPASGMNMSGMGGLGSLGDVS
KNMAPLPSAPRRKRRVLFSQAQVYELERRFKQQKYLSAPEREHLASMIHL
TPTQVKIWFQNHRYKMKRQAKDKAAQQQLQQDSGGGGGGGGGAGCPQQQQ
AQQQSPRRVAVPVLVKDGKPCQAGAPAPGAASLQSHAQQQAQQQAQAAQA
AAAAISVGSGGAGLGAHPGHQPGSAGQSPDLAHHAASPAGLQGQVSSLSH
LNSSGSDYGAMSCSTLLYGRTW
```

Figure 11 G

*NKX2-1 Homo sapiens*

***NKX2-1 Ad* : NM_003317, XM_002344771 (NCBI)**

***NKX2-1 Em* : NM_001079668 (NCBI)**

Score = 10270.0, Identities = 2122/2398 (88%), Positives = 2122/2398 (88%), Gaps = 247/2398 (10%)

```
Nkx2.1 Em      1 CTGACAGACACGTAGACCAACAGTGCGGCCCCAGGGT-------TCGTCCCCAG----
                       GA AC TA                    A GGT       T GTC   CAG
Nkx2.1 Ad      1 ------GAAACTTA-------------------AAGGTGTTTACCTTGTCATCAGCATG

Nkx2.1 Em     48 -----ACTCGCTCGCTCAT-------------------TTGTTGGCGACTGGGGCTCA
                      A T  CTCG  CA                    TTGTTG    CT     T A
Nkx2.1 Ad     37 AGCTAATTATCTCGGGCAAGATGTAGGCTTCTATTGTCTTGTTG----CT-----TTA

Nkx2.1 Em     84 GC---AGCGAAGCCCGATGTGGTCCGGAGGCAGTGGGAA----GGCGCGGGGCT----
                 GC    GC    GCC          TC GG GGC G    AA    GGCGC GGGCT
Nkx2.1 Ad     88 GCTTACGCCCCGCC--------TCTGGTGGCTGCCTAAAACCTGGCGCCGGGCTAAAA

Nkx2.1 Em    131 ---GGGAGGCCGC-----------------------------------------------
                    G GAGGC GC
Nkx2.1 Ad    140 AACGCGAGGCAGCCCCCGAGCCTCCACTCAAGCCAATTAAGGAGGACTCGGTCCACTC

Nkx2.1 Em    141 -----------------------GGCG----------------------GG---AGGG
                                        GGCG                      GG   AGGG
Nkx2.1 Ad    200 TTACGTGTACATCCAACAAGATCGGCGTTAAGGTAACACCAGAATATTTGGCAAAGGG

Nkx2.1 Em    153 G-------AGCAGCCCCGGCAGGCT---------------------------------
                         AGCAGC      AGGCT
Nkx2.1 Ad    260 AAAAAAAAAGCAGC-----GAGGCTTCGCCTTCCCCCTCTCCCTTTTTTTTCCTCCTC

Nkx2.1 Em    171 -----------CAGCCGCCGCCGAATCATGTCGATGAGTCCAAAGCACACGACTCCGT
                            CAGCCGCCGCCGAATCATGTCGATGAGTCCAAAGCACACGACTCCGT
Nkx2.1 Ad    315 CCTTCCTCCTCCAGCCGCCGCCGAATCATGTCGATGAGTCCAAAGCACACGACTCCGT

Nkx2.1 Em    220 TCAGTGTCTGACATCTTGAGTCCCCTGGAGGAAAGCTACAAGAAAGTGGGCATGGAGG
                 TCAGTGTCTGACATCTTGAGTCCCCTGGAGGAAAGCTACAAGAAAGTGGGCATGGAGG
Nkx2.1 Ad    375 TCAGTGTCTGACATCTTGAGTCCCCTGGAGGAAAGCTACAAGAAAGTGGGCATGGAGG

Nkx2.1 Em    280 GGCGGCCTCGGGGCTCCGCTGGCGGCGTACAGGCAGGGCCAGGCGGCACCGCCAACAG
                 GGCGGCCTCGGGGCTCCGCTGGCGGCGTACAGGCAGGGCCAGGCGGCACCGCCAACAG
Nkx2.1 Ad    435 GGCGGCCTCGGGGCTCCGCTGGCGGCGTACAGGCAGGGCCAGGCGGCACCGCCAACAG

Nkx2.1 Em    340 GCCATGCAGCAGCACGCCGTGGGGCACCACGGCGCCGTCACCGCCGCCTACCACATGA
                 GCCATGCAGCAGCACGCCGTGGGGCACCACGGCGCCGTCACCGCCGCCTACCACATGA
Nkx2.1 Ad    495 GCCATGCAGCAGCACGCCGTGGGGCACCACGGCGCCGTCACCGCCGCCTACCACATGA

Nkx2.1 Em    400 GCGGCGGGGGTGCCCCAGCTCTCGCACTCCGCCGTGGGGGGCTACTGCAACGGCAACC
                 GCGGCGGGGGTGCCCCAGCTCTCGCACTCCGCCGTGGGGGGCTACTGCAACGGCAACC
Nkx2.1 Ad    555 GCGGCGGGGGTGCCCCAGCTCTCGCACTCCGCCGTGGGGGGCTACTGCAACGGCAACC

Nkx2.1 Em    460 GGCAACATGAGCGAGCTGCCGCCGTACCAGGACACCATGAGGAACAGCGCCTCTGGCC
                 GGCAACATGAGCGAGCTGCCGCCGTACCAGGACACCATGAGGAACAGCGCCTCTGGCC
Nkx2.1 Ad    615 GGCAACATGAGCGAGCTGCCGCCGTACCAGGACACCATGAGGAACAGCGCCTCTGGCC
```

Figure 11 H

NKX2-1 Homo sapiens

NKX2-1 Ad : NM_003317, XM_002344771 (NCBI)

NKX2-1 Em : NM_001079668 (NCBI)

Score = 1956.0, Identities = 371/401 (92%), Positives = 371/401 (92%), Gaps = 30/401 (7%)

```
Nkx2.1 Em     1 ------------------------------MSMSPKHTTPFSVSDILSPLEESYKKVGM
                                              MSMSPKHTTPFSVSDILSPLEESYKKVGM
Nkx2.1 Ad     1 MWSGGSGKARGWEAAAGGRSSPGRLSRRRIMSMSPKHTTPFSVSDILSPLEESYKKVGM

Nkx2.1 Em    31 GGGLGAPLAAYRQGQAAPPTAAMQQHAVGHHGAVTAAYHMTAAGVPQLSHSAVGGYCNG
                GGGLGAPLAAYRQGQAAPPTAAMQQHAVGHHGAVTAAYHMTAAGVPQLSHSAVGGYCNG
Nkx2.1 Ad    61 GGGLGAPLAAYRQGQAAPPTAAMQQHAVGHHGAVTAAYHMTAAGVPQLSHSAVGGYCNG

Nkx2.1 Em    91 LGNMSELPPYQDTMRNSASGPGWYGANPDPRFPAISRFMGPASGMNMSGMGGLGSLGDV
                LGNMSELPPYQDTMRNSASGPGWYGANPDPRFPAISRFMGPASGMNMSGMGGLGSLGDV
Nkx2.1 Ad   121 LGNMSELPPYQDTMRNSASGPGWYGANPDPRFPAISRFMGPASGMNMSGMGGLGSLGDV

Nkx2.1 Em   151 KNMAPLPSAPRRKRRVLFSQAQVYELERRFKQQKYLSAPEREHLASMIHLTPTQVKIWF
                KNMAPLPSAPRRKRRVLFSQAQVYELERRFKQQKYLSAPEREHLASMIHLTPTQVKIWF
Nkx2.1 Ad   181 KNMAPLPSAPRRKRRVLFSQAQVYELERRFKQQKYLSAPEREHLASMIHLTPTQVKIWF

Nkx2.1 Em   211 NHRYKMKRQAKDKAAQQQLQQDSGGGGGGGGTGCPQQQQAQQQSPRRVAVPVLVKDGKP
                NHRYKMKRQAKDKAAQQQLQQDSGGGGGGGGTGCPQQQQAQQQSPRRVAVPVLVKDGKP
Nkx2.1 Ad   241 NHRYKMKRQAKDKAAQQQLQQDSGGGGGGGGTGCPQQQQAQQQSPRRVAVPVLVKDGKP

Nkx2.1 Em   271 QAGAPAPGAASLQGHAQQQAQHQAQAAQAAAAAISVGSGGAGLGAHPGHQPGSAGQSPD
                QAGAPAPGAASLQGHAQQQAQHQAQAAQAAAAAISVGSGGAGLGAHPGHQPGSAGQSPD
Nkx2.1 Ad   301 QAGAPAPGAASLQGHAQQQAQHQAQAAQAAAAAISVGSGGAGLGAHPGHQPGSAGQSPD

Nkx2.1 Em   331 AHHAASPAALQGQVSSLSHLNSSGSDYGTMSCSTLLYGRTW 371
                AHHAASPAALQGQVSSLSHLNSSGSDYGTMSCSTLLYGRTW
Nkx2.1 Ad   361 AHHAASPAALQGQVSSLSHLNSSGSDYGTMSCSTLLYGRTW 401
```

Figure 11 I

*Foxa2 Mus musuclus*

*Foxa2 Em (Var1):* Aceview (Isoform a)

*Foxa2 Ad (Var2):* NM_010446 (NCBI)

Score = 10116.0, Identities = 2040/2150 (94%), Positives = 2040/2150 (94%), Gaps = 103/2150 (4%)

```
Foxa2 var1      1 GGTCGTTTGTTGTGGCTG------------------------------------------   18
                                 CTG
Foxa2 var2      1 ---------------CTGACGACCAGGGCGGCCAGACCACGCGAGTCCTACGCGCCTCCT   45

Foxa2 var1     19 ----------------TTAAATTTTAAACCGCCATGCACTCGGCTTCC------------   50
                                  TTAA T T  AAC G  A G     GGC TCC
Foxa2 var2     46 GAGGCCGCCCCGGGACTTAACTGT--AACGGGGAGG-----GGCCTCCGGAGCAGCGGCC   98

Foxa2 var1     51 ----------AGTATGCTGGGAGCCGTGAAGATGGAAGGGCACGAGCCATCCGACTGGAG  100
                            AGTATGCTGGGAGCCGTGAAGATGGAAGGGCACGAGCCATCCGACTGGAG
Foxa2 var2     99 AGCGAGTTAAAGTATGCTGGGAGCCGTGAAGATGGAAGGGCACGAGCCATCCGACTGGAG  158

Foxa2 var1    101 CAGCTACTACGCGGAGCCCGAGGGCTACTCTTCCGTGAGCAACATGAACGCCGGCCTGGG  160
                  CAGCTACTACGCGGAGCCCGAGGGCTACTCTTCCGTGAGCAACATGAACGCCGGCCTGGG
Foxa2 var2    159 CAGCTACTACGCGGAGCCCGAGGGCTACTCTTCCGTGAGCAACATGAACGCCGGCCTGGG  218

Foxa2 var1    161 GATGAATGGCATGAACACATACATGAGCATGTCCGCGGCTGCCATGGGCGGCGGTTCCGG  220
                  GATGAATGGCATGAACACATACATGAGCATGTCCGCGGCTGCCATGGGCGGCGGTTCCGG
Foxa2 var2    219 GATGAATGGCATGAACACATACATGAGCATGTCCGCGGCTGCCATGGGCGGCGGTTCCGG  278

Foxa2 var1    221 CAACATGAGCGCGGGCTCCATGAACATGTCATCCTATGTGGGCGCTGGAATGAGCCCGTC  280
                  CAACATGAGCGCGGGCTCCATGAACATGTCATCCTATGTGGGCGCTGGAATGAGCCCGTC
Foxa2 var2    279 CAACATGAGCGCGGGCTCCATGAACATGTCATCCTATGTGGGCGCTGGAATGAGCCCGTC  338

Foxa2 var1    281 GCTAGCTGGCATGTCCCCGGGCGCCGGCGCCATGGCGGGCATGAGCGGCTCAGCCGGGGC  340
                  GCTAGCTGGCATGTCCCCGGGCGCCGGCGCCATGGCGGGCATGAGCGGCTCAGCCGGGGC
Foxa2 var2    339 GCTAGCTGGCATGTCCCCGGGCGCCGGCGCCATGGCGGGCATGAGCGGCTCAGCCGGGGC  398

Foxa2 var1    341 GGCCGGCGTGGCGGGCATGGGACCTCACCTGAGTCCGAGTCTGAGCCCGCTCGGGGGACA  400
                  GGCCGGCGTGGCGGGCATGGGACCTCACCTGAGTCCGAGTCTGAGCCCGCTCGGGGGACA
Foxa2 var2    399 GGCCGGCGTGGCGGGCATGGGACCTCACCTGAGTCCGAGTCTGAGCCCGCTCGGGGGACA  458

Foxa2 var1    401 GGCGGCCGGGGCCATGGGTGGCCTTGCCCCCTACGCCAACATGAACTCGATGAGCCCCAT  460
                  GGCGGCCGGGGCCATGGGTGGCCTTGCCCCCTACGCCAACATGAACTCGATGAGCCCCAT
Foxa2 var2    459 GGCGGCCGGGGCCATGGGTGGCCTTGCCCCCTACGCCAACATGAACTCGATGAGCCCCAT  518

Foxa2 var1    461 GTACGGGCAGGCCGGCCTGAGCCGCGCTCGGGACCCCAAGACATACCGACGCAGCTACAC  520
                  GTACGGGCAGGCCGGCCTGAGCCGCGCTCGGGACCCCAAGACATACCGACGCAGCTACAC
Foxa2 var2    519 GTACGGGCAGGCCGGCCTGAGCCGCGCTCGGGACCCCAAGACATACCGACGCAGCTACAC  578

Foxa2 var1    521 ACACGCCAAACCTCCCTACTCGTACATCTCGCTCATCACCATGGCCATCCAGCAGAGCCC  580
                  ACACGCCAAACCTCCCTACTCGTACATCTCGCTCATCACCATGGCCATCCAGCAGAGCCC
Foxa2 var2    579 ACACGCCAAACCTCCCTACTCGTACATCTCGCTCATCACCATGGCCATCCAGCAGAGCCC  638

Foxa2 var1    581 CAACAAGATGCTGACGCTGAGCGAGATCTATCAGTGGATCATGGACCTCTTCCCTTTCTA  640
                  CAACAAGATGCTGACGCTGAGCGAGATCTATCAGTGGATCATGGACCTCTTCCCTTTCTA
Foxa2 var2    639 CAACAAGATGCTGACGCTGAGCGAGATCTATCAGTGGATCATGGACCTCTTCCCTTTCTA  698

Foxa2 var1    641 CCGGCAGAACCAGCAGCGCTGGCAGAACTCCATCCGCCACTCTCTCTCCTTCAACGACTG  700
                  CCGGCAGAACCAGCAGCGCTGGCAGAACTCCATCCGCCACTCTCTCTCCTTCAACGACTG
Foxa2 var2    699 CCGGCAGAACCAGCAGCGCTGGCAGAACTCCATCCGCCACTCTCTCTCCTTCAACGACTG  758

Foxa2 var1    701 CTTTCTCAAGGTGCCCCGCTCGCCAGACAAGCCTGGCAAGGGCTCCTTCTGGACCCTGCA  760
                  CTTTCTCAAGGTGCCCCGCTCGCCAGACAAGCCTGGCAAGGGCTCCTTCTGGACCCTGCA
Foxa2 var2    759 CTTTCTCAAGGTGCCCCGCTCGCCAGACAAGCCTGGCAAGGGCTCCTTCTGGACCCTGCA  818

Foxa2 var1    761 CCCAGACTCGGGCAACATGTTCGAGAACGGCTGCTACCTGCGCCGCCAGAAGCGCTTCAA  820
                  CCCAGACTCGGGCAACATGTTCGAGAACGGCTGCTACCTGCGCCGCCAGAAGCGCTTCAA
Foxa2 var2    819 CCCAGACTCGGGCAACATGTTCGAGAACGGCTGCTACCTGCGCCGCCAGAAGCGCTTCAA  878
```

Figure 11 J

Foxa2 Mus musuclus

Foxa2 Em (Var1): Aceview (Isoform a)

Foxa2 Ad (Var2): NP_034576 (NCBI)

Score = 2460.0, Identities = 459/465 (98%), Positives = 459/465 (98%), Gaps = 6/465 (1%)

```
Foxa2 var1     1 MHSASSMLGAVKMEGHEPSDWSSYYAEPEGYSSVSNMNAGLGMNGMNTYMSMSAAAMG
                       MLGAVKMEGHEPSDWSSYYAEPEGYSSVSNMNAGLGMNGMNTYMSMSAAAMG
Foxa2 var2     1 ------MLGAVKMEGHEPSDWSSYYAEPEGYSSVSNMNAGLGMNGMNTYMSMSAAAMG

Foxa2 var1    61 SGNMSAGSMNMSSYVGAGMSPSLAGMSPGAGAMAGMSGSAGAAGVAGMGPHLSPSLSP
                 SGNMSAGSMNMSSYVGAGMSPSLAGMSPGAGAMAGMSGSAGAAGVAGMGPHLSPSLSP
Foxa2 var2    55 SGNMSAGSMNMSSYVGAGMSPSLAGMSPGAGAMAGMSGSAGAAGVAGMGPHLSPSLSP

Foxa2 var1   121 GQAAGAMGGLAPYANMNSMSPMYGQAGLSRARDPKTYRRSYTHAKPPYSYISLITMAI
                 GQAAGAMGGLAPYANMNSMSPMYGQAGLSRARDPKTYRRSYTHAKPPYSYISLITMAI
Foxa2 var2   115 GQAAGAMGGLAPYANMNSMSPMYGQAGLSRARDPKTYRRSYTHAKPPYSYISLITMAI

Foxa2 var1   181 SPNKMLTLSEIYQWIMDLFPFYRQNQQRWQNSIRHSLSFNDCFLKVPRSPDKPGKGSF
                 SPNKMLTLSEIYQWIMDLFPFYRQNQQRWQNSIRHSLSFNDCFLKVPRSPDKPGKGSF
Foxa2 var2   175 SPNKMLTLSEIYQWIMDLFPFYRQNQQRWQNSIRHSLSFNDCFLKVPRSPDKPGKGSF

Foxa2 var1   241 LHPDSGNMFENGCYLRRQKRFKCEKQLALKEAAGAASSGGKKTAPGSQASQAQLGEAA
                 LHPDSGNMFENGCYLRRQKRFKCEKQLALKEAAGAASSGGKKTAPGSQASQAQLGEAA
Foxa2 var2   235 LHPDSGNMFENGCYLRRQKRFKCEKQLALKEAAGAASSGGKKTAPGSQASQAQLGEAA

Foxa2 var1   301 ASETPAGTESPHSSASPCQEHKRGGLSELKGAPASALSPPEPAPSPGQQQQAAAHLLG
                 ASETPAGTESPHSSASPCQEHKRGGLSELKGAPASALSPPEPAPSPGQQQQAAAHLLG
Foxa2 var2   295 ASETPAGTESPHSSASPCQEHKRGGLSELKGAPASALSPPEPAPSPGQQQQAAAHLLG

Foxa2 var1   361 HHPGLPPEAHLKPEHHYAFNHPFSINNLMSSEQQHHHSHHHHQPHKMDLKAYEQVMHY
                 HHPGLPPEAHLKPEHHYAFNHPFSINNLMSSEQQHHHSHHHHQPHKMDLKAYEQVMHY
Foxa2 var2   355 HHPGLPPEAHLKPEHHYAFNHPFSINNLMSSEQQHHHSHHHHQPHKMDLKAYEQVMHY

Foxa2 var1   421 GYGSPMPGSLAMGPVTNKAGLDASPLAADTSYYQGVYSRPIMNSS 465
                 GYGSPMPGSLAMGPVTNKAGLDASPLAADTSYYQGVYSRPIMNSS
Foxa2 var2   415 GYGSPMPGSLAMGPVTNKAGLDASPLAADTSYYQGVYSRPIMNSS 459
```

Figure 11 K

*FOXA2 Homo sapiens*
*FOXA2 Em (Var1):* NM_021784.4 (NCBI)
*FOXA2Ad (Var2):* NM_153675.2 (NCBI)

Score = 11264.0, Identities = 2304/2517 (91%), Positives = 2304/2517 (91%), Gaps = 191/2517 (7%)

```
Foxa2 var1     1 CCCGCCCACTTC--------CAACTACCGC----CTCCGGCCTGCCCA------------  36
                   CG CC CT C        C  CT  CGC    C CCGGCC  CCCA
Foxa2 var2     1 --CGGCCGCTGCTAGAGGGGCTGCTTGCGCCAGGCGCCGGCCGCCCCACTGCGGGTCCCT  58

Foxa2 var1    37 -------GG-----GAGAGAGAGGGAGTGGAGCCCAGGG----AGAGGGAGCGC------  74
                        GG     GAG GAG  GGA   GAGCC AGG     AGA  G GCGC
Foxa2 var2    59 GGCGGCCGGTGTCTGAG-GAGTCGGA---GAGCCGAGGCGGCCAGACCGTGCGCCCCGCG  114

Foxa2 var1    75 --------GAG----------------------AGAGGGAGGG-------------AGGA  91
                         GAG                      A AGGGAGG              AG A
Foxa2 var2   115 CTTCTCCCGAGGCCGTTCCGGGTCTGAACTGTAACAGGGAGGGGCCTCGCAGGAGCAGCA  174

Foxa2 var1    92 GGGGACGGTGCTTTGGCTGACTTTTTTTTAAAAGAGGGTGGGGGTGGGGGGTGATTGCTG  151
                 G GG CG
Foxa2 var2   175 GCGGGCG-----------------------------------------------------  181

Foxa2 var1   152 GTCGTTTGTTGTGGCTGTTAAATTTTAAACTGCCATGCACTCGGCTTCCAGTATGCTGGG  211
                                  GTTAA                            AGTATGCTGGG
Foxa2 var2   182 ---------------AGTTAA----------------------------AGTATGCTGGG  198

Foxa2 var1   212 AGCGGTGAAGATGGAAGGGCACGAGCCGTCCGACTGGAGCAGCTACTATGCAGAGCCCGA  271
                 AGCGGTGAAGATGGAAGGGCACGAGCCGTCCGACTGGAGCAGCTACTATGCAGAGCCCGA
Foxa2 var2   199 AGCGGTGAAGATGGAAGGGCACGAGCCGTCCGACTGGAGCAGCTACTATGCAGAGCCCGA  258

Foxa2 var1   272 GGGCTACTCCTCCGTGAGCAACATGAACGCCGGCCTGGGGATGAACGGCATGAACACGTA  331
                 GGGCTACTCCTCCGTGAGCAACATGAACGCCGGCCTGGGGATGAACGGCATGAACACGTA
Foxa2 var2   259 GGGCTACTCCTCCGTGAGCAACATGAACGCCGGCCTGGGGATGAACGGCATGAACACGTA  318

Foxa2 var1   332 CATGAGCATGTCGGCGGCCGCCATGGGCAGCGGCTCGGGCAACATGAGCGCGGGCTCCAT  391
                 CATGAGCATGTCGGCGGCCGCCATGGGCAGCGGCTCGGGCAACATGAGCGCGGGCTCCAT
Foxa2 var2   319 CATGAGCATGTCGGCGGCCGCCATGGGCAGCGGCTCGGGCAACATGAGCGCGGGCTCCAT  378

Foxa2 var1   392 GAACATGTCGTCGTACGTGGGCGCTGGCATGAGCCCGTCCCTGGCGGGGATGTCCCCCGG  451
                 GAACATGTCGTCGTACGTGGGCGCTGGCATGAGCCCGTCCCTGGCGGGGATGTCCCCCGG
Foxa2 var2   379 GAACATGTCGTCGTACGTGGGCGCTGGCATGAGCCCGTCCCTGGCGGGGATGTCCCCCGG  438

Foxa2 var1   452 CGCGGGCGCCATGGCGGGCATGGGCGGCTCGGCCGGGGCGGCCGGCGTGGCGGGCATGGG  511
                 CGCGGGCGCCATGGCGGGCATGGGCGGCTCGGCCGGGGCGGCCGGCGTGGCGGGCATGGG
Foxa2 var2   439 CGCGGGCGCCATGGCGGGCATGGGCGGCTCGGCCGGGGCGGCCGGCGTGGCGGGCATGGG  498

Foxa2 var1   512 GCCGCACTTGAGTCCCAGCCTGAGCCCGCTCGGGGGGCAGGCGGCCGGGGCCATGGGCGG  571
                 GCCGCACTTGAGTCCCAGCCTGAGCCCGCTCGGGGGGCAGGCGGCCGGGGCCATGGGCGG
Foxa2 var2   499 GCCGCACTTGAGTCCCAGCCTGAGCCCGCTCGGGGGGCAGGCGGCCGGGGCCATGGGCGG  558

Foxa2 var1   572 CCTGGCCCCCTACGCCAACATGAACTCCATGAGCCCCATGTACGGGCAGGCGGGCCTGAG  631
                 CCTGGCCCCCTACGCCAACATGAACTCCATGAGCCCCATGTACGGGCAGGCGGGCCTGAG
Foxa2 var2   559 CCTGGCCCCCTACGCCAACATGAACTCCATGAGCCCCATGTACGGGCAGGCGGGCCTGAG  618

Foxa2 var1   632 CCGCGCCCGCGACCCCAAGACCTACAGGCGCAGCTACACGCACGCAAAGCCGCCCTACTC  691
                 CCGCGCCCGCGACCCCAAGACCTACAGGCGCAGCTACACGCACGCAAAGCCGCCCTACTC
Foxa2 var2   619 CCGCGCCCGCGACCCCAAGACCTACAGGCGCAGCTACACGCACGCAAAGCCGCCCTACTC  678

Foxa2 var1   692 GTACATCTCGCTCATCACCATGGCCATCCAGCAGAGCCCCAACAAGATGCTGACGCTGAG  751
                 GTACATCTCGCTCATCACCATGGCCATCCAGCAGAGCCCCAACAAGATGCTGACGCTGAG
Foxa2 var2   679 GTACATCTCGCTCATCACCATGGCCATCCAGCAGAGCCCCAACAAGATGCTGACGCTGAG  738

Foxa2 var1   752 CGAGATCTACCAGTGGATCATGGACCTCTTCCCCTTCTACCGGCAGAACCAGCAGCGCTG  811
                 CGAGATCTACCAGTGGATCATGGACCTCTTCCCCTTCTACCGGCAGAACCAGCAGCGCTG
Foxa2 var2   739 CGAGATCTACCAGTGGATCATGGACCTCTTCCCCTTCTACCGGCAGAACCAGCAGCGCTG  798
```

Figure 11 L

FOXA2 Homo sapiens

FOXA2 Em (Var1): NP_068556 (NCBI)

FOXA2Ad (Var2): NP_710141 (NCBI)

Score = 2453.0, Identities = 457/463 (98%), Positives = 457/463 (98%), Gaps = 6/463 (1%)

```
Foxa2 var1     1 MHSASSMLGAVKMEGHEPSDWSSYYAEPEGYSSVSNMNAGLGMNGMNTYMSMSAAAMG
                       MLGAVKMEGHEPSDWSSYYAEPEGYSSVSNMNAGLGMNGMNTYMSMSAAAMG
Foxa2 var2     1 ------MLGAVKMEGHEPSDWSSYYAEPEGYSSVSNMNAGLGMNGMNTYMSMSAAAMG

Foxa2 var1    61 SGNMSAGSMNMSSYVGAGMSPSLAGMSPGAGAMAGMGGSAGAAGVAGMGPHLSPSLSP
                 SGNMSAGSMNMSSYVGAGMSPSLAGMSPGAGAMAGMGGSAGAAGVAGMGPHLSPSLSP
Foxa2 var2    55 SGNMSAGSMNMSSYVGAGMSPSLAGMSPGAGAMAGMGGSAGAAGVAGMGPHLSPSLSP

Foxa2 var1   121 GQAAGAMGGLAPYANMNSMSPMYGQAGLSRARDPKTYRRSYTHAKPPYSYISLITMAI
                 GQAAGAMGGLAPYANMNSMSPMYGQAGLSRARDPKTYRRSYTHAKPPYSYISLITMAI
Foxa2 var2   115 GQAAGAMGGLAPYANMNSMSPMYGQAGLSRARDPKTYRRSYTHAKPPYSYISLITMAI

Foxa2 var1   181 SPNKMLTLSEIYQWIMDLFPFYRQNQQRWQNSIRHSLSFNDCFLKVPRSPDKPGKGSF
                 SPNKMLTLSEIYQWIMDLFPFYRQNQQRWQNSIRHSLSFNDCFLKVPRSPDKPGKGSF
Foxa2 var2   175 SPNKMLTLSEIYQWIMDLFPFYRQNQQRWQNSIRHSLSFNDCFLKVPRSPDKPGKGSF

Foxa2 var1   241 LHPDSGNMFENGCYLRRQKRFKCEKQLALKEAAGAAGSGKKAAAGAQASQAQLGEAAG
                 LHPDSGNMFENGCYLRRQKRFKCEKQLALKEAAGAAGSGKKAAAGAQASQAQLGEAAG
Foxa2 var2   235 LHPDSGNMFENGCYLRRQKRFKCEKQLALKEAAGAAGSGKKAAAGAQASQAQLGEAAG

Foxa2 var1   301 SETPAGTESPHSSASPCQEHKRGGLGELKGTPAAALSPPEPAPSPGQQQQAAAHLLGP
                 SETPAGTESPHSSASPCQEHKRGGLGELKGTPAAALSPPEPAPSPGQQQQAAAHLLGP
Foxa2 var2   295 SETPAGTESPHSSASPCQEHKRGGLGELKGTPAAALSPPEPAPSPGQQQQAAAHLLGP

Foxa2 var1   361 HPGLPPEAHLKPEHHYAFNHPFSINNLMSSEQQHHHSHHHHQPHKMDLKAYEQVMHYP
                 HPGLPPEAHLKPEHHYAFNHPFSINNLMSSEQQHHHSHHHHQPHKMDLKAYEQVMHYP
Foxa2 var2   355 HPGLPPEAHLKPEHHYAFNHPFSINNLMSSEQQHHHSHHHHQPHKMDLKAYEQVMHYP

Foxa2 var1   421 GSPMPGSLAMGPVTNKTGLDASPLAADTSYYQGVYSRPIMNSS 463
                 GSPMPGSLAMGPVTNKTGLDASPLAADTSYYQGVYSRPIMNSS
Foxa2 var2   415 GSPMPGSLAMGPVTNKTGLDASPLAADTSYYQGVYSRPIMNSS 457
```

Figure 11 M

*Id2 Mus musuclus*
*Id2 Em (Var1):* NM_010496.3 (NCBI)
*Id2 Ad (Var2):* Aceview Isoform b Score = 2872.0, Identities = 720/2348 (30%), Positives = 720/2348 (30%), Gaps = 1672/2348 (66%)

```
Id2 var2      1 AGCAAAACAAGAATTCAGAATTAAAGCATTGGAGTCAAGAGCTCTAAACTTTTTCAAAA

Id2 var1        ------------------------------------------------------------

Id2 var2     61 GTGGCTGCATCTAGGAAGGGTGCTGAAAGATTCCAAACCTCGTACGTAACAGAATTTTC

Id2 var1        ------------------------------------------------------------

Id2 var2    121 TTTAAAAACAGCGATAAGCTGTCAGTCAATAGCTAGGACCACCTACCTGACAAAGAGCT

Id2 var1        ------------------------------------------------------------

Id2 var2    181 CCCAAGAGCTCTAAGTGTTGGAATGTGACACCAGAAATCACGATTTGTGCATAATTAAT

Id2 var1        ------------------------------------------------------------

Id2 var2    241 GCATCACTTTGCCACCTACACTGAAGGGCACAGACCAAGGGCAGTGTATGTAAATGTAG

Id2 var1        ------------------------------------------------------------

Id2 var2    301 TCCAGTGTGCAAACCCCACTAATGACCTTCGATTAATGGAGTCATTATAGTAACCCTGC

Id2 var1        ------------------------------------------------------------

Id2 var2    361 TCATTCTTGGGGGTGGGGGGAGTTCCGAATGCACCGGGTCCCTCGGGGCTCCTCTGCGG

Id2 var1        ------------------------------------------------------------

Id2 var2    421 CTGAGGGAGACCGCACAGTGTTCCTACAATTCGTGTCACTGAGTTTCCGAGAAGGCCTC

Id2 var1        ------------------------------------------------------------

Id2 var2    481 CGCGTTGCTCCAAGTTGCAAAGCTTCACGCTAAACCTGTCGTGGACGTGTATGTGGGCA

Id2 var1        ------------------------------------------------------------

Id2 var2    541 TGGCTGCGAACGCGGAAGAACCGAGAGCTCATACTCACCAATGGGAGAATTCGCCTGGT

Id2 var1        ------------------------------------------------------------

Id2 var2    601 TGATGGACGGGAGCCCTTCCACCAATGGCAATTCAGGGATGCCCGATTGAGCGGCCAGG

Id2 var1        ------------------------------------------------------------

Id2 var2    661 CGAGTGCACATAAAAGACGCCCCGCCCGGCTCGCGCTTCATTCTGAACCGAGCCTGGTG
                                                   GCTTCATTCTGAACCGAGCCTGGTG
Id2 var1      1 -----------------------------------GCTTCATTCTGAACCGAGCCTGGTG

Id2 var2    721 CGCGCAGTCAGCTCAGCCCCCTGTGGCGGCTCCCTCCCGGTCTTCCTCCTACGAGCAGC
                CGCGCAGTCAGCTCAGCCCCCTGTGGCGGCTCCCTCCCGGTCTTCCTCCTACGAGCAGC
Id2 var1     27 CGCGCAGTCAGCTCAGCCCCCTGTGGCGGCTCCCTCCCGGTCTTCCTCCTACGAGCAGC

Id2 var2    781 TGAAAGCCTTCAGTCCGGTGAGGTCCGTTAGGAAAAACAGCCTGTCGGACCACAGCTTG
                TGAAAGCCTTCAGTCCGGTGAGGTCCGTTAGGAAAAACAGCCTGTCGGACCACAGCTTG
Id2 var1     87 TGAAAGCCTTCAGTCCGGTGAGGTCCGTTAGGAAAAACAGCCTGTCGGACCACAGCTTG

Id2 var2    841 GCATCTCCCGGAGCAAAACCCCGGTGGACGACCCGATGAGTCTGCTCTACAACATGAAC
                GCATCTCCCGGAGCAAAACCCCGGTGGACGACCCGATGAGTCTGCTCTACAACATGAAC
Id2 var1    147 GCATCTCCCGGAGCAAAACCCCGGTGGACGACCCGATGAGTCTGCTCTACAACATGAAC

Id2 var2    901 ACTGCTACTCCAAGCTCAAGGAACTGGTGCCCAGCATCCCCCAGAACAAGAAGGTGACC
                ACTGCTACTCCAAGCTCAAGGAACTGGTGCCCAGCATCCCCCAGAACAAGAAGGTGACC
Id2 var1    207 ACTGCTACTCCAAGCTCAAGGAACTGGTGCCCAGCATCCCCCAGAACAAGAAGGTGACC

Id2 var2    961 AGATGGAAATCCTGCAGCACGTCATCGATTACATCTTGGACCTGCAGATCGCCCTGGAC
                AGATGGAAATCCTGCAGCACGTCATCGATTACATCTTGGACCTGCAGATCGCCCTGGAC
Id2 var1    267 AGATGGAAATCCTGCAGCACGTCATCGATTACATCTTGGACCTGCAGATCGCCCTGGAC

Id2 var2   1021 CGCATCCCACTATCGTCAGCCTGCATCACCAGAGACCTGGACAGAACCAGGCGTCCAGG
                CGCATCCCACTATCGTCAGCCTGCATCACCAGAGACCTGGACAGAACCAGGCGTCCAGG
Id2 var1    327 CGCATCCCACTATCGTCAGCCTGCATCACCAGAGACCTGGACAGAACCAGGCGTCCAGG
```

Figure 11 N

Id2 Mus musuclus

Id2 Em (Var1): NP_034626 (NCBI)

Id2 Ad (Var2): Aceview Isoform b

Score = 575.0, Identities = 117/155 (75%), Positives = 119/155 (76%), Gaps = 21/155 (13%)

```
Id2 var2     1  MKAFSPVRSVRKNSLSDHSLGISRSKTPVDDPMSLLYNMNDCYSKLKELVPSIPQNKKVT
                MKAFSPVRSVRKNSLSDHSLGISRSKTPVDDPMSLLYNMNDCYSKLKELVPSIPQNKKVT
Id2 var1     1  MKAFSPVRSVRKNSLSDHSLGISRSKTPVDDPMSLLYNMNDCYSKLKELVPSIPQNKKVT

Id2 var2    61  KMEILQHVIDYILDLQIALDSHPTIVSLHHQRPGQNQASRTPLTTLNTDISILSLQVRLA
                KMEILQHVIDYILDLQIALDSHPTIVSLHHQRPGQNQASRTPLTTLNTDISILSLQ
Id2 var1    61  KMEILQHVIDYILDLQIALDSHPTIVSLHHQRPGQNQASRTPLTTLNTDISILSLQASEF

Id2 var2   121  CKYATAQTLRVSRAVTLKAHRRDRFINFIFEETVY 155
                     +   +V
Id2 var1   121  PSELMSNDSKVLCG--------------------- 134
```

Figure 11 O

*ID2 Homo sapiens*

*ID2 Em (Var1):* NM_002166 (NCBI)

*ID2 Ad (Var2):* Aceview Isoform b

Score = 6432.0, Identities = 1292/2509 (51%), Positives = 1292/2509 (51%), Gaps = 1217/2509 (48%)

```
Id2 var2        ------------------------------------------------------------

Id2 var1     1  GGGGACGAAGGGAAGCTCCAGCGTGTGGCCCCGGCGAGTGCGGATAAAAGCCGCCCCGC

Id2 var2     1  ----------TTCATTCTGAGCCGAGCCCGGTGCCAAGCGCAGCTAGCTCAGCAGGCGG
                          TTCATTCTGAGCCGAGCCCGGTGCCAAGCGCAGCTAGCTCAGCAGGCGG
Id2 var1    61  GGGCTCGGGCTTCATTCTGAGCCGAGCCCGGTGCCAAGCGCAGCTAGCTCAGCAGGCGG

Id2 var2    51  AGCGGCGGCCTGAGCTTCAGGGCAGCCAGCTCCCTCCCGGTCTCGCCTTCCCTCGCGGT
                AGCGGCGGCCTGAGCTTCAGGGCAGCCAGCTCCCTCCCGGTCTCGCCTTCCCTCGCGGT
Id2 var1   121  AGCGGCGGCCTGAGCTTCAGGGCAGCCAGCTCCCTCCCGGTCTCGCCTTCCCTCGCGGT

Id2 var2   111  AGCATGAAAGCCTTCAGTCCCGTGAGGTCCGTTAGGAAAAACAGCCTGTCGGACCACAG
                AGCATGAAAGCCTTCAGTCCCGTGAGGTCCGTTAGGAAAAACAGCCTGTCGGACCACAG
Id2 var1   181  AGCATGAAAGCCTTCAGTCCCGTGAGGTCCGTTAGGAAAAACAGCCTGTCGGACCACAG

Id2 var2   171  CTGGGCATCTCCCGGAGCAAAACCCCTGTGGACGACCCGATGAGCCTGCTATACAACAT
                CTGGGCATCTCCCGGAGCAAAACCCCTGTGGACGACCCGATGAGCCTGCTATACAACAT
Id2 var1   241  CTGGGCATCTCCCGGAGCAAAACCCCTGTGGACGACCCGATGAGCCTGCTATACAACAT

Id2 var2   231  AACGACTGCTACTCCAAGCTCAAGGAGCTGGTGCCCAGCATCCCCCAGAACAAGAAGGT
                AACGACTGCTACTCCAAGCTCAAGGAGCTGGTGCCCAGCATCCCCCAGAACAAGAAGGT
Id2 var1   301  AACGACTGCTACTCCAAGCTCAAGGAGCTGGTGCCCAGCATCCCCCAGAACAAGAAGGT

Id2 var2   291  AGCAAGATGGAAATCCTGCAGCACGTCATCGACTACATCTTGGACCTGCAGATCGCCCT
                AGCAAGATGGAAATCCTGCAGCACGTCATCGACTACATCTTGGACCTGCAGATCGCCCT
Id2 var1   361  AGCAAGATGGAAATCCTGCAGCACGTCATCGACTACATCTTGGACCTGCAGATCGCCCT

Id2 var2   351  GACTCGCATCCCACTATTGTCAGCCTGCATCACCAGAGACCCGGGCAGAACCAGGCGTC
                GACTCGCATCCCACTATTGTCAGCCTGCATCACCAGAGACCCGGGCAGAACCAGGCGTC
Id2 var1   421  GACTCGCATCCCACTATTGTCAGCCTGCATCACCAGAGACCCGGGCAGAACCAGGCGTC
```

Figure 11 P

ID2 Homo sapiens

ID2 Em (Var1): NP_002157.2 (NCBI)

ID2 Ad (Var2): Aceview Isoform b

>Protein alignment 11 Alignment of 2 sequences: Id2 var2, Id2 var1

Score = 578.0, Identities = 117/141 (82%), Positives = 118/141 (83%), Gaps = 7/141 (4%)

```
Id2 var2      1 MKAFSPVRSVRKNSLSDHSLGISRSKTPVDDPMSLLYNMNDCYSKLKELVPSIPQNKKVS
                MKAFSPVRSVRKNSLSDHSLGISRSKTPVDDPMSLLYNMNDCYSKLKELVPSIPQNKKVS
Id2 var1      1 MKAFSPVRSVRKNSLSDHSLGISRSKTPVDDPMSLLYNMNDCYSKLKELVPSIPQNKKVS

Id2 var2     61 KMEILQHVIDYILDLQIALDSHPTIVSLHHQRPGQNQASRTPLTTLNTDISILSLQVRPA
                KMEILQHVIDYILDLQIALDSHPTIVSLHHQRPGQNQASRTPLTTLNTDISILSLQ
Id2 var1     61 KMEILQHVIDYILDLQIALDSHPTIVSLHHQRPGQNQASRTPLTTLNTDISILSLQASEF

Id2 var2    121 PGSPPRRRTLPRSSGLSLGDP 141
                P       +
Id2 var1    121 PSELMSNDSKALCG------- 134
```

Figure 13
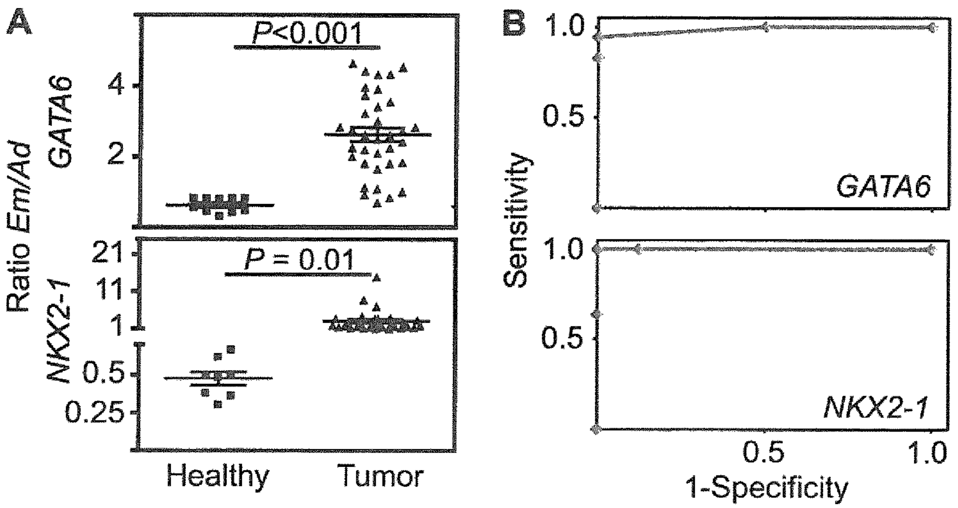
C.
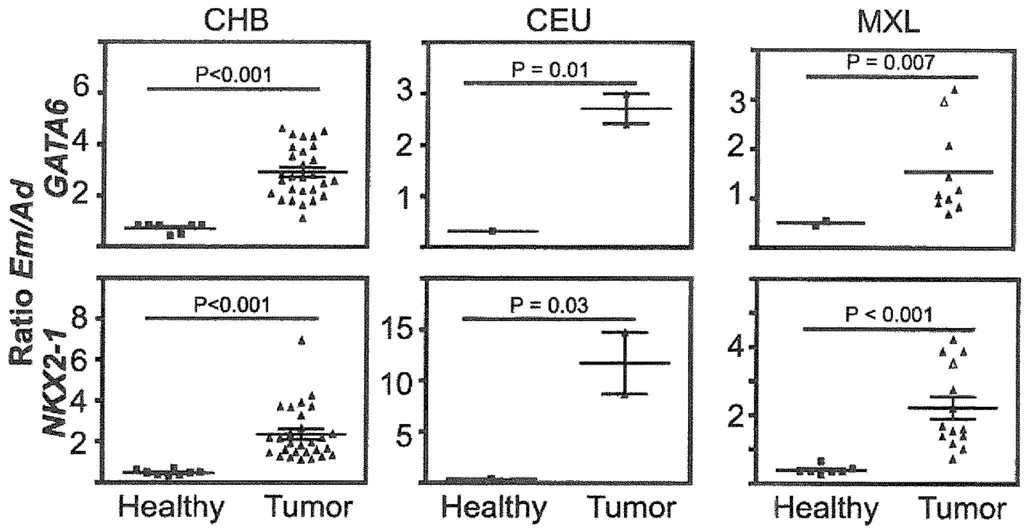

A.

D.

D

Figure 18
A B
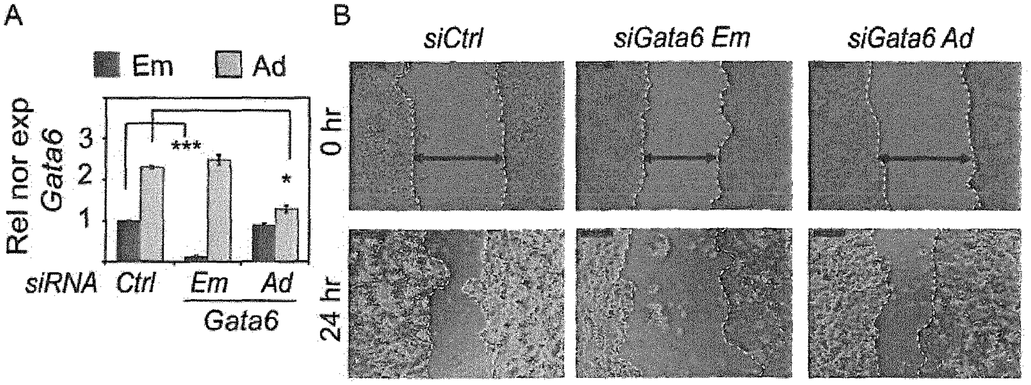
C.
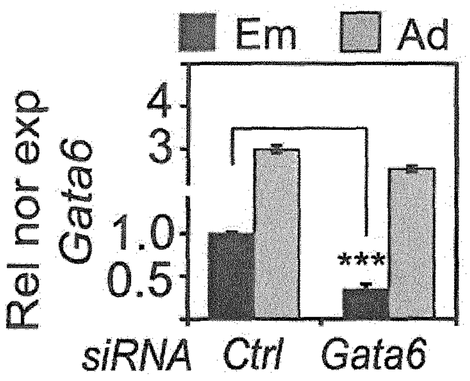
D.
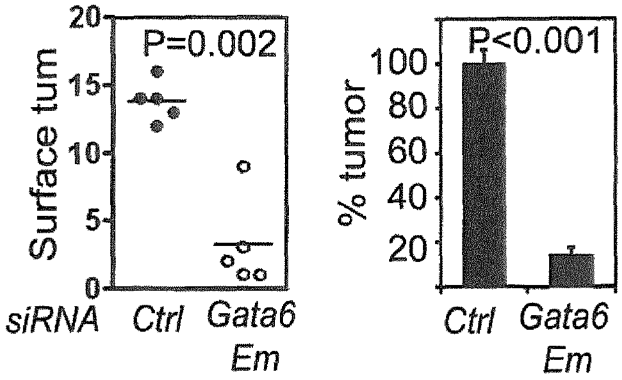

A

| Protein name | Log-2 Fold Change | Ratio H/L Lung versus ATII | Ratio H/L Lung versus MLE-12 | N. of peptides | N. of unique peptides | N. of peptides | N. of unique peptides |
|---|---|---|---|---|---|---|---|
| | | | | ATII cells | | MLE-12 cells | |
| COL1A2 | 0 | 0 | 4,8 | 6 | 6 | 2 | 2 |
| THBS1 | 0,01 | 0 | 2,3 | 16 | 16 | 4 | 4 |
| BASP1 | 0,01 | 0,1 | 8,1 | 9 | 9 | 2 | 2 |
| PTGIS | 0,01 | 0,2 | 18,4 | 7 | 7 | 4 | 4 |
| PDLIM4 | 0,01 | 0,2 | 12,3 | 2 | 2 | 1 | 1 |
| IGFBP7 | 0,01 | 0,4 | 29,8 | 6 | 6 | 5 | 5 |
| FBN1 | 0,01 | 0,4 | 23,6 | 24 | 24 | 19 | 19 |
| DES | 0,01 | 0,7 | 34,1 | 5 | 5 | 5 | 5 |
| ITGB2 | 0,01 | 0,30 | 16,70 | 9 | 9 | 4 | 4 |
| ITGA2 | 0,01 | 0,20 | 14,20 | 11 | 11 | 7 | 7 |
| OSMR | 0,02 | 0,2 | 4,6 | 6 | 6 | 1 | 1 |
| FILIP1L | 0,02 | 0,2 | 5,4 | 10 | 10 | 6 | 6 |
| CDH11 | 0,02 | 0,2 | 4,5 | 9 | 9 | 5 | 5 |
| MGLL | 0,02 | 0,4 | 10,4 | 2 | 2 | 2 | 2 |
| ANPEP | 0,02 | 0,7 | 18,8 | 8 | 8 | 6 | 6 |
| ASS1 | 0,02 | 0,8 | 22,9 | 7 | 7 | 6 | 6 |
| CTSS | 0,03 | 0,4 | 7,7 | 5 | 5 | 3 | 3 |
| CSPG4 | 0,03 | 0,5 | 10,6 | 3 | 3 | 3 | 3 |
| ITGB6 | 0,03 | 0,25 | 8,60 | 3 | 3 | 3 | 3 |
| AGPAT4 | 0,04 | 0,7 | 12,4 | 4 | 4 | 5 | 5 |
| FABP5 | 0,04 | 2,9 | 48,6 | 7 | 7 | 7 | 7 |
| CLU | 0,07 | 0,05 | 0,70 | 10 | 10 | 7 | 7 |
| SFTPC | 0,55 | 4 | 4,5 | 3 | 3 | 3 | 3 |
| EPHA2 | 1,00 | 0,30 | 0,30 | 4 | 4 | 6 | 6 |
| CD9 | 1,00 | 0,90 | 0,80 | 5 | 5 | 5 | 5 |
| F3 | n.d. | 0,02 | n.d. | 8 | 8 | 1 | 1 |
| COX2 | n.d. | 0,04 | n.d. | 7 | 7 | n.d. | n.d. |
| PTPRC | | | | | | | |

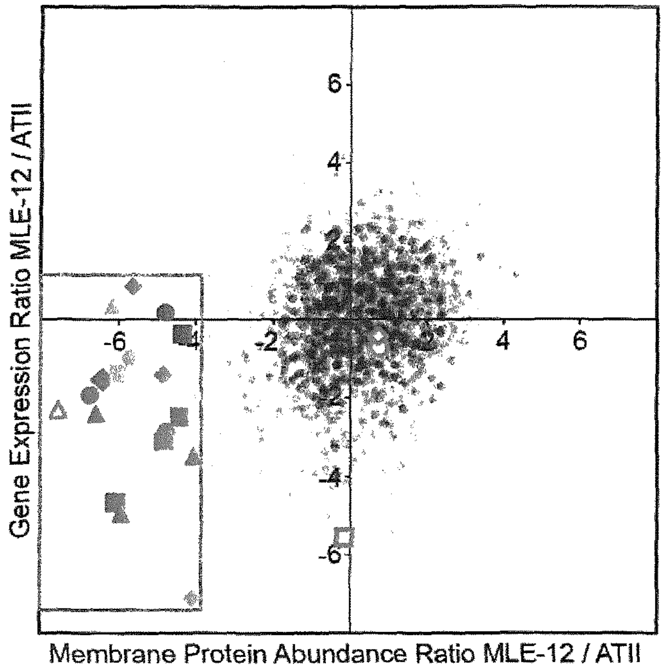

B

| Protein name | Single Uniprot | Cellular location | Prot Abud MLE12/ATII | Gene Exp MLE12/ATII | Figure |
|---|---|---|---|---|---|
| ITGB2 | P11835 | membrane part | -5,92 | -4,96 | ▲ |
| PTGIS | Q8BXC0 | ER membrane | -6,72 | -1,93 | ● |
| BASP1 | Q91XV3 | membrane part | -6,56 | -2,41 | ▲ |
| DES | P31001 | Z disc membrane | -5,68 | -0,99 | ● |
| ITGA2 | Q62469 | membrane part | -5,62 | 0,85 | ◆ |
| CTSS | Q3U5K1 | membrane part | -4,45 | -6,31 | |
| PTPRC | P06800 | integral to membrane | -4,84 | -5,74 | |
| ANPEP | P97449 | integral to membrane | -4,83 | -4,87 | |
| FILIP1L | Q6P6LO | membrane part | -4,69 | -3,59 | |
| MGLL | O35678 | membrane part | -4,81 | -3,12 | ■ |
| OSMR | O70458 | integral to membrane | -4,75 | -2,88 | ● |
| ITGB6 | Q9Z0T9 | membrane part | -4,40 | -2,50 | ■ |
| AGPAT4 | Q8K4X7 | integral to membrane | -4,05 | -3,50 | ▲ |
| ASS1 | P16460 | mitochondrion membran | -4,83 | -1,43 | ◆ |
| CSPG4 | Q8VHY0 | integral to membrane | -4,35 | -0,38 | ■ |
| CDH11 | P55288 | integral to membrane | -4,78 | 0,18 | ● |
| CD9 | P40240 | integral to membrane | 0,73 | -0,44 | ◇ |
| EPHA2 | Q03145 | integral to membrane | 0,75 | -0,73 | ○ |
| COL1A2 | Q01149 | extracellular space | -7,57 | -2,32 | △ |
| IGFBP7 | Q61581 | extracellular space | -6,08 | -4,67 | ■ |
| THBS1 | P35441 | extracellular space | -6,40 | -1,54 | ◆ |
| FBN1 | O88840 | extracellular space | -5,99 | -1,38 | |
| PDLIM4 | Q5SWV3 | Actin cytoskeleton | -6,15 | 0,37 | |
| FABP5 | Q05816 | cytoplasm | -4,09 | -7,11 | |
| SFTPC | P21841 | extracellular space | -0,15 | -5,57 | □ |

ISOFORMS OF GATA6 AND NKX2-1 AS MARKERS FOR DIAGNOSIS AND THERAPY OF CANCER AND AS TARGETS FOR ANTI-CANCER THERAPY

This application is a national phase application under 35 U.S.C. § 371 of International Application No. PCT/EP2014/060489, filed May 21, 2014, which claims benefit of European Application No. 13168629.7, filed May 21, 2013, and European Application No. 13168636.2, filed May 21, 2013.

The present invention relates to a method of assessing whether a subject suffers from cancer or is prone to suffering from cancer comprising the measurement of the amounts of specific isoforms of GATA6 and/or NKX2-1 in a sample of said subject. Accordingly, the present invention relates to the fields of medicine as well as diagnostics, in particular to personalized medicine and molecular biomarkers. Furthermore, the present invention relates to a composition for use in medicine, in particular in cancer therapy, said composition comprising an inhibitor of specific isoforms of GATA6 and/or NKX2-1. Additionally, the present invention relates to a kit for use in a method of assessing whether a subject suffers from cancer or is prone to suffering from cancer. Therefore, the present invention relates to means and methods for stratifying patients for the medical intervention with (a) anticancer therapy or specific additional close diagnostic screening for cancer development.

The term cancer covers a broad class of diseases, which is unified by the malignant hyperproliferation of cells. The term includes solid tumors as for example sarcoma and carcinoma as well as liquid tumors like leukemia, lymphoma and myeloma. Cancer can be initiated by the activation or deregulation of certain genes, so called proto-oncogenes. When upregulated and/or activated, these genes can initiate a cascade of molecular events eventually leading to a cell's ability to hyperproliferate thereby initiating the development of malignant neoplasms. The identification of novel specific proto-oncogenes provides novel targets for the treatment and/or the prevention of cancer.

Lung cancer is a typical model cancer with a very high prevalence. Lung cancer is the most frequent cause of cancer related deaths worldwide. There are two major classes of lung cancer, non small cell lung cancer (contributing to 85% of all lung cancers) and small cell lung cancer (the remaining 15%). Symptoms of lung cancer are often subtle in nascent stages (Herbst R S et al., (2008) N Engl J Med 359(13): 1367-80). Consequently, the majority of patients are diagnosed at advanced stages making successful therapeutic approaches challenging and prognosis poor. Therefore, early diagnosis of lung cancer is crucial to increase the probability of a successful therapy. A better understanding of the molecular mechanisms responsible for lung cancer initiation is extremely important.

Lung cancer cells show an enhanced expression of transcription factors that are present during embryonic development in the endoderm as GATA6 (GATA Binding Factor 6), NKX2-1 (NK2 homeobox 1, also known as Ttf-1, Thyroid transcription factor-1), FOXA2 (Forkhead box protein A2), and ID2 (Inhibitor of DNA binding 2) (Guo M et al., (2004) Clin Cancer Res. 10(23): 7917-24; Kendall J et al., (2007) Proc Natl Acad Sci USA. 104(42): 16663-8; Tang Y et al., (2011) Cell Res, 21(2): 316-26; Rollin J et al., (2009) PLoS One. 4(1): e4158). It was recently demonstrated that lung adenocarcinoma initiates from clonal expansion of cells expressing high levels of Nkx2-1 and progress to a more aggressive state with low expression of Nkx2-1 (see Winslow (2011) Nature 473(7345): 101-104).

GATA6 has been shown to be abundantly expressed in malignant mesotheliomas, and to a small extent, in metastatic adenocarcinomas (see Lindholm (2009) Journal of Clinical Pathology 62(4): 339-344). In addition, GATA6 regulates tumorigenesis related genes, such as KRAS, an oncogene activated by point mutations (see Gorshkove (2005) Biochemistry (Mosc):70: 1180-1184).

GATA6, FOXA2 and NKX2-1 are crucial for early lung development. Genetic analyses with knockout animals demonstrated their role in lung endoderm differentiation and postnatal repair and homeostasis. Nkx2-1, Gata6 and Foxa2 are expressed in respiratory epithelial cells throughout lung morphogenesis. They all have been shown to bind and trans-activate many lung specific promoters, including SftpA-, SftpB-, SftpC- and Scgb1a1-promoters (Bruno M D et al., (1995) 270(12): 6531-6; Margana R K and Boggaram V. (1997) J Biol Chem. 272(5): 3083-90). Mice harboring a Nkx2-1 null mutation show severe attenuation of lung airway branching. In addition, the lung epithelial cells present in these mice lack expression of putative targets like SftpC (Minoo P et al., (1999) Dev Biol. 209(1): 60-71). Conditional deletion of Gata6 in the lung endoderm demonstrated its central role in lung endoderm gene expression, proliferation and branching morphogenesis. (Keijzer R et al., (2001) Development 128(4): 503-11). A loss of Foxa2 in the lung can be compensated by Foxa1. However, a loss of both Foxa1/2 also dramatically inhibits endoderm differentiation and branching morphogenesis. (Wan H et al., (2005) J Biol Chem. 280(14): 13809-16). Foxa2 has also been shown to be essential for the transition to breathing air at birth (Wan H et al., (2004) Proc Natl Acad Sci USA. 101(40): 14449-54).

Current cancer therapy is such that it treats cancer cells as a homogenous cell population. However, in recent years, it has been demonstrated that most tumors contain a mixture of principally two populations, the majority of the cells are able to proliferate and only a small population of these cells has the potential for self renewal. This small population of cells is highly tumorigenic, resistant to chemotherapy and shows a de-differentiated phenotype. Malignant cells with these properties have been termed as 'cancer stem cells'. It has become clear that cancer treatment that fails to eliminate these cancer stem cells has a substantial risk of tumor relapse. Consequently, there is an enormous need to understand the origin of these cells and specifically target them for therapy (Eramo A et al., (2010) Oncogene 29(33): 4625-35).

As discussed above, late diagnosis of cancer is a main hindrance for successful cancer therapy. The prognosis of lung cancer patients depends on the severity of the disease. If detected early, at Stage I, the 5 year survival rate for lung cancer patients is about 80% and drops to about 1% if the disease is advanced to stage IV with the development of metastatic lesions (European Society for Medical Oncology (2009, May 9), *Early Detection Of Lung Cancer*, ScienceDaily, retrieved from the world wide web at sciencedaily.com/releases/2009/05/090502093211.htm). Therefore, early detection and subsequent treatment of lung cancer is the most promising strategy to reduce related mortality. This is not only true for lung cancer but also for a variety of further malignant neoplasms.

Accordingly, there is a need for new techniques allowing a reliable and early diagnosis of cancer as well as for further and/or alternative treatment options in cancer therapy. Thus, the technical problem underlying the present invention is the provision of reliable means and methods for the detection of cancer, in particular lung cancer, and for the determination of treatment options.

The solution to this technical problem is provided by the embodiments as defined herein and as characterized in the claims.

In accordance with this invention, a method of assessing whether a subject suffers from cancer or is prone to suffering from cancer is found, said method comprising the steps of a) measuring in a sample of said subject the amount of a specific transcription factor isoform wherein said specific transcription isoform is either
   i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; or
   ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2;
b) comparing the amount of said specific transcription factor Em isoform with the amount of said specific transcription factor Em isoform in a control sample;
c) assessing that said subject suffers from cancer or is prone to suffering from cancer if the amount of said specific transcription factor Em isoform in said sample from said subject is increased in comparison to the amount of said specific transcription factor Em isoform in (a)/(the) control sample.

It is demonstrated by the disclosure of this application that certain transcription factors share a common structure, with two promoters driving the expression of two distinct transcripts. It is surprisingly found that though different isoforms exist only one is oncogenic and is indicative of the presence/development of cancer (see Examples 2 and 3 of the present application). The embryonic GATA6 and NKX2-1 "Em" transcripts as defined by the present invention are found to be detectable in high levels in human lung cancer cell lines and patient lung cancer biopsies (see Examples 2 and 3 of the present application). Remarkably, these cancer specific isoforms are oncogenic and forced overexpression in cell lines as well as in mice results in a tumorigenic phenotype (see Examples 4, 6 and 7 of the present application). This is illustrated by the finding of the present invention that mice develop adenocarcinoma as early as 5 weeks after transfection with one of those specific embryonic "Em" isoforms. Further, it is surprisingly found that these specific "Em" isoforms can be detected in the blood of mice that are induced for tumor formation, showing their usability as early diagnostic markers for cancer, in particular lung cancer (see Example 3 of the present application).

The present invention has the technical advantage that the inventive means and methods provided herein enable the attending physician or medical personal to start preferably at an early point of time the relevant medicinal intervention, like anti-cancer medication and/or radiation therapy. Accordingly, the presence of an increased amount of the specific transcription factor Em (i.e. GATA6 Em and/or NKX2-1 Em isoform) in a (biological) sample as compared to a standard or control sample leads to (early) anti-cancer therapy and/or closer and more intense diagnostic cancer screening and/or cancer surveillance. An "increased amount"/"increased expression" of the specific transcription factor Em (i.e. GATA6 Em and/or NKX2-1 Em isoform) in a (biological) sample as compared to a standard or control sample can be, inter alia, an expression increase of at least about 1.3-fold in comparison to the control.

The present invention also provides in the appended examples for evidence that an increased amount (increased expression) of Ad (adult) isoform of e.g. Gata6 (in contrast to the embryonic "Em isoform" of Gata6) in comparison to a control sample can be indicative for fibrotic events, in particular for lung fibrosis; see also appended illustrative Example 9 and FIG. 8.

The method of assessing whether a subject suffers from cancer or is prone to suffering from cancer according to the present application preferably relates to an in vitro method of assessing whether a subject suffers from cancer or is prone to suffering from cancer. In accordance with the invention, the term "cancer" encompasses any malignant neoplasm. This includes but is not limited to solid tumors as for example sarcoma and carcinoma as well as to liquid tumors like leukemia, lymphoma and myeloma. Preferably, the present invention allows the detection of lung cancer.

The person skilled in the art understands that a subject which is prone to suffering from cancer is a subject which has an increased likelihood of developing cancer within the next 30 years or preferably within the next 20 or 10 years or even more preferably within the next 9, 8, 7, 6, 5, 4, 3 or 2 years or even furthermore preferably within the next year. An increased likelihood of a subject of developing cancer can be understood as that said subject has an increased likelihood of developing cancer within a given time period as if compared to the average likelihood that a subject of the same age or a subject of the same age and the same gender develops cancer.

The term "sample" according to the present invention relates to any kind of sample which can be obtained from a subject, preferably from a human subject. The sample is a biological sample. A sample according to the present invention can be for example, but is not limited to, a blood sample, a breath condensate sample, a bronchoalveolar lavage fluid sample, a mucus sample or a phlegm sample. Preferably, the sample according to the present invention is a blood sample or a breath condensate sample. The term "breath condensate sample" as used herein refers to an "exhaled breath condensate (sample)". The term "exhaled breath condensate (sample)" can be abbreviated as "EBC". Accordingly, the terms "breath condensate sample", "exhaled breath condensate", "exhaled breath condensate sample" and "EBC" are used interchangeably herein. The use of "breath condensate sample", in particular "exhaled breath condensate (sample)" allows the non-invasive obtaining of samples from a subject/patient and is therefore advantageous.

In accordance with this invention, a method of assessing whether a subject suffers from cancer or is prone to suffering from cancer is found, said method comprising the steps of a) measuring in a sample of said subject the amount of a specific transcription factor isoform selected from the group of specific transcription factor isoforms consisting of
   i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1;
   the NKX2-1 Em isoform comprising the nucleic acid sequence of SEQ ID No: 2 or the NKX2-1 Em isoform comprising the nucleic acid sequence with up to 39 additions, deletions or substitutions of SEQ ID NO: 2;
   iii) the FOXA2 Em isoform comprising the nucleic acid sequence of SEQ ID No: 3 or the FOXA2 Em isoform comprising nucleic acid sequence with up to 68 additions, deletions or substitutions of SEQ ID NO: 3; or
   iv) the ID2 Em isoform comprising the nucleic acid sequence of SEQ ID No: 4 or the ID2 Em isoform comprising nucleic acid sequence with up to 34 additions, deletions or substitutions of SEQ ID NO: 4;

b) comparing the amount of said specific transcription factor isoform with the amount of said specific transcription factor isoform in a control sample;

c) assessing that said subject suffers from cancer or is prone to suffering from cancer if the amount of said specific transcription factor isoform in said sample from said subject is increased in comparison to the amount of said specific transcription factor isoform in the control sample.

Again, as already pointed out herein above, the increased amount of said specific transcription factor isoform in said sample leads to fast medical intervention for example by means of corresponding anti-cancer therapy, like anti-cancer medication or radiation therapy. Early stage anti-cancer therapies include, but are not limited to, radiation therapy, such as external radiation therapy, photodynamic therapy (PDT) using an endoscope and surgery (i.e. wedge resection or segmental resection for carcinoma in situ and sleeve resection or lobectomy for StageI). In addition, chemotherapy is used alone or after surgery. The chemotherapy drugs may, inter alia, comprise compounds selected from the group consisting of Cisplatin, Carboplatin, Paclitaxel (Taxol®), Albumin-bound paclitaxel (nab-paclitaxel, Abraxane®), Docetaxel (Taxotere®), Gemcitabine (Gemzar®), Vinorelbine (Navelbine®), Irinotecan (Camptosar®, CPT-11), Etoposide (VP-16®)), Vinblastine and Pemetrexed (Alimta®).

The present invention provides also for a method for stratifying, subjecting or seek out subjects or groups of subjects (patients or patient groups) for the treatment with (a) anti-cancer drug(s) and/or radiation therapy, said method comprising the steps of a) measuring in a sample of said subject the amount of a specific transcription factor isoform wherein said specific transcription isoform is either
   i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; or
   ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2;

b) comparing the amount of said specific transcription factor Em isoform with the amount of said specific transcription factor Em isoform in a control sample; and c) assessing that said subject suffers from cancer or is prone to suffering from cancer if the amount of said specific transcription factor Em isoform in said sample from said subject is increased in comparison to the amount of said specific transcription factor Em isoform in the control sample.

wherein an increased amount of specific transcription factor Em (GATA6 Em isoform and/or NKX2-1 Em isoform) indicates that the subjects or groups of subjects is/are suitable and in need for therapy with (a) anti-cancer drug(s) and/or radiation therapy and that the subjects or groups of subjects should be treated with said anti-cancer drug and/or radiation therapy. Said subject is preferably a human subject/patient.

Also in this context of the invention of, i.e. the stratification of patients/patient groups for the need of anti-cancer therapy and/or radiation therapy, FOXA2 Em isoform and/or ID2 Em isoform may be determined as described herein.

The term "specific transcription factor Em isoform" according to the present application relates to specific isoforms of the transcription factors GATA6 (Uniprot-ID: Q92908; Gene-ID: 2627), NKX2-1 (Uniprot-ID: P43699; Gene-ID: 7080), FOXA2 (Uniprot-ID: Q9Y261; Gene-ID: 3170) and ID2 (Uniprot-ID: Q02363; Gene-ID: 3398). If, for example, the amount of a specific transcription factor is measured on mRNA level, the specific transcription factor can be mRNA molecules (or transcript or splice variants). In this context, the transcription factors can be defined as i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1;

ii) the NKX2-1 Em isoform comprising the nucleic acid sequence of SEQ ID No: 2 or the NKX2-1 Em isoform comprising the nucleic acid sequence with up to 39 additions, deletions or substitutions of SEQ ID NO: 2;

iii) the FOXA2 Em isoform comprising the nucleic acid sequence of SEQ ID No: 3 or the FOXA2 Em isoform comprising nucleic acid sequence with up to 68 additions, deletions or substitutions of SEQ ID NO: 3; or iv) the ID2 Em isoform comprising the nucleic acid sequence of SEQ ID No: 4 or the ID2 Em isoform comprising nucleic acid sequence with up to 34 additions, deletions or substitutions of SEQ ID NO: 4.

If, for example, the amount of a specific transcription factor is measured on protein level, the specific transcription factor can be protein molecules. For example, they can be defined as v) the GATA6 Em isoform comprising the polypeptide sequence of SEQ ID No: 50 or the GATA6 Em isoform comprising the polypeptide sequence with up to 30 additions, deletions or substitutions of SEQ ID NO: 50;

vi) the NKX2-1 Em isoform comprising the polypeptide sequence of SEQ ID No: 51 or the NKX2-1 Em isoform comprising the polypeptide sequence with up to 14 additions, deletions or substitutions of SEQ ID NO: 51;

vii) the FOXA2 Em isoform comprising the polypeptide sequence of SEQ ID No: 52 or the FOXA2 Em isoform comprising polypeptide sequence with up to 43 additions, deletions or substitutions of SEQ ID NO: 52; or viii) the ID2 Em isoform comprising the polypeptide sequence of SEQ ID No: 53 or the ID2 Em isoform comprising polypeptide sequence with up to 13 additions, deletions or substitutions of SEQ ID NO: 53.

The present invention relates to a method of assessing whether a subject suffers from cancer or is prone to suffering from cancer, said method comprising the steps of a) measuring in a sample of said subject the amount of a specific transcription factor isoform as a polypeptide wherein said specific transcription isoform is either
   i) the GATA6 Em isoform comprising the polypeptide sequence of SEQ ID No: 50 or the GATA6 Em isoform comprising the polypeptide sequence with up to 30 additions, deletions or substitutions of SEQ ID NO: 50; or
   ii) the NKX2-1 Em isoform comprising the polypeptide sequence of SEQ ID No: 51 or the NKX2-1 Em isoform comprising the polypeptide sequence with up to 14 additions, deletions or substitutions of SEQ ID NO: 51;

b) comparing the amount of said specific transcription factor Em isoform with the amount of said specific transcription factor Em isoform in a control sample; and c) assessing that said subject suffers from cancer or is prone to suffering from cancer if the amount of said specific transcription factor Em isoform in said sample from said subject is increased in comparison to the amount of said specific transcription factor Em isoform in the control sample.

Again, an increased amount or said specific transcription factor Em isoform as compared to a control sample leads to modified medical intervention and/or closer diagnostic surveillance.

The herein provided methods are primarily useful in the assessment whether a subject suffers from cancer or is prone to suffering from cancer before the subject undergoes therapeutic intervention. In other words, the sample of the subject is obtained from the subject and analyzed prior to therapeutic intervention, like conventional chemotherapy. If the subject is assessed "positive" in accordance with the present invention, i.e. assessed to suffer from cancer or prone to suffering from cancer, the appropriate therapy/therapeutic intervention can be chosen. For example, a subject may be suspected of suffering from cancer and the present methods can be used to assess whether the subject suffers indeed from said cancer in addition or in the alternative to conventional diagnostic methods.

Following positive diagnosis with the herein provided inventive method, the diagnosis may be elucidated/further verified with low-dose helical computed tomography and/or Chest X-Ray, by bronchoscopy and/or histological assessment. In early stage or Grade I tumors, surgery to remove the lobe or the section of the lung that contains the tumor would be the first choice of treatment. It is feasible to supplement the surgery with chemotherapy, known as 'adjuvant chemotherapy', to prevent cancer relapse (Howington J A et al. (2013) CHEST Journal 143: e278S-e313S). At later stages, surgery is no longer feasible and a combination of chemotherapy and radiation are advised. Further, for metastatic lesions, chemotherapy and radiation are suggested, mainly for palliation of the symptoms.

The term "isoform" according to the present invention encompasses transcript variants (which are mRNA molecules) as well as the corresponding polypeptide variants (which are polypeptides) of a gene. Such transcription variants result, for example, from alternative splicing or from a shifted transcription initiation. Based on the different transcript variants, different polypeptides are generated. It is possible that different transcript variants have different translation initiation sites. A person skilled in the art will appreciate that the amount of an isoform can be measured by adequate techniques for the quantification of mRNA as far as the isoform relates to a transcript variant which is an mRNA. Examples of such techniques are polymerase chain reaction-based methods, in situ hybridization-based methods, microarray-based techniques and whole transcriptome shotgun sequencing. Further, a person skilled in the art will appreciate that the amount of an isoform can be measured by adequate techniques for the quantification of polypeptides as far as the isoform relates to a polypeptide. Examples of such techniques for the quantification of polypeptides are ELISA (Enzyme-linked Immunosorbent Assay)-based, gel-based, blot-based, mass spectrometry-based, and flow cytometry-based methods.

It was surprisingly found by the inventors that those specific Em transcription factor isoforms are markers of the development of cancer. It was further surprisingly found that those specific Em isoforms of the transcription factors can be detected with an increased abundance in a sample obtained from a subject who suffers from cancer or is prone to suffering from cancer if compared to a control sample from healthy control subjects. Genes can contain single nucleotide polymorphisms (SNPs). The specific transcription factor Em isoform sequences of the present invention encompass (genetic) variants thereof, for example, variants having SNPs. Without deferring from the gist of the present invention, all naturally occurring sequences of the respective isoform independent of the number and nature of the SNPs in said sequence can be used herein. To relate to currently known SNPs, the transcription factor Em isoforms of the present invention are defined such that they contain up to 55 (in the case of GATA6), up to 39 (in the case of NKX2-1), up to 68 (in the case of FOXA2) or up to 34 (in the case of ID2) additions, deletions or substitutions of the nucleic acid sequences defined by SEQ ID NOs: 1, 2, 3 and 4, respectively. Thus, respective Em transcripts of carriers of different nucleotides at the respective SNPs are covered by the present application.

The GATA6 Em isoform according to the invention is the GATA6 Em isoform comprising the nucleic acid sequence of SEQ ID No: 1 or the GATA6 Em isoform comprising a nucleic acid sequence with up to 55; preferably up to 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21 or 20; even more preferably up to 19, 18, 17, 16, 15, 14, 13, 12, 11, 10, 9, 8, 7. 6, 5, 4, 3 or 2; or even furthermore preferably only 1 addition(s), deletion(s) or substitution(s) of SEQ ID NO: 1. The GATA6 Em isoform can also be defined as the GATA6 Em isoform comprising the nucleic acid sequence of SEQ ID No: 1 or the GATA6 Em isoform comprising the nucleic acid sequence of SEQ ID No: 1 with additions, deletions or substitutions at any of positions 163; 293; 320; 327; 339; 430; 462; 480; 759; 1128; 1256; 1304; 1589; 1597; 1627; 1651; 1652; 1803; 1844; 1849; 1879; 1882; 1911; 1940; 1949; 1982; 2000; 2002; 2008; 2026; 2031; 2106; 2137; 2142; 2163; 2294; 2390; 2391; 2627; 2691; 3036; 3102; 3240; 3265; 3266; 3290; 3358; 3366; 3578; 3632; 3646; 3670; 3690; 3708 and 3735. The GATA6 Em isoform according to the invention can also be defined as the GATA6 Em isoform comprising the nucleic acid sequence of SEQ ID No: 1 or the GATA6 Em isoform comprising a nucleic acid sequence with at least 85% homology to SEQ ID No: 1, preferably up to 86%, 87%, 88%, 89%, 90%, 91%, 92%, 93%, 94%, 95%, 96%, 97% or 98% homology to SEQ ID No: 1; even more preferably up to 99% homology to SEQ ID No: 1.

The NKX2-1 Em isoform according to the invention is the NKX2-1 Em isoform comprising the nucleic acid sequence of SEQ ID No: 2 or the NKX2-1 Em isoform comprising a nucleic acid sequence with up to 39; preferably up to 38, 37, 36, 35, 34, 33, 32, 31, 30, 29, 28, 27, 26, 25, 24, 23, 22, 21, 20, 19, 18, 17, 16, 15, 14, 13, 12, 11, or 10; even more preferably up to 9, 8, 7, 6, 5, 4, 3, or 2; or even furthermore preferably only 1 addition(s), deletion(s) or substitution(s) of SEQ ID NO: 2. The NKX2-1 Em isoform can also be defined as the NKX2-1 Em isoform comprising the nucleic acid sequence of SEQ ID No: 2 or the NKX2-1 Em isoform comprising the nucleic acid sequence of SEQ ID No: 2 with additions, deletions or substitutions at any of positions 269; 281; 305; 304; 420; 425; 439; 441; 450; 486; 781; 785; 825; 950; 1169; 1305; 1344; 1448; 1458; 1467; 1489; 1552; 1633; 1634; 1640; 1641; 1643; 1667; 1673; 1678; 1748; 1750; 1831; 1893; 1916; 1917; 1934; 2099 and 2319. The NKX2-1 Em isoform according to the invention can also be defined as the NKX2-1 Em isoform comprising the nucleic acid sequence of SEQ ID No: 2 or the NKX2-1 Em isoform comprising a nucleic acid sequence with at least 90% homology to SEQ ID No: 2, preferably up to 91%, 92%, 93%, 94%, 95%, 96%, 97% or 98% homology to SEQ ID No: 2; even more preferably up to 99% homology to SEQ ID No: 2.

The FOXA2 Em isoform according to the invention is the FOXA2 Em isoform comprising the nucleic acid sequence of SEQ ID No: 3 or the FOXA2 Em isoform comprising a nucleic acid sequence with up to 68; preferably up to 67, 66, 65, 64, 63, 62, 61, 60, 59, 58, 57, 56, 55, 54, 53 52, 51, 50, 49, 48 47, 46, 45, 44, 43, 42, 41, 40, 39, 38, 37, 36, 35, 34, 33, 32, 31, 30, 29, 28, 27, 26, 25, 24, 23, 22, 21 or 20; even more preferably up to 19, 18, 17, 16, 15, 14, 13, 12, 11, 10, 9, 8, 7. 6, 5, 4, 3 or 2; or even furthermore preferably only 1 addition(s), deletion(s) or substitution(s) of SEQ ID NO: 3. The FOXA2 Em isoform can also be defined as the FOXA2 Em isoform comprising the nucleic acid sequence of SEQ ID No: 3 or the FOXA2 Em isoform comprising the nucleic acid sequence of SEQ ID No: 3 with additions, deletions or substitutions at any of positions 168; 208; 289; 361; 368; 374; 379; 383; 404; 459; 481; 483; 494; 529; 564; 577; 584; 590; 610; 623; 641; 650; 659; 674; 773; 845; 1040; 1075; 1186; 1188; 1240; 1242; 1243; 1304; 1374; 1391; 1408; 1414; 1432; 1458; 1475; 1487; 1522; 1539; 1582; 1583; 1594; 1627; 1631; 1687; 1723; 1737; 1738; 1754; 1812; 1831; 1838; 1940; 1966; 1970; 2070; 2083; 2084; 2093; 2105; 2112; 2200 and 2388. The FOXA2 Em isoform according to the invention can also be defined as the FOXA2 Em isoform comprising the nucleic acid sequence of SEQ ID No: 3 or the FOXA2 Em isoform comprising a nucleic acid sequence with at least 93% homology to SEQ ID No: 3, preferably up to 94%, 95%, 96%, 97% or 98% homology to SEQ ID No: 3; even more preferably up to 99% homology to SEQ ID No: 3.

The ID2 Em isoform according to the invention is the ID2 Em isoform comprising the nucleic acid sequence of SEQ ID No: 4 or the ID2 Em isoform comprising a nucleic acid sequence with up to 34; preferably up to 33, 32, 31, 30, 29, 28, 27, 26, 25, 24, 23, 22, 21, 20, 19, 18, 17, 16, 15, 14, 13, 12, 11, or 10; even more preferably up to 9, 8, 7, 6, 5, 4, 3, or 2; or even furthermore preferably only 1 addition(s), deletion(s) or substitution(s) of SEQ ID NO: 4. The ID2 Em isoform can also be defined as the ID2 Em isoform comprising the nucleic acid sequence of SEQ ID No: 4 or the ID2 Em isoform comprising the nucleic acid sequence of SEQ ID No: 4 with additions, deletions or substitutions at any of positions 6; 43; 53; 55; 154; 195; 209; 224; 237; 263; 286; 360; 399; 405; 485; 501; 544; 547; 605; 662; 665; 716; 757; 871; 876; 975; 1085; 1115; 1119; 1149; 1151; 1251; 1333 and 1350. The ID2 Em isoform according to the invention can also be defined as the ID2 Em isoform comprising the nucleic acid sequence of SEQ ID No: 4 or the ID2 Em isoform comprising a nucleic acid sequence with at least 51% homology to SEQ ID No: 4, preferably up to 55%, 60%, 65%, 70%, 75%, 80%, 85% or 90% homology to SEQ ID No: 4; even more preferably up to 91%, 92%, 93%, 94%, 95%, 96%, 97%, 98% or 99% homology to SEQ ID No: 4.

Preferably, the above referred "addition(s), deletion(s) or substitution(s)" of the transcription factor isoforms are substitutions.

Tables 1, 2, 3, 4, 5, 6, 7 and 8 provide information on different SNPs of the transcription factors of the present invention. The present invention relates to the respective isoforms independently from the various SNPs which may occur at the different positions of the mRNAs or polypeptides. The SNPs of tables 1, 2, 3, 4, 5, 6, 7 and 8 may occur in the isoforms of the present invention in any combination. For example, a (genetic) variant of the GATA6 Em isoform to be used herein may comprise a nucleic acid sequence of SEQ ID NO:1, whereby the "G" residue at position 293 of SEQ ID NO:1 is substituted by "A". Further variants of the isoforms to be used herein are apparent from Tables 1 to 8 to the person skilled in the art. The respective SNP information has been retrieved using dbSNP (short genetic variations) database of the NCBI. The SNP information is based on Contig Label GRCh37.p5. A person skilled in the art will understand that also SNPs which are not mentioned in tables 1 to 8 are encompassed by the present invention.

TABLE 1

SNPs of the GATA6 Em isoform

| S. No. | Region | Position | Contig reference | Polymorphism | Codon Position | Function | Protein residue |
|---|---|---|---|---|---|---|---|
| 1 | 5' UTR | 163 | C | G | | | |
| 2 | CCDS | 293 | G | A | 6 | Missense | Gly-Ser |
| 3 | CCDS | 320 | G | C | 15 | Missense | Gly-Arg |
| 4 | CCDS | 327 | C | G | 17 | Missense | Ala-Gly |
| 5 | CCDS | 339 | C | G | 21 | Missense | Ala-Gly |
| 6 | CCDS | 430 | G | T | 51 | Missense | Glu-Asp |
| 7 | CCDS | 462 | — | T | 62 | Frameshift | TA-Thr |
| 8 | CCDS | 480 | A | T | 68 | Missense | Glu-Val |
| 9 | CCDS | 759 | C | T | 161 | Missense | Ala-Val |
| 10 | CCDS | 1128 | C | G | 284 | Missense | Ala-Gly |
| 11 | CCDS | 1256 | C | A | 327 | Missense | His-Asn |
| 12 | CCDS | 1304 | G | A | 343 | Missense | Ala-Thr |
| 13 | CCDS | 1589 | C | T | 438 | Missense | Arg-Trp |
| 14 | CCDS | 1597 | T | A | 440 | Synonymous | Leu-Leu |
| 15 | CCDS | 1627 | A | G | 450 | Synonymous | Thr-Thr |
| 16 | CCDS | 1651 | C | T | 458 | Synonymous | Asn-Asn |
| 17 | CCDS | 1652 | G | A | 459 | Missense | Ala-Thr |
| 18 | CCDS | 1803 | A | G | 509 | Missense | Asn-Ser |
| 19 | CCDS | 1844 | T | C | 523 | Missense | Ser-Pro |
| 20 | CCDS | 1849 | T | C | 524 | Synonymous | Asp-Asp |
| 21 | CCDS | 1879 | A | G | 534 | Synonymous | Thr-Thr |
| 22 | CCDS | 1882 | A | G | 535 | Synonymous | Gln-Gln |
| 23 | CCDS | 1911 | T | G | 545 | Missense | Val-Gly |
| 24 | CCDS | 1940 | C | G | 555 | Missense | Pro-Ala |
| 25 | CCDS | 1949 | A | G | 558 | Missense | Ser-Gly |
| 26 | CCDS | 1982 | T | C | 569 | Missense | Tyr-His |
| 27 | CCDS | 2000 | G | C | 575 | Missense | Ala-Pro |

TABLE 1-continued

| SNPs of the GATA6 Em isoform | | | | | | | |
|---|---|---|---|---|---|---|---|
| S. No. | Region | Position | Contig reference | Polymorphism | Codon Position | Function | Protein residue |
| 28 | CCDS | 2002 | C | T | 575 | Synonymous | Ala-Ala |
| 29 | CCDS | 2008 | G | C | 577 | Synonymous | Pro-Pro |
| 30 | CCDS | 2026 | C | T | 583 | Synonymous | Ser-Ser |
| 31 | CCDS | 2031 | G | T | 585 | Missense | Arg-Leu |
| 32 | 3'UTR | 2106 | C | T | | | |
| 33 | 3'UTR | 2137 | G | A | | | |
| 34 | 3'UTR | 2142 | A | G | | | |
| 35 | 3'UTR | 2163 | C | T | | | |
| 36 | 3'UTR | 2294 | C | T | | | |
| 37 | 3'UTR | 2390 | A | G | | | |
| 38 | 3'UTR | 2391 | T | A | | | |
| 39 | 3'UTR | 2627 | A | G | | | |
| 40 | 3'UTR | 2691 | G | T | | | |
| 41 | 3'UTR | 3036 | G | T | | | |
| 42 | 3'UTR | 3102 | A | G | | | |
| 43 | 3'UTR | 3240 | C | T | | | |
| 44 | 3'UTR | 3265 | C | G | | | |
| 45 | 3'UTR | 3266 | C | T | | | |
| 46 | 3'UTR | 3290 | A | G | | | |
| 47 | 3'UTR | 3358 | C | T | | | |
| 48 | 3'UTR | 3366 | A | T | | | |
| 49 | 3'UTR | 3578 | C | T | | | |
| 50 | 3'UTR | 3632 | — | C | | | |
| 51 | 3'UTR | 3646 | C | T | | | |
| 52 | 3'UTR | 3670 | A | G | | | |
| 53 | 3'UTR | 3690 | C | T | | | |
| 54 | 3'UTR | 3708 | A | G | | | |
| 55 | 3'UTR | 3735 | A | G | | | |

TABLE 2

| SNPs of the GATA6 Ad isoform | | | | | | | |
|---|---|---|---|---|---|---|---|
| S. No. | Region | Position | Contig reference | Polymorphism | Codon Position | Function | Protein residue |
| 1 | 5'UTR | 138 | C | G | | | |
| 2 | 5'UTR | 228 | G | A | | | |
| 3 | 5'UTR | 255 | G | C | | | |
| 4 | 5'UTR | 262 | C | G | | | |
| 5 | 5'UTR | 274 | C | G | | | |
| 6 | 5'UTR | 365 | G | T | | | |
| 7 | 5'UTR | 397 | — | T | | | |
| 8 | 5'UTR | 415 | A | T | | | |
| 9 | CCDS | 694 | C | T | 15 | Missense | Ala-Val |
| 10 | CCDS | 1063 | C | G | 138 | Missense | Ala-Gly |
| 11 | CCDS | 1191 | C | A | 181 | Missense | His-Asn |
| 12 | CCDS | 1239 | G | A | 197 | Missense | Ala-Thr |
| 13 | CCDS | 1524 | C | T | 292 | Missense | Arg-Trp |
| 14 | CCDS | 1532 | T | A | 294 | Synonymous | Leu-Leu |
| 15 | CCDS | 1562 | A | G | 304 | Synonymous | Thr-Thr |
| 16 | CCDS | 1586 | C | T | 312 | Synonymous | Asn-Asn |
| 17 | CCDS | 1587 | G | A | 313 | Missense | Ala-Thr |
| 18 | CCDS | 1738 | A | G | 363 | Missense | Asn-Ser |
| 19 | CCDS | 1779 | T | C | 377 | Missense | Ser-Pro |
| 20 | CCDS | 1784 | T | C | 378 | Synonymous | Asp-Asp |
| 21 | CCDS | 1814 | A | G | 388 | Synonymous | Thr-Thr |
| 22 | CCDS | 1817 | A | G | 389 | Synonymous | Gln-Gln |
| 23 | CCDS | 1846 | T | G | 399 | Missense | Val-Gly |
| 24 | CCDS | 1875 | C | G | 409 | Missense | Pro-Ala |
| 25 | CCDS | 1884 | A | G | 412 | Missense | Ser-Gly |
| 26 | CCDS | 1917 | T | C | 423 | Missense | Tyr-His |
| 27 | CCDS | 1935 | G | C | 429 | Missense | Ala-Pro |
| 28 | CCDS | 1937 | C | T | 429 | Synonymous | Ala-Ala |
| 29 | CCDS | 1943 | G | C | 431 | Synonymous | Pro-Pro |
| 30 | CCDS | 1961 | C | T | 437 | Synonymous | Ser-Ser |
| 31 | CCDS | 1966 | G | T | 439 | Missense | Arg-Leu |
| 32 | 3'UTR | 2041 | C | T | | | |
| 33 | 3'UTR | 2072 | G | A | | | |
| 34 | 3'UTR | 2077 | A | G | | | |
| 35 | 3'UTR | 2098 | C | T | | | |
| 36 | 3'UTR | 2229 | C | T | | | |

TABLE 2-continued

| SNPs of the GATA6 Ad isoform | | | | | | | |
|---|---|---|---|---|---|---|---|
| S. No. | Region | Position | Contig reference | Polymorphism | Codon Position | Function | Protein residue |
| 37 | 3'UTR | 2325 | A | G | | | |
| 38 | 3'UTR | 2326 | T | A | | | |
| 39 | 3'UTR | 2562 | A | G | | | |
| 40 | 3'UTR | 2626 | G | T | | | |
| 41 | 3'UTR | 2971 | G | T | | | |
| 42 | 3'UTR | 3037 | A | G | | | |
| 43 | 3'UTR | 3175 | C | T | | | |
| 44 | 3'UTR | 3200 | C | G | | | |
| 45 | 3'UTR | 3201 | C | T | | | |
| 46 | 3'UTR | 3225 | A | G | | | |
| 47 | 3'UTR | 3293 | C | T | | | |
| 48 | 3'UTR | 3301 | A | T | | | |
| 49 | 3'UTR | 3513 | C | T | | | |
| 50 | 3'UTR | 3567 | — | C | | | |
| 51 | 3'UTR | 3581 | C | T | | | |
| 52 | 3'UTR | 3605 | A | G | | | |
| 53 | 3'UTR | 3625 | C | T | | | |
| 54 | 3'UTR | 3643 | A | G | | | |
| 55 | 3'UTR | 3670 | A | G | | | |

TABLE 3

| SNPs of the NKX2-1 Em isoform | | | | | | | |
|---|---|---|---|---|---|---|---|
| S. No. | Region | Position | Contig reference | Polymorphism | Codon Position | Function | Protein residue |
| 1 | 5'UTR | 269 | C | T | | | |
| 2 | 5'UTR | 281 | A | G | | | |
| 3 | 5'UTR | 305 | — | A | | | |
| 4 | 5'UTR | 304 | — | AA | | | |
| 5 | CCDS | 420 | G | A | 27 | Missense | Val-Met |
| 6 | CCDS | 425 | C | T | 28 | Synonymous | Gly-Gly |
| 7 | CCDS | 439 | G | T | 33 | Missense | Gly-Val |
| 8 | CCDS | 441 | C | A | 34 | Missense | Leu-Ile |
| 9 | CCDS | 450 | C | T | 37 | Missense | Pro-Ser |
| 10 | CCDS | 486 | C | T | 49 | Missense | Pro-Ser |
| 11 | CCDS | 781 | G | T | 147 | Missense | Gly-Val |
| 12 | CCDS | 785 | C | T | 148 | Synonymous | Asp-Asp |
| 13 | CCDS | 825 | A | C | 162 | Synonymous | Arg-Arg |
| 14 | CCDS | 950 | G | T | 203 | Synonymous | Thr-Thr |
| 15 | CCDS | 1169 | G | A | 276 | Synonymous | Ala-Ala |
| 16 | CCDS | 1305 | G | A | 322 | Missense | Gly-Ser |
| 17 | CCDS | 1344 | G | T | 335 | Missense | Ala-Ser |
| 18 | CCDS | 1448 | G | A | 369 | Synonymous | Arg-Arg |
| 19 | 3'UTR | 1458 | C | T | | | |
| 20 | 3'UTR | 1467 | C | T | | | |
| 21 | 3'UTR | 1489 | G | T | | | |
| 22 | 3'UTR | 1552 | G | T | | | |
| 23 | 3'UTR | 1633 | A | G | | | |
| 24 | 3'UTR | 1634 | A | G | | | |
| 25 | 3'UTR | 1640 | — | T | | | |
| 26 | 3'UTR | 1641 | — | GT | | | |
| 27 | 3'UTR | 1643 | — | >6 bp | | | |
| 28 | 3'UTR | 1667 | A | T | | | |
| 29 | 3'UTR | 1673 | — | T | | | |
| 30 | 3'UTR | 1678 | — | T | | | |
| 31 | 3'UTR | 1748 | — | C | | | |
| 32 | 3'UTR | 1750 | — | C | | | |
| 33 | 3'UTR | 1831 | A | T | | | |
| 34 | 3'UTR | 1893 | G | T | | | |
| 35 | 3'UTR | 1916 | — | A | | | |
| 36 | 3'UTR | 1917 | — | A | | | |
| 37 | 3'UTR | 1934 | C | G/T | | | |
| 38 | 3'UTR | 2099 | C | G | | | |
| 39 | 3'UTR | 2319 | C | G | | | |

TABLE 4

SNPs of the NKX2-1 Ad isoform

| S. No. | Region | Position | Contig reference | Polymorphism | Codon Position | Function | Protein residue |
|---|---|---|---|---|---|---|---|
| 1 | 5'UTR | 12 | G | T | | | |
| 2 | CCDS | 125 | G | A | 10 | Missense | Arg-Gln |
| 3 | CCDS | 265 | G | A | 57 | Missense | Val-Met |
| 4 | CCDS | 270 | C | T | 58 | Synonymous | Gly-Gly |
| 5 | CCDS | 284 | G | T | 63 | Missense | Gly-Val |
| 6 | CCDS | 286 | C | A | 64 | Missense | Leu-Ile |
| 7 | CCDS | 295 | C | T | 67 | Missense | Pro-Ser |
| 8 | CCDS | 331 | C | T | 79 | Missense | Pro-Ser |
| 9 | CCDS | 626 | G | T | 177 | Missense | Gly-Val |
| 10 | CCDS | 630 | C | T | 178 | Synonymous | Asp-Asp |
| 11 | CCDS | 670 | A | C | 192 | Synonymous | Arg-Arg |
| 12 | CCDS | 795 | G | T | 233 | Synonymous | Thr-Thr |
| 13 | CCDS | 1014 | G | A | 306 | Synonymous | Ala-Ala |
| 14 | CCDS | 1150 | G | A | 352 | Missense | Gly-Ser |
| 15 | CCDS | 1189 | G | T | 365 | Missense | Ala-Ser |
| 16 | CCDS | 1293 | G | A | 399 | Synonymous | Arg-Arg |
| 17 | 3'UTR | 1303 | C | T | | | |
| 18 | 3'UTR | 1312 | C | T | | | |
| 19 | 3'UTR | 1334 | G | T | | | |
| 20 | 3'UTR | 1397 | G | T | | | |
| 21 | 3'UTR | 1478 | A | G | | | |
| 22 | 3'UTR | 1479 | A | G | | | |
| 23 | 3'UTR | 1478 | — | >6 bp | | | |
| 24 | 3'UTR | 1485 | — | T | | | |
| 25 | 3'UTR | 1486 | — | GT | | | |
| 26 | 3'UTR | 1488 | — | >6 bp | | | |
| 27 | 3'UTR | 1512 | A | T | | | |
| 28 | 3'UTR | 1518 | — | T | | | |
| 29 | 3'UTR | 1523 | — | T | | | |
| 30 | 3'UTR | 1593 | — | C | | | |
| 31 | 3'UTR | 1595 | — | C | | | |
| 32 | 3'UTR | 1676 | A | T | | | |
| 33 | 3'UTR | 1738 | G | T | | | |
| 34 | 3'UTR | 1761 | — | A | | | |
| 35 | 3'UTR | 1762 | — | A | | | |
| 36 | 3'UTR | 1779 | C | G/T | | | |
| 37 | 3'UTR | 1944 | C | G | | | |
| 38 | 3'UTR | 2164 | C | G | | | |

TABLE 5

SNPs of the FOXA2 Em isoform

| S. No. | Region | Position | Contig reference | Polymorphism | Codon Position | Function | Protein residue |
|---|---|---|---|---|---|---|---|
| 1 | 5'UTR | 168 | — | >6 bp | | | |
| 2 | CCDS | 208 | T | C | 8 | Missense | Leu-Pro |
| 3 | CCDS | 289 | G | A | 35 | Missense | Ser-Asn |
| 4 | CCDS | 361 | G | A | 59 | Missense | Ser-Asn |
| 5 | CCDS | 368 | G | A | 61 | Synonymous | Ser-Ser |
| 6 | CCDS | 374 | C | T | 63 | Synonymous | Asn-Asn |
| 7 | CCDS | 379 | G | A | 65 | Missense | Ser-Asn |
| 8 | CCDS | 383 | G | A | 66 | Synonymous | Ala-Ala |
| 9 | CCDS | 404 | G | T | 73 | Synonymous | Ser-Ser |
| 10 | CCDS | 459 | G | A | 92 | Missense | Ala-Thr |
| 11 | CCDS | 481 | C | T | 99 | Missense | Ser-Leu |
| 12 | CCDS | 483 | G | C | 100 | Missense | Ala-Pro |
| 13 | CCDS | 494 | C | T | 103 | Synonymous | Ala-Ala |
| 14 | CCDS | 529 | G | A | 115 | Missense | Ser-Asn |
| 15 | CCDS | 564 | A | G | 127 | Missense | Met-Val |
| 16 | CCDS | 577 | C | G | 131 | Missense | Ala-Gly |
| 17 | CCDS | 584 | C | T | 133 | Synonymous | Tyr-Tyr |
| 18 | CCDS | 590 | C | A | 135 | Missense | Asn-Lys |
| 19 | CCDS | 610 | T | C | 142 | Missense | Met-Thr |
| 20 | CCDS | 623 | G | C | 146 | Synonymous | Ala-Ala |
| 21 | CCDS | 641 | C | T | 152 | Synonymous | Arg-Arg |
| 22 | CCDS | 650 | G | A | 155 | Synonymous | Lys-Lys |
| 23 | CCDS | 659 | G | T | 158 | Missense | Arg-Ser |
| 24 | CCDS | 674 | C | T | 163 | Synonymous | His-His |
| 25 | CCDS | 773 | G | T | 196 | Missense | Met-Ile |
| 26 | CCDS | 845 | C | T | 220 | Synonymous | Asn-Asn |

TABLE 5-continued

SNPs of the FOXA2 Em isoform

| S. No. | Region | Position | Contig reference | Polymorphism | Codon Position | Function | Protein residue |
|---|---|---|---|---|---|---|---|
| 27 | CCDS | 1040 | A | G | 285 | Synonymous | Gly-Gly |
| 28 | CCDS | 1075 | C | T | 297 | Missense | Ala-Val |
| 29 | CCDS | 1186 | C | T | 334 | Missense | Ala-Val |
| 30 | CCDS | 1188 | G | C | 335 | Missense | Ala-Pro |
| 31 | CCDS | 1240 | C | T | 352 | Missense | Ala-Val |
| 32 | CCDS | 1242 | G | A | 353 | Missense | Ala-Thr |
| 33 | CCDS | 1243 | C | G | 353 | Missense | Ala-Gly |
| 34 | CCDS | 1304 | A | C | 373 | Missense | Glu-Asp |
| 35 | CCDS | 1374 | AG | — | 397 | Frameshift | Ser-Pro |
| 36 | CCDS | 1391 | A | G | 402 | Synonymous | Gln-Gln |
| 37 | CCDS | 1408 | T | C | 408 | Missense | Leu-Pro |
| 38 | CCDS | 1414 | C | T | 410 | Missense | Ala-Val |
| 39 | CCDS | 1432 | A | C | 416 | Missense | His-Pro |
| 40 | CCDS | 1458 | C | A | 425 | Missense | Pro-Thr |
| 41 | CCDS | 1475 | G | A | 430 | Missense | Met-Ile |
| 42 | CCDS | 1487 | G | C | 434 | Synonymous | Thr-Thr |
| 43 | CCDS | 1522 | C | G | 446 | Missense | Ala-Gly |
| 44 | CCDS | 1539 | C | G | 452 | Missense | Gln-Glu |
| 45 | 3'UTR | 1582 | G | T | | | |
| 46 | 3'UTR | 1583 | A | G | | | |
| 47 | 3'UTR | 1594 | C | T | | | |
| 48 | 3'UTR | 1627 | A | G | | | |
| 49 | 3'UTR | 1631 | A | G | | | |
| 50 | 3'UTR | 1687 | A | G | | | |
| 51 | 3'UTR | 1723 | A | C | | | |
| 52 | 3'UTR | 1737 | — | G | | | |
| 53 | 3'UTR | 1738 | — | G | | | |
| 54 | 3'UTR | 1754 | A | G | | | |
| 55 | 3'UTR | 1812 | A | G | | | |
| 56 | 3'UTR | 1831 | A | T | | | |
| 57 | 3'UTR | 1838 | — | T | | | |
| 58 | 3'UTR | 1940 | A | C | | | |
| 59 | 3'UTR | 1966 | — | G/T | | | |
| 60 | 3'UTR | 1970 | — | A | | | |
| 61 | 3'UTR | 2070 | A | T | | | |
| 62 | 3'UTR | 2083 | A | G | | | |
| 63 | 3'UTR | 2084 | — | T | | | |
| 64 | 3'UTR | 2093 | — | T | | | |
| 65 | 3'UTR | 2105 | A | C | | | |
| 66 | 3'UTR | 2112 | C | T | | | |
| 67 | 3'UTR | 2200 | C | T | | | |
| 68 | 3'UTR | 2388 | A | G | | | |

TABLE 6

SNPs of the FOXA2 Em isoform

| S. No. | Region | Position | Contig reference | Polymorphism | Codon Position | Function | Protein residue |
|---|---|---|---|---|---|---|---|
| 1 | 5'UTR | 5 | C | T | | | |
| 2 | 5'UTR | 37 | G | T | | | |
| 3 | 5'UTR | 65 | C | T | | | |
| 4 | 5'UTR | 68 | A | C | | | |
| 5 | 5'UTR | 70 | A | G | | | |
| 6 | 5'UTR | 88 | A | G | | | |
| 7 | 5'UTR | 128 | C | T | | | |
| 8 | CCDS | 195 | T | C | 2 | Missense | Leu-Pro |
| 9 | CCDS | 276 | G | A | 29 | Missense | Ser-Asn |
| 10 | CCDS | 348 | G | A | 53 | Missense | Ser-Asn |
| 11 | CCDS | 355 | G | A | 55 | Synonymous | Ser-Ser |
| 12 | CCDS | 361 | C | T | 57 | Synonymous | Asn-Asn |
| 13 | CCDS | 366 | G | A | 59 | Missense | Ser-Asn |
| 14 | CCDS | 370 | G | A | 60 | Synonymous | Ala-Ala |
| 15 | CCDS | 391 | G | T | 67 | Synonymous | Ser-Ser |
| 16 | CCDS | 446 | G | A | 86 | Missense | Ala-Thr |
| 17 | CCDS | 468 | C | T | 93 | Missense | Ser-Leu |
| 18 | CCDS | 470 | G | C | 94 | Missense | Ala-Pro |
| 19 | CCDS | 481 | C | T | 97 | Synonymous | Ala-Ala |
| 20 | CCDS | 516 | G | A | 109 | Missense | Ser-Asn |
| 21 | CCDS | 551 | A | G | 121 | Missense | Met-Val |
| 22 | CCDS | 564 | C | G | 125 | Missense | Ala-Gly |

TABLE 6-continued

SNPs of the FOXA2 Em isoform

| S. No. | Region | Position | Contig reference | Polymorphism | Codon Position | Function | Protein residue |
|---|---|---|---|---|---|---|---|
| 23 | CCDS | 571 | C | T | 127 | Synonymous | Tyr-Tyr |
| 24 | CCDS | 577 | C | A | 129 | Missense | Asn-Lys |
| 25 | CCDS | 597 | T | C | 136 | Missense | Met-Thr |
| 26 | CCDS | 610 | G | C | 140 | Synonymous | Ala-Ala |
| 27 | CCDS | 628 | C | T | 146 | Synonymous | Arg-Arg |
| 28 | CCDS | 637 | G | A | 149 | Synonymous | Lys-Lys |
| 29 | CCDS | 646 | G | T | 152 | Missense | Arg-Ser |
| 30 | CCDS | 661 | C | T | 157 | Synonymous | His-His |
| 31 | CCDS | 760 | G | T | 190 | Missense | Met-Ile |
| 32 | CCDS | 832 | C | T | 214 | Synonymous | Asn-Asn |
| 33 | CCDS | 1027 | A | G | 279 | Synonymous | Gly-Gly |
| 34 | CCDS | 1062 | C | T | 291 | Missense | Ala-Val |
| 35 | CCDS | 1173 | C | T | 328 | Missense | Ala-Val |
| 36 | CCDS | 1175 | G | C | 329 | Missense | Ala-Pro |
| 37 | CCDS | 1227 | C | T | 346 | Missense | Ala-Val |
| 38 | CCDS | 1229 | G | A | 347 | Missense | Ala-Thr |
| 39 | CCDS | 1230 | C | G | 347 | Missense | Ala-Gly |
| 40 | CCDS | 1291 | A | C | 367 | Missense | Gly-Glu |
| 41 | CCDS | 1361 | AG | — | 391 | Frameshift | Ser-Pro |
| 42 | CCDS | 1378 | A | G | 396 | Synonymous | Gln-Gln |
| 43 | CCDS | 1395 | T | C | 402 | Missense | Leu-Pro |
| 44 | CCDS | 1401 | C | T | 404 | Missense | Ala-Val |
| 45 | CCDS | 1419 | A | C | 410 | Missense | His-Pro |
| 46 | CCDS | 1445 | C | A | 419 | Missense | Pro-Thr |
| 47 | CCDS | 1462 | G | A | 424 | Missense | Met-Ile |
| 48 | CCDS | 1474 | G | C | 428 | Synonymous | Thr-Thr |
| 49 | CCDS | 1509 | C | G | 440 | Missense | Ala-Gly |
| 50 | CCDS | 1526 | C | G | 446 | Missense | Gln-Glu |
| 51 | 3'UTR | 1569 | G | T | | | |
| 52 | 3'UTR | 1570 | A | G | | | |
| 53 | 3'UTR | 1581 | C | T | | | |
| 54 | 3'UTR | 1614 | A | G | | | |
| 55 | 3'UTR | 1618 | A | G | | | |
| 56 | 3'UTR | 1674 | A | G | | | |
| 57 | 3'UTR | 1710 | A | C | | | |
| 58 | 3'UTR | 1724 | — | G | | | |
| 59 | 3'UTR | 1725 | — | G | | | |
| 60 | 3'UTR | 1741 | A | G | | | |
| 61 | 3'UTR | 1799 | A | G | | | |
| 62 | 3'UTR | 1818 | A | T | | | |
| 63 | 3'UTR | 1825 | — | T | | | |
| 64 | 3'UTR | 1927 | A | C | | | |
| 65 | 3'UTR | 1953 | — | G/T | | | |
| 66 | 3'UTR | 1957 | — | A | | | |
| 67 | 3'UTR | 2057 | A | T | | | |
| 68 | 3'UTR | 2070 | A | G | | | |
| 69 | 3'UTR | 2071 | — | T | | | |
| 70 | 3'UTR | 2080 | — | T | | | |
| 71 | 3'UTR | 2092 | A | C | | | |
| 72 | 3'UTR | 2099 | C | T | | | |
| 73 | 3'UTR | 2187 | C | T | | | |
| 74 | 3'UTR | 2375 | A | G | | | |

TABLE 7

SNPs of the ID2 Em isoform

| S. No. | Region | Position | Contig reference | Polymorphism | Codon Position | Function | Protein residue |
|---|---|---|---|---|---|---|---|
| 1 | 5'UTR | 6 | C | T | | | |
| 2 | 5'UTR | 43 | A | G | | | |
| 3 | 5'UTR | 53 | A | G | | | |
| 4 | 5'UTR | 55 | C | G | | | |
| 5 | 5'UTR | 154 | C | G/T | | | |
| 6 | CCDS | 195 | C | T | 4 | Missense | Phe-Phe |
| 7 | CCDS | 209 | C | T | 9 | Missense | Ser-Phe |
| 8 | CCDS | 224 | G | A | 14 | Missense | Ser-Asn |
| 9 | CCDS | 237 | C | T | 18 | Synonymous | His-His |
| 10 | CCDS | 263 | C | A | 27 | Missense | Thr-Asn |
| 11 | CCDS | 286 | C | T | 35 | Synonymous | Leu-Leu |

TABLE 7-continued

SNPs of the ID2 Em isoform

| S. No. | Region | Position | Contig reference | Polymorphism | Codon Position | Function | Protein residue |
|---|---|---|---|---|---|---|---|
| 12 | CCDS | 360 | G | A | 59 | Synonymous | Val-Val |
| 13 | CCDS | 399 | C | T | 72 | Synonymous | Ile-Ile |
| 14 | CCDS | 405 | C | T | 74 | Synonymous | Asp-Asp |
| 15 | CCDS | 485 | C | T | 101 | Missense | Thr-Met |
| 16 | CCDS | 501 | C | G/T | 106 | Synonymous | Leu-Leu |
| 17 | CCDS | 544 | C | T | 121 | Missense | Pro-Ser |
| 18 | CCDS | 547 | T | A | 122 | Missense | Ser-Thr |
| 19 | 3'UTR | 605 | A | G | | | |
| 20 | 3'UTR | 662 | C | G | | | |
| 21 | 3'UTR | 665 | G | T | | | |
| 22 | 3'UTR | 716 | A | T | | | |
| 23 | 3'UTR | 757 | C | T | | | |
| 24 | 3'UTR | 871 | A | G | | | |
| 25 | 3'UTR | 876 | A | G | | | |
| 26 | 3'UTR | 975 | — | >6 bp | | | |
| 27 | 3'UTR | 1085 | — | >6 bp | | | |
| 28 | 3'UTR | 1115 | A | G | | | |
| 29 | 3'UTR | 1119 | — | AT | | | |
| 30 | 3'UTR | 1149 | C | T | | | |
| 31 | 3'UTR | 1151 | A | T | | | |
| 32 | 3'UTR | 1251 | — | CA | | | |
| 33 | 3'UTR | 1333 | A | G | | | |
| 34 | 3'UTR | 1350 | C | G | | | |

TABLE 8

SNPs of the ID2 Ad isoform

| S. No. | Region | Position | Contig reference | Polymorphism | Codon Position | Function | Protein residue |
|---|---|---|---|---|---|---|---|
| 5 | 5'UTR | 93 | C | G/T | | | |
| 6 | CCDS | 134 | C | T | 4 | Missense | Phe-Phe |
| 7 | CCDS | 148 | C | T | 9 | Missense | Ser-Phe |
| 8 | CCDS | 163 | G | A | 14 | Missense | Ser-Asn |
| 9 | CCDS | 176 | C | T | 18 | Synonymous | His-His |
| 10 | CCDS | 202 | C | A | 27 | Missense | Thr-Asn |
| 11 | CCDS | 225 | C | T | 35 | Synonymous | Leu-Leu |
| 12 | CCDS | 299 | G | A | 59 | Synonymous | Val-Val |
| 13 | CCDS | 338 | C | T | 72 | Synonymous | Ile-Ile |
| 14 | CCDS | 344 | C | T | 74 | Synonymous | Asp-Asp |
| 15 | CCDS | 424 | C | T | 101 | Missense | Thr-Met |
| 16 | CCDS | 440 | C | G/T | 106 | Synonymous | Leu-Leu |
| 17 | CCDS | 483 | C | T | 121 | Missense | Pro-Ser |
| 18 | CCDS | 486 | T | A | 122 | Missense | Ser-Thr |
| 19 | 3'UTR | 544 | A | G | | | |
| 20 | 3'UTR | 601 | C | G | | | |
| 21 | 3'UTR | 604 | G | T | | | |
| 22 | 3'UTR | 655 | A | T | | | |
| 23 | 3'UTR | 696 | C | T | | | |
| 24 | 3'UTR | 810 | A | G | | | |
| 25 | 3'UTR | 815 | A | G | | | |
| 26 | 3'UTR | 914 | — | >6 bp | | | |
| 27 | 3'UTR | 1024 | — | >6 bp | | | |
| 28 | 3'UTR | 1054 | A | G | | | |
| 29 | 3'UTR | 1058 | — | AT | | | |
| 30 | 3'UTR | 1088 | C | T | | | |
| 31 | 3'UTR | 1090 | A | T | | | |
| 32 | 3'UTR | 1190 | — | CA | | | |
| 33 | 3'UTR | 1272 | A | G | | | |
| 34 | 3'UTR | 1289 | C | G | | | |

A control sample according to the present invention is a sample from a healthy control subject. Such a sample can be obtained for example from a subject known to be a healthy subject. It is also possible to generate a control sample according to the present invention as a mixture of samples obtained from several healthy subjects, for example from a group of 10, 20, 30, 50, 100 or even up to 1000 healthy subjects. A control sample according to the present invention can be generated for example from age-matched and or gender-matched healthy control subjects. A control sample according to the present invention can also be generated for example in vitro to mimic a control sample obtained from one or several healthy subjects.

Control samples used, inter alia, in appended Example 10 for the analysis of tumor biopsies were healthy tissues (i.e. biopsies) from diseased individuals/subjects. "Healthy tissue from diseased individuals/subjects" can refer to tissue that is pathologically classified as "normal" or "healthy" and/or that is distant or adjacent to a (suspected) tumor. For example, the "healthy tissue from diseased individuals/subjects" can be obtained e.g. by biopsy from adjacent healthy tissue of (suspected) cancer patients.

For example, the "healthy tissue" can be obtained from the subject(s) to be assessed in accordance with the present invention for suffering from cancer or being prone to suffering from cancer. In another example, the "healthy tissue" can be obtained from other diseased patients (e.g. patients that have already been diagnosed to suffer from cancer by conventional means and methods or patients that have a history of cancer); in that case, "healthy tissue" is not obtained from subject(s) to be assessed in accordance with the present invention for suffering from cancer or being prone to suffering from cancer.

Thus, also "healthy tissue from (a) diseased individual(s)" can be used as a control sample in accordance with the present invention.

Control samples used, inter alia, in appended Example 10 in the analysis of EBCs for assessing whether a subject suffers from cancer or is prone to suffer from cancer were samples from healthy individuals. The term "healthy individuals" as used herein can refer to individuals with no history of cancer, i.e. individuals that did not suffer from cancer or that do currently (i.e. at the time the control sample is obtained) not suffer from cancer. Thus, "healthy tissue/sample" (i.e. tissue (e.g. a biopsy) or another sample (e.g. EBC) obtained from a healthy individual" can be used as a control sample in accordance with the present invention.

A subject according to the present invention is preferably a human subject. The subject according to the present invention can be a human subject which has an increased likelihood of suffering from cancer. Such an increased likelihood of suffering from cancer can for example result from certain exposures to cancerogens, for example through the habit of smoking.

The "amount of said specific transcription isoform" according to the present invention can be a relative amount or an absolute amount. The relative amount can be determined relative to a control sample. To determine the "amount of said specific transcription isoform", the absolute or relative amount of a reference gene or reference protein can be determined in the sample from the subject and in the control sample. Non-limiting examples of reference genes/proteins are TUBA1A1 (Uniprot-ID: Q71U36, Gene-ID: 7846), HPRT1 (Uniprot-ID: P00492, Gene-ID: 3251), ACTB (Uniprot-ID: P60709, Gene-ID: 60), HMBS (Uniprot-ID: P08397, Gene-ID: 3145), RPL13A (Uniprot-ID: Q9BSQ6, Gene-ID: 23521) and UBE2A (Uniprot-ID: P49459, Gene-ID: 7319).

The term "is increased in comparison to the amount of said specific transcription factor isoform in the control sample" relates to an increase of the amount of the specific transcription factor isoform in the sample obtained from the subject in comparison to the amount of said specific transcription factor isoform in the control sample by at least 1.3-fold, by at least 1.4-fold, 1.5-fold, 1.6-fold, 1.7-fold, 1.8-fold, 1.9-fold or 2.0-fold, by at least 3-fold, 4-fold, 5-fold, 6-fold, 7-fold, 8-fold, 9-fold or 10-fold; by at least 20-fold, by at least 30-fold, by at least 40-fold; by at least 50-fold; or by at least 100-fold. Illustrative data provided herein for GATA6 and NKX2-1 are summarized in the following table and further illustrate the invention without being limiting:

| | Normal | Grade I | Grade II | Grade III |
|---|---|---|---|---|
| | | Gata6 | | |
| Em | 1.0 | 2.7 | 6.7 | 1.9 |
| Ad | 2.3 | 1.1 | 0.5 | 0.5 |
| Ratio (Em/Ad) | 0.435 | 2.5 | 13.4 | 3.8 |
| Fold increase of Em relative to control | | 2.7 | 6.7 | 1.9 |
| | | Nkx2-1 | | |
| Em | 1.0 | 1.6 | 5.3 | 5.7 |
| Ad | 2.9 | 1.6 | 0.9 | 1.8 |
| Ratio (Em/Ad) | 0.3 | 1.0 | 5.9 | 3.2 |
| Fold increase of Em related to ctrl | | 1.6 | 5.3 | 5.7 |

According to a more refined analysis in appended Example 10 the following thresholds were determined:

| | GATA6 Em | NKX2-1 Em |
|---|---|---|
| Mean ± s.e.m. | 2.240 ± 0.453 | 3.359 ± 1.053 |
| fold increase of Em relative to control (range) | 1.194-5.064 | 1.393-10.661 |

These data confirm that the methods provided herein allow a reliable assessment that a subject suffers from cancer, in particular lung cancer, such as NSCLC or small cell lung cancer (SLC), or is prone to suffering from said cancer, when the amount of the (analyzed) specific transcription factor Em isoform GATA6 Em and/or NKX2-1 Em is increased by at least about 1.3 fold in comparison to the amount of the analyzed specific transcription factor Em isoform(s) in the control sample. In relation to the Em isoform GATA6 Em a reliable assessment that a subject suffers from cancer, in particular lung cancer, such as NSCLC or small cell lung cancer (SLC), or is prone to suffering from said cancer, is possible, when the amount of the (analyzed) specific transcription factor Em isoform GATA6 Em and/or NKX2-1 Em is increased by at least about 1.2 fold in comparison to the amount of the analyzed specific transcription factor Em isoform(s) in the control sample.

Without being bound by theory and the concrete values provided herein in particular in the experimental part, for example for NKX2-1, an increase of at least 1.3 fold (over control) would be a reason to observe the subject in periodical manner (i.e. every 3 to 6 months). An increase of at least about 1.6 (over control) fold would be a reason for more detail analysis and elucidation of the most suitable treatment (i.e. targeting the isoform that is increased using, inter alia, but not limited to a "loss-of-function approach"; see also appended FIG. 2B and technical details provided in the appended examples. Potential and preferred treatment options have been provided herein above. Yet, the attending physician may also decide to make use of other and/or further medical and/or pharmaceutical intervention(s). For GATA6, as illustrated about, again, an increase of about 1.3-fold (over control) to about 2.7 (over control) merits closer observation of the subject/patient Potential and preferred treatment options have been provided herein above. Yet, the attending physician may also decide to make use of other and/or further medical and/or pharmaceutical intervention(s). Again, in accordance with the illustrative data provided herein for GATA6, an increase of at least about 27 (over control) merits a more detailed analysis and elucidation of the most suitable treatment form of the cancer.

The method according to the present invention may comprise the step of obtaining a sample from a patient, wherein this sample is preferably a blood sample.

The present invention relates to a method of assessing whether a subject suffers from cancer or is prone to suffering from cancer, said method comprising the steps of a) measuring in a sample of said subject the amount of two specific isoforms of a transcription factor, wherein said transcription factor is either GATA6 or NKX2-1 and wherein the two specific isoforms are either:
  i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; and the GATA6 Ad isoform comprising the nucleic acid sequence of SEQ ID No: 5 or the GATA6 Ad isoform nucleic acid sequence with up to 55 additions, deletions or substitutions of SEQ ID NO: 5; or
  ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2; and the NKX2-1 Ad isoform comprising the nucleic acid sequence of SEQ ID No: 6 or the NKX2-1 Ad isoform comprising a nucleic acid sequence with up to 38 additions, deletions or substitutions of SEQ ID NO: 6;
b) building the ratio of the amount of said Em and said Ad isoform of said transcription factor
c) assessing that said subject suffers from cancer or is prone to suffering from cancer if
  i) the transcription factor is GATA6 and the ratio of the amount of said Em and said Ad isoform of GATA6 is higher than 0.5; or
  ii) the transcription factor is NKX2-1 and the ratio of the amount of said Em and said Ad isoform of NKX2-1 is higher than 0.3.

It is surprisingly found that the ratio of the transcription factor Em isoform and the transcription factor Ad isoform according to the present invention is increasing in the process of the development of cancer (see Example 3 of the present application). This allows a very early detection of cancer using any of the methods of the present invention. Further, this surprising finding also allows the staging of cancer, i.e. to assess the stage of a cancer of a subject with a method of the present invention alone or with a method of the present invention in combination with further methods for the staging of cancer (see, inter alia, Example 3 appended herewith).

To compute the ratio of the amount of the Em isoform and the amount of the Ad isoform according to the present invention, the person skilled in the art preferably divides the amount of the Em isoform by the amount of the Ad isoform. This is possible if the amounts are absolute amounts as well as if the amounts are relative amounts, for examples amounts which are given in relation to one or several reference genes. As documented herein (see FIG. 2B of Example 3 of the present application), the corresponding ratio for GATA6 is deduced at about 0.5 (0.435 in table presented herein above), for NKX2-1 at about 0.3 and for FOXA2 at about 0.8 when (as done in the appended examples) quantitative measures are taken by real time PCR for the ratio of Em/Ad.

As documented herein (see, inter alia, FIG. 2B of Example 3 of the present application), the Em-isoforms are highly expressed in human lung cancer tissue. In the appended examples, isoform specific expression was monitored by (for example) qRT-PCR after total RNA isolation from human lung tumor and normal lung cryosections. The expression of the Em-isoform/Em-transcript of each one of the genes analyzed, in particular GATA6, NKX2-1 and FOXA2, was higher in the tested cancer samples when compared to the normal controls, documenting that indeed an increase in expression of the Em-isoforms of GATA6 and NKX2-1 and, in co-assessments also of FOXA3 and/or ID2 are relevant and indicative for the development/formation of cancer, in particular for lung cancer formation as documented herein. This was also confirmed in human cancer specimens, in particular when human lung biopsies from healthy donors and lung tumor patients were compared; see also appended FIG. 2B. The embryonic transcript of each one of the genes analyzed was enriched in the biopsies of lung tumor when compared to the healthy tissue. In accordance with the data presented herein for lung cancer, for GATA6 Em, NKX2-1 Em and FOXA2 Em isoforms, a diagnostic ratio for GATA6 is 0.5, for NKX2-1 is 0.3 and for FOXA2 is 0.8. In the following, non limiting examples for FOXA 2 as elucidated form the experimental part of this application are provided:

| | Normal | Grade I | Grade II | Grade III |
|---|---|---|---|---|
| | | Foxa2 | | |
| var1 | 0.8 | 3.19 | 15.34 | 5.59 |
| var2 | 1.00 | 1.44 | 1.50 | 0.45 |
| Ratio (Em/Ad) | 0.80 | 2.21 | 10.20 | 12.55 |
| | | 3.99 | 19.17 | 6.98 |
| | | Id2 | | |
| Em (Var 1) | 1 | 1.182787 | 3.831565 | 1.639342 |
| Ad (Var 2) | 1.08543 | 0.78787 | 1.12586 | 0.62216 |
| Ratio (Em/Ad) | 0.9 | 1.5 | 3.4 | 2.6 |
| | | 1.182787 | 3.831565 | 1.639342 |

As demonstrated in the appended examples, the thresholds/ratios of 0.5 in relation to GATA6 or 0.3 in relation to NKX2-1 are useful to assess whether a patient suffers from cancer or is prone to suffering from cancer. If the ratio of the amount of said Em and said Ad isoform of GATA6 is higher than 0.5 a subject is assessed herein as suffering from cancer or as being prone to suffering from cancer. If the ratio of the amount of said Em and said Ad isoform of NKX2-1 is higher than 0.3, a subject is assessed herein as suffering from cancer or as being prone to suffering from cancer.

It is understood that different ethnic groups can show a certain variation in these ratios. For example, appended example 10 provides an assessment of a large sample set including patients from all ethnic groups (CEU, Utah residents with ancestry from northern and western Europe; CHB, Han Chinese in Beijing, China and MXL, Mexican ancestry in Los Angeles, Calif.). It is demonstrated therein that healthy tissue (biopsies) from all diseased patients in all ethnic groups had a mean Em/Ad ratio of 0.642 for GATA6 and 0.475 for NKX2-1. These values are slightly increased compared to the threshold values of 0.5 and 0.3 respectively, which is due to the inclusion of a more heterogeneous population set (including all three ethnic groups). Importantly, however, the majority of the healthy samples lies in the range of 0.3-0.7 for GATA6 and 0.3-0.5 for NKX2-1.

The data provided inter alia in appended Example 10 employed control samples (biopsies) obtained from adjacent healthy tissue of lung cancer patients.

Also healthy donor tissue from unaffected, healthy individuals (no current or history of tumors) can be used as control samples in the herein provided methods as "control samples". It is demonstrated herein that the ratio of Em/Ad was <0.3 for GATA6 and <0.2 for NKX2-1 in these control samples, as shown below:

The ratios obtained using "healthy" donor lung tissues are 0.17±0.03 for GATA6 and 0.16±0.02 for NKX2-1, lower than the ones obtained from healthy tissues from diseased individuals; see the table below:

| | Em/Ad | |
|---|---|---|
| | GATA6 | NKX2-1 |
| | 0.219218 | 0.211487 |
| | 0.08244 | 0.271615 |
| | 0.06726 | 0.176477 |
| | 0.346862 | 0.164339 |
| | 0.224829 | 0.193047 |
| | 0.219752 | 0.123482 |
| | 0.06256 | 0.08117 |
| | 0.176477 | 0.047586 |
| Mean | 0.17 | 0.16 |
| s.e.m. | 0.03505 | 0.025586 |

This demonstrates that the threshold values/ratios of 0.5 in relation to GATA6 or 0.3 in relation to NKX2-1 are indeed useful to assess whether a patient suffers from cancer or is prone to suffering from cancer.

Again, it is understood that these thresholds/ratios can vary depending on the values determined in control samples due to variations within ethnic groups, due to variations in sample types (e.g. biopsy or EBC), or origin (e.g. obtained from a healthy individual or obtained from healthy tissue from a diseased individual/subject). It is of note that subjects suffering from cancer or prone to suffering from cancer can reliably be diagnosed herein, because samples obtained from these subjects (e.g. a biopsy from a suspected tumor or EBC, exhaled breath condensate) show, even and in particular at early stages of the tumor, an increased Em/Ad ratio compared to the control. As shown in the appended examples, the Em/Ad ratios in samples from diseased patients is consistently increased compared to that of control samples (irrespective of the ethnic groups, sample type or origin of sample). The Em/Ad ratios in samples from diseased patients was always shown to be higher than 1. The lowest Em/Ad ratio shown in a sample from diseased patients was about 1.5.

The data shown in appended example 10 are summarized in the following table:

| Mean values ± s.e.m. | | | | |
|---|---|---|---|---|
| Healthy | Tumor | Grade I | Grade II | Grade III |
| GATA6 Biopsies | | | | |
| 0.64 ± 0.05 | 2.63 ± 0.19 | 2.39 ± 0.25 | 3.43 ± 0.24 | 2.83 ± 0.59 |
| EBC | | | | |
| 0.47 ± 0.11 | 1.53 ± 0.27 | | | |
| NKX2-1 Biopsies | | | | |
| 0.46 ± 0.03 | 2.07 ± 0.22 | 1.87 ± 0.12 | 2.58 ± 0.25 | 3.78 ± 0.39 |
| EBC | | | | |
| 0.45 ± 0.05 | 2.77 ± 0.29 | | | |

The data show that the Em/Ad ratios obtained from EBCs and biopsies are comparable supporting that the EBCs can be used as a non-invasive, sensitive and specific cancer diagnostic method, in particular lung cancer diagnostic method, that is advantageous for screening in particular high risk patients compared to conventional methods including chest X-ray and low dose computed tomography.

This shows that the present invention provides a reliable diagnosis of cancer patients, in particular of lung cancer patients.

Accordingly, in one embodiment of the invention, the transcription factor to be verified is GATA6 and the ratio of the amount of said Em and said Ad isoform of GATA6 is higher than 0.5; at least higher than 0.6, 0.7, 0.8, 0.9 or preferably higher than 1. More preferably, the ratio of the amount of said Em and said Ad isoform of GATA6 is higher than 1.5. Thus, the ratio of the amount of said Em and said Ad isoform of GATA6 can be higher than 1.2, 1.4, 1.6, 1.8 or 2, or even higher, for example higher than 3, 4, 5, 6, 7, 8, 9 or 10.

In one embodiment, said transcription factor is NKX2-1 and the ratio of the amount of said Em and said Ad isoform of NKX2-1 is higher than 0.3, at least higher than 0.4, 0.5, 0.6, 0.7, 0.8, 0.9 or preferably higher than 1. More preferably, the ratio of the amount of said Em and said Ad isoform of NKX2-1 is higher than 1.7. Thus, the ratio of the amount of said Em and said Ad isoform of NKX2-1 can be higher than 1.2, 1.4, 1.6, 1.8 or 2; or even higher for example higher than 3, 4, 5, 6, 7, 8, 9 or 10 in order to be indicative for the development/formation of cancer, in particular for lung cancer formation.

In one embodiment, said transcription factor is FOXA2 and the ratio of the amount of said Em and said Ad isoform of FOXA2 is higher than 0.8; at least higher than 0.9, 1.0. 1.1, 1.2, 1.3, 1.4, 1.5, 1.6, 1.7, 1.8, 1.9 or 2; higher than 2.2, 2.4, 2.6, 2.8 or 3; higher than 4, 5, 6, 7, 8, 9, 10 or 15 in order to be indicative for the development/formation of cancer, in particular for lung cancer formation. In one embodiment, said the transcription factor is ID2 and the ratio of the amount of said Em and said Ad isoform of ID2 is higher than 1; at least higher than 1.1, 1.2, 1.3, 1.4, 1.5, 1.6, 1.7, 1.8, 1.9 or 2; higher than 2.2, 2.4, 2.6, 2.8 or 3; higher than 4, 5, 6, 7, 8, 9, 10 or 15 in order to be indicative for the development/formation of cancer, in particular for lung cancer formation.

Threshold values/ratios of the amount of said Em and said Ad isoform of GATA6 indicating that a subject suffers from cancer or is prone to suffering from cancer can be about 0.7 or higher (in particular 1.0 or higher), if control sample(s) is/are healthy tissue(s) (obtained preferably in this context by biopsy) from diseased patients. Threshold values/ratios of the amount of said Em and said Ad isoform of GATA6 indicating that a subject suffers from cancer or is prone to suffering from cancer can be about 0.25 or 0.3 or higher (in particular 1.0 or higher), if control sample(s) is/are healthy tissue(s) (obtained preferably in this context by biopsy) from healthy individuals. For example, ratios of the amount of said Em and said Ad isoform of GATA6 can be about 2.6 (or higher) in samples (in particular and preferred in this context biopsies) from a subject assessed to suffer from cancer or being prone to suffering from cancer in accordance with the present invention.

The herein provided method can be used to stratify/assess subjects according to the tumor/cancer grade. It can be helpful to assess whether a patient is suffering from Grade I, Grade II or Grade III tumor/cancer in order to decide which therapeutic intervention is warranted.

The definition of Grade I, Grade II and Grade III tumor is based on TNM classification recommended by the American Joint Committee on Cancer (Goldstraw P. et al. (2007) J Thorac Oncol. 2(8):706-14; Beadsmoore C J and Screaton N J (2003) Eur J Radiol. 45(1):8-17; Mountain C F (1997) Chest. 111(6):1710-7.), which is incorporated herein by reference.

Ratios of the amount of said Em and said Ad isoform of GATA6 can be about 2.4 (or higher) in samples (in particular and preferred in this context biopsies) from a subject assessed to suffer from Grade I cancer or being prone to suffering from Grade I cancer in accordance with the present invention. Ratios of the amount of said Em and said Ad isoform of GATA6 can be about 3.4 (or higher) in samples (in particular and preferred in this context biopsies) from a subject assessed to suffer from Grade II cancer or being prone to suffering from Grade II cancer in accordance with the present invention. Ratios of the amount of said Em and said Ad isoform of GATA6 can be about 2.8 (or higher) in samples (in particular and preferred in this context biopsies) from a subject assessed to suffer from Grade III cancer or being prone to suffering from Grade III cancer in accordance with the present invention.

Again, preferred herein is lung cancer, in particular non-small cell lung cancer or small cell lung cancer. Particularly preferred is non-small cell lung cancer.

Threshold values/ratios of the amount of said Em and said Ad isoform of GATA6 indicating that a subject suffers from cancer or is prone to suffering from cancer can be about 0.6 or higher (in particular 1.0 or higher), if control sample(s) is/are exhaled breath condensate(s) from healthy individuals. For example, ratios of the amount of said Em and said Ad isoform of GATA6 can be about 1.5 (or higher) in samples (in particular and preferred in this context exhaled breath condensate(s)) from a subject assessed to suffer from cancer or being prone to suffering from cancer in accordance with the present invention.

Also here, lung cancer is preferred, in particular non-small cell lung cancer or small cell lung cancer. Particularly preferred is non-small cell lung cancer.

Threshold values/ratios of the amount of said Em and said Ad isoform of NKX2-1 indicating that a subject suffers from cancer or is prone to suffering from cancer can be about 0.5 or higher (in particular 1.0 or higher), if control sample(s) is/are healthy tissue(s) (obtained preferably in this context by biopsy) from diseased patients. Threshold values/ratios of the amount of said Em and said Ad isoform of NKX2-1 indicating that a subject suffers from cancer or is prone to suffering from cancer can be about 0.2 or 0.3 or higher (in particular 1.0 or higher), if control sample(s) is/are healthy tissue(s) (obtained preferably in this context by biopsy) from healthy individuals. For example, ratios of the amount of said Em and said Ad isoform of NKX2-1 can be about 2.0 (or higher) in samples (in particular and preferred in this context biopsies) from a subject assessed to suffer from cancer or being prone to suffering from cancer in accordance with the present invention.

The herein provided method can be used to stratify/assess subjects according to the tumor/cancer grade. It can be helpful to assess whether a patient is suffering from Grade I, Grade II or Grade III tumor/cancer in order to decide which therapeutic intervention is warranted.

Ratios of the amount of said Em and said Ad isoform of NKX2-1 can be about 1.9 (or higher) in samples (in particular and preferred in this context biopsies) from a subject assessed to suffer from Grade I cancer or being prone to suffering from Grade I cancer in accordance with the present invention. Ratios of the amount of said Em and said Ad isoform of NKX2-1 can be about 2.6 (or higher) in samples (in particular and preferred in this context biopsies) from a subject assessed to suffer from Grade II cancer or being prone to suffering from Grade II cancer in accordance with the present invention. Ratios of the amount of said Em and said Ad isoform of NKX2-1 can be about 3.8 (or higher) in samples (in particular and preferred in this context biopsies) from a subject assessed to suffer from Grade III cancer or being prone to suffering from Grade III cancer in accordance with the present invention.

Again, preferred herein is lung cancer, in particular non-small cell lung cancer or small cell lung cancer. Particularly preferred is non-small cell lung cancer.

Threshold values/ratios of the amount of said Em and said Ad isoform of NKX2-1 indicating that a subject suffers from cancer or is prone to suffering from cancer can be about 0.5 or higher (in particular 1.0 or higher), if control sample(s) is/are exhaled breath condensate(s) from healthy individuals. For example, ratios of the amount of said Em and said Ad isoform of NKX2-1 can be about 2.8 (or higher) in samples (in particular and preferred in this context exhaled breath condensate(s)) from a subject assessed to suffer from cancer or being prone to suffering from cancer in accordance with the present invention.

Also here, lung cancer is preferred, in particular non-small cell lung cancer or small cell lung cancer. Particularly preferred is non-small cell lung cancer.

The appended examples demonstrate that the herein provided methods can be reliably used for assessing whether a subject suffers from cancer, preferably lung cancer, such as non-small cell lung cancer or small cell lung cancer. Though most of the data provided herein relate to non-small cell lung cancer, FIG. 13B and Example 10 demonstrate that the herein provided methods allow also for a reliable assessment whether a subject suffers from small cell lung cancer.

For example, the small cell lung cancer sample assessed herein showed the following ratios:

Em/Ad for Gata6—Biopsy—2.9743;
Em/Ad for Gata6 EBC—3.12
Em/Ad for Nkx2.1—Biopsy—3.544;
Em/Ad for Nkx2.1 EBC—3.584

Thus, ratios of the amount of said Em and said Ad isoform of GATA6 of 1.0 or higher and/or ratios of the amount of said Em and said Ad isoform of NKX2-1 of 1.0 or higher indicate that a subject suffers from small cell lung cancer or is prone to suffering from small cell lung cancer sample.

For example, ratios of the amount of said Em and said Ad isoform of GATA6 can be about 3.0 (or higher) in samples (in particular and preferred in this context biopsies) from a subject assessed to suffer from small cell lung cancer or being prone to suffering from small cell lung cancer in accordance with the present invention.

For example, ratios of the amount of said Em and said Ad isoform of GATA6 can be about 3.1 (or higher) in samples (in particular and preferred in this context exhaled breath condensate(s)) from a subject assessed to suffer from small cell lung cancer or being prone to suffering from small cell lung cancer in accordance with the present invention.

For example, ratios of the amount of said Em and said Ad isoform of NKX2-1 can be about 3.5 (or higher) in samples (in particular and preferred in this context biopsies) from a subject assessed to suffer from small cell lung cancer or being prone to suffering from small cell lung cancer in accordance with the present invention.

For example, ratios of the amount of said Em and said Ad isoform of NKX2-1 can be about 3.6 (or higher) in samples (in particular and preferred in this context exhaled breath condensate(s)) from a subject assessed to suffer from small cell lung cancer or being prone to suffering from small cell lung cancer in accordance with the present invention.

As explained above, the ratio of the amount of said Em and said Ad isoform of GATA6 and/or the ratio of the amount of said Em and said Ad isoform of NKX2-1 is increased in samples from patients assessed to suffer from or assessed as being prone to suffering from cancer compared with a control (sample).

The present invention relates to a method of assessing whether a subject suffers from cancer or is prone to suffering from cancer, said method comprising the steps of a) measuring in a sample of said subject the amount of two specific isoforms of a transcription factor, wherein said transcription factor is either GATA6 or NKX2-1 and wherein the two specific isoforms are either
   i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; and the GATA6 Ad isoform comprising the nucleic acid sequence of SEQ ID No: 5 or the GATA6 Ad isoform comprising a nucleic acid sequence with up to 55 additions, deletions or substitutions of SEQ ID NO: 5; or
   ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2; and the NKX2-1 Ad isoform comprising the nucleic acid sequence of SEQ ID No: 6 or the NKX2-1 Ad isoform comprising a nucleic acid sequence with up to 38 additions, deletions or substitutions of SEQ ID NO: 6;
b) building the ratio of the amount of said Em and said Ad isoform of said transcription factor; and
c) assessing that said subject suffers from cancer or is prone to suffering from cancer if
   i) the transcription factor is GATA6 and the ratio of the amount of said Em and said Ad isoform of GATA6 is increased in comparison to a control (sample); or
   ii) the transcription factor is NKX2-1 and the ratio of the amount of said Em and said Ad isoform of NKX2-1 is increased in comparison to a control (sample).

The present invention relates to a method of assessing whether a subject suffers from cancer or is prone to suffering from cancer, said method comprising the steps of a) measuring in a sample of said subject the amount of two specific isoforms of a transcription factor, wherein said transcription factors are GATA6 and NKX2-1 and wherein the two specific isoforms are
   i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; and the GATA6 Ad isoform comprising the nucleic acid sequence of SEQ ID No: 5 or the GATA6 Ad isoform comprising a nucleic acid sequence with up to 55 additions, deletions or substitutions of SEQ ID NO: 5; and
   ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2; and the NKX2-1 Ad isoform comprising the nucleic acid sequence of SEQ ID No: 6 or the NKX2-1 Ad isoform comprising a nucleic acid sequence with up to 38 additions, deletions or substitutions of SEQ ID NO: 6;
b) building the ratio of the amount of said Em and said Ad isoform of said transcription factor; and
c) assessing that said subject suffers from cancer or is prone to suffering from cancer if
   i) the transcription factor is GATA6 and the ratio of the amount of said Em and said Ad isoform of GATA6 is increased in comparison to a control (sample); and
   ii) the transcription factor is NKX2-1 and the ratio of the amount of said Em and said Ad isoform of NKX2-1 is increased in comparison to a control (sample).

Also here, lung cancer is preferred, in particular non-small cell lung cancer or small cell lung cancer. Particularly preferred is non-small cell lung cancer.

The definitions and explanations provided herein in relation to the method of "assessing whether a subject suffers from cancer or is prone to suffering from cancer" apply, mutatis mutandis, in this context.

The term "specific transcription factor Ad isoform" according to the present application relates to specific isoforms of the transcription factors GATA6 (Uniprot-ID: Q92908; Gene-ID: 2627), NKX2-1 (Uniprot-ID: P43699; Gene-ID: 7080), FOXA2 (Uniprot-ID: Q9Y261; Gene-ID: 3170) and ID2 (Uniprot-ID: Q02363; Gene-ID: 3398). If, for example, the amount of a specific transcription factor is measured on mRNA level, the specific transcription factor can be mRNA molecules (or transcript or splice variants). In this context, the transcription factors can be defined as i) the GATA6 Ad isoform comprising the nucleic acid sequence of SEQ ID No: 5 or the GATA6 Ad isoform nucleic acid sequence with up to 55 additions, deletions or substitutions of SEQ ID NO: 5;
ii) the NKX2-1 Ad isoform comprising the nucleic acid sequence of SEQ ID No: 2 or the NKX2-1 Ad isoform comprising the nucleic acid sequence with up to 38 additions, deletions or substitutions of SEQ ID NO: 6;
iii) the FOXA2 Ad isoform comprising the nucleic acid sequence of SEQ ID No: 7 or FOXA2 Ad isoform comprising the nucleic acid sequence with up to 74 additions, deletions or substitutions of SEQ ID NO: 3; or
iv) the ID2 Ad isoform consisting of the nucleic acid sequence of SEQ ID No: 8 or ID2 Ad isoform consisting of nucleic acid sequence with up to 30 additions, deletions or substitutions of SEQ ID NO: 8;

If, for example, the amount of a specific transcription factor is measure on protein level, the specific transcription factors can be proteins molecules. For example, they can be defined as v) the GATA6 Ad isoform comprising the polypeptide sequence of SEQ ID No: 54 or the GATA6 Ad isoform polypeptide sequence with up to 23 additions, deletions or substitutions of SEQ ID NO: 54;
vi) the NKX2-1 Ad isoform comprising the polypeptide sequence of SEQ ID No: 55 or the NKX2-1 Ad isoform comprising the polypeptide sequence with up to 15 additions, deletions or substitutions of SEQ ID NO: 55;
vii) the FOXA2 Ad isoform comprising the polypeptide sequence of SEQ ID No: 56 or FOXA2 Ad isoform comprising the polypeptide sequence with up to 43 additions, deletions or substitutions of SEQ ID NO: 56; or
viii) the ID2 Ad isoform consisting of the polypeptide sequence of SEQ ID No: 57 or ID2 Ad isoform consisting of polypeptide sequence with up to 13 additions, deletions or substitutions of SEQ ID NO: 57;

The present invention relates to a method of assessing whether a subject suffers from cancer or is prone to suffering from cancer, said method comprising the steps of a) measuring in a sample of said subject the amount of two specific isoforms of a transcription factor, wherein said transcription factor is either GATA6 or NKX2-1 and wherein the two specific isoforms are either:
   i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; and the GATA6 Ad isoform comprising the nucleic acid sequence of SEQ ID No: 5 or the GATA6 Ad isoform nucleic acid sequence with up to 55 additions, deletions or substitutions of SEQ ID NO: 5; or
   ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2; and the NKX2-1 Ad isoform comprising the nucleic acid sequence of SEQ ID No: 6 or the NKX2-1 Ad isoform comprising a nucleic acid sequence with up to 38 additions, deletions or substitutions of SEQ ID NO: 6;
b) building the ratio of the amount of said Em and said Ad isoform of said transcription factor
c) assessing that said subject suffers from cancer or is prone to suffering from cancer if
   i) the transcription factor is GATA6 and the ratio of the amount of said Em and said Ad isoform of GATA6 is higher than 0.5; preferably higher than 0.6, 0.7, 0.8, 0.9 or 1; more preferably higher than 1.2, 1.4, 1.6, 1.8 or 2; even more preferably higher than 3, 4, 5, 6, 7, 8, 9 or 10;
   ii) the transcription factor is NKX2-1 and the ratio of the amount of said Em and said Ad isoform of NKX2-1 is higher than 0.3 preferably higher than 0.4, 0.5, 0.6, 0.7, 0.8, 0.9 or 1; more preferably higher than 1.2, 1.4, 1.6, 1.8 or 2; even more preferably higher than 3, 4, 5, 6, 7, 8, 9 or 10;

The present invention relates to a method of assessing whether a subject suffers from cancer or is prone to suffering from cancer, said method comprising the steps of a) measuring in a sample of said subject the amount of two specific isoforms of a transcription factor, wherein the transcription factor is selected from the group GATA6, NKX2-1, FOXA2 and ID2, and wherein the two specific isoforms are either:
   i) the GATA6 Em isoform comprising the nucleic acid sequence of SEQ ID No: 1 or the GATA6 Em isoform comprising the nucleic acid sequence with up to 55 additions, deletions or substitutions of SEQ ID NO: 1; and the GATA6 Ad isoform comprising the nucleic acid sequence of SEQ ID No: 5 or the GATA6 Ad isoform nucleic acid sequence with up to 55 additions, deletions or substitutions of SEQ ID NO: 5;
   ii) the NKX2-1 Em isoform comprising the nucleic acid sequence of SEQ ID No: 2 or the NKX2-1 Em isoform comprising the nucleic acid sequence with up to 39 additions, deletions or substitutions of SEQ ID NO: 2; and the NKX2-1 Ad isoform comprising the nucleic acid sequence of SEQ ID No: 2 or the NKX2-1 Ad isoform comprising the nucleic acid sequence with up to 38 additions, deletions or substitutions of SEQ ID NO: 6;
   iii) the FOXA2 Em isoform comprising the nucleic acid sequence of SEQ ID No: 3 or the FOXA2 Em isoform comprising the nucleic acid sequence with up to 68 additions, deletions or substitutions of SEQ ID NO: 3; and the FOXA2 Ad isoform comprising the nucleic acid sequence of SEQ ID No: 7 or FOXA2 Ad isoform comprising the nucleic acid sequence with up to 74 additions, deletions or substitutions of SEQ ID NO: 3; or
   iv) the ID2 Em isoform comprising the nucleic acid sequence of SEQ ID No: 4 or the ID2 Em isoform comprising the nucleic acid sequence with up to 34 additions, deletions or substitutions of SEQ ID NO: 4; and the ID2 Ad isoform consisting of the nucleic acid sequence of SEQ ID No: 8 or ID2 Ad isoform consisting of nucleic acid sequence with up to 30 additions, deletions or substitutions of SEQ ID NO: 8;
b) building the ratio of the amount of said Em and said Ad isoform of said transcription factor
c) assessing that said subject suffers from cancer or is prone to suffering from cancer if
   i) the transcription factor is GATA6 and the ratio of the amount of said Em and said Ad isoform of GATA6 is higher than 0.5; preferably higher than 0.6, 0.7, 0.8, 0.9 or 1; higher than 1.2, 1.4, 1.6, 1.8 or 2; higher than 3, 4, 5, 6, 7, 8, 9 or 10;
   ii) the transcription factor is NKX2-1 and the ratio of the amount of said Em and said Ad isoform of NKX2-1 is higher than 0.3, preferably higher than 0.4, 0.5, 0.6, 0.7, 0.8, 0.9 or 1; higher than 1.2, 1.4, 1.6, 1.8 or 2; higher than 3, 4, 5, 6, 7, 8, 9 or 10;
   iii) the transcription factor is FOXA2 and the ratio of the amount of said Em and said Ad isoform of FOXA2 is higher than 0.8; preferably higher than 0.9, 1.0. 1.1, 1.2, 1.3, 1.4, 1.5, 1.6, 1.7, 1.8, 1.9 or 2; higher than 2.2, 2.4, 2.6, 2.8 or 3; higher than 4, 5, 6, 7, 8, 9, 10 or 15; or
   iv) the transcription factor is ID2 and the ratio of the amount of said Em and said Ad isoform of ID2 is higher than 1; preferably higher than 1.1, 1.2, 1.3, 1.4, 1.5, 1.6, 1.7, 1.8, 1.9 or 2; higher than 2.2, 2.4, 2.6, 2.8 or 3; higher than 4, 5, 6, 7, 8, 9, 10 or 15.

It is known by the person skilled in the art that genes can contain single nucleotide polymorphisms. The specific transcription factor Em isoform sequences of the present invention encompass all naturally occurring sequences of the respective isoform independent of the number and nature of the SNPs in said sequence. To relate to currently known SNPs, the specific transcription factor Ad isoform sequences of the present invention are defined such that they contain up to 55 (in the case of GATA6), up to 38 (in the case of NKX2-1), up to 74 (in the case of FOXA2) or up to 30 (in the case of ID2) additions, deletions or substitutions of the nucleic acid sequences defined by SEQ ID NOs: 5, 6, 7 and 8, respectively, to also cover the respective Ad transcripts of carriers of different nucleotides at the respective SNPs. The SNPs of tables 2, 4, 6 and 8 may occur in the Ad isoforms of the present invention in any combination. For example, a (genetic) variant of the GATA6 Ad isoform to be used herein may comprise a nucleic acid sequence of SEQ ID NO:5, whereby the "C" residue at position 694 of SEQ ID NO:5 is substituted by "T". Further variants of the isoforms to be used herein are apparent from Tables 1 to 8 to the person skilled in the art.

The GATA6 Ad isoform according to the invention is the GATA6 Ad isoform comprising the nucleic acid sequence of SEQ ID NO: 5 or the GATA6 Ad isoform comprising a nucleic acid sequence with up to 55; preferably up to 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21 or 20; even more preferably up to 19, 18, 17, 16, 15, 14, 13, 12, 11, 10, 9, 8, 7. 6, 5, 4, 3 or 2; or even furthermore preferably only 1 addition(s), deletion(s) or substitution(s) of SEQ ID NO: 5. The GATA6 Ad isoform can also be defined as the GATA6 Ad isoform comprising the nucleic acid sequence of SEQ ID NO: 5 or the GATA6 Ad isoform comprising the nucleic acid sequence of SEQ ID NO: 5 with additions, deletions or substitutions at any of positions 138; 228; 255; 262; 274; 365; 397; 415; 694; 1063; 1191; 1239; 1524; 1532; 1562; 1586; 1587; 1738; 1779; 1784; 1814; 1817; 1846; 1875; 1884; 1917; 1935; 1937; 1943; 1961; 1966; 2041; 2072; 2077; 2098; 2229; 2325; 2326; 2562; 2626; 2971; 3037; 3175; 3200; 3201; 3225; 3293; 3301; 3513; 3567; 3581; 3605; 3625; 3643 or 3670. The GATA6 Ad isoform according to the invention can also be defined as the GATA6 Ad isoform comprising the nucleic acid sequence of SEQ ID No: 5 or the GATA6 Ad isoform comprising a nucleic acid sequence with at least 85% homology to SEQ ID No: 5, preferably up to 86%, 87%, 88%, 89%, 90%, 91%, 92%, 93%, 94%, 95%, 96%, 97% or 98% homology to SEQ ID No: 5; even more preferably up to 99% homology to SEQ ID No: 5.

The NKX2-1 Ad isoform according to the invention is the NKX2-1 Ad isoform comprising the nucleic acid sequence of SEQ ID NO: 6 or the NKX2-1 Ad isoform comprising a nucleic acid sequence with up to 38; preferably up to 37, 36, 35, 34, 33, 32, 31, 30, 29, 28, 27, 26, 25, 24, 23, 22, 21, 20, 19, 18, 17, 16, 15, 14, 13, 12, 11, or 10; even more preferably up to 9, 8, 7, 6, 5, 4, 3, or 2; or even furthermore preferably only 1 addition(s), deletion(s) or substitution(s) of SEQ ID NO: 6. The NKX2-1 Ad isoform can also be defined as the NKX2-1 Ad isoform comprising the nucleic acid sequence of SEQ ID NO: 6 or the Nkx2-1 isoform Ad comprising the nucleic acid sequence of SEQ ID NO: 6 with additions, deletions or substitutions at any of positions 12; 125; 265; 270; 284; 286; 295; 331; 626; 630; 670; 795; 1014; 1150; 1189; 1293; 1303; 1312; 1334; 1397; 1478; 1479; 1478; 1485; 1486; 1488; 1512; 1518; 1523; 1593; 1595; 1676; 1738; 1761; 1762; 1779; 1944 or 2164. The NKX2-1 Ad isoform according to the invention can also be defined as the NKX2-1 Ad isoform comprising the nucleic acid sequence of SEQ ID No: 6 or the NKX2-1 Ad isoform comprising a nucleic acid sequence with at least 90% homology to SEQ ID No: 6, preferably up to 91%, 92%, 93%, 94%, 95%, 96%, 97% or 98% homology to SEQ ID No: 6; even more preferably up to 99% homology to SEQ ID No: 6.

The FOXA2 Ad isoform according to the invention is the FOXA2 Ad isoform comprising the nucleic acid sequence of SEQ ID NO: 7 or the FOXA2 Ad isoform comprising a nucleic acid sequence with up to 74; preferably up to 73, 72, 71, 70, 69, 68, 67, 66, 65, 64, 63, 62, 61, 60, 59, 58, 57, 56, 55, 54, 53 52, 51, 50, 49, 48 47, 46, 45, 44, 43, 42, 41, 40, 39, 38, 37, 36, 35, 34, 33, 32, 31, 30, 29, 28, 27, 26, 25, 24, 23, 22, 21 or 20; even more preferably up to 19, 18, 17, 16, 15, 14, 13, 12, 11, 10, 9, 8, 7. 6, 5, 4, 3 or 2; or even furthermore preferably only 1 addition(s), deletion(s) or substitution(s) of SEQ ID NO: 7. The FOXA2 Ad isoform can also be defined as the FOXA2 Ad isoform comprising the nucleic acid sequence of SEQ ID NO: 7 or the FOXA2 Ad isoform comprising the nucleic acid sequence of SEQ ID NO: 7 with additions, deletions or substitutions at any of positions 5; 37; 65; 68; 70; 88; 128; 195; 276; 348; 355; 361; 366; 370; 391; 446; 468; 470; 481; 516; 551; 564; 571; 577; 597; 610; 628; 637; 646; 661; 760; 832; 1027; 1062; 1173; 1175; 1227; 1229; 1230; 1291; 1361; 1378; 1395; 1401; 1419; 1445; 1462; 1474; 1509; 1526; 1569; 1570; 1581; 1614; 1618; 1674; 1710; 1724; 1725; 1741; 1799; 1818; 1825; 1927; 1953; 1957; 2057; 2070; 2071; 2080; 2092; 2099; 2187 or 2375. The FOXA2 Ad isoform according to the invention can also be defined as the FOXA2 Ad isoform comprising the nucleic acid sequence of SEQ ID No: 7 or the FOXA2 Ad isoform comprising a nucleic acid sequence with at least 93% homology to SEQ ID No: 7, preferably up to 92%, 93%, 94%, 95%, 96%, 97% or 98% homology to SEQ ID No: 7; even more preferably up to 99% homology to SEQ ID No: 7.

The ID2 Ad isoform according to the invention is the ID2 Ad isoform consisting the nucleic acid sequence of SEQ ID NO: 8 or the ID2 Ad isoform consisting of a nucleic acid sequence with up to 30; preferably up to 29, 28, 27, 26, 25, 24, 23, 22, 21, 20, 19, 18, 17, 16, 15, 14, 13, 12, 11, or 10; even more preferably up to 9, 8, 7, 6, 5, 4, 3, or 2; or even furthermore preferably only 1 addition(s), deletion(s) or substitution(s) of SEQ ID NO: 8. The ID2 Ad isoform can also be defined as the ID2 Ad isoform consisting the nucleic acid sequence of SEQ ID NO: 8 or the ID2 Ad isoform consisting the nucleic acid sequence of SEQ ID NO: 8 with additions, deletions or substitutions at any of positions 93; 134; 148; 163; 176; 202; 225; 299; 338; 344; 424; 440; 483; 486; 544; 601; 604; 655; 696; 810; 815; 914; 1024; 1054; 1058; 1088; 1090; 1190; 1272 or 1289. The ID2 Ad isoform according to the invention can also be defined as the ID2 Ad isoform comprising the nucleic acid sequence of SEQ ID No: 8 or the ID2 Ad isoform comprising a nucleic acid sequence with at least 51% homology to SEQ ID No: 8, preferably up to 55%, 60%, 65%, 70%, 75%, 80%, 85% or 90% homology to SEQ ID No: 8; even more preferably up to 91%, 92%, 93%, 94%, 95%, 96%, 97%, 98% or 99% homology to SEQ ID No: 8.

The present invention relates to a method of treating a patient, said method comprising a) selecting a cancer patient according to any of the above mentioned methods of assessing whether a subject suffers from cancer or is prone to suffering from cancer
b) administering to said cancer patient an effective amount of an anti-cancer agent.

The term "cancer patient" as used herein refers to a patient that is suspected to suffer from cancer or being prone to suffer from cancer. The cancer to be treated in accordance with the present invention can be a solid cancer or a liquid cancer. Non-limiting examples of cancers which can be treated according to the present invention are lung cancer, ovarian cancer, colorectal cancer, kidney cancer, bone cancer, bone marrow cancer, bladder cancer, prostate cancer, esophagus cancer, salivary gland cancer, pancreas cancer, liver cancer, head and neck cancer, CNS (especially brain) cancer, cervix cancer, cartilage cancer, colon cancer, genitourinary cancer, gastrointestinal tract cancer, pancreas cancer, synovium cancer, testis cancer, thymus cancer, thyroid cancer and uterine cancer.

Preferably, the cancer patient according to the present invention is a patient suffering from lung cancer, such as non-small cell lung cancer (NSCLC) or small cell lung cancer (SLC). Particularly preferably, the patient suffers non-small cell lung cancer (NSCLC). Even more preferably, the cancer patient is a patient suffering from adenocarcinoma. The patient may also suffer from a squamous cell carcinoma or a large ell carcinoma. The adenocarcinoma can be a bronchoalveolar carcinoma.

The amount of the specific transcription factor isoform according to the invention can be measured for example by a polymerase chain reaction-based method, an in situ hybridization-based method, or a microarray. If the amount of the specific transcription factor isoform according to the invention is measured via a polymerase chain reaction-based method, it is preferably measured via a quantitative reverse transcriptase polymerase chain reaction.

The method of assessing whether a subject suffers from cancer or is prone to suffering from cancer according to the invention may comprise the contacting of a sample with primers, wherein said primers can be used for amplifying the respective specific transcription factor isoforms.

Primers for the polymerase chain reaction-based measurement of the amount of the specific transcription factor isoforms according to the invention may encompass the use of primers being selected from the Table 9.

TABLE 9

Examples of primer pairs for the amplification, detection and/or quantification of the amount of specific transcription factor isoforms

| Gene | Primers for Human (5'→3') | Primers for Human (5'→3') (For RNA from tissue sections) |
|---|---|---|
| Gata6-Em Fwd | SEQ ID NO 9: CTCGGCTTCTCTCCGCGCCTG | SEQ ID NO 10: TTGACTGACGGCGGCTGGTG |
| Gata6-Em Rev | SEQ ID NO 11: AGCTGAGGCGTCCCGCAGTTG | SEQ ID NO 12: CTCCCGCGCTGGAAAGGCTC |
| Gata6-Ad Fwd | SEQ ID NO 13: GCGGTTTCGTTTTCGGGGAC | SEQ ID NO 14: AGGACCCAGACTGCTGCCCC |
| Gata6-Ad Rev | SEQ ID NO 15: AAGGGATGCGAAGCGTAGGA | SEQ ID NO 16: CTGACCAGCCCGAACGCGAG |
| Nkx2-1-Em Fwd | SEQ ID NO 17: AAACCTGGCGCCGGGCTAAA | SEQ ID NO 18: CAGCGAGGCTTCGCCTTCCC |
| Nkx2-1-Em Rev | SEQ ID NO 19: GGAGAGGGGGAAGGCGAAGCC | SEQ ID NO 20: TCGACATGATTCGGCGGCGG |
| Nkx2-1-Ad Fwd | SEQ ID NO 21: AGCGAAGCCCGATGTGGTCC | SEQ ID NO 22: TCCGGAGGCAGTGGGAAGGC |
| Nk2-1-Ad Rev | SEQ ID NO 23: CCGCCCTCCATGCCCACTTTC | SEQ ID NO 24: GACATGATTCGGCGGCGGCT |
| Foxa2-Var1 Fwd | SEQ ID NO 25: TGCCATGCACTCGGCTTCCAG | SEQ ID NO 26: CAGGGAGAGGGAGGGCGAGA |
| Foxa2-Var1 Rev | SEQ ID NO 27: TCATGTTGCCCGAGCCGCTG | SEQ ID NO 28: CCCCCACCCCCACCCTCTTT |
| Foxa2-Var2 Fwd | SEQ ID NO 29: CTGCTAGAGGGGCTGCTTGCG | SEQ ID NO 30: CGCTTCTCCCGAGGCCGTTC |
| Foxa2-Var2 Rev | SEQ ID NO 31: ACGGCTCGTGCCCTTCCATC | SEQ ID NO 32: TAACTCGCCCGCTGCTGCTC |
| Id2-Var1 Fwd | SEQ ID NO 33: AACCCCTGTGGACGACCCGA | SEQ ID NO 34: TGCGGATAAAAGCCGCCCCG |
| Id2-Var1 Rev | SEQ ID NO 35 GCCCGGGTCTCTGGTGATGC | SEQ ID NO 36: AGCTAGCTGCGCTTGGCACC |
| Id2-Var2 Fwd | SEQ ID NO 37: CTGCGGTGCTGAACTCGCCC | SEQ ID NO 38: CCCCCTGCGGTGCTGAACTC |
| Id2-Var 2 Rev | SEQ ID NO 39: GACGAGCGGGCGCTTCCATT | SEQ ID NO 40: TAACTCGCCCGCTGCTGCTC |

It lies within the scope of the invention to combine the measurement of several of the specific transcription factor Em isoforms of the present invention to allow assessing whether a subject suffers from cancer or is prone to suffering from cancer. In particular, the amount of two, three or up to all four of the specific transcription factor Em isoforms selected from i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; ii) the NKX2-1 Em isoform comprising the nucleic acid sequence of SEQ ID No: 2 or the NKX2-1 Em isoform comprising the nucleic acid sequence with up to 39 additions, deletions or substitutions of SEQ ID NO: 2; iii) the FOXA2 Em isoform comprising the nucleic acid sequence of SEQ ID No: 3 or the FOXA2 Em isoform comprising nucleic acid sequence with up to 68 additions, deletions or substitutions of 3E0 ID NO: 3; and iv) the ID2 Em isoform comprising the nucleic acid sequence of SEQ ID No: 4 or the ID2 Em isoform comprising nucleic acid sequence with up to 34 additions, deletions or substitutions of SEQ ID NO: 4 may be analyzed for assessing whether a subject suffers from cancer or is prone to suffering from cancer. Preferably, a combination of transcription factor Em isoforms analyzed for the assessment of whether a subject suffers from cancer or is prone to suffering from cancer according to the present invention includes the GATA6 Em isoform and the NKX2-1 Em isoform.

The method for assessing whether a subject suffers from cancer or is prone to suffering from cancer according to the present invention can be used for example for assessing whether a subject suffers from lung cancer or is prone to suffering from lung cancer. In particular, the method of the present invention allows assessing whether a subject suffers from adenocarcinoma or bronchoalveolar carcinoma or is prone to suffering from adenocarcinoma or bronchoalveolar carcinoma.

The diagnostic methods can be used, for example, in combination with (i.e. subsequently prior to or simultaneously with) other diagnostic techniques, like CT (short for computer tomography) and CXR (short for chest radiograph, colloquially called chest X-ray (CXR)).

The herein provided methods for the diagnosis of a patient group and the therapy of this selected patient group is particularly useful for high risk subjects/patients or patient groups, such as those that have a hereditary history and/or are exposed to tobacco smoke, environmental smoke, cooking fumes, indoor smoky coal emissions, asbestos, some metals (e.g. nickel, arsenic and cadmium), radon (particularly amongst miners) and ionizing radiation. These subjects/patients may particularly profit from an early diagnosis and, hence, treatment of the cancer in accordance with the present invention.

A method of treating a patient according to the present invention may comprise a) obtaining a sample from a patient;

b) selecting a cancer patient according to any of the above mentioned methods of assessing whether a subject suffers from cancer or is prone to suffering from cancer;

c) administering to said cancer patient an effective amount of an anti-cancer agent.

The present invention also provides a method of treating a patient, said method comprising a) selecting a cancer patient according to any of the above mentioned methods of assessing whether a subject suffers from cancer or is prone to suffering from cancer b) administering to said cancer patient an effective amount of an anti-cancer agent, wherein the cancer agent is for example selected from the group of agents comprising Oxalaplatin, Gemcitabine (Gemzar), Paclitaxel (Taxol), Vincristine (Oncovin) and a composition for use in medicine comprising an inhibitor of i) the GATA6 Em isoform comprising the nucleic acid sequence of SEQ ID No: 1 or the GATA6 Em isoform comprising the nucleic acid sequence with up to 55 additions, deletions or substitutions of SEQ ID NO: 1;

ii) the NKX2-1 Em isoform comprising the nucleic acid sequence of SEQ ID No:

2 or the NKX2-1 Em isoform comprising the nucleic acid sequence with up to 39 additions, deletions or substitutions of SEQ ID NO: 2.

iii) the FOXA2 Em isoform comprising the nucleic acid sequence of SEQ ID No: 3 or the FOXA2 Em isoform comprising nucleic acid sequence with up to 68 additions, deletions or substitutions of SEQ ID NO: 3; and/or iv) the ID2 Em isoform comprising the nucleic acid sequence of SEQ ID No: 4 or the ID2 Em isoform comprising nucleic acid sequence with up to 34 additions, deletions or substitutions of SEQ ID NO: 4.

The present invention relates to a pharmaceutical composition comprising an agent for the treatment or the prevention of cancer, wherein for the patient suffering from cancer has been determined by a method of the present invention and wherein the method of treatment comprises the step of determining whether or not the patient suffers from cancer. Preferably, the pharmaceutical composition according to the present invention comprises an agent for the treatment or the prevention of lung cancer, wherein for the patient lung cancer has been determined by a method of the present invention and wherein the method of treatment comprises the step of determining whether or not the patient suffers from lung cancer The present invention provides a composition for use in medicine comprising an inhibitor of i) the GATA6 Em isoform comprising the nucleic acid sequence of SEQ ID No: 1 or the GATA6 Em isoform comprising the nucleic acid sequence with up to 55 additions, deletions or substitutions of SEQ ID NO: 1;

ii) the NKX2-1 Em isoform comprising the nucleic acid sequence of SEQ ID No: 2 or the NKX2-1 Em isoform comprising the nucleic acid sequence with up to 39 additions, deletions or substitutions of SEQ ID NO: 2.

iii) the FOXA2 Em isoform comprising the nucleic acid sequence of SEQ ID No: 3 or the FOXA2 Em isoform comprising nucleic acid sequence with up to 68 additions, deletions or substitutions of SEQ ID NO: 3; or iv) the ID2 Em isoform comprising the nucleic acid sequence of SEQ ID No: 4 or the ID2 Em isoform comprising nucleic acid sequence with up to 34 additions, deletions or substitutions of SEQ ID NO: 4.

It is surprisingly found that the Em isoforms of the transcription factors of the present invention have an oncogenic potential (see Examples 4, 6 and 7). Further, it is shown that their reduction leads to the prevention of the development of tumors and allows treating cancer (see example 7). Thus, the present invention relates to inhibitors of the Em isoforms of the transcription factors GATA6, NKX2-1, FOXA2 and ID2. In particular, the present invention relates to agents that allow reducing the amount of the Em isoform of the transcription factors GATA6, NKX2-1, FOXA2 and ID2. The present invention also relates to activators of the Ad isoform of the transcription factors GATA6, NKX2-1, FOXA2 and ID2. Examples of such activators are agents, which activate the promoter of the Ad isoform of the respective transcription factors.

The present invention also relates to a composition for use in medicine comprising an inhibitor of i) the GATA6 Em isoform comprising the nucleic acid sequence of SEQ ID No: 1 or the GATA6 Em isoform comprising the nucleic acid sequence with up to 55 additions, deletions or substitutions of SEQ ID NO: 1;

ii) the NKX2-1 Em isoform comprising the nucleic acid sequence of SEQ ID No: 2 or the NKX2-1 Em isoform comprising the nucleic acid sequence with up to 39 additions, deletions or substitutions of SEQ ID NO: 2.

iii) the FOXA2 Em isoform comprising the nucleic acid sequence of SEQ ID No: 3 or the FOXA2 Em isoform comprising nucleic acid sequence with up to 68 additions, deletions or substitutions of SEQ ID NO: 3; and/or iv) the ID2 Em isoform comprising the nucleic acid sequence of SEQ ID No: 4 or the ID2 Em isoform comprising nucleic acid sequence with up to 34 additions, deletions or substitutions of SEQ ID NO: 4.

The inhibitors of i) the GATA6 Em isoform comprising the nucleic acid sequence of SEQ ID No: 1 or the GATA6 Em isoform comprising the nucleic acid sequence with up to 55 additions, deletions or substitutions of SEQ ID NO: 1;

ii) the NKX2-1 Em isoform comprising the nucleic acid sequence of SEQ ID No: 2 or the NKX2-1 Em isoform comprising the nucleic acid sequence with up to 39 additions, deletions or substitutions of SEQ ID NO: 2.

iii) the FOXA2 Em isoform comprising the nucleic acid sequence of SEQ ID No: 3 or the FOXA2 Em isoform comprising nucleic acid sequence with up to 68 additions, deletions or substitutions of SEQ ID NO: 3; or iv) the ID2 Em isoform comprising the nucleic acid sequence of SEQ ID No: 4 or the ID2 Em isoform comprising nucleic acid sequence with up to 34 additions, deletions or substitutions of SEQ ID NO: 4 according to the present invention can for example comprise siRNAs (small interfering RNAs) or shRNAs (small hairpin RNAs) targeting said specific transcription factor Em isoforms.

The person skilled in the art knows how to design siRNAs and shRNAs, which specifically target the specific transcription factor Em isoforms of the present invention. Examples of such specific siRNAs and shRNAs targeting the specific transcription factor Em isoforms of the present invention are depicted in Tables 10 and 11.

i) the GATA6 Em isoform comprising the polypeptide sequence of SEQ ID No: 50 or the GATA6 Em isoform comprising the polypeptide sequence with up to 30 additions, deletions or substitutions of SEQ ID NO: 50; or ii) the NKX2-1 Em isoform comprising the polypeptide sequence of SEQ ID No: 51 or the NKX2-1 Em isoform comprising the polypeptide sequence with up to 14 additions, deletions or substitutions of SEQ ID NO: 51;

b) comparing the amount of said specific transcription factor Em isoform with the amount of said specific transcription factor Em isoform in a control sample; and c) assessing that said subject suffers from cancer or is prone to suffering from cancer if the amount of said specific transcription factor Em isoform in said sample from said subject is increased in comparison to the amount of said specific transcription factor Em isoform in the control sample.

The invention relates to a method of assessing whether a subject suffers from cancer or is prone to suffering from cancer, said method comprising the steps of a) measuring in a sample of said subject the amount of two specific isoforms of a transcription factor on the polypeptide level, wherein said transcription factor is either GATA6 or NKX2-1 and wherein the two specific isoforms are either i) the GATA6 Em isoform comprising the polypeptide sequence of SEQ ID No: 50 or the GATA6 Em isoform comprising the polypeptide sequence with up to 30 additions, deletions or substitutions of SEQ ID NO: 50; and the GATA6 Ad isoform comprising the polypeptide sequence of SEQ ID No: 54 or the GATA6 Ad isoform polypeptide sequence with up to 23 additions, deletions or substitutions of SEQ ID NO: 54; or ii) the NKX2-1 Em isoform comprising the polypeptide sequence of SEQ ID No: 51 or the NKX2-1 Em isoform comprising the polypeptide sequence with up to 14 additions, deletions or substitutions of SEQ ID NO: 51; and the NKX2-1 Ad isoform comprising the polypeptide sequence of SEQ ID No: 55 or the NKX2-1 Ad isoform comprising the polypeptide sequence with up to 15 additions, deletions or substitutions of SEQ ID NO: 55;

b) building the ratio of the amount of said Em and said Ad isoform of said transcription factor; and c) assessing that said subject suffers from cancer or is prone to suffering from cancer if

TABLE 10

Examples of siRNA sequences for the knockdown of Gata6 Em and Foxa2 Em

| Target Sequence | Sense strand siRNA | Antisense strand siRNA |
|---|---|---|
| **Gata6** | | |
| AATCAGGAGCGCAGGCTGCAG (SEQ ID NO. 58) | SEQ ID NO: 41 UCAGGAGCGCAGGCUGCAGtt | SEQ ID NO: 43 CUGCAGCCUGCGCUCCUGAtt |
| AAGAGGCGCCTCCTCTCTCCT (SEQ ID NO. 59) | SEQ ID NO: 42 GAGGCGCCUCCUCUCUCCUtt | SEQ ID NO: 44 AGGAGAGAGGAGGCGCCUCtt |
| **Foxa2** | | |
| AAACCGCCATGCACTCGGCTT (SEQ ID NO. 60) | SEQ ID NO: 45 ACCGCCAUGCACUCGGCUUtt | SEQ ID NO: 46 AAGCCGAGUGCAUGGCGGUtt |

TABLE 11

Examples of shRNA sequences for the knockdown of Nkx2-1 Nkx2-1

| shHairpin sequence (5'-3') |
|---|
| SEQ ID NO: 47 CCGGCCCATGAAGAAGAAAGCAATTCTCGAGAATTGCTTTCTTCTTCATGGGTTTTTG |
| SEQ ID NO: 48 GTACCGGGGGATCATCCTTGTAGATAAACTCGAGTTTATCTACAAGGATGATCCCTTTTTTG |
| SEQ ID NO: 49 CCGGATTCGGAATCAGCTAGCAATTCTCGAGAATTGCTAGCTGATTCCGAATTTTTTG |

The amount of the specific transcription factor isoform according to the present invention can be determined on the polypeptide level. Thus, the invention relates to a method of assessing whether a subject suffers from cancer or is prone to suffering from cancer, said method comprising the steps of a) measuring in a sample of said subject the amount of a specific transcription factor isoform as a polypeptide wherein said specific transcription isoform is either i) the transcription factor is GATA6 and the ratio of the amount of said Em and said Ad isoform of GATA6 is higher than 0.5; or ii) the transcription factor is NKX2-1 and the ratio of the amount of said Em and said Ad isoform of NKX2-1 is higher than 0.3.

The amount of the specific transcription factor isoforms according to the invention can be assessed on the polypeptide level using known quantitative methods for the assessment of polypeptide levels. For example, ELISA (Enzyme-linked Immunosorbent Assay)-based, gel-based, blot-based, mass spectrometry-based, or flow cytometry-based methods can be used for measuring the amount of the specific transcription factor isoforms on the polypeptide level according to the invention.

The method according of the present invention may further comprise measuring in a sample of a subject the amount of one or two further specific transcription factor isoform(s) on the polypeptide level selected from the group of specific transcription factor isoforms consisting of i) the FOXA2 Em isoform comprising the polypeptide sequence of SEQ ID No: 52 or the FOXA2 Em isoform comprising polypeptide sequence with up to 43 additions, deletions or substitutions of SEQ ID NO: 52; and ii) the ID2 Em isoform comprising the polypeptide sequence of SEQ ID No: 53 or the ID2 Em isoform comprising polypeptide sequence with up to 13 additions, deletions or substitutions of SEQ ID NO: 53;

and wherein for assessing that said subject suffers from cancer or is prone to suffering from cancer the amount of all analyzed specific transcription factor Em isoforms has to be increased in comparison to the amount of the analyzed specific transcription factor Em isoforms in the control sample.

In accordance with this invention, a method of assessing whether a subject suffers from cancer or is prone to suffering from cancer is found, said method comprising the steps of a) measuring in a sample of said subject the amount of a specific transcription factor isoform selected from the group of specific transcription factor isoforms consisting of i) the GATA6 Em isoform comprising the polypeptide sequence of SEQ ID No: 50 or the GATA6 Em isoform comprising the polypeptide sequence with up to 30 additions, deletions or substitutions of SEQ ID NO: 50;

ii) the NKX2-1 Em isoform comprising the polypeptide sequence of SEQ ID No: 51 or the NKX2-1 Em isoform comprising the polypeptide sequence with up to 14 additions, deletions or substitutions of SEQ ID NO: 51;

iii) the FOXA2 Em isoform comprising the polypeptide sequence of SEQ ID No: 52 or the FOXA2 Em isoform comprising polypeptide sequence with up to 43 additions, deletions or substitutions of SEQ ID NO: 52; or iv) the ID2 Em isoform comprising the polypeptide sequence of SEQ ID No: 53 or the ID2 Em isoform comprising polypeptide sequence with up to 13 additions, deletions or substitutions of SEQ ID NO: 53;

b) comparing the amount of said specific transcription factor isoform with the amount of said specific transcription factor isoform in a control sample;

c) assessing that said subject suffers from cancer or is prone to suffering from cancer if the amount of said specific transcription factor isoform in said sample from said subject is increased in comparison to the amount of said specific transcription factor isoform in the control sample.

The invention provides a method of assessing whether a subject suffers from cancer or is prone to suffering from cancer, said method comprising the steps of a) measuring in a sample of said subject the amount of two specific isoforms of a transcription factor, wherein the transcription factor is selected from the group GATA6, NKX2-1, FOXA2 and ID2, and wherein the two specific isoforms are either:

i) the GATA6 Em isoform comprising the polypeptide sequence of SEQ ID No: 50 or the GATA6 Em isoform comprising the polypeptide sequence with up to 30 additions, deletions or substitutions of SEQ ID NO: 50; and the GATA6 Ad isoform comprising the polypeptide sequence of SEQ ID No: 54 or the GATA6 Ad isoform polypeptide sequence with up to 23 additions, deletions or substitutions of SEQ ID NO: 54;

ii) the NKX2-1 Em isoform comprising the polypeptide sequence of SEQ ID No: 51 or the NKX2-1 Em isoform comprising the polypeptide sequence with up to 14 additions, deletions or substitutions of SEQ ID NO: 51; and the NKX2-1 Ad isoform comprising the polypeptide sequence of SEQ ID No: 55 or the NKX2-1 Ad isoform comprising the polypeptide sequence with up to 15 additions, deletions or substitutions of SEQ ID NO: 55;

iii) the FOXA2 Em isoform comprising the polypeptide sequence of SEQ ID No: 52 or the FOXA2 Em isoform comprising the polypeptide sequence with up to 43 additions, deletions or substitutions of SEQ ID NO: 52; and the FOXA2 Ad isoform comprising the polypeptide sequence of SEQ ID No: 56 or FOXA2 Ad isoform comprising the polypeptide sequence with up to 43 additions, deletions or substitutions of SEQ ID NO: 56; or iv) the ID2 Em isoform comprising the polypeptide sequence of SEQ ID No: 53 or the ID2 Em isoform comprising the polypeptide sequence with up to 13 additions, deletions or substitutions of SEQ ID NO: 53; and the ID2 Ad isoform consisting of the polypeptide sequence of SEQ ID No: 57 or ID2 Ad isoform consisting of polypeptide sequence with up to 13 additions, deletions or substitutions of SEQ ID NO: 57;

b) building the ratio of the amount of said Em and said Ad isoform of said transcription factor c) assessing that said subject suffers from cancer or is prone to suffering from cancer if i) the transcription factor is GATA6 and the ratio of the amount of said Em and said Ad isoform of GATA6 is higher than 0.5;

ii) the transcription factor is NKX2-1 and the ratio of the amount of said Em and said Ad isoform of NKX2-1 is higher than 0.3;

iii) the transcription factor is FOXA2 and the ratio of the amount of said Em and said Ad isoform of FOXA2 is higher than 0.8; or iv) the transcription factor is ID2 and the ratio of the amount of said Em and said Ad isoform of ID2 is higher than 1.

The method according to the present invention may also comprise a) measuring in a sample of a subject the amount of two specific transcription factor isoforms on protein level, wherein the transcription factor isoform are i) the GATA6 Em isoform comprising the polypeptide sequence of SEQ ID No: 50 or the GATA6 Em isoform comprising the polypeptide sequence with up to 30 additions, deletions or substitutions of SEQ ID NO: 50; and ii) the NKX2-1 Em isoform comprising the polypeptide sequence of SEQ ID No: 51 or the NKX2-1 Em isoform comprising the polypeptide sequence with up to 14 additions, deletions or substitutions of SEQ ID NO: 51;

b) comparing the amount of said specific transcription factor isoform with the amount of said specific transcription factor isoform in a control sample;

c) assessing that said subject suffers from cancer or is prone to suffering from cancer if the amount of the GATA6 Em and the amount of the NKX2-1 Em isoform in said sample from said subject is increased in comparison to the amount of said specific transcription factor isoform in the control sample.

The method according to the present invention may allow assessing that a subject suffers from cancer or is prone to suffering from cancer if the amount of the analyzed specific transcription factor Em isoform(s) on polypeptide level is increased by at least 1.3-fold over control, at least 1.4-fold over control, at least 1.5-fold over control, at least 1.6-fold over control, at least 1.7-fold over control, at least 1.8-fold over control, at least 1.9-fold over control, at least 2-fold over control, at least 2.5 over control, at least 2.7 over control, at least 3-fold over control, at least 4-fold over control, at least 5-fold over control, wherein "over control" relates to the comparison of the amount of the analyzed specific transcription factor Em isoform(s) in the test/patient/subject sample to the amount of the analyzed specific transcription factor Em isoform(s) in a control sample.

The method according of the present invention may also comprise the step of measuring in a sample of a subject the amount of two specific isoforms of one or two further transcription factor(s) on the polypeptide level, wherein said one or two further transcription factor(s) are either Foxa2 and/or Id2 and wherein the two specific isoforms of said one or two further transcription factor(s) are:

i) the FOXA2 Em isoform comprising the polypeptide sequence of SEQ ID No: 52 or the FOXA2 Em isoform comprising the polypeptide sequence with up to 43 additions, deletions or substitutions of SEQ ID NO: 52; and the FOXA2 Ad isoform comprising the polypeptide sequence of SEQ ID No: 56 or FOXA2 Ad isoform comprising the polypeptide sequence with up to 43 additions, deletions or substitutions of SEQ ID NO: 56; or ii) the ID2 Em isoform comprising the polypeptide sequence of SEQ ID No: 53 or the ID2 Em isoform comprising the polypeptide sequence with up to 13 additions, deletions or substitutions of SEQ ID NO: 53; and the ID2 Ad isoform consisting of the polypeptide sequence of SEQ ID No: 57 or ID2 Ad isoform consisting of polypeptide sequence with up to 13 additions, deletions or substitutions of SEQ ID NO: 57;

and wherein said subject is assessed as suffering from cancer or as being prone to suffer from cancer if i) the transcription factor is GATA6 and the ratio of the amount of said Em and said Ad isoform of GATA6 is higher than 0.5; and/or ii) the transcription factor is NKX2-1 and the ratio of the amount of said Em and said Ad isoform of NKX2-1 is higher than 0.3; and iii) the transcription factor is FOXA2 and the ratio of the amount of said Em and said Ad isoform of FOXA2 is higher than 0.8; and/or iv) the transcription factor is ID2 and the ratio of the amount of said Em and said Ad isoform of ID2 is higher than 1.

It is obvious to the person skilled in the art that the specific transcription factor isoforms of the present invention can show certain sequence varieties between different subjects of the same ancestry and in particular between subjects of different ancestry. Non-limiting examples of the polymorphisms of the cancer specific isoforms of the present invention are given in Tables 12 and 13.

TABLE 12

Examples of polymorphisms in the sequences of GATA6, Em and Ad isoforms in dependence of the ancestry of a subject (CEU: Utah residents with Northern and Western European ancestry from the CEPH collection; CHB: Han Chinese in Beijing, China; JPT: Japanese in Tokyo, Japan; YRI: Yoruban in Ibadan, Nigeria)

| S. No | Region | Position in Gata6 Em | Position in Gata6 Ad | Polymorphism | Population | Frequency of T | Frequency of C |
|---|---|---|---|---|---|---|---|
| 1 | CCDS | 1982 | 1917 | T/C | CEU | 100% | 0% |
| | | | | | JPT | 100% | 0% |
| | | | | | YRI | 100% | 0% |
| **S. No** | **Region** | **Position in Gata6 Em** | **Position in Gata6 Ad** | **Polymorphism** | **Population** | **Frequency of G** | **Frequency of A** |
| 2 | 3'UTR | 2137 | 2072 | G/A | CEU | 56% | 44% |
| | | | | | CHB | 57% | 43% |
| | | | | | JPT | 65% | 35% |
| | | | | | YRI | 45% | 55% |
| **S. No** | **Region** | **Position in Gata6 Em** | **Position in Gata6 Ad** | **Polymorphism** | **Population** | **Frequency of A** | **Frequency of G** |
| 3 | 3'UTR | 2142 | 2077 | A/G | CEU | 97% | 3% |
| | | | | | CHB | 90% | 10% |
| | | | | | JPT | 100% | 0% |
| | | | | | YRI | 100% | 0% |

TABLE 12-continued

Examples of polymorphisms in the sequences of GATA6, Em and Ad isoforms in dependence of the ancestry of a subject (CEU: Utah residents with Northern and Western European ancestry from the CEPH collection; CHB: Han Chinese in Beijing, China; JPT: Japanese in Tokyo, Japan; YRI: Yoruban in Ibadan, Nigeria)

| S. No | Region | Position in Gata6 Em | Position in Gata6 Ad | Polymorphism | Population | Frequency of T | Frequency of A |
|---|---|---|---|---|---|---|---|
| 4 | 3'UTR | 2391 | 2326 | T/A | CEU | 100% | 0% |
| | | | | | CHB | 100% | 0% |
| | | | | | JPT | 100% | 0% |
| | | | | | YRI | 100% | 0% |

TABLE 13

Examples of polymorphisms in the sequences of FOXA2 variant 1 and 2 in dependence of the ancestry of a subject (ASW: African ancestry in Southwest USA; CEU: Utah residents with Northern and Western European ancestry from the CEPH collection; CHB: Han Chinese in Beijing, China; CHD: Chinese in Metropolitan Denver, Colorado; GIH: Gujarati Indians in Houston, Texas; JPT: Japanese in Tokyo, Japan; LWK: Luhya in Webuye, Kenya; MEX: Mexican ancestry in Los Angeles, California; MKK: Maasai in Kinyawa, Kenya; TSI: Tuscan in Italy; YRI: Yoruban in Ibadan, Nigeria)

| S. No | Region | Position in Foxa2 Em | Position in Foxa2 Ad | Polymorphism | Population | Frequency of T | Frequency of C |
|---|---|---|---|---|---|---|---|
| 1 | CCDS | 1408 | 1395 | T/C | CEU | 100% | 0% |
| | | | | | CHB | 100% | 0% |
| | | | | | JPT | 100% | 0% |
| | | | | | YRI | 100% | 0% |

| S. No | Region | Position in Foxa2 Em | Position in Foxa2 Ad | Polymorphism | Population | Frequency of A | Frequency of G |
|---|---|---|---|---|---|---|---|
| 1 | 3'UTR | 1627 | 1614 | A/G | ASW | 38% | 62% |
| | | | | | CEU | 96% | 4% |
| | | | | | CHB | 84% | 16% |
| | | | | | CHD | 84% | 16% |
| | | | | | JPT | 77% | 23% |
| | | | | | GIH | 89% | 11% |
| | | | | | LWK | 27% | 73% |
| | | | | | MEX | 92% | 8% |
| | | | | | MKK | 40% | 60% |
| | | | | | TSI | 91% | 9% |
| | | | | | YRI | 20% | 80% |

Interestingly, it was found by the inventors that an increased expression of the GATA6 Ad isoform comprising the nucleic acid sequence of SEQ ID No: 5 or the GATA6 Ad isoform nucleic acid sequence with up to 55 additions, deletions or substitutions of SEQ ID NO: 5 could be used for the diagnosis of non-cancer related lung disease, for example lung fibrosis (see Examples 8 and 9). Thus, the invention also relates to a method of assessing whether a subject suffers from fibrosis, in particular lung fibrosis, or is prone to suffering from fibrosis, in particular lung fibrosis, said method comprising the steps of a) measuring in a sample of said subject the amount of a specific transcription factor isoform wherein said specific transcription isoform is either
   i) the GATA6 Ad isoform comprising the nucleic acid sequence of SEQ ID No: 5 or the GATA6 Em isoform comprising a nucleic acid sequence with up to 55 additions, deletions or substitutions of SEQ ID NO: 5 or
b) comparing the amount of said specific GATA6 Ad isoform with the amount of said specific GATA6 Ad isoform in a control sample;
c) assessing that said subject suffers from lung fibrosis or is prone to suffering from lung fibrosis if the amount of said specific GATA6 Ad isoform in said sample from said subject is increased in comparison to the amount of said GATA6 Ad isoform isoform in the control sample.

As shown herein, it was surprisingly found that GATA6 Ad isoform is increased in comparison to the amount of the GATA6 Ad isoform in a control sample in fibrotic events, in particular in lung fibrosis. Accordingly, and increased amount of the GATA6 Ad isoform in a patient/subject sample as compared to a (healthy) control sample is indicative of the presence of lung fibrosis in said patient/subject.

The present invention provides a kit for use in any of the methods of the invention for assessing whether a subject suffers from cancer or is prone to suffering from cancer comprising reagents for measuring in a sample specifically the amount of one or several transcription factor isoforms selected from the group of specific transcription factor isoforms consisting of i) the GATA6 Em isoform comprising the nucleic acid sequence of SEQ ID No: 1 or the GATA6 Em isoform comprising the nucleic acid sequence with up to 55 additions, deletions or substitutions of SEQ ID NO: 1;
ii) the NKX2-1 Em isoform comprising the nucleic acid sequence of SEQ ID No: 2 or the NKX2-1 Em isoform comprising the nucleic acid sequence with up to 39 additions, deletions or substitutions of SEQ ID NO: 2;

iii) the FOXA2 Em isoform comprising the nucleic acid sequence of SEQ ID No: 3 or the FOXA2 Em isoform comprising the nucleic acid sequence with up to 68 additions, deletions or substitutions of SEQ ID NO: 3; or iv) the ID2 Em isoform comprising the nucleic acid sequence of SEQ ID No: 4 or the ID2 Em isoform comprising the nucleic acid sequence with up to 34 additions, deletions or substitutions of SEQ ID NO: 4.

The kit of the present invention may comprise primers and further reagents necessary for a qPCR analysis. The respective primers may be selected from the list in Table 9.

While the invention has been illustrated and described in detail in the drawings and foregoing description, such illustration and description are to be considered illustrative or exemplary and not restrictive. It will be understood that changes and modifications may be made by those of ordinary skill within the scope and spirit of the following claims. In particular, the present invention covers further embodiments with any combination of features from different embodiments described above and below.

The invention also covers all further features shown in the figures individually although they may not have been described in the afore or following description. Also, single alternatives of the embodiments described in the figures and the description and single alternatives of features thereof can be disclaimed from the subject matter of the other aspect of the invention.

Furthermore, in the claims the word “comprising” does not exclude other elements or steps, and the indefinite article “a” or “an” does not exclude a plurality. A single unit may fulfill the functions of several features recited in the claims. The terms “essentially”, “about”, “approximately” and the like in connection with an attribute or a value particularly also define exactly the attribute or exactly the value, respectively. Any reference signs in the claims should not be construed as limiting the scope.

The present invention is also characterized by the following items:

1. A method of assessing whether a subject suffers from cancer or is prone to suffering from cancer, said method comprising the steps of
   a) measuring in a sample of said subject the amount of a specific transcription factor isoform wherein said specific transcription isoform is either
      i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; or
      ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2;
   b) comparing the amount of said specific transcription factor Em isoform with the amount of said specific transcription factor Em isoform in a control sample; and
   c) assessing that said subject suffers from cancer or is prone to suffering from cancer if the amount of said specific transcription factor Em isoform in said sample from said subject is increased in comparison to the amount of said specific transcription factor Em isoform in the control sample.
2. A method of assessing whether a subject suffers from cancer or is prone to suffering from cancer, said method comprising the steps of
   a) measuring in a sample of said subject the amount of two specific isoforms of a transcription factor, wherein said transcription factor is either GATA6 or NKX2-1 and wherein the two specific isoforms are either
      i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; and the GATA6 Ad isoform comprising the nucleic acid sequence of SEQ ID No: 5 or the GATA6 Ad isoform comprising a nucleic acid sequence with up to 55 additions, deletions or substitutions of SEQ ID NO: 5; or
      ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2; and the NKX2-1 Ad isoform comprising the nucleic acid sequence of SEQ ID No: 6 or the NKX2-1 Ad isoform comprising a nucleic acid sequence with up to 38 additions, deletions or substitutions of SEQ ID NO: 6;
   b) building the ratio of the amount of said Em and said Ad isoform of said transcription factor; and
   c) assessing that said subject suffers from cancer or is prone to suffering from cancer if
      i) the transcription factor is GATA6 and the ratio of the amount of said Em and said Ad isoform of GATA6 is higher than 0.5; or
      ii) the transcription factor is NKX2-1 and the ratio of the amount of said Em and said Ad isoform of NKX2-1 is higher than 0.3.
3. The method according to item 1 or 2, wherein the amount of said specific transcription factor isoform(s) is measured via a polymerase chain reaction-based method, an in situ hybridization-based method, or a microarray.
4. The method according to item 3, wherein the amount of said specific transcription factor isoform(s) is measured via a polymerase chain reaction-based method and wherein said polymerase chain reaction-based method is a quantitative reverse transcriptase polymerase chain reaction.
5. The method according to item 4, wherein the step of measuring in a sample of said subject the amount of a specific transcription factor comprises the contacting of the sample with primers, wherein said primers can be used for amplifying at least one of the specific transcription factor isoforms.
6. The method according to item 5, wherein said primers are selected from the group of primers having a nucleic acid sequence as set forth in SEQ ID NOs 9 to 40.
7. The method according to items 1 and 3 to 6, wherein
   i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; and
   ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2;
   are analyzed for assessing whether said subject suffers from cancer or is prone to suffering from cancer and wherein the amount of both said specific transcription factor Em isoforms has to be increased in comparison to the amount of said two specific transcription factor Em isoforms in the control sample for assessing that said subject suffers from cancer or is prone to suffering from cancer.

8. The method according to items 1 and 3 to 7, wherein said step a) further comprises measuring in a sample of said subject the amount of one or two further specific transcription factor isoform(s) selected from the group of specific transcription factor isoforms consisting of
   i) the FOXA2 Em isoform comprising the nucleic acid sequence of SEQ ID No: 3 or the FOXA2 Em isoform comprising nucleic acid sequence with up to 68 additions, deletions or substitutions of SEQ ID NO: 3; and
   ii) the ID2 Em isoform comprising the nucleic acid sequence of SEQ ID No: 4 or the ID2 Em isoform comprising nucleic acid sequence with up to 34 additions, deletions or substitutions of SEQ ID NO: 4;
   and wherein for assessing that said subject suffers from cancer or is prone to suffering from cancer the amount of all analyzed specific transcription factor Em isoforms has to be increased in comparison to the amount of the analyzed specific transcription factor Em isoforms in the control sample.
9. The method according to items 1 and 3 to 8, wherein for assessing that said subject suffers from cancer or is prone to suffering from cancer the amount of said analyzed specific transcription factor Em isoform(s) has to be increased by at least 1.3-fold in comparison to the amount of the analyzed specific transcription factor Em isoform(s) in the control sample.
10. The method according to items 2 to 6, wherein
   i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; and the GATA6 Ad isoform comprising the nucleic acid sequence of SEQ ID No: 5 or the GATA6 Ad isoform comprising a nucleic acid sequence with up to 55 additions, deletions or substitutions of SEQ ID NO: 5; and
   ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2; and the NKX2-1 Ad isoform comprising the nucleic acid sequence of SEQ ID No: 2 or the NKX2-1 Ad isoform comprising a nucleic acid sequence with up to 38 additions, deletions or substitutions of SEQ ID NO: 6
   are analyzed for assessing whether said subject suffers from cancer or is prone to suffering from cancer and wherein it is assessed that said subject suffers from cancer if
   i) the ratio of the amount of said Em and said Ad isoform of GATA6 is higher than 0.5; and
   ii) the ratio of the amount of said Em and said Ad isoform of NKX2-1 is higher than 0.3.
11. The method according to items 2 to 6 and 10, wherein step a) further comprises measuring in a sample of said subject the amount of two specific isoforms of one or two further transcription factor(s), wherein said one or two further transcription factor(s) are either Foxa2 and/or Id2 and wherein the two specific isoforms of said one or two further transcription factor(s) are:
   i) the FOXA2 Em isoform comprising the nucleic acid sequence of SEQ ID No: 3 or the FOXA2 Em isoform comprising a nucleic acid sequence with up to 68 additions, deletions or substitutions of SEQ ID NO: 3; and the FOXA2 Ad isoform comprising the nucleic acid sequence of SEQ ID No: 7 or FOXA2 Ad isoform comprising a nucleic acid sequence with up to 74 additions, deletions or substitutions of SEQ ID NO: 3; or
   ii) the ID2 Em isoform comprising the nucleic acid sequence of SEQ ID No: 4 or the ID2 Em isoform comprising a nucleic acid sequence with up to 34 additions, deletions or substitutions of SEQ ID NO: 4; and the ID2 Ad isoform consisting of the nucleic acid sequence of SEQ ID No: 8 or ID2 Ad isoform consisting of nucleic acid sequence with up to 30 additions, deletions or substitutions of SEQ ID NO: 8;
   and wherein said subject is assessed as suffering from cancer or as being prone to suffer from cancer if
   i) the transcription factor is GATA6 and the ratio of the amount of said Em and said Ad isoform of GATA6 is higher than 0.5; and/or
   ii) the transcription factor is NKX2-1 and the ratio of the amount of said Em and said Ad isoform of NKX2-1 is higher than 0.3; and
   iii) the transcription factor is FOXA2 and the ratio of the amount of said Em and said Ad isoform of FOXA2 is higher than 0.8; and/or
   iv) the transcription factor is ID2 and the ratio of the amount of said Em and said Ad isoform of ID2 is higher than 1.
12. The method according to any of items 1, 2, or 7 to 10, wherein the amount of said specific transcription factor isoform(s) is measured on the polypeptide level.
13. The method according to item 12, wherein the amount of said specific transcription factor isoform(s) is measured by an ELISA, a gel- or blot-based method, mass spectrometry, flow cytometry or FACS.
14. The method according to items 1 to 13, wherein said cancer is a lung cancer.
15. The method according to item 14, wherein said lung cancer is an adenocarcinoma or a bronchoalveolar carcinoma.
16. The method according to items 1 to 15, wherein said sample comprises tumor cells.
17. The method according to items 1 to 16, wherein said sample is a blood sample, a breath condensate sample, a bronchoalveolar lavage fluid sample, a mucus sample or a phlegm sample.
18. The method according to items 1 to 17, wherein said subject is a human subject.
19. The method of item 18, wherein said human subject is a subject having an increased risk for developing cancer.
20. A method of treating a patient, said method comprising
   a) selecting a cancer patient according to the method of any of items 1 to 19
   b) administering to said cancer patient an effective amount of an anti-cancer agent and/or radiation therapy.
21. The method of treating a patient according to item 20, wherein said anti-cancer agent is an inhibitor of
   i) the GATA6 Em isoform comprising the nucleic acid sequence of SEQ ID No: 1 or the GATA6 Em isoform nucleic acid sequence with up to 55 additions, deletions or substitutions of SEQ ID NO: 1; or
   ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2.

22. The method of treating a patient according to item 20 or 21, wherein said cancer patient is a patient suffering from lung cancer.
23. The method of treating a patient according to item 22, wherein said lung cancer is a lung adenocarcinoma or a bronchoalveolar carcinoma.
24. A composition for use in medicine comprising an inhibitor of
   i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; or
   ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2.
25. The composition for use in medicine of item 24, wherein said inhibitor comprises a siRNA or shRNA specifically targeting
   i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1;
   ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2;
   iii) the FOXA2 Em isoform comprising the nucleic acid sequence of SEQ ID No: 3 or the FOXA2 Em isoform comprising nucleic acid sequence with up to 68 additions, deletions or substitutions of SEQ ID NO: 3; or
   iv) the ID2 Em isoform comprising the nucleic acid sequence of SEQ ID No: 4 or the ID2 Em isoform comprising nucleic acid sequence with up to 34 additions, deletions or substitutions of SEQ ID NO: 4.
26. The composition for use in medicine of item 25, wherein said siRNA is selected from the group of siRNAs consisting of SEQ ID No: 41 to SEQ ID NO: 46.
27. The composition for use in medicine of item 25, wherein said shRNA is selected from the group of shRNAs consisting of SEQ ID No: 47 to SEQ ID NO: 49.
28. A composition for use in medicine comprising an inhibitor of
   i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; and
   ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2.
29. The composition according to item 28 further comprising an inhibitor of
   i) the FOXA2 Em isoform comprising the nucleic acid sequence of SEQ ID No: 3 or the FOXA2 Em isoform comprising nucleic acid sequence with up to 68 additions, deletions or substitutions of SEQ ID NO: 3; or
   ii) the ID2 Em isoform comprising the nucleic acid sequence of SEQ ID No: 4 or the ID2 Em isoform comprising nucleic acid sequence with up to 34 additions, deletions or substitutions of SEQ ID NO: 4
30. The composition for use in medicine of items 24 to 29, wherein said inhibitor further comprises protamine.
31. The composition for use in medicine of items 24 to 29, wherein the inhibitor further comprises a fusion protein of protamine and an antigen-targeting polypeptide.
32. The composition for use in medicine of item 31, wherein said antigen-targeting polypeptide is targeting a protein selected from the group of proteins consisting of ITGB2, PTGIS, BASP1, DES, ITGA2, CTSS, PTPRC, ANPEP, FILIP1L, MGLL, OSMR, ITGB6, AGPAT4, ASS1, CSPG4, and CDH11.
33. The composition for use in medicine of item 31 or item 32, wherein said antigen-targeting polypeptide is a monoclonal antibody or a single chain variable fragment.
34. The composition of items 24 to 33 for the use in the treatment of a lung disease.
35. The composition of item 34 for the use in the treatment of a lung disease, wherein the lung disease is a lung cancer.
36. The composition of item 35 for the use in the treatment of a lung cancer, wherein said lung cancer is an adenocarcinoma or a bronchoalveolar carcinoma.
37. A kit for use in any of the methods according to items 1 to 23 comprising reagents for measuring in a sample specifically the amount of one or two transcription factor isoforms selected from the group of specific transcription factor isoforms consisting of
   i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; and
   ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2.
38. The kit according to item 37 further comprising reagents for measuring in a sample specifically the amount of one or two transcription factor isoforms selected from the group of specific transcription factor isoforms consisting of
   iii) the FOXA2 Em isoform comprising the nucleic acid sequence of SEQ ID No: 3 or the FOXA2 Em isoform comprising nucleic acid sequence with up to 68 additions, deletions or substitutions of SEQ ID NO: 3; and
   iv) the ID2 Em isoform comprising the nucleic acid sequence of SEQ ID No: 4 or the ID2 Em isoform comprising nucleic acid sequence with up to 34 additions, deletions or substitutions of SEQ ID NO: 4.
39. The kit according to item 37 or 38 further comprising reagents for measuring in a sample specifically the amount of one or several further transcription factor isoform(s) selected from the group of specific transcription factor isoforms consisting of
   i) the GATA6 Ad isoform comprising the nucleic acid sequence of SEQ ID No: 5 or the GATA6 Ad isoform comprising a nucleic acid sequence with up to 55 additions, deletions or substitutions of SEQ ID NO: 5;
   ii) the NKX2-1 Ad isoform comprising the nucleic acid sequence of SEQ ID No: 2 or the NKX2-1 Ad isoform comprising the nucleic acid sequence with up to 38 additions, deletions or substitutions of SEQ ID NO: 6;
   iii) the FOXA2 Ad isoform comprising the nucleic acid sequence of SEQ ID No: 7 or FOXA2 Ad isoform comprising the nucleic acid sequence with up to 74 additions, deletions or substitutions of SEQ ID NO: 3; and
   iv) the ID2 Ad isoform consisting of the nucleic acid sequence of SEQ ID No: 8 or ID2 Ad isoform consisting of nucleic acid sequence with up to 30 additions, deletions or substitutions of SEQ ID NO: 8;

40. The kit of items 37 to 39 wherein said sample is a blood or breath condensate sample.

41. The kit of items 37 to 40 wherein said sample is a sample from a human subject.

42. The kit of item 41 wherein the kit comprises one or several primers selected from the group of primers comprising the nucleic acid sequence of SEQ IDs 9 to 40.

Furthermore, the present invention relates to the following items:

1. A method of assessing whether a subject suffers from cancer or is prone to suffering from cancer, said method comprising the steps of
   a) measuring in a sample of said subject the amount of a specific transcription factor isoform wherein said specific transcription isoform is either
      i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; or
      ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2;
   b) comparing the amount of said specific transcription factor Em isoform with the amount of said specific transcription factor Em isoform in a control sample; and
   c) assessing that said subject suffers from cancer or is prone to suffering from cancer if the amount of said specific transcription factor Em isoform in said sample from said subject is increased in comparison to the amount of said specific transcription factor Em isoform in the control sample.
2. A method of assessing whether a subject suffers from cancer or is prone to suffering from cancer, said method comprising the steps of
   a) measuring in a sample of said subject the amount of two specific isoforms of a transcription factor, wherein said transcription factor is either GATA6 or NKX2-1 and wherein the two specific isoforms are either
      i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; and the GATA6 Ad isoform comprising the nucleic acid sequence of SEQ ID No: 5 or the GATA6 Ad isoform comprising a nucleic acid sequence with up to 55 additions, deletions or substitutions of SEQ ID NO: 5; or
      ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2; and the NKX2-1 Ad isoform comprising the nucleic acid sequence of SEQ ID No: 6 or the NKX2-1 Ad isoform comprising a nucleic acid sequence with up to 38 additions, deletions or substitutions of SEQ ID NO: 6;
   b) building the ratio of the amount of said Em and said Ad isoform of said transcription factor; and
   c) assessing that said subject suffers from cancer or is prone to suffering from cancer if
      i) the transcription factor is GATA6 and the ratio of the amount of said Em and said Ad isoform of GATA6 is higher than 0.5; or
      ii) the transcription factor is NKX2-1 and the ratio of the amount of said Em and said Ad isoform of NKX2-1 is higher than 0.3.
3. The method according to item 1 or 2, wherein the amount of said specific transcription factor isoform(s) is measured via a quantitative reverse transcriptase polymerase chain reaction.
4. The method according to item 3, wherein the step of measuring in a sample of said subject the amount of a specific transcription factor comprises the contacting of the sample with primers, wherein said primers can be used for amplifying at least one of the specific transcription factor isoforms and wherein said primers are selected from the group of primers having a nucleic acid sequence as set forth in SEQ ID NOs 9 to 40.
5. The method according to any one of items 1 and 3 to 4, wherein
   i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; and
   ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2;

are analyzed for assessing whether said subject suffers from cancer or is prone to suffering from cancer and wherein the amount of both said specific transcription factor Em isoforms has to be increased in comparison to the amount of said two specific transcription factor Em isoforms in the control sample for assessing that said subject suffers from cancer or is prone to suffering from cancer.
6. The method according to any one of items 1 and 3 to 5, wherein said step a) further comprises measuring in a sample of said subject the amount of one or two further specific transcription factor isoform(s) selected from the group of specific transcription factor isoforms consisting of
   i) the FOXA2 Em isoform comprising the nucleic acid sequence of SEQ ID No: 3 or the FOXA2 Em isoform comprising a nucleic acid sequence with up to 68 additions, deletions or substitutions of SEQ ID NO: 3; and
   ii) the ID2 Em isoform comprising the nucleic acid sequence of SEQ ID No: 4 or the ID2 Em isoform comprising a nucleic acid sequence with up to 34 additions, deletions or substitutions of SEQ ID NO: 4;

and wherein for assessing that said subject suffers from cancer or is prone to suffering from cancer the amount of all analyzed specific transcription factor Em isoforms has to be increased in comparison to the amount of the analyzed specific transcription factor Em isoforms in the control sample.
7. The method according to any of items 1, 2, or 5 to 6, wherein the amount of said specific transcription factor isoform(s) is measured on the polypeptide level and wherein the amount of said specific transcription factor isoform(s) is measured by an ELISA, a gel- or blot-based method, mass spectrometry, flow cytometry or FACS.
8. The method according to any one of items 1 to 7, wherein said cancer is a lung cancer.

9. The method according to item 8, wherein said lung cancer is an adenocarcinoma or a bronchoalveolar carcinoma.
10. The method according to any one of items 1 to 9, wherein said sample is a blood sample, a breath condensate sample, a bronchoalveolar lavage fluid sample, a mucus sample or a phlegm sample.
11. The method according to any one of items 1 to 10, wherein said subject is a human subject.
12. A composition for use in medicine comprising an inhibitor of
   i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; or
   ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2.
13. The composition for use in medicine of item 12, wherein said inhibitor comprises an siRNA selected from the group of siRNAs consisting of SEQ ID No: 41 to SEQ ID NO: 46.
14. The composition of item 12 or 13 for the use in the treatment of a lung cancer, wherein said lung cancer is an adenocarcinoma or a bronchoalveolar carcinoma.
15. A kit for use in any of the methods according to items 1 to 11 comprising reagents for measuring in a sample specifically the amount of one or two transcription factor isoforms selected from the group of specific transcription factor isoforms consisting of
   i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; and
   ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2.

The present invention is also characterized by the following items:

1. A method of assessing whether a subject suffers from cancer or is prone to suffering from cancer, said method comprising the steps of
   a) measuring in a sample of said subject the amount of a specific transcription factor isoform wherein said specific transcription isoform is either
      i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; or
      ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2;
   b) comparing the amount of said specific transcription factor Em isoform with the amount of said specific transcription factor Em isoform in a control sample; and
   c) assessing that said subject suffers from cancer or is prone to suffering from cancer if the amount of said specific transcription factor Em isoform in said sample from said subject is increased in comparison to the amount of said specific transcription factor Em isoform in the control sample.
2. A method of assessing whether a subject suffers from cancer or is prone to suffering from cancer, said method comprising the steps of
   a) measuring in a sample of said subject the amount of two specific isoforms of a transcription factor, wherein said transcription factor is either GATA6 or NKX2-1 and wherein the two specific isoforms are either
      i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; and the GATA6 Ad isoform comprising the nucleic acid sequence of SEQ ID No: 5 or the GATA6 Ad isoform comprising a nucleic acid sequence with up to 55 additions, deletions or substitutions of SEQ ID NO: 5; or
      ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2; and the NKX2-1 Ad isoform comprising the nucleic acid sequence of SEQ ID No: 6 or the NKX2-1 Ad isoform comprising a nucleic acid sequence with up to 38 additions, deletions or substitutions of SEQ ID NO: 6;
   b) building the ratio of the amount of said Em and said Ad isoform of said transcription factor; and
   c) assessing that said subject suffers from cancer or is prone to suffering from cancer if
      i) the transcription factor is GATA6 and the ratio of the amount of said Em and said Ad isoform of GATA6 is higher than 0.5, in particular higher than 1.0, more particularly higher than 1.5; or
      ii) the transcription factor is NKX2-1 and the ratio of the amount of said Em and said Ad isoform of NKX2-1 is higher than 0.3, in particular higher than 1.0, more particularly higher than 1.7.
3. The method according to item 1 or 2, wherein the amount of said specific transcription factor isoform(s) is measured via a polymerase chain reaction-based method, an in situ hybridization-based method, or a microarray.
4. The method according to item 3, wherein the amount of said specific transcription factor isoform(s) is measured via a polymerase chain reaction-based method and wherein said polymerase chain reaction-based method is a quantitative reverse transcriptase polymerase chain reaction.
5. The method according to item 4, wherein the step of measuring in a sample of said subject the amount of a specific transcription factor comprises the contacting of the sample with primers, wherein said primers can be used for amplifying at least one of the specific transcription factor isoforms.
6. The method according to item 5, wherein said primers are selected from the group of primers having a nucleic acid sequence as set forth in SEQ ID NOs 9 to 40.
7. The method according to items 1 and 3 to 6, wherein
   i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; and
   ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2;

are analyzed for assessing whether said subject suffers from cancer or is prone to suffering from cancer and wherein the amount of both said specific transcription factor Em isoforms has to be increased in comparison to the amount of said two specific transcription factor Em isoforms in the control sample for assessing that said subject suffers from cancer or is prone to suffering from cancer.

8. The method according to items 1 and 3 to 7, wherein said step a) further comprises measuring in a sample of said subject the amount of one or two further specific transcription factor isoform(s) selected from the group of specific transcription factor isoforms consisting of
   i) the FOXA2 Em isoform comprising the nucleic acid sequence of SEQ ID No: 3 or the FOXA2 Em isoform comprising nucleic acid sequence with up to 68 additions, deletions or substitutions of SEQ ID NO: 3; and
   ii) the ID2 Em isoform comprising the nucleic acid sequence of SEQ ID No: 4 or the ID2 Em isoform comprising nucleic acid sequence with up to 34 additions, deletions or substitutions of SEQ ID NO: 4; and wherein for assessing that said subject suffers from cancer or is prone to suffering from cancer the amount of all analyzed specific transcription factor Em isoforms has to be increased in comparison to the amount of the analyzed specific transcription factor Em isoforms in the control sample.
9. The method according to items 1 and 3 to 8, wherein for assessing that said subject suffers from cancer or is prone to suffering from cancer the amount of said analyzed specific transcription factor Em isoform(s) has to be increased by at least 1.3-fold in comparison to the amount of the analyzed specific transcription factor Em isoform(s) in the control sample.
10. The method according to items 2 to 6, wherein
   i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; and the GATA6 Ad isoform comprising the nucleic acid sequence of SEQ ID No: 5 or the GATA6 Ad isoform comprising a nucleic acid sequence with up to 55 additions, deletions or substitutions of SEQ ID NO: 5; and
   ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2; and the NKX2-1 Ad isoform comprising the nucleic acid sequence of SEQ ID No: 2 or the NKX2-1 Ad isoform comprising a nucleic acid sequence with up to 38 additions, deletions or substitutions of SEQ ID NO: 6 are analyzed for assessing whether said subject suffers from cancer or is prone to suffering from cancer and wherein it is assessed that said subject suffers from cancer if
   i) the ratio of the amount of said Em and said Ad isoform of GATA6 is higher than 0.5, in particular higher than 1.0, more particularly higher than 1.5; and
   ii) the ratio of the amount of said Em and said Ad isoform of NKX2-1 is higher than 0.3 in particular higher than 1.0, more particularly higher than 1.7.
11. The method according to items 2 to 6 and 10, wherein step a) further comprises measuring in a sample of said subject the amount of two specific isoforms of one or two further transcription factor(s), wherein said one or two further transcription factor(s) are either Foxa2 and/or Id2 and wherein the two specific isoforms of said one or two further transcription factor(s) are:
   i) the FOXA2 Em isoform comprising the nucleic acid sequence of SEQ ID No: 3 or the FOXA2 Em isoform comprising a nucleic acid sequence with up to 68 additions, deletions or substitutions of SEQ ID NO: 3; and the FOXA2 Ad isoform comprising the nucleic acid sequence of SEQ ID No: 7 or FOXA2 Ad isoform comprising a nucleic acid sequence with up to 74 additions, deletions or substitutions of SEQ ID NO: 3; or
   ii) the ID2 Em isoform comprising the nucleic acid sequence of SEQ ID No: 4 or the ID2 Em isoform comprising a nucleic acid sequence with up to 34 additions, deletions or substitutions of SEQ ID NO: 4; and the ID2 Ad isoform consisting of the nucleic acid sequence of SEQ ID No: 8 or ID2 Ad isoform consisting of nucleic acid sequence with up to 30 additions, deletions or substitutions of SEQ ID NO: 8;

and wherein said subject is assessed as suffering from cancer or as being prone to suffer from cancer if
   i) the transcription factor is GATA6 and the ratio of the amount of said Em and said Ad isoform of GATA6 is higher than 0.5, in particular higher than 1.0, more particularly higher than 1.5; and/or
   ii) the transcription factor is NKX2-1 and the ratio of the amount of said Em and said Ad isoform of NKX2-1 is higher than 0.3, in particular higher than 1.0, more particularly higher than 1.7; and
   iii) the transcription factor is FOXA2 and the ratio of the amount of said Em and said Ad isoform of FOXA2 is higher than 0.8; and/or
   iv) the transcription factor is ID2 and the ratio of the amount of said Em and said Ad isoform of ID2 is higher than 1.
12. The method according to items 1 to 11, wherein said sample comprises tumor cells.
13. The method according to items 1 to 12, wherein said sample is a breath condensate sample.
14. The method according to items 1 to 12, wherein said sample is a biopsy sample.
15. The method according to items 1 to 12, wherein said sample is a breath condensate sample, a biopsy sample, a blood sample, or a bronchoalveolar lavage fluid sample.
16. The method according to any of items 1, 2, or 7 to 10, wherein the amount of said specific transcription factor isoform(s) is measured on the polypeptide level.
17. The method according to item 16, wherein the amount of said specific transcription factor isoform(s) is measured by an ELISA, a gel- or blot-based method, mass spectrometry, flow cytometry or FACS.
18. The method according to item 16 or 17, wherein said sample comprises tumor cells.
19. The method according to any one of items 16 to 18, wherein said sample is a breath condensate sample.
20. The method according to any one of items 16 to 18, wherein said sample is a biopsy sample.
21. The method according to any one of items 16 to 18, wherein said sample is a breath condensate sample, a biopsy sample, a blood sample, a bronchoalveolar lavage fluid sample, a mucus sample or a phlegm sample.
22. The method according to items 1 to 21, wherein said cancer is a lung cancer.

23. The method according to item 22, wherein said lung cancer is non-small cell lung cancer (NSCLC).
24. The method according to item 23, wherein said NSCLC is an adenocarcinoma, a squamous cell carcinoma or a large cell carcinoma.
25. The method according to item 23, wherein said adenocarcinoma is a bronchoalveolar carcinoma.
26. The method according to item 23, wherein said adenocarcinoma is a bronchoalveolar carcinoma, an acinar adenocarcinoma, a papillary adenocarcinoma, a solid adenocarcinoma with mucin production, a adenocarcinoma with mixed subtypes, a variant adenocarcinomas, including well differentiated fetal adenocarcinoma, mucinous (colloid) adenocarcinoma, mucinous cystadenocarcinoma, signet ring adenocarcinoma, or clear cell adenocarcinoma.
27. The method according to item 22, wherein said lung cancer is small cell lung cancer.
28. The method according to any one of items 1 to 27, wherein said subject is a human subject.
29. The method of item 28, wherein said human subject is a subject having an increased risk for developing cancer.
30. A method of treating a patient, said method comprising
  a) selecting a cancer patient according to the method of any of items 1 to 29
  b) administering to said cancer patient an effective amount of an anti-cancer agent and/or radiation therapy.
31. The method of treating a patient according to item 30, wherein said anti-cancer agent is an inhibitor of
  i) the GATA6 Em isoform comprising the nucleic acid sequence of SEQ ID No: 1 or the GATA6 Em isoform nucleic acid sequence with up to 55 additions, deletions or substitutions of SEQ ID NO: 1; or
  ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2.
32. The method of treating a patient according to item 30 or 31, wherein said cancer patient is a patient suffering from lung cancer.
33. The method according to item 32, wherein said lung cancer is non-small cell lung cancer (NSCLC).
34. The method according to item 33, wherein said NSCLC is an adenocarcinoma, a squamous cell carcinoma or a large cell carcinoma.
35. The method according to item 33, wherein said adenocarcinoma is a bronchoalveolar carcinoma.
36. The method according to item 33, wherein said adenocarcinoma is a bronchoalveolar carcinoma, an acinar adenocarcinoma, a papillary adenocarcinoma, a solid adenocarcinoma with mucin production, a adenocarcinoma with mixed subtypes, a variant adenocarcinomas, including well differentiated fetal adenocarcinoma, mucinous (colloid) adenocarcinoma, mucinous cystadenocarcinoma, signet ring adenocarcinoma, or clear cell adenocarcinoma.
37. The method according to item 32, wherein said lung cancer is small cell lung cancer.
38. A composition for use in medicine comprising an inhibitor of
  i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; or
  ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2; or the method of treating a patient according to any one of items 30 to 37, wherein said anti-cancer agent comprises or is a composition for use in medicine comprising an inhibitor of
  i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; or
  ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2
39. The composition for use in medicine of item 38, or the method of treating a patient according to any one of items 30 to 38, wherein said inhibitor comprises a siRNA or shRNA specifically targeting
  i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1;
  ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2;
  iii) the FOXA2 Em isoform comprising the nucleic acid sequence of SEQ ID No: 3 or the FOXA2 Em isoform comprising nucleic acid sequence with up to 68 additions, deletions or substitutions of SEQ ID NO: 3; or
  iv) the ID2 Em isoform comprising the nucleic acid sequence of SEQ ID No: 4 or the ID2 Em isoform comprising nucleic acid sequence with up to 34 additions, deletions or substitutions of SEQ ID NO: 4.
40. The composition for use in medicine of item 39, or the method of treating a patient according to item 39, wherein said siRNA is selected from the group of siRNAs consisting of SEQ ID No: 41 to SEQ ID NO: 46.
41. The composition for use in medicine of item 39, or the method of treating a patient according to item 39, wherein said shRNA is selected from the group of shRNAs consisting of SEQ ID No: 47 to SEQ ID NO: 49.
42. A composition for use in medicine comprising an inhibitor of
  i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; and
  ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2;

or the method of treating a patient according to any one of items 30 to 37, wherein said anti-cancer agent comprises or is a composition for use in medicine comprising an inhibitor of
  i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; and ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2;

43. The composition according to item 42, or the method of treating a patient according to item 42, further comprising an inhibitor of i) the FOXA2 Em isoform comprising the nucleic acid sequence of SEQ ID No: 3 or the FOXA2 Em isoform comprising nucleic acid sequence with up to 68 additions, deletions or substitutions of SEQ ID NO: 3; or ii) the ID2 Em isoform comprising the nucleic acid sequence of SEQ ID No: 4 or the ID2 Em isoform comprising nucleic acid sequence with up to 34 additions, deletions or substitutions of SEQ ID NO: 4

44. The composition for use in medicine of items 38 to 43, or the method of treating a patient according to any one of items 38 to 43, wherein said inhibitor further comprises protamine.

45. The composition for use in medicine of items 38 to 43, or the method of treating a patient according to any one of items 38 to 43, wherein the inhibitor further comprises a fusion protein of protamine and an antigen-targeting polypeptide.

46. The composition for use in medicine of item 45, or the method of treating a patient according to item 45, wherein said antigen-targeting polypeptide is targeting a protein selected from the group of proteins consisting of ITGB2, PTGIS, BASP1, DES, ITGA2, CTSS, PTPRC, ANPEP, FILIP1L, MGLL, OSMR, ITGB6, AGPAT4, ASS1, CSPG4, and CDH11.

47. The composition for use in medicine of item 45 or item 46, or the method of treating a patient according to item 45 or 46, wherein said antigen-targeting polypeptide is a monoclonal antibody or a single chain variable fragment.

48. The composition of any one of items 38 to 47, or the method of treating a patient according to any one of items 38 to 47, for the use in the treatment of a lung disease.

49. The composition of item 48, or the method of treating a patient according to item 48 for the use in the treatment of a lung disease, wherein the lung disease is a lung cancer.

50. The composition of item 49 for the use in the treatment of a lung cancer, or the method of treating a patient according to item 49, wherein said lung cancer is non-small cell lung cancer (NSCLC).

51. The composition of item 50 for the use in the treatment of a lung cancer, or the method of treating a patient according to item 50, wherein said NSCLC is an adenocarcinoma, a squamous cell carcinoma or a large cell carcinoma.

52. The composition of item 51 for the use in the treatment of a lung cancer, or the method of treating a patient according to item 51, wherein said adenocarcinoma is a bronchoalveolar carcinoma.

53. The composition of item 51 for the use in the treatment of a lung cancer, or the method of treating a patient according to item 51, wherein said adenocarcinoma is a bronchoalveolar carcinoma, an acinar adenocarcinoma, a papillary adenocarcinoma, a solid adenocarcinoma with mucin production, a adenocarcinoma with mixed subtypes, a variant adenocarcinomas, including well differentiated fetal adenocarcinoma, mucinous (colloid) adenocarcinoma, mucinous cystadenocarcinoma, signet ring adenocarcinoma, or clear cell adenocarcinoma.

54. The composition of item 49 for the use in the treatment of a lung cancer, or the method of treating a patient according to item 49, wherein said lung cancer is small cell lung cancer.

55. A kit for use in any of the methods according to items 1 to 54 comprising reagents for measuring in a sample specifically the amount of one or two transcription factor isoforms selected from the group of specific transcription factor isoforms consisting of i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1; and ii) the NKX2-1 Em isoform comprising the nucleic acid sequence of SEQ ID No: 2 or the NKX2-1 Em isoform comprising a nucleic acid sequence with up to 39 additions, deletions or substitutions of SEQ ID NO: 2.

56. The kit according to item 55 further comprising reagents for measuring in a sample specifically the amount of one or two transcription factor isoforms selected from the group of specific transcription factor isoforms consisting of iii) the FOXA2 Em isoform comprising the nucleic acid sequence of SEQ ID No: 3 or the FOXA2 Em isoform comprising nucleic acid sequence with up to 68 additions, deletions or substitutions of SEQ ID NO: 3; and iv) the ID2 Em isoform comprising the nucleic acid sequence of SEQ ID No: 4 or the ID2 Em isoform comprising nucleic acid sequence with up to 34 additions, deletions or substitutions of SEQ ID NO: 4.

57. The kit according to item 54 or 55 further comprising reagents for measuring in a sample specifically the amount of one or several further transcription factor isoform(s) selected from the group of specific transcription factor isoforms consisting of i) the GATA6 Ad isoform comprising the nucleic acid sequence of SEQ ID No: 5 or the GATA6 Ad isoform comprising a nucleic acid sequence with up to 55 additions, deletions or substitutions of SEQ ID NO: 5;

ii) the NKX2-1 Ad isoform comprising the nucleic acid sequence of SEQ ID No: 2 or the NKX2-1 Ad isoform comprising the nucleic acid sequence with up to 38 additions, deletions or substitutions of SEQ ID NO: 6;

iii) the FOXA2 Ad isoform comprising the nucleic acid sequence of SEQ ID No: 7 or FOXA2 Ad isoform comprising the nucleic acid sequence with up to 74 additions, deletions or substitutions of SEQ ID NO: 3; and iv) the ID2 Ad isoform consisting of the nucleic acid sequence of SEQ ID No: 8 or ID2 Ad isoform consisting of nucleic acid sequence with up to 30 additions, deletions or substitutions of SEQ ID NO: 8;

58. The kit of any one of items 54 to 57, wherein said sample comprises tumor cells.

59. The kit of item 58, wherein said sample is a breath condensate sample.

60. The kit of item 58, wherein said sample is a biopsy sample.

61. The kit of item 58, wherein said sample is a breath condensate sample, a biopsy sample, a blood sample, a bronchoalveolar lavage fluid sample, a mucus sample or a phlegm sample.

62. The kit of any one of items 58 to 61, wherein said sample is a sample from a human subject.

63. The kit of item 62, wherein the kit comprises one or several primers selected from the group of primers comprising the nucleic acid sequence of SEQ IDs 9 to 40.

The proteins to be targeted in accordance with the above and mentioned in item 32 above can be selected from the group of proteins consisting of ITGB2, PTGIS, BASP1, DES, ITGA2, CTSS, PTPRC, ANPEP, FILIP1L, MGLL, OSMR, ITGB6, AGPAT4, ASS1, CSPG4, and CDH11. The proteins ITGB2, PTGIS, BASP1, DES, ITGA2, CTSS, PTPRC, ANPEP, FILIP1L, MGLL, OSMR, ITGB6, AGPAT4, ASS1, CSPG4, and CDH11 are preferably human. The proteins are known in the art and their respective amino acid sequences and nucleic acid sequences encoding the proteins can be retrieved from the corresponding databases, like Uniprot or NCBI. The following table provides an overview of human proteins ITGB2, PTGIS, BASP1, DES, ITGA2, CTSS, PTPRC, ANPEP, FILIP1L, MGLL, OSMR, ITGB6, AGPAT4, ASS1, CSPG4, and CDH11, showing the gene symbol as used above, the gene name and the accession numbers. By using this information a person skilled in the art is readily in the position to retrieve the sequence of any one of the human proteins ITGB2, PTGIS, BASP1, DES, ITGA2, CTSS, PTPRC, ANPEP, FILIP1L, MGLL, OSMR, ITGB6, AGPAT4, ASS1, CSPG4, and CDH11. These proteins are also described further below in more detail and also exemplary nucleotide and amino acid sequences thereof are provided herein.

| | | Human | | |
|---|---|---|---|---|
| Gene Symbol | Gene Name | Uniprot ID | NCBI Gene ID | NCBI (Transcript, Protein) |
| ITGB2 | Integrin beta-2 | P05107 | 3689 | NM_000211.3, NP_000202.2 |
| PTGIS | prostaglandin I2 (prostacyclin) synthase | Q16647 | 5740 | NM_000961.3, NP_000952.1 |
| BASP1 | brain abundant, membrane attached signal protein 1 | P80723 | 10409 | NM_001271606.1, NP_001258535.1 |
| DES | desmin | P17661 | 1674 | NM_001927.3, NP_001918.3 |
| ITGA2 | integrin, alpha 2 (CD49B, alpha 2 subunit of VLA-2 receptor) | P17301 | 3673 | NM_002203.3, NP_002194.2 |
| CTSS | cathepsin S | P25774 | 1520 | NM_001199739.1, NP_001186668.1 (isoform 2) NM_004079.4, NP_004070.3 (isoform 1) |
| PTPRC | protein tyrosine phosphatase, receptor type, C | Q6PJK7 | 5788 | NM_001267798.1, NP_001254727.1 (isoform 5) NM_002838.4, NP_002829.3 (isoform 1) NM_080921.3, NP_563578.2 (isoform 2) |
| ANPEP | aminopeptidase N precursor | P15144 | 290 | NM_001150.2, NP_001141.2 |
| FILIP1L | filamin A interacting protein 1-like | Q4L180 | 11259 | NM_182909.2, NP_878913.2 (isoform 1) NM_014890.2, NP_055705.2 (isoform 2) NM_001042459.1, NP_001035924.1 (isoform 3) |
| MGLL | monoglyceride lipase | Q99685 | 23945 | NM_011844.4, NP_035974.1 (isoform b) NM_001166251.1, NP_001159723.1 (isoform a) |
| OSMR | oncostatin M receptor | Q99650 | 9180 | NM_001168355.1, NP_001161827.1 (isoform 2) NM_003999.2, NP_003990.1 (isoform 1) |
| ITGB6 | integrin, beta 6 | P18564 | 3694 | NM_000888.3, NP_000879.2 |
| AGPAT4 | 1-acylglycerol-3-phosphate O-acyltransferase 4 | Q9NRZ5 | 56895 | NM_020133.2, NP_064518.1 |
| ASS1 | argininosuccinate synthetase 1 | P00966 | 445 | NM_000050.4, NP_000041.2 |
| CSPG4 | chondroitin sulfate proteoglycan 4 | Q6UVK1 | 1464 | NM_001897.4, NP_001888.2 |
| CDH11 | cadherin 11, type 2, OB-cadherin (osteoblast) | P55287 | 1009 | NM_001797.2, NP_001788.2 |

The following table provides an overview of murine proteins ITGB2, PTGIS, BASP1, DES, ITGA2, CTSS, PTPRC, ANPEP, FILIP1L, MGLL, OSMR, ITGB6, AGPAT4, ASS1, CSPG4, and CDH11, showing the gene symbol as used above, the gene name and the accession numbers. By using this information a person skilled in the art is readily in the position to retrieve the sequence of any one of the murine proteins ITGB2, PTGIS, BASP1, DES, ITGA2, CTSS, PTPRC, ANPEP, FILIP1L, MGLL, OSMR, ITGB6, AGPAT4, ASS1, CSPG4, and CDH11.

| | | Mouse | | |
|---|---|---|---|---|
| Gene Symbol | Gene Name | Uniprot | NCBI Gene ID | NCBI |
| Itgb2 | Integrin beta-2 | P11835 | 16414 | NM_008404.4, NP_032430.2 |
| Ptgis | prostaglandin I2 (prostacyclin) synthase | Q8BXC0 | 19223 | NM_008968.3, NP_032994.1 |
| Basp1 | brain abundant, membrane attached signal protein 1 | Q91XV3 | 70350 | NM_027395.2, NP_081671.1 |
| Des | desmin | P31001 | 13346 | NM_010043.1, NP_034173.1 |
| Itga2 | integrin, alpha 2 (CD49B, alpha 2 subunit of VLA-2 receptor) | Q62469 | 16398 | NM_008396.2, NP_032422.2 |
| Ctss | cathepsin S | Q3U5K1 | 13040 | NM_021281.2, NP_067256.3 NM_001267695.1, NP_001254624.1 |
| Ptprc | protein tyrosine phosphatase, receptor type, C | P06800 | 19264 | NM_001111316.2, NP_001104786.2 (isoform 1) NM_001268286.1, NP_001255215.1 NM_011210.4, NP_035340.3 (isoform 2) |
| Anpep | aminopeptidase N precursor | P97449 | 16790 | NM_008486.2, NP_032512.2 |
| Filip1l | filamin A interacting protein 1-like | Q6P6LO | 78749 | NM_001040397.4, NP_001035487.2 (isoform 1) NM_001177871.1, NP_001171342.1 (isoform 2) |
| Mgll | monoglyceride lipase | O35678 | 11343 | NM_007283.6, NP_009214.1 (isoform 1) NM_001256585.1, NP_001243514.1 (isoform 3) NM_001003794.2, NP_001003794.1 (isoform 2) |
| Osmr | oncostatin M receptor | O70458 | 18414 | NM_011019.3, NP_035149.2 |
| Itgb6 | integrin, beta 6 | Q9Z0T9 | 16420 | NM_001159564.1, NP_001153036.1 |
| Agpta4 | 1-acylglycerol-3-phosphate O-acyltransferase 4 | Q8K4X7 | 68262 | NM_026644.2, NP_080920.2 |
| Ass1 | argininosuccinate synthetase 1 | P16460 | 11898 | NM_007494.3, NP_031520.1 |
| Cspg4 | chondroitin sulfate proteoglycan 4 | Q8VHY0 | 121021 | NM_139001.2, NP_620570.2 |
| Cdh11 | cadherin 11, type 2, OB-cadherin (osteoblast) | P55288 | 12552 | NM_009866.4, NP_033996.4 |

Herein above, markers, in particular GATA6 Em isoform and NKX2-1 Em isoform, for the diagnosis of cancer, particularly lung cancer, have been provided and described. These markers are highly expressed in cancer and are therefore useful as targets in the therapy of cancer. The following provide nucleic acid delivery systems that can be used in the therapy of these cancers or as research tools, inter alia, targeting GATA6 Em isoform and NKX2-1 Em isoform. Accordingly, the present invention relates also to a nucleic acid delivery system, in particular, an alveolar type II cell directed nucleic acid delivery system for the treatment of lung diseases. Provided is a nucleic acid delivery system for the delivery of nucleic acids specifically into an alveolar type II epithelial cell (ATII cells), wherein said system comprises a polypeptide binding to a specific surface marker of ATII cells, wherein said specific surface marker is ITGB2 or ITGB6. Moreover, the present invention relates to the use of the nucleic acid delivery system in the treatment of a lung disease.

The lung is a complex organ consisting of different epithelial and mesenchymal cell lineages organized in a proximal-distal manner, with several specialized cell types that form the functional gas exchange interface required for postnatal respiration (FIG. 19, [21639799, 20531299]). The lung shows slow homeostatic turnover but rapid repair after injury, and tissue-resident lung-endogenous progenitor cell niches located in specific regions along the proximal-distal axis of the airways are thought to be responsible for both processes (Rawlins and Hogan, 2006). ATII cells represent one of these regional progenitor cell populations and are located in the alveoli. ATII cells are responsible for regeneration of alveolar epithelium during homeostatic turnover and in response to injury [PMID: 4812806, 163758, 12922980, 21079581]. ATII cells have been related to a diversity of lung diseases including lung cancer, pulmonary fibrosis, chronic obstructive pulmonary disease (COPD), emphysema and cystic fibrosis [PMID: 22411819, 23134111, 19934355, 16888288, 19335897]. Thus, characterization of the regulatory mechanisms controlling the proper balance between expansion and differentiation of ATII cells will have a profound impact on our understanding and treatment of lung disease. However, detailed characterization of ATII cells has been challenging since the most specific known cellular marker for these cells (surfactant associated protein C, SFTPC or SP-C) is a secreted molecule making difficult the enrichment of a homogenous population of these cells. Furthermore, a lack of reliable cell markers of ATII cells hampers the specific targeting of said cells using siRNAs or alternative agents. Thus, there is a great need to identify specific ATII cell markers to provide means and methods to target ATII cells specifically. Accordingly, the technical problem underlying the present invention is the provision of means and methods to target ATII cells specifically.

The technical problem is solved by provision of the embodiments herein, inter alia, in the items below.

1. A nucleic acid delivery system for the delivery of nucleic acids specifically into an alveolar type-II epithelial cell, wherein said system comprises a polypeptide binding to a specific surface marker of alveolar type-II epithelial cells, wherein said specific surface marker is Itgb2 or Itgb6.
2. The nucleic acid delivery system according to item 1, wherein said polypeptide is a monoclonal antibody or a single chain variable fragment.
3. The nucleic acid delivery system according to item 1 or 2, wherein said polypeptide is fused to a nucleic acid binding molecule.
4. The nucleic acid delivery system according to item 3, wherein said nucleic acid binding molecule is protamine or a polypeptide having at least 90% identity with protamine and having nucleic acid binding activity.
5. The nucleic acid delivery system according to any one of items 1 to 4, wherein said system comprises a nucleic acid, such as an siRNA or shRNA.
6. The nucleic acid delivery system according to item 5, wherein said siRNA is specifically targeting an mRNA being upregulated in a lung disease, like lung cancer, such as adenocarcinoma or a bronchoalveolar carcinoma.
7. The nucleic acid delivery system according to item 5 or 6, wherein said siRNA is targeting
   i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1;
   ii) the NKX2-1 Em isoform comprising the nucleic acid sequence of SEQ ID No: 2 or the NKX2-1 Em isoform comprising the nucleic acid sequence with up to 39 additions, deletions or substitutions of SEQ ID NO: 2;
   iii) the FOXA2 Em isoform comprising the nucleic acid sequence of SEQ ID No: 3 or the FOXA2 Em isoform comprising nucleic acid sequence with up to 68 additions, deletions or substitutions of SEQ ID NO: 3; or
   iv) the ID2 Em isoform comprising the nucleic acid sequence of SEQ ID No: 4 or the ID2 Em isoform comprising nucleic acid sequence with up to 34 additions, deletions or substitutions of SEQ ID NO: 4;
8. The nucleic acid delivery system according to any one of items 1 to 7, wherein said surface marker Itgb2 has the amino acid sequence as shown in SEQ ID NO. 110, and wherein said surface marker Itgb6 has the amino acid sequence as shown in SEQ ID NO. 150.
9. Use of the nucleic acid delivery systems of any one of items 1 to 8 for the transfection of specifically alveolar type-II epithelial cells.
10. A composition comprising (an) siRNA(s) targeting
   i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1;
   ii) the NKX2-1 Em isoform comprising the nucleic acid sequence of SEQ ID No: 2 or the NKX2-1 Em isoform comprising the nucleic acid sequence with up to 39 additions, deletions or substitutions of SEQ ID NO: 2;
   iii) the FOXA2 Em isoform comprising the nucleic acid sequence of SEQ ID No: 3 or the FOXA2 Em isoform comprising nucleic acid sequence with up to 68 additions, deletions or substitutions of SEQ ID NO: 3; or
   iv) the ID2 Em isoform comprising the nucleic acid sequence of SEQ ID No: 4 or the ID2 Em isoform comprising nucleic acid sequence with up to 34 additions, deletions or substitutions of SEQ ID NO: 4;

and a fusion protein of protamine and an Itgb2-, or Itgb6-targeting monoclonal antibody or single chain variable fragment.
11. A composition for use in medicine comprising the nucleic acid delivery system of any one of items 1 to 8 or the composition of item 10.
12. The composition according to item 11 for the use in the treatment of a lung disease.
13. The composition according to item 11 for the use in the treatment of lung cancer.
14. The composition according to item 11 for the use in the treatment of lung adenocarcinoma or lung bronchoalveolar carcinoma.
15. A nucleic acid delivery system for the delivery of nucleic acids into an alveolar type-II epithelial cell according to any of items 1 to 8, wherein the nucleic acid delivery system is a non-viral nucleic acid delivery system; or the composition according to any of items 10 to 14, wherein the composition is characterized by being a substantially non-viral composition.

Furthermore, the present invention relates to the following items:

1. A nucleic acid delivery system for the delivery of nucleic acids specifically into an alveolar type-II epithelial cell, wherein said system comprises a polypeptide binding to a specific surface marker of alveolar type-II epithelial cells, wherein said specific surface marker is Itgb2 or Itgb6.
2. The nucleic acid delivery system according to item 1, wherein said polypeptide is a monoclonal antibody or a single chain variable fragment.

3. The nucleic acid delivery system according to items 1 or 2, wherein said polypeptide is fused to a nucleic acid binding molecule.
4. The nucleic acid delivery system according to item 3, wherein said nucleic acid binding molecule is protamine or a polypeptide having at least 70%, 75%, 80%, 85% or at least 90%, 95%, 96%, 97%, 98% or at least 99% identity with protamine and having nucleic acid binding activity.
5. The nucleic acid delivery system according to items 1 to 4, wherein said system comprises a nucleic acid, such as an siRNA or shRNA.
6. The nucleic acid delivery system according to item 5, wherein said siRNA is specifically targeting an mRNA being upregulated in a lung disease.
7. The nucleic acid delivery system according to item 6, wherein said lung disease is lung cancer.
8. The nucleic acid delivery system according to item 7, wherein said lung cancer is an adenocarcinoma or a bronchoalveolar carcinoma.
9. The nucleic acid delivery system according to item 7 or 8, wherein said mRNA being upregulated in a lung disease is upregulated in lung cancer.
10. The nucleic acid delivery system according to items 5 to 9, wherein said siRNA is targeting
    i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1;
    ii) the NKX2-1 Em isoform comprising the nucleic acid sequence of SEQ ID No: 2 or the NKX2-1 Em isoform comprising the nucleic acid sequence with up to 39 additions, deletions or substitutions of SEQ ID NO: 2;
    iii) the FOXA2 Em isoform comprising the nucleic acid sequence of SEQ ID No: 3 or the FOXA2 Em isoform comprising nucleic acid sequence with up to 68 additions, deletions or substitutions of SEQ ID NO: 3; or
    iv) the ID2 Em isoform comprising the nucleic acid sequence of SEQ ID No: 4 or the ID2 Em isoform comprising nucleic acid sequence with up to 34 additions, deletions or substitutions of SEQ ID NO: 4;
11. A composition comprising (an) siRNA(s) targeting
    i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1;
    ii) the NKX2-1 Em isoform comprising the nucleic acid sequence of SEQ ID No: 2 or the NKX2-1 Em isoform comprising the nucleic acid sequence with up to 39 additions, deletions or substitutions of SEQ ID NO: 2;
    iii) the FOXA2 Em isoform comprising the nucleic acid sequence of SEQ ID No: 3 or the FOXA2 Em isoform comprising nucleic acid sequence with up to 68 additions, deletions or substitutions of SEQ ID NO: 3; or
    iv) the ID2 Em isoform Em comprising the nucleic acid sequence of SEQ ID No: 4 or the ID2 Em isoform Em comprising nucleic acid sequence with up to 34 additions, deletions or substitutions of SEQ ID NO: 4;

and a fusion protein of protamine and an Itgb2-, or Itgb6-targeting monoclonal antibody or single chain variable fragment.
12. A kit for the delivery of a nucleic acid into an alveolar type-II epithelial cell comprising any of the nucleic acid delivery systems of items 1 to 10 or the composition of item 11.
13. Use of the nucleic acid delivery systems of items 1 to 10 for the transfection of specifically alveolar type-II epithelial cells.
14. A composition for use in medicine comprising any of the nucleic acid delivery systems of items 1 to 10 or the composition of item 11.
15. The composition according to item 14 for the use in the treatment of a lung disease.
16. The composition according to item 14 for the use in the treatment of lung cancer.
17. The composition according to item 14 for the use in the treatment of lung adenocarcinoma or lung bronchoalveolar carcinoma.
18. A nucleic acid delivery system for the delivery of nucleic acids into an alveolar type-II epithelial cell according to any of items 1 to 10, wherein the nucleic acid delivery system is a non-viral nucleic acid delivery system.
19. The composition according to any of items 11 or 14 to 17, wherein the composition is characterized by being a substantially non-viral composition.
20. A method of treating a subject suffering from cancer or a subject with an increased risk of suffering from cancer comprising the step of administering to said subject the nucleic acid delivery system according to items 1 to 10 or 18.
21. The method of item 20, wherein the subject is a human subject.
22. The method of item 20, wherein said cancer is a lung cancer.
23. The method of item 22, wherein said lung cancer is an adenocarcinoma or a bronchoalveolar carcinoma.

The present invention relates to a nucleic acid delivery system for the delivery of nucleic acids specifically into an alveolar type-II epithelial cell (ATII cells), wherein said system comprises a polypeptide binding to a specific surface marker of alveolar type-II epithelial cell (ATII cells), wherein said specific surface marker is ITGB2 or ITGB6.

Furthermore, the present invention relates to a nucleic acid delivery system for the delivery of nucleic acids specifically into an alveolar type-II epithelial cell (ATII cell), wherein said system comprises a polypeptide binding to a specific surface marker of alveolar type-II epithelial cell (ATII cells), wherein said specific surface marker is selected from the group consisting of ITGB2, PTGIS, BASP1, DES, ITGA2, CTSS, PTPRC, ANPEP, FILIP1L, MGLL, OSMR, ITGB6, AGPAT4, ASS1, CSPG4, and CDH11.

The terms “alveolar type II cell”, “alveolar type II epithelial cell”, “alveolar type-II epithelial cell”, “AT-II cell”, “ATII cell” and the like can be used interchangeably herein.

Metabolic labeling of living organisms with stable isotopes has become a powerful tool for global protein quantitation. The SILAC (stable isotope labeling with amino acids in cell culture) approach is based on the incorporation of nonradioactive-labeled isotopic forms of amino acids into cellular proteins [PMID: 12118079]. The effective SILAC labeling of immortalized cells and single-cell organisms (e.g., yeast and bacteria) was recently extended to more complex organisms, including worms, flies, and even rodents [PMID: 18662549]. The administration of a $^{13}C_6$-lysine (Lys6—heavy) containing diet for one mouse generation leads to a complete exchange of the natural isotope $^{12}C_6$-lysine (Lys0-light). Here we used the lung of the fully labeled SILAC mice as a heavy “spike-in” standard into nonlabeled samples of murine ATII or MLE-12 cells (mouse lung epithelial cell line) in combination with high-performance mass spectrometry to analyze fractions of membrane proteins. By a comparison of the membrane protein fractions of ATII cells, MLE-12 cells and whole adult lung derived from the SILAC mouse, we were able to identify membrane proteins that are enriched in ATII cells. A comparison of the results obtained by the proteomic approach with an Affymetrix microarray based expression analysis of ATII cells led us to the identification of 16 membrane proteins that are present and highly expressed in ATII cells; see FIG. 22. These 16 membrane proteins are ITGB2, PTGIS, BASP1, DES, ITGA2, CTSS, PTPRC, ANPEP, FILIP1L, MGLL, OSMR, ITGB6, AGPAT4, ASS1, CSPG4, and CDH11. Exemplary amino acid sequences and nucleic acid sequences encoding same are shown in SEQ ID NO. 108 to 126 and 128 to 159.

The 16 membrane proteins described above constitute surface markers of ATII cells that will be recognized by the nucleic acid delivery system of the present invention thereby allowing ATII cell specific targeting. Upon recognition, it is believed that the above described surface proteins of ATII cells will facilitate the internalization of the nucleic acid delivery system of the present invention thereby mediating ATII cell specific delivery. The potential of nucleic acids delivery systems into specific cells using antibodies recognizing cell surface proteins has been previously demonstrated (Schneider (2012) Molecular Therapy-Nucleic Acids. 1, e46; Dou (2012) Journal of Controlled Release. 16, 875-883; Song (2005) NATURE BIOTECHNOLOGY 23(6), 709-717).

It is envisaged herein that the nucleic acid delivery systems can be administered by using an aerosol that will be inhaled thereby ensuring ATII cell specific targeting. The aerosol contains the nucleic acid delivery provided herein.

The herein provided nucleic acid delivery systems are not only useful as a research tool to further characterize ATII cells. The nucleic acid delivery systems can also be used in medical intervention in diseases associated with ATII cells. For example, ATII cells have been related to a diversity of lung diseases including lung cancer (like lung adenocarcinoma), pulmonary fibrosis, chronic obstructive pulmonary disease (COPD), emphysema and cystic fibrosis [PMID: 22411819, 23134111, 19934355, 16888288, 19335897]. Thus, the present invention allows the targeting of the ATII cells to provide means for the treatment of lung diseases (including lung cancer (like lung adenocarcinoma), pulmonary fibrosis, chronic obstructive pulmonary disease (COPD), emphysema and cystic fibrosis) that arise from or are associated with ATII cells. For example, antibodies against any of the 16 membrane proteins that were identified as ATII cell specific can be used in context of the herein provided nucleic acid delivery system. A combination of the nucleic acid delivery system of the present invention with known as well as newly identified specific agents will help to prevent and to treat a diversity of lung diseases, to which ATII cells have been or will be related, including but not limited to lung cancer, pulmonary fibrosis, chronic obstructive pulmonary disease (COPD), emphysema and cystic fibrosis.

Recently, it was shown that ATII cells are the cells of origin of lung adenocarcinoma (Xu et al 2012, PNAS, word wide web at pnas.org/cgi/doi/10.1073/pnas.1112499109). In addition, data are provided herein (see Example 12 and FIGS. 25 and 26) which support that lung adenocarcinoma originates from ATII cells.

Lung cancer is a typical model cancer with a very high prevalence. Lung cancer is the most frequent cause of cancer related deaths worldwide. There are two major classes of lung cancer, non small cell lung cancer (contributing to 85% of all lung cancers) and small cell lung cancer (the remaining 15%). Lung cancer cells show an enhanced expression of transcription factors that are present during embryonic development in the endoderm as GATA6 (GATA Binding Factor 6), NKX2-1 (NK2 homeobox 1, also known as Ttf-1, Thyroid transcription factor-1), FOXA2 (Forkhead box protein A2), and ID2 (Inhibitor of DNA binding 2) (Guo M et al., (2004) Clin Cancer Res. 10(23): 7917-24; Kendall J et al, (2007) Proc Natl Acad Sci USA. 104(42): 16663-8; Tang Y et al., (2011) Cell Res. 21(2): 316-26; Rollin J et al., (2009) PLoS One. 4(1): e4158). It was recently demonstrated that lung adenocarcinoma initiates from clonal expansion of cells expressing high levels of Nkx2-1 and progress to a more aggressive state with low expression of Nkx2-1 (see Winslow (2011) Nature 473(7345): 101-104). GATA6 has been shown to be abundantly expressed in malignant mesotheliomas, and to a small extent, in metastatic adenocarcinomas (see Lindholm (2009) Journal of Clinical Pathology 62(4): 339-344). In addition, GATA6 regulates tumorigenesis related genes, such as KRAS, an oncogene activated by point mutations (see Gorshkove (2005) Biochemistry (Mosc):70: 1180-1184).

GATA6, FOXA2 and NKX2-1 are crucial for early lung development. Genetic analyses with knockout animals demonstrated their role in lung endoderm differentiation and post natal repair and homeostasis. Nkx2-1, Gata6 and Foxa2 are expressed in respiratory epithelial cells throughout lung morphogenesis. They all have been shown to bind and trans-activate many lung specific promoters, including SftpA-, SftpB-, SftpC- and Scgb1a1-promoters (Bruno M D et al., (1995) 270(12): 6531-6; Margana R K and Boggaram V. (1997) J Biol Chem. 272(5): 3083-90). Mice harboring a Nkx2-1 null mutation show severe attenuation of lung airway branching. In addition, the lung epithelial cells present in these mice lack expression of putative targets like SftpC (Minoo P et al., (1999) Dev Biol. 209(1): 60-71). Conditional deletion of Gata6 in the lung endoderm demonstrated its central role in lung endoderm gene expression, proliferation and branching morphogenesis. (Keijzer R et al., (2001) Development 128(4): 503-11). A loss of Foxa2 in the lung can be compensated by Foxa1. However, a loss of both Foxa1/2 also dramatically inhibits endoderm differentiation and branching morphogenesis. (Wan H et al., (2005) J Biol Chem. 280(14): 13809-16). Foxa2 has also been shown to be essential for the transition to breathing air at birth (Wan H et al., (2004) Proc Natl Acad Sci USA. 101(40): 14449-54).

It was demonstrated by the disclosure of a patent application that will be submitted back-to-back with the present application that GATA6, NKX2-1, FOXA2 and ID2 share a common gene structure, with two promoters driving the expression of two distinct transcripts. It is surprisingly found that though different isoforms exist only one is oncogenic and is indicative of the presence/development of cancer (see Examples 2 and 3). The embryonic GATA6 and NKX2-1 “Em” transcripts as defined herein are found to be detectable in high levels in human lung cancer cell lines and patient lung cancer biopsies (see Examples 2 and 3). Remarkably, these cancer specific isoforms are oncogenic and forced overexpression in cell lines as well as in mice results in a tumorigenic phenotype (see Examples 4, 6 and 7). This is illustrated by the finding that mice develop adenocarcinoma as early as 5 weeks after transfection with one of those specific embryonic “Em” isoforms. Further, it is surprisingly found that these specific “Em” isoforms can be detected in the blood of mice that are induced for tumor formation, showing their usability as early diagnostic markers for cancer, in particular lung cancer (see Example 3). In addition, overexpression of hyperactive KRAS G12D mutant increases the expression of embryonic Gata6 and Nkx2-1 (FIG. 9), supporting the involvement of the embryonic isoforms in KRAS induced malignant transformation. Furthermore, siRNA mediated loss-of-function of Gata6 Em reduces the number and the size of lung tumors after tail vein injection of LLC1 cells (FIG. 8), demonstrating the therapeutic potential of targeting the embryonic isoforms. In a normal, healthy ATII cell, the embryonic isoforms should be expressed at very low level. Only after transformation of a normal cell into a cancer cell the expression of the embryonic isoforms increases dramatically.

Therefore, it is plausible that the nucleic acid delivery system provided herein can be used to treat ATII relates lung diseases, like lung adenocarcinoma, for example via an ATII cell directed loss-of-function of the embryonic isoforms of GATA6, NKX2-1, FOXA2 and/or ID2.

Furthermore, it was confirmed that integrin beta 2 and 6 (ITGB2 and ITGB6) are indeed present in ATII cells. Integrins are heterodimeric cell adhesion molecules that are formed by specific non-covalent associations of an alpha and a beta subunit [22819514]. In general each integrin subunit has a large extracellular region, a single pass transmembrane domain and a short cytoplasmic tail [PMID: 21421922]. Integrins mediate cell-cell and cell-ECM (extracellular matrix) interaction and transmit signals across the plasma membrane in both directions between their extracellular ligand binding adhesion sites and their cytoplasmic domain [PMID: 12297042, 22458844], thereby linking the cytoskeleton to several signal transduction pathways [21900405, 18441324, 15863032, 15554942, 15053919]. Surprisingly, a close analysis of the membrane protein fraction of ATII cells showed an enrichment of proteins that are involved in WNT signaling. Therefore WNT signaling was analyzed in the lung of Itgb2$^{-}$/$^{-}$ mice [8700894]. Enhanced expression and increased protein levels of WNT targets were found in the lung of Itgb2$^{-}$/$^{-}$ mice. It was found that Itgb2 seems to be required for a negative regulation of WNT signaling in the adult lung. Moreover, ectopic expression of Itgb2 in MLE-12 cells counteracted the lithium chloride (LiCl) induced enhancement of WNT signaling. It is shown herein that ITGB2 and ITGB6 are cell surface markers for a subpopulation of ATII cells. Proteins that are involved in WNT signaling are enriched in the membrane of ATII cells, showing an important role of this pathway. Furthermore, Itgb2 is required for a negative regulation of WNT signaling in the lung.

Integrins have been involved in lung development, lung epithelial cell differentiation and epithelial repair after lung injury [PMID: 12242717; 18725542; 12843406, 16169900, 20363851]. The epithelial cells of the airways express multiple members of the integrin family. Although the multiple integrins on airway epithelial cells may have overlapping ligand binding specificities thereby supporting adhesion to the same molecules of the extracellular matrix (ECM), the functional roles of each integrin that has been examined in detail are quite distinct. Several integrins are able to activate latent transforming growth factor beta 1 (TGFB1) located in the ECM thereby showing a critical role of ECM and integrins in regulating TGFB signaling [PMID 21900405, 23046811]. Integrins play a role in fibroblast growth factor (FGF) signaling through cross-talk with FGF receptors [18441324; 15863032].

A regulation of WNT signaling by cell-cell and cell-ECM adhesion has been suggested to be mediated by integrin outside-in signaling [PMID: 15554942; 15053919]. Although the majority of recent studies in embryonic stem cells and organ progenitor cells have focused on the role of growth factors, such as TGFB, FGF and WNT, relatively little is known about the role of ECM-integrin signaling. Recent data provide evidence that ECM-integrin signaling promotes differentiation of human embryonic stem cells toward definitive endoderm [PMID 23154389], an early embryonic cell population fated to give rise to specific organs such as the lung, liver, pancreas, stomach, and intestine. In the mouse adult lung, a subpopulation of alveolar epithelial cells expressing Itga6 and Itgb4 has been reported to have regenerative potential after lung injury making it a strong candidate as progenitor cells during alveolar epithelium repair [21701069; 21701072]. The data provided herein confirmed that integrin beta 2 and 6 (ITGB2 and ITGB6) are indeed present in ATII cells.

Further characterization of these cells after sorting and enrichment of a homogenous cell population could have a profound impact on our understanding on the regulatory mechanisms controlling the proper balance between expansion and differentiation of ATII cells. In addition, it will be relevant for clinical applications to determine the regenerative potential of these ITGB2- and ITGB6-positive cells using lung injury models. The herein described surface markers of ATII cells (ITGB2, PTGIS, BASP1, DES, ITGA2, CTSS, PTPRC, ANPEP, FILIP1L, MGLL, OSMR, ITGB6, AGPAT4, ASS1, CSPG4, and CDH11) can be used in accordance with the present invention to sort and/or enrich ATII cells. Accordingly, a cell population enriched in ATII cells is provided herein.

ATII cells have been related to a diversity of lung diseases including lung cancer, pulmonary fibrosis, chronic obstructive pulmonary disease (COPD), emphysema and cystic fibrosis [PMID: 22411819, 23134111, 19934355, 16888288, 19335897]. On the other hand, integrins have been related to different processes in the lung like regulation of lung inflammation, macrophage protease expression, pulmonary fibrosis, the pulmonary edema that follows acute lung injury and malignant transformation [PMID: 12843406, 23046811, 18378634, 14527926, 22802286]. Thus our data suggest that Itgb2 and Itgb6 are attractive as diagnostic and therapeutic targets for intervention in a number of common lung disorders (like lung cancer, pulmonary fibrosis, chronic obstructive pulmonary disease (COPD), emphysema and cystic fibrosis, lung inflammation, macrophage protease expression, pulmonary fibrosis, the pulmonary edema that follows acute lung injury and malignant transformation. Indeed, significant efforts have been directed towards the development of advanced molecular tools for an integrin-mediated drug delivery in cancer and cardiovascular diseases with peptide-functionalized nanoparticles [22612699].

The present invention relates to a nucleic acid delivery system for the delivery of nucleic acids specifically into an alveolar type-II epithelial cell (ATII cell), wherein said system comprises a polypeptide binding to a specific surface marker of alveolar type-II epithelial cell (ATII cells), wherein said specific surface marker is selected from the group consisting of ITGB2, PTGIS, BASP1, DES, ITGA2, CTSS, PTPRC, ANPEP, FILIP1L, MGLL, OSMR, ITGB6, AGPAT4, ASS1, CSPG4, and CDH11.

The present invention relates to a nucleic acid delivery system for the delivery of nucleic acids specifically into an alveolar type-II epithelial cell (ATII cell), wherein said system comprises a polypeptide binding to a specific surface marker of alveolar type-II epithelial cell (ATII cells), wherein said specific surface marker is ITGB2 or ITGB6.

In accordance with the above, the present invention provides a nucleic acid delivery system for the delivery of nucleic acids into an alveolar type-II epithelial cell (ATII cell), wherein said system comprises a polypeptide binding to a specific surface marker of alveolar type-II epithelial cell (ATII cells). Preferably, the nucleic acid delivery system is for the delivery of nucleic acids specifically into an alveolar type-II epithelial cell (ATII cell).

A "nucleic acid delivery system" according to the present invention can be any system capable of introducing or transferring a nucleic acid into a cell. Suitable systems taking advantage of surface markers are described in the art, such as (Schneider (2012) loc. cit.; Dou (2012) loc. cit., or Song (2005) loc. cit. (see also PMID: 12067443 PMID 9862854 PMID: 16146351 PMID: 16606824 PMID: 16778167 PMID: 16823371 PMID: 11156528 PMID: 15908939 PMID: 21902630) which are incorporated herein by reference in their entirety.

The term "specific surface marker of alveolar type-II epithelial cell (ATII cells)" as used herein refers to a membrane protein. The membrane protein is primarily found at the surface of alveolar type-II epithelial cells (ATII cells). The "specific surface marker of alveolar type-II epithelial cell (ATII cells)" is therefore characteristic or specific for alveolar type-II epithelial cell (ATII cells). For example, other lung cell types do not have such a "specific surface marker of alveolar type-II epithelial cell (ATII cells)" (e.g. other lung cell types do not have such a "specific surface marker of alveolar type-II epithelial cell (ATII cells)" in detectable amounts). Other lung cell types than alveolar type-II epithelial cell (ATII cells) can, for example, have significantly less "specific surface marker of alveolar type-II epithelial cell (ATII cells)" than alveolar type-II epithelial cell (ATII cells).

Exemplary "specific surface markers of alveolar type-II epithelial cell (ATII cells)" of the present invention are ITGB2, ITGB6, PTGIS, BASP1, DES, ITGA2, CTSS, PTPRC, ANPEP, FILIP1L, MGLL, OSMR, AGPAT4, ASS1, CSPG4, and CDH11. Preferred specific surface markers are ITGB2 and ITGB6. Exemplary amino acid sequences of the surface markers and nucleic acid sequences encoding these surface markers are shown in SEQ ID NO:s 108-126 and 128 to 159. Also the use of variants of these surface markers (like variants with SNP polymorphisms or other genetic variants, like mutants) is envisaged herein without deferring from the gist of the present invention. Furthermore, also membrane proteins having a certain level of identity (like at least 80%, at least 90%, at least 91%, at least 92%, at least 93%, at least 94%, at least 95%, at least 96%, at least 97%, at least 98%, or at least 99%) to any of these membrane proteins as shown in the above SEQ ID NO.s is envisaged in accordance with the present invention.

The "nucleic acid delivery system" according to the present invention comprises a polypeptide binding to a specific surface marker of alveolar type-II epithelial cell (ATII cells) as described herein. The "nucleic acid delivery system" according to the present invention can be used as a transfection system for the targeted transfection of alveolar type-II epithelial cell (ATII cells). Said polypeptide can induce internalization of the surface marker(s), thereby allowing or facilitating or enhancing the transport/delivery of (a) nucleic acid(s) into the alveolar type-II epithelial cell(s) (ATII cell(s)) (s). Alternatively, the polypeptide binds to the specific surface marker without inducing its internalization. The delivery of the nucleic acids can be achieved by taking advantage of the naturally occurring internalization procedure of the surface markers. It is believed that the entire surface marker-polypeptide-complex (including e.g. nucleic acids bound to the polypeptide either directly or indirectly) is internalized and that thereby the nucleic acid is delivered into the ATII cell. It is envisaged that the nucleic acids to be delivered into the ATII cells are bound either directly or indirectly to the polypeptide. Indirect binding can involve the use of a nucleic acid binding molecule like protamine, histones, high mobility group proteins, a cell-permeant RNA-binding protein, a HIV-1 TAT peptide, or a polypeptide sharing at least 60% identity with one of those polypeptides, at least 65%, 70%, 75%, 80%, 85%, preferably at least 90%, 95%, 96%, 97%, 98% or 99% and having nucleic acid binding capability. A "nucleic acid binding molecule" according to the present invention can be protamine. A "nucleic acid binding molecule" according to the present invention can be digoxigenin or nano particles.

A "polypeptide binding to a specific surface marker of alveolar type-II epithelial cell (ATII cells)" according to the present invention can be any polypeptide (e.g. haptens or antibodies and the like) which shows binding capacity to a "specific surface marker" of an alveolar type-II epithelial cell (ATII cells). In particular, such a polypeptide can be an antibody or a fragment of an antibody, like for example a Fab fragment an F(ab)' fragment of an antibody, or a $F(ab)_2$-fragment. The antibody can be a full antibody (immunoglobulin), a murine antibody, a chimeric antibody, a humanized antibody, a human antibody, a deimmunized antibody, a single-chain antibody, a CDR-grafted antibody, a bivalent antibody-construct, a synthetic antibody, a bispecific single chain antibody or a cross-cloned antibody. A "polypeptide binding to a specific surface marker of alveolar type-II epithelial cell (ATII cells)" according to the present invention can be a monoclonal antibody or a single chain variable fragment.

A person skilled in the art is readily in the position to generate antibodies binding to a specific surface maker. Polyclonal or monoclonal antibodies or other antibodies (derived therefrom) can be routinely prepared using, inter alia, standard immunization protocols; see Ed Harlow, David Lane, (December 1988), Antibodies: A Laboratory Manual, Cold Spring Harbor Laboratory; or Ed Harlow, David Lane, (December 1998), Portable Protocols (Using Antibodies): A Laboratory Manual 2nd edition, Cold Spring Harbor Laboratory.

For example, immunization may involve the intraperitoneal or subcutaneous administration of the surface marker (and/or fragments, isoforms, homologues and so on) as defined herein to a mammal (e.g. rodents such as mice, rats, hamsters and the like). Preferably, fragments of the surface marker are used, wherein the fragment preferably comprises the extracellular domain of the surface marker (or a part thereof). For example, a fragment, e.g. of the extracellular domain, of the surface marker ITGB2 (preferably ITGB2 shown in SEQ ID NO: 110) may be used. For example, a fragment, e.g. of the extracellular domain, of the surface marker ITGB6 (preferably ITGB6 shown in SEQ ID NO: 150) may be used.

The fragment can consist of five, six, seven, eight, nine, ten, eleven, twelve, thirteen, fourteen, fifteen or sixteen or more of the entire surface marker, particularly of the extraceullar domain thereof. Corresponding fragments (peptides) may be prepared by enzymatic hydrolysis or by chemical synthesis.

For example, antibodies recognizing the surface marker may be affinity purified. ELISA is commonly used for screening sera and/or assaying affinity column fractions. Western Blots can be used to demonstrate that the antibody can detect the actual protein of interest and to evaluate whether the antibody only recognizes the protein of interest, or if it cross-reacts with other proteins.

A person skilled in the art is in the position to apply and to adapt the teaching of these documents for the generation and validation of antibodies specifically binding to or specifically recognizing the polypeptides as defined herein in context of the present invention.

"Alveolar type-II epithelial cell (ATII cells)" and their characteristics are well known [PMID: 4812806; PMID: 163758; PMID: 21079581; PMID: 62893; PMID: 12922980; PMID: 9151120; PMID: 8770063; PMID: 7917310] An "alveolar type-II epithelial cell (ATII cells)" according to the present invention is an "alveolar type-II epithelial cell (ATII cells)" having at least one surface marker of the group consisting of ITGB2, ITGB6, PTGIS, BASP1, DES, ITGA2, CTSS, PTPRC, ANPEP, FILIP1L, MGLL, OSMR, ITGB6, AGPAT4, ASS1, CSPG4, and CDH11. An "alveolar type-II epithelial cell (ATII cells)" according to the present invention can have at least the surface marker ITGB2 and/or ITGB6. The one or more surface marker can be enriched on the cell surface of an "alveolar type-II epithelial cell (ATII cells)" according to the present invention. The one or more surface marker can be enriched on the cell surface of an "alveolar type-II epithelial cell (ATII cells)" according to the present invention compared to other lung cell lines, e.g. in MLE-12 cells.

An exemplary nucleic delivery system for use in the present invention, wherein the nucleic acid is directly (via a digoxigenin label) bound to a polypeptide is described in Schneider (2012) loc. cit. This delivery system can be used in context of the present invention: A bispecific antibody (e.g. a bispecific monoclonal antibody or bispecific single chain variable fragment or bispecific single chain antibody) can be used, wherein a first variable domain is capable of binding to a surface marker and a second variable domain is capable of binding to digoxigenin. The nucleic acids (like siRNAs and the like) can be labeled with digoxigenin e.g. at its 3' ends. The bispecific antibody binds to both the surface marker and the digoxigenin labeled nucleic acid and thereby effects delivery of the siRNA into the ATII cells.

The "polypeptide binding to a specific surface marker of alveolar type-II epithelial cell (ATII cells)" according to the present invention can be fused to or otherwise bound to a nucleic acid binding molecule. For example, the nucleic acid(s) to be delivered is (are) bound to or associated with the binding molecule(s) and the binding molecule(s) is(are), in turn, bound by the polypeptide(s). Upon binding of the polypeptide(s) to the surface marker(s), the nucleic acid(s) is(are) delivered into the ATII cell(s).

A "nucleic acid binding molecule" according to the present invention can be any molecule which is capable of binding nucleic acids, like a polypeptide. A "nucleic acid binding molecule" according to the present invention can be a polypeptide selected from the group consisting of protamine, histones, high mobility group proteins, a cell-permeant RNA-binding protein, a HIV-1 TAT peptide, or a polypeptide sharing at least 60% identity with one of those polypeptides, at least 65%, 70%, 75%, 80%, 85%, preferably at least 90%, 95%, 96%, 97%, 98% or 99% and having nucleic acid binding capability. A "nucleic acid binding molecule" according to the present invention can be a protamine. A "nucleic acid binding molecule" according to the present invention can be digoxigenin or nano particles.

An exemplary nucleic acid delivery system that takes advantage of a nucleic acid binding molecule is described in Song (2012), loc. cit. or Dou (2012) loc. cit. These delivery systems can be used in accordance with the present invention. For example, a nucleic acid sequence encoding a nucleic acid binding molecule (like protamine and the like) can be fused in frame to a e.g. a sequence encoding the C-terminus of a polypeptide binding to a specific surface marker (e.g. the C-terminus of the heavy chain of an antibody). Expression can be performed in appropriate host systems (like eukaryotic host cells, e.g. CHO cells). Because the nucleic acid (e.g. siRNA) binds to the binding molecule fused to the polypeptide, the nucleic acid can be delivered to the ATII cell upon binding of the polypeptide-binding molecule-nucleic acid complex to the surface marker.

A "nucleic acid" according to the present invention can be any nucleic acid. If for example, it is aimed to overexpress a gene in a alveolar type-II epithelial cell (ATII cells) according to the present invention, the nucleic acid may be a nucleic acid encoding said polypeptide linked to regulatory elements for the expression and/or translation of said polypeptide. If, for example, the aim is to reduce or abandon the expression of a gene product in a alveolar type-II epithelial cell (ATII cells) according to the present invention, the nucleic acid may be an antisense DNA or RNA molecule or be an siRNA molecule specifically targeting the gene of which the product should be reduced in its expression. The nucleic acid may also encode an antisense RNA molecule or a shRNA molecule.

The nucleic acid delivery system to be used herein comprises a nucleic acid molecule to be delivered, such as the afore-mentioned DNA or RNA molecules, like siRNA, shRNA, miRNA (or DNA molecules encoding same) and so forth. Also modified forms of these molecules to improve characteristic of these molecules as stability and or specificity are envisaged herein.

The nucleic acid delivery system according to the present invention may comprise an siRNA. This siRNA is preferably an siRNA specifically targeting an mRNA being upregulated in a lung disease. The nucleic acid delivery system according to the present invention may comprise an shRNA. This shRNA is preferably an shRNA specifically targeting an mRNA being upregulated in a lung disease.

A "lung disease" according to the present invention can be any lung disease. Preferably, it is a "lung disease" which is associated with malfunction or disregulation of ATII cells. Examples of such diseases are lung cancer, pulmonary fibrosis, chronic obstructive pulmonary disease (COPD), emphysema and cystic fibrosis [PMID: 22411819, 23134111, 19934355, 16888288, 19335897].

A "lung cancer" according to the present invention can be any "lung cancer". Preferably, it is a "lung cancer" which is associated with or derived from alveolar type-II epithelial cells (ATII cells). Examples of such "lung cancers" are adenocarcinoma or bronchoalveolar carcinoma. According to a preferred embodiment of the present invention, "lung cancer" is "lung adenocarcinoma".

The nucleic acid system of the present invention can be used to treat lung cancer, for example, when it comprises an siRNA specifically targeting an mRNA being upregulated in lung cancer. Examples of such mRNAs being upregulated in lung cancer are i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1;
ii) the NKX2-1 Em isoform comprising the nucleic acid sequence of SEQ ID No: 2 or the NKX2-1 Em isoform comprising the nucleic acid sequence with up to 39 additions, deletions or substitutions of SEQ ID NO: 2;
iii) the FOXA2 Em isoform comprising the nucleic acid sequence of SEQ ID No: 3 or the FOXA2 Em isoform comprising nucleic acid sequence with up to 68 additions, deletions or substitutions of SEQ ID NO: 3; or iv) the ID2 Em isoform comprising the nucleic acid sequence of SEQ ID No: 4 or the ID2 Em isoform comprising nucleic acid sequence with up to 34 additions, deletions or substitutions of SEQ ID NO: 4.

Thus, the siRNAs according to the present invention may be siRNAs targeting said mRNAs being upregulated in lung cancer.

The present invention relates to a composition comprising (an) siRNA(s) targeting i) the GATA6 Em isoform comprising the nucleic acid sequence of SEQ ID No: 1 or the GATA6 Em isoform comprising a nucleic acid sequence with up to 55 additions, deletions or substitutions of SEQ ID NO: 1;

ii) the NKX2-1 Em isoform comprising the nucleic acid sequence of SEQ ID No: 2 or the NKX2-1 Em isoform comprising the nucleic acid sequence with up to 39 additions, deletions or substitutions of SEQ ID NO: 2;

iii) the FOXA2 Em isoform comprising the nucleic acid sequence of SEQ ID No: 3 or the FOXA2 Em isoform comprising nucleic acid sequence with up to 68 additions, deletions or substitutions of SEQ ID NO: 3; or iv) the ID2 Em isoform comprising the nucleic acid sequence of SEQ ID No: 4 or the ID2 Em isoform comprising nucleic acid sequence with up to 34 additions, deletions or substitutions of SEQ ID NO: 4;

and a fusion protein of a nucleic acid binding molecule (like the polypeptides described herein, such as protamine) and an surface marker (e.g. Itgb2- or Itgb6-)-targeting antibody (e.g. monoclonal antibody or single chain variable fragment).

Genes can contain single nucleotide polymorphisms (SNPs). The specific transcription factor Em isoform sequences of the present invention encompass (genetic) variants thereof, for example, variants having SNPs. Without deferring from the gist of the present invention, all naturally occurring sequences of the respective isoform independent of the number and nature of the SNPs in said sequence can be used herein. To relate to currently known SNPs, the transcription factor Em isoforms of the present invention are defined such that they contain up to 55 (in the case of GATA6), up to 39 (in the case of NKX2-1), up to 68 (in the case of FOXA2) or up to 34 (in the case of ID2) additions, deletions or substitutions of the nucleic acid sequences defined by SEQ ID NOs: 1, 2, 3 and 4, respectively. Thus, respective Em transcripts of carriers of different nucleotides at the respective SNPs are covered by the present application.

These "specific transcription factor Em isoform" (like GATA6 Em isoform, NKX2-1 Em isoform, FOXA2 Em isoform and ID2 Em isoform) have been described herein above in detail. These definitions and explanations apply, mutatis mutandis, in this context.

The person skilled in the art knows how to design siRNAs and shRNAs which specifically target the specific transcription factor Em isoforms of the present invention. Examples of such specific siRNAs and shRNAs targeting the specific transcription factor Em isoforms of the present invention are depicted in Tables 6 and 7.

TABLE 10

Examples of siRNA sequences for the knockdown of Gata6 Em and Foxa2 Em

| Target Sequence | Sense strand siRNA | Antisense strand siRNA |
|---|---|---|
| **Gata6** | | |
| SEQ ID NO: 58 AATCAGGAGCGCAGGCTGCAG | SEQ ID NO: 41 UCAGGAGCGCAGGCUGCAGtt | SEQ ID NO: 43 CUGCAGCCUGCGCUCCUGAtt |
| SEQ ID NO: 59 AAGAGGCGCCTCCTCTCTCCT | SEQ ID NO: 42 GAGGCGCCUCCUCUCUCCUtt | SEQ ID NO: 44 AGGAGAGAGGAGGCGCCUCtt |
| **Foxa2** | | |
| SEQ ID NO: 60 AAACCGCCATGCACTCGGCTT | SEQ ID NO: 45 ACCGCCAUGCACUCGGCUUtt | SEQ ID NO: 46 AAGCCGAGUGCAUGGCGGUtt |

TABLE 11

Examples of DNA sequences encoding hairpin sequences from which shRNA sequences are cleaved that can be used for the knockdown of Nkx2-1
Nkx2-1

| shHairpin sequence (5'-3') |
|---|
| SEQ ID NO: 47 CCGGCCCATGAAGAAGAAAGCAATTCTCGAGAA TTGCTTTCTTCTTCATGGGTTTTTG |
| SEQ ID NO: 48 GTACCGGGGGATCATCCTTGTAGATAAACTC GAGTTTATCTACAAGGATGATCCCTTTTTTG |
| SEQ ID NO: 49 CCGGATTCGGAATCAGCTAGCAATTCTCGAGAA TTGCTAGCTGATTCCGAATTTTTTG |

The use of corresponding shRNA molecules is envisaged herein (i.e. the shRNA molecules are cleaved from hairpin sequences which are identical to the above DNA sequences of Table 11 with the exception that the "T" residues are replaced by "U" residues).

The siRNA to be used herein can comprise a nucleic acid molecule comprising at least ten contiguous bases of a sequence as shown in the sequence of SEQ ID NOs 41, 43, 42, 44, 45 or 46. It is to be understood that an siRNA molecule consists of an antisense and a sense strand. For example, an siRNA targeting a GATA6 Em isoform can consist of a nucleic acid molecule comprising at least ten contiguous bases of a sequence as shown in the sequence of SEQ ID NOs 41, and a nucleic acid molecule comprising at least ten contiguous bases of a sequence as shown in the sequence 43. For example, an siRNA targeting a GATA6 Em isoform can consist of a nucleic acid molecule comprising at least ten contiguous bases of a sequence as shown in the sequence of SEQ ID NOs 42, and a nucleic acid molecule comprising at least ten contiguous bases of a sequence as shown in the sequence 44. For example, an siRNA targeting a FOXA2 Em isoform can consist of a nucleic acid molecule comprising at least ten contiguous bases of a sequence as shown in the sequence of SEQ ID NOs 45, and a nucleic acid molecule comprising at least ten contiguous bases of a sequence as shown in the sequence 46.

Up to 10% of the contiguous bases of the above-mentioned nucleic acid-molecule can be non-complementary. The nucleic acid molecule may further comprise at least one base at the 5' end and/or at least one base at the 3' end. The siRNA to be used herein can consist of a molecule as shown in SEQ ID No. 41 and 43; SEQ ID NO. 42 and 44; or SEQ ID NO. 45 and 46.

The present invention relates to a kit for the delivery of a nucleic acid into an alveolar type-II epithelial cell comprising any the nucleic acid delivery system. The kit according to the present invention is a kit which contains all the components which are necessary to deliver nucleic acids into alveolar type-II epithelial cells. In particular, the kit may contain a fusion protein of a nucleic acid binding protein and a polypeptide specifically binding to a specific surface marker of alveolar type-II epithelial cells. As an example, the kit may comprise a fusion protein of protamine and a monoclonal antibody or a single chain variable fragment, wherein the antibody or the single chain variable fragment specifically binds to a cell surface marker of alveolar type-II epithelial cells, wherein this cell surface marker of alveolar type-II epithelial cells is preferably selected from the group of proteins consisting of ITGB2, ITGB6, PTGIS, BASP1, DES, ITGA2, CTSS, PTPRC, ANPEP, FILIP1L, MGLL, OSMR, AGPAT4, ASS1, CSPG4, and CDH11.

The present invention relates to the use of the nucleic acid delivery system of the present invention for the transfection of alveolar type-II epithelial cells. In other words, the present invention provides a method for delivering nucleic acid molecules (such as DNA molecules or RNA molecules (e.g. siRNA) into ATII cells, wherein the nucleic acid is bound directly or indirectly (e.g. via a nucleic binding molecule) to a polypeptides binding to a specific surface marker of ATII cells. The nucleic acid delivery system may be used to deliver nucleic acid molecules into healthy or diseased ATII cells (e.g. tumor or cancer cells). The use or method may be employed in vitro, for example as a research tool to deliver nucleic acid molecules into healthy ATII cells.

The present invention relates to a composition for use in medicine comprising any of the nucleic acid delivery systems or the compositions of the present invention. The composition can be for use in the treatment of a lung disease, like lung cancer. Said lung cancer can be a lung adenocarcinoma or a lung bronchoalveolar carcinoma.

The present invention relates to a nucleic acid delivery system for the delivery of nucleic acids specifically into an alveolar type-II epithelial cell, wherein said system comprises a polypeptide binding to a specific surface marker of alveolar type-II epithelial cells. Preferably, the nucleic acid system according to the present invention is a non-viral nucleic acid delivery system. In the context of the present invention, the term "non-viral" defines the nucleic acid delivery system as not using viruses for the delivery of the nucleic acid. This does not necessary imply that no viral particles can be detected in the nucleic acid delivery system but only that they are not of functional relevance for the delivery of the nucleic acid of the present invention.

The present invention relates to a method of treating a subject suffering from a lung disease, like lung cancer, or a subject with an increased risk of suffering from a lung disease, like lung cancer, comprising the step of administering to said subject the nucleic acid delivery system of the present invention. Preferably, said cancer is lung cancer. Even more preferably, said lung cancer is adenocarcinoma or a lung bronchoalveolar carcinoma. The subject according to the present invention is preferably a human.

The method of treating a subject suffering from cancer or a subject with an increased risk of suffering from cancer may comprise the step of contacting an alveolar type-II epithelial cell of said subject with a nucleic acid delivery system of the present invention.

The following relates to pharmaceutical compositions which may comprise the nucleic acid delivery system and compositions described and defined herein above.

The pharmaceutical composition will be formulated and dosed in a fashion consistent with good medical practice, taking into account the clinical condition of the individual patient, the site of delivery of the pharmaceutical composition, the method of administration, the scheduling of administration, and other factors known to practitioners. The "effective amount" of the nucleic acid delivery system or the pharmaceutical composition for purposes herein is thus determined by such considerations.

The skilled person knows that the effective amount of pharmaceutical composition administered to an individual will, inter alia, depend on the nature of the compound. For example, if said compound is a an nucleic acid molecule the total pharmaceutically effective amount of pharmaceutical composition administered parenterally per dose will be in the range of about 1 μg/kg/day to 100 mg/kg/day of patient body weight, although, as noted above, this will be subject to therapeutic discretion. More preferably, this dose is at least 0.01 mg/kg/day, and most preferably for humans between about 0.01 and 1 mg/kg/day. The presently recommended dose for nucleic acid molecules lies in a range of between 8 and 80 mg per/kg/day. However, this dose may be further decreased subject to therapeutic discretion, in particular if concomitantly certain lipids are applied or if the nucleic acid molecule is subject to certain chemical modifications. If given continuously, the pharmaceutical composition is typically administered at a dose rate of about 1 μg/kg/hour to about 40 μg/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect. The particular amounts may be determined by conventional tests which are well known to the person skilled in the art.

Pharmaceutical compositions of the invention may be administered orally, rectally, parenterally, intracisternally, intravaginally, intraperitoneally, topically (as by powders, ointments, drops or transdermal patch), bucally, or as an oral or nasal spray. Preferably the pharmaceutical compositions of the invention are administered as a spray. The term "pharmaceutical composition" and "composition for use in medicine" and the like can be used interchangeably herein. It is envisaged and preferred herein that the nucleic acid delivery systems and compositions comprising same can be administered by using a spray (like an oral or nasal spry). For example, they can be administered in form of an aerosol that will be inhaled thereby ensuring ATII cell specific targeting. The aerosol contains the nucleic acid delivery provided herein.

Pharmaceutical compositions of the invention preferably comprise a pharmaceutically acceptable carrier. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The pharmaceutical composition is also suitably administered by sustained release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547-556 (1983)), poly (2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP 133,988). Sustained release pharmaceutical composition also include liposomally entrapped compound. Liposomes containing the pharmaceutical composition are prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapy.

For parenteral administration, the pharmaceutical composition is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

Generally, the formulations are prepared by contacting the components of the pharmaceutical composition uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non aqueous vehicles such as fixed oils and ethyl oleate are also useful herein, as well as liposomes. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The components of the pharmaceutical composition to be used for therapeutic administration must be sterile. Sterility is readily accomplished by filtration through sterile filtration membranes (e.g., 0.2 micron membranes). Therapeutic components of the pharmaceutical composition generally are placed into a container having a sterile access port, for example, an intravenous solution bag or vial having a stopper pierceable by a hypodermic injection needle.

The components of the pharmaceutical composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized compound(s) using bacteriostatic Water-for-Injection.

The nucleic acid molecules may be delivered as follows: for example, the nucleic acid molecules can be injected directly into a cell, such as by microinjection. Alternatively, the molecules can be contacted with a cell, preferably aided by a delivery system as provided herein. Further useful delivery systems include, for example, liposomes and charged lipids. Liposomes typically encapsulate oligonucleotide molecules within their aqueous center. Charged lipids generally form lipid-oligonucleotide molecule complexes as a result of opposing charges. Yet, the delivery by internalization via the herein provided and defined surface markers is preferred herein.

These liposomes-oligonucleotide molecule complexes or lipid-oligonucleotide molecule complexes are usually internalized in cells by endocytosis. The liposomes or charged lipids generally comprise helper lipids which disrupt the endosomal membrane and release the oligonucleotide molecules.

Other methods for introducing nucleic acid molecules into a cell include use of delivery vehicles, such as dendrimers, biodegradable polymers, polymers of amino acids, polymers of sugars, and oligonucleotide-binding nanoparticles. In addition, pluoronic gel as a depot reservoir can be used to deliver the anti-microRNA oligonucleotide molecules over a prolonged period. The above methods are described in, for example, Hughes et al., Drug Discovery Today 6, 303-315 (2001); Liang et al. Eur. J. Biochem. 269 5753-5758 (2002); and Becker et al., In Antisense Technology in the Central Nervous System (Leslie, R. A., Hunter, A. J. & Robertson, H. A., eds), pp. 147-157, Oxford University Press.

Targeting of nucleic acid molecules to a particular cell can be performed by any method known to those skilled in the art. For example, nucleic acid molecules can be conjugated to an antibody or ligand specifically recognized by receptors on the cell.

The terms "treatment", "treating" and the like are used herein to generally mean obtaining a desired pharmacological and/or physiological effect. The effect may be prophylactic in terms of completely or partially preventing fibrosis or symptom thereof and/or may be therapeutic in terms of partially or completely curing a lung disease and/or adverse effect attributed to a lung disease. The term "treatment" as used herein covers any treatment of a disease in a subject and includes: (a) preventing a lung disease from occurring in a subject which may be predisposed to a lung disease; (b) inhibiting a lung disease, i.e. arresting its development; or (c) relieving lung disease, i.e. causing regression of a lung disease.

The nucleic acid molecule can be introduced into the mammal by any method known to those in the art. For example, the above described methods for introducing the nucleic acid molecule into a cell can also be used for introducing the molecules into a mammal.

It is envisaged herein that the above described and defined nucleic acid molecules can also be applied in combination with conventional therapies. For example, one or more additional pharmaceutical agents can be used. Non-limiting examples of additional pharmaceutical agents are diuretics (e.g. sprionolactone, eplerenone, furosemide), inotropes (e.g. dobutamine, milrinone), digoxin, vasodilators, angiotensin II converting enzyme (ACE) inhibitors (e.g. are captopril, enalapril, lisinopril, benazepril, quinapril, fosinopril, and ramipril), angiotensin II receptor blockers (ARB) (e.g. candesartan, irbesartan, olmesartan, losartan, valsartan, telmisartan, eprosartan), calcium channel blockers, isosorbide dinitrate, hydralazine, nitrates (e.g. isosorbide mononitrate, isosorbide dinitrate), hydralazine, beta-blockers (e.g. carvedilol, metoprolol), and natriuretic peptides (e.g. nesiritide).

An additional pharmaceutical agent may also enhance the body's immune system, and may, therefore, include low-dose cyclophosphamide, thymostimulin, vitamins and nutritional supplements (e.g., antioxidants, including vitamins A, C, E, beta-carotene, zinc, selenium, glutathione, coenzyme Q-10 and echinacea), and vaccines, e.g., the immunostimulating complex (ISCOM), which comprises a vaccine formulation that combines a multimeric presentation of antigen and an adjuvant.

The additional therapy can also be selected to treat or ameliorate a side effect of one or more pharmaceutical compositions of the present invention. Such side effects include, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

Moreover, one or more pharmaceutical compositions of the present invention and one or more other pharmaceutical agents can be administered at the same time. The one or more pharmaceutical compositions of the present invention and one or more other pharmaceutical agents can also be prepared together in a single formulation.

While the invention has been illustrated and described in detail in the drawings and foregoing description, such illustration and description are to be considered illustrative or exemplary and not restrictive. It will be understood that changes and modifications may be made by those of ordinary skill within the scope and spirit of the items and claims provided herein. In particular, the present invention covers further embodiments with any combination of features from different embodiments described above and below.

The invention also covers all further features shown in the figures individually although they may not have been described in the afore or following description. Also, single alternatives of the embodiments described in the figures and the description and single alternatives of features thereof can be disclaimed from the subject matter of the other aspect of the invention.

Furthermore, in the claims the word "comprising" does not exclude other elements or steps, and the indefinite article "a" or "an" does not exclude a plurality. A single unit may fulfill the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of." Thus, the terms "comprising"/"including"/"having" mean that any further component (or likewise features, integers, steps and the like) can be present.

The term "consisting of" means that no further component (or likewise features, integers, steps and the like) can be present.

The term "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

Thus, the term "consisting essentially of" means that specific further components (or likewise features, integers, steps and the like) can be present, namely those not materially affecting the essential characteristics of the composition, device or method. In other words, the term "consisting essentially of" (which can be interchangeably used herein with the term "comprising substantially"), allows the presence of other components in the composition, device or method in addition to the mandatory components (or likewise features, integers, steps and the like), provided that the essential characteristics of the device or method are not materially affected by the presence of other components.

As used herein the term "about" refers to ±10%.

The present invention is also illustrated by the following figures. The figures show:

(A) In silico analysis of the indicated genes shows an identical arrangement with two promoters (hatched boxes), surrounded by CpG islands ( ), driving the expression of two distinct transcripts (exons as black boxes, shown in right panel; coding region in white). Gata6, GATA Binding Factor 6; Nkx2-1, also known as Ttf1, Thyroid transcription factor 1; Foxa2, Foxhead box protein A2; Id2, Inhibitor of DNA binding 2; Em, Embryonic; Ad, Adult; Var1, Variant 1; Var2, Variant 2. (B) The two transcript isoforms are differentially regulated during embryonic lung development and show complementary expression. Expression of both isoforms of each gene was analyzed by quantitative reverse transcriptase (q-RT) PCR in embryonic lungs isolated at different days post coitum (dpc; 11, 12, 13 and 14). Data are represented as mean+/−standard error mean (s.e.m.), n=5

Figure 2:
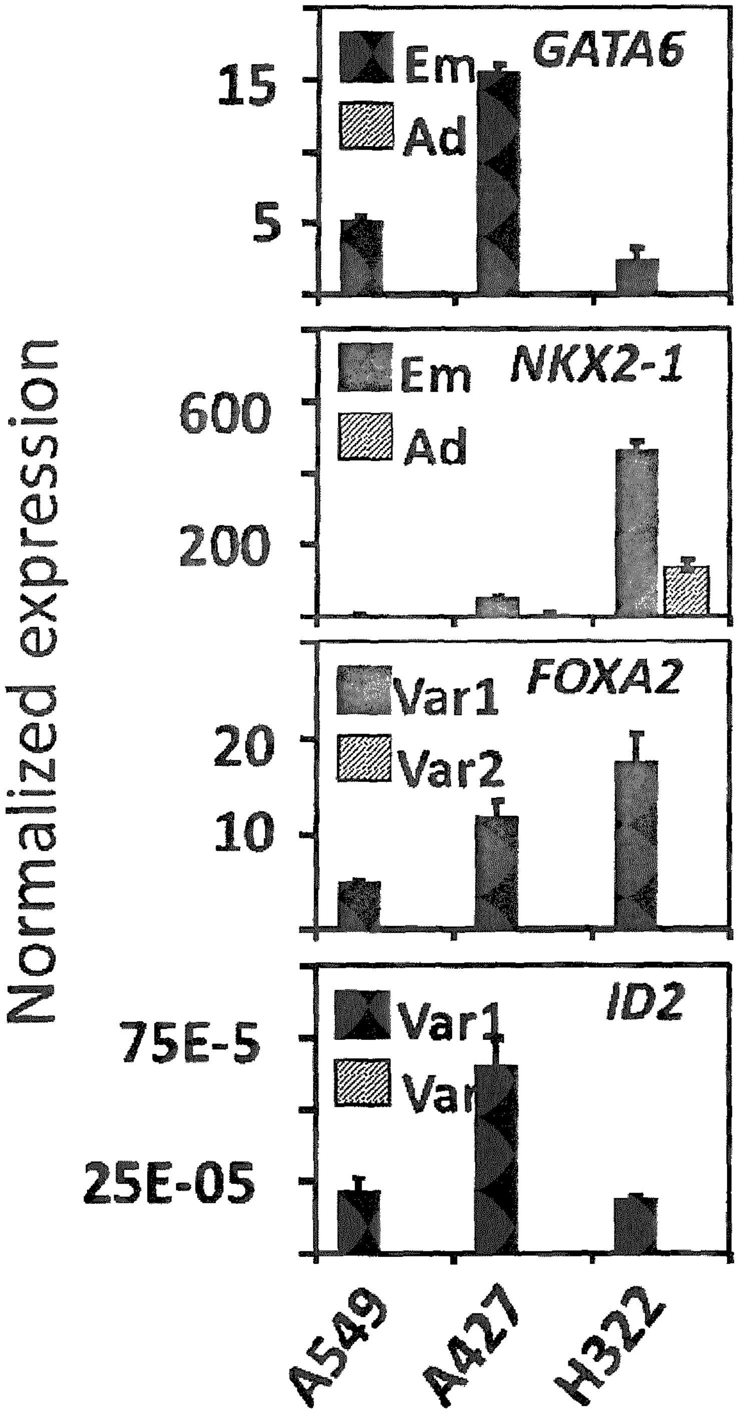
Figure 2:
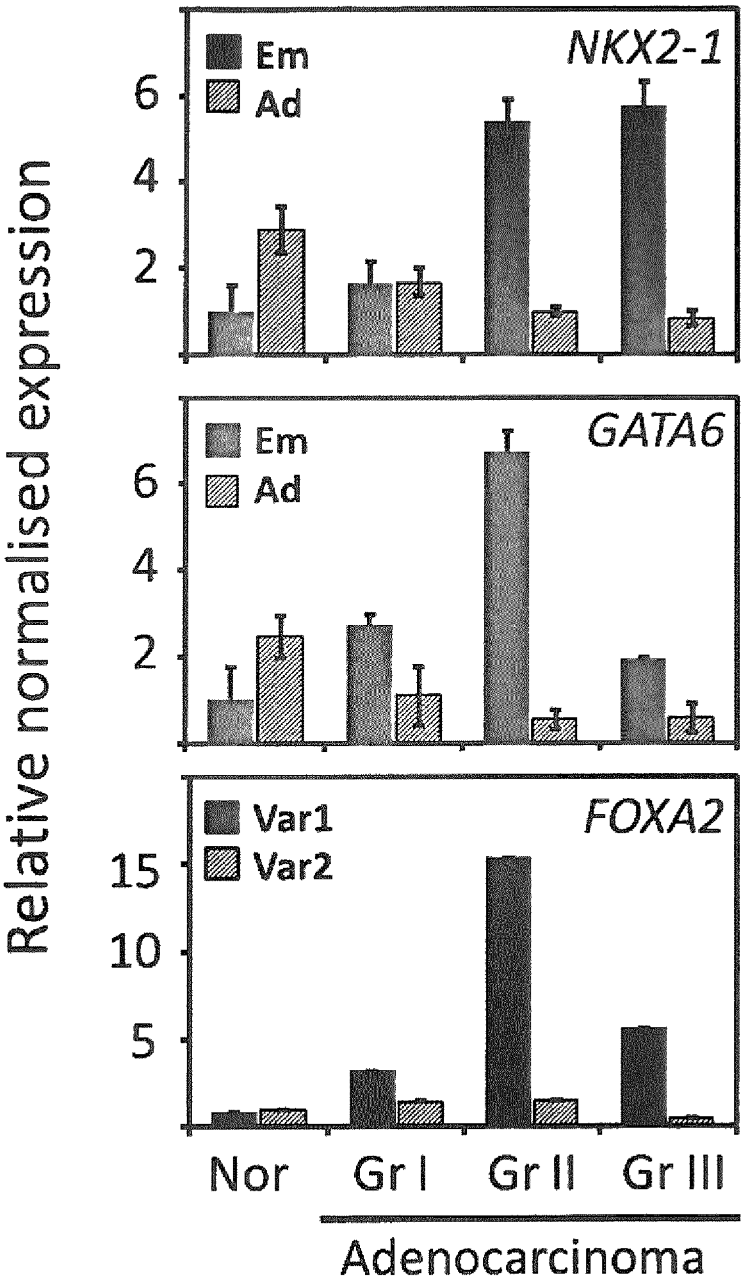
Figure 2:
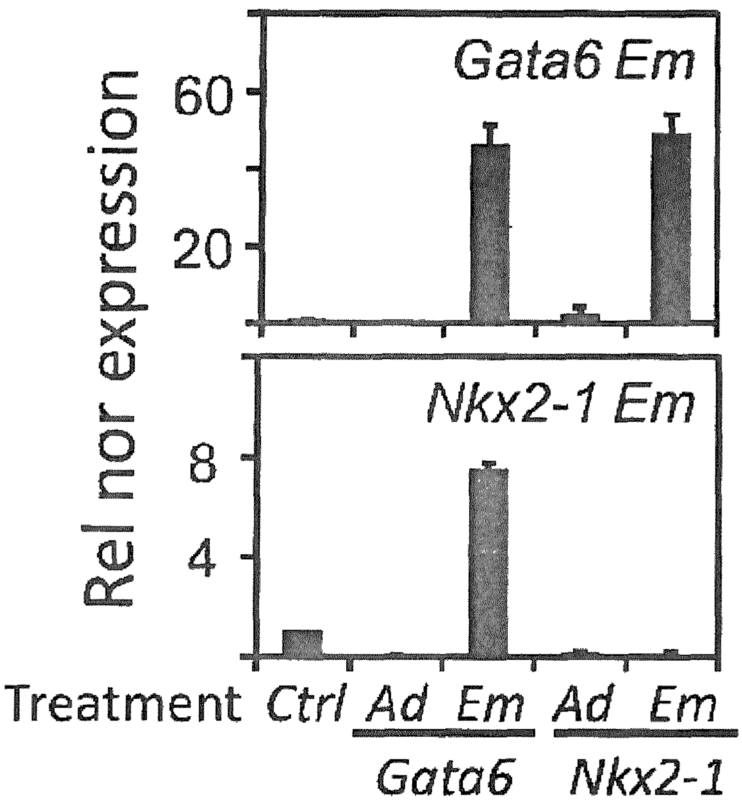

FIG. 2: High expression of embryonic isoforms in human lung cancer samples as well as their detection in mouse blood at early stage of tumor initiation supports the potential of the Em-isoforms as markers for early lung cancer diagnosis.

(A) Em-isoforms are predominantly expressed in human lung cancer cell lines. Isoform specific expression analysis of the indicated genes by qRT-PCR in human lung adenocarcinoma (A549, A427) and bronchoalveolar carcinoma (H322) cell lines. Data are represented as mean+/−standard error mean (s.e.m.), n=5 (B) Em-isoforms are highly expressed in human lung cancer tissue. Isoform specific expression was monitored by qRT-PCR after total RNA isolation from human lung tumor and normal lung cryosections. Data are represented as in A. (C) Embryonic transcripts of the indicated genes were detected in blood of mice at early stage of tumor initiation. Isoform specific expression analysis of the indicated genes by qRT-PCR in blood isolated from mouse hearts. Data are represented as in A.

Figure 3:
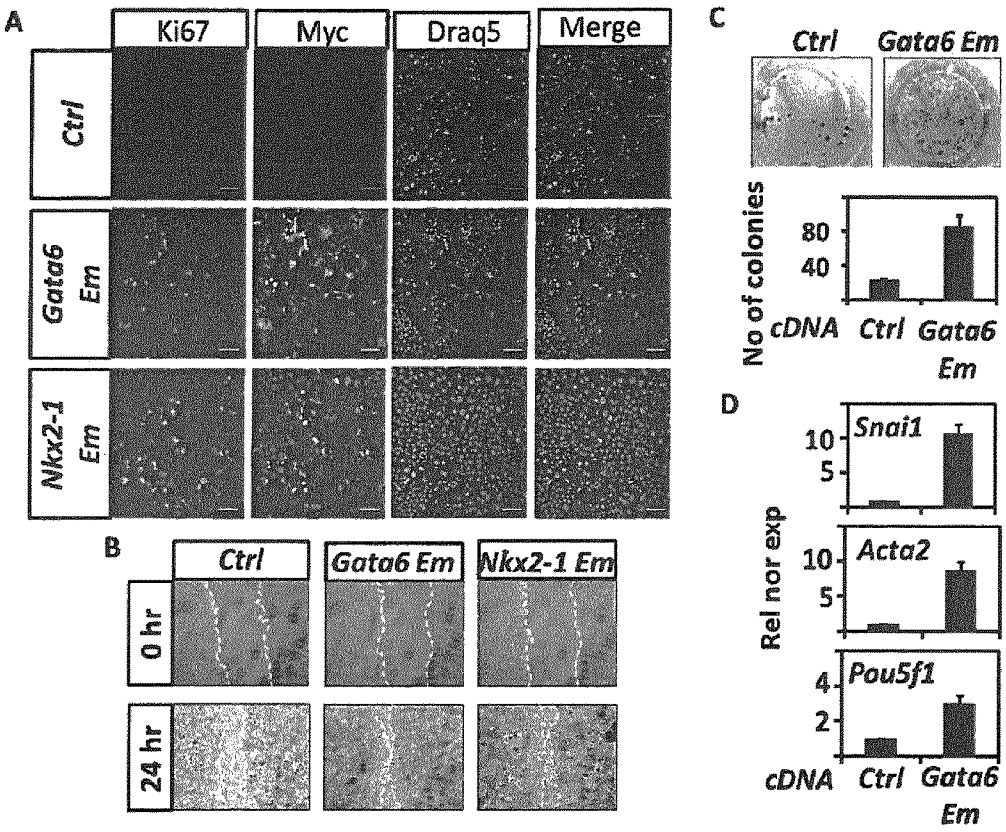

FIG. 3: Embryonic isoforms mediate oncogenic transformation in cell lines.

(A) MLE-12 cells transfected with Gata6 Em or Nkx2-1 Em are highly proliferative. Cells were analyzed by immunofluorescence microscopy after immunostaining with MKI67- or MYC-specific antibodies. Draq5, nuclear staining. Scale bars, 20 μm. (B) Enhanced cell migration in MLE-12 cells transfected with Gata6 Em and Nkx2-1 Em. Scratch was made in 100% confluent monolayer culture 24 hours after transfection. Cells were observed by bright field microscopy every 6 hours after making the scratch, till the scratch was filled. Scale bar, 200 μm. (C) Increased colony formation in MLE-12 cells stable transfected with Gata6 Em. Control (Ctrl) and Gata6 Em stable transfected cells were plated at a density of 500 cells per well. Cells were cultured till colonies were observed (2 weeks), fixed in 4% Paraformaldehyde, stained by Haematoxylin and colonies counted. Data are represented as mean+/−standard error mean (s.e.m.), n=3. (D) MLE-12 cells stable transfected with Gata6 Em undergo epithelial mesenchymal transition (EMT). Analysis of EMT by expression analysis of Snail homolog 1 (Snail), alpha smooth muscle actin (Acta2) and POU domain class 5 transcription factor 1 (Pou5f1) was monitored by qRT-PCR after total RNA isolation from MLE-12 cells stable transfected with Gata6 Em. Data are represented as in FIG. 1B.

Figure 5:
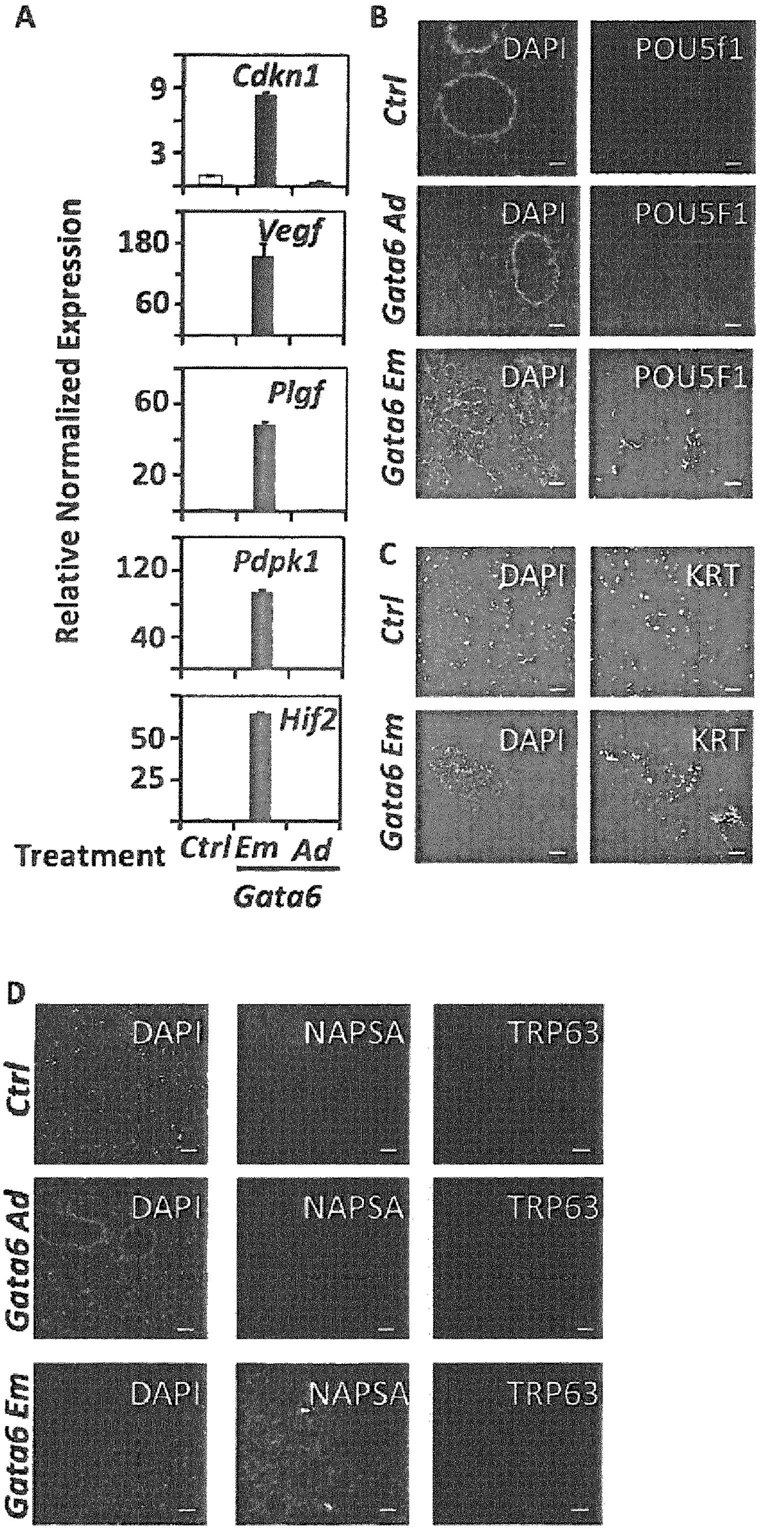

FIG. 4: Embryonic isoforms are oncogenic (A) Forced expression of Em-isoforms in adult lung induced hyperplasia. Haematoxylin and Eosin staining on sections of mice lungs in vivo transfected with control (Ctrl), isoform specific expression constructs (Em or Ad, Gata6 or Nkx2-1). Scale bars, 50 μm. (B) Isoform specific in vivo overexpression of Gata6 and Nkx2-1 was performed as in A. Isoform specific expression analysis by qRT-PCR was performed on total lung RNA 5 weeks after transfection. Data are represented as in FIG. 1B FIG. 5: Gata6 Em-isoform induces adenocarcinomas in adult lung (A) Gata6 Em GOF specifically increased expression of markers for cancer. Expression analysis of the indicated genes by qRT-PCR after in vivo transfection of adult lung with the indicated constructs. Cdkn1, Cyclin dependent kinase 1 (proliferation marker); Vegf, Vascular endothelial growth factor; Plgf, Placental growth factor (angiogenesis markers); Pdpk1, 3-phosphoinositide dependent protein kinase 1 (metabolic/migration marker) and Hif2, Hypoxia inducible factor 2 (Hypoxia marker). Data are represented as mean+/−standard error mean (s.e.m.), n=5. (B-D) Atypical hyperplasia observed in adult lungs after overexpression of Em isoforms consists of small clusters of dedifferentiated ‘stem’ cells which are epithelial and are positive for lung adenocarcinoma diagnostic markers. Sections of treated lungs were analyzed by confocal microscopy after immunostaining with POU5F1, Pan-cytokeratin (KRT), NapsinA (NAPSA) and tumor protein 63 (TRP63)-specific antibodies. DAPI, nuclear staining. Scale bars, 50 μm.

Figure 6:
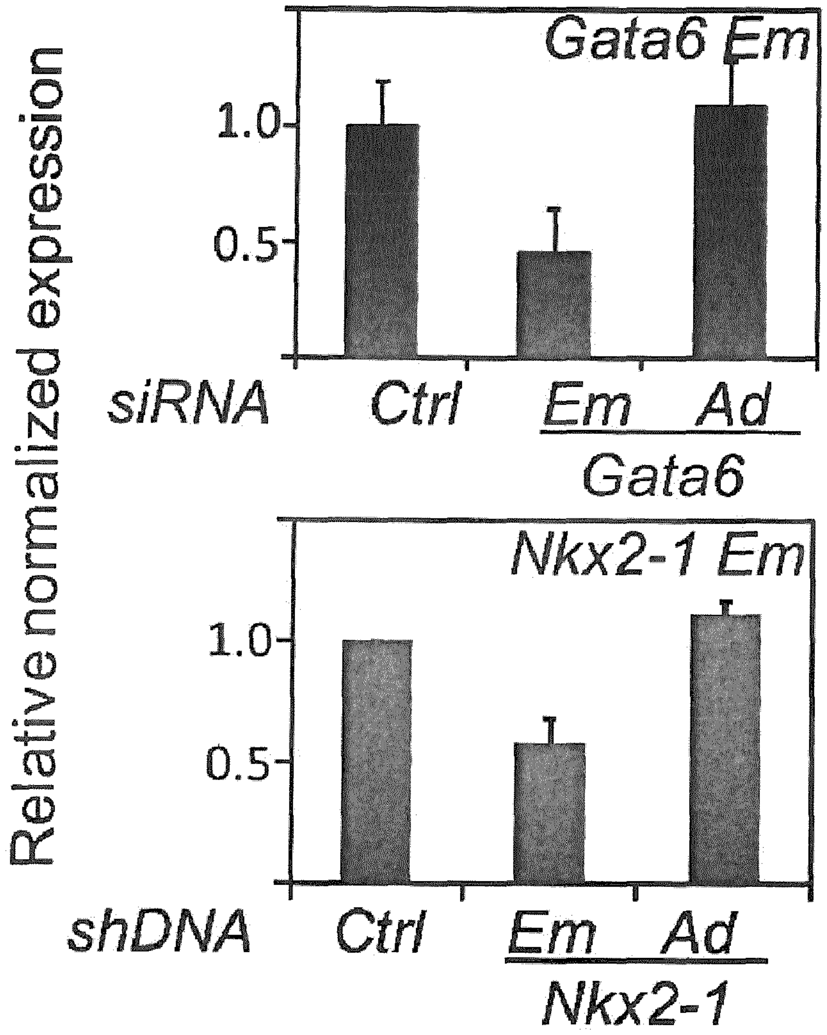

FIG. 6: Efficiency of siRNA mediated knockdown of Gata6 Em and Nkx2-1 Em (A) Isoform specific siRNAs can be used to exclusively target the Embryonic isoform transcripts. Expression analysis of both isoforms of Gata6 and Nkx2-1 in MLE-12 cells 48 hours after transfection with indicated siRNA or shDNA plasmids. Additional siRNA/shRNA sequences (SEQ ID NOs: 58, 59, 41-44, and 47-49) tested are listed (B). Data are represented as in FIG. 1B.

Figure 7:
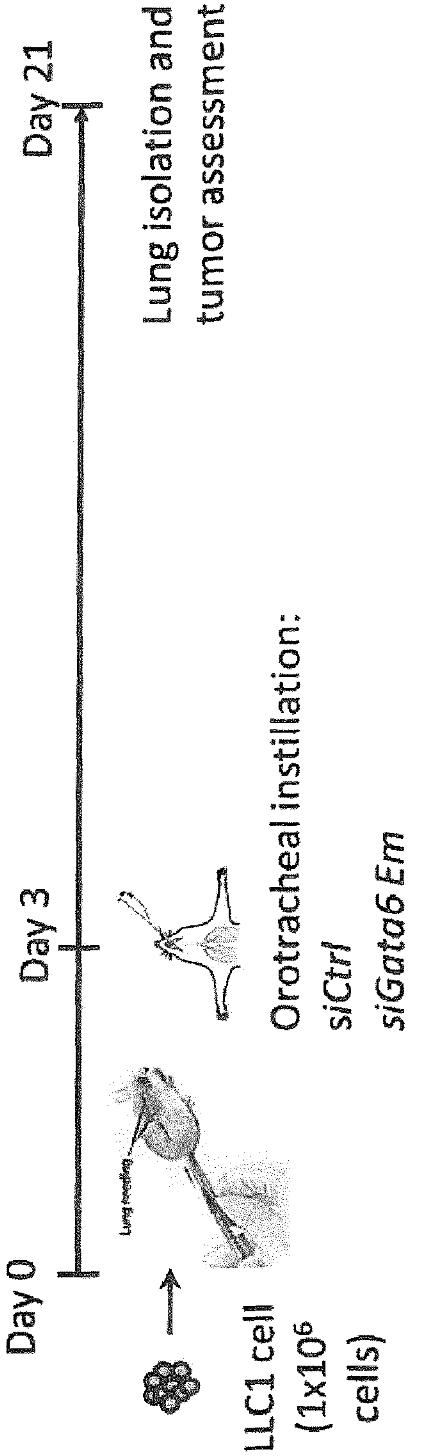
Figure 7:
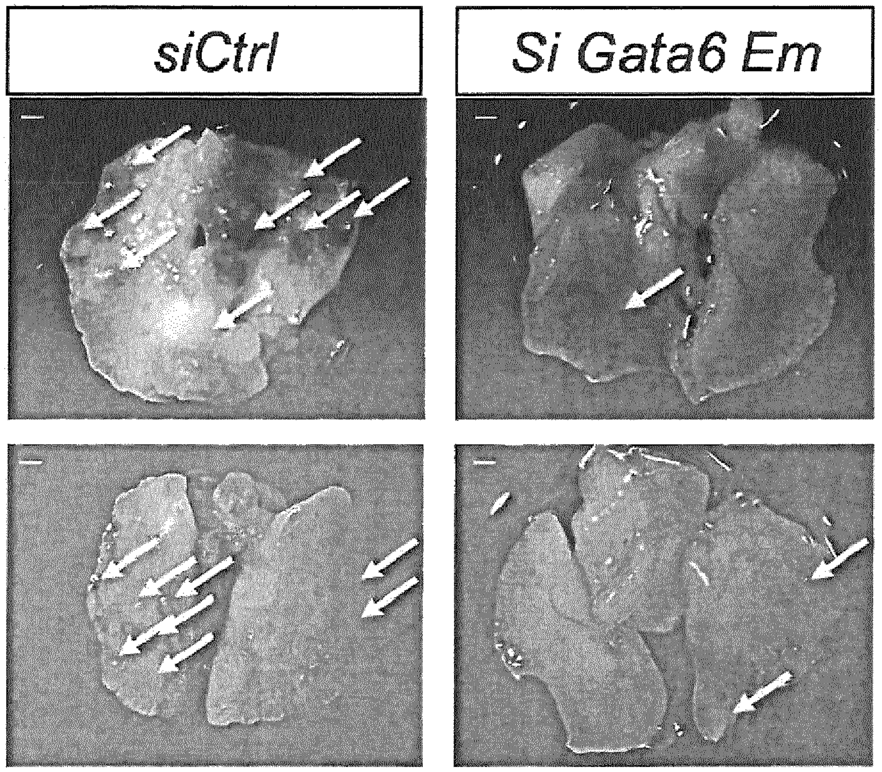
Figure 7:
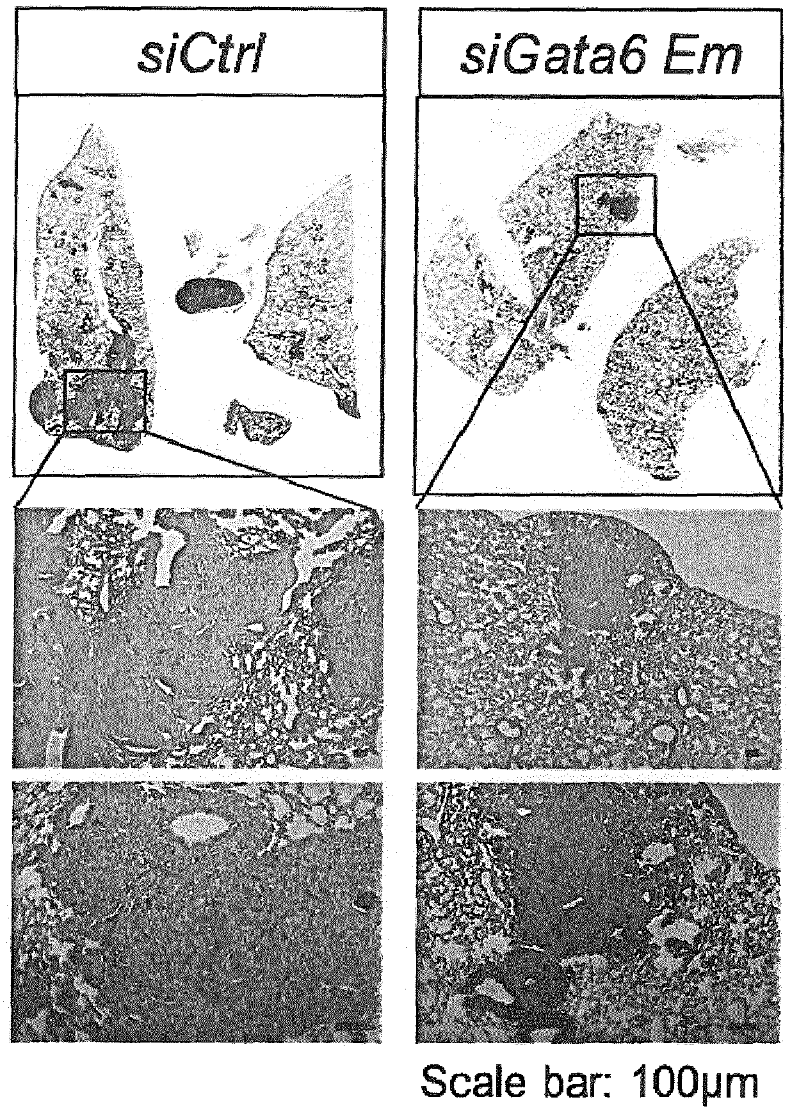

FIG. 7: Targeted knock down of Gata6 Em decreases tumor metastasis (A) Schematic representation of experiment design. Lewis Lung Carcinoma (LLC) cells were injected into the mouse tail vein at a density of 1 million cells. Three days after injection, control (siCtrl) or Gata6 Em specific (si-Gata6) siRNA was administered orotracheally. Lungs were harvested 21 days after injection and tumor foci were monitored. (B and C) Knockdown of Gata6 Em reduces lung tumor metastasis. (B) Images of lungs treated as in A. Arrows indicate tumor nodules. Scale bars, 1 mm. (C) Haematoxylin Eosin staining of mice lungs treated as in A. Scale bars, 100 μm.

Figure 8:
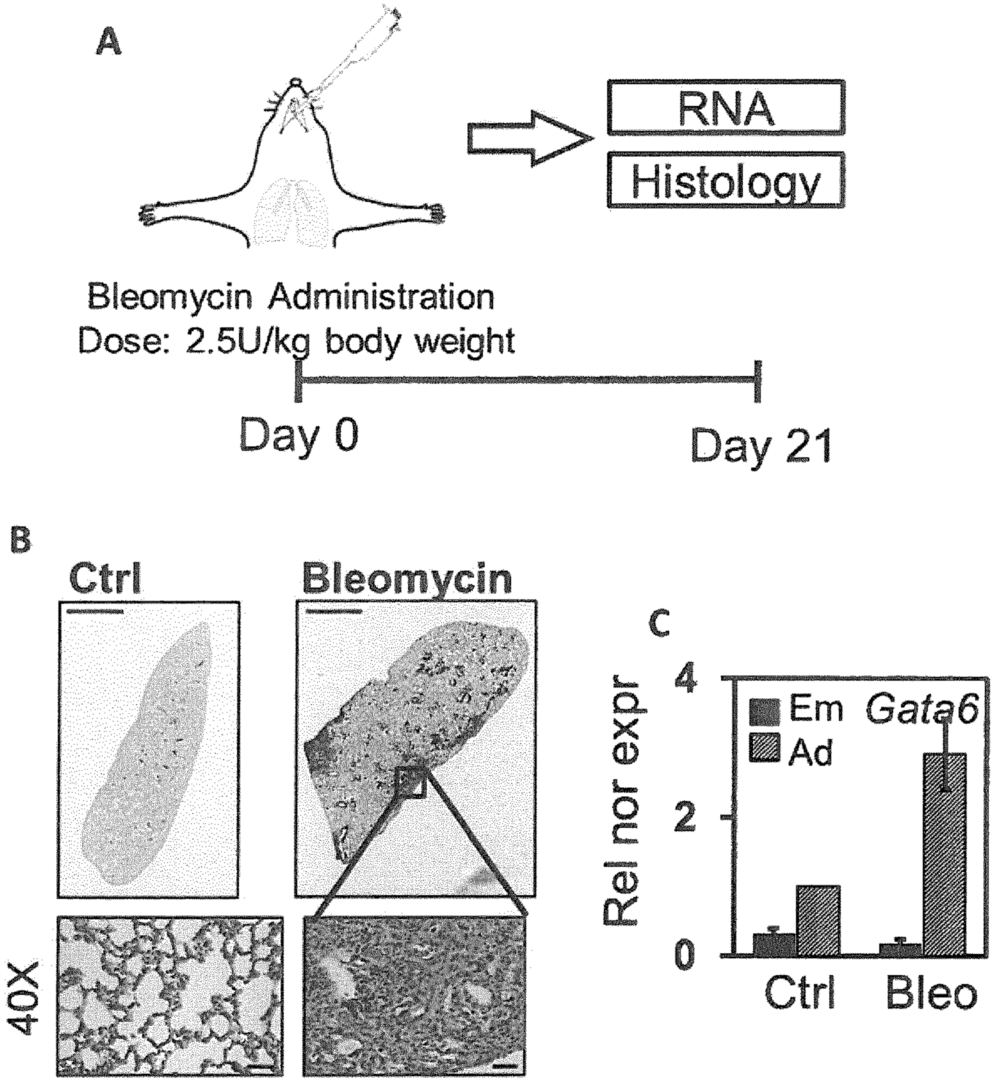

FIG. 8: Gata6 Ad is specifically expressed in lung fibrosis (A) Schematic representation of experiment design. Mice were treated with 2.5 U/kg body weight of Bleomycin. The lungs were harvested for RNA isolation and histology 21 days after treatment. (B) Bleomycin treatment induced lung fibrosis. Masson’s Trichrome staining of mouse lungs 21 days after Bleomycin treatment. Scale bar, 2 mm (upper panel) 50 μm (lower panel). (C) Gata6 Ad expression increased specifically in fibrotic lungs. Expression of both isoforms of Gata6 was monitored by qRT-PCR 21 days after Bleomycin treatment. Data are represented as mean+/− standard error mean (s.e.m.), n=3

Figure 9:
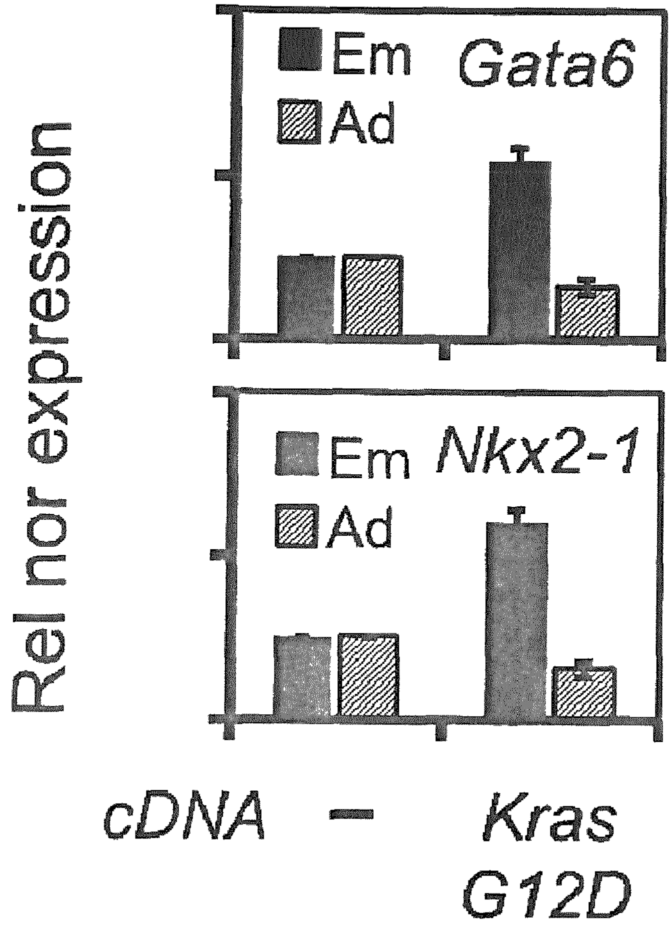

FIG. 9: Oncogenic Kras mutant G12D specifically induced the expression of the embryonic isoforms of Gata6 and Nkx2-1

MLE-12 cells were transfected with control (Ctrl) or KrasG12D plasmid DNA. Expression of isoform specific transcripts was monitored by qRT-PCR 48 hours after transfection. Data are represented as mean+/−standard error mean (s.e.m.), n=3

Figure 10:
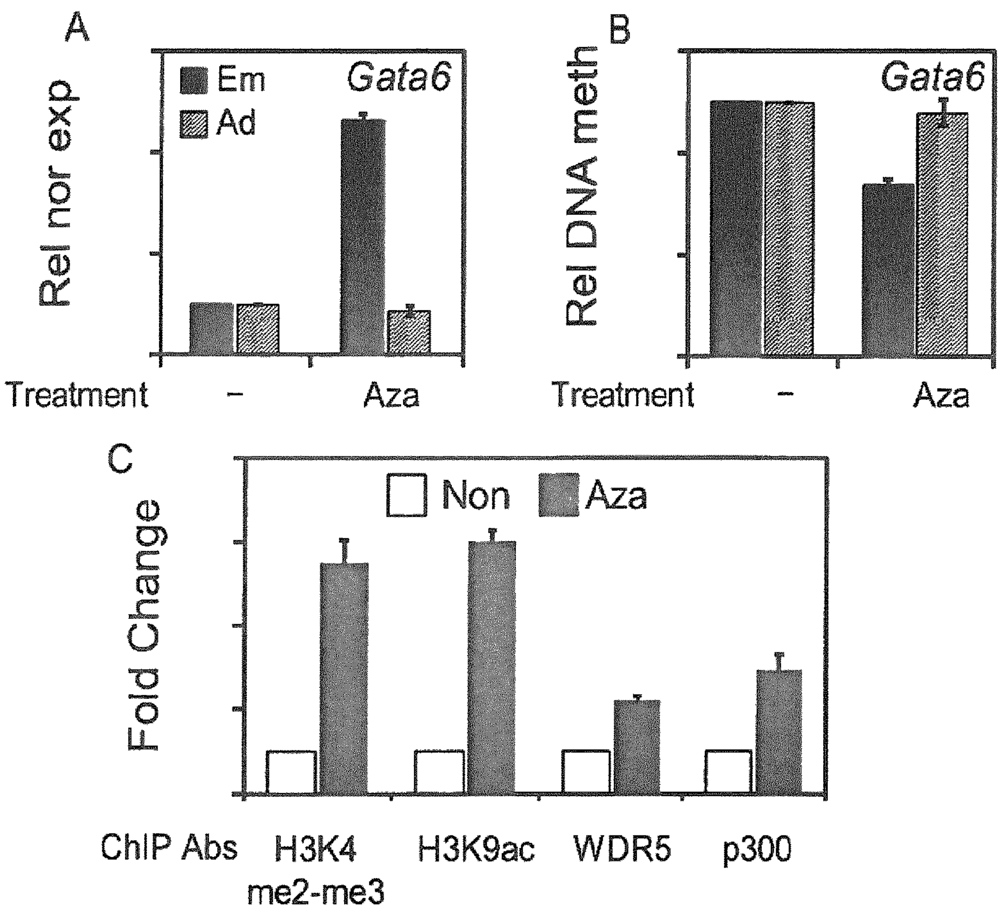

FIG. 10: Gata6 Em expression is epigenetically regulated.

(A) Specific induction of Gata6 Em after DNA demethylation. Passive DNA demethylation was induced in MLE-12 cells by 5'Azadeoxycytidine (Aza) treatment. Isoform specific expression of Gata6 was analysed by qRT-PCR 48 hours after AZA treatment. (B) Aza treatment induces Gata6 Em promoter demethylation. MLE-12 cells were treated as in A. DNA methylation was analyzed by Methylation Sensitive (MS) PCR 48 hours after Aza treatment. (C) Active histone marks accumulated in Gata6 Em promoter after Aza treatment. MLE-12 cells were treated as in A. Chromatin Immunoprecipitation (ChIP) was performed 48 hours after Aza treatment with antibodies against H3K4me2-me3, H3K9Ac, WDR5 and p300. Enrichment was monitored by qPCR after DNA purification. Data are represented as mean+/−standard error mean (s.e.m.), n=3 (A-C)

FIG. 11: Alignment of the Em and the Ad isoform of GATA6, NKX2-1, FOXA2 and ID2

Sequence alignment of Em and Ad isoforms of GATA6, NKX2-1, FOXA2 and ID2 (A, SEQ ID NOs: 160-162; B, SEQ ID NOs: 101-102; C, SEQ ID NOs: 163-165; D, SEQ ID NOs: 50 and 54; E, SEQ ID NOs: 166-168; F, SEQ ID NO: 103; G, SEQ ID NOs: 169-171; H, SEQ ID NOs: 51 and 55; I, SEQ ID NOs: 172-174; J, SEQ ID NOs: 104 and 105; K, SEQ ID NOs: 175-177; L, SEQ ID NOs: 52 and 56; M, SEQ ID NOs: 178 and 179; N, SEQ ID NOs: 107, 180, and 106; O, SEQ ID NOs: 181 and 182; P, SEQ ID NOs: 57, 183, and 53) was performed for both, mouse (*Mus musculus*) and human (*Homo sapiens*) sequences. Nucleotide sequences were obtained from NCBI or from its public mRNA database Aceview. Protein sequences were obtained from Uniprot or NCBI. The sequences were aligned pair-wise using Needleman-Wunsch Algorithm for global alignment (with free and gaps). The settings used for generating these alignments were: Cost Matrix: 65% similarity (5.0/−4.0); Gap open penalty: 14; Gap extension penalty: 0. All alignments were performed with Geneious (Geneious version R6 created by Biomatters.

Figure 12:
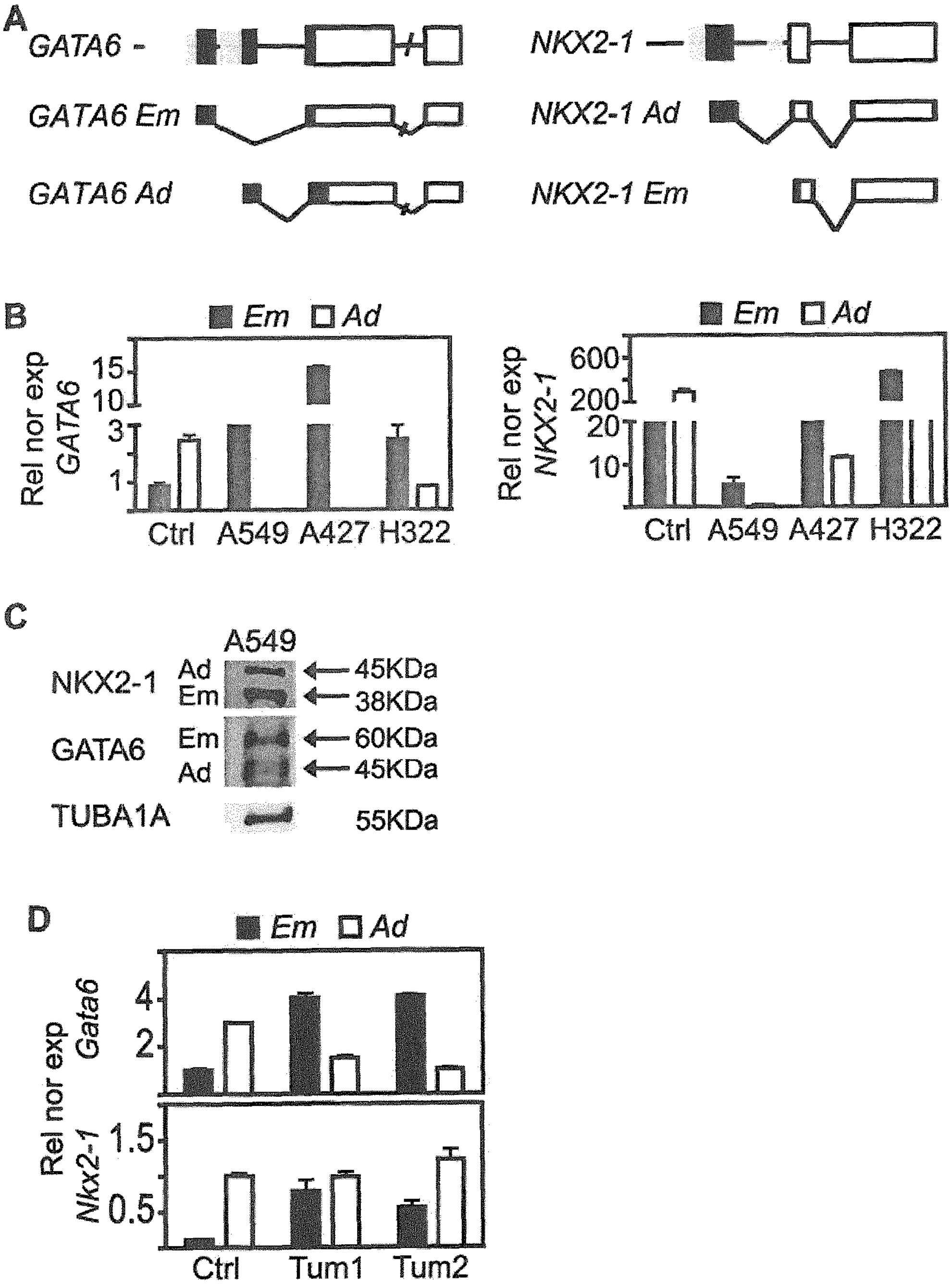

FIG. 12: Two distinct isoforms of GATA6 and NKX2-1.

(A) Schematic representation of the gene structure of human GATA6 and NKX2-1. In silico analysis of the indicated genes (upper panel) shows an identical arrangement with two promoters (grey boxes) driving the expression of two distinct transcripts (exons as black boxes; coding region in white, lower panel). GATA6, GATA Binding Factor 6; NKX2-1, also known as Ttf1, Thyroid transcription factor 1; Em, Embryonic; Ad, Adult. (B) The two transcript isoforms are differentially regulated during lung cancer and show complementary expression. Isoform specific gene expression analysis was performed for both genes by quantitative reverse transcriptase polymerase chain reaction (q-RT PCR) in healthy donor lungs (Ctrl) and lung cancer cell lines, A549, A427 (Adenocarcinoma) and H322 (Bronchoalveolar carcinoma). Rel nor exp, relative expression normalized to TUBA1A. Error bars, standard error mean (s.e.m.), n=5. (C) The two transcript isoforms encode two distinct proteins. Expression of both isoforms at the protein level was analyzed by western blot in A549 cell lines using antibodies against indicated proteins. TUBA1A, Tubulin, alpha 1a. (D) High expression of Em isoform of Gata6 and Nkx2.1 in lung cancer. Isoform specific expression analysis was performed in healthy mouse lungs (Ctrl) and lung tumors that developed in mice after tail vein injection of Lewis lung carcinoma (LLC1) cell lines (Tum1, 2), n=5 mice each and Tum1, 2 represent tumors from two different mice. Data are represented as in (B).

Figure 13:
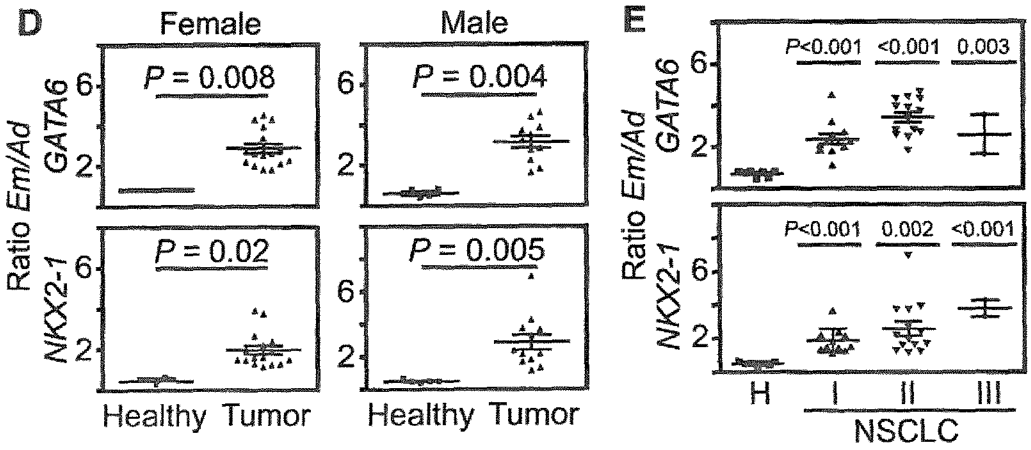

FIG. 13: High expression of Em isoform in human lung cancer tissues.

(A) Isoform specific expression of GATA6 and NKX2-1 was monitored by qRT-PCR after total RNA isolation from human lung tumor and normal lung formalin fixed paraffin embedded (FFPE) sections. The Em/Ad ratio for both genes is plotted. Samples are normalized to TUB1A1. Each point represents one sample, horizontal line in the middle represents the mean and the error bars represent the standard error mean (s.e.m). n=20 Healthy, n=39 Tumor. P values after one-way ANOVA. (B) Unadjusted Receiver-Operating-Characteristics (ROC) Curves for GATA6 and NKX2-1. Sensitivity and 1 minus specificity (ROC curves) are shown for different values for Em/Ad ratio of GATA6 and NKX2-1. (C and D) High Em/Ad ratio is conserved among ethnic groups (C) and gender (D). CHB, Han Chinese in Beijing; CEU, Utah residents with ancestry from northern and western Europe; MXL, Mexican ancestry in Los Angeles. n=10 Healthy, 28 Tumor (CHB); n=7 Healthy, 3 Tumor (CEU); n=3 Healthy, 14 Tumor (MXL); n=5 Healthy, 15 Tumor (Male) and n=2 Healthy and 16 Tumor (Female); Data are represented as in (A). The filled triangles in (C) (MXL) represent NSCLC tumor samples. The empty triangle in (C) (MXL) represents a small cell lung cancer sample. (E) Expression of Em isoform correlates with tumor grade. Ratio of Em/Ad isoform was monitored in lung cancer biopsies of Grade I, II and III. n=10 Healthy, n=12 GradeI, n=14 GradeII and 2 Grade III. Samples were staged according to the TNM Classification recommended by the American Joint Committee on Cancer. Data are represented as in (A).

Figure 14:
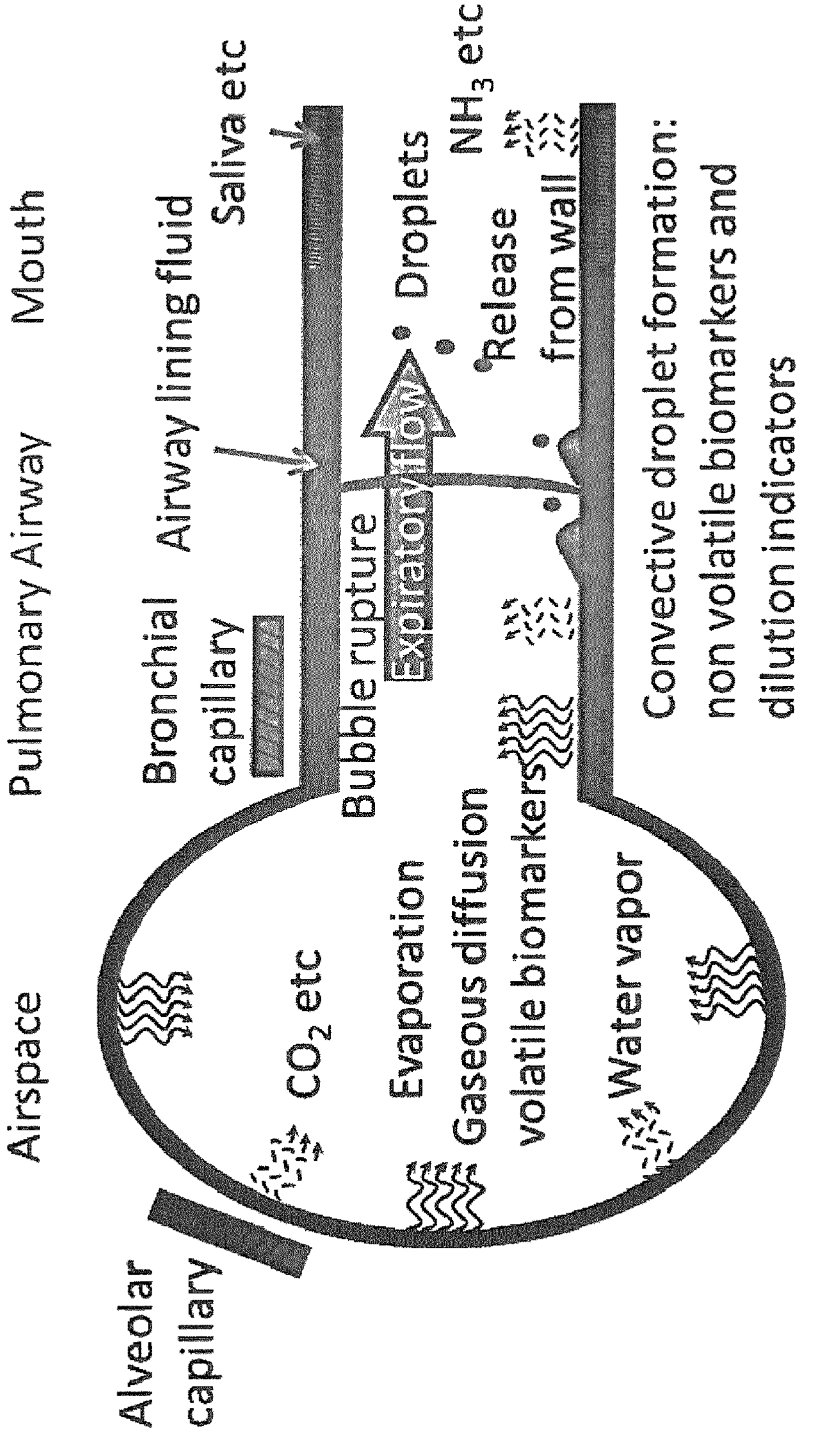
Figure 14:
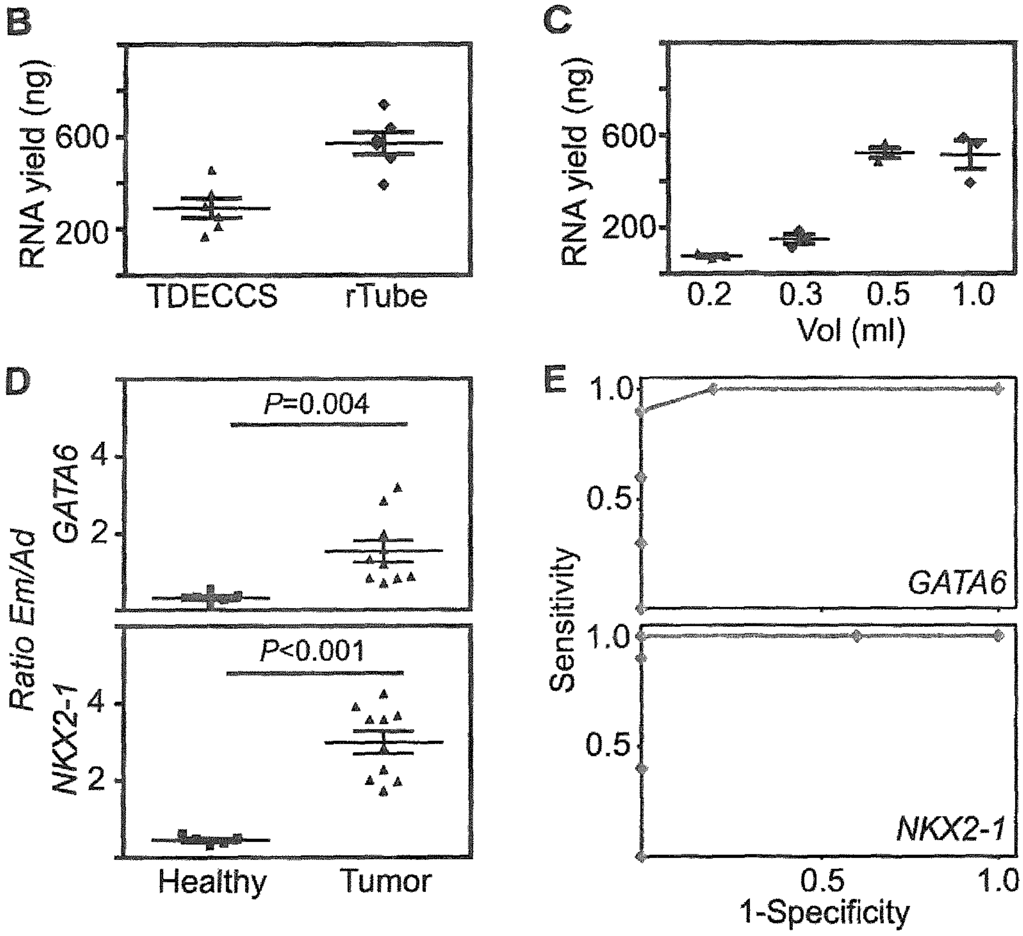

FIG. 14: Noninvasive lung cancer diagnosis using Exhaled breath condensate (EBC).

(A) Exhaled breath condensate (EBC) as a promising source of biomarkers for lung diseases. Water vapour is rapidly diffused from the airway lining fluid (both bronchial and alveolar) into the expiratory flow. Droplet formation (nonvolatile biomarkers) takes place in the airway lining fluid, while respiratory gases (volatile biomarkers) are from both the airspaces and the airways. Adapted from Effros et al. (2012) Am J Respir Crit Care Med. 185(8): 803-804) (B) RTube is more suitable for RNA isolation as compared to TurboDECCS. Two main EBC collection devices were compared for the total RNA yield (y-axis, ng) obtained using the QIAGEN RNeasy Micro column using 500 μl EBC as starting material. Data are represented as mean±s.e.m, n=6. (C) 500 μl of EBC is optimal for RNA isolation. Total RNA isolation with the RNeasy Micro kit was compared using 200, 350, 500 and 1000 μl starting EBC volume. Data are represented as in (B), n=3.

Figure 15:
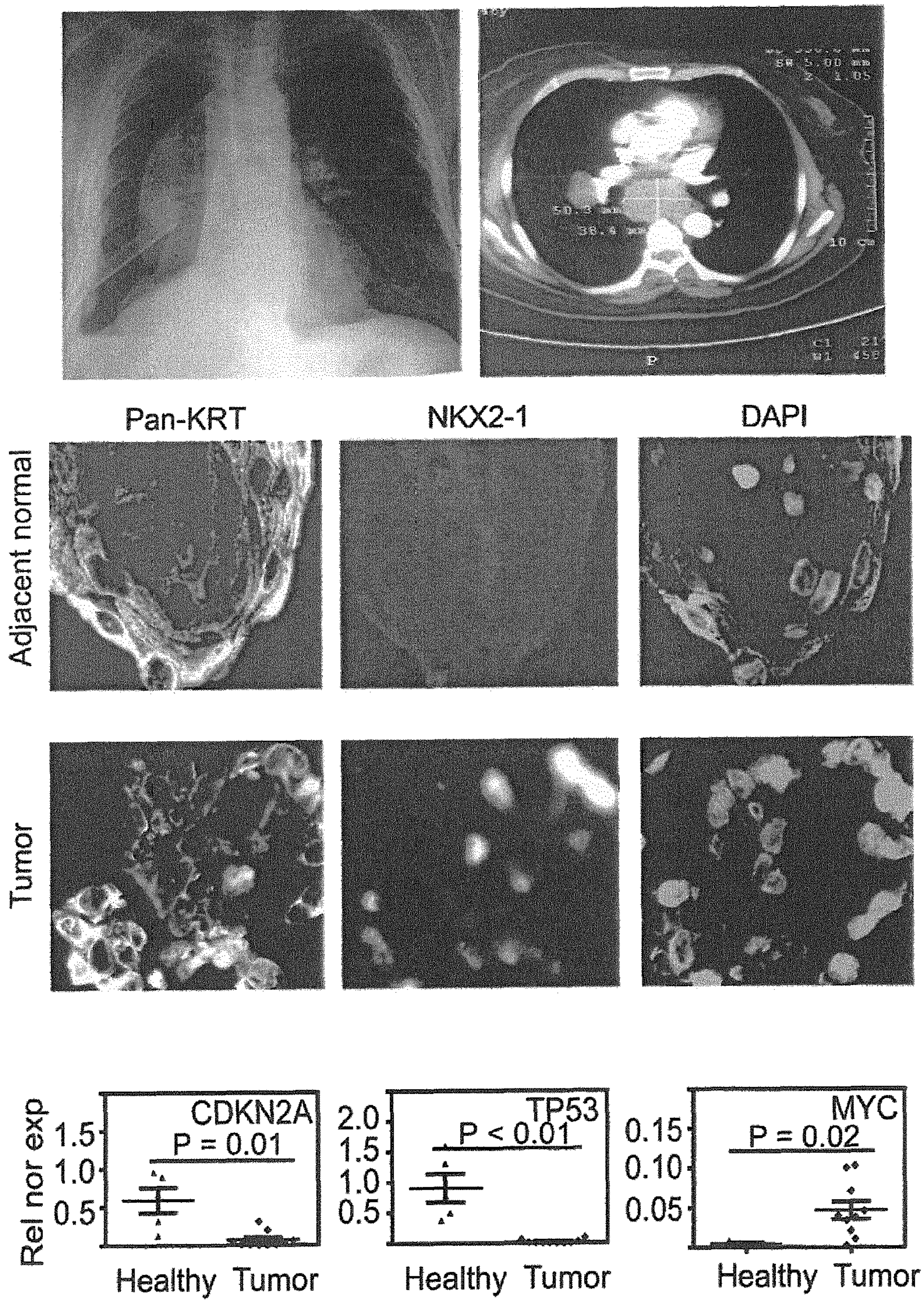

FIG. 15: EBC based lung cancer diagnosis correlates with classical methods.

Representative pictures of (A) chest X-ray and (B) low-dose helical computed tomography (CT) scans for patients with lung cancer. (C) Immunohistochemistry analysis for adjacent normal (upper panel) and tumor (lower panel) from a lung cancer patient sample with the indicated antibodies. PAN-KRT, Pan Cytokeratin; NKX2-1, also known as TTF1, Thyroid transcription factor 1; DAPI, nucleus. Scale bar, 10 μm. (D) Expression analysis of known tumor suppressor and oncogenes in EBCs of healthy donors and tumor patients. CDKNA2, also known as P16, cyclin-dependent kinase inhibitor 2A; TP53, tumor protein p5.3; MYC, v-myc avian myelocytomatosis viral oncogene homolog. Data are represented as in FIG. 13.

Figure 16:
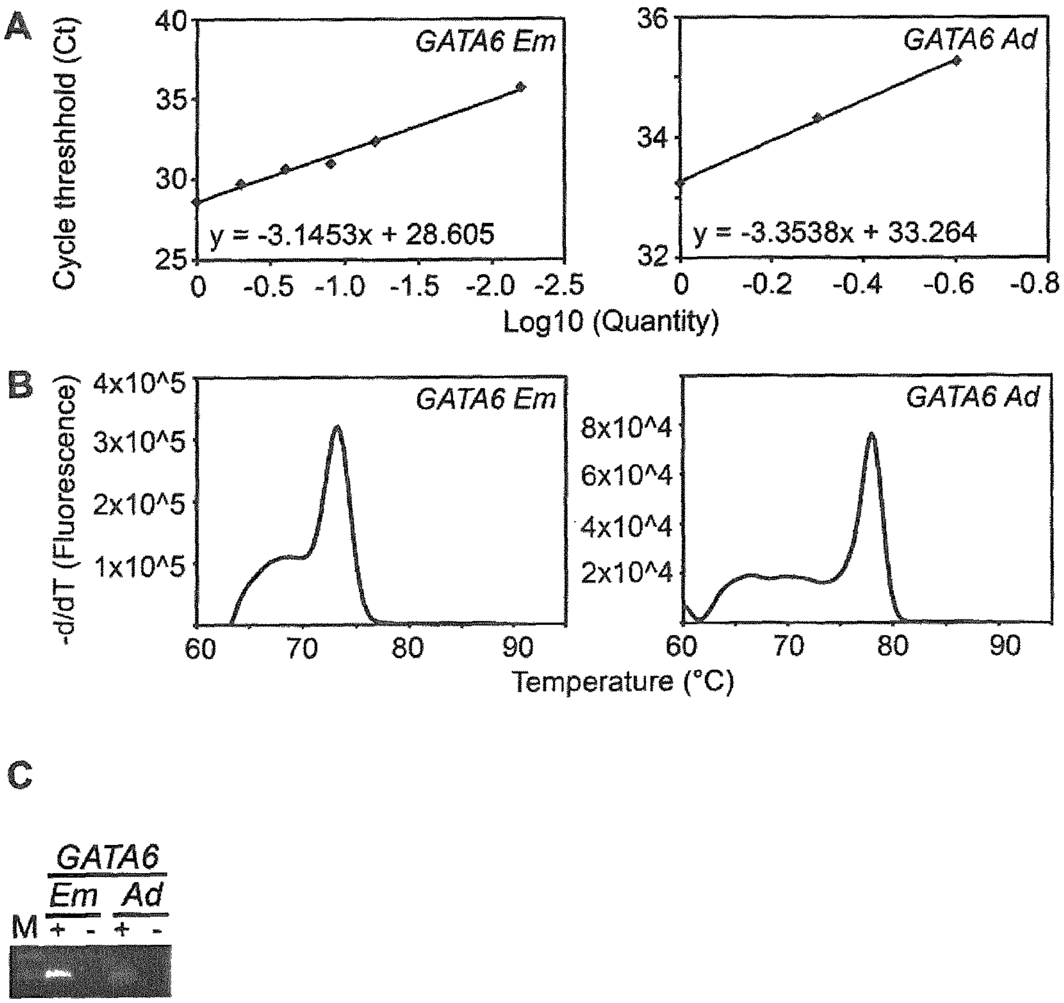
Figure 16:
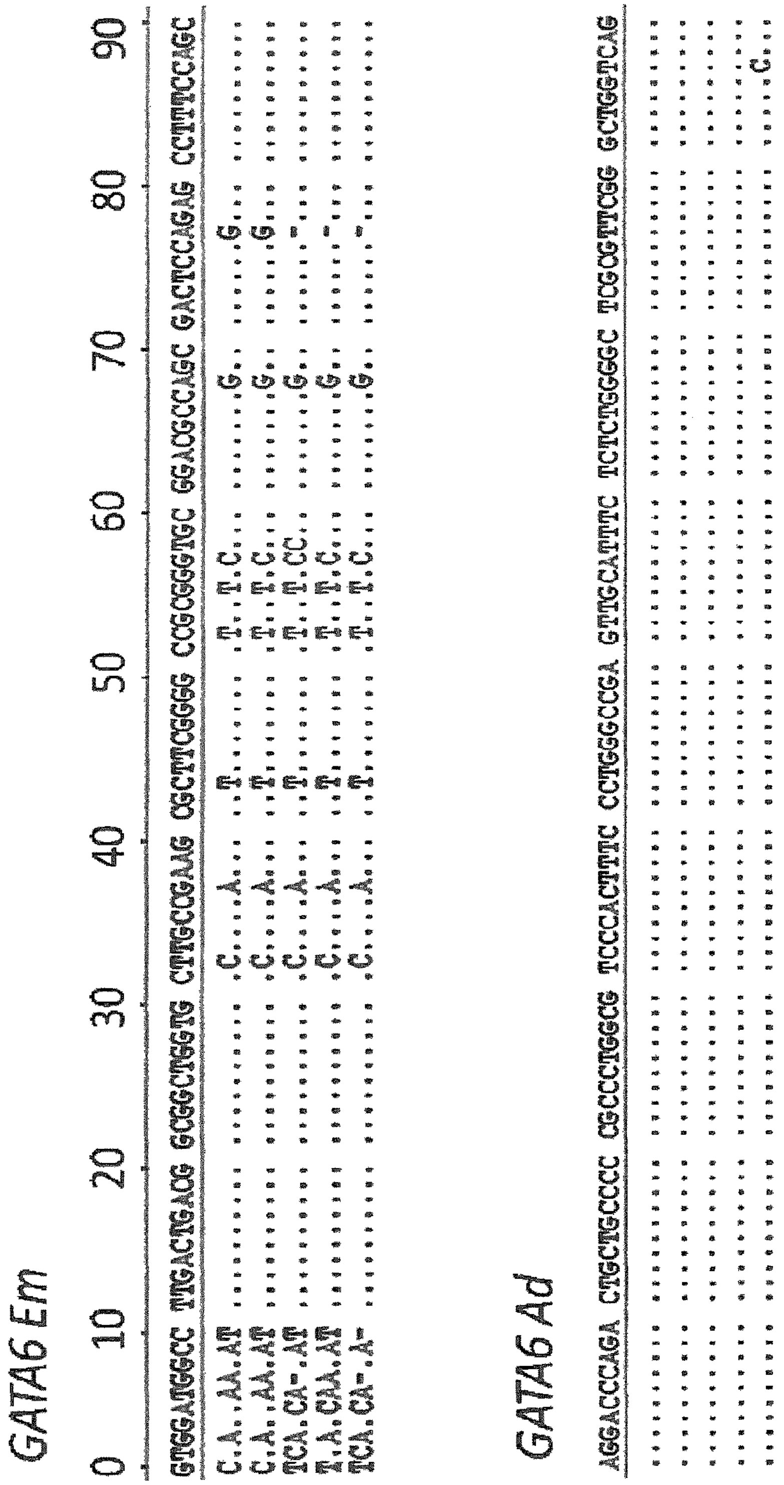

FIG. 16: Specific PCR amplification of both isoforms of GATA6. (A) Amplification efficiency for each primer pair was calculated using serial dilutions of the cDNA template. Primer efficiency was assessed by plotting the cycle threshold values (Ct, y-axis) against the logarithm (base 10) of the fold dilution (log (Quantity), x-axis). Primer efficiency was calculated using the slope of the linear function. Data points represent mean Ct values of triplicates. (B) Dissociation curve analysis of the PCR products was performed by constantly monitoring the fluorescence with increasing temperatures from 60° C. to 95° C. Melt curves were generated by plotting the negative first derivative of the fluorescence (d/d T (Fluorescence) 520 nm) versus temperature (degree Celsius, ° C.). (C) Specific PCR amplification was also demonstrated by agarose gel electrophoresis. PCR products after quantitative RT-PCR were analyzed by agarose gel electrophoresis. +, specific PCR reaction using EBC template; −, no RT control; M, 100 bp DNA ladder. (D) Sequencing of the PCR products of GATA6 Em and Ad (SEQ ID NOs: 184 and 185) demonstrates specific PCR amplification of both isoforms using EBC as template. Five clones for each primer pair (GATA6 Em and Ad) were sequenced and aligned to the reference sequence (top row, yellow highlighted). Sequence similarities are represented as dots.

Figure 17:
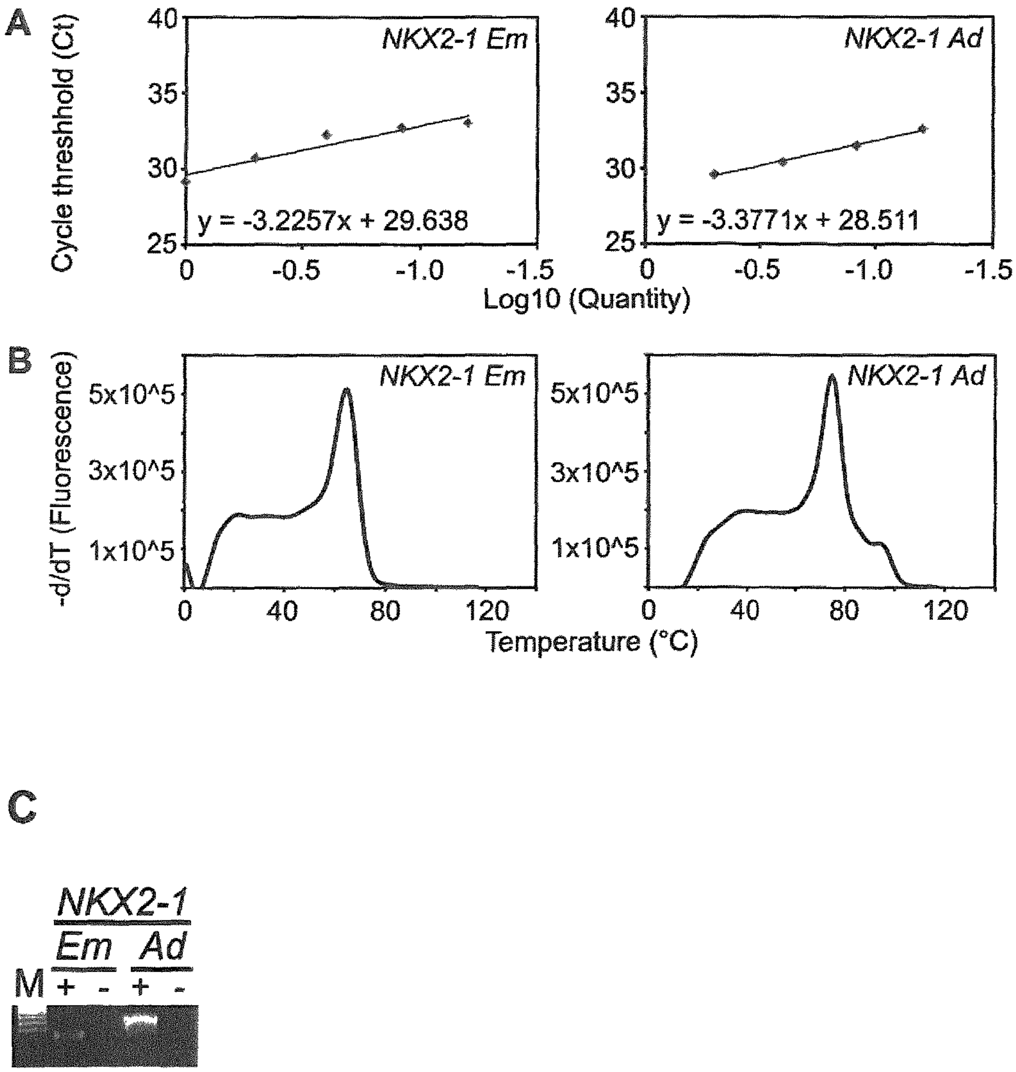
Figure 17:
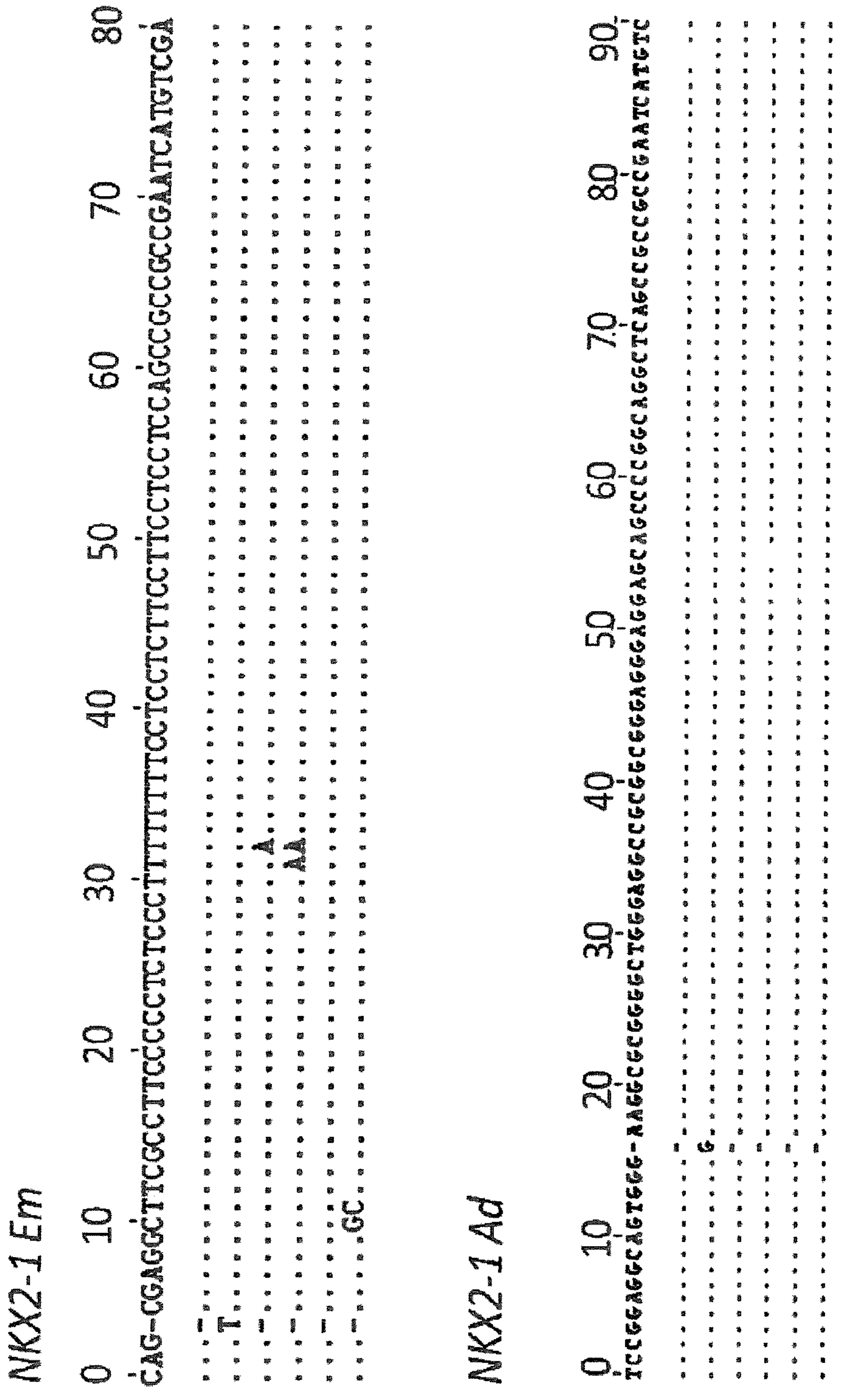

FIG. 17: Specific PCR amplification of both isoforms of NKX2-1.

(A) Amplification efficiency for each primer pair was calculated using serial dilutions of the cDNA template. Primer efficiency was assessed by plotting the cycle threshold values (Ct, y-axis) against the logarithm (base 10) of the fold dilution (log (Quantity), x-axis). Primer efficiency was calculated using the slope of the linear function. Data points represent mean Ct values of triplicates. (B) Dissociation curve analysis of the PCR products was performed by constantly monitoring the fluorescence with increasing temperatures from 60° C. to 95° C. Melt curves were generated by plotting the negative first derivative of the fluorescence (−d/dT (Fluorescence) 520 nm) versus temperature (degree Celsius, ° C.). (C) Specific PCR amplification was also demonstrated by agarose gel electrophoresis. PCR products after quantitative RT-PCR were analyzed by agarose gel electrophoresis. +, specific PCR reaction using EBC template; −, no RT control; M, 100 bp DNA ladder. (D) Sequencing of the PCR products of NKX2-1 Em and Ad (SEQ ID NOs: 186 and 187) demonstrates specific PCR amplification of both isoforms using EBC as template. Five clones for each primer pair (NKX2-1 Em and Ad) were sequenced and aligned to the reference sequence (top row, yellow highlighted). Sequence similarities are represented as dots.

FIG. 18—Loss-of-function (LOF) of embryonic Gata6 counteracts lung tumor formation.

(A) SiRNA mediated Gata6 depletion is isoform-specific and efficient. MLE-12 cells were transiently transfected with control siRNA (Ctrl) or siRNA specific against Gata6 embryonic (Em) or adult (Ad) isoforms. Isoform specific Gata6 expression analysis was performed by qRT-PCR. Rel nor exp Gata6, relative expression of Gata6 normalized to Tuba1a, n=3, Asterix, P values after one-way ANOVA, * P<0.001;  P<0.01; * P<0.05. (B) Gata6 Em specific LOF results in reduced migration of MLE-12 cells. MLE-12 cells were transfected as in A. Transfected cells were grown till a confluent monolayer was formed and a scratch (dashed lines) was made in the center (0 hr). The closure of the scratch or wound healing by the growth of a confluent monolayer of cells was monitored 24 hr later. siCtrl, control siRNA; siGata6 Em and siGata6 Ad, embryonic and adult isoform specific siRNAs. (C) Orotracheal administration of siRNA results in Gata6 Em specific loss of function in adult mouse lung. Lungs of mice that were orotrachealy administered with siCtrl and siGata6 Em were harvested for total lung RNA isolation. Isoform specific expression analysis was performed by qRT-PCR. Data are represented as in A. (D) Macroscopic tumor analysis revealed significant reduction of tumor formation in mice treated with siGata6 Em. Lungs were isolated from mice injected with LLC1 cells and treated with siCtrl or siGata6 as in C. Macroscopic surface tumors (Surface tum, arrows) were counted and percentage tumor reduction was analyzed. Scale bar, 1 mm; n=5; P values as in A.

Figure 19:
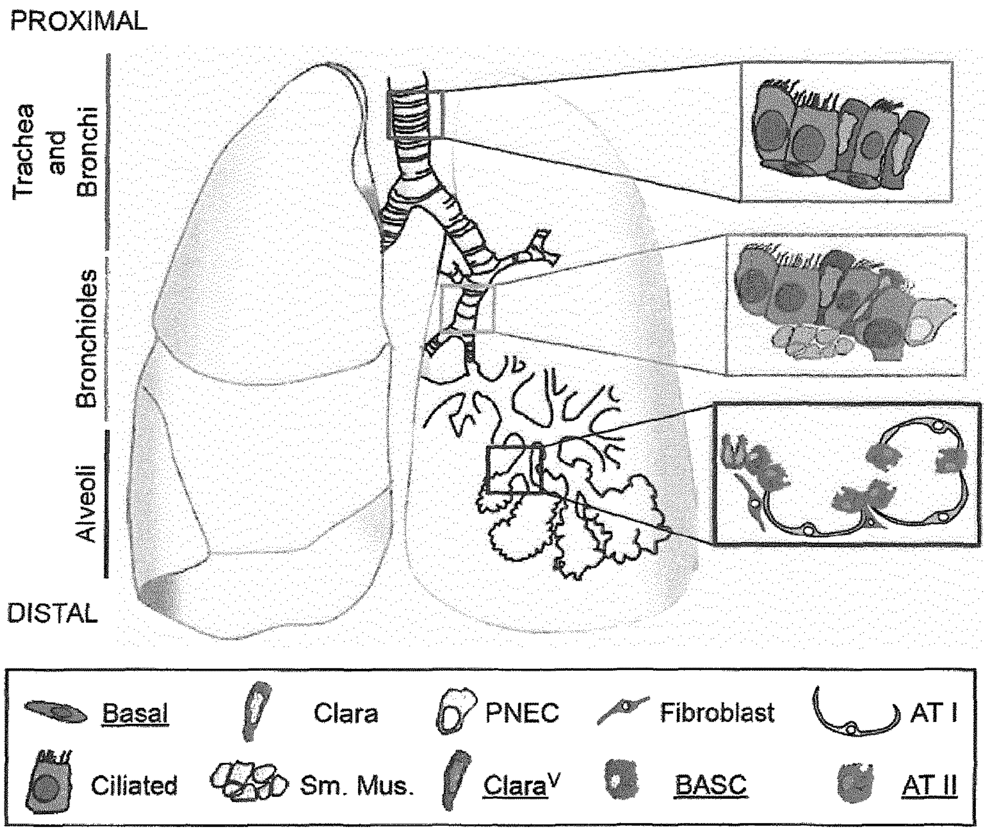

FIG. 19. Schematic representation of the lung structure.

The lung consists of different structural regions organized along a proximal-distal axis. Each of these regions is characterized by specialized cell types of epithelial or mesenchymal origin (listed in the square). Different tissue-resident lung-endogenous progenitor cells (underlined in the list) are located in specific regions along the proximal-distal axis of the airways. They are responsible for homeostatic turnover and repair after injury. Alveolar type II (ATII) cells represent one of these regional progenitor cell populations and are located in the alveoli. Sm. Mus., smooth muscle cells; Clarav, variant Clara cells; PNEC, pulmonary neuroendocrine cells; BASC, bronchoalveolar stem cells; AT I, alveolar type I cells.

FIG. 20.

(A) Schematic representation of experimental procedure. Spike-in based relative quantification of ATII versus MLE-12 cells using (13)C6-lysine labeled lung (Lys-6 labeled, heavy labeled lung) as standard. (B) Quality analysis of membrane protein isolation. Distribution of Gene Ontology cellular component (GOCC) terms based analysis of identified proteins after mass spectrometric measurement. (C) Calculation of direct abundance ratio between MLE-12 and ATII cells (MLE-12/ATII). (D) (Top) Histogram of spike-in SILAC-ratios (log 2) between heavy labeled lung and ATII (right) or MLE-12 (left) cells. (Bottom) Histogram of direct ratio between MLE-12 versus ATII cells (MLE-12/ATII, log 2, left) and the direct ratio plotted against intensity (log 10, right).

FIG. 21.

(A) Table of selected proteins enriched in ATII cells. (B) MS spectra of ITGB2 specific SILAC-pairs derived from ATII or MLE-12 cells mixed with labeled heavy lung. H, heavy, L, light; N., number; n.d., not determined; m/z, xyz FIG. 22. Identification of potential ATII cell specific membrane proteins.

(A) Scatter plot between membrane protein abundance ratio (MLE-12/ATII) and gene expression ratio (MLE-12/ATII). Proteins enriched in the membrane of ATII cells are indicated in the marked section and listed in the table (B). Prot Abud, protein abundance; Gene Exp, gene expression.

Figure 23:
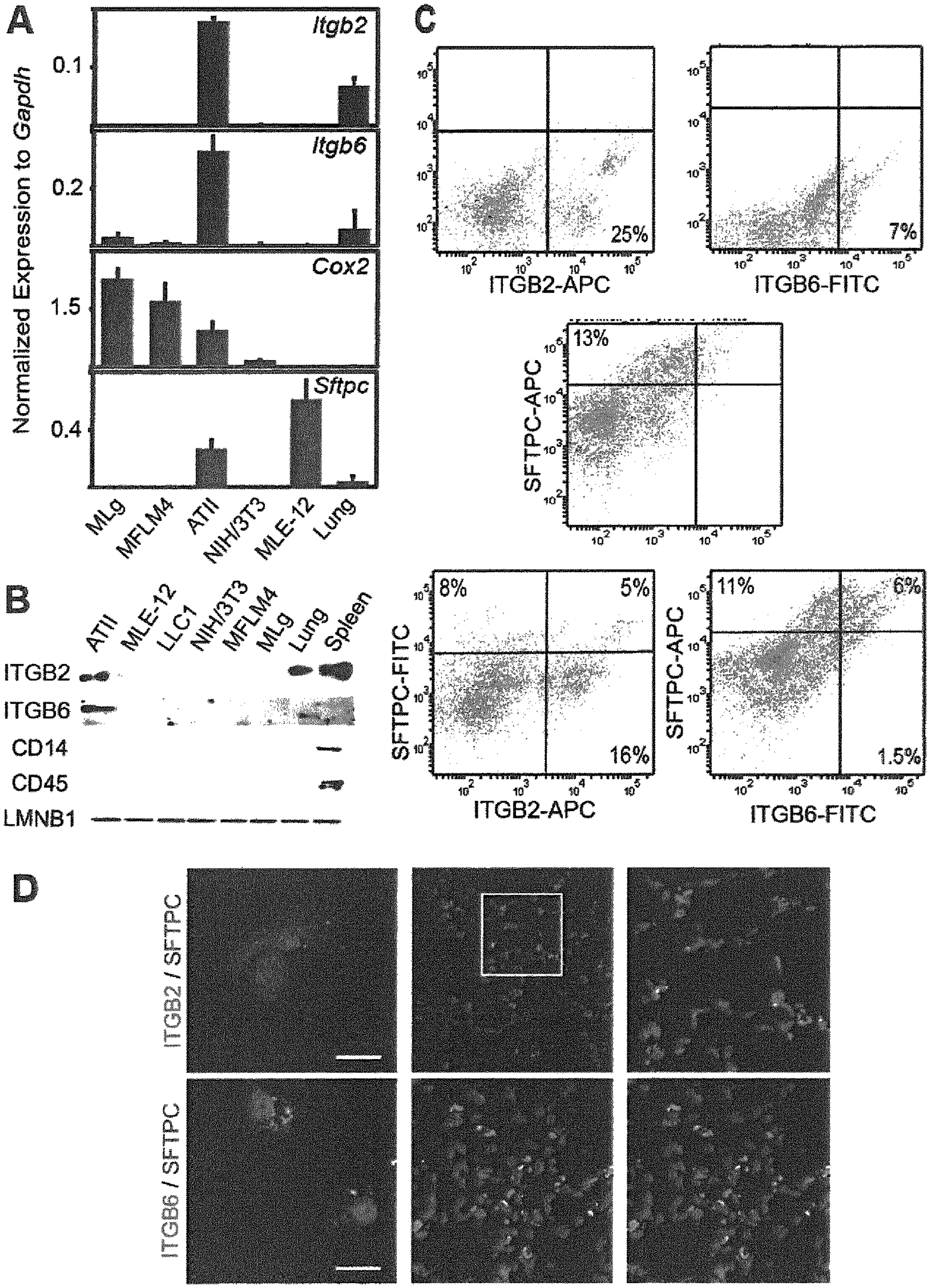

FIG. 23. Integrin beta 2 and 6 are membrane proteins of a sub-population of alveolar type II cells.

(A) Itgb2 and Itgb6 are specifically expressed in ATII cells. Expression of the indicated genes was analyzed in different cell lines and in adult lung by qRT-PCR. Gene expression was normalized after Gapdh. Data are represented as mean±s.e.m. (n=6). (B) ITGB2 and ITGB6 are ATII cells specific proteins. Protein extracts of different cell lines, adult lung and spleen were analyzed by western blot using antibodies specific for the indicated proteins. CD14 and CD45 were used as controls for blood cells specific antigens. LMNB1, Lamin B1, loading control. (C) A sub-population of alveolar type II cells is positive for ITGB2 or ITGB6. Cell suspensions of adult lung were analyzed by flow cytometry after single (top and middle) or double (bottom) immunostaining using SFTPC- and either ITGB2- or ITGB6-specific antibodies. The numbers indicate the percentage of positive stained cells in the relevant quadrants. (D) SFTPC and ITGB2 or ITGB6 co-localized in alveolar type II cells. Confocal microscopy of isolated alveolar type II cells (left) and adult lung sections (middle and right) after double immunostaining using SFTPC- and either ITGB2- or ITGB6-specific antibodies. Nuclear staining with Draq5. Squares show regions presented at higher magnification on the right. Scale bars, 20 μm.

Figure 24:
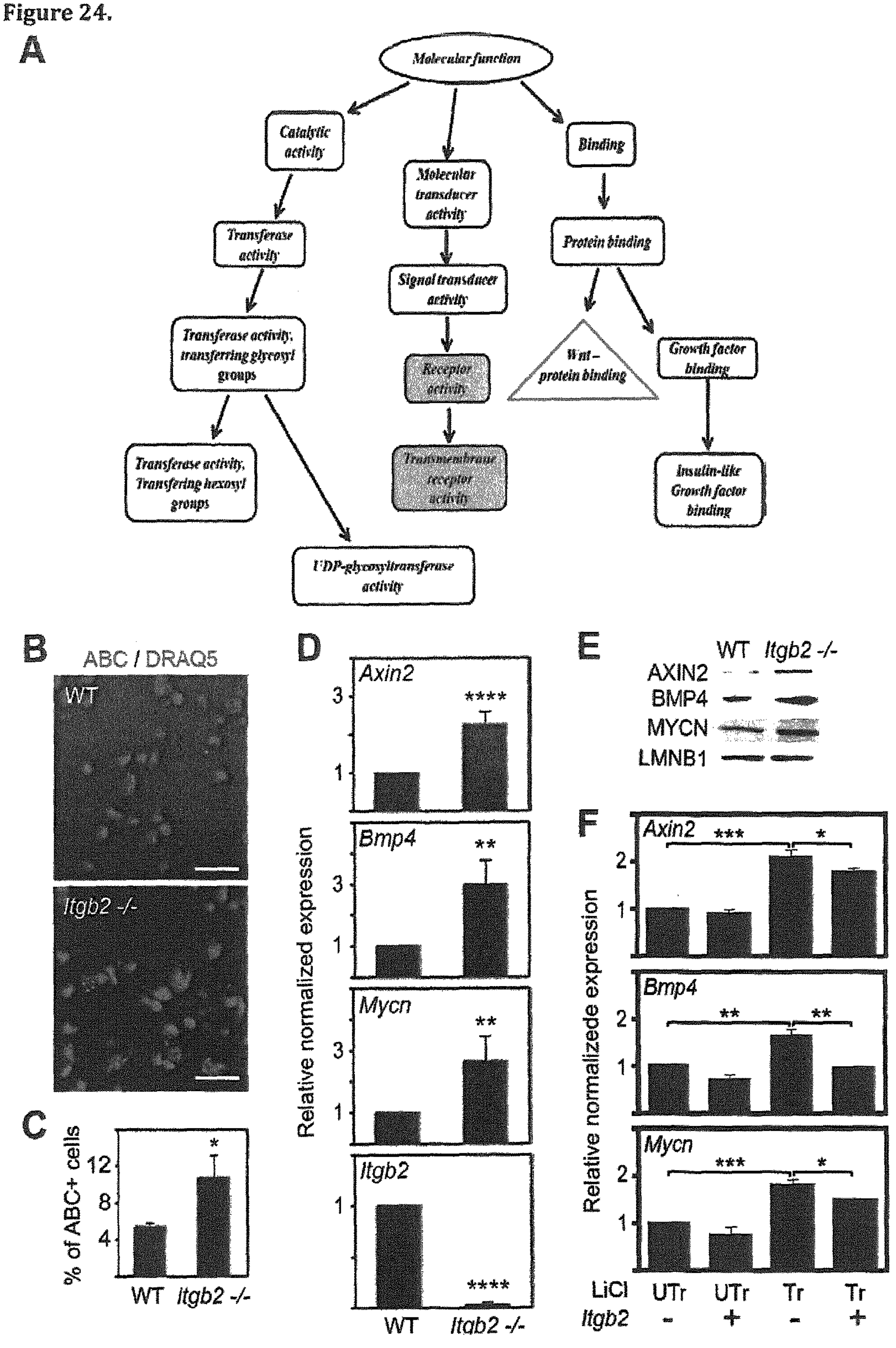

FIG. 24. Integrin beta 2 antagonizes WNT signaling pathway.

(A) WNT signaling pathway related proteins are enriched in the membrane of ATII cells. Schematic representation of Gene Ontology biological process (GOBP) terms based analysis of identified proteins after mass spectrometric measurement using the GORILLA online-tool (Eden, BMC Bioinformatics, 2009). The color represents the frequency of ATII enriched membrane proteins involved in the indicated biological processes (red, high; orange, middle; white, low). (B) Itgb2 knockout (Itgb2−/−) increased activated-beta-catenin immunostaining (ABC) in adult lung. Sections of adult lung of wild type (WT) and Itgb2−/− mice were analyzed by confocal microscopy after immunostaining using ABC specific antibodies. Nuclear staining with Draq5. Scale bars, 20 μm. (C) Quantification of ABC positive cells in adult lung of WT and Itgb2−/− mice after immunostaining as in B. Axis of ordinates show percentage of ABC positive cells relative to total counted cells. Data are represented as mean±s.e.m. (n=3). Asterisks, P values after one-way ANOVA, * P<0.001;  P<0.01; * P<0.05 (D) Itgb2 knockout enhanced expression of canonical WNT pathway markers. Expression analysis of the indicated genes by qRT-PCR in adult lung of WT and Itgb2−/− mice. Data are represented as mean±s.e.m. (n=3). Asterisks as in C. (E) Itgb2 knockout increased in adult lung the level of proteins encoded by genes that are targets of WNT signaling. Lung protein extracts from WT or Itgb2−/− mice were analyzed by western blot using antibodies specific for the indicated proteins. (F) Itgb2 gain-of-function antagonized the positive effect of lithium chloride (LiCl) on expression of canonical Wnt targets. Expression analysis of the indicated genes by qRT-PCR in MLE-12 cells that were untreated (UTr) or treated (Tr) with LiCl and transfected with either control (−) or mouse Itgb2 expression plasmid as indicated. Data are represented as mean±s.e.m. (n=3). Asterisks as in C.

FIG. 25:

(A) Schematic representation of experiment design. Sftpc-rtTA/TetOP-Cre//TK-LoxP-LacZ-LoxP-GFP triple transgenic mice were treated with Control (Ctrl) or Gata6 Em expression vectors as in FIG. 10. 3 days after the first treatment, doxycycline was administered via water. After 7 weeks, lungs were isolated and single cell homogenate was made and following negative selection for blood cells using CD16, CD45/32 antibodies, a pupe population of lung epithelial cells was obtained. These cells were cultured in low attachment dishes in serum free conditions, supplemented with basic fibroblast growth factor (bFGF), epidermal growth factor (EGF) and heparin. (B) Diagrammatic representation of the transgenic mice. Surfactant protein C (SftpC) promoter drives the expression of rtTA which in the presence of doxyclycine binds to the Tet operator (Tet OP) and activates downstream expression of Cre recombinase (Cre). Cre recombinase is essential for homologous recombination at the LoxP sites, resulting in the deletion of the LacZ gene, and the expression of EGFP in SftpC expressing cells.

Figure 26:
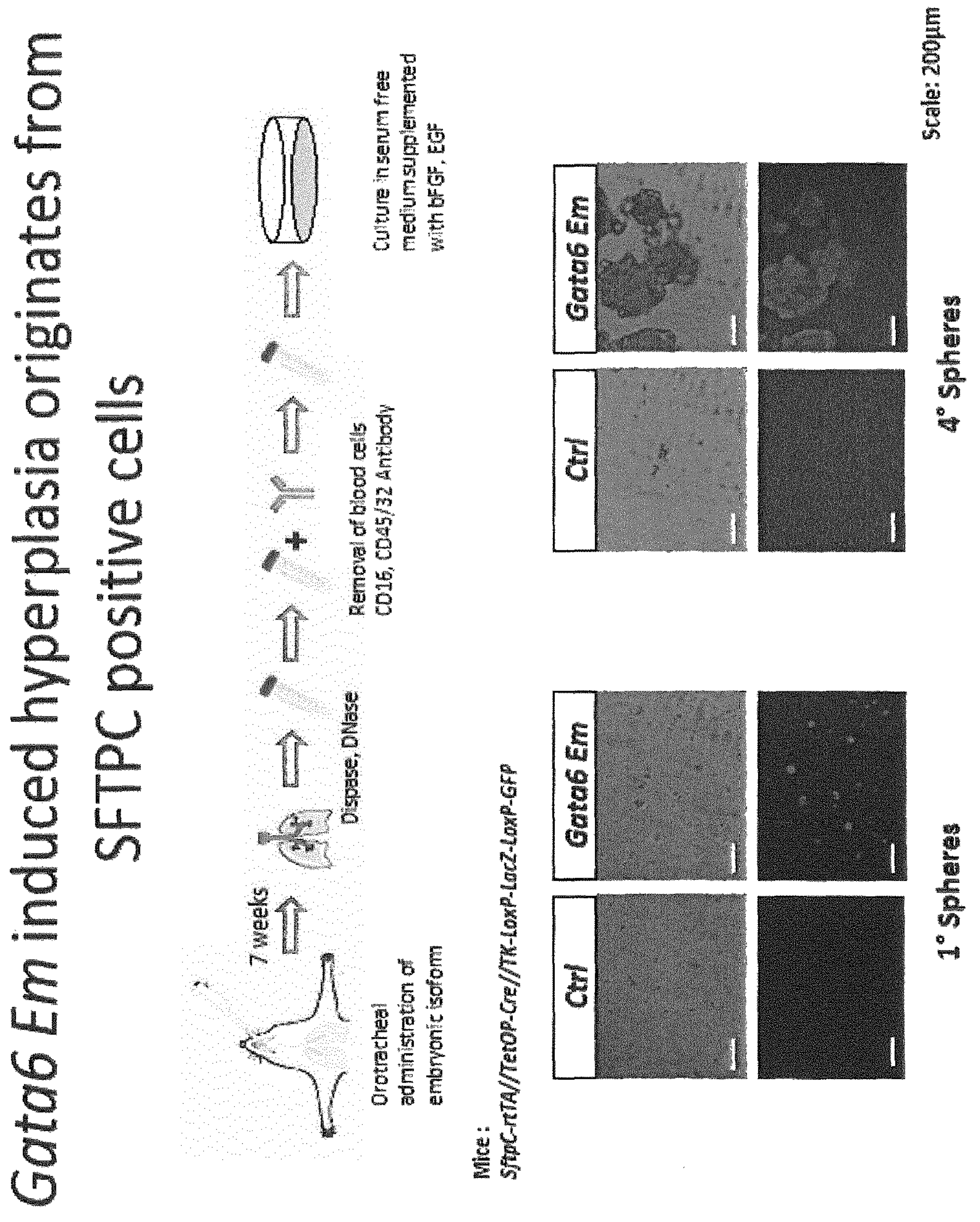

FIG. 26: Gata6 Em Induced hyperplasia originates from SFTPC positive cells.

Isolated primary cultures of Gata6 Em treated lungs form clusters of cells within 10 days of culture as compared to Ctrl treated lungs (Left panel). These clusters of cells express EGFP. Following subsequent dissociation and replating, these clusters were able to maintain in culture for 4 passages and continuously expressed EGFP (Right panel). Scale 200 μm.

A number of documents including patent applications, manufacturer's manuals and scientific publications are cited herein. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The present invention is additionally described by way of the following illustrative non-limiting examples that provide a better understanding of the present invention and of its many advantages. The following examples are included to demonstrate preferred embodiments of the invention. It should be appreciated by those of skill in the art that the techniques disclosed in the examples which follow represent techniques used in the present invention to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Materials and Methods

In Silico Analysis of Gene Structure

Genomic sequences for lung relevant genes (Gata6, Nkx2-1, Foxa2 and Id2) were obtained from the NCBI Gene database. Sequences analysed for promoter identification and CpG island analysis included up to 5 kb upstream of the transcription start site. Promoters were predicted using WWW Promoter Scan online tool using the PROSCAN Version 1.7 Suite of programs (see Prestridge (1995) Journal of Molecular Biology 249: 923-932). Promoters chosen for further analysis had a score greater than 60 based on transcription factor binding sites and RNA Pol II eukaryotic promoter sequences. The EMBL online tool, CpG Plot (http://www.ebi.ac.uk/Tools/emboss/cpgplot/) was used to identify CpG islands surrounding the identified or known promoter sequences. The CpG islands were identified as regions containing more than 50% CG content over a minimum region of 200 bp. Promoter predictions were then compared to mRNA sequences for these genes obtained from Aceview (Thierry-Mieg (2006) Genome Biology 7 (Suppl 1):s12) which provides a comprehensive and non-redundant sequence representation of all human and mouse mRNA sequences (mRNAs from GenBank or RefSeq, and single pass cDNA sequences from dbEST and Trace). Isoforms that were identified based on mRNA sequences corresponding to predicted promoters with CpG islands at their 5' end were taken for further analysis.

TABLE 1

| Accession Numbers | | |
|---|---|---|
| Gene | Mouse | Human |
| Gata6, GATA6 | NC_000084.6 (11052510 . . . 11085635) | NC_000018.9 (19749404 . . . 19782491) |
| Nkx2-1, NKX2-1 | NC_000078.6 (56531935 . . . 56536908, complement) | NC_000014.8 (36985602 . . . 36989430, complement) |
| Foxa2, FOXA2 | NC_000068.7 (148042878 . . . 148046969, complement) | NC_000020.10 (22561642 . . . 22566101, complement) |
| Id2, ID2 | NC_000078.6 (25093799 . . . 25096092, complement) | NC_000002.11 (8822113 . . . 8824583) |

DNA Constructs

Expression plasmid for Gata6 Em was purchased from Origene (MR222974) in vector pCMV6-Entry containing a Myc and DDK tag. The Gata6 Ad was PCR amplified using the embryonic isoform as template and sub cloned into pcDNA3.1 Myc His B (Invitrogen). The Nkx2-1 Em was purchased from Addgene (Plasmid 15540) and subcloned into pCS2-Myc. The Nkx2-1 Ad was PCR amplified and cloned into pcDNA3.1 Myc His A (Invitrogen).

Cell Culture

Cell lines used in this study were A549 (CCL-185), A427 (HTB-53), H322 and MLE-12 (CRL-2110). Cell lines were cultured in medium and conditions recommended by the American Type Culture Collection (ATCC). Cells were used for the preparation of RNA (QIAGEN RNeasy plus mini kit).

MLE-12 cells were transfected using Lipofectamine 2000 (Invitrogen) with the expression vectors for Gata6 Em and Nkx2-1 Em in a ratio of 1:2 DNA:Lipofectamine. The cells were washed and the medium was changed on the following day. For the generation of stable transfected cells, 48 hours after transfection, the cells were plated at clonal density and selection medium supplemented with 1 mg/ml G418 (Sigma) was added. Cells were maintained in selection medium for subsequent passages.

In Vitro Scratch Assay

The in vitro scratch assay was performed as previously described (Liang C C et al., (2007) Nat Protoc. 2007; 2(2): 329-33). Briefly, MLE-12 cells were transfected with Gata6 Em, Nkx2-1 Em and Control plasmids as above. The cells were grown at 37° C. till they reached 100% confluence to form a monolayer. A p200 pipette tip was used to create a scratch of the cell monolayer. The plate was then washed to remove the floating cells and the medium was replaced. The cells were then observed after every 6 hours to check migration.

Colony Formation Assay

For the clonogenecity assay, control and Gata6 Em stable transfected cells were trypsinized with 0.005% trypsin and counted. Cells were plated at a density of 500 and 1000 cells/well of a 12 well plate in medium supplemented with 1 mg/ml G418 (Sigma-Aldrich). The total number of colonies was counted after 2 weeks following Haematoxylin staining.

RNA Isolation and Expression Analysis

Timed pregnant (C57B16 WT) mice were sacrificed on post coitum days 11.5, 12.5, 13.5 and 14.5. Lungs were dissected from these embryos, as previously described. Total RNA was isolated from 5 lungs for each stage using the RNeasy plus mini kit (Qiagen). Human lung tumor tissues were obtained as cryoblocks. Six sections of 10 μm were used for total RNA isolation with the RNeasy plus micro kit (Qiagen). The High Capacity cDNA Reverse Transcription kit (Applied Biosystem) was used for cDNA synthesis according to manufacturer's instructions. The PCR results were normalized with respect to the housekeeping gene Gapdh. Quantitative real time PCR reactions were performed using SYBR® Green on the Step One plus Real-time PCR system (Applied Biosystem).

Table 2: Primer Sequences

| Gene | Primers for Mouse (5'→3') | Primers for Human (5'→3') | Primers for Human (5'→3') (For RNA from tissue sections) |
|---|---|---|---|
| HPRT Fwd | | TGACCTTGATTTATTTTG CATACC (SEQ ID NO. 61) | TTTGCTTTCCTTGGTCAG GCAGT (SEQ ID NO. 62) |
| HPRT Rev | | CGAGCAAGACGTTCAGTC CT(SEQ ID NO. 63) | CGTGGGGTCCTTTTCACC AGCA (SEQ ID NO. 64) |
| Gapdh Fwd | TGAGTATGTCGTGGAGT CTAC (SEQ ID NO. 65) | GCAAATTCCATGGCACCG T (SEQ ID NO. 66) | GGCCCGATTTCTCCTCCG GGT (SEQ ID NO. 67) |
| Gapdh Rev | TGGACTGTGGTCATGAG CC (SEQ ID NO. 68) | TCGCCCCACTTGATTTTGG (SEQ ID NO. 69) | GGTGACCAGGCGCCCAAT ACG (SEQ ID NO. 70) |
| Gata6-Em Fwd | GCTAGCGCTGTTTGTTT AGGGCTCG (SEQ ID NO. 71) | SEQ ID NO 9: CTCGGCTTCTCTCCGCGCC TG | SEQ ID NO 10: TTGACTGACGGCGGCTGG TG |
| Gata6-Em Rev | GCCCCGAAACGCTTCGG CAG (SEQ ID NO. 72) | SEQ ID NO 11: AGCTGAGGCGTCCCGCAG TTG | SEQ ID NO 12: CTCCCGCGCTGGAAAGGC TC |
| Gata6-Ad Fwd | TTTGGGGTGGCCTCGGC TCT (SEQ ID NO. 73) | SEQ ID NO 13: GCGGTTTCGTTTTCGGGG AC | SEQ ID NO 14: AGGACCCAGACTGCTGCC CC |
| Gata6-Ad Rev | CCAGGCCAACCGCACAC CTT (SEQ ID NO. 74) | SEQ ID NO 15: AAGGGATGCGAAGCGTAG GA | SEQ ID NO 16: CTGACCAGCCCGAACGCG AG |
| Nkx2-1-Em Fwd | GCGGCCATGCAGCAGCA C (SEQ ID NO. 75) | SEQ ID NO 17: AAACCTGGCGCCGGGCTA AA | SEQ ID NO 18: CAGCGAGGCTTCGCCTTC CC |
| Nkx2-1-Em Rev | CCATGTTCTTGCTCACG TCC (SEQ ID NO. 76) | SEQ ID NO 19: GGAGAGGGGGAAGGCGAA GCC | SEQ ID NO 20: TCGACATGATTCGGCGGC GG |
| Nkx2-1-Ad Fwd | ACTCTTTTGGTGGTGAC TGGG (SEQ ID NO. 77) | SEQ ID NO 21: AGCGAAGCCCGATGTGGT CC | SEQ ID NO 21: TCCGGAGGCAGTGGGAAG GC |
| Nk2-1-Ad Rev | CTCATGTTGCCCAGGTT GCC (SEQ ID NO. 78) | SEQ ID NO 22: CCGCCCTCCATGCCCACTT TC | SEQ ID NO 23: GACATGATTCGGCGGCGG CT |

-continued

| Gene | Primers for Mouse (5'→3') | Primers for Human (5'→3') | Primers for Human (5'→3') (For RNA from tissue sections) |
|---|---|---|---|
| Foxa2-Var1 Fwd | ACCGCCATGCACTCGGC TTC (SEQ ID NO. 79) | SEQ ID NO 24: TGCCATGCACTCGGCTTCC AG | SEQ ID NO 25: CAGGGAGAGGGAGGGCG AGA |
| Foxa2-Var1 Rev | GGCTCATTCCAGCGCCC ACA (SEQ ID NO. 80) | SEQ ID NO 26: TCATGTTGCCCGAGCCGCT G | SEQ ID NO 27: CCCCCACCCCCACCCTCT TT |
| Foxa2-Var2 Fwd | GGCACTGCGCTTCACTC CCC (SEQ ID NO. 81) | SEQ ID NO 28: CTGCTAGAGGGGCTGCTT GCG | SEQ ID NO 29: CGCTTCTCCCGAGGCCGT TC |
| Foxa2-Var2 Rev | GGCTCATTCCAGCGCCC ACA (SEQ ID NO. 82) | SEQ ID NO 30: ACGGCTCGTGCCCTTCCAT C | SEQ ID NO 31: TAACTCGCCCGCTGCTGC TC |
| Id2-Var1 Fwd | CTGAACCGAGCCTGGTG CCG (SEQ ID NO. 83) | SEQ ID NO 32: AACCCCTGTGGACGACCCG A | SEQ ID NO 33: TGCGGATAAAAGCCGCCC CG |
| Id2-Var1 Rev | GCTCCGGGAGATGCCCA AGC (SEQ ID NO. 84) | SEQ ID NO 34 GCCCGGGTCTCTGGTGAT GC | SEQ ID NO 35: AGCTAGCTGCGCTTGGCA CC |
| Id2-Var2 Fwd | GGGTGCTGAAAGATTCC AAACCTCG (SEQ ID NO. 85) | SEQ ID NO 36: CTGCGGTGCTGAACTCGCC C | SEQ ID NO 37: CCCCCTGCGGTGCTGAAC TC |
| 1d2-Var 2 Rev | TGTGCCCTTCAGTGTAG GTGGCA (SEQ ID NO. 86) | SEQ ID NO 38: GACGAGCGGGCGCTTCCA TT | SEQ ID NO 39: TAACTCGCCCGCTGCTGC TC |
| Snai1 Fwd | CCGAAGCCACACGCTGC CTT (SEQ ID NO. 87) | | |
| Snai1 Rev | AGCACGGTTGCAGTGGG AGC (SEQ ID NO. 88) | | |
| Acta2 Fwd | GCTGGTGATGATGCTC CCA (SEQ ID NO. 89) | | |
| Acta2 Rev | GCCCATTCCAACCATT ACTCC (SEQ ID NO. 90) | | |
| Pou5f1 Fwd | TGTGGACCTCAGGTTGG ACT (SEQ ID NO. 91) | | |
| Pou5f1 Rev | CTTCTGCAGGGCTTTCA TGTC (SEQ ID NO. 92) | | |

Animal Experiments

Five to 6 weeks old C57BL6 mice were used throughout this study. Animals were housed under controlled temperature and lighting [12/12-hour light/dark cycle], fed with commercial animal feed and water ad libitum. All experiments were performed according to the institutional guidelines that comply with national and international regulations. The mice were administered orotracheally control (pBLSK, Ctrl) or plasmids specific to isoforms (Em, Embryonic or Ad, Adult) of Gata6 and Nkx2-1 prepared in PEI transfection reagent (Sigma-Aldrich, 408727) at 50 μg/kg body weight of the mouse, three times (Day 0, 3, 7). Lungs were harvested at 5, 7 and 12 weeks after administration of plasmid, for RNA (QIAGEN Rneasy Mini Kit) and protein isolation and histology. For histology, the lungs were fixed overnight in 1% Paraformaldehyde (PFA) followed by overnight incubation in PBS. The lungs were dehydrated over a graded series of alcohol changes and embedded in paraffin. In addition, blood was isolated from the mice by cardiac puncture and processed immediately for RNA isolation (QIAGEN Rneasy Mini Kit). A minimum of 200 μl of blood was taken for RNA isolation.

Histology and Haematoxylin Staining

Paraffin embedded lung tissues were analysed by Haematoxylin and Eosin staining. 4 μm sections were prepared and standard staining protocols were followed.

For colony formation assay, cells were fixed in 4% Paraformaldehyde (PFA) for 20 minutes followed by three washes with Phosphate buffered saline (PBS) for 5 minutes. The cells were then incubated in haemaxylin for 20 minutes, followed by two washes in PBS for 5 minutes.

Immunochemistry

For paraffin embedded mouse lung tissue, sections of 4 μm were prepared on a microtome (Leica Germany). Antigen retrieval was performed by boiling in 10 mM Citrate Buffer followed by incubation at sub boiling temperatures for 10 minutes. Antibody staining was performed following standard procedures. All incubations and washes were done with 1×TBS/0.1% Tween-20 (1×TBST). Non-specific binding was blocked by incubating in 5% donkey serum in TBST for 60 minutes. The sections were then incubated with primary and secondary antibodies for 60 min followed by nuclear staining. Antibodies were specific to Pan-cytokeratin (Dako, Code Z0622, 1:200 dilution), Napsin A (Abcam, ab9868; 1:100 dilution) and TRP63 (Cell Signaling Techn., 4984; 1:150 dilution). For cell lines, MLE-12 cells were cultured on coverslips and transfected with Control, Gata6 Em and Nkx2-1 Em plasmids. Cells were fixed 48 hours after transfection with 1% PFA for 20 minutes and washed 3 times, for 5 minutes, with 1×PBS. Antibody staining was performed as above. Antibodies were specific to MKI67 (Abcam, ab15580; 1:200 dilution) and MYC (Abcam, ab9132, 1:500 dilution)

Example 2: In Silico Analysis of Gata6. Nkx2-1, Foxa2 and Id2

Figure 1:
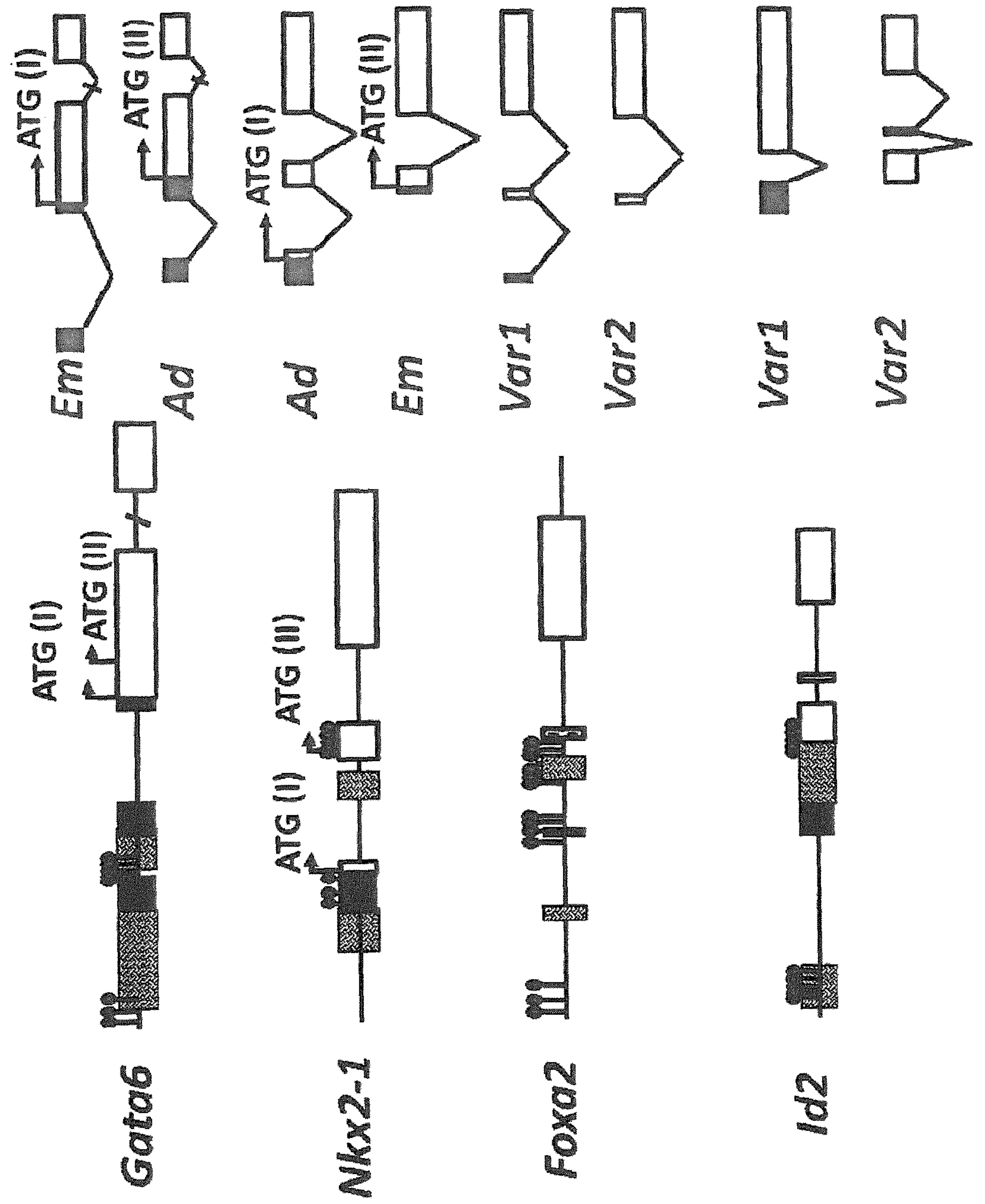
FIG. 1: Lung relevant genes share similar structure.
Figure 1:
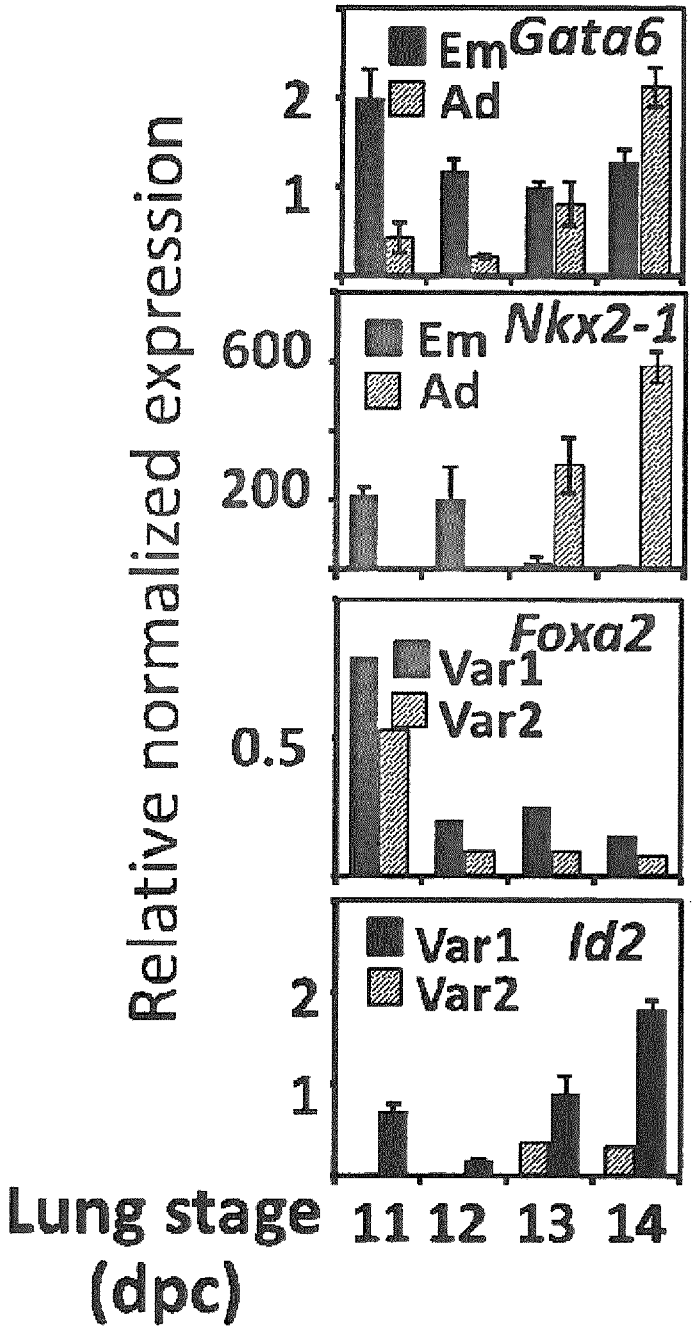

In silico analysis of lung important genes revealed a common structure of Gata6, Nkx2-1, Foxa2 and Id2 (FIG. 1A, left). Promoter analysis showed the presence of two promoters, one 5' of the first exon and the other in the first intron. Further analysis showed that each of the predicted promoters was surrounded by CpG islands (greater than 200 bp, with more than 50% CG), suggesting that these in fact are functional promoters and that they might be epigenetically regulated. Expression analysis showed that each gene gave rise to two distinct transcripts driven by different promoters. (FIG. 1A, right). In silico analysis of the same genes in humans demonstrated a similar structure as in mice, which clearly highlights that the identified gene structure was maintained during evolution and is conserved among species, reflecting its relevance. Isoform specific expression analysis was carried out during the pseudoglandular stage of mouse lung development (E11-14, FIG. 1B). Expression of both isoforms of the same gene was complementary with one isoform mainly expressed at early stages (E11, 12) while the other at later stages (E13, 14). In the adult lung mainly the transcript that is expressed at late stages of embryonic development can be detected (data not show). Our data suggest that the expression of both transcripts is developmentally regulated with an Em-isoform expressed at early stages of embryonic lung development and an Ad-isoform expressed at late stages of embryonic lung development and in the adult lung.

Example 3: Expression of Specific Gata6, Nkx2-1, Foxa2 and Id2 Isoforms in Cancer Cell Lines, Biopsy Samples and Blood Isoform specific expression analysis was carried out in human lung adenocarcinoma (A549, A427) and human bronchoalveolar carcinoma (H322) cell lines (FIG. 2A). The expression of the Em-isoform of each one of the genes analyzed was higher in all three cell lines tested, suggesting that the Em-isoforms are relevant during lung cancer formation. To confirm this hypothesis, human lung biopsies from healthy donors and lung tumor patients were analyzed (FIG. 2B). Consistent with the expression analysis in cell culture, the embryonic transcript of each one of the genes analyzed was enriched in the biopsies of lung tumor when compared to the healthy tissue. To confirm the diagnostic potential of the Em-isoforms of the genes analyzed here, it was attempted to detect these isoforms in the blood of genetic mouse models of lung cancer at early stage of cancer formation as well as in blood of lung cancer patients. Preliminary results after hyperplasia induced by in vivo gain-of-function (GOF; see example 6, FIG. 4) showed that transcripts of Gata6 Em and Nkx2-1 Em can be detected in the blood of mice after forced expression of Gata6 Em (FIG. 2C, middle) whereas only Gata6 Em transcript can be detected in the blood of mice after forced expression of Nkx2-1 Em (right).

Example 4: Analysis of the Oncogenic Potential of Gata6 Em or Nkx2-1 Em (I)

To analyze the potential role of the Em-isoforms in oncogenic transformation, the primary characteristics of cancer cells, enhanced proliferation and migration, were analyzed after transient transfection of Gata6 Em or Nkx2-1 Em in Mouse Lung Epithelial-12 (MLE) cells. Immunostaining of transient transfected MLE-12 cells using antibodies specific for cell proliferation markers MKI67 and MYC (FIG. 3A) showed enhanced cell proliferation after transfection of Gata6 Em or Nkx2-1 Em when compared to the control transfected cells (Ctrl). In addition, migration was assessed by standard in vitro scratch assay (FIG. 3B). The Em-isoforms transfected MLE-12 cells were able to close the scratch faster (after 24 h) than control transfected cells (Ctrl; 48 h) demonstrating enhanced cell migration. To assess clonogenicity, other characteristic of cancer cells, control (Ctrl) and Gata6 Em stable transfected MLE-12 cells were plated at clonal density and colonies were counted after 2 weeks (FIG. 3C). The ability to form colonies increased more than four times in cells expressing Gata6 Em when compared to control transfected cells, clearly supporting the oncogenic potential of this Em-isoform.

Example 5: Analysis of the of the Role of Gata6 Em in Metastasis

Epithelial-mesenchymal transition (EMT) is a process characterized by loss of cell adhesion and increased cell motility. EMT is essential for numerous developmental processes including mesoderm formation and neural tube formation. However, initiation of metastasis involves invasion, which has many phenotypic similarities to EMT, including a loss of cell-cell adhesion and an increase in cell mobility. Recent evidence suggests that EMT results in formation of cells with stem cell like properties (see Mani (2008) Cell 133(4): 704-715). Such cells are proposed to persist in tumors as a distinct population and cause relapse and metastasis by giving rise to new tumors. In control (Ctrl) and Gata6 Em stable transfected MLE-12 cells, EMT was monitored by expression analysis of Snail homolog 1 (Snail) and alpha smooth muscle actin (Acta2) (FIG. 3D, top), whereas 'stemness' was monitored by expression analysis of the stem cell marker POU domain class 5 transcription factor 1 (Pou5f1, also known as Oct4; FIG. 3D, bottom). Gata6 Em increased the expression of all three markers indicating EMT and a potential role of this Em-isoform in metastasis.

Example 6: Analysis of the Oncogenic Potential of Gata6 Em or Nkx2-1 Em (II)

To confirm the oncogenic potential of the Em-isoforms, isoform specific in vivo GOF was carried out in wild type C57/Bl6 mice (FIG. 4). The mice were induced by orotracheal administration of a transfection mix containing Polyethylenimine (PEI, transfection reagent) and either a control plasmid (Ctrl) or plasmids for specific expression of each isoform (embryonic, Em or adult, Ad) of Nkx2-1 or Gata6.

Isoform specific GOF was monitored by qRT-PCR (FIG. 4B). As early as 5 weeks after transfection, histological analysis of the lungs by Haematoxylin and Eosin staining revealed atypical hyperplasia exclusively in Em-isoform treated lungs while the Ad-isoform treated lungs were apparently normal, demonstrating the oncogenic potential of the Gata6 Em and Nkx2-1 Em (FIG. 4A).

To further characterize the phenotype induced after forced expression of the Em-isoforms in the adult lung, the expression of markers for all four hallmarks of cancer was analyzed: proliferation, angiogenesis, migration and hypoxic growth (FIG. 5A). Forced expression of Gata6 Em isoform in adult lung led to increased expression of Cdkn1 (Cyclin dependent kinase, proliferation marker); Vegf (Vascular endothelial growth factor) and Plgf (Placental growth factor, angiogenesis markers); Pdpk1 (3-phosphoinositide dependent protein kinase 1, migration/metabolic marker) and Hif2 (Hypoxia inducible factor 2, hypoxic marker), supporting the oncogenic potential of the Em-isoform in this in vivo model. To assess the formation of cancer stem cells in vivo, immunostaining using POU5F1 specific antibody on sections of Gata6 Em treated lungs was performed (FIG. 5B). Small clusters of POU5F1 positive cells were observed within regions of the lung with atypical hyperplasia after Gata6 Em in vivo GOF supporting the formation of high tumorigenic dedifferentiated cells. Furthermore, immunohistochemistry using Pan-cytokeratin (KRT) specific antibody on sections of Gata6 Em treated lungs (FIG. 5C) showed the presence of cytokeratin filaments, which are markers for both major classes of epithelial lung tumors, i.e. squamous cell carcinoma and adenocarcinoma. Clinical diagnosis of lung adenocarcinoma includes positive staining for NKX2-1 and Napsin A (NAPSA) (Bishop J A et al., (2010) Hum Pathol. 41(1): 20-5) as well as cytoplasmatic staining for tumor protein 63 (TRP63) (see Kalhor (2006) Modern Pathology 19: 1117-1123). Immunohistochemistry on sections of Gata6 Em treated lungs (FIG. 5D) demonstrated strong staining for NAPSA as well as for cytoplasmic TRP63 in the regions of hyperplasia, indicating that these regions correlate well with adenocarcinomas of the lung.

Enhanced colony formation and Pou5f1 expression in cell lines transfected with Gata6 Em as well as clusters of POU5F1 positive cells within tumors resulting from forced overexpression of Gata6 Em in the adult lung show the formation of cancer stem cells. Targeting these cancer stem cells by cell-specific knockdown of the embryonic/cancer specific isoform of the genes analyzed here provides a therapeutic strategy to prevent frequent tumor relapse.

Example 7: Analysis of the Oncogenic Potential of Gata6 Em or Nkx2-1 Em (III)

To exploit the use of the Em isoform in cancer therapeutics, isoform specific knockdown was carried out (FIG. 6A). MLE-12 cells were transfected with different siRNAs against Gata6 Em or Ad (top) or shDNA plasmids against Nkx2-1 Em or Ad (bottom). The best siRNAs or shDNAs by showing the maximum knockdown with the least off target effects were selected (FIG. 6B) for further use in vivo.

In order to demonstrate the therapeutic property of blocking the embryonic isoform, isoform specific knockdown was carried out in a highly aggressive tumor metastasis model. Lewis lung carcinoma (LLC1) cells were injected into the mouse tail vein. These cells would seed into the lung and form local tumors within 10-21 days. Three days after injection, the mice were treated with either a control (siCtrl) or Gata6 Em specific siRNAs (siGata6 Em) by orotracheal administration. The lungs were examined for both number and size tumor foci 21 days after injection (FIG. 7B-C). It was observed that after treatment with siGata6 Em tumor formation was dramatically reduced as compared to the siCtrl treatment. These results supported the therapeutic potential of targeting the Em isoform in lung cancer.

Example 8: Material and Methods of In Vivo Lung Fibrosis Model

Adult C57BL/6N mice (Charles River Laboratories) were used throughout this study. Animals were housed under controlled temperature and lighting [12/12-hour light/dark cycle], fed with commercial animal feed and water ad libitum. All experiments were performed according to the institutional guidelines that comply with national and international regulations. Bleomycin sulphate (2.5 U/Kg; Hexal AG, Germany) or sterile saline was administered as orotracheal instillation method as described earlier.

At day 21 after bleomycin instillation, mice were anaesthetized with 30-60 mg/kg ketamine (Pfizer, Germany) and 5-10 mg/kg, xylazine (Bayer, Germany). In anaesthetized mice, the thorax was opened and lung was then perfused with 1×PBS. The lung was either frozen for mRNA isolation or perfusion-fixed with 4% paraformaldehyde for 15 min with a pressure of 20 cm $H_2O$ for immunohistology

Example 9: Gata6 Ad Expression Increases Dramatically after Lung Fibrosis Induction by Bleomycin Treatment Interestingly it was found in an in vivo model of lung fibrosis (FIG. 8B) that the expression of Gata6 Ad increased dramatically after induction of lung fibrosis by Bleomycin treatment when compared with the control treated mice (FIG. 8C), suggesting that increased expression of the adult isoform could be used for the diagnosis of lung fibrosis.

Example 10: Embryonic Isoforms of GATA6 and NKX2-1 in Lung Cancer Diagnosis

Materials and Methods

Study Population

All patients were studied according to a protocol approved by the local institutional research ethics committee. Transbronchial biopsy specimens were obtained from the 45 patients who had primary lung tumors in the last five years. Inclusion criteria included primary lung tumor samples including lung adenocarcinoma (Grades 1, 2, 3), lung squamous cell carcinoma (Grades 1, 2, 3) and lung small cell carcinoma (Grades 1, 2, 3). All tumors were graded according to the Bloom-Richardson and the TNM grading system recommended by the American Joint Committee on Cancer. In addition, from 13 patients adjacent normal tissues were also obtained. Secondary lung tumors and lung cancer samples older than 5 years were excluded.

All cases were reviewed by an expert panel of pulmonologists and oncologists according to the current diagnostic criteria for morphological features and immunophenotypes. Specifically, for immunohistochemistry, reactivity to NKX2-1, Cytokeratins (specifically CK5/6/7/8) and MKI67 was evaluated. In addition, for some samples, genetic analysis for EGFR mutations was also performed.

TABLE 1

| Classification of cases | | | | | | | |
|---|---|---|---|---|---|---|---|
| Original diagnosis | No. Of Cases | Pathological Diagnosis* | No. Of Cases | Gender | No. Of Cases | Gender | No. Of Cases |
| Non Small Cell Lung Cancer | 50 | Adenocarcinoma | 47 | Female | 19 | Male | 20 |
| | | Squamous Cell Carcinoma | 1 | Female | 1 | Male | 0 |
| | | Large Cell Carcinoma | 1 | Female | 0 | Male | 1 |
| | | AdenoSquamous Carcinoma | 1 | Female | 1 | Male | 0 |
| Small Cell Lung Cancer | 1 | Small cell lung cancer | 1 | Female | 1 | Male | 0 |

*Pathological diagnosis is according to the current diagnostic criteria for morphology, immunohistochemistry and genetic findings.

SUPPLEMENT TABLE 1

| Clinical characteristics of patients with lung cancer | |
|---|---|
| Clinical Characteristic | % Patients |
| Age | |
| <50 | 8.8 |
| 50-70 | 46.6% |
| >70 | 35.5% |
| Gender | |
| Male | 46.6% |
| Female | 53.3% |
| Ethnic group | |
| CEU | 6.6% |
| CHB | 62.2% |
| MXL | 31.1% |
| Stage* | |
| I-II | 50.9% |
| III-IV | 49.0% |
| Recurrent disease | 6.6% |
| Treatment ongoing at biopsy collection | 6.5% |

*Stage of tumor according to the Bloom Richardson and TNM staging criteria.
Percentages may not round up to 100% because of rounding.

Exhaled Breath Condensate (EBC) Collection

From 10 samples that were currently undergoing diagnostic evaluation for lung cancer, EBC collection was also performed just prior to biopsy collection. Further, healthy EBC was also collected from donor individuals. All participants provided written informed consent.

EBC collection was performed using the RTube (Respiratory Research) as described online (http://www.respiratoryresearch.com/products-rtube-how.htm). Briefly, the aluminum cooling sleeve was cooled to −20° C. and the disposable, sterile RTube was placed in the cooling sleeve. The apparatus was the covered by the insulating cover provided. All donors used a nose clamp to avoid nasal contaminants and breathing was only through the mouthpiece. The collection device consists of a one way valve that directs the air to the collection chamber where vapors, aerosols and moisture in the breath are condensed. Exhaled breath was collected for 10 min for each donor. After this, the mouthpiece was removed and a plunger was used to collect the EBCs. The RTube was placed on top of the standard plunger and slowly pushed down until the RTube reached the bottom of the plunger. Exhaled breath condensates were collected with a pipette and 500 µl aliquots were prepared. EBCs were stored at −80° C. until further use. As a precaution to avoid contaminants from the mouth, subjects were asked to refrain from eating, drinking (except water) and smoking up to 3 hours before EBC collection and were asked to rinse their mouth with fresh water just prior to collection.

Cell Culture and Mouse Experiments

Cell lines used in this study were A549 (CCL-185), A427 (HTB-53), H322 (CRL-5806) and LLC1 (CRL-1642). Cell lines were cultured in medium and conditions recommended by the American Type Culture Collection (ATCC). Cells were used for the preparation of RNA (QIAGEN RNeasy plus mini kit) and protein extracts.

Five to 6 weeks old C57BL6 mice were used throughout this study. Animals were housed under controlled temperature and lighting [12/12-hour light/dark cycle], fed with commercial animal feed and water ad libitum. All experiments were performed according to the institutional guidelines that comply with national and international regulations. For LLC1 cell injection, a cell suspension of 1 million cells/1000 of medium was prepared. 100 µl of cell suspension was injected into the tail vein of each mouse. The development of tumors was observed after 21 days and lung tumors were harvested for RNA isolation.

RNA Isolation, cDNA Synthesis and Gene Expression Analysis

Total RNA was isolated from cell lines using the RNeasy Mini kit (Qiagen). Human lung tumor biopsies were obtained as formalin fixed paraffin embedded (FFPE) tissues. 80 µm of tissue in sections of 10 µm was cut and total RNA was isolated using the RecoverAll™ Total Nucleic Acid Isolation Kit for FFPE (Ambion). For exhaled breath condensates, 500 µl of EBC was used for RNA isolation using the RNeasy Micro Kit (Qiagen) following manufacturer's instructions. cDNA was synthesized from total RNA using the High Capacity cDNA Reverse Transcription kit (Applied Biosystem) according to manufacturer's instructions. The cDNA was 6 fold diluted and 3.5 µl of the diluted cDNA was used for SYBR green based expression analysis for EBCs and 1 µl for cDNA from cell lines, mice and tumor biopsies (Applied biosystems, power SYBR green). Briefly, 1× concentration of the SYBR green master mix was used with 250 nM each forward and reverse primer. The PCR results were normalized with respect to the housekeeping gene TUBA1A. Quantitative real time PCR reactions were performed using SYBR® Green on the Step One plus Real-time PCR system (Applied Biosystems) using the primers specified in the supplementary table 2.

Supplement Table 2
Primer sequences used for the analysis of GATA6 and NKX2-1. Estimation of Receiver-operating-characteristic (ROC) curves

| Gene | Primer Sequence for cell lines (5'-3') | Primer Sequence for tissue, EBC (5'-3') |
|---|---|---|
| Gata6 Em Fwd | CTCGGCTTCTCTCCGCGCCTG (SEQ ID NO: 9) | TTGACTGACGGCGGCTGGTG (SEQ ID NO: 10) |
| Gata6 Em Rev | AGCTGAGGCGTCCCGCAGTTG (SEQ ID NO: 11) | CTCCCGCGCTGGAAAGGCTC (SEQ ID NO: 12) |
| Gata6 Ad Fwd | GCGGTTTCGTTTTCGGGGAC (SEQ ID NO: 13) | AGGACCCAGACTGCTGCCCC (SEQ ID NO: 14) |
| Gata6 Ad Rev | AAGGGATGCGAAGCGTAGGA (SEQ ID NO: 15) | CTGACCAGCCCGAACGCGAG (SEQ ID NO: 16) |
| Nkx2-1 Em Fwd | AAACCTGGCGCCGGGCTAAA (SEQ ID NO: 17) | CAGCGAGGCTTCGCCTTCCC (SEQ ID NO: 18) |
| Nkx2-1 Em Rev | GGAGAGGGGGAAGGCGAAGCC (SEQ ID NO: 19) | TCGACATGATTCGGCGGCGG (SEQ ID NO: 20) |
| Nkx2-1 Ad Fwd | AGCGAAGCCCGATGTGGTCC (SEQ ID NO: 21) | TCCGGAGGCAGTGGGAAGGC (SEQ ID NO: 22) |
| Nk2-1 Ad Rev | CCGCCCTCCATGCCCACTTTC (SEQ ID NO: 23) | GACATGATTCGGCGGCGGCT (SEQ ID NO: 24) |

Receiver-operating-characteristic (ROC) curves were estimated for the 59 biopsies. Em/Ad ratios were categorized into five groups, in order to adequately separate the points on the ROC curve. (For GATA6, the range was <0.5; 0.5-0.8; 0.8-1.1; 1.1-2; and >2 while for NKX2-1, <0.4; 0.4-0.8; 0.8-1.2; 1.2-2; >2.)

ROC curve analysis was performed using the web based calculator for ROC curves, ROC Analysis (Eng J. ROC analysis: web-based calculator for ROC curves. Baltimore: Johns Hopkins University [updated 2014 March 19; cited Apr. 25, 2014]. The area under the empirical ROC curve was calculated by the trapezoid (nonparametric) method.

Statistical Analysis

Samples were analyzed at least in triplicates and cell line and mouse experiments experiments were performed three times. Statistical analyses were performed using Excel Solver. The data are represented as mean±Standard Error (mean±s.e.m) and for human samples, each point on the graph represents an individual sample while the horizontal line represents the median±Standard Error (median±s.e.m.). One-way analysis of variance (ANOVA) was used to determine the levels of difference between the groups and P values for significance.

Lung cancer is the leading cause of cancer related deaths worldwide, accounting for an estimated 1.6 million deaths out of 1.8 million cases in 2012 (Globacon 2012). The incidence pattern of lung cancer closely parallels the mortality rate because of persistently low patient survival. There are two major classes of lung cancer, non-small cell lung cancer (NSCLC, representing 85% of all lung cancers) and small cell lung cancer (SCLC, the remaining 15%) (Herbst R S et al., (2008) N Engl J Med 359(13): 1367-80). Depending on the histological characteristics, NSCLC is further divided into three major subtypes; squamous cell carcinoma, adenocarcinoma and large cell carcinoma. Adenocarcinoma is the most common form and has approximately 40% prevalence, followed by squamous cell and large cell carcinoma that have 25% and 10% prevalence respectively (Hoffman P C et al., (2000) Lancet 355(9202): 479-85).

Clinical manifestations of lung cancer are diverse and patients are mostly asymptomatic at early stages. Symptoms, even when present, are non-specific and mimic more common benign etiologies, including persistent cough, dyspnea, hoarseness, chest pain, weight loss and fatigue (Hyde L and Hyde Cl, (1974) Chest 65(3): 299-306). Traditional diagnostic strategies for lung cancer include imaging tests, including chest X-rays, histological analysis, including sputum cytology, and tissue biopsies (Strauss G M and Dominioni L, (2013) J Surg Oncol 108(5): 294-300; D'Urso V et al., (2013) J Cell Physiol 228(5): 945-51; Travis W D et al., (2013) Arch Pathol Lab Med 137(5): 668-84). Most of these tests are performed only after the development of symptoms, frequently at advanced stages of the disease when patient prognosis is poor as shown by a low five-year patient survival of 1-5% (Herbst R S et al., (2008) N Engl J Med 359(13): 1367-80). Strikingly, patient survival increases to almost 52% if lung cancer is diagnosed early (Herbst R S et al., (2008) N Engl J Med 359(13): 1367-80), demonstrating that early diagnosis of lung cancer is decisive to increase the probability of a successful therapy. Thus, a better understanding of the molecular mechanisms responsible for lung cancer initiation is extremely important.

It is proposed herein that many of the mechanisms involved in embryonic development are recapitulated in lung cancer initiation. Therefore, new experimental approaches based on studies of embryonic development are provided herein to elucidate the molecular mechanisms responsible for lung cancer initiation.

Consistently, two transcription factors that are key regulators of embryonic lung development, such as GATA6 (GATA Binding Factor 6) and NKX2-1 (NK2 homeobox 1, also known as Ttf-1, Thyroid transcription factor-1) (Keijzer R et al., (2001) Development 128(4): 503-11; Kolla V et al., (2007) Am J Respir Cell Mol Biol 36(2): 213-25; Zhang Y et al., (2007) Development 134(1): 189-98; Tian Y et al., (2011) Development 138(7): 1235-45), have been implicated in lung cancer formation and metastasis (Guo M et al., (2004) Clin Cancer Res 10(23): 7917-24; Gorshkova E V et al., (2005) Biochemistry (Mosc) 70(10): 1180-4; Lindholm P M et al., (2009) J Clin Pathol 62(4): 339-44; Winslow M M et al., (2011) Nature 473(7345): 101-4; Cheung W K et al., (2013) Cancer Cell 23(6): 725-38; Chen P M et al., (2013) Carcinogenesis 34(11): 2655-63).

Here it is shown that two different mRNAs are expressed from both GATA6 and NKX2-1. Furthermore the expression of both transcripts from the same gene is complementary and differentially regulated during embryonic lung development as well as in lung cancer. One transcript is expressed in early stages of embryonic lung development (embryonic isoform, Em-isoform), whereas the second transcript is expressed in late stages and in adult lung (adult isoform, Ad-isoform). Herein an enrichment of the Em-isoform in lung tumors is demonstrated, even at early stages of cancer, making the detection of these embryonic specific transcripts a powerful tool for early cancer diagnosis. Moreover, isoform specific expression analysis of GATA6 and NKX2-1 is demonstrated herein in exhaled breath condensates (EBCs). The Em-by Ad-expression ratio in each sample can be used as a non-invasive, specific and sensitive method for both early lung cancer diagnosis and identification of high risk patients.

Study Population.

59 lung biopsies and 20 EBCs that were collected in three different cohorts located in different continents (America, Asia and Europe) were analyzed allowing us to investigate ethnic differences. The patients were studied according to a protocol approved by the institutional review board and ethical committee of the Hospital Regional de Alta Especialidad de Oaxaca (HRAEO), C.P. 71256, Oaxaca, Mexico; Union Hospital, Hong Kong; and Universitätsklinikum Gießen and Marburg, Germany. The cases were reviewed by our panel of expert lung pathologists in the different cohorts according to current criteria of the WHO.

To develop a diagnostic test based on the Em-Ad-expression ratio of GATA6 and NKX2-1, initially 39 cases were analysed that were originally diagnosed as NSCLC and confirmed as such by the pathological review. The qRT-PCR based expression analysis of the samples was in accord with the pathological diagnosis in all of the 39 cases.

Embryonic Isoforms of GATA6 and NKX2-1 are Highly Expressed in Human Lung Cancer Cell Lines and in a Mouse Model of Experimental Metastasis.

In silico analysis of GATA6 and NKX2-1 revealed a common gene structure (FIG. 12A, top). Two promoters were predicted in each of the genes, one 5' of the first exon and the other in the first intron. Further analysis showed that each of the predicted promoters was surrounded by CpG islands (greater than 200 bp, with more than 50% CG), suggesting that these might be epigenetically regulated functional promoters. Indeed, expression analysis showed that each gene gave rise to two distinct transcripts driven by different promoters (FIG. 12A, bottom). In silico analysis of the same genes in mice demonstrated a similar structure as in humans, which highlights that the identified gene structure was maintained during evolution and is conserved among species, reflecting its relevance.

Quantitative PCR after reverse transcription (qRT-PCR) based expression analysis during mouse lung development revealed that the expression of both isoforms of the same gene was complementary and differentially regulated, with the Em-isoform mainly expressed at early developmental stages while the Ad-isoform at later stages and in adult lung. Isoform specific expression analysis (FIG. 12B) in healthy human lung tissue (Ctrl), human lung adenocarcinoma (A549, A427) and human bronchoalveolar carcinoma (H322) cell lines showed that the expression of the Em-isoform of each one of the genes analyzed was higher than the expression of the Ad-isoform only in the lung cancer cell lines. In the healthy human lung tissue, we observed the opposite results, in which the Ad-isoforms expression was higher than the Em-isoforms expression. In addition, western blot (WB) analysis of protein extracts from A549 cells using NKX2-1- or GATA6-specific antibodies (FIG. 12C) confirmed that both transcripts of each one of the genes were translated into proteins of different molecular weight.

In a mouse model of experimental metastasis (FIG. 12D) (Elkin M and Vlodaysky I, (2001) Curr Protoc Cell Biol Chapter 19: Unit 19.2), in which lewis lung carcinoma (LLC1) cells were injected into the tail vein to induce 21 days later tumor formation in the mouse lung, elevated expression of the Em-isoforms of Gata6 and Nkx2-1 in the tumors was detected when compared to healthy lung tissue (Ctrl).

Summarizing, these results support the hypothesis that the Em-isoforms of GATA6 and NKX2-1 are relevant during lung cancer formation.

Em/Ad Expression Ratios of GATA6 and NKX2-1 as Marker for Lung Cancer Diagnosis.

To confirm that the Em-isoform of GATA6 and NKX2-1 are markers for detection of lung cancer, we turned to human lung biopsies from healthy donors and lung tumor patients (FIG. 13A). The pathological diagnosis of the 59 lung-biopsy specimens was considered the standard against which the molecular diagnosis based on the gene expression analysis was compared. Isoform specific expression analysis based on qRT-PCR showed that the Em-isoforms of GATA6 and NKX2-1 were enriched in the biopsies of lung tumor when compared to the healthy tissue, consistent with the expression analysis in cell culture and in the mouse model of experimental metastasis.

The Ad-isoform expression was used as internal control to minimize the effect of individual variations among the different lung-tumor-biopsy specimens by calculating the Em- by Ad-expression ratio (Em/Ad) of each sample. In healthy lung tissue biopsies, the Em/Ad was 0.642±0.065 (n=20) for GATA6 and 0.475±0.044 (n=20) for NKX2-1. The Em/Ad increased in the lung cancer biopsies to 2.63±0.194 (n=39, P<0.001) for GATA6 and to 2.075±0.22 (n=39; P=0.01) for NKX2-1, supporting that an increased Em/Ad of GATA6 and NKX2-1 can be used as marker for lung cancer diagnosis.

To estimate the sensitivity and specificity of the herein provided method for lung cancer diagnosis, a mathematical model was used to perform an unadjusted Receiver-Operating-Characteristics (ROC) curve analysis (FIG. 13B) [12878740] of the 59 biopsies that were analyzed in FIG. 13A. A ROC curve is a plot of the sensitivity versus 1 minus the specificity. Each point along the curve is specific for a particular Em/Ad value from the lung biopsies. The estimated ROC curves showed high sensitivity and high specificity predicting high accuracy for lung cancer diagnosis by using the Em/Ad values of GATA6 and NKX2-1. The elevated Em/Ad values of GATA6 and NKX2-1 in the lung tumor biopsies when compared to the healthy lung tissue were maintained after sample grouping by ethnicity (FIG. 13C) or by gender (FIG. 13D). Furthermore, sample grouping based on TNM classification recommended by the American Joint Committee on Cancer (FIG. 13D) revealed that the Em/Ad of GATA6 and NKX2-1 increased progressively with advancing stages of lung cancer from Grade I (2.395±0.257; P<0.001 for GATA6 and 1.878±0.129; P<0.001 for NKX2-1) through Grade II (3.436±0.243; P<0.001 for GATA6 and 2.589±0.257; P=0.002 for NKX2-1) till Grade III (2.838±0.598; P=0.003 for GATA6 and 3.787±0.392; P<0.001 for NKX2-1).

Detection of Em- and Ad-Isoforms of GATA6 and NKX2-1 in Exhaled Breath Condensate.

EBCs consist of three main components (FIG. 14A): distilled water condensed from the gas phase (>99%), droplets aerosolized from the airway lining fluid and water soluble respiratory gases (the last two make the remaining 1%) (Horvath I et al., (2005) Eur Respir J 26(3): 523-48; Montuschi P, (2007) Ther Adv Respir Dis 1(1): 5-23). EBC is a promising source of biomarkers for, but not only, lung diseases since the droplets contain nonvolatile biomarkers such as adenosine, prostaglandins, leukotriene, cytokines, etc. whereas the respiratory gases should be considered as water soluble volatile biomarkers such as nitrogen oxides that diffuse from both airspace and airway lining fluid (Ho L P et al., (1998) Thorax 53(8): 680-4; Shahid S K et al., (2002) Am J Respir Crit Care Med 165(9): 1290-3; Huszar E et al., (2002) Eur Respir J 20(6): 1393-8; Effros R M et al., (2002) Am J Respir Crit Care Med 165(5): 663-9; Montuschi P et al., (2003) Thorax 58(7): 585-8; Kostikas K et al., (2003) Eur Respir J 22(5): 743-7; Effros R M et al., (2012) Am J Respir Crit Care Med 185(8): 803-4; Davis M D et al., (2012) Immunol Allergy Clin North Am 32(3): 363-75). EBCs are typically collected through cooling devices. Here, two of the most broadly used devices for EBC collection were tested for their suitability for subsequent RNA extraction (FIG. 14B).

Using the same conditions for EBC collection and RNA extraction, the RTube showed a yield of 573±48 ng RNA per 500 μl EBC (n=6) whereas the TurboDECCS showed a lower yield of 292±42 ng RNA per 500 μl EBC (n=6). Thus, we continued collecting the samples with the RTube and tested different EBC volumes to determine the best for RNA extraction (FIG. 14C). The RNA yield increased with the EBC volume following a sigmoid curve that reached a plateau at 573±48 ng RNA using 500 μl EBC. RNA extraction from more than 500 μl EBC did not improve the RNA yield. In addition, conditions for cDNA synthesis by reverse transcription and qPCR amplification were optimized using 500 μl EBC collected with the RTube (data not shown). Using the optimized conditions, we performed an isoform specific expression analysis of GATA6 and NKX2-1 in EBCs from healthy donors and lung cancer patients (FIG. 14D). In healthy donors EBCs, the Em/Ad was 0.475±0.113 (n=20) for GATA6 and 0.456±0.054 (n=20) for NKX2-1. Correlating with the expression analysis in the biopsies, the Em/Ad increased in the EBCs from lung cancer patients to 1.532±0.274 (n=10, P<0.001) for GATA6 and to 2.778±0.292 (n=10; P=0.01) for NKX2-1.

These results support that an increased Em/Ad of GATA6 and NKX2-1 in the EBCs can be used as marker for early lung cancer diagnosis. The specificity of the different qRT-PCR products detected in the EBCs was demonstrated by dissociation curve analysis, electrophoretic gel analysis and sequencing of the different qRT-PCR products (FIGS. 16A-D and 17A-D). Moreover, the estimated ROC curves of the 10 EBCs that were analyzed in FIG. 14D showed high sensitivity and high specificity predicting high accuracy for early lung cancer diagnosis by using the Em/Ad values of GATA6 and NKX2-1.

Correlation of EBC Based Lung Cancer Diagnosis with Classical Methods.

To confirm that an increased Em/Ad of GATA6 and/or NKX2-1 in the EBCs can be used as marker for early lung cancer diagnosis, the patients from which the EBC were obtained were diagnosed using classical methods. FIG. 15 shows representative results. Pulmonary nodules were clearly identified by chest X-ray radiography (CXR, FIG. 15A left) and low-dose helical computed tomography (CT, right) in the patients with elevated Em/Ad of GATA6 and NKX2-1. Furthermore, immunostaining on sections of biopsies from the same patients (FIG. 15B) using antibodies specific for the epithelial maker KRT (pan-cytokeratin) and NKX2-1 demonstrated that the nodules were primary adenocarcinomas of the lung.

To determine that markers that are used for the molecular diagnosis of cancer can be detected in EBC, we analyzed the expression of the oncogene MYC and the tumor suppressor genes CDKN2A (also known as P16 or INK4A) and TP53 in EBCs from healthy donors and tumor patients (FIG. 15C). In healthy donors, expression level of CDKNA2 was 0.6±0.36 (n=5) and it decreased to 0.068±0.09 (n=10; P=0.001). Similarly, for TP53 the expression level in healthy donors was 0.908±0.52 (n=5) which decreased to 0.021±0.03 (n=10; P<0.001) in tumor samples. Consistently, the expression of MYC increased in tumor patients to 0.046±0.034 (n=10) from 0.004±0.002 (n=5; P=0.01). The pathological and molecular diagnosis correlated with the increased Em/Ad of GATA6 and NKX2-1 in all of the 10 cases from which we obtained the EBCs.

EBC is a promising source of biomarkers for lung diseases. In chronic obstructive pulmonary diseases (COPD) and asthma, increase of several inflammatory mediators like adenosines, prostaglandins, leukotriene and cytokines has been determined in EBCs of patients (Huszar E et al., (2002) Eur Respir J 20(6): 1393-8; Shahid S K et al., (2002) Am J Respir Crit Care Med 165(9): 1290-3; Kostikas K et al., (2003) Eur Respir J 22(5): 743-7; Montuschi P et al., (2003) Thorax 58(7): 585-8). In lung cancer, it was shown that cytokines, survivin and cycloxygenase-2, the last two being associated with poor survival in NSCLC, were enriched in EBCs of patients (Kullmann T et al., (2008) Pathol Oncol Res 14(4): 481-3; Carpagnano G E et al., (2010) Lung Cancer 76(1): 108-13). In addition to small mediators, nucleic acid from pathogens has been isolated from EBCs with diagnostic purposes (Zakharkina T et al., (2011) Respirology 16(6): 932-8; Xu Z et al., (2012) Plos One 7(7): e41137). Furthermore, using genomic DNA isolated from EBCs from lung cancer patients, both promoter hypermethylation of the tumor suppressor gene CDKN2A and gene mutations in TP53 were detected (Gessner C et al., (2004) Lung Cancer 43(2): 215-22; Xiao P et al., (2014) Lung Cancer 83(1): 56-60).

Herein it is demonstrated that RNA isolated from EBC can be used for qRT-PCR based isoform specific expression analysis of GATA6 and NKX2-1 to determine the Em- by Ad-expression ratio as a non-invasive, specific and sensitive method for early lung cancer diagnosis. 59 lung biopsies and 20 EBCs from three cohorts located in different continents were analyzed and an increased Em/Ad of GATA6 and NKX2-1 was determined in NSCLC samples independent of the ethnic group, the gender and NSCLC subtype. Furthermore, a direct correlation between the Em/Ad value and the cancer stage was determined suggesting that the level of increase of Em/Ad may be an indicator for the stage of the disease.

Early lung cancer diagnosis is crucial to improve patient prognosis. The ROC curve analysis presented herein showed high sensitivity and high specificity predicting high accuracy for lung cancer diagnosis by using the Em/Ad values of GATA6 and NKX2-1. Thus, the method provided herein can be used in the screening of high risk groups, such as those that have a hereditary history and/or are exposed to tobacco smoke, environmental smoke, cooking fumes, indoor smoky coal emissions, asbestos, some metals (e.g. nickel, arsenic and cadmium), radon (particularly amongst miners) and ionizing radiation (IARC Monogr Eval Carcinog Risk Chem Hum (1986) 38:35-394; Xu Z Y et al., (1989) J Natl Cancer Inst 81(23): 1800-6; Zhong L et al., (1999) Cancer Causes Control 10(6): 607-16). Currently, CT and CXR are used to screen such high risk group individuals. CT imaging has been shown to be considerably superior to CXR in the identification of small pulmonary nodules (Henschke Cl et al., (1999) Lancet 354(9173): 99-105). However, despite the success of CT imaging for early lung cancer diagnosis, it suffers from serious limitations, including a high detection rate of benign non calcified nodules (>50% of participants) resulting in follow-up CT scans, biopsies and frequently unnecessary resection of the benign non calcified nodules (Jett J R, (2005) Clin Cancer Res 11(13 Pt 2): 4988s-4992s). Implementation of the herein provided (EBC) based molecular diagnosis will improve and complement the success of CT and CXR for early lung cancer diagnosis.

Microarray based analysis of tumor samples not only led to identification of gene expression profiles that are associated with NSCLC subtypes (Bhattacharjee A et al., (2001) Proc Natl Acad Sci USA 98(24): 13790-5; Meyerson M and Carbone D, (2005) J Clin Oncol 23(14): 3219-26) but also predicted with relatively high accuracy the clinical outcome (Beer D G et al., (2002) Nat Med 8(8): 816-24; Chen H Y et al., (2007) N Engl J Med 356(1): 11-20). Although the method provided herein did not discriminate between different NSCLC subtypes, it will be superior to previous approaches of molecular and clinical lung cancer diagnosis due to its higher sensitivity and accuracy, straightforward and fast protocol, non-invasiveness and relative low price. A combination of the method provided herein with the existing clinical and molecular methods of lung cancer diagnosis can help to predict the response to specific therapies with the goal of tailoring personalized treatments. The diagnostic method may also be useful to monitor the effect of an anti-cancer therapy by detecting a reduction of the Em/Ad ratio of GATA6 and NKX2-1, thereby allowing to determine whether the therapy has a positive effect.

Example 10: Inhibitors of emGata6 in the Treatment of Cancer

In order to analyze the specificity and efficiency of siRNAs targeted to each isoform (FIG. 18A), mouse lung epithelial cell line (MLE-12) cells were transiently transfected with siRNAs directed to each isoform (siGata6 Em, siGata6 Ad) and a scrambled siRNA (siCtrl). Cells were harvested 48 hours after transfection and total RNA was isolated. Isoform specific gene expression analysis showed that the siRNA against each isoforms were highly specific and efficient, resulting in significant reduction of their respective target transcript with minimal off target effects to the other isoform. For instance, siGata6 Em induced 90% reduction of Gata6Em transcript while no significant reduction of the Gata6Ad transcript was observed (12%) when compared to the siCtrl transfected cells. Similarly, siGata6 Ad induced 50% reduction of its target transcript while no change for the Gata6 Em transcript was observed. To further analyse the functional role of the isoforms, MLE-12 were transfected with siCtrl, siGata6 Em or siGata6 Ad and allowed to grow to form a confluent monolayer (FIG. 12B). A scratch was made (0 hr) and cells were observed microscopically every 12 hours for closure of the scratch or "wound healing". It was observed that while the cells transfected with siCtrl and siGata6 Ad were comparable in their ability to close the scratch at 24 hr, cells transfected with siGata6 Em showed reduced ability to close the scratch suggesting reduced cell proliferation and/or reduced cell migration.

In a mouse model of experimental metastasis (FIG. 7A) (Elkin M and Vlodaysky I, (2001) Curr Protoc Cell Biol Chapter 19: Unit 19.2), in which Lewis lung carcinoma (LLC1) cells were injected into the tail vein to induce 21 days later tumor formation in the mouse lung, elevated expression of the Em-isoform of Gata6 in the tumors was detected when compared to healthy lung tissue (Ctrl) (FIG. 12D). Thus, to analyze the therapeutic potential of isoform specific loss of function (LOF) of Gata6 Em, adult mice were injected with LLC1 cells in the tail vein. Three days after tail vein injection, mice were orotracheally administered siCtrl or siGata6 Em. At day 21, lungs were prepared from the mice and isoform specific gene expression analysis was performed using total lung RNA (FIG. 18C). Gata6 Em expression was reduced approximately 70% after orotracheal administration of siGata6 Em when compared to the mice that were treated with siCtrl. Expression of Gata6 Ad was not significantly affected by Gata6 Em LOF supporting the specificity of the herein provided system.

Further, macroscopic gross tumor formation (FIG. 7B, top, arrows) was significantly reduced in mice treated with siGata6 Em when compared to the mice treated with siCtrl. In addition, a more than 80% reduction in the number of surface tumors was observed (bottom left; P=0.002; n=5) in mice treated with siGata Em. Microscopic (bottom right) and histological analysis (Figure XF) revealed that in addition to the number of tumors, the size of tumors was also significantly reduced in mice treated with siGata6 Em. Summarizing, the data presented herein support that the inhibition of Gata6 Em is a good approach for targeted therapy against lung cancer.

Example 11: Integrin Beta 2 and 6 are Membrane Proteins of Alveolar Type H Cells

Material and Methods

Cell Culture

Primary alveolar type II cells (ATII cells) were isolated from C57BL/6 mice as previously described [PMID: 22856132] with minor modifications. Crude cells suspensions from the lungs were prepared by intratracheal instillation of agarose containing Dispase (BD Heidelberg, cat.#354235) followed by mechanical disaggregation of the lungs. Crude cell suspensions were purified by negative selection using a system consisting of biotinylated antibodies (Biotin anti-mouse CD16/CD32, cat.#553143; Biotin anti-mouse CD45 (30-F11), cat.#553078, both from BD Biosciences), streptavidin coated magnetic beads (Promega, cat.# Z5481) and a magnetic separator stand (Promega, cat# Z5410). Purified ATII cells were seeded on fibronectin coated cell culture dishes and cultured up to 3 days in D-MEM/F-12 (1:1) (Life Technologies GmbH, cat.#31330038) supplemented with 10% FCS and 1% Penicillin/Streptomycin (Pen/Strep, Gibco, 15070) in an atmosphere of 5% $CO_2$ at 37° C.

Mouse epithelial lung cells (MLE-12, ATCC CRL-2110), mouse normal lung cells (MLg, ATCC CCL-206) and mouse fibroblast (NIH/3T3, ATCC CRL-1658) were obtained from the American Type Culture Collection. Mouse fetal lung mesenchyme cells (MFLM-4) were obtained from Seven Hills Bioreagents. All cell lines were cultured following the supplier instructions. MLE-12 cells were transiently transfected with Itgb2-YFP expression plasmid (Addgene, cat.#8638) using Lipofectamine 2000 transfection reagent (Invitrogen) at a ratio of 1:2 of DNA:Lipofectamine according to the manufacturer instructions. Cells were harvested 48 h after transfection for further analysis. Where indicated, MLE-12 cells were treated with Lithium Chloride (LiCl, 20 mM for 8 h) to activate the WNT signaling pathway.

Animal Experiments

C57BL/6 mice (stock #002644, Jackson Laboratories; (Xiang et al., 1990) were obtained from Charles River Laboratories at 5 to 6 week of age and Itgb2$^{-}$/$^{-}$ (β2 Integrin-deficient, B6.129S7-Itgb2$^{tm2Bay}$/J, stock #003329, [8700894]) were obtained from Jackson Laboratory. Animals were housed and bred under controlled temperature and lighting [12/12-hour light/dark cycle], fed with commercial animal feed and water ad libitum. All experiments were performed with 6-8 week old mice according to the institutional guidelines that comply with national and international regulations. The lungs of wild type and Itgb2$^{-}$/$^{-}$ mice were harvested and used for RNA isolation, protein isolation, flow cytometry analysis and/or immunohistochemistry.

Metabolic labeling of living C57BL/6 mice was achieved by a diet containing a nonradioactive-labeled isotopic form of the amino acid lysine ((13)C6-lysine, heavy). The administration of a heavy lysine containing diet for one mouse generation leads to a complete exchange of the natural isotope (12)C6-lysine (light) in the cellular proteins. The fully labeled SILAC (stable isotope labeling with amino acids in cell culture) mice were used as a heavy "spike-in" standard into nonlabeled ATII- or MLE-12 cells samples during global proteomic screening with high-performance mass spectrometers.

Membrane Protein Isolation

ATII cells or MLE-12 cells were mixed with lung tissue from SILAC-mice at a ratio of 1:1 (wet weight:wet weight). The membrane proteins of these mixtures were isolated as previously described [PMID: 19848406 and 19153689]. After isolation, membrane protein fractions were solubilized in 0.1 M TRIS/HCl pH 7.6 containing 2% SDS and 50 mM DTT.

Mass Spectrometry: Sample Preparation, Methods and Data Analysis

Solubilized membrane protein fractions were prepared for proteome analysis by FASP (filter-aided sample preparation) as previously described [PMID: 19377485].

Reverse phase nano-LC-MS/MS was performed by using an Agilent 1200 nanoflow LC system (Agilent Technologies, Santa Clara, Calif.) using a cooled thermostated 96-well autosampler. The LC system was coupled to LTQ-Orbitrap instrument (Thermo Fisher Scientific) equipped with a nano-electro-spray source (Proxeon, Denmark). Chromatographic separation of peptides was performed in a 10 cm long and 75 μm C18 capillary needle. The column was custom-made with methanol slurry of reverse-phase ReproSil-Pur C18-AQ 3 μm resin (Dr. Maisch GmbH). The tryptic peptide mixtures were auto-sampled at a flow rate of 0.5 μl/min and then eluted with a linear gradient at a flow rate 0.25 μl/min. The mass spectrometer was operated in the data-dependent mode to automatically measure MS and MS/MS spectra. LTQ-FT full scan MS spectra (from m/z 350 to 1750) were acquired with a resolution of r=60,000 at m/z=400. The five most intense ions were sequentially isolated and fragmented in the linear ion trap by using collision-induced dissociation with collision energy of 35%. Further mass spectrometric parameters: spray voltage of 2.4 kV, no sheath gas flow, and capillary temperature was 200° C.

For data analysis we used the MaxQuant software tool (Version 1.2.0.8). The measured raw data were processed and quantitated as described [Cox et al. Nature Biotech 2009 & nature protocols 2009]. For Gene Ontology functional analysis of the data, the GORILLA online-tool was used in target and background mode for ATII enriched proteins (Eden, BMC Bioinformatics, 2009).

Semiquantitative and Quantitative RT-PCR.

Total RNA was isolated with RNeasy® plus mini kit (Qiagen). cDNA was synthesized from total RNA using the High Capacity cDNA Reverse Transcription kit (Applied Biosystem) according to manufacturer's instructions. The PCR results were normalized with respect to the housekeeping gene Gapdh. Quantitative real time PCR reactions were performed using SYBR® Green on the Step One plus Real-time PCR system (Applied Biosystem).

Western Blot

Protein concentrations were determined using BCA kit (Sigma). Western blot was performed using standard methods [22753500]. Immunodetection of blotted proteins was performed using ITGB2-, ITGB6-, CD14-, CD45-, AXIN2-, BMP4-, MYCN-, ABC- (all from Millipore) and LMNB1- (Santa Cruz) specific primary antibodies, the corresponding HRP-conjugated secondary antibodies, an enhanced chemiluminescent substrate (SuperSignal West Femto, Thermo Scientific) and a luminescent image analyzer (Las 4000, Fujifilm).

Flow Cytometry Analysis of Single Cell Suspension of the Lungs

Lung single cell suspensions were generated and analyzed by flow cytometry as previously described [21985786] with minor modifications. Primary antibodies used were Pro-SFTPC (Millipore), ITGB2-CD18/APC (BioLegend, 0.5 mg/mL), ITGB6/FITC (R&D). Secondary antibodies used were Alexa 488 (BIOTIUM) and Alexa 633 (BIOTIUM). After immunostaining, single cell suspensions were quantified using the 5.0 Zflow cytometer. Data were analyzed with the BD FACS DIVA™ Software Version 3.0. Cells were analysed using BD LSRII flow cytometry. Data were analysed with Weasel or FlowJo software (FlowJo version 7.6.5, USA).

Immunohistochemistry

For cryosections, mouse lungs were harvested and embedded in tissue freezing medium (Polyfreeze, Polysciences Inc.). Sections of 10 μm were prepared on a cryostat (Leica Germany). and post-fixed in 4% PFA for 20 min. Antibody staining was performed following standard procedures. All incubations were performed with histobuffer containing 3% BSA and 0.2% Triton X-100 in 1×PBS, pH 7.4. Non-specific binding was blocked by incubating with 10% donkey serum and histobuffer (1:1 (v/v) ratio) for 45-60 minutes. The sections were then incubated with primary and secondary antibodies for 60 min followed by nuclear staining. The sections were examined with a Zeiss confocal microscope (Zeiss, Germany). Antibodies used were specific against Pro-SFTPC (Millipore), ITGB2/CD18 (R&D system), ITGB6 (R&D system). Secondary antibodies used were Alexa 488 and Alexa 594 (Invitrogen). Draq5 (Invitrogen) was used as nuclear dye.

For paraffin embedded mouse lung tissue, lungs were post-fixed overnight in 1% PFA at 4° C., dehydrated over a graded series of alcohol, and paraffin embedded. Sections of 4 μm were prepared on a microtome (Leica Germany). Antigen retrieval was performed by cooking using a rice-cooker for 20 min in citrate buffer containing 10 mM Sodium citrate, 0.05% Tween 20, pH 6.0. Antibody staining was performed following standard procedures. All incubations and washes were done with 1×PBS. Non-specific binding was blocked by incubating with 5% BSA in 1×PBS for 60 minutes at room temperature. The sections were then incubated with primary and secondary antibodies for 60 min each followed by nuclear staining. Primary antibody used was specific against activated β-CATENIN (Millipore). The sections were examined with a Zeiss confocal microscope (Zeiss Germany).

Statistical Analysis

Statistical analyses were performed using Excel Solver. All data are represented as mean±Standard Error (mean±s.e.m). One-way analyses of variance (ANOVA) were used to determine the levels of difference between the groups and P values for significance. P values after one-way ANOVA,* P≤0.05;  P<0.01 and * P<0.001

Results

Mass Spectrometry Analysis of Membrane Proteins of ATII and MLE-12 Cells.

Figure 20:
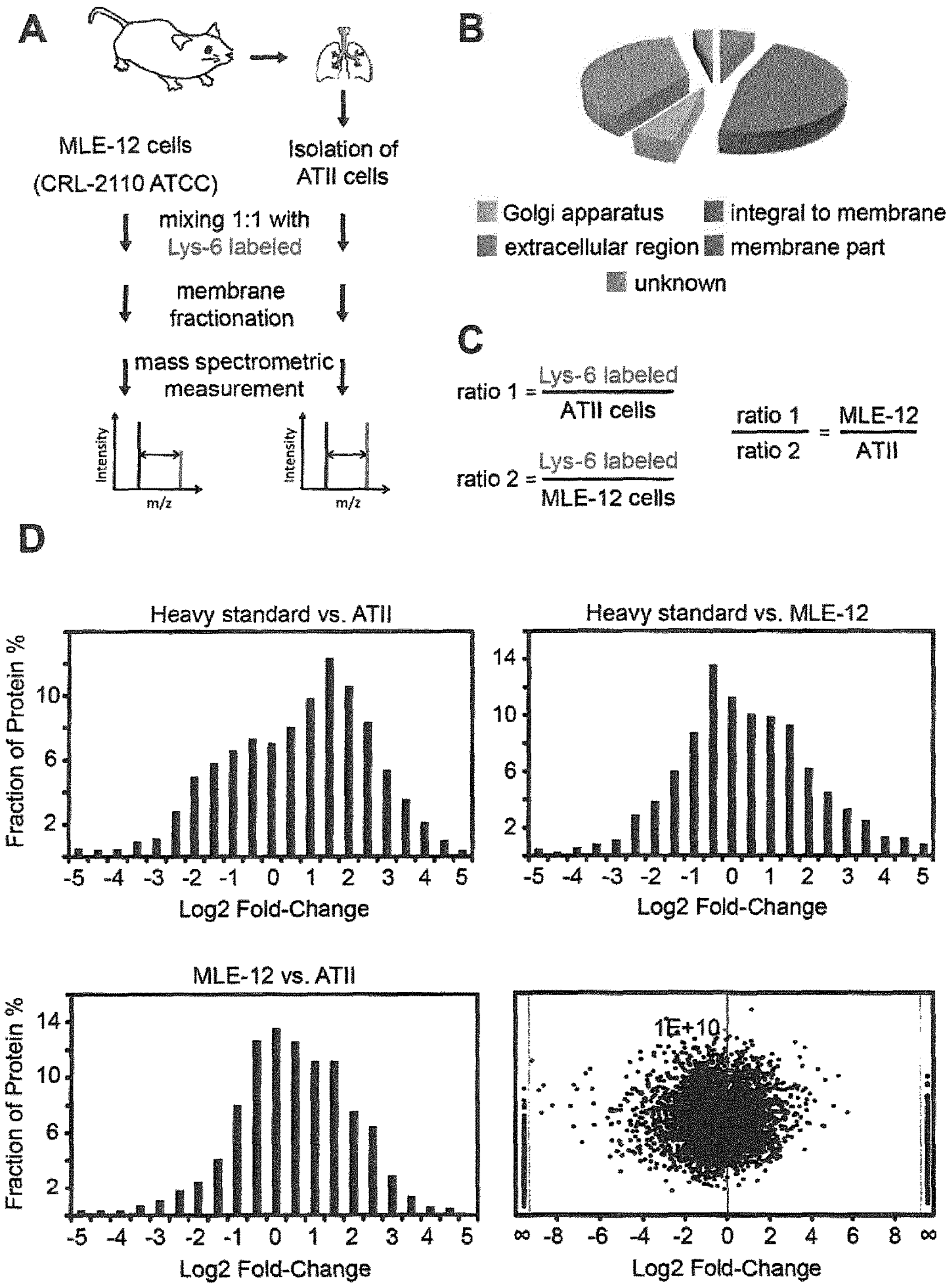
Figure 21:
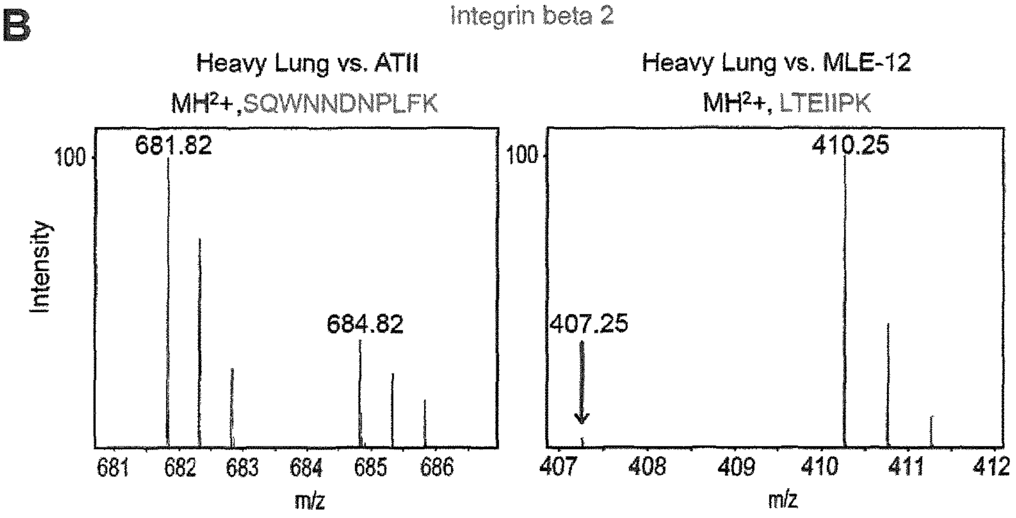

FIG. 20A shows a schematic representation of the experimental procedure. Primary ATII cells from adult mouse lung were isolated and cultured as previously described [PMID: 22856132]. ATII cells or MLE-12 cells were mixed with lung tissue from SILAC-mice at a ratio of 1:1 (wet weight: wet weight). Membrane proteins of these mixtures were isolated [PMID: 19848406 and 19153689] and after adequate sample preparation [PMID: 19377485] analyzed by high-resolution mass spectrometry based proteomic approach. Gene Ontology cellular component (GOCC) terms based analysis of identified proteins after mass spectrometric measurement (FIG. 20B) revealed that over 90% of the proteins are either membrane proteins or related to the Golgi apparatus, a cellular organelle with a high content of endomembrane that is particularly important in the processing of membrane proteins and proteins for secretion. These results support the high efficiency of our membrane protein fractionation; FIGS. 20C and 20D XYZ and FIG. 21 XYZ.

Identification of Potential ATII Cell Specific Membrane Proteins.

The transcriptomes of ATII and MLE-12 cells were determined by Affymetrix microarray based expression analysis. The transcriptome databases and the membrane proteome databases of both cells were cross analyzed (FIG. 22A) by calculating the ratios of expression of the genes in MLE-12 versus ATII cells and comparing them with the respective protein abundance ratio. This cross databases query led to the identification of 16 genes that are highly expressed in ATII cells whose gene products are enriched in the membrane of ATII cells (FIG. 22B). These 16 genes are ITGB2, PTGIS, BASP1, DES, ITGA2, CTSS, PTPRC, ANPEP, FILIP1L, MGLL, OSMR, ITGB6, AGPAT4, ASS1, CSPG4, and CDH11. The identified genes are potential ATII cell surface markers.

Integrin Beta 2 and 6 are Membrane Proteins of a Subpopulation of Alveolar Type II Cells.

We focused our attention on ITGB2 and ITGB6 for further analysis to confirm our results from the membrane proteome and transcriptome analysis. The expression of Itgb2 and Itgb6 was determined in MLg (mouse normal lung cells), MFLM-4 (mouse fetal lung mesenchyme cells), NIH/3T3 (mouse fibroblast), MLE-12 and ATII cells as well as in adult mouse lung by quantitative PCR after reverse transcription (qRT-PCR, FIG. 23A). Itgb2 and Itgb6 are highly expressed only in ATII cells when compared to the other cell lines tested. In contrast, Cox2 expression, another gene that was identified in the membrane proteome approach, was detected not only in ATII but also in MLg and MFLM-4 cells. Sftpc was expressed in ATII and MLE-12 cells, as expected. Consistently, western blot analysis of protein extracts (FIG. 23B) showed that the level of ITGB2 and ITGB6 is high in spleen, lung and ATII cells but not in any of the other cell lines tested. Our results support certain cellular specificity for the expression of Itgb2 and Itgb6. Since ITGB2 and ITGB6 are known to be present in blood cells, we decided to discard the possibility that our data are the result of contamination of the isolated ATII cells with remaining blood cells. Therefore, we tested the presence of two blood cell proteins, CD14 and CD45, in our protein extracts. CD14 and CD45 are present in the spleen protein extract, as expected, but absent in any of the other protein extracts analyzed, ruling out the possibility that our results are due to a contamination of the isolated ATII cells with remaining blood cells.

Flow cytometry analysis after single immunostaining in cell suspensions of adult lungs (FIG. 23C, top and middle) showed that 25% of the cells were ITGB2-positive, 7% were ITGB6-positive and 13% were SFTPC-positive (for each antibody P<0.01; n=4). Interestingly, similar analysis after double immunostaining (FIG. 23C, bottom) revealed that only 5% of the analyzed cells were SFTPC- and ITGB2-positive whereas 6% of the cells were SFTPC- and ITGB6-positive (for each antibody combination P<0.05; n=5), suggesting the existence of at least two different subpopulation of ATII cells in the adult lung. Our results were validated by double immunostaining in sections of adult lung (FIG. 23D) using SFTPC- and either ITGB2-(top) or ITGB6-(bottom) specific antibodies. SFTPC and ITGB2 co-localized in a subpopulation of SFTPC-positive cells of the adult lung. A similar result was obtained for ITGB6.

Integrin Beta 2 Antagonizes WNT Signaling Pathway.

Gene Ontology biological process (GOBP) terms based analysis of identified proteins after mass spectrometric measurement (FIG. 24A) revealed an enrichment of WNT signaling pathway proteins in the membrane of ATII cells. To identify a functional link between our results, we decided to monitor the WNT signaling pathway in the lung of Itgb2$^{-/-}$ mice. Activated beta catenin (ABC) is a mediator of and an indicator for active WNT signaling. Immunostaining for ABC in sections of adult lungs (FIG. 24B-C) demonstrated an enhancement of canonical WNT signaling after Itgb2 knockout (KO) that was further validated by enhanced expression (FIG. 24D) as well as increased protein levels (FIG. 24E) of canonical WNT targets in the adult lung of Itgb2$^{-/-}$ mice when compared to wild type mice (WT). Our results suggest a block release of WNT signaling after Itgb2-KO. To confirm an Itgb2 mediated negative regulation of WNT signaling, we transfected Itgb2 into MLE-12 cells that were either untreated or treated with LiCl to activate WNT signaling (FIG. 24F). Itgb2 reduced the basal level of expression of the WNT targets Axing, Bmp4 and Mycn. Moreover, Itgb2 antagonized the activation of the WNT signaling pathway induced by LiCl-treatment. Our results support the hypothesis of an Itgb2 mediated negative regulation of WNT signaling in the adult lung.

It is shown herein that Itgb2 is required for a negative regulation of WNT signaling in the lung. The previously reported integrin mediated activation of TGFB signaling

[21900405, 23046811] suggest the possibility of an integrin mediated counteracting effect between these two signaling pathways that would be of interest for further investigation. A recent publication links a cross talk between WNT and TGFB signaling to pulmonary epithelial cell fate specification [23562608]. A potential integrin mediated cross talk between TGFB and WNT signaling becomes even more interesting within the context of an important biological paradigm, how is the balance between differentiation and self-renewal of progenitor cells. Moreover, given the ability of integrins to modulate both signaling pathways, it may be possible to use them as potential targets to activate these pathways to increase repair and regeneration after lung injury. However, due to the fact that integrins, TGFB and WNT have been involved in pulmonary fibrosis and lung cancer one has to be careful before modulating both signaling pathways for this purpose.

Example 12

Figure 25:
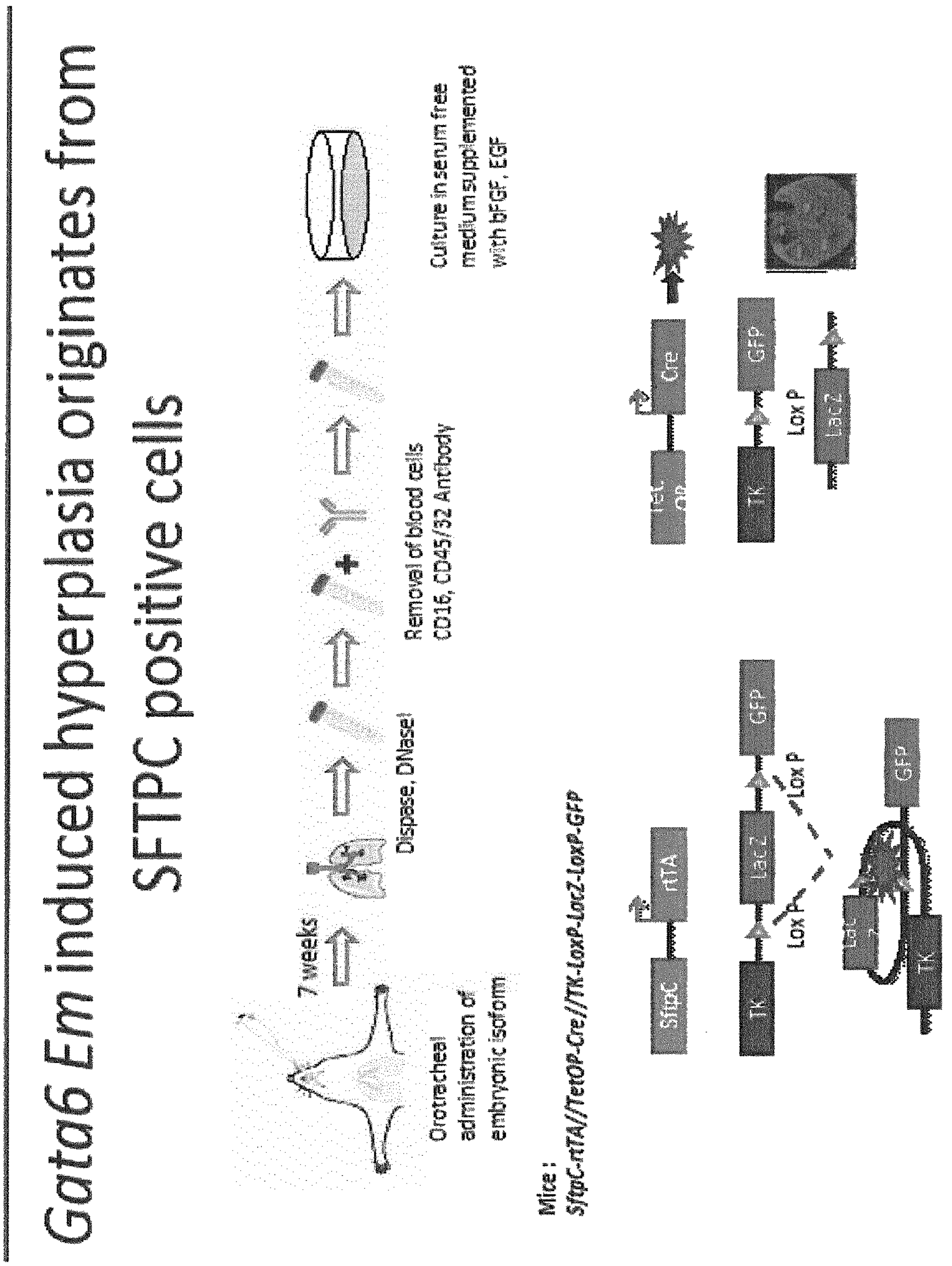

In order to determine whether ATII cells were the cells of origin of the Gata6 Em induced hyperplasia observed we used inducible reporter lines for ATII cells. Sftpc-rtTA/TetOP-Cre//TK-LoxP-LacZ-LoxP-GFP, a triple transgenic mouse that specifically labels ATII cells with green fluorescent protein after induction with Doxycycline (FIG. 25). In these mice; expression of Tet-O transactivator (rtTA) gene is under the control of the surfactant protein C (sftpc) promoter. Sftpc is the most specific marker of lung epithelial Alveolar type II cells. In a Tet-On system, the rtTA protein is capable of binding the operator (TetOP) only if bound by a tetracycline or its derivative doxycycline. Thus the introduction of doxycycline to the system initiates the transcription of the CRE recombinase protein in the ATII cells triple transgenic mice lung and then CRE recombinase protein deletes LacZ flanked by LoxP sites which leads to expression of green fluorescent protein gene (GFP) under the control of thymidine kinase gene (TK) promoter specifically into Alveolar type II cells.

These mice were treated with a Control (Ctrl) or Gata6 Em expression vector mixed with Polyethyleneimine (as in FIG. 4) and 3 days after the first treatment, doxyclycine was administered via water at a concentration of 4 mg/ml. After 7 weeks, we harvested and homogenized the lung from these mice and prepared single cell suspensions (FIG. 25). Lung epithelial cells were isolated following negative selection using antibodies against blood cells, CD16, CD45/32. The isolated cells were cultured in serum free medium supplemented with basic fibroblast growth factor (bFGF), epidermal growth factor (EGF) and heparin in low attachment dishes, allowing the growth of only those cells that have a stem cell like phenotype, or in this case, the highly tumorigenic cancer stem cells. As compared to the cells isolated from the control (Ctrl) treated lungs, Gata6 Em treated lung cells contained a subpopulation of cells that was able to stay in culture for several passages suggesting that these cells have undergone malignant transformation (FIG. 26). In addition, these cell clusters expressed EGFP supporting the hypothesis that these cells originated from ATII cells. To confirm the formation of cancer stem cells, we will investigate the two hallmarks of these cells, i.e. resistance to chemotherapeutic agents (in vitro) and subsequent tumor inducing potential after sub cutaneous injection in mice.

The present invention refers to the following nucleotide and amino acid sequences:

The sequences provided herein are available in the NCBI database and can be retrieved for example from world wide web at ncbi.nlm.nih.gov/sites/entrez?db=gene; Theses sequences also relate to annotated and modified sequences. The present invention also provides techniques and methods wherein homologous sequences, and variants of the concise sequences provided herein are used. Preferably, such "variants" are genetic variants.

SEQ ID No. 108:

Nucleotide sequence encoding *Homo sapiens* ITGB2 (integrin beta 2): Transcript var 1: NM_000211

SEQ ID No. 109:

Nucleotide sequence encoding *Homo sapiens* ITGB2 (integrin beta 2): Transcript var 2: NM_001127491.1

SEQ ID No. 110:

Amino acid sequence of *Homo sapiens* ITGB2 (integrin beta 2): Protein: NP_000202.2, NP_001120963.1

SEQ ID NO. 111:

Nucleotide sequence encoding *Homo sapiens* PTGIS (prostaglandin 12 (prostacyclin) synthase (PTGIS)): Transcript: NM_000961.3

SEQ ID NO. 112:

Amino acid sequence of *Homo sapiens* PTGIS (prostaglandin 12 (prostacyclin) synthase (PTGIS)): Protein: NP_000952.1

SEQ ID NO. 113:

Nucleic acid sequence encoding *Homo sapiens* BASP1 (brain abundant, membrane attached signal protein 1): Transcript Variant 1: NM_006317

SEQ ID NO. 114:

Nucleic acid sequence encoding *Homo sapiens* BASP1 (brain abundant, membrane attached signal protein 1): Transcript variant 2: NM_001271606

SEQ ID NO. 115:

Amino acid sequences of *Homo sapiens* BASP1 (brain abundant, membrane attached signal protein 1): Protein: NP_001258535, NP_006308

SEQ ID NO. 116:

Nucleic acid sequence encoding *Homo sapiens* DES (Desmin):Transcript: NM_001927

SEQ ID NO. 117:

Amino acid sequence of *Homo sapiens* DES (Desmin): Protein: NP_001918

SEQ ID NO. 118:

Nucleic acid sequence encoding *Homo sapiens* ITGA2 (integrin, alpha 2): Transcript: NM_002203

SEQ ID NO. 119:

Amino acid sequence of *Homo sapiens* ITGA2 (integrin, alpha 2): Protein: NP_002194

SEQ ID NO. 120:

Nucleic acid sequence encoding *Homo sapiens* CTSS (Cathepsin S): Transcript variant 1: NM_004079

SEQ ID NO. 121:

Nucleic acid sequence encoding *Homo sapiens* CTSS (Cathepsin S): Transcript variant 2: NM_001199739

SEQ ID NO. 122:

Amino acid sequence of *Homo sapiens* CTSS (Cathepsin S): Protein variant 1: NP_004070

SEQ ID NO. 123:

Amino acid sequence of *Homo sapiens* CTSS (Cathepsin S): Protein variant 2: NP_001186668

SEQ ID NO. 124:

Nucleic acid sequence encoding *Homo sapiens* PTPRC (protein tyrosine phosphatase, receptor type, C): Transcript variant 5: NM_001267798

SEQ ID NO. 125:

Nucleic acid sequence encoding *Homo sapiens* PTPRC (protein tyrosine phosphatase, receptor type, C): Transcript variant 1: NM_002838

SEQ ID NO. 126:

Nucleic acid sequence encoding *Homo sapiens* PTPRC (protein tyrosine phosphatase, receptor type, C): Transcript variant 2: NM_080921

SEQ ID NO. 127:

Nucleic acid sequence of *Homo sapiens* PTPRC (protein tyrosine phosphatase, receptor type, C): Transcript variant 4 (Non coding RNA): NR_052021

SEQ ID NO. 128:

Amino acid sequence of *Homo sapiens* PTPRC (protein tyrosine phosphatase, receptor type, C): Protein variant 5: NP_001254727

SEQ ID NO. 129:

Amino acid sequence of *Homo sapiens* PTPRC (protein tyrosine phosphatase, receptor type, C): Protein variant 1: NP_002829

SEQ ID NO. 130:

Amino acid sequence of *Homo sapiens* PTPRC (protein tyrosine phosphatase, receptor type, C): Protein variant 2: NP_563578

SEQ ID NO. 131:

Nucleic acid sequence encoding *Homo sapiens* ANPEP (alanyl (membrane) aminopeptidase): Transcript: NM_001150

SEQ ID NO. 132:

Amino acid sequence of *Homo sapiens* ANPEP (alanyl (membrane) aminopeptidase): Protein: NP_001141

SEQ ID NO. 133:

Nucleic acid sequence encoding *Homo sapiens* FILIP1L (filamin A interacting protein 1-like): Transcript variant 1: NM_182909

SEQ ID NO. 134:

Nucleic acid sequence encoding *Homo sapiens* FILIP1L (filamin A interacting protein 1-like): Transcript variant 2: NM_014890

SEQ ID NO. 135:

Nucleic acid sequence encoding *Homo sapiens* FILIP1L (filamin A interacting protein 1-like): Transcript variant 3: NM_001042459

SEQ ID NO. 136:

Amino acid sequence of *Homo sapiens* FILIP1L (filamin A interacting protein 1-like): Protein variant 1: NP_878913

SEQ ID NO. 137:

Amino acid sequence of *Homo sapiens* FILIP1L (filamin A interacting protein 1-like): Protein variant 2: NP_055705

SEQ ID NO. 138:

Amino acid sequence of *Homo sapiens* FILIP1L (filamin A interacting protein 1-like): Protein variant 3: NP_001035924

SEQ ID NO. 139:

Nucleic acid sequence encoding *Homo sapiens* MGLL (monoglyceride lipase): Transcript variant 1: NM_007283

SEQ ID NO. 140:

Nucleic acid sequence encoding *Homo sapiens* MGLL (monoglyceride lipase): Transcript variant 2: NM 001003794

SEQ ID NO. 141:

Nucleic acid sequence encoding *Homo sapiens* MGLL (monoglyceride lipase): Transcript variant 3: NM 001256585

SEQ ID NO. 142:

Amino acid sequence of *Homo sapiens* MGLL (monoglyceride lipase): Protein variant 1: NP_009214

SEQ ID NO. 143:

Amino acid sequence of *Homo sapiens* MGLL (monoglyceride lipase): Protein variant 2: NP_001003794

SEQ ID NO. 144:

Amino acid sequence of *Homo sapiens* MGLL (monoglyceride lipase): Protein variant 3: NP_001243514

SEQ ID NO. 145:

Nucleic acid sequence encoding *Homo sapiens* OSMR (oncostatin M receptor): Transcript variant 1: NM_003999

SEQ ID NO. 146:

Nucleic acid sequence encoding *Homo sapiens* OSMR (oncostatin M receptor): Transcript variant 2: NM_001168355

SEQ ID NO. 147:

Amino acid sequence of *Homo sapiens* OSMR (oncostatin M receptor): Protein Variant 1: NP_003990

SEQ ID NO. 148:

Amino acid sequence of *Homo sapiens* OSMR (oncostatin M receptor): Protein variant 2: NP_001161827

SEQ ID NO. 149:

Nucleic acid sequence encoding *Homo sapiens* ITGB6 (integrin, beta 6): Transcript: NM_000888

SEQ ID NO. 150:

Amino acid sequence of *Homo sapiens* ITGB6 (integrin, beta 6): Protein: NP_000879

SEQ ID NO. 151:

Nucleic acid sequence encoding *Homo sapiens* AGPAT4 (1-acylglycerol-3-phosphate O-acyltransferase 4): Transcript: NM_020133

SEQ ID NO. 152:

Amino acid sequence of *Homo sapiens* AGPAT4 (1-acylglycerol-3-phosphate O-acyltransferase 4): Protein: NP_064518

SEQ ID NO. 153:

Nucleic acid sequence encoding *Homo sapiens* ASS1 (argininosuccinate synthase 1): Transcript variant 1: NM_000050

SEQ ID NO. 154:

Nucleic acid sequence encoding *Homo sapiens* ASS1 (argininosuccinate synthase 1): Transcript variant 2: NM_054012

SEQ ID NO. 155:

Amino acid sequence of *Homo sapiens* ASS1 (argininosuccinate synthase 1): Protein: NP_000041, NP_446464

SEQ ID NO. 156:

Nucleic acid sequence encoding *Homo sapiens* CSPG4 (chondroitin sulfate proteoglycan 4): Transcript: NM_001897

SEQ ID NO. 157:

Amino acid sequence of *Homo sapiens* CSPG4 (chondroitin sulfate proteoglycan 4): Protein: NP_001888

SEQ ID NO. 158:

Nucleic acid sequence encoding *Homo sapiens* CDH11 (cadherin 11, type 2, OB-cadherin): Transcript: NM_001797

SEQ ID NO. 159:

Amino acid sequence of *Homo sapiens* CDH11 (cadherin 11, type 2, OB-cadherin): Protein: NP_001788

The invention claimed is:

1. A method of assessing a lung cell sample or a breath condensate from a subject, said method comprising a) measuring in the lung cell sample or breath condensate of said subject the amount of specific transcription factor isoforms by performing detection assay to specifically detect said specific transcription factor isoforms, wherein said specific transcription isoforms are i) the GATA6 Em isoform comprising the nucleic acid sequence of SEQ ID No: 1 or the GATA6 Em isoform comprising a nucleic acid sequence of SEQ ID NO:1 with at least one of the SNPs selected from
G at position 293 is substituted with A;
G at position 320 is substituted with C;
C at position 327 is substituted with G;
C at position 339 is substituted with G;
G at position 430 is substituted with U;
position 462 is inserted with U;
A at position 480 is substituted with U;
C at position 759 is substituted with U;
C at position 1128 is substituted with G;
C at position 1256 is substituted with A;
G at position 1304 is substituted with A;
C at position 1589 is substituted with U;
U at position 1597 is substituted with A;
A at position 1627 is substituted with G;
C at position 1651 is substituted with U;
G at position 1652 is substituted with A;
A at position 1803 is substituted with G;
U at position 1844 is substituted with C;
U at position 1849 is substituted with C;
A at position 1879 is substituted with G;
A at position 1882 is substituted with G;
U at position 1911 is substituted with G;
C at position 1940 is substituted with G;
A at position 1949 is substituted with G;
U at position 1982 is substituted with C;
G at position 2000 is substituted with C;
C at position 2002 is substituted with U;
G at position 2008 is substituted with C;
C at position 2026 is substituted with U;
G at position 2031 is substituted with U;
C at position 2106 is substituted with U;
G at position 2137 is substituted with A;
A at position 2142 is substituted with G
C at position 2163 is substituted with U;
C at position 2294 is substituted with U;
A at position 2390 is substituted with G;
U at position 2391 is substituted with A;
A at position 2627 is substituted with G;
A at position 3102 is substituted with G;
C at position 3240 is substituted with U;
A at position 3290 is substituted with G;
C at position 3358 is substituted with U;
A at position 3366 is substituted with U;
C at position 3578 is substituted with U;
position 3632 is inserted with C;
C at position 3646 is substituted with U;
A at position 3670 is substituted with G; and
C at position 3690 is substituted with U;
and ii) the NKX2-1 Em isoform comprising the nucleic acid sequence of SEQ ID No: 2 or the NKX2-1 Em isoform comprising a nucleic acid sequence of SEQ ID NO: 2 with at least one of the SNPs selected from
position 305 is inserted with A;
position 304 is inserted with AA;
G at position 420 is substituted with A;
C at position 425 is substituted with U;
G at position 439 is substituted with U;
C at position 441 is substituted with A;
C at position 450 is substituted with U;

C at position 486 is substituted with U;
G at position 781 is substituted with U;
C at position 785 is substituted with U;
A at position 825 is substituted with C;
G at position 950 is substituted with U;
G at position 1169 is substituted with A;
G at position 1305 is substituted with A;
G at position 1344 is substituted with U;
G at position 1448 is substituted with A;
position 1640 is inserted with U;
position 1641 is inserted with GU;
position 1643 is inserted with >6 bp;
position 1673 is inserted with U;
position 1678 is inserted with U;
position 1748 is inserted with C;
position 1750 is inserted with C;
position 1916 is inserted with A;
position 1917 is inserted with A;
C at position 1934 is substituted with G or U; and
C at position 2099 is substituted with G.

2. The method according to claim 1, wherein the amount of said specific transcription factor isoforms is measured via a polymerase chain reaction based method.

3. The method according to claim 2, wherein the step of measuring in a lung cell sample or a breath condensate of said subject the amount of a specific transcription factor comprises the contacting of the sample with primers, wherein said primers can be used for amplifying at least one of the specific transcription factor isoforms.

4. The method according to claim 3, wherein said primers are selected from the group of primers having a nucleic acid sequence as set forth in SEQ ID NOs 9 to 40.

5. The method according to claim 1, wherein said step a) further comprises measuring in the lung cell sample or the breath condensate of said subject the amount of one or two further specific transcription factor isoform(s) selected from the group of specific transcription factor isoforms consisting of i) the FOXA2 Em isoform comprising the nucleic acid sequence of SEQ ID No: 3 or the FOXA2 Em isoform comprising a nucleic acid sequence of SEQ ID NO: 3 with at least one of the SNPs selected from
position 168 is inserted with >6 bp;
U at position 208 is substituted with C;
G at position 289 is substituted with A;
G at position 361 is substituted with A;
G at position 368 is substituted with A;
C at position 374 is substituted with U;
G at position 379 is substituted with A;
G at position 383 is substituted with A;
G at position 404 is substituted with U;
G at position 459 is substituted with A;
C at position 481 is substituted with U;
G at position 483 is substituted with C;
C at position 494 is substituted with U;
G at position 529 is substituted with A;
A at position 564 is substituted with G;
C at position 577 is substituted with G;
C at position 584 is substituted with U;
C at position 590 is substituted with A;
U at position 610 is substituted with C;
G at position 623 is substituted with C;
C at position 641 is substituted with U;
G at position 650 is substituted with A;
G at position 659 is substituted with U;
C at position 674 is substituted with U;
G at position 773 is substituted with U;
C at position 845 is substituted with U;
A at position 1040 is substituted with G;
C at position 1075 is substituted with U;
C at position 1186 is substituted with U;
G at position 1188 is substituted with C;
C at position 1240 is substituted with U;
G at position 1242 is substituted with A;
C at position 1243 is substituted with G;
A at position 1304 is substituted with C;
AG at position 1374-1375 is deleted;
A at position 1391 is substituted with G;
U at position 1408 is substituted with C;
C at position 1414 is substituted with U;
A at position 1432 is substituted with C;
C at position 1458 is substituted with A;
G at position 1475 is substituted with A;
G at position 1487 is substituted with C;
C at position 1522 is substituted with G;
C at position 1539 is substituted with G;
position 1737 is inserted with G;
position 1738 is inserted with G;
A at position 1831 is substituted with U;
position 1838 is inserted with U;
position 1966 is inserted with G or U;
position 1970 is inserted with A
A at position 2070 is substituted with U;
A at position 2083 is substituted with G;
position 2084 is inserted with U;
position 2093 is inserted with U;
C at position 2112 is substituted with U; and
C at position 2200 is substituted with U;
and ii) the ID2 Em isoform comprising the nucleic acid sequence of SEQ ID No: 4 or the ID2 Em isoform comprising a nucleic acid sequence of SEQ ID NO: 4 with at least one of the SNPs selected from:
C at position 6 is substituted with U;
C at position 55 is substituted with G;
C at position 154 is substituted with G or U;
C at position 195 is substituted with U;
C at position 209 is substituted with U;
G at position 224 is substituted with A;
C at position 237 is substituted with U;
C at position 263 is substituted with A;
C at position 286 is substituted with U;
G at position 360 is substituted with A;
C at position 399 is substituted with U;
C at position 405 is substituted with U;
C at position 485 is substituted with U;
C at position 501 is substituted with G or U;
C at position 544 is substituted with U;
U at position 547 is substituted with A;
A at position 605 is substituted with G;
G at position 665 is substituted with U;
A at position 876 is substituted with G;
position 975 is inserted with >6 bp;
position 1085 is inserted with >6 bp;
position 1119 is inserted with AU;
A at position 1151 is substituted with U;
position 1251 is inserted with CA;
A at position 1333 is substituted with G; and
C at position 1350 is substituted with G.

6. The method according to claim 1, wherein the amount of said specific transcription factor isoform(s) is measured on the polypeptide level.

7. The method according to claim 6, wherein the amount of said specific transcription factor isoform(s) is measured by an ELISA, a gel- or blot-based method, mass spectrometry, flow cytometry or FACS.

8. The method according to claim 1, wherein the subject has a lung cancer.

9. The method according to claim 8, wherein said lung cancer is an adenocarcinoma or a bronchoalveolar carcinoma.

10. The method according to claim 1, wherein said lung cell sample comprises tumor cells.

11. The method according to claim 1, wherein said lung cell sample is a blood sample, a bronchoalveolar lavage fluid sample, a mucus sample or a phlegm sample.

12. The method according to claim 1, wherein said subject is a human subject.

13. The method of claim 12, wherein said human subject is a subject having an increased risk for developing cancer.

14. A method of treating a subject, said method comprising a) assessing a lung cell sample or a breath condensate from the subject according to the method of claim 1; and b) administering to said subject an effective amount of an anti-cancer agent and/or radiation therapy.

15. The method of treating a subject according to claim 14, wherein said anti-cancer agent is an isoform specific siRNA of i) the GATA6 Em isoform comprising the nucleic acid sequence of SEQ ID No: 1 or the GATA6 Em isoform nucleic acid sequence of SEQ ID NO: 1 with at least one of the SNPs selected from G at position 293 is substituted with A;
G at position 320 is substituted with C;
C at position 327 is substituted with G;
C at position 339 is substituted with G;
G at position 430 is substituted with U;
position 462 is inserted with U;
A at position 480 is substituted with U;
C at position 759 is substituted with U;
C at position 1128 is substituted with G;
C at position 1256 is substituted with A;
G at position 1304 is substituted with A;
C at position 1589 is substituted with U;
U at position 1597 is substituted with A;
A at position 1627 is substituted with G;
C at position 1651 is substituted with U;
G at position 1652 is substituted with A;
A at position 1803 is substituted with G;
U at position 1844 is substituted with C;
U at position 1849 is substituted with C;
A at position 1879 is substituted with G;
A at position 1882 is substituted with G;
U at position 1911 is substituted with G;
C at position 1940 is substituted with G;
A at position 1949 is substituted with G;
U at position 1982 is substituted with C;
G at position 2000 is substituted with C;
C at position 2002 is substituted with U;
G at position 2008 is substituted with C;
C at position 2026 is substituted with U;
G at position 2031 is substituted with U;
C at position 2106 is substituted with U;
G at position 2137 is substituted with A;
A at position 2142 is substituted with G
C at position 2163 is substituted with U;
C at position 2294 is substituted with U;
A at position 2390 is substituted with G;
U at position 2391 is substituted with A;
A at position 2627 is substituted with G;
A at position 3102 is substituted with G;
C at position 3240 is substituted with U;
A at position 3290 is substituted with G;
C at position 3358 is substituted with U;
A at position 3366 is substituted with U;
C at position 3578 is substituted with U;
position 3632 is inserted with C;
C at position 3646 is substituted with U;
A at position 3670 is substituted with G; and
C at position 3690 is substituted with U;
or ii) the NKX2-1 Em isoform comprising the nucleic acid sequence of SEQ ID No: 2 or the NKX2-1 Em isoform comprising a nucleic acid sequence of SEQ ID NO:2 with at least one of the SNPs selected from:

position 305 is inserted with A;
position 304 is inserted with AA;
G at position 420 is substituted with A;
C at position 425 is substituted with U;
G at position 439 is substituted with U;
C at position 441 is substituted with A;
C at position 450 is substituted with U;
C at position 486 is substituted with U;
G at position 781 is substituted with U;
C at position 785 is substituted with U;
A at position 825 is substituted with C;
G at position 950 is substituted with U;
G at position 1169 is substituted with A;
G at position 1305 is substituted with A;
G at position 1344 is substituted with U;
G at position 1448 is substituted with A;
position 1640 is inserted with U;
position 1641 is inserted with GU;
position 1643 is inserted with >6 bp;
position 1673 is inserted with U;
position 1678 is inserted with U;
position 1748 is inserted with C;
position 1750 is inserted with C;
position 1916 is inserted with A;
position 1917 is inserted with A;
C at position 1934 is substituted with G or U; and
C at position 2099 is substituted with G.

16. The method of treating a subject according to claim 14, wherein said subject is a subject suffering from lung cancer.

17. The method of treating a subject according to claim 16, wherein said lung cancer is a lung adenocarcinoma or a bronchoalveolar carcinoma.

18. The method according to claim 4, wherein said primers comprise primers having a nucleic acid sequence as set forth in:

(i) SEQ ID NO: 10 and SEQ ID NO: 12;
(ii) SEQ ID NO: 14 and SEQ ID NO: 16;
(iii) SEQ ID NO: 18 and SEQ ID NO: 20; or
(iv) SEQ ID NO: 22 and SEQ ID NO: 24.

19. The method according to claim 2, wherein said polymerase chain reaction-based method is a quantitative reverse transcriptase polymerase chain reaction.

20. The method according to claim 1, wherein the measuring is performed on the nucleic acid level by contacting the lung cell sample or the breath condensate with primers specific for said specific transcription isoforms; or wherein the measuring is performed on the polypeptide level by an ELISA, a gel- or blot-based method, mass spectrometry, flow cytometry or FACS.

21. The method according to claim 14, wherein the lung cell sample or a breath condensate is a breath condensate from the subject.

22. The method according to claim 14, wherein the lung cell sample is a blood sample, a bronchoalveolar lavage fluid sample, a mucus sample or a phlegm sample.

* * * * *

SEQUENCE LISTING

```
<160> NUMBER OF SEQ ID NOS: 187

<210> SEQ ID NO 1
<211> LENGTH: 3770
<212> TYPE: RNA
```

<213> ORGANISM: Homo sapiens

<400> SEQUENCE: 1
gacccacagc cuggcacccu ucggcgagcg cuguuuguuu agggcucggu gaguccaauc 60
aggagcccag gcugcaguuu uccggcagag caguaagagg cgccuccucu cuccuuuuua 120
uucaccagca gcgcggcgca gaccccggac ucgcgcucgc ccgcuggcgc ccucggcuuc 180
ucuccgcgcc ugggagcacc cuccgccgcg gccguucucc augcgcagcg cccgcccgag 240
gagcuagacg ucagcuugga gcggcgccgg accguggaug gccuugacug acggcggcug 300
gugcuugccg aagcgcuucg gggccgcggg ugcggacgcc agcgacucca gagccuuucc 360
agcgcgggag cccuccacgc cgccuucccc caucucuucc ucguccuccu ccugcucccg 420
gggcggagag cggggccccg gcggcgccag caacugcggg acgccucagc ucgacacgga 480
ggcggcggcc ggacccccgg cccgcucgcu gcugcucagu uccuacgcuu cgcaucccuu 540
cggggcuccc cacggaccuu cggcgccugg ggucgcgggc cccgggggca accugucgag 600
cugggaggac uugcugcugu ucacugaccu cgaccaagcc gcgaccgcca gcaagcugcu 660
gugguccagc cgcggcgcca agcugagccc cuucgcaccc gagcagccgg aggagaugua 720
ccagacccuc gccgcucucu ccagccaggg uccggccgcc uacgacggcg cgcccggcgg 780
cuucgugcac ucugcggccg cggcggcagc agccgcggcg gcggccagcu ccccggucua 840
cgugcccacc acccgcgugg guuccaugcu gcccggccua ccguaccacc ugcagggguc 900
gggcaguggg ccagccaacc acgcgggcgg cgcgggcgcg caccccggcu ggccucaggc 960
cucggccgac agcccuccau acggcagcgg aggcggcgcg gcuggcggcg gggccgcggg 1020
gccuggcggc gcuggcucag ccgcggcgca cgucucggcg cgcuuccccu acucucccag 1080
cccgcccaug gccaacggcg ccgcgcggga gccgggaggc uacgcggcgg cgggcagugg 1140
gggcgcggga ggcgugagcg gcggcggcag uagccuggcg gccaugggcg gccgcgagcc 1200
ccaguacagc ucgcugucgg ccgcgcggcc gcugaacggg acguaccacc accaccacca 1260
ccaccaccac caccauccga gccccuacuc gcccuacgug gggcgccac ugacgccugc 1320 cuggcccgcc ggacccuucg agaccccggu gcugcacagc cugcagagcc gcgccggagc 1380
cccgcucccg gugccccggg gucccagugc agaccugcug gaggaccugu ccgagagccg 1440
cgagugcgug aacugcggcu ccauccagac gccgcugugg cggcgggacg gcaccggcca 1500
cuaccugugc aacgccugcg ggcucuacag caagaugaac ggccucagcc ggccccucau 1560
caagccgcag aagcgcgugc cuucaucacg gcggcuugga uuguccugug ccaacuguca 1620
caccacaacu accaccuuau ggcgcagaaa cgccgagggu gaacccgugu gcaaugcuug 1680
uggacucuac augaaacucc auggggugcc cagaccacuu gcuaugaaaa aagagggaau 1740
ucaaaccagg aaacgaaaac cuaagaacau aaauaaauca aagacuugcu cugguaauag 1800
caauaauucc auucccauga cuccaacuuc caccucuucu aacucagaug auugcagcaa 1860
aaauacuucc cccacaacac aaccuacagc cucagggggcg ggugccccgg ugaugacugg 1920
ugcgggagag agcaccaauc ccgagaacag cgagcucaag uauucggguc aagaugggcu 1980
cuacauaggc gucagucucg ccucgccggc cgaagucacg uccuccgugc gaccggauuc 2040
cuggugcgcc cuggcccugg ccugagccca cgccgccagg aggcagggag ggcuccgccg 2100
cgggccucac uccacucgug ucugcuuuug ugcagcgguc cagacagugg cgacugcgcu 2160
gacagaacgu gauucucgug ccuuuauuuu gaaagagaug uuuuucccaa gaggcuugcu 2220
gaaagaguga gagaagaugg aagggaaggg ccagugcaac ugggcgcuug ggccacucca 2280

-continued gccagcccgc cucccggggcg gacccugcuc cacuuccaga agccaggacu aggaccuggg 2340
ccuugccugc uauggaauau ugagagagau uuuuuaaaaa agauuuugca uuuuguccaa 2400
aaucaugugc uucuucugau caauuuuggu uguuccagaa uuucuucaua ccuuuuccac 2460
auccagauuu caugugcguu cauggagaag aucacuugag gccauuuggu acacaucucu 2520
ggaggcugag ucgguucaug aggucucuua ucaaaaauau uacucaguuu gcaagacugc 2580
auuguaacuu uaacauacac ugugacugac guuucucaaa guucauauug uguggcugau 2640
cugaagucag ucggaauuug uaaacagggu agcaaacaag auauuuuucu uccauguaua 2700
caauaauuuu uuuaaaaagu gcaauuugcg uugcagcaau caguguuaaa ucauuugcau 2760
aagauuuaac agcauuuuuu auaaugaaug uaaacauuuu aacuuaaugg uacuuaaaau 2820
aauuuaaaag aaaaauguua acuuagacau ucuuaugcuu cuuuuacaac uacaucccau 2880
uuuauauuuc caauuguuaa agaaaaauau uucaagaaca aaucuucucu caggaaaauu 2940
gccuuucucu auuuguuaag aauuuuuaua caagaacacc aauauacccc cuuuauuuua 3000
cuguggaaua ugugcuggaa aaauugcaac aacacuuuac uaccuaacgg auagcauuug 3060
uaaauacucu agguaucugu aaacacucug augaagucug uauaguguga cuaacccaca 3120
ggcagguugg uuuacauuaa uuuuuuuuuu ugaaugggau guccuaugga aaccuauuuc 3180
accagaguuu uaaaaauaaa aaggguauug uuuugucuuc uguacaguga guuccuuccc 3240
uuuucaaagc uuucuuuuua ugcuguaugu gacuauagau auucauauaa aacaagugca 3300
cgugaaguuu gcaaaaugcu uuaaggccuu ccuuucaaag cauaguccuu uuggagccgu 3360
uuuguaccuu uuauaccuug gcuuauuuga aguugacaca ugggguuagu uacuacucuc 3420
caugugcauu ggggacaguu uuuauaagug ggaaggacuc aguauuauua uauuugagau 3480
gauaagcauu uuguuuggga acaaugcuua aaaauauucc agaaaguuca gauuuuuuuu 3540
cuuugugaau gaaauauauu cuggcccacg aacagggcga uuuccuuuca guuuuuuccu 3600
uuugcaacgu gccuugaagu cucaaagcuc accugagguu gcagacguua cccccaacag 3660
aagauaggua gaaaugauuc caguggccuc uuuguauuuu cuucauuguu gaguagauuu 3720
caggaaauca ggagguguuu cacaauacag aaugauggcc uuuaacugug 3770

<210> SEQ ID NO 2
<211> LENGTH: 2352
<212> TYPE: RNA
<213> ORGANISM: Homo sapiens

<400> SEQUENCE: 2
gaaacuuaaa gguguuuacc uugucaucag cauguaagcu aauuaucucg ggcaagaugu 60
aggcuucuau ugucuuguug cuuuagcgcu uacgccccgc cucugguggc ugccuaaaac 120
cuggcgccgg gcuaaaacaa acgcgaggca gcccccgagc cuccacucaa gccaauuaag 180
gaggacucgg uccacuccgu uacguguaca uccaacaaga ucggcguuaa gguaacacca 240
gaauauuugg caaagggaga aaaaaaaagc agcgaggcuu cgccuucccc cucucccuuu 300
uuuuuccucc ucuuccuucc uccuccagcc gccgccgaau caugucgaug aguccaaagc 360
acacgacucc guucucagug ucugacaucu ugaguccccu ggaggaaagc uacaagaaag 420
ugggcaugga gggcggcggc cucggggcuc cgcuggcggc guacaggcag ggccaggcgg 480
caccgccaac agcggccaug cagcagcacg ccguggggca ccacggcgcc gucaccgccg 540
ccuaccacau gacggcggcg gggguguccc agcucucgca cuccgccgug gggggcuacu 600

```
gcaacggcaa ccugggcaac augagcgagc ugccgccgua ccaggacacc augaggaaca    660

gcgccucugg ccccggaugg uacggcgcca acccagaccc gcgcuucccc gccaucuccc    720

gcuucauggg cccggcgagc ggcaugaaca ugagcggcau gggcggccug ggcucgcugg    780

gggacgugag caagaacaug gccccgcugc caagcgcgcc gcgcaggaag cgccgggugc    840

ucuucucgca ggcgcaggug uacgagcugg agcgacgcuu caagcaacag aaguaccugu    900

cggcgccgga gcgcgagcac cuggccagca ugauccaccu gacgcccacg caggucaaga    960

ucugguucca gaaccaccgc uacaaaauga agcgccaggc caaggacaag gcggcgcagc   1020

agcaacugca gcaggacagc ggcggcggcg ggggcggcgg gggcaccggg ugcccgcagc   1080

agcaacaggc ucagcagcag ucgccgcgac gcguggcggu gccgguccug gugaaagacg   1140

gcaaaccgug ccaggcgggu gcccccgcgc cgggcgccgc cagccuacaa ggccacgcgc   1200

agcagcaggc gcagcaccag gcgcaggccg cgcaggcggc ggcagcggcc aucuccgugg   1260

gcagcggugg cgccggccuu ggcgcacacc cgggccacca gccaggcagc gcaggccagu   1320

cuccggaccu ggcgcaccac gccgccagcc ccgcggcgcu gcagggccag guauccagcc   1380

ugucccaccu gaacuccucg ggcucggacu acggcaccau guccugcucc accuugcuau   1440

acggucggac cuggugagag gacgccgggc cggcccuagc ccagcgcucu gccucaccgc   1500

uucccuccug cccgccacac agaccaccau ccaccgcugc uccacgcgcu ucgacuuuuc   1560

uuaacaaccu ggccgcguuu agaccaagga acaaaaaaac cacaaaggcc aaacugcugg   1620

acgucuuucu uuuuuucccc cccuaaaauu uguggguuuu uuuuuuuaaa aaaagaaaau   1680

gaaaaacaac caagcgcauc caaucucaag gaaucuuuaa gcagagaagg gcauaaaaca   1740

gcuuuggggu gucuuuuuuu ggugauucaa augggguuuuc cacgcuaggg cggggcacag   1800

auuggagagg gcucugugcu gacauggcuc uggacucuaa agaccaaacu ucacucuggg   1860

cacacucugc cagcaaagag gacucgcuug uaaauaccag gauuuuuuuu uuuuuuugaa   1920

gggaggacgg gagcugggga gaggaaagag ucuucaacau aacccacuug ucacugacac   1980

aaaggaagug cccccucccc ggcacccucu ggccgccuag gcucagcggc gaccgcccuc   2040

cgcgaaaaua guuuguuuaa ugugaacuug uagcuguaaa acgcugucaa aaguuggacu   2100

aaaugccuag uuuuuaguaa ucuguacauu uuguuguaaa aagaaaaacc acucccaguc   2160

cccagcccuu cacauuuuuu augggcauug acaaaucugu guauauuauu uggcaguuug   2220

guauuugcgg cgucagucuu uuucuguugu aacuuaugua gauauuuggc uuaaauauag   2280

uuccuaagaa gcuucuaaua aauuauacaa auuaaaaaga uucuuuuucu gauuaaaaaa   2340

aaaaaaaaaa aa                                                       2352
```

```
<210> SEQ ID NO 3
<211> LENGTH: 2428
<212> TYPE: RNA
<213> ORGANISM: Homo sapiens

<400> SEQUENCE: 3

cccgcccacu uccaacuacc gccuccggcc ugcccaggga gagagaggga guggagccca     60

gggagaggga gcgcgagaga gggagggagg aggggacggu gcuuuggcug acuuuuuuuu    120

aaaagagggu gggggugggg ggugauugcu ggucguuugu uguggcuguu aaauuuuaaa    180

cugccaugca cucggcuucc aguaugcugg gagcggugaa gauggaaggg cacgagccgu    240

ccgacuggag cagcuacuau gcagagcccg agggcuacuc cuccgugagc aacaugaacg    300

ccggccuggg gaugaacggc augaacacgu acaugagcau gucggcggcc gccaugggca    360
```

gcggcucggg caacaugagc gcgggcucca ugaacauguc gucguacgug ggcgcuggca 420
ugagcccguc ccuggcgggg auguccccg gcgcgggcgc cauggcgggc augggcggcu 480
cggccggggc ggccggcgug gcgggcaugg ggccgcacuu gagucccagc cugagcccgc 540
ucggggggca ggcggccggg gccaugggcg gccuggcccc cuacgccaac augaacucca 600
ugagccccau guacgggcag gcgggccuga gccgcgcccg cgaccccaag accuacaggc 660
gcagcuacac gcacgcaaag ccgcccuacu cguacaucuc gcucaucacc auggccaucc 720
agcagagccc caacaagaug cugacgcuga gcgagaucua ccaguggauc auggaccucu 780
uccccuucua ccggcagaac cagcagcgcu ggcagaacuc cauccgccac ucgcucuccu 840
ucaacgacug uuuccugaag gugccccgcu cgcccgacaa gcccggcaag ggcuccuucu 900
ggacccugca cccugacucg ggcaacaugu ucgagaacgg cugcuaccug cgccgccaga 960
agcgcuucaa gugcgagaag cagcuggcgc ugaaggaggc cgcaggcgcc gccggcagcg 1020
gcaagaaggc ggccgccgga gcccaggccu cacaggcuca acucggggag gccgccgggc 1080
cggccuccga gacuccggcg ggcaccgagu cgccucacuc gagcgccucc ccgugccagg 1140
agcacaagcg aggggggcug ggagagcuga aggggacgcc ggcugcggcg cugagccccc 1200
cagagccggc gcccucuccc gggcagcagc agcaggccgc ggcccaccug cugggcccgc 1260
cccaccaccc gggccugccg ccugaggccc accugaagcc ggaacaccac uacgccuuca 1320
accacccguu cuccaucaac aaccucaugu ccucggagca gcagcaccac cacagccacc 1380
accaccacca accccacaaa auggaccuca aggccuacga acaggugaug cacuaccccg 1440
gcuacgguuc cccaugccu ggcagcuugg ccaugggccc ggucacgaac aaaacgggcc 1500
uggacgccuc gccccuggcc gcagauaccu ccuacuacca gggggguguac ucccggccca 1560 uuaugaacuc cucuuaagaa gacgacggcu ucaggcccgg cuaacucugg caccccggau 1620
cgaggacaag ugagagagca agugggggguc gagacuuugg ggagacggug uugcagagac 1680
gcaagggaga agaaauccau aacacccca ccccaacacc cccaagacag cagucuucuu 1740
cacccgcugc agccguuccg ucccaaacag agggccacac agauacccca cguucuauau 1800
aaggaggaaa acgggaaaga auauaaaguu aaaaaaaagc cuccgguuuc cacuacugug 1860
uagacuccug cuucuucaag caccugcaga uucugauuuu uuuguuguug uuguucuccu 1920
ccauugcugu uguugcaggg aagucuuacu uaaaaaaaaa aaaaaauuuu gugagugacu 1980
cgguguaaaa ccauguaguu uuaacagaac cagaggguug uacuauuguu uaaaaacagg 2040
aaaaaaaaua auguaagggu cuguuguaaa ugaccaagaa aaagaaaaaa aaagcauucc 2100
caaucuugac acggugaaau ccaggucucg gguccgauua auuuaugguu ucugcgugcu 2160
uuauuuaugg cuuauaaaug uguauucugg cugcaagggc cagaguucca caaaucuaua 2220
uuaaaguguu auacccgguu uuaucccuug aaucuuuucu uccagauuuu ucuuuucuuu 2280
acuuggcuua caaaauauac aggcuuggaa auuauuucaa gaaggaggga gggauacccu 2340
gucugguugc agguuguauu uuauuuuggc ccagggagug uugcuguuuu cccaacauuu 2400
uauuaauaaa auuuucagac auaaaaaa 2428

<210> SEQ ID NO 4
<211> LENGTH: 1402
<212> TYPE: RNA
<213> ORGANISM: Homo sapiens

<400> SEQUENCE: 4

-continued

```
ggggacgaag ggaagcucca gcguguggcc ccggcgagug cggauaaaag ccgccccgcc      60

gggcucgggc uucauucuga gccgagcccg gugccaagcg cagcuagcuc agcaggcggc     120

agcggcggcc ugagcuucag ggcagccagc ucccucccgg ucucgccuuc ccucgcgguc     180

agcaugaaag ccuucagucc cgugaggucc guuaggaaaa acagccuguc ggaccacagc     240

cugggcaucu cccggagcaa aaccccugug gacgacccga ugagccugcu auacaacaug     300

aacgacugcu acuccaagcu caaggagcug gugcccagca ucccccagaa caagaaggug     360

agcaagaugg aaauccugca gcacgucauc gacuacaucu uggaccugca gaucgcccug     420

gacucgcauc ccacuauugu cagccugcau caccagagac ccgggcagaa ccaggcgucc     480

aggacgccgc ugaccacccu caacacggau aucagcaucc uguccuugca ggcuucugaa     540

uucccuucug aguuaauguc aaaugacagc aaagcacugu guggcugaau aagcggiguu     600

caugauuucu uuuauucuuu gcacaacaac aacaacaaca aauucacgga aucuuuuaag     660

ugcugaacuu auuuuucaac cauuucacaa ggaggacaag uugaauggac cuuuuuaaaa     720

agaaaaaaaa aauggaagga aaacuaagaa ugaucaucuu cccagggugu ucucuuacuu     780

ggacugugau auucguuauu uaugaaaaag acuuuuaaau gcccuuucug caguuggaag     840

guuuucuuua uauacuauuc ccaccauggg gagcgaaaac guuaaaauca caaggaauug     900

cccaaucuaa gcagacuuug ccuuuuuuca aagguggagc gugaauacca gaaggaucca     960

guauucaguc acuuaaauga agucuuuugg ucagaaauua ccuuuuugac acaagccuac    1020

ugaaugcugu guauauauuu auauauaaau auaucuauuu gagugaaacc uugugaacuc    1080

uuuaauuaga guuuucuugu auaguggcag agaugucuau uucugcauuc aaaaguguaa    1140

ugauguacuu auucaugcua aacuuuuuau aaaaguuuag uuguaaacuu aacccuuuua    1200

uacaaaauaa aucaagugug uuuauugaau ggugauugcc ugcuuuauuu cagaggacca    1260

gugcuuugau uuuuauuaug cuauguuaua acugaaccca aauaaauaca aguucaaauu    1320

uauguagacu guauaagauu auaauaaaac augucugaag ucaaaaaaaa aaaaaaaaaa    1380

aaaaaaaaaa aaaaaaaaaa aa                                             1402
```

<210> SEQ ID NO 5
<211> LENGTH: 3158
<212> TYPE: RNA
<213> ORGANISM: Homo sapiens

<400> SEQUENCE: 5

```
auugaucucc acgcccgggg cagaaauagg aucuuugaga agucucaaau gggaucuuug      60

agaagucaga ucccauuuga acuagaaaaa ggaguggagg cgagguagcg ugcagccuac     120

gcucuuguua acccgucgau cuccuaccau acccgucucc cccaccccac cucaggagcu     180

agacgucagc uuggagcggc gccggaccgu ggauggccuu gacugacggc ggcuggugcu     240

ugccgaagcg cuucggggcc gcgggugcgg acgccagcga cuccagagcc uuuccagcgc     300

gggagcccuc cacgccgccu ucccccaucu cuuccucguc cuccuccugc ucccggggcg     360

gagagcgggg ccccggcggc gccagcaacu gcgggacgcc ucagcucgac acggaggcgg     420

cggccggacc cccggcccgc ucgcugcugc ucaguuccua cgcuucgcau cccuucgggg     480

cuccccacgg accuucggcg ccuggggucg cgggccccgg gggcaaccug ucgagcuggg     540

aggacuugcu gcuguucacu gaccucgacc aagccgcgac cgccagcaag cugcuguggu     600

ccagccgcgg cgccaagcug agccccuucg cacccgagca gccggaggag auguaccaga     660

cccucgccgc ucucuccagc cagggguccgg ccgccuacga cggcgcgccc ggcggcuucg     720
```

-continued ugcacucugc ggccgcggcg gcagcagccg cggcggcggc cagcuccccg gucuacgugc 780
ccaccacccg cgugggguucc augcugcccg gccuaccgua ccaccugcag gggucgggca 840
gugggccagc caaccacgcg ggcggcgcgg gcgcgcaccc cggcuggccu caggccucgg 900
ccgacagccc uccauacggc agcggaggcg gcgcggcugg cggcggggcc gcggggccug 960
gcggcgcugg cucagccgcg gcgcacgucu cggcgcgcuu ccccuacucu cccagcccgc 1020
ccauggccaa cggcgccgcg cgggagccgg gaggcuacgc ggcggcgggc agugggggcg 1080
cgggaggcgu gagcggcggc ggcaguagcc uggcggccau gggcggccgc gagccccagu 1140
acagcucgcu gucggccgcg cggccgcuga acgggacgua ccaccaccac caccaccacc 1200
accaccacca uccgagcccc uacucgcccu acgugggggc gccacugacg ccugccuggc 1260
ccgccggacc cuucgagacc ccggugcugc acagccugca gagccgcgcc ggagccccgc 1320
ucccggugcc ccgggguccc agugcagacc ugcuggagga ccuguccgag agccgcgagu 1380
gcgugaacug cggcuccauc cagacgccgc uguggcggcg ggacggcacc ggccacuacc 1440
ugugcaacgc cugcgggcuc uacagcaaga ugaacggccu cagccggccc cucaucaagc 1500
cgcagaagcg cgugccuuca ucacggcggc uuggauuguc cugugccaac ugucacacca 1560
caacuaccac cuuauggcgc agaaacgccg agggugaacc cgugugcaau gcuuguggac 1620
ucuacaugaa acuccauggg gugcccagac cacuugcuau gaaaaaagag ggaauucaaa 1680
ccaggaaacg aaaaccuaag aacauaaaua aaucaaagac uugcucuggu aauagcaaua 1740
auuccauucc caugacucca acuuccaccu cuucuaacuc agaugauugc agcaaaaaua 1800
cuucccccac aacacaaccu acagccucag ggcgcggugc cccggugaug acuggugcgg 1860
gagagagcac caaucccgag aacagcgagc ucaaguauuc gggucaagau gggcucuaca 1920
uaggcgucag ucucgccucg ccggccgaag ucacguccuc cgugcgaccg gauuccuggu 1980
gcgcccuggc ccuggccuga gcccacgccg ccaggaggca gggagggcuc cgccgcgggc 2040
cucacuccac ucgugucugc uuuugugcag cgguccagac aguggcgacu gcgcugacag 2100
aacgugauuc ucgugccuuu auuuugaaag agauguuuuu cccaagaggc uugcugaaag 2160
agugagagaa gauggaaggg aagggccagu gcaacugggc gcuugggcca cuccagccag 2220
cccgccuccg gggcggaccc ugcuccacuu ccagaagcca ggacuaggac cugggccuug 2280
ccugcuaugg aauauugaga gagauuuuuu aaaaaagauu uugcauuuug uccaaaauca 2340
ugugcuucuu cugaucaauu uugguuguuc cagaauuucu ucauaccuuu uccacaucca 2400
gauuucaugu gcguucaugg agaagaucac uugaggccau uugguacaca ucucuggagg 2460
cugagucggu ucaugagguc ucuuaucaaa aauauuacuc aguuugcaag acugcauugu 2520
aacuuuaaca uacacuguga cugacguuuc ucaaaguuca uauugugugg cugaucugaa 2580
gucagucgga auuuguaaac aggguagcaa acaagauauu uuucuuccau guauacaaua 2640
auuuuuuuaa aaagugcaau uugcguugca gcaaucagug uuaaaucauu ugcauaagau 2700
uuaacagcau uuuuuauaau gaauguaaac auuuuaacuu aaugguacuu aaaauaauuu 2760
aaaagaaaaa uguuaacuua gacauucuua ugcuucuuuu acaacuacau cccauuuuau 2820
auuuccaauu guuaaagaaa aauauuucaa gaacaaaucu ucucucagga aaauugccuu 2880
ucucuauuug uuaagaauuu uuauacaaga acaccaauau acccccuuua uuuuacugug 2940
gaauaugugc uggaaaaauu gcaacaacac uuuacuaccu aacggauagc auuuguaaau 3000
acucuaggua ucuguaaaca cucugaugaa gucuguauag ugugacuaac ccacaggcag 3060
guugguuuac auuaauuuuu uuuuuugaau gggauguccu auggaaaccu auuucaccag 3120
aguuuuaaaa auaaaaaggg uauuguuuug ucuucugu 3158

<210> SEQ ID NO 6
<211> LENGTH: 2197
<212> TYPE: RNA
<213> ORGANISM: Homo sapiens

<400> SEQUENCE: 6
cugacagaca cguagaccaa cagugcggcc ccaggguucg uccccagacu cgcucgcuca 60
uuuguuggcg acuggggcuc agcgcagcga agcccgaugu gguccggagg cagugggaag 120
gcgcggggcu gggaggccgc ggcgggaggg aggagcagcc ccggcaggcu cagccgccgc 180
cgaaucaugu cgaugagucc aaagcacacg acuccguucu cagugucuga caucuugagu 240
ccccuggagg aaagcuacaa gaaagugggc auggagggcg gcggccucgg ggcuccgcug 300
gcggcguaca ggcagggcca ggcggcaccg ccaacagcgg ccaugcagca gcacgccgug 360
gggcaccacg gcgccgucac cgccgccuac cacaugacgg cggcgggggu gccccagcuc 420
ucgcacuccg ccguggggggg cuacugcaac ggcaaccugg gcaacaugag cgagcugccg 480
ccguaccagg acaccaugag gaacagcgcc ucuggccccg gaugguacgg cgccaaccca 540
gacccgcgcu uccccgccau cucccgcuuc augggcccgg cgagcggcau gaacaugagc 600
ggcaugggcg gccugggcuc gcugggggac gugagcaaga acauggcccc gcugccaagc 660
gcgccgcgca ggaagcgccg ggugcucuuc ucgcaggcgc agguguacga gcuggagcga 720
cgcuucaagc aacagaagua ccugucggcg ccggagcgcg agcaccuggc cagcaugauc 780
caccugacgc ccacgcaggu caagaucugg uuccagaacc accgcuacaa aaugaagcgc 840
caggccaagg acaaggcggc gcagcagcaa cugcagcagg acagcggcgg cggcgggggc 900
ggcgggggca ccgggugccc gcagcagcaa caggcucagc agcagucgcc gcgacgcgug 960
gcggugccgg uccuggugaa agacggcaaa ccgugccagg cgggugcccc cgcgccgggc 1020
gccgccagcc uacaaggcca cgcgcagcag caggcgcagc accaggcgca ggccgcgcag 1080
gcggcggcag cggccaucuc cgugggcagc gguggcgccg gccuuggcgc acacccgggc 1140
caccagccag gcagcgcagg ccagucuccg gaccuggcgc accacgccgc cagccccgcg 1200
gcgcugcagg gccagguauc cagccugucc caccugaacu ccucgggcuc ggacuacggc 1260
accaugcccu gcuccaccuu gcuauacggu cggaccuggu gagaggacgc cgggccggcc 1320
cuagcccagc gcucugccuc accgcuuccc uccugcccgc cacacagacc accauccacc 1380
gcugcuccac gcgcuucgac uuuucuuaac aaccuggccg cguuuagacc aaggaacaaa 1440
aaaaccacaa aggccaaacu gcuggacguc uuucuuuuuu uccccccccua aaauuugugg 1500 guuuuuuuuu uuaaaaaaag aaaaugaaaa acaaccaagc gcauccaauc ucaaggaauc 1560
uuuaagcaga gaagggcaua aaacagcuuu ggggugucuu uuuuugguga uucaaauggg 1620
uuuuccacgc uagggcgggg cacagauugg agagggcucu gugcugacau ggcucuggac 1680
ucuaaagacc aaacuucacu cugggcacac ucugccagca aagaggacuc gcuuguaaau 1740
accaggauuu uuuuuuuuuu uugaagggag gacgggagcu ggggagagga aagagucuuc 1800
aacauaaccc acuugucacu gacacaaagg aagugccccc uccccggcac ccucuggccg 1860
ccuaggcuca gcggcgaccg cccuccgcga aaauaguuug uuuaauguga acuuguagcu 1920
guaaaacgcu gucaaaaguu ggacuaaaug ccuaguuuuu aguaaucugu acauuuuguu 1980
guaaaaagaa aaaccacucc caguccccag cccuucacau uuuuuauggg cauugacaaa 2040
ucuguguaua uuauuuggca guuugguauu ugcggcguca gucuuuuucu guuguaacuu 2100
auguagauau uuggcuuaaa uauaguuccu aagaagcuuc uaauaaauua uacaaauuaa 2160
aaagauucuu uuucugauua aaaaaaaaaa aaaaaaa 2197

<210> SEQ ID NO 7
<211> LENGTH: 2415
<212> TYPE: RNA
<213> ORGANISM: Homo sapiens

<400> SEQUENCE: 7
cggccgcugc uagagggggcu gcuugcgcca ggcgccggcc gccccacugc ggguccc ugg 60 cggccggugu cugaggaguc ggagagccga ggcggccaga ccgugcgccc cgcgcuucuc 120
ccgaggccgu uccgggucug aacuguaaca gggaggggcc ucgcaggagc agcagcgggc 180
gaguuaaagu augcugggag cggugaagau ggaagggcac gagccguccg acuggagcag 240
cuacuaugca gagcccgagg gcuacuccuc cgugagcaac augaacgccg gccuggggau 300
gaacggcaug aacacguaca ugagcauguc ggcggccgcc augggcagcg gcucgggcaa 360
caugagcgcg ggcuccauga acaugucguc guacgugggc gcuggcauga gcccgucccu 420
ggcggggaug ucccccggcg cgggcgccau ggcgggcaug ggcggcucgg ccggggcggc 480
cggcguggcg ggcauggggc cgcacuugag ucccagccug agcccgcucg gggggcaggc 540
ggccggggcc augggcggcc uggcccccua cgccaacaug aacuccauga gccccaugua 600
cgggcaggcg ggccugagcc gcgcccgcga ccccaagacc uacaggcgca gcuacacgca 660
cgcaaagccg cccuacucgu acaucucgcu caucaccaug gccauccagc agagccccaa 720
caagaugcug acgcugagcg agaucuacca guggaucaug gaccucuucc ccuucuaccg 780
gcagaaccag cagcgcuggc agaacuccau ccgccacucg cucuccuuca acgacuguuu 840
ccugaaggug ccccgcucgc ccgacaagcc cggcaagggc uccuucugga cccugcaccc 900
ugacucgggc aacauguucg agaacggcug cuaccugcgc cgccagaagc gcuucaagug 960
cgagaagcag cuggcgcuga aggaggccgc aggcgccgcc ggcagcggca agaaggcggc 1020
cgccggagcc caggccucac aggcucaacu cggggaggcc gccgggccgg ccuccgagac 1080
uccggcgggc accgagucgc cucacucgag cgccuccccg ugccaggagc acaagcgagg 1140
gggccuggga gagcugaagg ggacgccggc ugcggcgcug agcccccag agccggcgcc 1200 cucucccggg cagcagcagc aggccgcggc ccaccugcug ggcccgcccc accacccggg 1260
ccugccgccu gaggcccacc ugaagccgga acaccacuac gccuucaacc acccguucuc 1320
caucaacaac cucauguccu cggagcagca gcaccaccac agccaccacc accaccaacc 1380
ccacaaaaug gaccucaagg ccuacgaaca ggugaugcac uaccccggcu acgguucccc 1440
caugccuggc agcuuggcca ugggcccggu cacgaacaaa acgggccugg acgccucgcc 1500
ccuggccgca gauaccuccu acuaccaggg gguguacucc cggcccauua ugaacuccuc 1560
uuaagaagac gacggcuuca ggcccggcua acucuggcac ccccggaucga ggacaaguga 1620 gagagcaagu gggggucgag acuuugggga gacgguguug cagagacgca agggagaaga 1680
aauccauaac accccccaccc caacacccccc aagacagcag ucuucuucac ccgcugcagc 1740
cguuccgucc caaacagagg gccacacaga uaccccacgu ucuauauaag gaggaaaacg 1800
ggaaagaaua uaaaguuaaa aaaaagccuc cgguuuccac uacuguguag acuccugcuu 1860
cuucaagcac cugcagauuc ugauuuuuuu guuguuguug uucuccucca uugcuguugu 1920

-continued

```
ugcagggaag ucuuacuuaa aaaaaaaaaa aaauuuugug agugacucgg uguaaaacca   1980

uguaguuuua acagaaccag aggguuguac uauuguuuaa aaacaggaaa aaaaauaaug   2040

uaagggucug uuguaaauga ccaagaaaaa gaaaaaaaaa gcauucccaa ucuugacacg   2100

gugaaaucca ggucucgggu ccgauuaauu uaugguuucu gcgugcuuua uuuauggcuu   2160

auaaaaugugu auucuggcug caagggccag aguuccacaa aucuauauua aaguguuaua   2220

cccgguuuua ucccuugaau cuuuucuucc agauuuuucu uuucuuuacu uggcuuacaa   2280

aauauacagg cuuggaaauu auuucaagaa ggagggaggg auacccuguc ugguugcagg   2340

uuguauuuua uuuuggccca gggaguguug cuguuuuccc aacauuuuau uaauaaaauu   2400

uucagacaua aaaaa                                                  2415
```

<210> SEQ ID NO 8
<211> LENGTH: 1681
<212> TYPE: RNA
<213> ORGANISM: Homo sapiens

<400> SEQUENCE: 8

```
caaaggcggc cuggccagcg cggagcuccc ggcccggagc ugcuucugau uaccgcgagg     60

ggcccggacg cgagagccgc cgcggggccu gcccuagagg cggagugaug aacuguggcu    120

uccccccugc ggugcugaac ucgcccgugu agcugugauu uuagagcugc cgacagcucu    180

aagcugggcu cgcgccccgc ccacccccgcg gggauuggcu gcgaacgcgg aagaaccaag    240

cccacgcccc gcgcccgcgc ccaccaaugg aagcgcccgc ucgucuugau agacgugcca    300

ccuuccgcca auggggacga agggaagcuc cagcgugugg ccccggcgag ugcggauaaa    360

agccgccccg ccgggcucgg gcuucauucu gagccgagcc cggugccaag cgcagcuagc    420

ucagcaggcg gcagcggcgg ccugagcuuc agggcagcca gcucccuccc ggucucgccu    480

ucccucgcgg ucagcaugaa agccuucagu cccgugaggu ccguuaggaa aaacagccug    540

ucggaccaca gccugggcau cucccggagc aaaaccccug uggacgaccc gaugagccug    600

cuauacaaca ugaacgacug cuacuccaag cucaaggagc uggugcccag cauccccccag    660

aacaagaagg ugagcaagau ggaaauccug cagcacguca ucgacuacau cuuggaccug    720

cagaucgccc uggacucgca ucccacuauu gucagccugc aucaccagag acccgggcag    780

aaccaggcgu ccaggacgcc gcugaccacc cucaacacgg auaucagcau ccuguccuug    840

caggcuucug aauucccuuc ugaguuaaug ucaaaugaca gcaaagcacu gugu ggcuga    900

auaagcggug uucaugauuu cuuuuauucu uugcacaaca acaacaacaa caaauucacg    960

gaaucuuuua agugcugaac uuauuuuuca accauuucac aaggaggaca aguugaaugg   1020

accuuuuuaa aaagaaaaaa aaaauggaag gaaaacuaag aaugaucauc uucccagggu   1080

guucucuuac uuggacugug auauucguua uuuaugaaaa agacuuuuaa augcccuuuc   1140

ugcaguugga agguuuucuu uauauacuau ucccaccaug gggagcgaaa acguuaaaau   1200

cacaaggaau ugcccaaucu aagcagacuu ugccuuuuuu caaaggugga gcgugaaauac   1260

cagaaggauc caguauucag ucacuuaaau gaagucuuuu ggucagaaau uaccuuuuug   1320

acacaagccu acugaaugcu guguauauau uuauauauaa auauaucuau uugagugaaa   1380

ccuugugaac ucuuuaauua gaguuuucuu guauaguggc agagaugucu auuucugcau   1440

ucaaaagugu aaugauguac uuauucaugc uaaacuuuuu auaaaaguuu aguuguaaac   1500

uuaacccuuu uauacaaaau aaaucaagug uguuuauuga auggugauug ccugcuuuau   1560

uucagaggac cagugcuuug auuuuuauua ugcuauguua uaacugaacc caaauaaaua   1620
```

caaguucaaa uuuauguaga cuguauaaga uuauaauaaa acaugucuga agucaauacc 1680
u 1681

<210> SEQ ID NO 9
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 9
ctcggcttct ctccgcgcct g 21

<210> SEQ ID NO 10
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 10
ttgactgacg gcggctggtg 20

<210> SEQ ID NO 11
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 11
agctgaggcg tcccgcagtt g 21

<210> SEQ ID NO 12
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 12
ctcccgcgct ggaaaggctc 20

<210> SEQ ID NO 13
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 13
gcggtttcgt tttcggggac 20

<210> SEQ ID NO 14
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 14
aggacccaga ctgctgcccc 20

<210> SEQ ID NO 15

-continued

<211> LENGTH: 20
<212> TYPE: DNA
<213> ORGANISM: Artificial sequence
<220> FEATURE:
<223> OTHER INFORMATION: Synthetic nucleotide

<400> SEQUENCE: 15
aagggatgcg aagcgtagga 20

<210> SEQ ID NO 16
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 16
ctgaccagcc cgaacgcgag 20

<210> SEQ ID NO 17
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 17
aaacctggcg ccgggctaaa 20

<210> SEQ ID NO 18
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 18
cagcgaggct tcgccttccc 20

<210> SEQ ID NO 19
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 19
ggagaggggg aaggcgaagc c 21

<210> SEQ ID NO 20
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 20
tcgacatgat tcggcggcgg 20

<210> SEQ ID NO 21
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 21
agcgaagccc gatgtggtcc 20

<210> SEQ ID NO 22
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 22
tccggaggca gtgggaaggc 20

<210> SEQ ID NO 23
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 23
ccgccctcca tgcccacttt c 21

<210> SEQ ID NO 24
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 24
gacatgattc ggcggcggct 20

<210> SEQ ID NO 25
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 25
tgccatgcac tcggcttcca g 21

<210> SEQ ID NO 26
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 26
cagggagagg gagggcgaga 20

<210> SEQ ID NO 27
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 27
tcatgttgcc cgagccgctg 20

<210> SEQ ID NO 28
<211> LENGTH: 20
<212> TYPE: DNA

<213> ORGANISM: Artificial sequence
<220> FEATURE:
<223> OTHER INFORMATION: Synthetic nucleotide

<400> SEQUENCE: 28
cccccacccc caccctcttt 20

<210> SEQ ID NO 29
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 29
ctgctagagg ggctgcttgc g 21

<210> SEQ ID NO 30
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 30
cgcttctccc gaggccgttc 20

<210> SEQ ID NO 31
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 31
acggctcgtg cccttccatc 20

<210> SEQ ID NO 32
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 32
taactcgccc gctgctgctc 20

<210> SEQ ID NO 33
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 33
aacccctgtg gacgacccga 20

<210> SEQ ID NO 34
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 34
tgcggataaa agccgccccg 20

<210> SEQ ID NO 35
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 35
gcccgggtct ctggtgatgc 20

<210> SEQ ID NO 36
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 36
agctagctgc gcttggcacc 20

<210> SEQ ID NO 37
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 37
ctgcggtgct gaactcgccc 20

<210> SEQ ID NO 38
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 38
ccccctgcgg tgctgaactc 20

<210> SEQ ID NO 39
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 39
gacgagcggg cgcttccatt 20

<210> SEQ ID NO 40
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 40
taactcgccc gctgctgctc 20

<210> SEQ ID NO 41
<211> LENGTH: 21
<212> TYPE: DNA
<213> ORGANISM: Artificial sequence
<220> FEATURE:

<223> OTHER INFORMATION: Synthetic nucleotide

<400> SEQUENCE: 41
ucaggagcgc aggcugcagt t 21

<210> SEQ ID NO 42
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 42
gaggcgccuc cucucuccut t 21

<210> SEQ ID NO 43
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 43
cugcagccug cgcuccugat t 21

<210> SEQ ID NO 44
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 44
aggagagagg aggcgccuct t 21

<210> SEQ ID NO 45
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 45
accgccaugc acucggcuut t 21

<210> SEQ ID NO 46
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 46
aagccgagug cauggcggut t 21

<210> SEQ ID NO 47
<211> LENGTH: 58
<212> TYPE: DNA
<213> ORGANISM: Artificial sequence
<220> FEATURE:
<223> OTHER INFORMATION: Synthetic nucleotide

<400> SEQUENCE: 47
ccggcccatg aagaagaaag caattctcga gaattgcttt cttcttcatg ggtttttg 58

<210> SEQ ID NO 48
<211> LENGTH: 62
<212> TYPE: DNA
<213> ORGANISM: Artificial sequence
<220> FEATURE:
<223> OTHER INFORMATION: Synthetic nucleotide

<400> SEQUENCE: 48
gtaccggggg atcatccttg tagataaact cgagtttatc tacaaggatg atcccttttt 60
tg 62

<210> SEQ ID NO 49
<211> LENGTH: 58
<212> TYPE: DNA
<213> ORGANISM: Artificial sequence
<220> FEATURE:
<223> OTHER INFORMATION: Synthetic nucleotide

<400> SEQUENCE: 49
ccggattcgg aatcagctag caattctcga gaattgctag ctgattccga atttttg 58

<210> SEQ ID NO 50
<211> LENGTH: 595
<212> TYPE: PRT
<213> ORGANISM: Homo sapiens

<400> SEQUENCE: 50

Met Ala Leu Thr Asp Gly Gly Trp Cys Leu Pro Lys Arg Phe Gly Ala
1 5 10 15

Ala Gly Ala Asp Ala Ser Asp Ser Arg Ala Phe Pro Ala Arg Glu Pro
20 25 30

Ser Thr Pro Pro Ser Pro Ile Ser Ser Ser Ser Ser Ser Cys Ser Arg
35 40 45

Gly Gly Glu Arg Gly Pro Gly Gly Ala Ser Asn Cys Gly Thr Pro Gln
50 55 60

Leu Asp Thr Glu Ala Ala Ala Gly Pro Pro Ala Arg Ser Leu Leu Leu
65 70 75 80

Ser Ser Tyr Ala Ser His Pro Phe Gly Ala Pro His Gly Pro Ser Ala
85 90 95

Pro Gly Val Ala Gly Pro Gly Gly Asn Leu Ser Ser Trp Glu Asp Leu
100 105 110

Leu Leu Phe Thr Asp Leu Asp Gln Ala Ala Thr Ala Ser Lys Leu Leu
115 120 125

Trp Ser Ser Arg Gly Ala Lys Leu Ser Pro Phe Ala Pro Glu Gln Pro
130 135 140

Glu Glu Met Tyr Gln Thr Leu Ala Ala Leu Ser Ser Gln Gly Pro Ala
145 150 155 160

Ala Tyr Asp Gly Ala Pro Gly Gly Phe Val His Ser Ala Ala Ala Ala
165 170 175

Ala Ala Ala Ala Ala Ala Ala Ser Ser Pro Val Tyr Val Pro Thr Thr
180 185 190

Arg Val Gly Ser Met Leu Pro Gly Leu Pro Tyr His Leu Gln Gly Ser
195 200 205

Gly Ser Gly Pro Ala Asn His Ala Gly Gly Ala Gly Ala His Pro Gly
210 215 220

Trp Pro Gln Ala Ser Ala Asp Ser Pro Pro Tyr Gly Ser Gly Gly Gly
225 230 235 240

Ala Ala Gly Gly Gly Ala Ala Gly Pro Gly Gly Ala Gly Ser Ala Ala

```
                245                 250                 255

Ala His Val Ser Ala Arg Phe Pro Tyr Ser Pro Ser Pro Pro Met Ala
            260                 265                 270

Asn Gly Ala Ala Arg Glu Pro Gly Gly Tyr Ala Ala Ala Gly Ser Gly
        275                 280                 285

Gly Ala Gly Gly Val Ser Gly Gly Gly Ser Ser Leu Ala Ala Met Gly
    290                 295                 300

Gly Arg Glu Pro Gln Tyr Ser Ser Leu Ser Ala Ala Arg Pro Leu Asn
305                 310                 315                 320

Gly Thr Tyr His His His His His His His His His His Pro Ser Pro
            325                 330                 335

Tyr Ser Pro Tyr Val Gly Ala Pro Leu Thr Pro Ala Trp Pro Ala Gly
            340                 345                 350

Pro Phe Glu Thr Pro Val Leu His Ser Leu Gln Ser Arg Ala Gly Ala
        355                 360                 365

Pro Leu Pro Val Pro Arg Gly Pro Ser Ala Asp Leu Leu Glu Asp Leu
    370                 375                 380

Ser Glu Ser Arg Glu Cys Val Asn Cys Gly Ser Ile Gln Thr Pro Leu
385                 390                 395                 400

Trp Arg Arg Asp Gly Thr Gly His Tyr Leu Cys Asn Ala Cys Gly Leu
            405                 410                 415

Tyr Ser Lys Met Asn Gly Leu Ser Arg Pro Leu Ile Lys Pro Gln Lys
            420                 425                 430

Arg Val Pro Ser Ser Arg Arg Leu Gly Leu Ser Cys Ala Asn Cys His
        435                 440                 445

Thr Thr Thr Thr Thr Leu Trp Arg Arg Asn Ala Glu Gly Glu Pro Val
    450                 455                 460

Cys Asn Ala Cys Gly Leu Tyr Met Lys Leu His Gly Val Pro Arg Pro
465                 470                 475                 480

Leu Ala Met Lys Lys Glu Gly Ile Gln Thr Arg Lys Arg Lys Pro Lys
            485                 490                 495

Asn Ile Asn Lys Ser Lys Thr Cys Ser Gly Asn Ser Asn Asn Ser Ile
            500                 505                 510

Pro Met Thr Pro Thr Ser Thr Ser Ser Asn Ser Asp Asp Cys Ser Lys
        515                 520                 525

Asn Thr Ser Pro Thr Thr Gln Pro Thr Ala Ser Gly Ala Gly Ala Pro
    530                 535                 540

Val Met Thr Gly Ala Gly Glu Ser Thr Asn Pro Glu Asn Ser Glu Leu
545                 550                 555                 560

Lys Tyr Ser Gly Gln Asp Gly Leu Tyr Ile Gly Val Ser Leu Ala Ser
            565                 570                 575

Pro Ala Glu Val Thr Ser Ser Val Arg Pro Asp Ser Trp Cys Ala Leu
            580                 585                 590

Ala Leu Ala
        595


<210> SEQ ID NO 51
<211> LENGTH: 371
<212> TYPE: PRT
<213> ORGANISM: Homo sapiens

<400> SEQUENCE: 51

Met Ser Met Ser Pro Lys His Thr Thr Pro Phe Ser Val Ser Asp Ile
1               5                   10                  15
```

-continued

```
Leu Ser Pro Leu Glu Glu Ser Tyr Lys Lys Val Gly Met Glu Gly Gly
            20                  25                  30

Gly Leu Gly Ala Pro Leu Ala Ala Tyr Arg Gln Gly Gln Ala Ala Pro
        35                  40                  45

Pro Thr Ala Ala Met Gln Gln His Ala Val Gly His His Gly Ala Val
    50                  55                  60

Thr Ala Ala Tyr His Met Thr Ala Ala Gly Val Pro Gln Leu Ser His
65                  70                  75                  80

Ser Ala Val Gly Gly Tyr Cys Asn Gly Asn Leu Gly Asn Met Ser Glu
                85                  90                  95

Leu Pro Pro Tyr Gln Asp Thr Met Arg Asn Ser Ala Ser Gly Pro Gly
            100                 105                 110

Trp Tyr Gly Ala Asn Pro Asp Pro Arg Phe Pro Ala Ile Ser Arg Phe
        115                 120                 125

Met Gly Pro Ala Ser Gly Met Asn Met Ser Gly Met Gly Gly Leu Gly
    130                 135                 140

Ser Leu Gly Asp Val Ser Lys Asn Met Ala Pro Leu Pro Ser Ala Pro
145                 150                 155                 160

Arg Arg Lys Arg Arg Val Leu Phe Ser Gln Ala Gln Val Tyr Glu Leu
                165                 170                 175

Glu Arg Arg Phe Lys Gln Gln Lys Tyr Leu Ser Ala Pro Glu Arg Glu
            180                 185                 190

His Leu Ala Ser Met Ile His Leu Thr Pro Thr Gln Val Lys Ile Trp
        195                 200                 205

Phe Gln Asn His Arg Tyr Lys Met Lys Arg Gln Ala Lys Asp Lys Ala
    210                 215                 220

Ala Gln Gln Gln Leu Gln Gln Asp Ser Gly Gly Gly Gly Gly Gly Gly
225                 230                 235                 240

Gly Thr Gly Cys Pro Gln Gln Gln Gln Ala Gln Gln Gln Ser Pro Arg
                245                 250                 255

Arg Val Ala Val Pro Val Leu Val Lys Asp Gly Lys Pro Cys Gln Ala
            260                 265                 270

Gly Ala Pro Ala Pro Gly Ala Ala Ser Leu Gln Gly His Ala Gln Gln
        275                 280                 285

Gln Ala Gln His Gln Ala Gln Ala Ala Gln Ala Ala Ala Ala Ala Ile
    290                 295                 300

Ser Val Gly Ser Gly Gly Ala Gly Leu Gly Ala His Pro Gly His Gln
305                 310                 315                 320

Pro Gly Ser Ala Gly Gln Ser Pro Asp Leu Ala His His Ala Ala Ser
                325                 330                 335

Pro Ala Ala Leu Gln Gly Gln Val Ser Ser Leu Ser His Leu Asn Ser
            340                 345                 350

Ser Gly Ser Asp Tyr Gly Thr Met Ser Cys Ser Thr Leu Leu Tyr Gly
        355                 360                 365

Arg Thr Trp
    370
```

<210> SEQ ID NO 52
<211> LENGTH: 463
<212> TYPE: PRT
<213> ORGANISM: Homo sapiens

<400> SEQUENCE: 52

```
Met His Ser Ala Ser Ser Met Leu Gly Ala Val Lys Met Glu Gly His
1               5                   10                  15
```

-continued

```
Glu Pro Ser Asp Trp Ser Ser Tyr Tyr Ala Glu Pro Glu Gly Tyr Ser
            20                  25                  30

Ser Val Ser Asn Met Asn Ala Gly Leu Gly Met Asn Gly Met Asn Thr
        35                  40                  45

Tyr Met Ser Met Ser Ala Ala Ala Met Gly Ser Gly Ser Gly Asn Met
    50                  55                  60

Ser Ala Gly Ser Met Asn Met Ser Ser Tyr Val Gly Ala Gly Met Ser
65                  70                  75                  80

Pro Ser Leu Ala Gly Met Ser Pro Gly Ala Gly Ala Met Ala Gly Met
                85                  90                  95

Gly Gly Ser Ala Gly Ala Ala Gly Val Ala Gly Met Gly Pro His Leu
            100                 105                 110

Ser Pro Ser Leu Ser Pro Leu Gly Gly Gln Ala Ala Gly Ala Met Gly
        115                 120                 125

Gly Leu Ala Pro Tyr Ala Asn Met Asn Ser Met Ser Pro Met Tyr Gly
    130                 135                 140

Gln Ala Gly Leu Ser Arg Ala Arg Asp Pro Lys Thr Tyr Arg Arg Ser
145                 150                 155                 160

Tyr Thr His Ala Lys Pro Pro Tyr Ser Tyr Ile Ser Leu Ile Thr Met
                165                 170                 175

Ala Ile Gln Gln Ser Pro Asn Lys Met Leu Thr Leu Ser Glu Ile Tyr
            180                 185                 190

Gln Trp Ile Met Asp Leu Phe Pro Phe Tyr Arg Gln Asn Gln Gln Arg
        195                 200                 205

Trp Gln Asn Ser Ile Arg His Ser Leu Ser Phe Asn Asp Cys Phe Leu
    210                 215                 220

Lys Val Pro Arg Ser Pro Asp Lys Pro Gly Lys Gly Ser Phe Trp Thr
225                 230                 235                 240

Leu His Pro Asp Ser Gly Asn Met Phe Glu Asn Gly Cys Tyr Leu Arg
                245                 250                 255

Arg Gln Lys Arg Phe Lys Cys Glu Lys Gln Leu Ala Leu Lys Glu Ala
            260                 265                 270

Ala Gly Ala Ala Gly Ser Gly Lys Lys Ala Ala Ala Gly Ala Gln Ala
        275                 280                 285

Ser Gln Ala Gln Leu Gly Glu Ala Ala Gly Pro Ala Ser Glu Thr Pro
    290                 295                 300

Ala Gly Thr Glu Ser Pro His Ser Ser Ala Ser Pro Cys Gln Glu His
305                 310                 315                 320

Lys Arg Gly Gly Leu Gly Glu Leu Lys Gly Thr Pro Ala Ala Ala Leu
                325                 330                 335

Ser Pro Pro Glu Pro Ala Pro Ser Pro Gly Gln Gln Gln Gln Ala Ala
            340                 345                 350

Ala His Leu Leu Gly Pro Pro His His Pro Gly Leu Pro Pro Glu Ala
        355                 360                 365

His Leu Lys Pro Glu His His Tyr Ala Phe Asn His Pro Phe Ser Ile
    370                 375                 380

Asn Asn Leu Met Ser Ser Glu Gln Gln His His His Ser His His His
385                 390                 395                 400

His Gln Pro His Lys Met Asp Leu Lys Ala Tyr Glu Gln Val Met His
                405                 410                 415

Tyr Pro Gly Tyr Gly Ser Pro Met Pro Gly Ser Leu Ala Met Gly Pro
            420                 425                 430
```

```
Val Thr Asn Lys Thr Gly Leu Asp Ala Ser Pro Leu Ala Ala Asp Thr
        435                 440                 445

Ser Tyr Tyr Gln Gly Val Tyr Ser Arg Pro Ile Met Asn Ser Ser
    450                 455                 460


<210> SEQ ID NO 53
<211> LENGTH: 134
<212> TYPE: PRT
<213> ORGANISM: Homo sapiens

<400> SEQUENCE: 53

Met Lys Ala Phe Ser Pro Val Arg Ser Val Arg Lys Asn Ser Leu Ser
1               5                   10                  15

Asp His Ser Leu Gly Ile Ser Arg Ser Lys Thr Pro Val Asp Asp Pro
            20                  25                  30

Met Ser Leu Leu Tyr Asn Met Asn Asp Cys Tyr Ser Lys Leu Lys Glu
        35                  40                  45

Leu Val Pro Ser Ile Pro Gln Asn Lys Lys Val Ser Lys Met Glu Ile
    50                  55                  60

Leu Gln His Val Ile Asp Tyr Ile Leu Asp Leu Gln Ile Ala Leu Asp
65                  70                  75                  80

Ser His Pro Thr Ile Val Ser Leu His His Gln Arg Pro Gly Gln Asn
                85                  90                  95

Gln Ala Ser Arg Thr Pro Leu Thr Thr Leu Asn Thr Asp Ile Ser Ile
            100                 105                 110

Leu Ser Leu Gln Ala Ser Glu Phe Pro Ser Glu Leu Met Ser Asn Asp
        115                 120                 125

Ser Lys Ala Leu Cys Gly
    130


<210> SEQ ID NO 54
<211> LENGTH: 449
<212> TYPE: PRT
<213> ORGANISM: Homo sapiens

<400> SEQUENCE: 54

Met Tyr Gln Thr Leu Ala Ala Leu Ser Ser Gln Gly Pro Ala Ala Tyr
1               5                   10                  15

Asp Gly Ala Pro Gly Gly Phe Val His Ser Ala Ala Ala Ala Ala Ala
            20                  25                  30

Ala Ala Ala Ala Ala Ser Ser Pro Val Tyr Val Pro Thr Thr Arg Val
        35                  40                  45

Gly Ser Met Leu Pro Gly Leu Pro Tyr His Leu Gln Gly Ser Gly Ser
    50                  55                  60

Gly Pro Ala Asn His Ala Gly Gly Ala Gly Ala His Pro Gly Trp Pro
65                  70                  75                  80

Gln Ala Ser Ala Asp Ser Pro Pro Tyr Gly Ser Gly Gly Gly Ala Ala
                85                  90                  95

Gly Gly Gly Ala Ala Gly Pro Gly Gly Ala Gly Ser Ala Ala Ala His
            100                 105                 110

Val Ser Ala Arg Phe Pro Tyr Ser Pro Ser Pro Pro Met Ala Asn Gly
        115                 120                 125

Ala Ala Arg Glu Pro Gly Gly Tyr Ala Ala Ala Gly Ser Gly Gly Ala
    130                 135                 140

Gly Gly Val Ser Gly Gly Gly Ser Ser Leu Ala Ala Met Gly Gly Arg
145                 150                 155                 160
```

```
Glu Pro Gln Tyr Ser Ser Leu Ser Ala Ala Arg Pro Leu Asn Gly Thr
            165                 170                 175

Tyr His His His His His His His His His His Pro Ser Pro Tyr Ser
            180                 185                 190

Pro Tyr Val Gly Ala Pro Leu Thr Pro Ala Trp Pro Ala Gly Pro Phe
        195                 200                 205

Glu Thr Pro Val Leu His Ser Leu Gln Ser Arg Ala Gly Ala Pro Leu
    210                 215                 220

Pro Val Pro Arg Gly Pro Ser Ala Asp Leu Leu Glu Asp Leu Ser Glu
225                 230                 235                 240

Ser Arg Glu Cys Val Asn Cys Gly Ser Ile Gln Thr Pro Leu Trp Arg
            245                 250                 255

Arg Asp Gly Thr Gly His Tyr Leu Cys Asn Ala Cys Gly Leu Tyr Ser
            260                 265                 270

Lys Met Asn Gly Leu Ser Arg Pro Leu Ile Lys Pro Gln Lys Arg Val
        275                 280                 285

Pro Ser Ser Arg Arg Leu Gly Leu Ser Cys Ala Asn Cys His Thr Thr
    290                 295                 300

Thr Thr Thr Leu Trp Arg Arg Asn Ala Glu Gly Glu Pro Val Cys Asn
305                 310                 315                 320

Ala Cys Gly Leu Tyr Met Lys Leu His Gly Val Pro Arg Pro Leu Ala
            325                 330                 335

Met Lys Lys Glu Gly Ile Gln Thr Arg Lys Arg Lys Pro Lys Asn Ile
            340                 345                 350

Asn Lys Ser Lys Thr Cys Ser Gly Asn Ser Asn Asn Ser Ile Pro Met
        355                 360                 365

Thr Pro Thr Ser Thr Ser Ser Asn Ser Asp Asp Cys Ser Lys Asn Thr
    370                 375                 380

Ser Pro Thr Thr Gln Pro Thr Ala Ser Gly Ala Gly Ala Pro Val Met
385                 390                 395                 400

Thr Gly Ala Gly Glu Ser Thr Asn Pro Glu Asn Ser Glu Leu Lys Tyr
            405                 410                 415

Ser Gly Gln Asp Gly Leu Tyr Ile Gly Val Ser Leu Ala Ser Pro Ala
            420                 425                 430

Glu Val Thr Ser Ser Val Arg Pro Asp Ser Trp Cys Ala Leu Ala Leu
        435                 440                 445

Ala


<210> SEQ ID NO 55
<211> LENGTH: 401
<212> TYPE: PRT
<213> ORGANISM: Homo sapiens

<400> SEQUENCE: 55

Met Trp Ser Gly Gly Ser Gly Lys Ala Arg Gly Trp Glu Ala Ala Ala
1               5                   10                  15

Gly Gly Arg Ser Ser Pro Gly Arg Leu Ser Arg Arg Arg Ile Met Ser
            20                  25                  30

Met Ser Pro Lys His Thr Thr Pro Phe Ser Val Ser Asp Ile Leu Ser
        35                  40                  45

Pro Leu Glu Glu Ser Tyr Lys Lys Val Gly Met Glu Gly Gly Gly Leu
    50                  55                  60

Gly Ala Pro Leu Ala Ala Tyr Arg Gln Gly Gln Ala Ala Pro Pro Thr
65                  70                  75                  80
```

-continued

```
Ala Ala Met Gln Gln His Ala Val Gly His His Gly Ala Val Thr Ala
                85                  90                  95

Ala Tyr His Met Thr Ala Ala Gly Val Pro Gln Leu Ser His Ser Ala
            100                 105                 110

Val Gly Gly Tyr Cys Asn Gly Asn Leu Gly Asn Met Ser Glu Leu Pro
        115                 120                 125

Pro Tyr Gln Asp Thr Met Arg Asn Ser Ala Ser Gly Pro Gly Trp Tyr
    130                 135                 140

Gly Ala Asn Pro Asp Pro Arg Phe Pro Ala Ile Ser Arg Phe Met Gly
145                 150                 155                 160

Pro Ala Ser Gly Met Asn Met Ser Gly Met Gly Gly Leu Gly Ser Leu
                165                 170                 175

Gly Asp Val Ser Lys Asn Met Ala Pro Leu Pro Ser Ala Pro Arg Arg
            180                 185                 190

Lys Arg Arg Val Leu Phe Ser Gln Ala Gln Val Tyr Glu Leu Glu Arg
        195                 200                 205

Arg Phe Lys Gln Gln Lys Tyr Leu Ser Ala Pro Glu Arg Glu His Leu
    210                 215                 220

Ala Ser Met Ile His Leu Thr Pro Thr Gln Val Lys Ile Trp Phe Gln
225                 230                 235                 240

Asn His Arg Tyr Lys Met Lys Arg Gln Ala Lys Asp Lys Ala Ala Gln
                245                 250                 255

Gln Gln Leu Gln Gln Asp Ser Gly Gly Gly Gly Gly Gly Gly Gly Thr
            260                 265                 270

Gly Cys Pro Gln Gln Gln Gln Ala Gln Gln Gln Ser Pro Arg Arg Val
        275                 280                 285

Ala Val Pro Val Leu Val Lys Asp Gly Lys Pro Cys Gln Ala Gly Ala
    290                 295                 300

Pro Ala Pro Gly Ala Ala Ser Leu Gln Gly His Ala Gln Gln Gln Ala
305                 310                 315                 320

Gln His Gln Ala Gln Ala Ala Gln Ala Ala Ala Ala Ala Ile Ser Val
                325                 330                 335

Gly Ser Gly Gly Ala Gly Leu Gly Ala His Pro Gly His Gln Pro Gly
            340                 345                 350

Ser Ala Gly Gln Ser Pro Asp Leu Ala His His Ala Ala Ser Pro Ala
        355                 360                 365

Ala Leu Gln Gly Gln Val Ser Ser Leu Ser His Leu Asn Ser Ser Gly
    370                 375                 380

Ser Asp Tyr Gly Thr Met Ser Cys Ser Thr Leu Leu Tyr Gly Arg Thr
385                 390                 395                 400

Trp
```

<210> SEQ ID NO 56
<211> LENGTH: 457
<212> TYPE: PRT
<213> ORGANISM: Homo sapiens

<400> SEQUENCE: 56

```
Met Leu Gly Ala Val Lys Met Glu Gly His Glu Pro Ser Asp Trp Ser
1               5                   10                  15

Ser Tyr Tyr Ala Glu Pro Glu Gly Tyr Ser Ser Val Ser Asn Met Asn
            20                  25                  30

Ala Gly Leu Gly Met Asn Gly Met Asn Thr Tyr Met Ser Met Ser Ala
        35                  40                  45
```

```
Ala Ala Met Gly Ser Gly Ser Gly Asn Met Ser Ala Gly Ser Met Asn
    50                  55                  60

Met Ser Ser Tyr Val Gly Ala Gly Met Ser Pro Ser Leu Ala Gly Met
65                  70                  75                  80

Ser Pro Gly Ala Gly Ala Met Ala Gly Met Gly Gly Ser Ala Gly Ala
                85                  90                  95

Ala Gly Val Ala Gly Met Gly Pro His Leu Ser Pro Ser Leu Ser Pro
            100                 105                 110

Leu Gly Gly Gln Ala Ala Gly Ala Met Gly Gly Leu Ala Pro Tyr Ala
        115                 120                 125

Asn Met Asn Ser Met Ser Pro Met Tyr Gly Gln Ala Gly Leu Ser Arg
    130                 135                 140

Ala Arg Asp Pro Lys Thr Tyr Arg Arg Ser Tyr Thr His Ala Lys Pro
145                 150                 155                 160

Pro Tyr Ser Tyr Ile Ser Leu Ile Thr Met Ala Ile Gln Gln Ser Pro
                165                 170                 175

Asn Lys Met Leu Thr Leu Ser Glu Ile Tyr Gln Trp Ile Met Asp Leu
            180                 185                 190

Phe Pro Phe Tyr Arg Gln Asn Gln Gln Arg Trp Gln Asn Ser Ile Arg
        195                 200                 205

His Ser Leu Ser Phe Asn Asp Cys Phe Leu Lys Val Pro Arg Ser Pro
    210                 215                 220

Asp Lys Pro Gly Lys Gly Ser Phe Trp Thr Leu His Pro Asp Ser Gly
225                 230                 235                 240

Asn Met Phe Glu Asn Gly Cys Tyr Leu Arg Arg Gln Lys Arg Phe Lys
                245                 250                 255

Cys Glu Lys Gln Leu Ala Leu Lys Glu Ala Ala Gly Ala Ala Gly Ser
            260                 265                 270

Gly Lys Lys Ala Ala Ala Gly Ala Gln Ala Ser Gln Ala Gln Leu Gly
        275                 280                 285

Glu Ala Ala Gly Pro Ala Ser Glu Thr Pro Ala Gly Thr Glu Ser Pro
    290                 295                 300

His Ser Ser Ala Ser Pro Cys Gln Glu His Lys Arg Gly Gly Leu Gly
305                 310                 315                 320

Glu Leu Lys Gly Thr Pro Ala Ala Ala Leu Ser Pro Pro Glu Pro Ala
                325                 330                 335

Pro Ser Pro Gly Gln Gln Gln Gln Ala Ala Ala His Leu Leu Gly Pro
            340                 345                 350

Pro His His Pro Gly Leu Pro Pro Glu Ala His Leu Lys Pro Glu His
        355                 360                 365

His Tyr Ala Phe Asn His Pro Phe Ser Ile Asn Asn Leu Met Ser Ser
    370                 375                 380

Glu Gln Gln His His His Ser His His His His Gln Pro His Lys Met
385                 390                 395                 400

Asp Leu Lys Ala Tyr Glu Gln Val Met His Tyr Pro Gly Tyr Gly Ser
                405                 410                 415

Pro Met Pro Gly Ser Leu Ala Met Gly Pro Val Thr Asn Lys Thr Gly
            420                 425                 430

Leu Asp Ala Ser Pro Leu Ala Ala Asp Thr Ser Tyr Tyr Gln Gly Val
        435                 440                 445

Tyr Ser Arg Pro Ile Met Asn Ser Ser
    450                 455
```

<210> SEQ ID NO 57
<211> LENGTH: 141
<212> TYPE: PRT
<213> ORGANISM: Homo sapiens

<400> SEQUENCE: 57

```
Met Lys Ala Phe Ser Pro Val Arg Ser Val Arg Lys Asn Ser Leu Ser
1               5                   10                  15

Asp His Ser Leu Gly Ile Ser Arg Ser Lys Thr Pro Val Asp Asp Pro
            20                  25                  30

Met Ser Leu Leu Tyr Asn Met Asn Asp Cys Tyr Ser Lys Leu Lys Glu
        35                  40                  45

Leu Val Pro Ser Ile Pro Gln Asn Lys Lys Val Ser Lys Met Glu Ile
    50                  55                  60

Leu Gln His Val Ile Asp Tyr Ile Leu Asp Leu Gln Ile Ala Leu Asp
65                  70                  75                  80

Ser His Pro Thr Ile Val Ser Leu His His Gln Arg Pro Gly Gln Asn
                85                  90                  95

Gln Ala Ser Arg Thr Pro Leu Thr Thr Leu Asn Thr Asp Ile Ser Ile
            100                 105                 110

Leu Ser Leu Gln Val Arg Pro Ala Pro Gly Ser Pro Pro Arg Arg Arg
        115                 120                 125

Thr Leu Pro Arg Ser Ser Gly Leu Ser Leu Gly Asp Pro
    130                 135                 140
```

<210> SEQ ID NO 58
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 58
aatcaggagc gcaggctgca g 21

<210> SEQ ID NO 59
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 59
aagaggcgcc tcctctctcc t 21

<210> SEQ ID NO 60
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 60
aaaccgccat gcactcggct t 21

<210> SEQ ID NO 61
<211> LENGTH: 24
<212> TYPE: DNA
<213> ORGANISM: Artificial sequence
<220> FEATURE:
<223> OTHER INFORMATION: Synthetic nucleotide

<400> SEQUENCE: 61
tgaccttgat ttattttgca tacc 24

<210> SEQ ID NO 62
<211> LENGTH: 23
<212> TYPE: DNA
<213> ORGANISM: Artificial sequence
<220> FEATURE:
<223> OTHER INFORMATION: Synthetic nucleotide

<400> SEQUENCE: 62
tttgctttcc ttggtcaggc agt 23

<210> SEQ ID NO 63
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 63
cgagcaagac gttcagtcct 20

<210> SEQ ID NO 64
<211> LENGTH: 22
<212> TYPE: DNA
<213> ORGANISM: Artificial sequence
<220> FEATURE:
<223> OTHER INFORMATION: Synthetic nucleotide

<400> SEQUENCE: 64
cgtggggtcc ttttcaccag ca 22

<210> SEQ ID NO 65
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 65
tgagtatgtc gtggagtcta c 21

<210> SEQ ID NO 66
<211> LENGTH: 19
<212> TYPE: DNA
<213> ORGANISM: Artificial sequence
<220> FEATURE:
<223> OTHER INFORMATION: Synthetic nucleotide

<400> SEQUENCE: 66
gcaaattcca tggcaccgt 19

<210> SEQ ID NO 67
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 67
ggcccgattt ctcctccggg t 21

<210> SEQ ID NO 68
<211> LENGTH: 19
<212> TYPE: DNA

<213> ORGANISM: Artificial sequence
<220> FEATURE:
<223> OTHER INFORMATION: Synthetic nucleotide

<400> SEQUENCE: 68
tggactgtgg tcatgagcc 19

<210> SEQ ID NO 69
<211> LENGTH: 19
<212> TYPE: DNA
<213> ORGANISM: Artificial sequence
<220> FEATURE:
<223> OTHER INFORMATION: Synthetic nucleotide

<400> SEQUENCE: 69
tcgccccact tgattttgg 19

<210> SEQ ID NO 70
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 70
ggtgaccagg cgcccaatac g 21

<210> SEQ ID NO 71
<211> LENGTH: 25
<212> TYPE: DNA
<213> ORGANISM: Artificial sequence
<220> FEATURE:
<223> OTHER INFORMATION: Synthetic nucleotide

<400> SEQUENCE: 71
gctagcgctg tttgtttagg gctcg 25

<210> SEQ ID NO 72
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 72
gccccgaaac gcttcggcag 20

<210> SEQ ID NO 73
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 73
tttggggtgg cctcggctct 20

<210> SEQ ID NO 74
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 74
ccaggccaac cgcacacctt 20

<210> SEQ ID NO 75
<211> LENGTH: 18
<212> TYPE: DNA
<213> ORGANISM: Artificial sequence
<220> FEATURE:
<223> OTHER INFORMATION: Synthetic nucleotide

<400> SEQUENCE: 75
gcggccatgc agcagcac 18

<210> SEQ ID NO 76
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 76
ccatgttctt gctcacgtcc 20

<210> SEQ ID NO 77
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 77
actcttttgg tggtgactgg g 21

<210> SEQ ID NO 78
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 78
ctcatgttgc ccaggttgcc 20

<210> SEQ ID NO 79
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 79
accgccatgc actcggcttc 20

<210> SEQ ID NO 80
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 80
ggctcattcc agcgcccaca 20

<210> SEQ ID NO 81
<211> LENGTH: 20
<212> TYPE: DNA
<213> ORGANISM: Artificial sequence
<220> FEATURE:

<223> OTHER INFORMATION: Synthetic nucleotide

<400> SEQUENCE: 81
ggcactgcgc ttcactcccc 20

<210> SEQ ID NO 82
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 82
ggctcattcc agcgcccaca 20

<210> SEQ ID NO 83
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 83
ctgaaccgag cctggtgccg 20

<210> SEQ ID NO 84
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 84
gctccgggag atgcccaagc 20

<210> SEQ ID NO 85
<211> LENGTH: 25
<212> TYPE: DNA
<213> ORGANISM: Artificial sequence
<220> FEATURE:
<223> OTHER INFORMATION: Synthetic nucleotide

<400> SEQUENCE: 85
gggtgctgaa agattccaaa cctcg 25

<210> SEQ ID NO 86
<211> LENGTH: 23
<212> TYPE: DNA
<213> ORGANISM: Artificial sequence
<220> FEATURE:
<223> OTHER INFORMATION: Synthetic nucleotide

<400> SEQUENCE: 86
tgtgcccttc agtgtaggtg gca 23

<210> SEQ ID NO 87
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 87
ccgaagccac acgctgcctt 20

<210> SEQ ID NO 88
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 88
agcacggttg cagtgggagc 20

<210> SEQ ID NO 89
<211> LENGTH: 19
<212> TYPE: DNA
<213> ORGANISM: Artificial sequence
<220> FEATURE:
<223> OTHER INFORMATION: Synthetic nucleotide

<400> SEQUENCE: 89
gctggtgatg atgctccca 19

<210> SEQ ID NO 90
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 90
gcccattcca accattactc c 21

<210> SEQ ID NO 91
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 91
tgtggacctc aggttggact 20

<210> SEQ ID NO 92
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 92
cttctgcagg gctttcatgt c 21

<210> SEQ ID NO 93
<211> LENGTH: 3270
<212> TYPE: DNA
<213> ORGANISM: Mus musculus

<400> SEQUENCE: 93
ttcacctccg cacccagcag cttgtagaga gcagttccga cccacagcct ggcacccttc 60
ggctagcgct gtttgtttag ggctcggtga gtccaatcag gagcgcaggc tgcagttttc 120
cggcagagca gtaagaggcg cctcctctct cctttttatt caccagcagc gactagcaga 180
ccccggactc tcgctctccc gccggcgccc tccgcctctc tccgcgcccc ggagcaccct 240
cggtcgcggc cgttcttctc gcacatcgct cgaggaatca aaagtcaggt tggagtagcg 300
ccggacagtg gatggccttg actgacggcg gctggtgcct gccaaagcgt ttcggggctg 360

-continued

```
ctgctgcgga cgccggcgac tccgggccct ttccagcgcg ggagccctcc tcgccgcttt    420
cccccatctc gtcttcgtcc tcctcctgct cccggggcgg ggatcgcggt ccctgcggcg    480
ccagcaactg caggacgccg cagctcgacg ccgaggcggt ggcgggacct ccgggccgct    540
cgctcttgct cagcccctac gcctcgcatc ccttcgccgc tgcccacgga gccgcggcgc    600
ccggggtcgc aggccccggg agcgccctgt cgacttggga ggacctgttg ctcttcactg    660
acctcgatca ggccgcgacc gccagcaagc tgttgtggtc cagccggggc gccaaactga    720
gccccttcgc ggccgagcag ccggaggaaa tgtaccagac cctcgccgcc ctgtccagcc    780
aggggcccgc cgcttacgac ggcgcgcccg gcggcttcgt gcactccgca gcggcggcgg    840
ccgctgccgc cgcggcagcc agctccccgg tctacgtgcc caccacgcgc gtgggctcca    900
tgctgtccgg cctgccctac cttcaagggg cgggcagcgg gcccagcaat cacgcgggcg    960
gagcgggtgc ccacccaggc tggtcccagg cctccgccga cagcccccg tatggcgggg    1020
gtggcgcagc cggcggcggc gcggccggac ctggaggtgc gggatcggct acggcccacg   1080
cctctgcacg ctttccctac tcgcccagcc cgcccatggc caacggcgcc gcgcgagacc   1140
ccgggggcta cgtggctgcg ggcggcacgg gcgcaggcag tgtgagtgga ggtggcggca   1200
gcctggcggc catgggtggc cgggagcacc agtacagctc gctgtccgca gctcggccgc   1260
tgaacggaac gtaccaccac caccatcacc atcacccgac ctactcgccc tacatggccg   1320
caccgctgac tcctgcctgg ccagcaggac ccttcgaaac gccggtgctc cacagcttac   1380
agggccgcgc gggagctcca ctcccggtgc cacggggccc cagcacagac ctgttggagg   1440
acctgtcgga gagccgcgag tgcgtgaact gcggctccat ccagacgcca ctgtggagac   1500
gagacggcac cggtcattac ctgtgcaatg catgcggtct ctacagcaag atgaatggcc   1560
tcagcaggcc cctcatcaag ccacagaagc gcgtgccttc atcacggcgg cttggactgt   1620
cctgtgccaa ctgtcacacc acaaccacta ccttatggcg tagaaatgct gagggtgagc   1680
ctgtgtgcaa tgcttgcggg ctctatatga aactccatgg ggtgcctcga ccacttgcta   1740
tgaaaaaaga aggaattcaa accaggaaac gaaaacctaa aaatataaat aagtcaaaag   1800
cttgctccgg taacagcagt ggctctgtcc ctatgactcc tacttcctct tcttctaatt   1860
cagatgactg caccaaaaat acttctcctt ctacacaagc gaccacctca ggggtagggg   1920
catcagtgat gtctgcagtg ggagaaaacg ccaaccccga gaacagtgac ctcaagtatt   1980
caggtcaaga cggcctctac ataggtgtca gtctgtcctc ccctgccgaa gtcacatcct   2040
ccgtgcgaca ggattcttgg tgtgctctgg ccctggcctg agctggtgct accaagaggc   2100
aaggagggct ctgaaggcct cataccactt gtgtctgata ttgtccagca gtccagatgg   2160
cagcaaaaat gcagacataa cattccttcg atgcgtgatt tctgtgcctt tgttttgaaa   2220
gagatatatt tctcaagaag cttactgaag taagaagaga tgggcttttg caggaagggc   2280
cagcaccgtg ggcatgtggc ctgctcctgc cagcctgggc tgcttcctgc ctctgactct   2340
gccccatacc agtgggagaa actgtgacaa tgaccggggc cttgtctgct aaggaagatt   2400
gagagattta agagaaaatg tttgtgtatt gctccaaatc atgtgcttct tgtgatcaac   2460
ctcggttatc ccagaaccca ttcatccccg accaccgtgc acatttcaca agcgttcgtg   2520
gagaggagca ctgggagcca tttggtctat cctggaggcg gagtgcattc ctggggtctc   2580
aacaagaata ttaatttgca agattgcatc atgacagaca ctgactgact tatctcaacg   2640
ttcatcgtaa cgtggctgat ctgaggtcac ttggaatttg taaacagggt agcaaacaag   2700
atatttttct tccatgtaca caataatttt tttaagtgca atttgcgttg cagcaatcag   2760
```

tgttaaatca tttgcataag atttaacagc atttttataa tgaatgtaaa cattttaact 2820
taatggtact taaaataatt taaaaaaaag ttaactttag acatatgctt cttacactca 2880
cagcccactt ctgtgttccc aattgtttaa aagaaaaaaa aaaagatttc aagaacaaat 2940
cttctctcag gaaattgcct tttctccatt tatgaatttt tatacaagaa caccaacaca 3000
gtccccgttc ttttactgag gaaaaagtgc tggaaattgc aacaaacctt tactacctag 3060
agaatagcat ttgtaaatat tctaagtatc tgtaacactc ttgacgcctg taccacgtga 3120
ccaacccaca ggttggttta cattattatt ttttttaatg ggatatcata tggaaaccta 3180
tttcaccaga gttttaaaaa ataaaaaggg tattgttttg tgttctgtac agtgagatcc 3240
ttccttttca tcttatttca atgctgtgtg 3270

<210> SEQ ID NO 94
<211> LENGTH: 2097
<212> TYPE: DNA
<213> ORGANISM: Mus musculus

<400> SEQUENCE: 94
tgggcattaa ttttagtgtg gttatctccg atgagcctaa gcgatttgga aaagcagccc 60
ggtggaggcc tgcctggttc cccacccccct ccaagtctcc ctgtcattct tcctgctctc 120
ccctttgggg tggcctcggc tctggggcgg tctcaccccc ctcccctcct gcgttttccc 180
ctccttttct ctgcgctctg ctccacccta ctatgaccaa ttccagaacg atctggcctt 240
tcccctgctg ggttgacca tggggtgggc caggggtggc ccggcccgcc tgagtacgca 300
cgctggtggt tgtaaggcgg tttgtgttta aggaatcaaa agtcaggttg gagtagcgcc 360
ggacagtgga tggccttgac tgacggcggc tggtgcctgc caaagcgttt cggggctgct 420
gctgcggacg ccggcgactc cggccccttt ccagcgcggg agccctcctc gccgctttcc 480
cccatctcgt cttcgtcctc ctcctgctcc cggggcgggg atcgcggtcc ctgcggcgcc 540
agcaactgca ggacgccgca gctcgacgcc gaggcggtgg cgggacctcc gggccgctcg 600
ctcttgctca gcccctacgc ctcgcatccc ttcgccgctg cccacggagc cgcggcgccc 660
ggggtcgcag gccccgggag cgccctgtcg acttgggagg acctgttgct cttcactgac 720
ctcgatcagg ccgcgaccgc cagcaagctg ttgtggtcca gccggggcgc caaactgagc 780
cccttcgcgg ccgagcagcc ggaggaaatg taccagaccc tcgccgccct gtccagccag 840
gggcccgccg cttacgacgg cgcgcccggc ggcttcgtgc actccgcagc ggcggcggcc 900
gctgccgccg cggcagccag ctccccggtc tacgtgccca ccacgcgcgt gggctccatg 960
ctgtccggcc tgccctacct tcaaggggcg ggcagcgggc ccagcaatca cgcgggcgga 1020
gcgggtgccc acccaggctg gtcccaggcc tccgccgaca gcccccccgta tggcgggggt 1080 ggcgcagccg gcggcggcgc ggccggacct ggaggtgcgg gatcggctac ggcccacgcc 1140
tctgcacgct ttccctactc gcccagcccg cccatggcca acggcgccgc gcgagacccc 1200
gggggctacg tggctgcggg cggcacgggc gcaggcagtg tgagtggagg tggcggcagc 1260
ctggcggcca tgggtggccg ggagcaccag tacagctcgc tgtccgcagc tcggccgctg 1320
aacggaacgt accaccacca ccatcaccat cacccgacct actcgcccta catggccgca 1380
ccgctgactc ctgcctggcc agcaggaccc ttcgaaacgc cggtgctcca cagcttacag 1440
ggccgcgcgg gagctccact cccggtgcca cggggcccca gcacagacct gttggaggac 1500
ctgtcggaga gccgcgagtg cgtgaactgc ggctccatcc agacgccact gtggagacga 1560

```
gacggcaccg gtcattacct gtgcaatgca tgcggtctct acagcaagat gaatggcctc   1620
agcaggcccc tcatcaagcc acagaagcgc gtgccttcat cacggcggct tggactgtcc   1680
tgtgccaact gtcacaccac aaccactacc ttatggcgta gaaatgctga gggtgagcct   1740
gtgtgcaatg cttgcgggct ctatatgaaa ctccatgggg tatgttgctc ctgtttatcc   1800
atacatacaa ctagcacctg aattgtaaat ttttagttat aagacagaat cagcaaatga   1860
aaaaaggtgt aaaagtgtgt acatatgcct tgtagcgaat tcaagctgct cttaattgta   1920
atgtgaccag tcagttcagc cactaaggag ccaggagata aaacccacta ccaaccaatc   1980
cggcactaac attctctgtg aaacatctct acattttaga aatgtgaaaa tgagccaagt   2040
gtaactgtga atgcctttaa tccaagatag ccagggctac acggagaaac ctgtagc      2097
```

<210> SEQ ID NO 95
<211> LENGTH: 2265
<212> TYPE: DNA
<213> ORGANISM: Mus musculus

<400> SEQUENCE: 95

```
ttttttttt cctcctcttc cttcctcctc cagccgacgc cgaatcatgt cgatgagtcc     60
aaagcacacg actccgttct cagtgtctga catcttgagt cccctggagg aaagctacaa    120
gaaagtgggc atggagggcg gcggcctcgg ggctccgctc gcagcgtaca gacagggcca    180
ggcggcccca ccggccgcgg ccatgcagca gcacgccgtg gggcaccacg gcgccgtcac    240
cgccgcctac cacatgacgg cggcggggt gccccagctc tcgcactccg ccgtgggggg    300
ctactgcaac ggcaacctgg gcaacatgag cgagctgccg ccttaccagg acaccatgcg    360
gaacagcgct tcgggccccg gatggtacgg cgccaaccca gacccgcgct tccccgccat    420
ctcccgcttc atgggcccgg cgagcggcat gaatatgagt ggcatgggcg gcctgggctc    480
gctgggggac gtgagcaaga acatggcccc gctgcccagt gcgccccgcc ggaagcgccg    540
ggtgctcttc tcccaggcgc aggtgtacga gctcgagcga cgtttcaagc aacagaagta    600
cctgtcggcg ccggagcgcg agcatctggc cagcatgatt cacctgacac ccacgcaggt    660
caagatctgg ttccagaacc accgctacaa gatgaagcgc caggctaagg acaaggcggc    720
gcagcaacaa ctgcagcagg acagcggcgg cggcggaggc ggcggtggcg gtgcgggatg    780
cccgcagcag cagcaagctc agcagcagtc gccgcgccgg gtggccgtgc cggtcctagt    840
caaagacggc aaaccctgcc aggcgggcgc ccctgccccg ggagccgcaa gcctgcaaag    900
ccacgcgcag caacaagctc agcagcaggc gcaggcggcg caagcggctg ccgcggccat    960
ctcagtgggc agcggtggcg cgggtctagg agcacaccca ggccaccagc cgggcagcgc   1020
agggcagtcc ccggacctgg cgcaccacgc agccagcccc gcggggctgc agggccaggt   1080
ctccagccta tcccatctga actcctcggg ctcggactat ggcgccatgt cttgttctac   1140
cttgctttat ggtcggacct ggtgagacgt gagatgcgct tgagccccgc gcgacctcaa   1200
cgcttcccct ctgccttccg caaagaccac cattcgcccg ctgctccacg cgcttctact   1260
ttttttaaga atctgtttat gtttagacca aggaaaagta cacaaagacc aaactgctgg   1320
acgacttctt cttcttcttc ttcttcttct tcttcttctt cttcttcttc ttcttcttct   1380
tcttcttctt cttcttcttc ttcttcttct tctcctcctc ctcctcctcc tcctcctcct   1440
cctcctcttc ctccttcttg tccccgctcg ttcttttctt tctccccctc ctcttctgtt   1500
tccttcttcc ttcatctttc ccccttcct ttctctttac tatctaaaac ttgcagactt   1560
tttgtttttt aacataaaaa gaaaatagaa acagccaagc aaattcaacc ctttacggat   1620
```

tctttaaaca gagaaggaca gagaacaaat ttggggtgtc tttctggtag ttcaaatggg 1680
ttcccaagct taggcatggc acagttttgg agcctgttct atgcttccat ggccctgaac 1740
tctaaagacg gaaaactttt ctgtggatgc accctgccag caaagtgagc ttgcttgtaa 1800
ataccaggat ttttcgtttg tttgtatgtt tcagaaggga ggacagacgc tggagatagg 1860
aaagtcttca gcataaccca tttgtacctg acacaaagga agtgtcccct cccaggcgcc 1920
ctctggccct acaggttcag tccaggctgg cctttcagaa aattgtttta ggtttgatgt 1980
gaacttgtag ctgtaaaatg ctgttaaaag ttggactaaa tgcctagttt ttagtaacct 2040
gtacattatg ttgtaaaaag aaccccagtc ccagtcccta gtccctcact ttttcaaggg 2100
gcattgacaa acctgtgtat attatttggc agtttggtat ttgcagcacc aatccttttt 2160
ttttttctgt tgtaacttat gtagatattt ggcttaaata tagttcctaa gaagcttcta 2220
ataaattata cgaattaaaa aagatggttt ttttcctgat taaaa 2265

<210> SEQ ID NO 96
<211> LENGTH: 2832
<212> TYPE: DNA
<213> ORGANISM: Mus musculus

<400> SEQUENCE: 96
ctggtaacag caatgaggct gacgccccccg ggcccgctag ggagcacagc ccacagctcc 60
cccttgccag gcgcccaagg accctcaagg cgcggggctc acacttgaag cctgggaacg 120
ctcagacagg aaacccactt cctcctaagc agtttcttcc tagccggatg agaggcgccc 180
aattgaagca gaatgatcct catctactaa tatccagcgt ggccacaaag cgaccggcca 240
tttacgccgc cactttagac aaagatattt ggttattccc ggggaagcaa gtgcactttt 300
gcatggctga gctccgggag gaggcgagcc tcagcccagc ctcccgcccg ctgggctgcg 360
ggcgtcgaga tattcgcctc ctcccggaca acgagttcca cccgggttca gactcagttc 420
cactctgcaa cggatctgcg ggcgctcacg cggctccccg cccgggcttt cactgaagca 480
tcggaaggga aaactgcggg gatctgagct ggggtgctgg gactgggatg tcctcggaaa 540
gacagcatca gcttctgaag ccgaagtatc caggccatgg gcaagggtca ggggcaccag 600
ccgacgccga atcatgtcga tgagtccaaa gcacacgact ccgttctcag tgtctgacat 660
cttgagtccc ctggaggaaa gctacaagaa agtgggcatg gagggcggcg gcctcggggc 720
tccgctcgca gcgtacagac agggccaggc ggccccaccg gccgcggcca tgcagcagca 780
cgccgtgggg caccacggcg ccgtcaccgc cgcctaccac atgacggcgg cgggggtgcc 840
ccagctctcg cactccgccg tggggggcta ctgcaacggc aacctgggca acatgagcga 900
gctgccgcct taccaggaca ccatgcggaa cagcgcttcg ggccccggat ggtacggcgc 960
caacccagac ccgcgcttcc ccgccatctc ccgcttcatg ggcccggcga gcggcatgaa 1020
tatgagtggc atgggcggcc tgggctcgct gggggacgtg agcaagaaca tggccccgct 1080
gcccagtgcg ccccgccgga agcgccgggt gctcttctcc caggcgcagg tgtacgagct 1140
cgagcgacgt ttcaagcaac agaagtacct gtcggcgccg gagcgcgagc atctggccag 1200
catgattcac ctgacaccca cgcaggtcaa gatctggttc cagaaccacc gctacaagat 1260
gaagcgccag gctaaggaca aggcggcgca gcaacaactg cagcaggaca gcggcggcgg 1320
cggaggcggc ggtggcggtg cgggatgccc gcagcagcag caagctcagc agcagtcgcc 1380
gcgccgggtg gccgtgccgg tcctagtcaa agacggcaaa ccctgccagg cgggcgcccc 1440
tgccccggga gccgcaagcc tgcaaagcca cgcgcagcaa caagctcagc agcaggcgca 1500
ggcggcgcaa gcggctgccg cggccatctc agtgggcagc ggtggcgcgg gtctaggagc 1560
acacccaggc caccagccgg gcagcgcagg gcagtccccg gacctggcgc accacgcagc 1620
cagccccgcg gggctgcagg gccaggtctc cagcctatcc catctgaact cctcgggctc 1680
ggactatggc gccatgtctt gttctacctt gctttatggt cggacctggt gagacgtgag 1740
atgcgcttga gccccgcgcg acctcaacgc ttcccctctg ccttccgcaa agaccaccat 1800
tcgcccgctg ctccacgcgc ttctactttt tttaagaatc tgtttatgtt tagaccaagg 1860
aaaagtacac aaagaccaaa ctgctggacg acttcttctt cttcttcttc ttcttcttct 1920
tcttcttctt cttcttcttc ttcttcttct tcttcttctt cttcttcttc ttcttcttct 1980
cctcctcctc ctcctcctcc tcctcctcct cctcttcctc cttcttgtcc ccgctcgttc 2040
ttttctttct cccccctcctc ttctgtttcc ttcttccttc atctttcccc ccttcctttc 2100
tctttactat ctaaaacttg cagacttttt gtttttttaac ataaaaagaa aatagaaaca 2160
gccaagcaaa ttcaaccctt tacggattct ttaaacagag aaggacagag aacaaatttg 2220
gggtgtcttt ctggtagttc aaatgggttc ccaagcttag gcatggcaca gttttggagc 2280
ctgttctatg cttccatggc cctgaactct aaagacggaa aactttttctg tggatgcacc 2340 ctgccagcaa agtgagcttg cttgtaaata ccaggatttt tcgtttgttt gtatgtttca 2400
gaagggagga cagacgctgg agataggaaa gtcttcagca taacccattt gtacctgaca 2460
caaaggaagt gtcccctccc aggcgccctc tggccctaca ggttcagtcc aggctggcct 2520
ttcagaaaat tgttttaggt ttgatgtgaa cttgtagctg taaaatgctg ttaaaagttg 2580
gactaaatgc ctagttttta gtaacctgta cattatgttg taaaaagaac cccagtccca 2640
gtccctagtc cctcactttt tcaaggggca ttgacaaacc tgtgtatatt atttggcagt 2700
ttggtatttg cagcaccaat cctttttttt tttctgttgt aacttatgta gatatttggc 2760
ttaaatatag ttcctaagaa gcttctaata aattatacga attaaaaaag atggtttttt 2820
tcctgattaa aa 2832

<210> SEQ ID NO 97
<211> LENGTH: 2070
<212> TYPE: DNA
<213> ORGANISM: Mus musculus

<400> SEQUENCE: 97
ggtcgtttgt tgtggctgtt aaattttaaa ccgccatgca ctcggcttcc agtatgctgg 60
gagccgtgaa gatggaaggg cacgagccat ccgactggag cagctactac gcggagcccg 120
agggctactc ttccgtgagc aacatgaacg ccggcctggg gatgaatggc atgaacacat 180
acatgagcat gtccgcggct gccatgggcg gcggttccgg caacatgagc gcgggctcca 240
tgaacatgtc atcctatgtg ggcgctggaa tgagcccgtc gctagctggc atgtccccgg 300
gcgccggcgc catggcgggc atgagcggct cagccggggc ggccggcgtg gcgggcatgg 360
gacctcacct gagtccgagt ctgagcccgc tcgggggaca ggcggccggg gccatgggtg 420
gccttgcccc ctacgccaac atgaactcga tgagccccat gtacgggcag gccggcctga 480
gccgcgctcg ggaccccaag acataccgac gcagctacac acacgccaaa cctccctact 540
cgtacatctc gctcatcacc atggccatcc agcagagccc caacaagatg ctgacgctga 600
gcgagatcta tcagtggatc atggacctct tccctttcta ccggcagaac cagcagcgct 660
ggcagaactc catccgccac tctctctcct tcaacgactg ctttctcaag gtgccccgct 720

```
cgccagacaa gcctggcaag ggctccttct ggaccctgca cccagactcg ggcaacatgt    780
tcgagaacgg ctgctacctg cgccgccaga agcgcttcaa gtgtgagaag caactggcac    840
tgaaggaagc cgcgggtgcg gccagtagcg gaggcaagaa gaccgctcct gggtcccagg    900
cctctcaggc tcagctcggg gaggccgcgg gctcggcctc cgagactccg gcgggcaccg    960
agtcccccca ttccagcgct tctccgtgtc aggagcacaa gcgaggtggc ctaagcgagc   1020
taaagggagc acctgcctct gcgctgagtc ctcccgagcc ggcgccctcg cctgggcagc   1080
agcagcaggc tgcagcccac ctgctgggcc cacctcacca cccaggcctg ccaccagagg   1140
cccacctgaa gcccgagcac cattacgcct tcaaccaccc cttctctatc aacaacctca   1200
tgtcgtccga gcagcaacat caccacagcc accaccacca tcagccccac aaaatggacc   1260
tcaaggccta cgaacaggtc atgcactacc caggggggcta tggttccccc atgccaggca   1320
gcttggccat gggcccagtc acgaacaaag cgggcctgga tgcctcgccc ctggctgcag   1380
acacttccta ctaccaagga gtgtactcca ggcctattat gaactcatcc taagaagatg   1440
gctttcaggc cctgctagct ctggtcactg gggacaaggg aaatgagagg ctgagtggag   1500
actttgggag agctttgagg aaaagtagcc accacacttc aggcctcaag ggagcagtct   1560
cacctgtctg tgtccctaaa tagatgggcc acagtgatct gtcattctaa atagggaagg   1620
gaatggaaat atatatgtat acatataaac ttgttttaaa ggagcctttg gtctcctcta   1680
tgtagactac tgcttctcaa gacatctgca gagtttgatt tttgttgttg ttctctattg   1740
ctgttgttgc agaaaagtct gactttaaaa acaaacaaac aaacaaaaaa cttttgtgag   1800
tgacttggtg taaaaccatg tagttttaac agaaaaccag agggttgtac tgatgttgaa   1860
aagaggaaag aaaaataatg taagagtctg gtgtaccgga ccaggagaaa ggagaaaaac   1920
acatcccatt ctggacatgg tgaaatccag gtctcgggtc tgatttaatt tatggtttct   1980
gcgtgcttta tttatggctt ataaatgtgt gttctggcta gaatggccag aattccacaa   2040
atctatatta aagtgttatt gccgatttta                                     2070

<210> SEQ ID NO 98
<211> LENGTH: 2127
<212> TYPE: DNA
<213> ORGANISM: Mus musculus

<400> SEQUENCE: 98

ctgacgacca gggcggccag accacgcgag tcctacgcgc ctcctgaggc cgccccggga      60
cttaactgta acggggaggg gcctccggag cagcggccag cgagttaaag tatgctggga     120
gccgtgaaga tggaagggca cgagccatcc gactggagca gctactacgc ggagcccgag     180
ggctactctt ccgtgagcaa catgaacgcc ggcctgggga tgaatggcat gaacacatac     240
atgagcatgt ccgcggctgc catgggcggc ggttccggca acatgagcgc gggctccatg     300
aacatgtcat cctatgtggg cgctggaatg agcccgtcgc tagctggcat gtccccgggc     360
gccggcgcca tggcgggcat gagcggctca gccggggcgg ccggcgtggc gggcatggga     420
cctcacctga gtccgagtct gagcccgctc gggggacagg cggccggggc catgggtggc     480
cttgcccccct acgccaacat gaactcgatg agccccatgt acgggcaggc cggcctgagc     540
cgcgctcggg accccaagac ataccgacgc agctacacac acgccaaacc tccctactcg     600
tacatctcgc tcatcaccat ggccatccag cagagcccca acaagatgct gacgctgagc     660
gagatctatc agtggatcat ggacctcttc cctttctacc ggcagaacca gcagcgctgg     720
```

```
cagaactcca tccgccactc tctctccttc aacgactgct ttctcaaggt gccccgctcg    780

ccagacaagc ctggcaaggg ctccttctgg accctgcacc cagactcggg caacatgttc    840

gagaacggct gctacctgcg ccgccagaag cgcttcaagt gtgagaagca actggcactg    900

aaggaagccg cgggtgcggc cagtagcgga ggcaagaaga ccgctcctgg gtcccaggcc    960

tctcaggctc agctcgggga ggccgcgggc tcggcctccg agactccggc gggcaccgag   1020

tccccccatt ccagcgcttc tccgtgtcag gagcacaagc gaggtggcct aagcgagcta   1080

aagggagcac ctgcctctgc gctgagtcct cccgagccgg cgccctcgcc tgggcagcag   1140

cagcaggctg cagcccacct gctgggccca cctcaccacc caggcctgcc accagaggcc   1200

cacctgaagc ccgagcacca ttacgccttc aaccacccct tctctatcaa caacctcatg   1260

tcgtccgagc agcaacatca ccacagccac caccaccatc agccccacaa aatggacctc   1320

aaggcctacg aacaggtcat gcactaccca gggggctatg gttcccccat gccaggcagc   1380

ttggccatgg gcccagtcac gaacaaagcg ggcctggatg cctcgcccct ggctgcagac   1440

acttcctact accaaggagt gtactccagg cctattatga actcatccta agaagatggc   1500

tttcaggccc tgctagctct ggtcactggg gacaagggaa atgagaggct gagtggagac   1560

tttgggagag ctttgaggaa aagtagccac cacacttcag gcctcaaggg agcagtctca   1620

cctgtctgtg tccctaaata gatgggccac agtgatctgt cattctaaat agggaaggga   1680

atggaaatat atatgtatac atataaactt gttttaaagg agcctttggt ctcctctatg   1740

tagactactg cttctcaaga catctgcaga gtttgatttt tgttgttgtt ctctattgct   1800

gttgttgcag aaaagtctga ctttaaaaac aaacaaacaa acaaaaaact tttgtgagtg   1860

acttggtgta aaaccatgta gttttaacag aaaaccagag ggttgtactg atgttgaaaa   1920

gaggaaagaa aaataatgta agagtctggt gtaccggacc aggagaaagg agaaaaacac   1980

atcccattct ggacatggtg aaatccaggt ctcgggtctg atttaattta tggtttctgc   2040

gtgctttatt tatggcttat aaatgtgtgt tctggctaga atggccagaa ttccacaaat   2100

ctatattaaa gtgttattgc cgatttt                                       2127
```

<210> SEQ ID NO 99
<211> LENGTH: 1285
<212> TYPE: DNA
<213> ORGANISM: Mus musculus

<400> SEQUENCE: 99

```
gcttcattct gaaccgagcc tggtgccgcg cagtcagctc agccccctgt ggcggctccc     60

tcccggtctt cctcctacga gcagcatgaa agccttcagt ccggtgaggt ccgttaggaa    120

aaacagcctg tcggaccaca gcttgggcat ctcccggagc aaaaccccgg tggacgaccc    180

gatgagtctg ctctacaaca tgaacgactg ctactccaag ctcaaggaac tggtgcccag    240

catcccccag aacaagaagg tgaccaagat ggaaatcctg cagcacgtca tcgattacat    300

cttggacctg cagatcgccc tggactcgca tcccactatc gtcagcctgc atcaccagag    360

acctggacag aaccaggcgt ccaggacgcc gctgaccacc ctgaacacgg acatcagcat    420

cctgtccttg caggcatctg aattcccttc tgagcttatg tcgaatgata gcaaagtact    480

ctgtggctaa ataaatggca tttggggact tttttttttc tttttacttt ctctttttct    540

tttgcacaag aagaagtcta caagatcttt taagactttt gttatcagcc atttcaccag    600

gagaacacgt tgaatggacc tttttaaaaa gaaagcggaa ggaaaactaa ggatgatcgt    660

cttgcccagg tgtcgttctc cggcctggac tgtgataccg ttatttatga gagactttca    720
```

```
gtgccctttc tacagttgga aggttttctt tatatactat tcccaccatg gggagcgaaa    780

acgttaaaaa aaaaagaaaa aaatcacaag gaattgccca atgtaagcag actttgcctt    840

ttcacaaagg tggagcgtga ataccagaag gacccagtat tcggttactt aaatgaagtc    900

ttcggtcaga aatggccttt ttgacacgag cctactgaat gctgtgtata tatttatata    960

taaatatata tatattgagt gaaccttgtg gactctttaa ttagagtttt cttgtatagt   1020

ggcagaaata acctatttct gcattaaaat gtaatgacgt acttatgcta aactttttat   1080

aaaagtttag ttgtaaactt aaccctttta tacaaaataa atcaagtgtg tttattgaat   1140

gttgattgct tgctttattt cagacaacca gtgctttgat ttttttatg ctatgttata    1200

actgaaccca aataaatacc agttcaaatt tatgtagact gtattaagat tataataaaa   1260

tgtgtctgac atcaatgccg ggatt                                         1285
```

<210> SEQ ID NO 100
<211> LENGTH: 1839
<212> TYPE: DNA
<213> ORGANISM: Mus musculus

<400> SEQUENCE: 100

```
agcaaaacaa gaattcagaa ttaaagcatt ggagtcaaga gctctaaact ttttcaaaat     60

gtggctgcat ctaggaaggg tgctgaaaga ttccaaacct cgtacgtaac agaattttct    120

tttaaaaaca gcgataagct gtcagtcaat agctaggacc acctacctga caaagagctt    180

cccaagagct ctaagtgttg gaatgtgaca ccagaaatca cgatttgtgc ataattaatc    240

gcatcacttt gccacctaca ctgaagggca cagaccaagg gcagtgtatg taaatgtagt    300

tccagtgtgc aaaccccact aatgaccttc gattaatgga gtcattatag taaccctgcc    360

tcattcttgg gggtgggggg agttccgaat gcaccgggtc cctcggggct cctctgcggt    420

ctgagggaga ccgcacagtg ttcctacaat tcgtgtcact gagtttccga gaaggcctcc    480

cgcgttgctc caagttgcaa agcttcacgc taaacctgtc gtggacgtgt atgtgggcat    540

tggctgcgaa cgcggaagaa ccgagagctc atactcacca atgggagaat tcgcctggta    600

tgatggacgg gagcccttcc accaatggca attcagggat gcccgattga gcggccaggg    660

cgagtgcaca taaaagacgc cccgcccggc tcgcgcttca ttctgaaccg agcctggtgc    720

cgcgcagtca gctcagcccc ctgtggcggc tccctcccgg tcttcctcct acgagcagca    780

tgaaagcctt cagtccggtg aggtccgtta ggaaaaacag cctgtcggac cacagcttgg    840

gcatctcccg gagcaaaacc ccggtggacg acccgatgag tctgctctac aacatgaacg    900

actgctactc caagctcaag gaactggtgc ccagcatccc ccagaacaag aaggtgacca    960

agatggaaat cctgcagcac gtcatcgatt acatcttgga cctgcagatc gccctggact   1020

cgcatcccac tatcgtcagc ctgcatcacc agagacctgg acagaaccag gcgtccagga   1080

cgccgctgac caccctgaac acggacatca gcatcctgtc cttgcaggtg agactagctt   1140

gcaagtacgc cactgcccag acgctccggg tctcccgagc tgtcactctt aaagcccatc   1200

gtagagacag gttcattaac tttatttttg aggaaactgt atattgagcg tcatgtgaaa   1260

tcgctactta taagttctgt gtgggttgca tctggatctg cgctgtagca tgatcctgtt   1320

tcatgggact tgttggcact tttgtgaaag gaggaggggg gctaccttcc tttaagatta   1380

cctaatatcc tgccttttat cctctttctc cccaggcatc tgaattccct tctgagctta   1440

tgtcgaatga tagcaaagta ctctgtggct aaataaatgg tgagtgttgc gggtgcctcc   1500
```

-continued tgtgtgcgcg tttcggtaat gtgcttgtgt gtctgttaaa tgtttggttt ggtaaatgca 1560
tgcttacttc actgtgttac gggtgccgct tgacttacca cataggcatg aaggggcttg 1620
tagctgtggt tgctcaggac tacagaacag ttgcctttac aaaaacagaa aagaaagaaa 1680
aaaaagaaag aaaagaaatg ccagtaactt actatgaagg tgtcaggacc aagtgtggct 1740
gacttttatg agcccagtgg cggtacactg aggtggtaac ctcagctgta attaatctta 1800
tcgccacaaa ttccatagtg attctctttt cccaaaact 1839

<210> SEQ ID NO 101
<211> LENGTH: 589
<212> TYPE: PRT
<213> ORGANISM: Mus musculus

<400> SEQUENCE: 101

Met Ala Leu Thr Asp Gly Gly Trp Cys Leu Pro Lys Arg Phe Gly Ala
1 5 10 15

Ala Ala Ala Asp Ala Gly Asp Ser Gly Pro Phe Pro Ala Arg Glu Pro
20 25 30

Ser Ser Pro Leu Ser Pro Ile Ser Ser Ser Ser Ser Ser Cys Ser Arg
35 40 45

Gly Gly Asp Arg Gly Pro Cys Gly Ala Ser Asn Cys Arg Thr Pro Gln
50 55 60

Leu Asp Ala Glu Ala Val Ala Gly Pro Pro Gly Arg Ser Leu Leu Leu
65 70 75 80

Ser Pro Tyr Ala Ser His Pro Phe Ala Ala Ala His Gly Ala Ala Ala
85 90 95

Pro Gly Val Ala Gly Pro Gly Ser Ala Leu Ser Thr Trp Glu Asp Leu
100 105 110

Leu Leu Phe Thr Asp Leu Asp Gln Ala Ala Thr Ala Ser Lys Leu Leu
115 120 125

Trp Ser Ser Arg Gly Ala Lys Leu Ser Pro Phe Ala Ala Glu Gln Pro
130 135 140

Glu Glu Met Tyr Gln Thr Leu Ala Ala Leu Ser Ser Gln Gly Pro Ala
145 150 155 160

Ala Tyr Asp Gly Ala Pro Gly Gly Phe Val His Ser Ala Ala Ala Ala
165 170 175

Ala Ala Ala Ala Ala Ala Ala Ser Ser Pro Val Tyr Val Pro Thr Thr
180 185 190

Arg Val Gly Ser Met Leu Ser Gly Leu Pro Tyr Leu Gln Gly Ala Gly
195 200 205

Ser Gly Pro Ser Asn His Ala Gly Gly Ala Gly Ala His Pro Gly Trp
210 215 220

Ser Gln Ala Ser Ala Asp Ser Pro Pro Tyr Gly Gly Gly Gly Ala Ala
225 230 235 240

Gly Gly Gly Ala Ala Gly Pro Gly Gly Ala Gly Ser Ala Thr Ala His
245 250 255

Ala Ser Ala Arg Phe Pro Tyr Ser Pro Ser Pro Pro Met Ala Asn Gly
260 265 270

Ala Ala Arg Asp Pro Gly Gly Tyr Val Ala Ala Gly Gly Thr Gly Ala
275 280 285

Gly Ser Val Ser Gly Gly Gly Gly Ser Leu Ala Ala Met Gly Gly Arg
290 295 300

Glu His Gln Tyr Ser Ser Leu Ser Ala Ala Arg Pro Leu Asn Gly Thr
305 310 315 320

```
Tyr His His His His His His His Pro Thr Tyr Ser Pro Tyr Met Ala
                325                 330                 335

Ala Pro Leu Thr Pro Ala Trp Pro Ala Gly Pro Phe Glu Thr Pro Val
            340                 345                 350

Leu His Ser Leu Gln Gly Arg Ala Gly Ala Pro Leu Pro Val Pro Arg
        355                 360                 365

Gly Pro Ser Thr Asp Leu Leu Glu Asp Leu Ser Glu Ser Arg Glu Cys
    370                 375                 380

Val Asn Cys Gly Ser Ile Gln Thr Pro Leu Trp Arg Arg Asp Gly Thr
385                 390                 395                 400

Gly His Tyr Leu Cys Asn Ala Cys Gly Leu Tyr Ser Lys Met Asn Gly
                405                 410                 415

Leu Ser Arg Pro Leu Ile Lys Pro Gln Lys Arg Val Pro Ser Ser Arg
            420                 425                 430

Arg Leu Gly Leu Ser Cys Ala Asn Cys His Thr Thr Thr Thr Thr Leu
        435                 440                 445

Trp Arg Arg Asn Ala Glu Gly Glu Pro Val Cys Asn Ala Cys Gly Leu
    450                 455                 460

Tyr Met Lys Leu His Gly Val Pro Arg Pro Leu Ala Met Lys Lys Glu
465                 470                 475                 480

Gly Ile Gln Thr Arg Lys Arg Lys Pro Lys Asn Ile Asn Lys Ser Lys
                485                 490                 495

Ala Cys Ser Gly Asn Ser Ser Gly Ser Val Pro Met Thr Pro Thr Ser
            500                 505                 510

Ser Ser Ser Asn Ser Asp Asp Cys Thr Lys Asn Thr Ser Pro Ser Thr
        515                 520                 525

Gln Ala Thr Thr Ser Gly Val Gly Ala Ser Val Met Ser Ala Val Gly
    530                 535                 540

Glu Asn Ala Asn Pro Glu Asn Ser Asp Leu Lys Tyr Ser Gly Gln Asp
545                 550                 555                 560

Gly Leu Tyr Ile Gly Val Ser Leu Ser Ser Pro Ala Glu Val Thr Ser
                565                 570                 575

Ser Val Arg Gln Asp Ser Trp Cys Ala Leu Ala Leu Ala
            580                 585


<210> SEQ ID NO 102
<211> LENGTH: 443
<212> TYPE: PRT
<213> ORGANISM: Mus musculus

<400> SEQUENCE: 102

Met Tyr Gln Thr Leu Ala Ala Leu Ser Ser Gln Gly Pro Ala Ala Tyr
1               5                   10                  15

Asp Gly Ala Pro Gly Gly Phe Val His Ser Ala Ala Ala Ala Ala Ala
            20                  25                  30

Ala Ala Ala Ala Ala Ser Ser Pro Val Tyr Val Pro Thr Thr Arg Val
        35                  40                  45

Gly Ser Met Leu Ser Gly Leu Pro Tyr Leu Gln Gly Ala Gly Ser Gly
    50                  55                  60

Pro Ser Asn His Ala Gly Gly Ala Gly Ala His Pro Gly Trp Ser Gln
65                  70                  75                  80

Ala Ser Ala Asp Ser Pro Pro Tyr Gly Gly Gly Gly Ala Ala Gly Gly
                85                  90                  95

Gly Ala Ala Gly Pro Gly Gly Ala Gly Ser Ala Thr Ala His Ala Ser
```

```
            100                 105                 110

Ala Arg Phe Pro Tyr Ser Pro Ser Pro Pro Met Ala Asn Gly Ala Ala
        115                 120                 125

Arg Asp Pro Gly Gly Tyr Val Ala Ala Gly Gly Thr Gly Ala Gly Ser
    130                 135                 140

Val Ser Gly Gly Gly Gly Ser Leu Ala Ala Met Gly Gly Arg Glu His
145                 150                 155                 160

Gln Tyr Ser Ser Leu Ser Ala Ala Arg Pro Leu Asn Gly Thr Tyr His
                165                 170                 175

His His His His His His Pro Thr Tyr Ser Pro Tyr Met Ala Ala Pro
            180                 185                 190

Leu Thr Pro Ala Trp Pro Ala Gly Pro Phe Glu Thr Pro Val Leu His
        195                 200                 205

Ser Leu Gln Gly Arg Ala Gly Ala Pro Leu Pro Val Pro Arg Gly Pro
    210                 215                 220

Ser Thr Asp Leu Leu Glu Asp Leu Ser Glu Ser Arg Glu Cys Val Asn
225                 230                 235                 240

Cys Gly Ser Ile Gln Thr Pro Leu Trp Arg Arg Asp Gly Thr Gly His
                245                 250                 255

Tyr Leu Cys Asn Ala Cys Gly Leu Tyr Ser Lys Met Asn Gly Leu Ser
            260                 265                 270

Arg Pro Leu Ile Lys Pro Gln Lys Arg Val Pro Ser Ser Arg Arg Leu
        275                 280                 285

Gly Leu Ser Cys Ala Asn Cys His Thr Thr Thr Thr Thr Leu Trp Arg
    290                 295                 300

Arg Asn Ala Glu Gly Glu Pro Val Cys Asn Ala Cys Gly Leu Tyr Met
305                 310                 315                 320

Lys Leu His Gly Val Pro Arg Pro Leu Ala Met Lys Lys Glu Gly Ile
                325                 330                 335

Gln Thr Arg Lys Arg Lys Pro Lys Asn Ile Asn Lys Ser Lys Ala Cys
            340                 345                 350

Ser Gly Asn Ser Ser Gly Ser Val Pro Met Thr Pro Thr Ser Ser Ser
        355                 360                 365

Ser Asn Ser Asp Asp Cys Thr Lys Asn Thr Ser Pro Ser Thr Gln Ala
    370                 375                 380

Thr Thr Ser Gly Val Gly Ala Ser Val Met Ser Ala Val Gly Glu Asn
385                 390                 395                 400

Ala Asn Pro Glu Asn Ser Asp Leu Lys Tyr Ser Gly Gln Asp Gly Leu
                405                 410                 415

Tyr Ile Gly Val Ser Leu Ser Ser Pro Ala Glu Val Thr Ser Ser Val
            420                 425                 430

Arg Gln Asp Ser Trp Cys Ala Leu Ala Leu Ala
        435                 440


<210> SEQ ID NO 103
<211> LENGTH: 372
<212> TYPE: PRT
<213> ORGANISM: Mus musculus

<400> SEQUENCE: 103

Met Ser Met Ser Pro Lys His Thr Thr Pro Phe Ser Val Ser Asp Ile
1               5                   10                  15

Leu Ser Pro Leu Glu Glu Ser Tyr Lys Lys Val Gly Met Glu Gly Gly
            20                  25                  30
```

Gly Leu Gly Ala Pro Leu Ala Ala Tyr Arg Gln Gly Gln Ala Ala Pro
35 40 45

Pro Ala Ala Ala Met Gln Gln His Ala Val Gly His His Gly Ala Val
50 55 60

Thr Ala Ala Tyr His Met Thr Ala Ala Gly Val Pro Gln Leu Ser His
65 70 75 80

Ser Ala Val Gly Gly Tyr Cys Asn Gly Asn Leu Gly Asn Met Ser Glu
85 90 95

Leu Pro Pro Tyr Gln Asp Thr Met Arg Asn Ser Ala Ser Gly Pro Gly
100 105 110

Trp Tyr Gly Ala Asn Pro Asp Pro Arg Phe Pro Ala Ile Ser Arg Phe
115 120 125

Met Gly Pro Ala Ser Gly Met Asn Met Ser Gly Met Gly Gly Leu Gly
130 135 140

Ser Leu Gly Asp Val Ser Lys Asn Met Ala Pro Leu Pro Ser Ala Pro
145 150 155 160

Arg Arg Lys Arg Arg Val Leu Phe Ser Gln Ala Gln Val Tyr Glu Leu
165 170 175

Glu Arg Arg Phe Lys Gln Gln Lys Tyr Leu Ser Ala Pro Glu Arg Glu
180 185 190

His Leu Ala Ser Met Ile His Leu Thr Pro Thr Gln Val Lys Ile Trp
195 200 205

Phe Gln Asn His Arg Tyr Lys Met Lys Arg Gln Ala Lys Asp Lys Ala
210 215 220

Ala Gln Gln Gln Leu Gln Gln Asp Ser Gly Gly Gly Gly Gly Gly Gly
225 230 235 240

Gly Gly Ala Gly Cys Pro Gln Gln Gln Gln Ala Gln Gln Gln Ser Pro
245 250 255

Arg Arg Val Ala Val Pro Val Leu Val Lys Asp Gly Lys Pro Cys Gln
260 265 270

Ala Gly Ala Pro Ala Pro Gly Ala Ala Ser Leu Gln Ser His Ala Gln
275 280 285

Gln Gln Ala Gln Gln Gln Ala Gln Ala Ala Gln Ala Ala Ala Ala Ala
290 295 300

Ile Ser Val Gly Ser Gly Gly Ala Gly Leu Gly Ala His Pro Gly His
305 310 315 320

Gln Pro Gly Ser Ala Gly Gln Ser Pro Asp Leu Ala His His Ala Ala
325 330 335

Ser Pro Ala Gly Leu Gln Gly Gln Val Ser Ser Leu Ser His Leu Asn
340 345 350

Ser Ser Gly Ser Asp Tyr Gly Ala Met Ser Cys Ser Thr Leu Leu Tyr
355 360 365

Gly Arg Thr Trp
370

<210> SEQ ID NO 104
<211> LENGTH: 465
<212> TYPE: PRT
<213> ORGANISM: Mus musculus

<400> SEQUENCE: 104

Met His Ser Ala Ser Ser Met Leu Gly Ala Val Lys Met Glu Gly His
1 5 10 15

Glu Pro Ser Asp Trp Ser Ser Tyr Tyr Ala Glu Pro Glu Gly Tyr Ser
20 25 30

-continued

```
Ser Val Ser Asn Met Asn Ala Gly Leu Gly Met Asn Gly Met Asn Thr
        35                  40                  45

Tyr Met Ser Met Ser Ala Ala Ala Met Gly Gly Gly Ser Gly Asn Met
    50                  55                  60

Ser Ala Gly Ser Met Asn Met Ser Ser Tyr Val Gly Ala Gly Met Ser
65                  70                  75                  80

Pro Ser Leu Ala Gly Met Ser Pro Gly Ala Gly Ala Met Ala Gly Met
                85                  90                  95

Ser Gly Ser Ala Gly Ala Ala Gly Val Ala Gly Met Gly Pro His Leu
            100                 105                 110

Ser Pro Ser Leu Ser Pro Leu Gly Gly Gln Ala Ala Gly Ala Met Gly
        115                 120                 125

Gly Leu Ala Pro Tyr Ala Asn Met Asn Ser Met Ser Pro Met Tyr Gly
    130                 135                 140

Gln Ala Gly Leu Ser Arg Ala Arg Asp Pro Lys Thr Tyr Arg Arg Ser
145                 150                 155                 160

Tyr Thr His Ala Lys Pro Pro Tyr Ser Tyr Ile Ser Leu Ile Thr Met
                165                 170                 175

Ala Ile Gln Gln Ser Pro Asn Lys Met Leu Thr Leu Ser Glu Ile Tyr
            180                 185                 190

Gln Trp Ile Met Asp Leu Phe Pro Phe Tyr Arg Gln Asn Gln Gln Arg
        195                 200                 205

Trp Gln Asn Ser Ile Arg His Ser Leu Ser Phe Asn Asp Cys Phe Leu
    210                 215                 220

Lys Val Pro Arg Ser Pro Asp Lys Pro Gly Lys Gly Ser Phe Trp Thr
225                 230                 235                 240

Leu His Pro Asp Ser Gly Asn Met Phe Glu Asn Gly Cys Tyr Leu Arg
                245                 250                 255

Arg Gln Lys Arg Phe Lys Cys Glu Lys Gln Leu Ala Leu Lys Glu Ala
            260                 265                 270

Ala Gly Ala Ala Ser Ser Gly Gly Lys Lys Thr Ala Pro Gly Ser Gln
        275                 280                 285

Ala Ser Gln Ala Gln Leu Gly Glu Ala Ala Gly Ser Ala Ser Glu Thr
    290                 295                 300

Pro Ala Gly Thr Glu Ser Pro His Ser Ser Ala Ser Pro Cys Gln Glu
305                 310                 315                 320

His Lys Arg Gly Gly Leu Ser Glu Leu Lys Gly Ala Pro Ala Ser Ala
                325                 330                 335

Leu Ser Pro Pro Glu Pro Ala Pro Ser Pro Gly Gln Gln Gln Gln Ala
            340                 345                 350

Ala Ala His Leu Leu Gly Pro Pro His His Pro Gly Leu Pro Pro Glu
        355                 360                 365

Ala His Leu Lys Pro Glu His His Tyr Ala Phe Asn His Pro Phe Ser
    370                 375                 380

Ile Asn Asn Leu Met Ser Ser Glu Gln Gln His His His Ser His His
385                 390                 395                 400

His His Gln Pro His Lys Met Asp Leu Lys Ala Tyr Glu Gln Val Met
                405                 410                 415

His Tyr Pro Gly Gly Tyr Gly Ser Pro Met Pro Gly Ser Leu Ala Met
            420                 425                 430

Gly Pro Val Thr Asn Lys Ala Gly Leu Asp Ala Ser Pro Leu Ala Ala
        435                 440                 445
```

```
Asp Thr Ser Tyr Tyr Gln Gly Val Tyr Ser Arg Pro Ile Met Asn Ser
    450                 455                 460

Ser
465


<210> SEQ ID NO 105
<211> LENGTH: 459
<212> TYPE: PRT
<213> ORGANISM: Mus musculus

<400> SEQUENCE: 105

Met Leu Gly Ala Val Lys Met Glu Gly His Glu Pro Ser Asp Trp Ser
1               5                   10                  15

Ser Tyr Tyr Ala Glu Pro Glu Gly Tyr Ser Ser Val Ser Asn Met Asn
            20                  25                  30

Ala Gly Leu Gly Met Asn Gly Met Asn Thr Tyr Met Ser Met Ser Ala
        35                  40                  45

Ala Ala Met Gly Gly Gly Ser Gly Asn Met Ser Ala Gly Ser Met Asn
    50                  55                  60

Met Ser Ser Tyr Val Gly Ala Gly Met Ser Pro Ser Leu Ala Gly Met
65                  70                  75                  80

Ser Pro Gly Ala Gly Ala Met Ala Gly Met Ser Gly Ser Ala Gly Ala
                85                  90                  95

Ala Gly Val Ala Gly Met Gly Pro His Leu Ser Pro Ser Leu Ser Pro
            100                 105                 110

Leu Gly Gly Gln Ala Ala Gly Ala Met Gly Gly Leu Ala Pro Tyr Ala
        115                 120                 125

Asn Met Asn Ser Met Ser Pro Met Tyr Gly Gln Ala Gly Leu Ser Arg
    130                 135                 140

Ala Arg Asp Pro Lys Thr Tyr Arg Arg Ser Tyr Thr His Ala Lys Pro
145                 150                 155                 160

Pro Tyr Ser Tyr Ile Ser Leu Ile Thr Met Ala Ile Gln Gln Ser Pro
                165                 170                 175

Asn Lys Met Leu Thr Leu Ser Glu Ile Tyr Gln Trp Ile Met Asp Leu
            180                 185                 190

Phe Pro Phe Tyr Arg Gln Asn Gln Gln Arg Trp Gln Asn Ser Ile Arg
        195                 200                 205

His Ser Leu Ser Phe Asn Asp Cys Phe Leu Lys Val Pro Arg Ser Pro
    210                 215                 220

Asp Lys Pro Gly Lys Gly Ser Phe Trp Thr Leu His Pro Asp Ser Gly
225                 230                 235                 240

Asn Met Phe Glu Asn Gly Cys Tyr Leu Arg Arg Gln Lys Arg Phe Lys
                245                 250                 255

Cys Glu Lys Gln Leu Ala Leu Lys Glu Ala Ala Gly Ala Ala Ser Ser
            260                 265                 270

Gly Gly Lys Lys Thr Ala Pro Gly Ser Gln Ala Ser Gln Ala Gln Leu
        275                 280                 285

Gly Glu Ala Ala Gly Ser Ala Ser Glu Thr Pro Ala Gly Thr Glu Ser
    290                 295                 300

Pro His Ser Ser Ala Ser Pro Cys Gln Glu His Lys Arg Gly Gly Leu
305                 310                 315                 320

Ser Glu Leu Lys Gly Ala Pro Ala Ser Ala Leu Ser Pro Pro Glu Pro
                325                 330                 335

Ala Pro Ser Pro Gly Gln Gln Gln Gln Ala Ala Ala His Leu Leu Gly
            340                 345                 350
```

```
Pro Pro His His Pro Gly Leu Pro Pro Glu Ala His Leu Lys Pro Glu
        355                 360                 365

His His Tyr Ala Phe Asn His Pro Phe Ser Ile Asn Asn Leu Met Ser
    370                 375                 380

Ser Glu Gln Gln His His His Ser His His His His Gln Pro His Lys
385                 390                 395                 400

Met Asp Leu Lys Ala Tyr Glu Gln Val Met His Tyr Pro Gly Gly Tyr
                405                 410                 415

Gly Ser Pro Met Pro Gly Ser Leu Ala Met Gly Pro Val Thr Asn Lys
            420                 425                 430

Ala Gly Leu Asp Ala Ser Pro Leu Ala Ala Asp Thr Ser Tyr Tyr Gln
        435                 440                 445

Gly Val Tyr Ser Arg Pro Ile Met Asn Ser Ser
    450                 455


<210> SEQ ID NO 106
<211> LENGTH: 134
<212> TYPE: PRT
<213> ORGANISM: Mus musculus

<400> SEQUENCE: 106

Met Lys Ala Phe Ser Pro Val Arg Ser Val Arg Lys Asn Ser Leu Ser
1               5                   10                  15

Asp His Ser Leu Gly Ile Ser Arg Ser Lys Thr Pro Val Asp Asp Pro
            20                  25                  30

Met Ser Leu Leu Tyr Asn Met Asn Asp Cys Tyr Ser Lys Leu Lys Glu
        35                  40                  45

Leu Val Pro Ser Ile Pro Gln Asn Lys Lys Val Thr Lys Met Glu Ile
    50                  55                  60

Leu Gln His Val Ile Asp Tyr Ile Leu Asp Leu Gln Ile Ala Leu Asp
65                  70                  75                  80

Ser His Pro Thr Ile Val Ser Leu His His Gln Arg Pro Gly Gln Asn
                85                  90                  95

Gln Ala Ser Arg Thr Pro Leu Thr Thr Leu Asn Thr Asp Ile Ser Ile
            100                 105                 110

Leu Ser Leu Gln Ala Ser Glu Phe Pro Ser Glu Leu Met Ser Asn Asp
        115                 120                 125

Ser Lys Val Leu Cys Gly
    130


<210> SEQ ID NO 107
<211> LENGTH: 155
<212> TYPE: PRT
<213> ORGANISM: Mus musculus

<400> SEQUENCE: 107

Met Lys Ala Phe Ser Pro Val Arg Ser Val Arg Lys Asn Ser Leu Ser
1               5                   10                  15

Asp His Ser Leu Gly Ile Ser Arg Ser Lys Thr Pro Val Asp Asp Pro
            20                  25                  30

Met Ser Leu Leu Tyr Asn Met Asn Asp Cys Tyr Ser Lys Leu Lys Glu
        35                  40                  45

Leu Val Pro Ser Ile Pro Gln Asn Lys Lys Val Thr Lys Met Glu Ile
    50                  55                  60

Leu Gln His Val Ile Asp Tyr Ile Leu Asp Leu Gln Ile Ala Leu Asp
65                  70                  75                  80
```

```
Ser His Pro Thr Ile Val Ser Leu His His Gln Arg Pro Gly Gln Asn
                85                  90                  95

Gln Ala Ser Arg Thr Pro Leu Thr Thr Leu Asn Thr Asp Ile Ser Ile
            100                 105                 110

Leu Ser Leu Gln Val Arg Leu Ala Cys Lys Tyr Ala Thr Ala Gln Thr
        115                 120                 125

Leu Arg Val Ser Arg Ala Val Thr Leu Lys Ala His Arg Arg Asp Arg
    130                 135                 140

Phe Ile Asn Phe Ile Phe Glu Glu Thr Val Tyr
145                 150                 155
```

<210> SEQ ID NO 108
<211> LENGTH: 2977
<212> TYPE: DNA
<213> ORGANISM: Homo sapiens

<400> SEQUENCE: 108

```
gggccgctct ctgacatcag agctgctgta gagcggagag gggcaggggt gaagggccac     60

ggtggtgcaa cccaccactt cctccaagga ggagctgaga ggaacaggaa gtgtcaggac    120

tttacgaccc gcgcctccag ctgaggtttc tagacgtgac ccagggcaga ctggtagcaa    180

agccccccacg cccagccagg agcaccgccg aggactccag cacaccgagg gacatgctgg    240

gcctgcgccc cccactgctc gccctggtgg ggctgctctc cctcgggtgc gtcctctctc    300

aggagtgcac gaagttcaag gtcagcagct gccgggaatg catcgagtcg gggcccggct    360

gcacctggtg ccagaagctg aacttcacag ggccgggga tcctgactcc attcgctgcg    420

acacccggcc acagctgctc atgaggggct gtgcggctga cgacatcatg gaccccacaa    480

gcctcgctga aacccaggaa gaccacaatg gggccagaa gcagctgtcc ccacaaaaag    540

tgacgcttta cctgcgacca ggccaggcag cagcgttcaa cgtgaccttc cggcgggcca    600

agggctaccc catcgacctg tactatctga tggacctctc ctactccatg cttgatgacc    660

tcaggaatgt caagaagcta ggtggcgacc tgctccgggc cctcaacgag atcaccgagt    720

ccggccgcat tggcttcggg tccttcgtgg acaagaccgt gctgccgttc gtgaacacgc    780

accctgataa gctgcgaaac ccatgcccca acaaggagaa agagtgccag cccccgtttg    840

ccttcaggca cgtgctgaag ctgaccaaca actccaacca gtttcagacc gaggtcggga    900

agcagctgat ttccggaaac ctggatgcac ccgagggtgg gctggacgcc atgatgcagg    960

tcgccgcctg cccggaggaa atcggctggc gcaacgtcac gcggctgctg gtgtttgcca   1020

ctgatgacgg cttccatttc gcgggcgacg ggaagctggg cgccatcctg acccccaacg   1080

acggccgctg tcacctggag gacaacttgt acaagaggag caacgaattc gactacccat   1140

cggtgggcca gctggcgcac aagctggctg aaaacaacat ccagcccatc ttcgcggtga   1200

ccagtaggat ggtgaagacc tacgagaaac tcaccgagat catccccaag tcagccgtgg   1260

gggagctgtc tgaggactcc agcaatgtgg tccaactcat taagaatgct tacaataaac   1320

tctcctccag ggtcttcctg gatcacaacg ccctccccga caccctgaaa gtcacctacg   1380

actccttctg cagcaatgga gtgacgcaca ggaaccagcc cagaggtgac tgtgatggcg   1440

tgcagatcaa tgtcccgatc accttccagg tgaaggtcac ggccacagag tgcatccagg   1500

agcagtcgtt tgtcatccgg gcgctgggct tcacggacat agtgaccgtg caggttcttc   1560

cccagtgtga gtgccggtgc cgggaccaga gcagagaccg cagcctctgc catggcaagg   1620

gcttcttgga gtgcggcatc tgcaggtgtg acactggcta cattgggaaa aactgtgagt   1680
```

gccagacaca gggccggagc agccaggagc tggaaggaag ctgccggaag gacaacaact 1740
ccatcatctg ctcagggctg ggggactgtg tctgcgggca gtgcctgtgc cacaccagcg 1800
acgtccccgg caagctgata tacgggcagt actgcgagtg tgacaccatc aactgtgagc 1860
gctacaacgg ccaggtctgc ggcggcccgg ggaggggggct ctgcttctgc gggaagtgcc 1920
gctgccaccc gggctttgag ggctcagcgt gccagtgcga gaggaccact gagggctgcc 1980
tgaacccgcg gcgtgttgag tgtagtggtc gtggccggtg ccgctgcaac gtatgcgagt 2040
gccattcagg ctaccagctg cctctgtgcc aggagtgccc cggctgcccc tcaccctgtg 2100
gcaagtacat ctcctgcgcc gagtgcctga agttcgaaaa gggccccttt gggaagaact 2160
gcagcgcggc gtgtccgggc ctgcagctgt cgaacaaccc cgtgaagggc aggacctgca 2220
aggagaggga ctcagagggc tgctgggtgg cctacacgct ggagcagcag gacgggatgg 2280
accgctacct catctatgtg gatgagagcc gagagtgtgt ggcaggcccc aacatcgccg 2340
ccatcgtcgg gggcaccgtg gcaggcatcg tgctgatcgg cattctcctg ctggtcatct 2400
ggaaggctct gatccacctg agcgacctcc gggagtacag gcgctttgag aaggagaagc 2460
tcaagtccca gtggaacaat gataatcccc ttttcaagag cgccaccacg acggtcatga 2520
accccaagtt tgctgagagt taggagcact tggtgaagac aaggccgtca ggacccacca 2580
tgtctgcccc atcacgcggc cgagacatgg cttgccacag ctcttgagga tgtcaccaat 2640
taaccagaaa tccagttatt ttccgccctc aaaatgacag ccatggccgg ccgggtgctt 2700
ctgggggctc gtcgggggga cagctccact ctgactggca cagtctttgc atggagactt 2760
gaggagggag ggcttgaggt tggtgaggtt aggtgcgtgt ttcctgtgca agtcaggaca 2820
tcagtctgat taaaggtggt gccaatttat ttacatttaa acttgtcagg gtataaaatg 2880
acatcccatt aattatattg ttaatcaatc acgtgtatag aaaaaaaata aaacttcaat 2940
acaggctgtc catggaaaaa aaaaaaaaaa aaaaaaa 2977

<210> SEQ ID NO 109
<211> LENGTH: 2932
<212> TYPE: DNA
<213> ORGANISM: Homo sapiens

<400> SEQUENCE: 109
atccagggtg aggaaggcag cccacacttt tcttggagac acatccccaa agaagtcctc 60
acgtggctcc gtttgggcag aaaccatgaa ttgaacggga aaagaaatat gtcaagtatc 120
agaaagaaga gtggcatgct ttgacagcaa gtggactccg agtccagggc agagcctcag 180
ttagggacat gctgggcctg cgccccccac tgctcgccct ggtggggctg ctctccctcg 240
ggtgcgtcct ctctcaggag tgcacgaagt tcaaggtcag cagctgccgg gaatgcatcg 300
agtcggggcc cggctgcacc tggtgccaga agctgaactt cacagggccg gggggatcctg 360 actccattcg ctgcgacacc cggccacagc tgctcatgag ggctgtgcg gctgacgaca 420 tcatggaccc cacaagcctc gctgaaaccc aggaagacca caatgggggc cagaagcagc 480
tgtccccaca aaaagtgacg ctttacctgc gaccaggcca ggcagcagcg ttcaacgtga 540
ccttccggcg ggccaagggc taccccatcg acctgtacta tctgatggac ctctcctact 600
ccatgcttga tgacctcagg aatgtcaaga agctaggtgg cgacctgctc cgggccctca 660
acgagatcac cgagtccggc cgcattggct tcgggtcctt cgtggacaag accgtgctgc 720
cgttcgtgaa cacgcaccct gataagctgc gaaacccatg ccccaacaag gagaaagagt 780

-continued

```
gccagccccc gtttgccttc aggcacgtgc tgaagctgac caacaactcc aaccagtttc    840
agaccgaggt cgggaagcag ctgatttccg gaaacctgga tgcacccgag ggtgggctgg    900
acgccatgat gcaggtcgcc gcctgcccgg aggaaatcgg ctggcgcaac gtcacgcggc    960
tgctggtgtt tgccactgat gacggcttcc atttcgcggg cgacgggaag ctgggcgcca   1020
tcctgacccc caacgacggc cgctgtcacc tggaggacaa cttgtacaag aggagcaacg   1080
aattcgacta cccatcggtg ggccagctgg cgcacaagct ggctgaaaac aacatccagc   1140
ccatcttcgc ggtgaccagt aggatggtga agacctacga gaaactcacc gagatcatcc   1200
ccaagtcagc cgtggggggag ctgtctgagg actccagcaa tgtggtccaa ctcattaaga   1260
atgcttacaa taaactctcc tccagggtct tcctggatca caacgccctc cccgacaccc   1320
tgaaagtcac ctacgactcc ttctgcagca atggagtgac gcacaggaac cagcccagag   1380
gtgactgtga tggcgtgcag atcaatgtcc cgatcacctt ccaggtgaag gtcacggcca   1440
cagagtgcat ccaggagcag tcgtttgtca tccgggcgct gggcttcacg gacatagtga   1500
ccgtgcaggt tcttccccag tgtgagtgcc ggtgccggga ccagagcaga gaccgcagcc   1560
tctgccatgg caagggcttc ttggagtgcg gcatctgcag gtgtgacact ggctacattg   1620
ggaaaaactg tgagtgccag acacagggcc ggagcagcca ggagctggaa ggaagctgcc   1680
ggaaggacaa caactccatc atctgctcag ggctggggga ctgtgtctgc gggcagtgcc   1740
tgtgccacac cagcgacgtc cccggcaagc tgatatacgg gcagtactgc gagtgtgaca   1800
ccatcaactg tgagcgctac aacggccagg tctgcggcgg cccggggagg gggctctgct   1860
tctgcgggaa gtgccgctgc cacccgggct ttgagggctc agcgtgccag tgcgagagga   1920
ccactgaggg ctgcctgaac ccgcggcgtg ttgagtgtag tggtcgtggc cggtgccgct   1980
gcaacgtatg cgagtgccat tcaggctacc agctgcctct gtgccaggag tgccccggct   2040
gcccctcacc ctgtggcaag tacatctcct gcgccgagtg cctgaagttc gaaaagggcc   2100
cctttgggaa gaactgcagc gcggcgtgtc cgggcctgca gctgtcgaac aaccccgtga   2160
agggcaggac ctgcaaggag agggactcag agggctgctg ggtggcctac acgctggagc   2220
agcaggacgg gatggaccgc tacctcatct atgtggatga gagccgagag tgtgtggcag   2280
gccccaacat cgccgccatc gtcgggggca ccgtggcagg catcgtgctg atcggcattc   2340
tcctgctggt catctggaag gctctgatcc acctgagcga cctccgggag tacaggcgct   2400
ttgagaagga gaagctcaag tcccagtgga acaatgataa tccccttttc aagagcgcca   2460
ccacgacggt catgaacccc aagtttgctg agagttagga gcacttggtg aagacaaggc   2520
cgtcaggacc caccatgtct gccccatcac gcggccgaga catggcttgc cacagctctt   2580
gaggatgtca ccaattaacc agaaatccag ttattttccg ccctcaaaat gacagccatg   2640
gccggccggg tgcttctggg ggctcgtcgg ggggacagct ccactctgac tggcacagtc   2700
tttgcatgga gacttgagga gggagggctt gaggttggtg aggttaggtg cgtgtttcct   2760
gtgcaagtca ggacatcagt ctgattaaag gtggtgccaa tttatttaca tttaaacttg   2820
tcagggtata aaatgacatc ccattaatta tattgttaat caatcacgtg tatagaaaaa   2880
aaataaaact tcaatacagg ctgtccatgg aaaaaaaaaa aaaaaaaaaa aa           2932
```

<210> SEQ ID NO 110
<211> LENGTH: 769
<212> TYPE: PRT
<213> ORGANISM: Homo sapiens

<400> SEQUENCE: 110

-continued

```
Met Leu Gly Leu Arg Pro Pro Leu Leu Ala Leu Val Gly Leu Leu Ser
1               5                   10                  15

Leu Gly Cys Val Leu Ser Gln Glu Cys Thr Lys Phe Lys Val Ser Ser
            20                  25                  30

Cys Arg Glu Cys Ile Glu Ser Gly Pro Gly Cys Thr Trp Cys Gln Lys
        35                  40                  45

Leu Asn Phe Thr Gly Pro Gly Asp Pro Asp Ser Ile Arg Cys Asp Thr
    50                  55                  60

Arg Pro Gln Leu Leu Met Arg Gly Cys Ala Ala Asp Asp Ile Met Asp
65                  70                  75                  80

Pro Thr Ser Leu Ala Glu Thr Gln Glu Asp His Asn Gly Gly Gln Lys
                85                  90                  95

Gln Leu Ser Pro Gln Lys Val Thr Leu Tyr Leu Arg Pro Gly Gln Ala
            100                 105                 110

Ala Ala Phe Asn Val Thr Phe Arg Arg Ala Lys Gly Tyr Pro Ile Asp
        115                 120                 125

Leu Tyr Tyr Leu Met Asp Leu Ser Tyr Ser Met Leu Asp Asp Leu Arg
    130                 135                 140

Asn Val Lys Lys Leu Gly Gly Asp Leu Leu Arg Ala Leu Asn Glu Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Asp Lys Leu Arg Asn Pro Cys Pro
            180                 185                 190

Asn Lys Glu Lys Glu Cys Gln Pro Pro Phe Ala Phe Arg His Val Leu
        195                 200                 205

Lys Leu Thr Asn Asn Ser Asn Gln Phe Gln Thr Glu Val Gly Lys Gln
    210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
            260                 265                 270

Gly Lys Leu Gly Ala Ile Leu Thr Pro Asn Asp Gly Arg Cys His Leu
        275                 280                 285

Glu Asp Asn Leu Tyr Lys Arg Ser Asn Glu Phe Asp Tyr Pro Ser Val
    290                 295                 300

Gly Gln Leu Ala His Lys Leu Ala Glu Asn Asn Ile Gln Pro Ile Phe
305                 310                 315                 320

Ala Val Thr Ser Arg Met Val Lys Thr Tyr Glu Lys Leu Thr Glu Ile
                325                 330                 335

Ile Pro Lys Ser Ala Val Gly Glu Leu Ser Glu Asp Ser Ser Asn Val
            340                 345                 350

Val Gln Leu Ile Lys Asn Ala Tyr Asn Lys Leu Ser Ser Arg Val Phe
        355                 360                 365

Leu Asp His Asn Ala Leu Pro Asp Thr Leu Lys Val Thr Tyr Asp Ser
    370                 375                 380

Phe Cys Ser Asn Gly Val Thr His Arg Asn Gln Pro Arg Gly Asp Cys
385                 390                 395                 400

Asp Gly Val Gln Ile Asn Val Pro Ile Thr Phe Gln Val Lys Val Thr
                405                 410                 415
```

```
Ala Thr Glu Cys Ile Gln Glu Gln Ser Phe Val Ile Arg Ala Leu Gly
            420                 425                 430

Phe Thr Asp Ile Val Thr Val Gln Val Leu Pro Gln Cys Glu Cys Arg
        435                 440                 445

Cys Arg Asp Gln Ser Arg Asp Arg Ser Leu Cys His Gly Lys Gly Phe
    450                 455                 460

Leu Glu Cys Gly Ile Cys Arg Cys Asp Thr Gly Tyr Ile Gly Lys Asn
465                 470                 475                 480

Cys Glu Cys Gln Thr Gln Gly Arg Ser Ser Gln Glu Leu Glu Gly Ser
                485                 490                 495

Cys Arg Lys Asp Asn Asn Ser Ile Ile Cys Ser Gly Leu Gly Asp Cys
            500                 505                 510

Val Cys Gly Gln Cys Leu Cys His Thr Ser Asp Val Pro Gly Lys Leu
        515                 520                 525

Ile Tyr Gly Gln Tyr Cys Glu Cys Asp Thr Ile Asn Cys Glu Arg Tyr
    530                 535                 540

Asn Gly Gln Val Cys Gly Gly Pro Gly Arg Gly Leu Cys Phe Cys Gly
545                 550                 555                 560

Lys Cys Arg Cys His Pro Gly Phe Glu Gly Ser Ala Cys Gln Cys Glu
                565                 570                 575

Arg Thr Thr Glu Gly Cys Leu Asn Pro Arg Arg Val Glu Cys Ser Gly
            580                 585                 590

Arg Gly Arg Cys Arg Cys Asn Val Cys Glu Cys His Ser Gly Tyr Gln
        595                 600                 605

Leu Pro Leu Cys Gln Glu Cys Pro Gly Cys Pro Ser Pro Cys Gly Lys
    610                 615                 620

Tyr Ile Ser Cys Ala Glu Cys Leu Lys Phe Glu Lys Gly Pro Phe Gly
625                 630                 635                 640

Lys Asn Cys Ser Ala Ala Cys Pro Gly Leu Gln Leu Ser Asn Asn Pro
                645                 650                 655

Val Lys Gly Arg Thr Cys Lys Glu Arg Asp Ser Glu Gly Cys Trp Val
            660                 665                 670

Ala Tyr Thr Leu Glu Gln Gln Asp Gly Met Asp Arg Tyr Leu Ile Tyr
        675                 680                 685

Val Asp Glu Ser Arg Glu Cys Val Ala Gly Pro Asn Ile Ala Ala Ile
    690                 695                 700

Val Gly Gly Thr Val Ala Gly Ile Val Leu Ile Gly Ile Leu Leu Leu
705                 710                 715                 720

Val Ile Trp Lys Ala Leu Ile His Leu Ser Asp Leu Arg Glu Tyr Arg
                725                 730                 735

Arg Phe Glu Lys Glu Lys Leu Lys Ser Gln Trp Asn Asn Asp Asn Pro
            740                 745                 750

Leu Phe Lys Ser Ala Thr Thr Thr Val Met Asn Pro Lys Phe Ala Glu
        755                 760                 765

Ser
```

<210> SEQ ID NO 111
<211> LENGTH: 5603
<212> TYPE: DNA
<213> ORGANISM: Homo sapiens

<400> SEQUENCE: 111

```
ggagtgggcc aggccgccag ccccgccagc cccgccagcc ccgccagccc cgcgatggct      60

tgggccgcgc tcctcggcct cctggccgca ctgttgctgc tgctgctact gagccgccgc     120
```

-continued

```
cgcacgcggc gacctggtga gcctcccctg gacctgggca gcatcccctg gttggggtat    180
gccttggact ttggaaaaga tgctgccagc ttcctcacga ggatgaagga gaagcacggt    240
gacatcttta ctatactggt tgggggcagg tatgtcaccg ttctcctgga cccacactcc    300
tacgacgcgg tggtgtggga gcctcgcacc aggctcgact tccatgccta tgccatcttc    360
ctcatggaga ggatttttga tgtgcagctt ccacattaca gccccagtga tgaaaaggcc    420
aggatgaaac tgactcttct ccacagagag ctccaggcac tcacagaagc catgtatacc    480
aacctccatg cagtgctgtt gggcgatgct acagaagcag gcagtggctg gcacgagatg    540
ggtctcctcg acttctccta cagcttcctg ctcagagccg gctacctgac tctttacgga    600
attgaggcgc tgccacgcac ccatgaaagc caggcccagg accgcgtcca ctcagctgat    660
gtcttccaca cctttcgcca gctcgaccgg ctgctcccca aactggcccg tggctccctg    720
tcagtggggg acaaggacca catgtgcagt gtcaaaagtc gcctgtggaa gctgctatcc    780
ccagccaggc tggccaggcg ggcccaccgg agcaaatggc tggagagtta cctgctgcac    840
ctggaggaga tgggtgtgtc agaggagatg caggcacggg ccctggtgct gcagctgtgg    900
gccacacagg ggaatatggg tcccgctgcc ttctggctcc tgctcttcct tctcaagaat    960
cctgaagccc tggctgctgt ccgcggagag ctcgagagta tcctttggca agcggagcag   1020
cctgtctcgc agacgaccac tctcccacag aaggttctag acagcacacc tgtgcttgat   1080
agcgtgctga gtgagagcct caggcttaca gctgccccct tcatcacccg cgaggttgtg   1140
gtggacctgg ccatgcccat ggcagacggg cgagaattca acctgcgacg tggtgaccgc   1200
ctcctcctct tccccttcct gagcccccag agagacccag aaatctacac agacccagag   1260
gtatttaaat acaaccgatt cctgaaccct gacggatcag agaagaaaga cttttacaag   1320
gatgggaaac ggctgaagaa ttacaacatg ccctgggggg cggggcacaa tcactgcctg   1380
gggaggagtt atgcggtcaa cagcatcaaa caatttgtgt tccttgtgct ggtgcacttg   1440
gacttggagc tgatcaacgc agatgtggag atccctgagt ttgacctcag caggtacggc   1500
ttcggtctga tgcagccgga acacgacgtg cccgtccgct accgcatccg cccatgacac   1560
agggagcaga tggatccacg tgctcgcctc tgcccagcct gccccagcct gccccagcct   1620
cccagctttc tgtgtgcaca gttggcccgg gtgcaggtgc tagcattacc acttccctgc   1680
ttttctccca gaaggctggg tccaggggag ggaaaagcta agagggtgaa caaagaaaag   1740
acattgaaag ctctatggat tatccactgc aaagttttct ttccaaaatc aggctttgtc   1800
tgctcccaat tcacctcgtt actctcacct cgtgatatcc acaaatgcta ttcagataag   1860
gcagaactag gagtcttcac tgctctgccc ccaactcccg gaggtgtcac cttcctagtt   1920
cttatgagct agcatggccc gggccttatc cagtcaaagc ggatgctggc cacagaaagg   1980
ccactcagga tgtcctttgt gtccattgat gtcattcagc agtcagtccc ccaataatcc   2040
ttaaactagc taaaaccaaa ggagtccctt agaagatctg cttccctggg gccccatttg   2100
ccagattgcc ccattgctca cactacttga gaaaatgcag gagagcttcc cccaaggctg   2160
atgcattccc ggtgcagaac aggggcaccc tccaaacact gggctctgag gagtggagtt   2220
ctctgttcta gagtgacagg caccagatgg gatgggcttt ctcagtgtca gcactcaggt   2280
agggagctaa ggaagacaca gcccagacaa gatggctgga aggagccagc caggactcct   2340
tagactgatc aagccaaaaa agaaggtgcc gatttcatgc attctagtgc agaagcccca   2400
actgtgatca cgatccagtc tgcagacgtg ttttgtttgg acttcactta aaaaaatgcc   2460
```

ttagttgtta tcatctttgg gagagttcat tcaaaatgtc cagcttctct tgaaaacttg 2520
gtatatctgg ccacactggg ctcacattcc caagggtaac tcttggccag agctgagtgg 2580
cagccgcctc ccttatgcag gacatgtgct ctcggcttca ccagggttct gaccgggtct 2640
gcttctgcat tcacagcgcc tcctggacct gaaggcatct gagtgtgaga ccctgttcta 2700
actcttagaa gtgacattgt aagaggtggt ggggaccagc taattggtcc aacccagcct 2760
gagtgcacca ccctttgaac aaatgtatca gtgatgaaaa tttgcctttg ccccggcttg 2820
cctgtaatcc cagcactttg ggaggccgag gtgggcggat cacttgaggt cgggagttca 2880
agaccagcct ggccaacatg gcgaaacccc gtctctacta aacataaaaa aattagtcag 2940
gtgtggcggt gcgtgcctgt aatcccagct attcaggagg ctgaggcacc agaattgctt 3000
gaacccagga ggtggaggtt gcagtgaact gagactgcgc cacggcactc cagcctgggc 3060
gacagagcaa gactctgtct caataaataa ataattaatt aaaataaaaa acagcttaaa 3120
gagaaaaatg gcctgcaaac ctttttttatg atgctatttt tattaatata aagtcctgtt 3180
tattgagacc ctttaaatgc ctgcgagaga ccctacagac agtatgtcta ctcctcacag 3240
catctctatg aagagaagga gggttgtgcc cacttcatag atgagaaaac tgagaggtga 3300
ggtgacttgc ctggggccac atagctcata agctgtagaa ctctgcaggc agatttactg 3360
tcccaggagc aaatgctgga tgagcaactc ctgttctttg ggctcaaggg gactggtgat 3420
gggacaattc ttctcgactt caggagctga cagagccaga ggcacctaaa cttgggtaca 3480
tcttgtaaga cacataatga ggtccctcta gctttagctg gagggagata aaagaacccc 3540
agacctctga atgtcccaga ggctagtctc ttctcagagc agcactgggg tttgggggct 3600
tccctgggcc tcagcctcca ggcacccccca ggattcccag agagacgctg tgattggcag 3660
gaggcaggat atccccaggg aaacccatct tcacgcctgg gtgacccccca ctgccgcctc 3720
cttcttaact ctgcaggaaa tcagagctgg cagcctccag tgggaggaca gagccggttt 3780
ccgtggcaac cctcagctgc ctcatcgtgg ctgggaaggg aaggaagcaa gccggcagaa 3840
atagctatgg aaggtcttgc gcaggctgca accctggtgt gctgggcgaa aacccttatg 3900
actccccccct tccaaatcag gctgggttgt cactgagact agattctcac ctgccttcaa 3960
agaagggcca attcccttta aaggtcgcac ctccttggaa ccacagtcat tagtgaatta 4020
cactcaagga aaagatgtgc tcccaccagg cagctccagc tgttacctga gatactgaag 4080
tgcagctcag gagacgatta tttaaacctg cccttgtttt aatcgttatt tttctcttta 4140
aaaaaaatag aagctataaa gaaaagaggg agagatgagt gggttagcta cctgctatgc 4200
gctagttagg aagttacctg gatgccattg tatttcttca tcccttgctt aagaatcaaa 4260
attactggac atatgttagg aatactcttt ctttctttct ttctttttaa gctcagtggc 4320
aagaatgaaa tactcttttt tttttttttt ttttgagatg gagtctcgct ctgctgccca 4380
ggctagagtg cagtggcgtg atctcggctc actgcaagct ctgcctcccg tgttcacacc 4440
attctcctgc ctcagcctcc tgagtagctg ggactacagg cacccgccac cacacccggc 4500
taatttttgg atttttagta gagatgggat ttcaccgtat tagccaggat ggtcttgatc 4560
tcctgagctc gtgatctgcc cgcctcggcc tcccaaagtg ctgggattac aggtgtgagc 4620
caccgcgccc agccaagaat aaaatactct taagttgatc taatgaagtg tttccttacc 4680
attgtgatta ttgttactat tatttgctat attttaatat tgttgtttac caaatattct 4740
cctttaaaca gactcgcttt ttaaactttt tttttttttt ttgagacgga gtttcacgct 4800
tattgcccag gctggagtgc aatggcacga tctcagctca ccacaacctc cacctcctgg 4860
gtttaagcaa tgcttctgcc tcagcttccc aagtagctga gattacaggc gcacaccacc 4920
acgcccaact gatttttgta tttttagtag agacggggtt tccccatgtt ggtcaggctg 4980
gtctcgaact cctgacctcg tgatttgcct gcctgggcct cccaaagtgc taggattaca 5040
ggcatgagcc accatgcccg gcctaaactt tgtttttaaa atgaactttt tttcccccca 5100
attgctgcca atagtggata acatgtatca ctcactgcca aaaatagaaa gtgaccatga 5160
aaaataaatt cgctggggaa gggggctcca tgctggtgtg gccaaggctg agagctctct 5220
cttctctgtt acaaaacgag ataagcaagt gttagaattg ccttaaggcc acactggcat 5280
ctccctgacc ttctccaggg acagaagcag gagtaagttt ctcatcccat gggcgaccag 5340
ggccatctcc tcccaccagt ggcccccact cacagggagc tggcaatgcc ctacctgcct 5400
gttctccaga tggagaaaca ggctctgaga tttcacaggt cttgcccaaa gtcattgatt 5460
ttgatgatta aaaagaataa acacagtgtt tcctgagtag cagtgattgt tatgccttgc 5520
tattttaata aagattctat tttcgtataa cattgtcaag tggaaacatg ctgaaatcta 5580
ttaaaccatc tttgtttgtg gaa 5603

<210> SEQ ID NO 112
<211> LENGTH: 500
<212> TYPE: PRT
<213> ORGANISM: Homo sapiens

<400> SEQUENCE: 112

Met Ala Trp Ala Ala Leu Leu Gly Leu Leu Ala Ala Leu Leu Leu Leu
1 5 10 15

Leu Leu Leu Ser Arg Arg Arg Thr Arg Arg Pro Gly Glu Pro Pro Leu
20 25 30

Asp Leu Gly Ser Ile Pro Trp Leu Gly Tyr Ala Leu Asp Phe Gly Lys
35 40 45

Asp Ala Ala Ser Phe Leu Thr Arg Met Lys Glu Lys His Gly Asp Ile
50 55 60

Phe Thr Ile Leu Val Gly Gly Arg Tyr Val Thr Val Leu Leu Asp Pro
65 70 75 80

His Ser Tyr Asp Ala Val Val Trp Glu Pro Arg Thr Arg Leu Asp Phe
85 90 95

His Ala Tyr Ala Ile Phe Leu Met Glu Arg Ile Phe Asp Val Gln Leu
100 105 110

Pro His Tyr Ser Pro Ser Asp Glu Lys Ala Arg Met Lys Leu Thr Leu
115 120 125

Leu His Arg Glu Leu Gln Ala Leu Thr Glu Ala Met Tyr Thr Asn Leu
130 135 140

His Ala Val Leu Leu Gly Asp Ala Thr Glu Ala Gly Ser Gly Trp His
145 150 155 160

Glu Met Gly Leu Leu Asp Phe Ser Tyr Ser Phe Leu Leu Arg Ala Gly
165 170 175

Tyr Leu Thr Leu Tyr Gly Ile Glu Ala Leu Pro Arg Thr His Glu Ser
180 185 190

Gln Ala Gln Asp Arg Val His Ser Ala Asp Val Phe His Thr Phe Arg
195 200 205

Gln Leu Asp Arg Leu Leu Pro Lys Leu Ala Arg Gly Ser Leu Ser Val
210 215 220

Gly Asp Lys Asp His Met Cys Ser Val Lys Ser Arg Leu Trp Lys Leu
225 230 235 240

```
Leu Ser Pro Ala Arg Leu Ala Arg Arg Ala His Arg Ser Lys Trp Leu
            245                 250                 255

Glu Ser Tyr Leu Leu His Leu Glu Glu Met Gly Val Ser Glu Glu Met
            260                 265                 270

Gln Ala Arg Ala Leu Val Leu Gln Leu Trp Ala Thr Gln Gly Asn Met
        275                 280                 285

Gly Pro Ala Ala Phe Trp Leu Leu Leu Phe Leu Leu Lys Asn Pro Glu
    290                 295                 300

Ala Leu Ala Ala Val Arg Gly Glu Leu Glu Ser Ile Leu Trp Gln Ala
305                 310                 315                 320

Glu Gln Pro Val Ser Gln Thr Thr Thr Leu Pro Gln Lys Val Leu Asp
                325                 330                 335

Ser Thr Pro Val Leu Asp Ser Val Leu Ser Glu Ser Leu Arg Leu Thr
            340                 345                 350

Ala Ala Pro Phe Ile Thr Arg Glu Val Val Val Asp Leu Ala Met Pro
        355                 360                 365

Met Ala Asp Gly Arg Glu Phe Asn Leu Arg Arg Gly Asp Arg Leu Leu
    370                 375                 380

Leu Phe Pro Phe Leu Ser Pro Gln Arg Asp Pro Glu Ile Tyr Thr Asp
385                 390                 395                 400

Pro Glu Val Phe Lys Tyr Asn Arg Phe Leu Asn Pro Asp Gly Ser Glu
                405                 410                 415

Lys Lys Asp Phe Tyr Lys Asp Gly Lys Arg Leu Lys Asn Tyr Asn Met
            420                 425                 430

Pro Trp Gly Ala Gly His Asn His Cys Leu Gly Arg Ser Tyr Ala Val
        435                 440                 445

Asn Ser Ile Lys Gln Phe Val Phe Leu Val Leu Val His Leu Asp Leu
    450                 455                 460

Glu Leu Ile Asn Ala Asp Val Glu Ile Pro Glu Phe Asp Leu Ser Arg
465                 470                 475                 480

Tyr Gly Phe Gly Leu Met Gln Pro Glu His Asp Val Pro Val Arg Tyr
                485                 490                 495

Arg Ile Arg Pro
            500


<210> SEQ ID NO 113
<211> LENGTH: 1902
<212> TYPE: DNA
<213> ORGANISM: Homo sapiens

<400> SEQUENCE: 113

ggcactgggc aggaagggga gggggagcga gcgcgagaaa tgcagaggct gcagcggcgg      60

cggcggcggc agtagcggca gcggcgacga cggcggcggc agcgctccaa ctggctcctc     120

gctccgggct ccgccgtcga gccgggagag agcctccgcc agcggccagg caccagccag     180

acgacgccag cgaccccggc ctctcggcgg caccgcgcta actcaggggc tgcataggca     240

cccagagccg aactccaaga tgggaggcaa gctcagcaag aagaagaagg gctacaatgt     300

gaacgacgag aaagccaagg agaaagacaa gaaggccgag ggcgcggcga cggaagagga     360

ggggaccccg aaggagagtg agccccaggc ggccgcagag cccgccgagg ccaaggaggg     420

caaggagaag cccgaccagg acgccgaggg caaggccgag gagaaggagg gcgagaagga     480

cgcggcggct gccaaggagg aggccccgaa ggcggagccc gagaagacgg agggcgcggc     540

agaggccaag gctgagcccc cgaaggcgcc cgagcaggag caggcggccc ccggccccgc     600
```

tgcgggcggc gaggccccca aagctgctga ggccgccgcg gccccggccg agagcgcggc 660
ccctgccgcc ggggaggagc ccagcaagga ggaaggggaa cccaaaaaga ctgaggcgcc 720
cgcagctcct gccgcccagg agaccaaaag tgacggggcc ccagcttcag actcaaaacc 780
cggcagctcg gaggctgccc cctcttccaa ggagaccccc gcagccacgg aagcgcctag 840
ttccacaccc aaggcccagg gccccgcagc ctctgcagaa gagcccaagc cggtggaggc 900
cccggcagct aattccgacc aaaccgtaac cgtgaaagag tgacaaggac agcctatagg 960
aaaaacaata ccacttaaaa caatctcctc tctctctctc tctctctctc tctatctctc 1020
tctctatctc ctctctctct ctcctctcct atctctcctc tctctctctc ctatactaac 1080
ttgtttcaaa ttggaagtaa tgatatgtat tgcccaagga aaaatacagg atgttgtccc 1140
atcaagggag ggagggggtg ggagaatcca aatagtattt ttgtggggaa atatctaata 1200
taccttcagt caactttacc aagaagtcct ggatttccaa gatccgcgtc tgaaagtgca 1260
gtacatcgtt tgtacctgaa actgccgcca catgcactcc tccaccgctg agagttgaat 1320
agcttttctt ctgcaatggg agttgggagt gatgcgtttg attctgccca cagggcctgt 1380
gccaaggcaa tcagatcttt atgagagcag tatttttctgt gttttctttt taatttacag 1440
cctttcttat tttgatattt ttttaatgtt gtggatgaat gccagctttc agacagagcc 1500
cacttagctt gtccacatgg atctcaatgc caatcctcca ttcttcctct ccagatattt 1560
ttgggagtga caaacattct ctcatcctac ttagcctacc tagatttctc atgacgagtt 1620
aatgcatgtc cgtggttggg tgcacctgta gttctgttta ttggtcagtg gaaatgaaaa 1680
aaaaaaaaaa aaaaagtctg cgttcattgc agttccagtt tctcttccat tctgtgtcac 1740
agacaccaac acaccactca ttggaaaatg gaaaaaaaaa acaaaaaaaa aacaaaaaaa 1800
tgtacaatgg atgcattgaa attatatgta attgtataaa tggtgcaaca gtaataaagt 1860
taaacaatta aaaagaagta ataaagacaa aaaaaaaaaa aa 1902

<210> SEQ ID NO 114
<211> LENGTH: 1727
<212> TYPE: DNA
<213> ORGANISM: Homo sapiens

<400> SEQUENCE: 114
gcgcaactcg tttgcagcgg cgcagcccag acgcgcctgc agctggggct caccccaacc 60
tcgctgccag ccgagaactc caagatggga ggcaagctca gcaagaagaa gaagggctac 120
aatgtgaacg acgagaaagc caaggagaaa gacaagaagg ccgagggcgc ggcgacggaa 180
gaggagggga ccccgaagga gagtgagccc caggcggccg cagagcccgc cgaggccaag 240
gagggcaagg agaagcccga ccaggacgcc gagggcaagg ccgaggagaa ggagggcgag 300
aaggacgcgg cggctgccaa ggaggaggcc ccgaaggcgg agcccgagaa gacggagggc 360
gcggcagagg ccaaggctga gcccccgaag gcgcccgagc aggagcaggc ggcccccggc 420
cccgctgcgg gcggcgaggc ccccaaagct gctgaggccg ccgcggcccc ggccgagagc 480
gcggcccctg ccgccgggga ggagcccagc aaggaggaag gggaacccaa aaagactgag 540
gcgcccgcag ctcctgccgc ccaggagacc aaaagtgacg gggccccagc ttcagactca 600
aaacccggca gctcggaggc tgccccctct tccaaggaga cccccgcagc cacggaagcg 660
cctagttcca cacccaaggc ccagggcccc gcagcctctg cagaagagcc caagccggtg 720
gaggccccgg cagctaattc cgaccaaacc gtaaccgtga aagagtgaca aggacagcct 780

-continued

```
ataggaaaaa caataccact taaaacaatc tcctctctct ctctctctct ctctctctat    840

ctctctctct atctcctctc tctctctcct ctcctatctc tcctctctct ctctcctata    900

ctaacttgtt tcaaattgga agtaatgata tgtattgccc aaggaaaaat acaggatgtt    960

gtcccatcaa gggagggagg gggtgggaga atccaaatag tatttttgtg gggaaatatc   1020

taatatacct tcagtcaact ttaccaagaa gtcctggatt tccaagatcc gcgtctgaaa   1080

gtgcagtaca tcgtttgtac ctgaaactgc cgccacatgc actcctccac cgctgagagt   1140

tgaatagctt ttcttctgca atgggagttg ggagtgatgc gtttgattct gcccacaggg   1200

cctgtgccaa ggcaatcaga tctttatgag agcagtattt tctgtgtttt ctttttaatt   1260

tacagccttt cttattttga tattttttta atgttgtgga tgaatgccag ctttcagaca   1320

gagcccactt agcttgtcca catggatctc aatgccaatc ctccattctt cctctccaga   1380

tatttttggg agtgacaaac attctctcat cctacttagc ctacctagat ttctcatgac   1440

gagttaatgc atgtccgtgg ttgggtgcac ctgtagttct gtttattggt cagtggaaat   1500

gaaaaaaaaa aaaaaaaaaa gtctgcgttc attgcagttc cagtttctct tccattctgt   1560

gtcacagaca ccaacacacc actcattgga aaatggaaaa aaaaaacaaa aaaaaaacaa   1620

aaaaatgtac aatggatgca ttgaaattat atgtaattgt ataaatggtg caacagtaat   1680

aaagttaaac aattaaaaag aagtaataaa gacaaaaaaa aaaaaaa                 1727
```

```
<210> SEQ ID NO 115
<211> LENGTH: 227
<212> TYPE: PRT
<213> ORGANISM: Homo sapiens

<400> SEQUENCE: 115

Met Gly Gly Lys Leu Ser Lys Lys Lys Lys Gly Tyr Asn Val Asn Asp
1               5                   10                  15

Glu Lys Ala Lys Glu Lys Asp Lys Lys Ala Glu Gly Ala Ala Thr Glu
            20                  25                  30

Glu Glu Gly Thr Pro Lys Glu Ser Glu Pro Gln Ala Ala Ala Glu Pro
        35                  40                  45

Ala Glu Ala Lys Glu Gly Lys Glu Lys Pro Asp Gln Asp Ala Glu Gly
    50                  55                  60

Lys Ala Glu Glu Lys Glu Gly Glu Lys Asp Ala Ala Ala Ala Lys Glu
65                  70                  75                  80

Glu Ala Pro Lys Ala Glu Pro Glu Lys Thr Glu Gly Ala Ala Glu Ala
                85                  90                  95

Lys Ala Glu Pro Pro Lys Ala Pro Glu Gln Glu Gln Ala Ala Pro Gly
            100                 105                 110

Pro Ala Ala Gly Gly Glu Ala Pro Lys Ala Ala Glu Ala Ala Ala Ala
        115                 120                 125

Pro Ala Glu Ser Ala Ala Pro Ala Ala Gly Glu Glu Pro Ser Lys Glu
    130                 135                 140

Glu Gly Glu Pro Lys Lys Thr Glu Ala Pro Ala Ala Pro Ala Ala Gln
145                 150                 155                 160

Glu Thr Lys Ser Asp Gly Ala Pro Ala Ser Asp Ser Lys Pro Gly Ser
                165                 170                 175

Ser Glu Ala Ala Pro Ser Ser Lys Glu Thr Pro Ala Ala Thr Glu Ala
            180                 185                 190

Pro Ser Ser Thr Pro Lys Ala Gln Gly Pro Ala Ala Ser Ala Glu Glu
        195                 200                 205
```

```
Pro Lys Pro Val Glu Ala Pro Ala Ala Asn Ser Asp Gln Thr Val Thr
    210                 215                 220

Val Lys Glu
225


<210> SEQ ID NO 116
<211> LENGTH: 2268
<212> TYPE: DNA
<213> ORGANISM: Homo sapiens

<400> SEQUENCE: 116

gtctcccctc gccgcatcca ctctccggcc ggccgcctgc ccgccgcctc ctccgtgcgc      60

ccgccagcct cgcccgcgcc gtcaccatga gccaggccta ctcgtccagc cagcgcgtgt     120

cctcctaccg ccgcaccttc ggcggggccc cgggcttccc actcggctcc ccgctgagtt     180

cgcccgtgtt cccgcgggcg ggtttcggct ctaagggctc ctccagctcg gtgacgtccc     240

gcgtgtacca ggtgtcgcgc acgtcgggcg gggccggggg cctggggtcg ctgcgggcca     300

gccggctggg gaccacccgc acgccctcct cctacggcgc aggcgagctg ctggacttct     360

cactggccga cgcggtgaac caggagtttc tgaccacgcg caccaacgag aaggtggagc     420

tgcaggagct caatgaccgc ttcgccaact acatcgagaa ggtgcgcttc ctggagcagc     480

agaacgcggc gctcgccgcc gaagtgaacc ggctcaaggg ccgcgagccg acgcgagtgg     540

ccgagctcta cgaggaggag ctgcgggagc tgcggcgcca ggtggaggtg ctcactaacc     600

agcgcgcgcg cgtcgacgtc gagcgcgaca acctgctcga cgacctgcag cggctcaagg     660

ccaagctgca ggaggagatt cagttgaagg aagaagcaga gaacaatttg gctgccttcc     720

gagcggacgt ggatgcagct actctagctc gcattgacct ggagcgcaga attgaatctc     780

tcaacgagga gatcgcgttc cttaagaaag tgcatgaaga ggagatccgt gagttgcagg     840

ctcagcttca ggaacagcag gtccaggtgg agatggacat gtctaagcca gacctcactg     900

ccgccctcag ggacatccgg gctcagtatg agaccatcgc ggctaagaac atttctgaag     960

ctgaggagtg gtacaagtcg aaggtgtcag acctgaccca ggcagccaac aagaacaacg    1020

acgccctgcg ccaggccaag caggagatga tggaataccg acaccagatc cagtcctaca    1080

cctgcgagat tgacgccctg aagggcacta acgattccct gatgaggcag atgcgggaat    1140

tggaggaccg atttgccagt gaggccagtg gctaccagga caacattgcg cgcctggagg    1200

aggaaatccg gcacctcaag gatgagatgg cccgccatct gcgcgagtac caggacctgc    1260

tcaacgtgaa gatggccctg gatgtggaga ttgccaccta ccggaagctg ctggagggag    1320

aggagagccg gatcaatctc cccatccaga cctactctgc cctcaacttc cgagaaacca    1380

gccctgagca aaggggttct gaggtccata ccaagaagac ggtgatgatc aagaccatcg    1440

agacacggga tggggaggtc gtcagtgagg ccacacagca gcagcatgaa gtgctctaaa    1500

gacagagacc ctctgccacc agagaccgtc ctcacccctg tcctcactgc tccctgaagc    1560

cagccttctt ccatcccagg acaccacacc cagcctcagt cctcccctca cagcctctga    1620

cccctcctca ctggccatcc ctcgtggtcc ccaacagcga catagcccat ccctgcctgg    1680

tcacagggca tgccccggcc acctctgcgg accccagctg tgagccttgg ctgttggcag    1740

tgagtgagcc tggctcttgt gctggatgga gcccaggcgg gagcggtggc cctgtccctc    1800

ccacctctgt gacctcaggc actagccttt ggctctggag acagccccag agcagggtgt    1860

tgggatactg cagggccagg actgagcccc gcagacctcc ccagccccta gcccaggaga    1920

gagaaagcca ggcaggtagc caggggggact agcccctgtg gagactgggg ggcttgaaat    1980
```

```
tgtccccgtg gtctcttact ttcctttccc cagcccaggg tggacttaga aagcaggggc   2040

tacaagaggg aatccccgaa ggtgctggag gtgggagcag gagattgaga aggagagaaa   2100

gtgggtgaga tgctggagaa gagaggagag gagagaggca gagagcggtc tcaggctggt   2160

gggaggggcg cccacctccc cacgccctcc cctcccctgc tgcaggggct ctggagagaa   2220

acaataaaga gattcacaca caagccaaaa aaaaaaaaaa aaaaaaaa                2268


<210> SEQ ID NO 117
<211> LENGTH: 470
<212> TYPE: PRT
<213> ORGANISM: Homo sapiens

<400> SEQUENCE: 117

Met Ser Gln Ala Tyr Ser Ser Ser Gln Arg Val Ser Ser Tyr Arg Arg
1               5                   10                  15

Thr Phe Gly Gly Ala Pro Gly Phe Pro Leu Gly Ser Pro Leu Ser Ser
            20                  25                  30

Pro Val Phe Pro Arg Ala Gly Phe Gly Ser Lys Gly Ser Ser Ser Ser
        35                  40                  45

Val Thr Ser Arg Val Tyr Gln Val Ser Arg Thr Ser Gly Gly Ala Gly
    50                  55                  60

Gly Leu Gly Ser Leu Arg Ala Ser Arg Leu Gly Thr Thr Arg Thr Pro
65                  70                  75                  80

Ser Ser Tyr Gly Ala Gly Glu Leu Leu Asp Phe Ser Leu Ala Asp Ala
                85                  90                  95

Val Asn Gln Glu Phe Leu Thr Thr Arg Thr Asn Glu Lys Val Glu Leu
            100                 105                 110

Gln Glu Leu Asn Asp Arg Phe Ala Asn Tyr Ile Glu Lys Val Arg Phe
        115                 120                 125

Leu Glu Gln Gln Asn Ala Ala Leu Ala Ala Glu Val Asn Arg Leu Lys
    130                 135                 140

Gly Arg Glu Pro Thr Arg Val Ala Glu Leu Tyr Glu Glu Glu Leu Arg
145                 150                 155                 160

Glu Leu Arg Arg Gln Val Glu Val Leu Thr Asn Gln Arg Ala Arg Val
                165                 170                 175

Asp Val Glu Arg Asp Asn Leu Leu Asp Asp Leu Gln Arg Leu Lys Ala
            180                 185                 190

Lys Leu Gln Glu Glu Ile Gln Leu Lys Glu Glu Ala Glu Asn Asn Leu
        195                 200                 205

Ala Ala Phe Arg Ala Asp Val Asp Ala Ala Thr Leu Ala Arg Ile Asp
    210                 215                 220

Leu Glu Arg Arg Ile Glu Ser Leu Asn Glu Glu Ile Ala Phe Leu Lys
225                 230                 235                 240

Lys Val His Glu Glu Glu Ile Arg Glu Leu Gln Ala Gln Leu Gln Glu
                245                 250                 255

Gln Gln Val Gln Val Glu Met Asp Met Ser Lys Pro Asp Leu Thr Ala
            260                 265                 270

Ala Leu Arg Asp Ile Arg Ala Gln Tyr Glu Thr Ile Ala Ala Lys Asn
        275                 280                 285

Ile Ser Glu Ala Glu Glu Trp Tyr Lys Ser Lys Val Ser Asp Leu Thr
    290                 295                 300

Gln Ala Ala Asn Lys Asn Asn Asp Ala Leu Arg Gln Ala Lys Gln Glu
305                 310                 315                 320
```

-continued

```
Met Met Glu Tyr Arg His Gln Ile Gln Ser Tyr Thr Cys Glu Ile Asp
                325                 330                 335

Ala Leu Lys Gly Thr Asn Asp Ser Leu Met Arg Gln Met Arg Glu Leu
            340                 345                 350

Glu Asp Arg Phe Ala Ser Glu Ala Ser Gly Tyr Gln Asp Asn Ile Ala
        355                 360                 365

Arg Leu Glu Glu Glu Ile Arg His Leu Lys Asp Glu Met Ala Arg His
    370                 375                 380

Leu Arg Glu Tyr Gln Asp Leu Leu Asn Val Lys Met Ala Leu Asp Val
385                 390                 395                 400

Glu Ile Ala Thr Tyr Arg Lys Leu Leu Glu Gly Glu Glu Ser Arg Ile
                405                 410                 415

Asn Leu Pro Ile Gln Thr Tyr Ser Ala Leu Asn Phe Arg Glu Thr Ser
            420                 425                 430

Pro Glu Gln Arg Gly Ser Glu Val His Thr Lys Lys Thr Val Met Ile
        435                 440                 445

Lys Thr Ile Glu Thr Arg Asp Gly Glu Val Val Ser Glu Ala Thr Gln
    450                 455                 460

Gln Gln His Glu Val Leu
465                 470


<210> SEQ ID NO 118
<211> LENGTH: 7878
<212> TYPE: DNA
<213> ORGANISM: Homo sapiens

<400> SEQUENCE: 118

ttttccctgc tctcaccggg cgggggagag aagccctctg gacagcttct agagtgtgca      60

ggttctcgta tccctcggcc aagggtatcc tctgcaaacc tctgcaaacc cagcgcaact     120

acggtccccc ggtcagaccc aggatggggc cagaacggac aggggccgcg ccgctgccgc     180

tgctgctggt gttagcgctc agtcaaggca ttttaaattg ttgtttggcc tacaatgttg     240

gtctcccaga agcaaaaata ttttccggtc cttcaagtga acagtttggc tatgcagtgc     300

agcagtttat aaatccaaaa ggcaactggt tactggttgg ttcaccctgg agtggctttc     360

ctgagaaccg aatgggagat gtgtataaat gtcctgttga cctatccact gccacatgtg     420

aaaaactaaa tttgcaaact tcaacaagca ttccaaatgt tactgagatg aaaaccaaca     480

tgagcctcgg cttgatcctc accaggaaca tgggaactgg aggttttctc acatgtggtc     540

ctctgtgggc acagcaatgt gggaatcagt attacacaac gggtgtgtgt tctgacatca     600

gtcctgattt tcagctctca gccagcttct cacctgcaac tcagccctgc ccttccctca     660

tagatgttgt ggttgtgtgt gatgaatcaa atagtattta tccttgggat gcagtaaaga     720

attttttgga aaaatttgta caaggcctgg atataggccc cacaaagaca caggtggggt     780

taattcagta tgccaataat ccaagagttg tgtttaactt gaacacatat aaaaccaaag     840

aagaaatgat tgtagcaaca tcccagacat cccaatatgg tggggacctc acaaacacat     900

tcggagcaat tcaatatgca agaaaatatg cttattcagc agcttctggt gggcgacgaa     960

gtgctacgaa agtaatggta gttgtaactg acggtgaatc acatgatggt tcaatgttga    1020

aagctgtgat tgatcaatgc aaccatgaca atatactgag gtttggcata gcagttcttg    1080

ggtacttaaa cagaaacgcc cttgatacta aaaatttaat aaaagaaata aaagcaatcg    1140

ctagtattcc aacagaaaga tactttttca atgtgtctga tgaagcagct ctactagaaa    1200

aggctgggac attaggagaa caaattttca gcattgaagg tactgttcaa ggaggagaca    1260
```

-continued

```
actttcagat ggaaatgtca caagtgggat tcagtgcaga ttactcttct caaaatgata   1320
ttctgatgct gggtgcagtg ggagcttttg gctggagtgg gaccattgtc cagaagacat   1380
ctcatggcca tttgatcttt cctaaacaag cctttgacca aattctgcag gacagaaatc   1440
acagttcata tttaggttac tctgtggctg caatttctac tggagaaagc actcactttg   1500
ttgctggtgc tcctcgggca aattataccg gccagatagt gctatatagt gtgaatgaga   1560
atggcaatat cacggttatt caggctcacc gaggtgacca gattggctcc tattttggta   1620
gtgtgctgtg ttcagttgat gtggataaag acaccattac agacgtgctc ttggtaggtg   1680
caccaatgta catgagtgac ctaaagaaag aggaaggaag agtctacctg tttactatca   1740
aagagggcat tttgggtcag caccaatttc ttgaaggccc cgagggcatt gaaaacactc   1800
gatttggttc agcaattgca gctctttcag acatcaacat ggatggcttt aatgatgtga   1860
ttgttggttc accactagaa aatcagaatt ctggagctgt atacatttac aatggtcatc   1920
agggcactat ccgcacaaag tattcccaga aaatcttggg atccgatgga gcctttagga   1980
gccatctcca gtactttggg aggtccttgg atggctatgg agatttaaat ggggattcca   2040
tcaccgatgt gtctattggt gcctttggac aagtggttca actctggtca caaagtattg   2100
ctgatgtagc tatagaagct tcattcacac cagaaaaaat cactttggtc aacaagaatg   2160
ctcagataat tctcaaactc tgcttcagtg caaagttcag acctactaag caaaacaatc   2220
aagtggccat tgtatataac atcacacttg atgcagatgg attttcatcc agagtaacct   2280
ccaggggggtt atttaaagaa aacaatgaaa ggtgcctgca gaagaatatg gtagtaaatc   2340
aagcacagag ttgccccgag cacatcattt atatacagga gccctctgat gttgtcaact   2400
ctttggattt gcgtgtggac atcagtctgg aaaaccctgg cactagccct gcccttgaag   2460
cctattctga gactgccaag gtcttcagta ttcctttcca caaagactgt ggtgaggacg   2520
gactttgcat ttctgatcta gtcctagatg tccgacaaat accagctgct caagaacaac   2580
cctttattgt cagcaaccaa aacaaaaggt taacattttc agtaacgctg aaaaataaaa   2640
gggaaagtgc atacaacact ggaattgttg ttgatttttc agaaaacttg ttttttgcat   2700
cattctccct gccggttgat gggacagaag taacatgcca ggtggctgca tctcagaagt   2760
ctgttgcctg cgatgtaggc taccctgctt taaagagaga acaacaggtg acttttacta   2820
ttaactttga cttcaatctt caaaaccttc agaatcaggc gtctctcagt ttccaagcct   2880
taagtgaaag ccaagaagaa aacaaggctg ataatttggt caacctcaaa attcctctcc   2940
tgtatgatgc tgaaattcac ttaacaagat ctaccaacat aaatttttat gaaatctctt   3000
cggatgggaa tgttccttca atcgtgcaca gttttgaaga tgttggtcca aaattcatct   3060
tctccctgaa ggtaacaaca ggaagtgttc cagtaagcat ggcaactgta atcatccaca   3120
tccctcagta taccaaagaa aagaacccac tgatgtacct aactggggtg caaacagaca   3180
aggctggtga catcagttgt aatgcagata tcaatccact gaaaatagga caaacatctt   3240
cttctgtatc tttcaaaagt gaaaatttca ggcacaccaa agaattgaac tgcagaactg   3300
cttcctgtag taatgttacc tgctggttga aagacgttca catgaaagga gaatactttg   3360
ttaatgtgac taccagaatt tggaacggga ctttcgcatc atcaacgttc cagacagtac   3420
agctaacggc agctgcagaa atcaacacct ataaccctga gatatatgtg attgaagata   3480
acactgttac gattcccctg atgataatga aacctgatga gaaagccgaa gtaccaacag   3540
gagttataat aggaagtata attgctggaa tccttttgct gttagctctg gttgcaattt   3600
```

-continued

```
tatggaagct cggcttcttc aaaagaaaat atgaaaagat gaccaaaaat ccagatgaga   3660
ttgatgagac cacagagctc agtagctgaa ccagcagacc tacctgcagt gggaaccggc   3720
agcatcccag ccagggtttg ctgtttgcgt gaatggattt ctttttaaat cccatatttt   3780
ttttatcatg tcgtaggtaa actaacctgg tattttaaga gaaaactgca ggtcagtttg   3840
gaatgaagaa attgtggggg gtgggggagg tgcggggggc aggtagggaa ataataggga   3900
aaatacctat tttatatgat ggggggaaaa aagtaatctt taaactggct ggcccagagt   3960
ttacattcta atttgcattg tgtcagaaac atgaaatgct tccaagcatg acaactttta   4020
aagaaaaata tgatactctc agattttaag ggggaaaact gttctcttta aaatatttgt   4080
ctttaaacag caactacaga agtggaagtg cttgatatgt aagtacttcc acttgtgtat   4140
attttaatga atattgatgt taacaagagg ggaaaacaaa acacaggttt tttcaattta   4200
tgctgctcat ccaaagttgc cacagatgat acttccaagt gataatttta tttataaact   4260
aggtaaaatt tgttgttggt tccttttaga ccacggctgc cccttccaca ccccatcttg   4320
ctctaatgat caaaacatgc ttgaataact gagcttagag tatacctcct atatgtccat   4380
ttaagttagg agagggggcg atatagagaa taaggcacaa aattttgttt aaaactcaga   4440
atataacatg taaaatccca tctgctagaa gcccatcctg tgccagagga aggaaaagga   4500
ggaaatttcc tttctctttt aggaggcaca acagttctct tctaggattt gtttggctga   4560
ctggcagtaa cctagtgaat ttctgaaaga tgagtaattt ctttggcaac cttcctcctc   4620
ccttactgaa ccactctccc acctcctggt ggtaccatta ttatagaagc cctctacagc   4680
ctgactttct ctccagcggt ccaaagttat cccctccttt acccctcatc caaagttccc   4740
actccttcag gacagctgct gtgcattaga tattaggggg gaaagtcatc tgtttaattt   4800
acacacttgc atgaattact gtatataaac tccttaactt cagggagcta ttttcattta   4860
gtgctaaaca agtaagaaaa ataagctcga gtgaatttct aaatgttgga atgttatggg   4920
atgtaaacaa tgtaaagtaa gacatctcag gatttcacca gaagttacag atgaggcact   4980
ggaagccacc aaattagcag gtgcaccttc tgtggctgtc ttgtttctga agtacttaaa   5040
cttccacaag agtgaatttg acctaggcaa gtttgttcaa aaggtagatc ctgagatgat   5100
ttggtcagat tgggataagg cccagcaatc tgcattttaa caagcacccc agtcactagg   5160
atgcagatgg accacacttt gagaaacacc acccatttct actttttgca ccttattttc   5220
tctgttcctg agcccccaca ttctctagga gaaacttaga ggaaaagggc acagacacta   5280
catatctaaa gctttggaca agtccttgac ctctataaac ttcagagtcc tcattataaa   5340
atgggaagac tgagctggag ttcagcagtg atgcttttag ttttaaaagt ctatgatctg   5400
gacttcctat aatacaaata cacaatcctc caagaatttg acttggaaaa aaatgtcaaa   5460
ggaaaacagg ttatctgccc atgtgcatat ggacaacctt gactaccctg gcctggcccg   5520
tggtggcagt ccagggctat ctgtactgtt tacagaatta ctttgtagtt gacaacacaa   5580
aacaaacaaa aaaggcataa aatgccagcg gtttatagaa aaaacagcat ggtattctcc   5640
agttaggtat gccagagtcc aattctttta acagctgtga gaatttgctg cttcattcca   5700
acaaaatttt atttaaaaaa aaaaaaaaaa gactggagaa actagtcatt agcttgataa   5760
agaatattta acagctagtg gtgctggtgt gtacctgaag ctccagctac ttgagagact   5820
gagacaggaa gatcgcttga gcccaggagt tcaagtccag cctaagcaac atagcaagac   5880
cctgtctcaa aaaaatgact atttaaaaag acaatgtggc caggcacggt ggctcacacc   5940
tgtaatccca acactttggg aggctgaggc cggtggatca cgaggtcagg agtttgagac   6000
```

-continued

```
tagcctggcc aacatggtga aaccccatct ctaataatat aaaaattagc tgggcgtagt   6060

agcaggtgcc tgtaatccca gttactcggg aagctgaggc aggagaatca cttgaacccg   6120

ggaggcagag gtttcagtga gccgagatcg cgccactgca ctccagcctg ggtgacaggg   6180

caagactctg tctcaaacaa acaaacaaaa aaaaagttag tactgtatat gtaaatacta   6240

gcttttcaat gtgctataca aacaattata gcacatcctt ccttttactc tgtctcacct   6300

cctttaggtg agtacttcct taaataagtg ctaaacatac atatacggaa cttgaaagct   6360

ttggttagcc ttgccttagg taatcagcct agtttacact gtttccaggg agtagttgaa   6420

ttactataaa ccattagcca cttgtctctg caccatttat cacaccagga cagggtctct   6480

caacctgggc gctactgtca tttggggcca ggtgattctt ccttgcaggg gctgtcctgt   6540

accttgtagg acagcagccc tgtcctagaa ggtatgttta gcagcattcc tggcctctag   6600

ctacccgatg ccagagcatg ctcccccgc agtcatgaca atcaaaaaat gtctccagac   6660

attgtcaaat gcctcctggg ggcagtattt tctcaagcac ttttaagcaa aggtaagtat   6720

tcatacaaga aatttagggg gaaaaaacat tgtttaaata aaagctatgt gttcctattc   6780

aacaatattt ttgctttaaa agtaagtaga gggcataaaa gatgtcatat tcaaatttcc   6840

atttcataaa tggtgtacag acaaggtcta tagaatgtgg taaaaacttg actgcaacac   6900

aaggcttata aaatagtaag atagtaaaat agcttatgaa gaaactacag agatttaaaa   6960

ttgtgcatga ctcatttcag cagcaaaata agaactccta actgaacaga aatttttcta   7020

cctagcaatg ttattcttgt aaaatagtta cctattaaaa ctgtgaagag taaaactaaa   7080

gccaatttat tatagtcaca caagtgatta tactaaaaat tattataaag gttataattt   7140

tataatgtat ttacctgtcc tgatatatag ctataaccca atatatgaaa atctcaaaaa   7200

ttaagacatc atcatacaga aggcaggatt ccttaaactg agatccctga tccatcttta   7260

atatttcaat ttgcacacat aaaacaatgc ccttttgtgt acattcaggc atacccattt   7320

taatcaattt gaaaggttaa tttaaacctc tagaggtgaa tgagaaacat gggggaaaag   7380

tatgaaatag gtgaaaatct taactatttc tttgaactct aaagactgaa actgtagcca   7440

ttatgtaaat aaagtttcat atgtacctgt ttattttggc agattaagtc aaaatatgaa   7500

tgtatatatt gcataactat gttagaattg tatatatttt aaagaaattg tcttggatat   7560

tttcctttat acataataga taagtctttt ttcaaatgtg gtgtttgatg tttttgatta   7620

aatgtgtttt gcctctttcc acaaaaactg taaaaataaa tgcatgtttg tacaaaaagt   7680

tgcagaattc atttgattta tgagaaacaa aaattaaatt gtagtcaaca gttagtagtt   7740

tttctcatat ccaagtataa caaacagaaa agtttcatta ttgtaaccca ctttttttcat   7800

accacattat tgaatattgt tacaattgtt ttgaaaataa agccattttc tttgggcttt   7860

tataagttaa aaaaaaaa                                                 7878
```

<210> SEQ ID NO 119
<211> LENGTH: 1181
<212> TYPE: PRT
<213> ORGANISM: Homo sapiens

<400> SEQUENCE: 119

```
Met Gly Pro Glu Arg Thr Gly Ala Ala Pro Leu Pro Leu Leu Leu Val
1               5                   10                  15

Leu Ala Leu Ser Gln Gly Ile Leu Asn Cys Cys Leu Ala Tyr Asn Val
            20                  25                  30
```

-continued

```
Gly Leu Pro Glu Ala Lys Ile Phe Ser Gly Pro Ser Ser Glu Gln Phe
        35                  40                  45

Gly Tyr Ala Val Gln Gln Phe Ile Asn Pro Lys Gly Asn Trp Leu Leu
    50                  55                  60

Val Gly Ser Pro Trp Ser Gly Phe Pro Glu Asn Arg Met Gly Asp Val
65                  70                  75                  80

Tyr Lys Cys Pro Val Asp Leu Ser Thr Ala Thr Cys Glu Lys Leu Asn
                85                  90                  95

Leu Gln Thr Ser Thr Ser Ile Pro Asn Val Thr Glu Met Lys Thr Asn
            100                 105                 110

Met Ser Leu Gly Leu Ile Leu Thr Arg Asn Met Gly Thr Gly Gly Phe
        115                 120                 125

Leu Thr Cys Gly Pro Leu Trp Ala Gln Gln Cys Gly Asn Gln Tyr Tyr
    130                 135                 140

Thr Thr Gly Val Cys Ser Asp Ile Ser Pro Asp Phe Gln Leu Ser Ala
145                 150                 155                 160

Ser Phe Ser Pro Ala Thr Gln Pro Cys Pro Ser Leu Ile Asp Val Val
                165                 170                 175

Val Val Cys Asp Glu Ser Asn Ser Ile Tyr Pro Trp Asp Ala Val Lys
            180                 185                 190

Asn Phe Leu Glu Lys Phe Val Gln Gly Leu Asp Ile Gly Pro Thr Lys
        195                 200                 205

Thr Gln Val Gly Leu Ile Gln Tyr Ala Asn Asn Pro Arg Val Val Phe
    210                 215                 220

Asn Leu Asn Thr Tyr Lys Thr Lys Glu Glu Met Ile Val Ala Thr Ser
225                 230                 235                 240

Gln Thr Ser Gln Tyr Gly Gly Asp Leu Thr Asn Thr Phe Gly Ala Ile
                245                 250                 255

Gln Tyr Ala Arg Lys Tyr Ala Tyr Ser Ala Ala Ser Gly Gly Arg Arg
            260                 265                 270

Ser Ala Thr Lys Val Met Val Val Val Thr Asp Gly Glu Ser His Asp
        275                 280                 285

Gly Ser Met Leu Lys Ala Val Ile Asp Gln Cys Asn His Asp Asn Ile
    290                 295                 300

Leu Arg Phe Gly Ile Ala Val Leu Gly Tyr Leu Asn Arg Asn Ala Leu
305                 310                 315                 320

Asp Thr Lys Asn Leu Ile Lys Glu Ile Lys Ala Ile Ala Ser Ile Pro
                325                 330                 335

Thr Glu Arg Tyr Phe Phe Asn Val Ser Asp Glu Ala Ala Leu Leu Glu
            340                 345                 350

Lys Ala Gly Thr Leu Gly Glu Gln Ile Phe Ser Ile Glu Gly Thr Val
        355                 360                 365

Gln Gly Gly Asp Asn Phe Gln Met Glu Met Ser Gln Val Gly Phe Ser
    370                 375                 380

Ala Asp Tyr Ser Ser Gln Asn Asp Ile Leu Met Leu Gly Ala Val Gly
385                 390                 395                 400

Ala Phe Gly Trp Ser Gly Thr Ile Val Gln Lys Thr Ser His Gly His
                405                 410                 415

Leu Ile Phe Pro Lys Gln Ala Phe Asp Gln Ile Leu Gln Asp Arg Asn
            420                 425                 430

His Ser Ser Tyr Leu Gly Tyr Ser Val Ala Ala Ile Ser Thr Gly Glu
        435                 440                 445

Ser Thr His Phe Val Ala Gly Ala Pro Arg Ala Asn Tyr Thr Gly Gln
```

```
    450                 455                 460

Ile Val Leu Tyr Ser Val Asn Glu Asn Gly Asn Ile Thr Val Ile Gln
465                 470                 475                 480

Ala His Arg Gly Asp Gln Ile Gly Ser Tyr Phe Gly Ser Val Leu Cys
                485                 490                 495

Ser Val Asp Val Asp Lys Asp Thr Ile Thr Asp Val Leu Leu Val Gly
            500                 505                 510

Ala Pro Met Tyr Met Ser Asp Leu Lys Lys Glu Glu Gly Arg Val Tyr
        515                 520                 525

Leu Phe Thr Ile Lys Glu Gly Ile Leu Gly Gln His Gln Phe Leu Glu
    530                 535                 540

Gly Pro Glu Gly Ile Glu Asn Thr Arg Phe Gly Ser Ala Ile Ala Ala
545                 550                 555                 560

Leu Ser Asp Ile Asn Met Asp Gly Phe Asn Asp Val Ile Val Gly Ser
                565                 570                 575

Pro Leu Glu Asn Gln Asn Ser Gly Ala Val Tyr Ile Tyr Asn Gly His
            580                 585                 590

Gln Gly Thr Ile Arg Thr Lys Tyr Ser Gln Lys Ile Leu Gly Ser Asp
        595                 600                 605

Gly Ala Phe Arg Ser His Leu Gln Tyr Phe Gly Arg Ser Leu Asp Gly
    610                 615                 620

Tyr Gly Asp Leu Asn Gly Asp Ser Ile Thr Asp Val Ser Ile Gly Ala
625                 630                 635                 640

Phe Gly Gln Val Val Gln Leu Trp Ser Gln Ser Ile Ala Asp Val Ala
                645                 650                 655

Ile Glu Ala Ser Phe Thr Pro Glu Lys Ile Thr Leu Val Asn Lys Asn
            660                 665                 670

Ala Gln Ile Ile Leu Lys Leu Cys Phe Ser Ala Lys Phe Arg Pro Thr
        675                 680                 685

Lys Gln Asn Asn Gln Val Ala Ile Val Tyr Asn Ile Thr Leu Asp Ala
    690                 695                 700

Asp Gly Phe Ser Ser Arg Val Thr Ser Arg Gly Leu Phe Lys Glu Asn
705                 710                 715                 720

Asn Glu Arg Cys Leu Gln Lys Asn Met Val Val Asn Gln Ala Gln Ser
                725                 730                 735

Cys Pro Glu His Ile Ile Tyr Ile Gln Glu Pro Ser Asp Val Val Asn
            740                 745                 750

Ser Leu Asp Leu Arg Val Asp Ile Ser Leu Glu Asn Pro Gly Thr Ser
        755                 760                 765

Pro Ala Leu Glu Ala Tyr Ser Glu Thr Ala Lys Val Phe Ser Ile Pro
    770                 775                 780

Phe His Lys Asp Cys Gly Glu Asp Gly Leu Cys Ile Ser Asp Leu Val
785                 790                 795                 800

Leu Asp Val Arg Gln Ile Pro Ala Ala Gln Glu Gln Pro Phe Ile Val
                805                 810                 815

Ser Asn Gln Asn Lys Arg Leu Thr Phe Ser Val Thr Leu Lys Asn Lys
            820                 825                 830

Arg Glu Ser Ala Tyr Asn Thr Gly Ile Val Val Asp Phe Ser Glu Asn
        835                 840                 845

Leu Phe Phe Ala Ser Phe Ser Leu Pro Val Asp Gly Thr Glu Val Thr
    850                 855                 860

Cys Gln Val Ala Ala Ser Gln Lys Ser Val Ala Cys Asp Val Gly Tyr
865                 870                 875                 880
```

```
Pro Ala Leu Lys Arg Glu Gln Gln Val Thr Phe Thr Ile Asn Phe Asp
                885                 890                 895

Phe Asn Leu Gln Asn Leu Gln Asn Gln Ala Ser Leu Ser Phe Gln Ala
            900                 905                 910

Leu Ser Glu Ser Gln Glu Glu Asn Lys Ala Asp Asn Leu Val Asn Leu
        915                 920                 925

Lys Ile Pro Leu Leu Tyr Asp Ala Glu Ile His Leu Thr Arg Ser Thr
    930                 935                 940

Asn Ile Asn Phe Tyr Glu Ile Ser Ser Asp Gly Asn Val Pro Ser Ile
945                 950                 955                 960

Val His Ser Phe Glu Asp Val Gly Pro Lys Phe Ile Phe Ser Leu Lys
                965                 970                 975

Val Thr Thr Gly Ser Val Pro Val Ser Met Ala Thr Val Ile Ile His
            980                 985                 990

Ile Pro Gln Tyr Thr Lys Glu Lys  Asn Pro Leu Met Tyr  Leu Thr Gly
        995                 1000                1005

Val Gln  Thr Asp Lys Ala Gly  Asp Ile Ser Cys Asn  Ala Asp Ile
    1010                1015                1020

Asn Pro  Leu Lys Ile Gly Gln  Thr Ser Ser Ser Val  Ser Phe Lys
    1025                1030                1035

Ser Glu  Asn Phe Arg His Thr  Lys Glu Leu Asn Cys  Arg Thr Ala
    1040                1045                1050

Ser Cys  Ser Asn Val Thr Cys  Trp Leu Lys Asp Val  His Met Lys
    1055                1060                1065

Gly Glu  Tyr Phe Val Asn Val  Thr Thr Arg Ile Trp  Asn Gly Thr
    1070                1075                1080

Phe Ala  Ser Ser Thr Phe Gln  Thr Val Gln Leu Thr  Ala Ala Ala
    1085                1090                1095

Glu Ile  Asn Thr Tyr Asn Pro  Glu Ile Tyr Val Ile  Glu Asp Asn
    1100                1105                1110

Thr Val  Thr Ile Pro Leu Met  Ile Met Lys Pro Asp  Glu Lys Ala
    1115                1120                1125

Glu Val  Pro Thr Gly Val Ile  Ile Gly Ser Ile Ile  Ala Gly Ile
    1130                1135                1140

Leu Leu  Leu Leu Ala Leu Val  Ala Ile Leu Trp Lys  Leu Gly Phe
    1145                1150                1155

Phe Lys  Arg Lys Tyr Glu Lys  Met Thr Lys Asn Pro  Asp Glu Ile
    1160                1165                1170

Asp Glu  Thr Thr Glu Leu Ser  Ser
    1175                1180
```

<210> SEQ ID NO 120
<211> LENGTH: 4107
<212> TYPE: DNA
<213> ORGANISM: Homo sapiens

<400> SEQUENCE: 120

```
gacaagggct cttcttgatg gcttactgta tccactttgt ccccaagacc atagggaaat      60

gactagaggt gactgtacta gctagatttt aaatgaaact gaaatgaaag ttcacttcct     120

cattttgagt acctcatgtg acaagttcca atttcttttc aagtcaattg aactgaaatc     180

tccttgttgc tttgaaatct tagaagagag cccactaatt caaggactct tactgtggga     240

gcaactgctg gttctatcac aatgaaacgg ctggtttgtg tgctcttggt gtgctcctct     300
```

-continued

```
gcagtggcac agttgcataa agatcctacc ctggatcacc actggcatct ctggaagaaa    360
acctatggca aacaatacaa ggaaaagaat gaagaagcag tacgacgtct catctgggaa    420
aagaatctaa agtttgtgat gcttcacaac ctggagcatt caatgggaat gcactcatac    480
gatctgggca tgaaccacct gggagacatg accagtgaag aagtgatgtc tttgatgagt    540
tccctgagag ttcccagcca gtggcagaga aatatcacat ataagtcaaa ccctaatcgg    600
atattgcctg attctgtgga ctggagagag aaagggtgtg ttactgaagt gaaatatcaa    660
ggttcttgtg gtgcttgctg ggctttcagt gctgtggggg ccctggaagc acagctgaag    720
ctgaaaacag gaaagctggt gtctctcagt gcccagaacc tggtggattg ctcaactgaa    780
aaatatggaa acaaaggctg caatggtggc ttcatgacaa cggctttcca gtacatcatt    840
gataacaagg gcatcgactc agacgcttcc tatccctaca aagccatgga tcagaaatgt    900
caatatgact caaaatatcg tgctgccaca tgttcaaagt acactgaact tccttatggc    960
agagaagatg tcctgaaaga agctgtggcc aataaaggcc cagtgtctgt tggtgtagat   1020
gcgcgtcatc cttctttctt cctctacaga agtggtgtct actatgaacc atcctgtact   1080
cagaatgtga atcatggtgt acttgtggtt ggctatggtg atcttaatgg gaaagaatac   1140
tggcttgtga aaaacagctg ggccacaac tttggtgaag aaggatatat tcggatggca   1200
agaaataaag gaaatcattg tgggattgct agctttccct cttacccaga aatctagagg   1260
atctctcctt tttataacaa atcaagaaat atgaagcact ttctcttaac ttaatttttc   1320
ctgctgtatc cagaagaaat aattgtgtca tgattaatgt gtatttactg tactaattag   1380
aaaatatagt ttgaggccgg gcacggtggc tcacgcctgt aatcccagta cttgggaggc   1440
caaggcaggc atatcaactt gaggccagga gttaaagagc agcctggcta acatggtgaa   1500
accccatctc tactaaaaat acaaaaaatt agccgagcac ggtggtgcat gcctgtaatc   1560
ccagctactt gggaggctga ggcacgagat tccttgaacc caagaggttg aggctatgtt   1620
gagctgagat cacaccactg tactccagcc tggatgacag agtggagact ctgtttcaaa   1680
aaaacagaaa agaaaatata gtttgattct tcattttttt aaatttgcaa atctcaggat   1740
aaagtttgct aagtaaatta gtaatgtact atagatataa ctgtacaaaa attgttcaac   1800
ctaaaacaat ctgtaattgc ttattgtttt attgtatact ctttgtcttt ttaagacccc   1860
taatagcctt ttgtaacttg atggcttaaa aatacttaat aaatctgcca tttcaaattt   1920
ctatcattgc cacataccat tcttattcct aggcaactat taataatcta tcctgagaat   1980
attaattgtg gtattctggt gatggggttt agcaactttg atggaagaaa atattaggct   2040
ataaatgtcc taaggactca gattgtatct ttgtacagaa gaggattcaa aacgccacgt   2100
gtagtggctc atgcctgtaa tcccaacact ttgggaggct gaagtaggag gatcgtcttg   2160
agcccaggag ttcaagacca gcctggacaa catagtgaga ccttgtctcc acaaaaataa   2220
aaaagaaact atccaggagt ggtggtgtgt gcctgtggtc cctgctatgc agatgtctaa   2280
gacaggagga tcacaagagc ccaggaggtt gagaatgcag tgagcttgta attgcaccac   2340
tgcactccag cctgggtgac agagcaagac cctgtcttaa aaaaagagga ttcaacacat   2400
atttttatat tatgttaaag taaagaaatg cataaaagac aagcactttg gaagaattat   2460
tttaatgatc aacaatttaa tgtattagtc caaattattt ttacgtagtc atcaacaatt   2520
tgaccagggc ctttatttgg caaataactg agccaaccag aataaaataa ccaatactcc   2580
actgctcata tttttatcta attcagatgg atcttcctta caactgctct agattagtag   2640
atgcatctaa gcaggcagca ggaactttaa attttttaag ttcatgtcta tgacatgaac   2700
```

```
aatgtgtggg ataatgtcat taatatatcc taaattaacc taaacgtatt tcactaactc   2760
tggctccttc tccataaagc acattttaag gaacaagaat tgctaaatat aaaaacataa   2820
ataataccat aatacatggc tatcatcaaa agtgtataga atattatagt ttaaaagtat   2880
ttagttgatt acttttcagt tttgttttgt tttttgagac ggagtctcac tctgttgccc   2940
aggctggagt gcagtggcac catctcagtt cactgcaact tctgcctccc gagttcaagc   3000
gattctcctg cctcagcctc ccgagtagct ggaattatag gcgtgcacca ccacgcccag   3060
ctaatttttg tatttttagt aaagacaggg ttttgccaca ttagccaggc tggtctcaaa   3120
ctcctgacct caggtgatcc acccacccca gcctcccaaa gtgctaagat tacaggcgtg   3180
agccactgag cccagcctac ttttcagttt ttaacataat ttttgtttta tccacaactt   3240
ttcaagtatt gaaagtagaa taaaaacatg ggttcttagt ctttagctat ctgttaaagc   3300
ctatgaatgc cttcttaaaa tcatgttttt aaatgcataa aatatatagg attacaaagg   3360
aatctaatta tatcgaaata cagttattaa aatgttaaaa gataagtttg ttatatatta   3420
atatgcatgc ttctttataa atgcattaaa taagagttaa tagctatcct aaatttgaaa   3480
tagtgataag cataatgaaa atagatgcaa aaaactaatg tgatatgaaa atatctgggt   3540
ttttcttttg atgatgaagt attgctaata ttaccgtggt ttatgaacta tgttcagaat   3600
tgaagaaaat cctaactttc agttagaggt tagtgacggg gttcaggaca ccctacacaa   3660
aatacagcac tttgacatat tgaatatttt aagctgaagg catttgagga aattgcagaa   3720
gcaggaaggt gactctgacc ttctgcctgc tgttctcccc agaagcagcc ataaaacctg   3780
ggaaggattt tctgaccttc ccctgaagta gatcataaga ctgtcatgta agaggtgctc   3840
tcctggcacc cagagaaaag gagcatcctt acctccaaaa gcacagggac acaaagagga   3900
atctaaacaa acaggcctct cagtttcccc cagtttatta catttagctt gttcacactt   3960
tgccctatga catttctaca tcactggctg ctcttcatca aacctactat aaaaaacatt   4020
caagttcaac tgtttctttg ggcctttatt tccttatgga gcccctcgtg tcgtgtaaaa   4080
cttatattaa ataaatgtgc atgcttt                                       4107
```

<210> SEQ ID NO 121
<211> LENGTH: 3957
<212> TYPE: DNA
<213> ORGANISM: Homo sapiens

<400> SEQUENCE: 121

```
gacaagggct cttcttgatg gcttactgta tccactttgt ccccaagacc atagggaaat     60
gactagaggt gactgtacta gctagatttt aaatgaaact gaaatgaaag ttcacttcct    120
cattttgagt acctcatgtg acaagttcca atttcttttc aagtcaattg aactgaaatc    180
tccttgttgc tttgaaatct tagaagagag cccactaatt caaggactct tactgtggga    240
gcaactgctg gttctatcac aatgaaacgg ctggtttgtg tgctcttggt gtgctcctct    300
gcagtggcac agttgcataa agatcctacc ctggatcacc actggcatct ctggaagaaa    360
acctatggca aacaatacaa ggaaaagaat gaagaagcag tacgacgtct catctgggaa    420
aagaatctaa agtttgtgat gcttcacaac ctggagcatt caatgggaat gcactcatac    480
gatctgggca tgaaccacct gggagacatg ggttcttgtg gtgcttgctg ggctttcagt    540
gctgtggggg ccctggaagc acagctgaag ctgaaaacag gaaagctggt gtctctcagt    600
gcccagaacc tggtggattg ctcaactgaa aaatatggaa acaaaggctg caatggtggc    660
```

-continued

```
ttcatgacaa cggctttcca gtacatcatt gataacaagg gcatcgactc agacgcttcc    720

tatccctaca aagccatgga tcagaaatgt caatatgact caaaatatcg tgctgccaca    780

tgttcaaagt acactgaact tccttatggc agagaagatg tcctgaaaga agctgtggcc    840

aataaaggcc cagtgtctgt tggtgtagat gcgcgtcatc cttctttctt cctctacaga    900

agtggtgtct actatgaacc atcctgtact cagaatgtga atcatggtgt acttgtggtt    960

ggctatggtg atcttaatgg gaaagaatac tggcttgtga aaaacagctg gggccacaac   1020

tttggtgaag aaggatatat tcggatggca agaaataaag gaaatcattg tgggattgct   1080

agctttccct cttacccaga aatctagagg atctctcctt tttataacaa atcaagaaat   1140

atgaagcact ttctcttaac ttaatttttc ctgctgtatc cagaagaaat aattgtgtca   1200

tgattaatgt gtatttactg tactaattag aaaatatagt ttgaggccgg gcacggtggc   1260

tcacgcctgt aatcccagta cttgggaggc caaggcaggc atatcaactt gaggccagga   1320

gttaaagagc agcctggcta acatggtgaa accccatctc tactaaaaat acaaaaaatt   1380

agccgagcac ggtggtgcat gcctgtaatc ccagctactt gggaggctga ggcacgagat   1440

tccttgaacc caagaggttg aggctatgtt gagctgagat cacaccactg tactccagcc   1500

tggatgacag agtggagact ctgtttcaaa aaaacagaaa agaaaatata gtttgattct   1560

tcattttttt aaatttgcaa atctcaggat aaagtttgct aagtaaatta gtaatgtact   1620

atagatataa ctgtacaaaa attgttcaac ctaaaacaat ctgtaattgc ttattgtttt   1680

attgtatact ctttgtcttt ttaagacccc taatagcctt ttgtaacttg atggcttaaa   1740

aatacttaat aaatctgcca tttcaaattt ctatcattgc cacataccat tcttattcct   1800

aggcaactat taataatcta tcctgagaat attaattgtg gtattctggt gatggggttt   1860

agcaactttg atggaagaaa atattaggct ataaatgtcc taaggactca gattgtatct   1920

ttgtacagaa gaggattcaa aacgccacgt gtagtggctc atgcctgtaa tcccaacact   1980

ttgggaggct gaagtaggag gatcgtcttg agcccaggag ttcaagacca gcctggacaa   2040

catagtgaga ccttgtctcc acaaaaaataa aaaagaaact atccaggagt ggtggtgtgt   2100

gcctgtggtc cctgctatgc agatgtctaa gacaggagga tcacaagagc ccaggaggtt   2160

gagaatgcag tgagcttgta attgcaccac tgcactccag cctgggtgac agagcaagac   2220

cctgtcttaa aaaaagagga ttcaacacat atttttatat tatgttaaag taaagaaatg   2280

cataaaagac aagcactttg gaagaattat tttaatgatc aacaatttaa tgtattagtc   2340

caaattattt ttacgtagtc atcaacaatt tgaccagggc ctttatttgg caaataactg   2400

agccaaccag aataaaataa ccaatactcc actgctcata tttttatcta attcagatgg   2460

atcttcctta caactgctct agattagtag atgcatctaa gcaggcagca ggaactttaa   2520

attttttaag ttcatgtcta tgacatgaac aatgtgtggg ataatgtcat taatatatcc   2580

taaattaacc taaacgtatt tcactaactc tggctccttc tccataaagc acattttaag   2640

gaacaagaat tgctaaatat aaaaacataa ataataccat aatacatggc tatcatcaaa   2700

agtgtataga atattatagt ttaaaagtat ttagttgatt acttttcagt tttgttttgt   2760

tttttgagac ggagtctcac tctgttgccc aggctggagt gcagtggcac catctcagtt   2820

cactgcaact tctgcctccc gagttcaagc gattctcctg cctcagcctc ccgagtagct   2880

ggaattatag gcgtgcacca ccacgcccag ctaatttttg tatttttagt aaagacaggg   2940

ttttgccaca ttagccaggc tggtctcaaa ctcctgacct caggtgatcc acccaccccca   3000

gcctcccaaa gtgctaagat tacaggcgtg agccactgag cccagcctac ttttcagttt   3060
```

-continued

```
ttaacataat ttttgtttta tccacaactt ttcaagtatt gaaagtagaa taaaaacatg   3120

ggttcttagt ctttagctat ctgttaaagc ctatgaatgc cttcttaaaa tcatgttttt   3180

aaatgcataa aatatatagg attacaaagg aatctaatta tatcgaaata cagttattaa   3240

aatgttaaaa gataagtttg ttatatatta atatgcatgc ttctttataa atgcattaaa   3300

taagagttaa tagctatcct aaatttgaaa tagtgataag cataatgaaa atagatgcaa   3360

aaaactaatg tgatatgaaa atatctgggt ttttcttttg atgatgaagt attgctaata   3420

ttaccgtggt ttatgaacta tgttcagaat tgaagaaaat cctaactttc agttagaggt   3480

tagtgacggg gttcaggaca ccctacacaa aatacagcac tttgacatat tgaatatttt   3540

aagctgaagg catttgagga aattgcagaa gcaggaaggt gactctgacc ttctgcctgc   3600

tgttctcccc agaagcagcc ataaaacctg ggaaggattt tctgaccttc ccctgaagta   3660

gatcataaga ctgtcatgta agaggtgctc tcctggcacc cagagaaaag gagcatcctt   3720

acctccaaaa gcacagggac acaaagagga atctaaacaa acaggcctct cagtttcccc   3780

cagtttatta catttagctt gttcacactt tgccctatga catttctaca tcactggctg   3840

ctcttcatca aacctactat aaaaaacatt caagttcaac tgtttctttg ggcctttatt   3900

tccttatgga gcccctcgtg tcgtgtaaaa cttatattaa ataaatgtgc atgcttt      3957
```

```
<210> SEQ ID NO 122
<211> LENGTH: 331
<212> TYPE: PRT
<213> ORGANISM: Homo sapiens

<400> SEQUENCE: 122

Met Lys Arg Leu Val Cys Val Leu Leu Val Cys Ser Ser Ala Val Ala
1               5                   10                  15

Gln Leu His Lys Asp Pro Thr Leu Asp His His Trp His Leu Trp Lys
            20                  25                  30

Lys Thr Tyr Gly Lys Gln Tyr Lys Glu Lys Asn Glu Glu Ala Val Arg
        35                  40                  45

Arg Leu Ile Trp Glu Lys Asn Leu Lys Phe Val Met Leu His Asn Leu
    50                  55                  60

Glu His Ser Met Gly Met His Ser Tyr Asp Leu Gly Met Asn His Leu
65                  70                  75                  80

Gly Asp Met Thr Ser Glu Glu Val Met Ser Leu Met Ser Ser Leu Arg
                85                  90                  95

Val Pro Ser Gln Trp Gln Arg Asn Ile Thr Tyr Lys Ser Asn Pro Asn
            100                 105                 110

Arg Ile Leu Pro Asp Ser Val Asp Trp Arg Glu Lys Gly Cys Val Thr
        115                 120                 125

Glu Val Lys Tyr Gln Gly Ser Cys Gly Ala Cys Trp Ala Phe Ser Ala
    130                 135                 140

Val Gly Ala Leu Glu Ala Gln Leu Lys Leu Lys Thr Gly Lys Leu Val
145                 150                 155                 160

Ser Leu Ser Ala Gln Asn Leu Val Asp Cys Ser Thr Glu Lys Tyr Gly
                165                 170                 175

Asn Lys Gly Cys Asn Gly Gly Phe Met Thr Thr Ala Phe Gln Tyr Ile
            180                 185                 190

Ile Asp Asn Lys Gly Ile Asp Ser Asp Ala Ser Tyr Pro Tyr Lys Ala
        195                 200                 205

Met Asp Gln Lys Cys Gln Tyr Asp Ser Lys Tyr Arg Ala Ala Thr Cys
```

-continued

```
    210                 215                 220

Ser Lys Tyr Thr Glu Leu Pro Tyr Gly Arg Glu Asp Val Leu Lys Glu
225                 230                 235                 240

Ala Val Ala Asn Lys Gly Pro Val Ser Val Gly Val Asp Ala Arg His
                245                 250                 255

Pro Ser Phe Phe Leu Tyr Arg Ser Gly Val Tyr Tyr Glu Pro Ser Cys
            260                 265                 270

Thr Gln Asn Val Asn His Gly Val Leu Val Val Gly Tyr Gly Asp Leu
        275                 280                 285

Asn Gly Lys Glu Tyr Trp Leu Val Lys Asn Ser Trp Gly His Asn Phe
    290                 295                 300

Gly Glu Glu Gly Tyr Ile Arg Met Ala Arg Asn Lys Gly Asn His Cys
305                 310                 315                 320

Gly Ile Ala Ser Phe Pro Ser Tyr Pro Glu Ile
                325                 330


<210> SEQ ID NO 123
<211> LENGTH: 281
<212> TYPE: PRT
<213> ORGANISM: Homo sapiens

<400> SEQUENCE: 123

Met Lys Arg Leu Val Cys Val Leu Leu Val Cys Ser Ser Ala Val Ala
1               5                   10                  15

Gln Leu His Lys Asp Pro Thr Leu Asp His His Trp His Leu Trp Lys
            20                  25                  30

Lys Thr Tyr Gly Lys Gln Tyr Lys Glu Lys Asn Glu Glu Ala Val Arg
        35                  40                  45

Arg Leu Ile Trp Glu Lys Asn Leu Lys Phe Val Met Leu His Asn Leu
    50                  55                  60

Glu His Ser Met Gly Met His Ser Tyr Asp Leu Gly Met Asn His Leu
65                  70                  75                  80

Gly Asp Met Gly Ser Cys Gly Ala Cys Trp Ala Phe Ser Ala Val Gly
                85                  90                  95

Ala Leu Glu Ala Gln Leu Lys Leu Lys Thr Gly Lys Leu Val Ser Leu
            100                 105                 110

Ser Ala Gln Asn Leu Val Asp Cys Ser Thr Glu Lys Tyr Gly Asn Lys
        115                 120                 125

Gly Cys Asn Gly Gly Phe Met Thr Thr Ala Phe Gln Tyr Ile Ile Asp
    130                 135                 140

Asn Lys Gly Ile Asp Ser Asp Ala Ser Tyr Pro Tyr Lys Ala Met Asp
145                 150                 155                 160

Gln Lys Cys Gln Tyr Asp Ser Lys Tyr Arg Ala Ala Thr Cys Ser Lys
                165                 170                 175

Tyr Thr Glu Leu Pro Tyr Gly Arg Glu Asp Val Leu Lys Glu Ala Val
            180                 185                 190

Ala Asn Lys Gly Pro Val Ser Val Gly Val Asp Ala Arg His Pro Ser
        195                 200                 205

Phe Phe Leu Tyr Arg Ser Gly Val Tyr Tyr Glu Pro Ser Cys Thr Gln
    210                 215                 220

Asn Val Asn His Gly Val Leu Val Val Gly Tyr Gly Asp Leu Asn Gly
225                 230                 235                 240

Lys Glu Tyr Trp Leu Val Lys Asn Ser Trp Gly His Asn Phe Gly Glu
                245                 250                 255
```

```
Glu Gly Tyr Ile Arg Met Ala Arg Asn Lys Gly Asn His Cys Gly Ile
            260                 265                 270

Ala Ser Phe Pro Ser Tyr Pro Glu Ile
        275                 280


<210> SEQ ID NO 124
<211> LENGTH: 1477
<212> TYPE: DNA
<213> ORGANISM: Homo sapiens

<400> SEQUENCE: 124

agaacaactt ttttgacttc ctgcaaagag gacccttaca gtatttttgg agaagttagt      60

aaaaccgaat ctgacatcat cacctagcag ttcatgcagc tagcaagtgg tttgttctta     120

gggtaacaga ggaggaaatt gttcctcgtc tgataagaca acagtggaga aaggacgcat     180

gctgtttctt agggacacgg ctgacttcca gatatgacca tgtatttgtg gcttaaactc     240

ttggcatttg gctttgcctt tctggacaca gaagtatttg tgacagggca aagcccaaca     300

ccttcccccca ctggccatct gcaagctgag gagcaaggaa gccaatccaa gtcaccaaac    360

ctcaaaagta gggaagctga cagttcagcc ttcagttggt ggccaaaggc ccgagagccc     420

ctcacaaacc actggagtaa gtccaagagt ccaaaagctg aggaacttgg agtctgatgt     480

tcaagagcag gaagcagcca gcacgagaga aagatgaaga ccagaagact cagcaagctc     540

acttctccta ccttcttgtg cctgcttttt ctagccgtgc tggcagttgc ttggatgatg     600

cccactcata ttgggtgggg gtgggggggt tggggagggt ctgcctcccc cagtccactg     660

actcaaatgt taatctccct tggcaatacg ctcacaggca cacccaggaa caatactttg     720

catccttcaa tccaatcaag ttgacactca atattaacca tcaaatacta ttataaggag     780

aatgttgcat gattttcctt ctagtctgtt tgtaattcac atctaatgaa agagtgagag     840

tggacgataa agggaacttg ttgaaacatt tctctcaaag caaaagggat cattggaagc     900

aggcagacac cagaattggt ttaacctaaa aataacaaat taataattat caagtctata     960

atgatgacag tgacttaatg tgaatagaaa gaattctaaa ctctctcctt ccttcctccc    1020

tcccttcttt cctactttct ttccactccc tttctcccac cccctttct tttcctttct    1080

tttctcccac cctctctccc tccctttctt ttattcaatg catagtagtt gaaaaaatct    1140

aaagttagac ctgattttac actgaagact agaggtagtt actatcctat tactgtactt    1200

agttggctat gctggcatgt cattatgggt aaaagtttga tggatttatt tgtgagttat    1260

ttggttatga aaatctagag attgaagttt ttcattagaa aataacacac ataacaagtc    1320

tatgatcatt ttgcatttct gtaatcacag aatagttctg caatatttca tgtatattgg    1380

aattgaagtt caattgaatt ttatctgtat ttagtaaaaa ttaactttag ctttgatact    1440

aatgaataaa gctgggtttt ttatttaaaa aaaaaaa                             1477


<210> SEQ ID NO 125
<211> LENGTH: 5429
<212> TYPE: DNA
<213> ORGANISM: Homo sapiens

<400> SEQUENCE: 125

agaacaactt ttttgacttc ctgcaaagag gacccttaca gtatttttgg agaagttagt      60

aaaaccgaat ctgacatcat cacctagcag ttcatgcagc tagcaagtgg tttgttctta     120

gggtaacaga ggaggaaatt gttcctcgtc tgataagaca acagtggaga aaggacgcat     180

gctgtttctt agggacacgg ctgacttcca gatatgacca tgtatttgtg gcttaaactc     240
```

```
ttggcatttg gctttgcctt tctggacaca gaagtatttg tgacagggca aagcccaaca    300
ccttccccca ctggattgac tacagcaaag atgcccagtg ttccactttc aagtgacccc    360
ttacctactc acaccactgc attctcaccc gcaagcacct ttgaaagaga aaatgacttc    420
tcagagacca caacttctct tagtccagac aatacttcca cccaagtatc cccggactct    480
ttggataatg ctagtgcttt taataccaca ggtgtttcat cagtacagac gcctcacctt    540
cccacgcacg cagactcgca gacgccctct gctggaactg acacgcagac attcagcggc    600
tccgccgcca atgcaaaact caaccctacc ccaggcagca atgctatctc agatgtccca    660
ggagagagga gtacagccag cacctttcct acagacccag tttccccatt gacaaccacc    720
ctcagccttg cacaccacag ctctgctgcc ttacctgcac gcacctccaa caccaccatc    780
acagcgaaca cctcagatgc ctaccttaat gcctctgaaa caaccactct gagcccttct    840
ggaagcgctg tcatttcaac cacaacaata gctactactc catctaagcc aacatgtgat    900
gaaaaatatg caaacatcac tgtggattac ttatataaca aggaaactaa attatttaca    960
gcaaagctaa atgttaatga gaatgtggaa tgtggaaaca atacttgcac aaacaatgag   1020
gtgcataacc ttacagaatg taaaaatgcg tctgtttcca tatctcataa ttcatgtact   1080
gctcctgata agacattaat attagatgtg ccaccagggg ttgaaaagtt tcagttacat   1140
gattgtacac aagttgaaaa agcagatact actatttgtt taaaatggaa aaatattgaa   1200
acctttactt gtgatacaca gaatattacc tacagatttc agtgtggtaa tatgatattt   1260
gataataaag aaattaaatt agaaaacctt gaacccgaac atgagtataa gtgtgactca   1320
gaaatactct ataataacca caagtttact aacgcaagta aaattattaa aacagatttt   1380
gggagtccag gagagcctca gattattttt tgtagaagtg aagctgcaca tcaaggagta   1440
attacctgga atcccccctca aagatcattt cataatttta ccctctgtta tataaaagag   1500
acagaaaaag attgcctcaa tctggataaa aacctgatca aatatgattt gcaaaattta   1560
aaaccttata cgaaatatgt tttatcatta catgcctaca tcattgcaaa agtgcaacgt   1620
aatggaagtg ctgcaatgtg tcatttcaca actaaaagtg ctcctccaag ccaggtctgg   1680
aacatgactg tctccatgac atcagataat agtatgcatg tcaagtgtag gcctcccagg   1740
gaccgtaatg gcccccatga acgttaccat ttggaagttg aagctggaaa tactctggtt   1800
agaaatgagt cgcataagaa ttgcgatttc cgtgtaaaag atcttcaata ttcaacagac   1860
tacactttta aggcctattt tcacaatgga gactatcctg gagaaccctt tattttacat   1920
cattcaacat cttataattc taaggcactg atagcatttc tggcatttct gattattgtg   1980
acatcaatag ccctgcttgt tgttctctac aaaatctatg atctacataa gaaaagatcc   2040
tgcaatttag atgaacagca ggagcttgtt gaaagggatg atgaaaaaca actgatgaat   2100
gtggagccaa tccatgcaga tattttgttg gaaacttata agaggaagat tgctgatgaa   2160
ggaagacttt ttctggctga atttcagagc atcccgcggg tgttcagcaa gtttcctata   2220
aaggaagctc gaaagccctt taaccagaat aaaaaccgtt atgttgacat tcttccttat   2280
gattataacc gtgttgaact ctctgagata aacggagatg cagggtcaaa ctacataaat   2340
gccagctata ttgatggttt caaagaaccc aggaaataca ttgctgcaca aggtcccagg   2400
gatgaaactg ttgatgattt ctggaggatg atttgggaac agaaagccac agttattgtc   2460
atggtcactc gatgtgaaga aggaaacagg aacaagtgtg cagaatactg gccgtcaatg   2520
gaagagggca ctcgggcttt tggagatgtt gttgtaaaga tcaaccagca caaaagatgt   2580
```

ccagattaca tcattcagaa attgaacatt gtaaataaaa aagaaaaagc aactggaaga 2640
gaggtgactc acattcagtt caccagctgg ccagaccacg ggtgcctga ggatcctcac 2700
ttgctcctca aactgagaag gagagtgaat gccttcagca atttcttcag tggtcccatt 2760
gtggtgcact gcagtgctgg tgttgggcgc acaggaacct atatcggaat tgatgccatg 2820
ctagaaggcc tggaagccga gaacaaagtg gatgtttatg gttatgttgt caagctaagg 2880
cgacagagat gcctgatggt tcaagtagag gcccagtaca tcttgatcca tcaggctttg 2940
gtggaataca atcagtttgg agaaacagaa gtgaatttgt ctgaattaca tccatatcta 3000
cataacatga agaaaaggga tccacccagt gagccgtctc cactagaggc tgaattccag 3060
agacttcctt catataggag ctggaggaca cagcacattg gaaatcaaga agaaaataaa 3120
agtaaaaaca ggaattctaa tgtcatccca tatgactata acagagtgcc acttaaacat 3180
gagctggaaa tgagtaaaga gagtgagcat gattcagatg aatcctctga tgatgacagt 3240
gattcagagg aaccaagcaa atacatcaat gcatctttta taatgagcta ctggaaacct 3300
gaagtgatga ttgctgctca gggaccactg aaggagacca ttggtgactt ttggcagatg 3360
atcttccaaa gaaaagtcaa agttattgtt atgctgacag aactgaaaca tggagaccag 3420
gaaatctgtg ctcagtactg gggagaagga aagcaaacat atggagatat tgaagttgac 3480
ctgaaagaca cagacaaatc ttcaacttat acccttcgtg tctttgaact gagacattcc 3540
aagaggaaag actctcgaac tgtgtaccag taccaatata caaactggag tgtggagcag 3600
cttcctgcag aacccaagga attaatctct atgattcagg tcgtcaaaca aaaacttccc 3660
cagaagaatt cctctgaagg gaacaagcat cacaagagta cacctctact cattcactgc 3720
agggatggat ctcagcaaac gggaatattt tgtgctttgt taaatctctt agaaagtgcg 3780
gaaacagaag aggtagtgga tatttttcaa gtggtaaaag ctctacgcaa agctaggcca 3840
ggcatggttt ccacattcga gcaatatcaa ttcctatatg acgtcattgc cagcacctac 3900
cctgctcaga atggacaagt aaagaaaaac aaccatcaag aagataaaat tgaatttgat 3960
aatgaagtgg acaaagtaaa gcaggatgct aattgtgtta atccacttgg tgccccagaa 4020
aagctccctg aagcaaagga acaggctgaa ggttctgaac ccacgagtgg cactgagggg 4080
ccagaacatt ctgtcaatgg tcctgcaagt ccagctttaa atcaaggttc ataggaaaag 4140
acataaatga ggaaactcca aacctcctgt tagctgttat ttctattttt gtagaagtag 4200
gaagtgaaaa taggtataca gtggattaat taaatgcagc gaaccaatat ttgtagaagg 4260
gttatatttt actactgtgg aaaaatattt aagatagttt tgccagaaca gtttgtacag 4320
acgtatgctt attttaaaat tttatctctt attcagtaaa aaacaacttc tttgtaatcg 4380
ttatgtgtgt atatgtatgt gtgtatgggt gtgtgtttgt gtgagagaca gagaaagaga 4440
gagaattctt tcaagtgaat ctaaaagctt ttgcttttcc tttgttttta tgaagaaaaa 4500
atacatttta tattagaagt gttaacttag cttgaaggat ctgtttttaa aaatcataaa 4560
ctgtgtgcag actcaataaa atcatgtaca tttctgaaat gacctcaaga tgtcctcctt 4620
gttctactca tatatatcta tcttatatag tttactattt tacttctaga gatagtacat 4680
aaaggtggta tgtgtgtgta tgctactaca aaaaagttgt taactaaatt aacattggga 4740
aatcttatat tccatatatt agcatttagt ccaatgtctt tttaagctta tttaattaaa 4800
aaatttccag tgagcttatc atgctgtctt tacatggggt tttcaatttt gcatgctcga 4860
ttattccctg tacaatattt aaaatttatt gcttgatact tttgacaaca aattaggttt 4920
tgtacaattg aacttaaata aatgtcatta aaataaataa atgcaatatg tattaatatt 4980

```
cattgtataa aaatagaaga atacaaacat atttgttaaa tatttacata tgaaatttaa   5040
tatagctatt tttatggaat ttttcattga tatgaaaaat atgatattgc atatgcatag   5100
ttcccatgtt aaatcccatt cataactttc attaaagcat ttactttgaa tttctccaat   5160
gcttagaatg tttttaccag gaatggatgt cgctaatcat aataaaattc aaccattatt   5220
tttttcttgt ttataataca ttgtgttata tgttcaaata tgaaatgtgt atgcacctat   5280
tgaaatatgt ttaatgcatt tattaacatt tgcaggacac ttttacaggc cccaattatc   5340
caatagtcta ataattgttt aagatctaga aaaaaaaaat caagaatagt ggtatttttc   5400
atgaagtaat aaaaactcgt tttggtgaa                                     5429
```

```
<210> SEQ ID NO 126
<211> LENGTH: 4946
<212> TYPE: DNA
<213> ORGANISM: Homo sapiens

<400> SEQUENCE: 126
```

```
agaacaactt ttttgacttc ctgcaaagag gacccttaca gtatttttgg agaagttagt     60
aaaaccgaat ctgacatcat cacctagcag ttcatgcagc tagcaagtgg tttgttctta    120
gggtaacaga ggaggaaatt gttcctcgtc tgataagaca acagtggaga aaggacgcat    180
gctgtttctt agggacacgg ctgacttcca gatatgacca tgtatttgtg gcttaaactc    240
ttggcatttg gctttgcctt tctggacaca gaagtatttg tgacagggca aagcccaaca    300
ccttcccccca ctgatgccta ccttaatgcc tctgaaacaa ccactctgag cccttctgga    360
agcgctgtca tttcaaccac aacaatagct actactccat ctaagccaac atgtgatgaa    420
aaatatgcaa acatcactgt ggattactta tataacaagg aaactaaatt atttacagca    480
aagctaaatg ttaatgagaa tgtggaatgt ggaaacaata cttgcacaaa caatgaggtg    540
cataacctta cagaatgtaa aaatgcgtct gtttccatat ctcataattc atgtactgct    600
cctgataaga cattaatatt agatgtgcca ccaggggttg aaaagtttca gttacatgat    660
tgtacacaag ttgaaaaagc agatactact atttgtttaa aatggaaaaa tattgaaacc    720
tttacttgtg atacacagaa tattacctac agatttcagt gtggtaatat gatatttgat    780
aataaagaaa ttaaattaga aaaccttgaa cccgaacatg agtataagtg tgactcagaa    840
atactctata ataaccacaa gtttactaac gcaagtaaaa ttattaaaac agattttggg    900
agtccaggag agcctcagat tattttttgt agaagtgaag ctgcacatca aggagtaatt    960
acctggaatc cccctcaaag atcatttcat aattttaccc tctgttatat aaaagagaca   1020
gaaaaagatt gcctcaatct ggataaaaac ctgatcaaat atgatttgca aaatttaaaa   1080
ccttatacga aatatgtttt atcattacat gcctacatca ttgcaaaagt gcaacgtaat   1140
ggaagtgctg caatgtgtca tttcacaact aaaagtgctc ctccaagcca ggtctggaac   1200
atgactgtct ccatgacatc agataatagt atgcatgtca agtgtaggcc tcccagggac   1260
cgtaatggcc cccatgaacg ttaccatttg gaagttgaag ctggaaatac tctggttaga   1320
aatgagtcgc ataagaattg cgatttccgt gtaaaagatc ttcaatattc aacagactac   1380
acttttaagg cctattttca caatggagac tatcctggag aaccctttat tttacatcat   1440
tcaacatctt ataattctaa ggcactgata gcatttctgg catttctgat tattgtgaca   1500
tcaatagccc tgcttgttgt tctctacaaa atctatgatc tacataagaa aagatcctgc   1560
aatttagatg aacagcagga gcttgttgaa agggatgatg aaaaacaact gatgaatgtg   1620
```

-continued

```
gagccaatcc atgcagatat tttgttggaa acttataaga ggaagattgc tgatgaagga   1680
agactttttc tggctgaatt tcagagcatc ccgcgggtgt tcagcaagtt tcctataaag   1740
gaagctcgaa agccctttaa ccagaataaa aaccgttatg ttgacattct tccttatgat   1800
tataaccgtg ttgaactctc tgagataaac ggagatgcag ggtcaaacta cataaatgcc   1860
agctatattg atggtttcaa agaacccagg aaatacattg ctgcacaagg tcccagggat   1920
gaaactgttg atgatttctg gaggatgatt tgggaacaga aagccacagt tattgtcatg   1980
gtcactcgat gtgaagaagg aaacaggaac aagtgtgcag aatactggcc gtcaatggaa   2040
gagggcactc gggcttttgg agatgttgtt gtaaagatca accagcacaa aagatgtcca   2100
gattacatca ttcagaaatt gaacattgta aataaaaaag aaaaagcaac tggaagagag   2160
gtgactcaca ttcagttcac cagctggcca gaccacgggg tgcctgagga tcctcacttg   2220
ctcctcaaac tgagaaggag agtgaatgcc ttcagcaatt tcttcagtgg tcccattgtg   2280
gtgcactgca gtgctggtgt tgggcgcaca ggaacctata tcggaattga tgccatgcta   2340
gaaggcctgg aagccgagaa caaagtggat gtttatggtt atgttgtcaa gctaaggcga   2400
cagagatgcc tgatggttca agtagaggcc cagtacatct tgatccatca ggctttggtg   2460
gaatacaatc agtttggaga aacagaagtg aatttgtctg aattacatcc atatctacat   2520
aacatgaaga aaagggatcc acccagtgag ccgtctccac tagaggctga attccagaga   2580
cttccttcat ataggagctg gaggacacag cacattggaa atcaagaaga aaataaaagt   2640
aaaaacagga attctaatgt catcccatat gactataaca gagtgccact taaacatgag   2700
ctggaaatga gtaaagagag tgagcatgat tcagatgaat cctctgatga tgacagtgat   2760
tcagaggaac caagcaaata catcaatgca tcttttataa tgagctactg gaaacctgaa   2820
gtgatgattg ctgctcaggg accactgaag gagaccattg gtgacttttg gcagatgatc   2880
ttccaaagaa aagtcaaagt tattgttatg ctgacagaac tgaaacatgg agaccaggaa   2940
atctgtgctc agtactgggg agaaggaaag caaacatatg gagatattga agttgacctg   3000
aaagacacag acaaatcttc aacttatacc cttcgtgtct ttgaactgag acattccaag   3060
aggaaagact ctcgaactgt gtaccagtac caatatacaa actggagtgt ggagcagctt   3120
cctgcagaac ccaaggaatt aatctctatg attcaggtcg tcaaacaaaa acttccccag   3180
aagaattcct ctgaagggaa caagcatcac aagagtacac ctctactcat tcactgcagg   3240
gatggatctc agcaaacggg aatattttgt gctttgttaa atctcttaga aagtgcggaa   3300
acagaagagg tagtggatat ttttcaagtg gtaaaagctc tacgcaaagc taggccaggc   3360
atggtttcca cattcgagca atatcaattc ctatatgacg tcattgccag cacctaccct   3420
gctcagaatg gacaagtaaa gaaaaacaac catcaagaag ataaaattga atttgataat   3480
gaagtggaca aagtaaagca ggatgctaat tgtgttaatc cacttggtgc cccagaaaag   3540
ctccctgaag caaaggaaca ggctgaaggt tctgaaccca cgagtggcac tgaggggcca   3600
gaacattctg tcaatggtcc tgcaagtcca gctttaaatc aaggttcata ggaaaagaca   3660
taaatgagga aactccaaac ctcctgttag ctgttatttc tatttttgta gaagtaggaa   3720
gtgaaaatag gtatacagtg gattaattaa atgcagcgaa ccaatatttg tagaagggtt   3780
atattttact actgtggaaa aatatttaag atagttttgc cagaacagtt tgtacagacg   3840
tatgcttatt ttaaaatttt atctcttatt cagtaaaaaa caacttcttt gtaatcgtta   3900
tgtgtgtata tgtatgtgtg tatgggtgtg tgtttgtgtg agagacagag aaagagagag   3960
aattctttca agtgaatcta aaagcttttg cttttccttt gtttttatga agaaaaaata   4020
```

```
cattttatat tagaagtgtt aacttagctt gaaggatctg tttttaaaaa tcataaactg   4080

tgtgcagact caataaaatc atgtacattt ctgaaatgac ctcaagatgt cctccttgtt   4140

ctactcatat atatctatct tatatagttt actattttac ttctagagat agtacataaa   4200

ggtggtatgt gtgtgtatgc tactacaaaa aagttgttaa ctaaattaac attgggaaat   4260

cttatattcc atatattagc atttagtcca atgtcttttt aagcttattt aattaaaaaa   4320

tttccagtga gcttatcatg ctgtctttac atggggtttt caattttgca tgctcgatta   4380

ttccctgtac aatatttaaa atttattgct tgatactttt gacaacaaat taggttttgt   4440

acaattgaac ttaaataaat gtcattaaaa taaataaatg caatatgtat taatattcat   4500

tgtataaaaa tagaagaata caaacatatt tgttaaatat ttacatatga aatttaatat   4560

agctattttt atggaatttt tcattgatat gaaaaatatg atattgcata tgcatagttc   4620

ccatgttaaa tcccattcat aactttcatt aaagcattta ctttgaattt ctccaatgct   4680

tagaatgttt ttaccaggaa tggatgtcgc taatcataat aaaattcaac cattattttt   4740

ttcttgttta taatacattg tgttatatgt tcaaatatga aatgtgtatg cacctattga   4800

aatatgttta atgcatttat taacatttgc aggacacttt tacaggcccc aattatccaa   4860

tagtctaata attgtttaag atctagaaaa aaaaaatcaa gaatagtggt atttttcatg   4920

aagtaataaa aactcgtttt ggtgaa                                        4946
```

<210> SEQ ID NO 127
<211> LENGTH: 1156
<212> TYPE: DNA
<213> ORGANISM: Homo sapiens

<400> SEQUENCE: 127

```
agaacaactt ttttgacttc ctgcaaagag gacccttaca gtatttttgg agaagttagt     60

aaaaccgaat ctgacatcat cacctagcag ttcatgcagc tagcaagtgg tttgttctta    120

gggtaacaga ggaggaaatt gttcctcgtc tgataagaca acagtggaga aaggacgcat    180

gctgtttctt agggacacgg ctgacttcca gatatgacca tgtatttgtg gcttaaactc    240

ttggcatttg gctttgcctt tctggacaca gaagtatttg tgacagggca aagcccaaca    300

ccttcccccca ctggtaagaa ttaatattta tatttttact aattttattt tcttgttgca    360

aagtttatat atttaactac aattttctat tattaacact gaaattattt ttaaggataa    420

attttataat catgagtgat tcttgacatt cacttgttct taaactttct gcttatacgt    480

tatagagttt aataactacc taaacatgtt attaaatttg tatatatatt ttgtgtataa    540

atagtaactt ttcccaaact tgacagtaaa tcacacaaca ggtttctact ctcttttaat    600

atttaagac tataaaaaaa tgcatttaaa ttagataaca aaattttata gtctgaaagc    660

aggttaacag ctgtctatgt atgttataga tatgtagata acagatttgc atatgtctat    720

atttctttaa gagtatgttg ctttttttcaa tggtatgcaa aacctttgag actattgaga    780

tatttttaaa taataatttt caaattctac tgaacacttc aatagtcctt ataaatgtct    840

taatcatgag ataaatttaa aacacagaga tgctgcaaat aaattcatac atagtacata    900

caaaataaga gaaaaaatta aattgcagat ggttaaatat cacatcactt aactgatgtt    960

actgaaaatg tattttcctg cataatcata tggttgacag tatgcattaa gaaggtaagt   1020

aaaacaatga agacaatttt gatttaatat ggtaatgcac aattccaact aacgtacatt   1080

caacagatca tgaaattggg ttattaaaat gaatattttt gtcattaaat aaaaaattccg   1140
```

tccaaaaaaa aaaaaa 1156

<210> SEQ ID NO 128
<211> LENGTH: 87
<212> TYPE: PRT
<213> ORGANISM: Homo sapiens

<400> SEQUENCE: 128

Met Thr Met Tyr Leu Trp Leu Lys Leu Leu Ala Phe Gly Phe Ala Phe
1 5 10 15

Leu Asp Thr Glu Val Phe Val Thr Gly Gln Ser Pro Thr Pro Ser Pro
20 25 30

Thr Gly His Leu Gln Ala Glu Glu Gln Gly Ser Gln Ser Lys Ser Pro
35 40 45

Asn Leu Lys Ser Arg Glu Ala Asp Ser Ser Ala Phe Ser Trp Trp Pro
50 55 60

Lys Ala Arg Glu Pro Leu Thr Asn His Trp Ser Lys Ser Lys Ser Pro
65 70 75 80

Lys Ala Glu Glu Leu Gly Val
85

<210> SEQ ID NO 129
<211> LENGTH: 1306
<212> TYPE: PRT
<213> ORGANISM: Homo sapiens

<400> SEQUENCE: 129

Met Thr Met Tyr Leu Trp Leu Lys Leu Leu Ala Phe Gly Phe Ala Phe
1 5 10 15

Leu Asp Thr Glu Val Phe Val Thr Gly Gln Ser Pro Thr Pro Ser Pro
20 25 30

Thr Gly Leu Thr Thr Ala Lys Met Pro Ser Val Pro Leu Ser Ser Asp
35 40 45

Pro Leu Pro Thr His Thr Thr Ala Phe Ser Pro Ala Ser Thr Phe Glu
50 55 60

Arg Glu Asn Asp Phe Ser Glu Thr Thr Thr Ser Leu Ser Pro Asp Asn
65 70 75 80

Thr Ser Thr Gln Val Ser Pro Asp Ser Leu Asp Asn Ala Ser Ala Phe
85 90 95

Asn Thr Thr Gly Val Ser Ser Val Gln Thr Pro His Leu Pro Thr His
100 105 110

Ala Asp Ser Gln Thr Pro Ser Ala Gly Thr Asp Thr Gln Thr Phe Ser
115 120 125

Gly Ser Ala Ala Asn Ala Lys Leu Asn Pro Thr Pro Gly Ser Asn Ala
130 135 140

Ile Ser Asp Val Pro Gly Glu Arg Ser Thr Ala Ser Thr Phe Pro Thr
145 150 155 160

Asp Pro Val Ser Pro Leu Thr Thr Thr Leu Ser Leu Ala His His Ser
165 170 175

Ser Ala Ala Leu Pro Ala Arg Thr Ser Asn Thr Thr Ile Thr Ala Asn
180 185 190

Thr Ser Asp Ala Tyr Leu Asn Ala Ser Glu Thr Thr Thr Leu Ser Pro
195 200 205

Ser Gly Ser Ala Val Ile Ser Thr Thr Thr Ile Ala Thr Thr Pro Ser
210 215 220

Lys Pro Thr Cys Asp Glu Lys Tyr Ala Asn Ile Thr Val Asp Tyr Leu

-continued

```
225                 230                 235                 240

Tyr Asn Lys Glu Thr Lys Leu Phe Thr Ala Lys Leu Asn Val Asn Glu
                245                 250                 255

Asn Val Glu Cys Gly Asn Asn Thr Cys Thr Asn Asn Glu Val His Asn
            260                 265                 270

Leu Thr Glu Cys Lys Asn Ala Ser Val Ser Ile Ser His Asn Ser Cys
        275                 280                 285

Thr Ala Pro Asp Lys Thr Leu Ile Leu Asp Val Pro Pro Gly Val Glu
    290                 295                 300

Lys Phe Gln Leu His Asp Cys Thr Gln Val Glu Lys Ala Asp Thr Thr
305                 310                 315                 320

Ile Cys Leu Lys Trp Lys Asn Ile Glu Thr Phe Thr Cys Asp Thr Gln
                325                 330                 335

Asn Ile Thr Tyr Arg Phe Gln Cys Gly Asn Met Ile Phe Asp Asn Lys
            340                 345                 350

Glu Ile Lys Leu Glu Asn Leu Glu Pro Glu His Glu Tyr Lys Cys Asp
        355                 360                 365

Ser Glu Ile Leu Tyr Asn Asn His Lys Phe Thr Asn Ala Ser Lys Ile
    370                 375                 380

Ile Lys Thr Asp Phe Gly Ser Pro Gly Glu Pro Gln Ile Ile Phe Cys
385                 390                 395                 400

Arg Ser Glu Ala Ala His Gln Gly Val Ile Thr Trp Asn Pro Pro Gln
                405                 410                 415

Arg Ser Phe His Asn Phe Thr Leu Cys Tyr Ile Lys Glu Thr Glu Lys
            420                 425                 430

Asp Cys Leu Asn Leu Asp Lys Asn Leu Ile Lys Tyr Asp Leu Gln Asn
        435                 440                 445

Leu Lys Pro Tyr Thr Lys Tyr Val Leu Ser Leu His Ala Tyr Ile Ile
    450                 455                 460

Ala Lys Val Gln Arg Asn Gly Ser Ala Ala Met Cys His Phe Thr Thr
465                 470                 475                 480

Lys Ser Ala Pro Pro Ser Gln Val Trp Asn Met Thr Val Ser Met Thr
                485                 490                 495

Ser Asp Asn Ser Met His Val Lys Cys Arg Pro Pro Arg Asp Arg Asn
            500                 505                 510

Gly Pro His Glu Arg Tyr His Leu Glu Val Glu Ala Gly Asn Thr Leu
        515                 520                 525

Val Arg Asn Glu Ser His Lys Asn Cys Asp Phe Arg Val Lys Asp Leu
    530                 535                 540

Gln Tyr Ser Thr Asp Tyr Thr Phe Lys Ala Tyr Phe His Asn Gly Asp
545                 550                 555                 560

Tyr Pro Gly Glu Pro Phe Ile Leu His His Ser Thr Ser Tyr Asn Ser
                565                 570                 575

Lys Ala Leu Ile Ala Phe Leu Ala Phe Leu Ile Ile Val Thr Ser Ile
            580                 585                 590

Ala Leu Leu Val Val Leu Tyr Lys Ile Tyr Asp Leu His Lys Lys Arg
        595                 600                 605

Ser Cys Asn Leu Asp Glu Gln Gln Glu Leu Val Glu Arg Asp Asp Glu
    610                 615                 620

Lys Gln Leu Met Asn Val Glu Pro Ile His Ala Asp Ile Leu Leu Glu
625                 630                 635                 640

Thr Tyr Lys Arg Lys Ile Ala Asp Glu Gly Arg Leu Phe Leu Ala Glu
                645                 650                 655
```

-continued

```
Phe Gln Ser Ile Pro Arg Val Phe Ser Lys Phe Pro Ile Lys Glu Ala
            660                 665                 670

Arg Lys Pro Phe Asn Gln Asn Lys Asn Arg Tyr Val Asp Ile Leu Pro
        675                 680                 685

Tyr Asp Tyr Asn Arg Val Glu Leu Ser Glu Ile Asn Gly Asp Ala Gly
    690                 695                 700

Ser Asn Tyr Ile Asn Ala Ser Tyr Ile Asp Gly Phe Lys Glu Pro Arg
705                 710                 715                 720

Lys Tyr Ile Ala Ala Gln Gly Pro Arg Asp Glu Thr Val Asp Asp Phe
                725                 730                 735

Trp Arg Met Ile Trp Glu Gln Lys Ala Thr Val Ile Val Met Val Thr
            740                 745                 750

Arg Cys Glu Glu Gly Asn Arg Asn Lys Cys Ala Glu Tyr Trp Pro Ser
        755                 760                 765

Met Glu Glu Gly Thr Arg Ala Phe Gly Asp Val Val Val Lys Ile Asn
    770                 775                 780

Gln His Lys Arg Cys Pro Asp Tyr Ile Ile Gln Lys Leu Asn Ile Val
785                 790                 795                 800

Asn Lys Lys Glu Lys Ala Thr Gly Arg Glu Val Thr His Ile Gln Phe
                805                 810                 815

Thr Ser Trp Pro Asp His Gly Val Pro Glu Asp Pro His Leu Leu Leu
            820                 825                 830

Lys Leu Arg Arg Arg Val Asn Ala Phe Ser Asn Phe Phe Ser Gly Pro
        835                 840                 845

Ile Val Val His Cys Ser Ala Gly Val Gly Arg Thr Gly Thr Tyr Ile
    850                 855                 860

Gly Ile Asp Ala Met Leu Glu Gly Leu Glu Ala Glu Asn Lys Val Asp
865                 870                 875                 880

Val Tyr Gly Tyr Val Val Lys Leu Arg Arg Gln Arg Cys Leu Met Val
                885                 890                 895

Gln Val Glu Ala Gln Tyr Ile Leu Ile His Gln Ala Leu Val Glu Tyr
            900                 905                 910

Asn Gln Phe Gly Glu Thr Glu Val Asn Leu Ser Glu Leu His Pro Tyr
        915                 920                 925

Leu His Asn Met Lys Lys Arg Asp Pro Pro Ser Glu Pro Ser Pro Leu
    930                 935                 940

Glu Ala Glu Phe Gln Arg Leu Pro Ser Tyr Arg Ser Trp Arg Thr Gln
945                 950                 955                 960

His Ile Gly Asn Gln Glu Glu Asn Lys Ser Lys Asn Arg Asn Ser Asn
                965                 970                 975

Val Ile Pro Tyr Asp Tyr Asn Arg Val Pro Leu Lys His Glu Leu Glu
            980                 985                 990

Met Ser Lys Glu Ser Glu His Asp  Ser Asp Glu Ser Ser  Asp Asp Asp
        995                 1000                 1005

Ser Asp  Ser Glu Glu Pro Ser  Lys Tyr Ile Asn Ala  Ser Phe Ile
    1010                 1015                 1020

Met Ser  Tyr Trp Lys Pro Glu  Val Met Ile Ala Ala  Gln Gly Pro
    1025                 1030                 1035

Leu Lys  Glu Thr Ile Gly Asp  Phe Trp Gln Met Ile  Phe Gln Arg
    1040                 1045                 1050

Lys Val  Lys Val Ile Val Met  Leu Thr Glu Leu Lys  His Gly Asp
    1055                 1060                 1065
```

```
Gln Glu  Ile Cys Ala Gln Tyr  Trp Gly Glu Gly Lys  Gln Thr Tyr
    1070                 1075                 1080

Gly Asp  Ile Glu Val Asp Leu  Lys Asp Thr Asp Lys  Ser Ser Thr
    1085                 1090                 1095

Tyr Thr  Leu Arg Val Phe Glu  Leu Arg His Ser Lys  Arg Lys Asp
    1100                 1105                 1110

Ser Arg  Thr Val Tyr Gln Tyr  Gln Tyr Thr Asn Trp  Ser Val Glu
    1115                 1120                 1125

Gln Leu  Pro Ala Glu Pro Lys  Glu Leu Ile Ser Met  Ile Gln Val
    1130                 1135                 1140

Val Lys  Gln Lys Leu Pro Gln  Lys Asn Ser Ser Glu  Gly Asn Lys
    1145                 1150                 1155

His His  Lys Ser Thr Pro Leu  Leu Ile His Cys Arg  Asp Gly Ser
    1160                 1165                 1170

Gln Gln  Thr Gly Ile Phe Cys  Ala Leu Leu Asn Leu  Leu Glu Ser
    1175                 1180                 1185

Ala Glu  Thr Glu Glu Val Val  Asp Ile Phe Gln Val  Val Lys Ala
    1190                 1195                 1200

Leu Arg  Lys Ala Arg Pro Gly  Met Val Ser Thr Phe  Glu Gln Tyr
    1205                 1210                 1215

Gln Phe  Leu Tyr Asp Val Ile  Ala Ser Thr Tyr Pro  Ala Gln Asn
    1220                 1225                 1230

Gly Gln  Val Lys Lys Asn Asn  His Gln Glu Asp Lys  Ile Glu Phe
    1235                 1240                 1245

Asp Asn  Glu Val Asp Lys Val  Lys Gln Asp Ala Asn  Cys Val Asn
    1250                 1255                 1260

Pro Leu  Gly Ala Pro Glu Lys  Leu Pro Glu Ala Lys  Glu Gln Ala
    1265                 1270                 1275

Glu Gly  Ser Glu Pro Thr Ser  Gly Thr Glu Gly Pro  Glu His Ser
    1280                 1285                 1290

Val Asn  Gly Pro Ala Ser Pro  Ala Leu Asn Gln Gly  Ser
    1295                 1300                 1305
```

<210> SEQ ID NO 130
<211> LENGTH: 1145
<212> TYPE: PRT
<213> ORGANISM: Homo sapiens

<400> SEQUENCE: 130

```
Met Thr Met Tyr Leu Trp Leu Lys Leu Leu Ala Phe Gly Phe Ala Phe
1               5                   10                  15

Leu Asp Thr Glu Val Phe Val Thr Gly Gln Ser Pro Thr Pro Ser Pro
            20                  25                  30

Thr Asp Ala Tyr Leu Asn Ala Ser Glu Thr Thr Thr Leu Ser Pro Ser
        35                  40                  45

Gly Ser Ala Val Ile Ser Thr Thr Thr Ile Ala Thr Thr Pro Ser Lys
    50                  55                  60

Pro Thr Cys Asp Glu Lys Tyr Ala Asn Ile Thr Val Asp Tyr Leu Tyr
65                  70                  75                  80

Asn Lys Glu Thr Lys Leu Phe Thr Ala Lys Leu Asn Val Asn Glu Asn
                85                  90                  95

Val Glu Cys Gly Asn Asn Thr Cys Thr Asn Asn Glu Val His Asn Leu
            100                 105                 110

Thr Glu Cys Lys Asn Ala Ser Val Ser Ile Ser His Asn Ser Cys Thr
        115                 120                 125
```

-continued

```
Ala Pro Asp Lys Thr Leu Ile Leu Asp Val Pro Pro Gly Val Glu Lys
    130                 135                 140

Phe Gln Leu His Asp Cys Thr Gln Val Glu Lys Ala Asp Thr Thr Ile
145                 150                 155                 160

Cys Leu Lys Trp Lys Asn Ile Glu Thr Phe Thr Cys Asp Thr Gln Asn
                165                 170                 175

Ile Thr Tyr Arg Phe Gln Cys Gly Asn Met Ile Phe Asp Asn Lys Glu
            180                 185                 190

Ile Lys Leu Glu Asn Leu Glu Pro Glu His Glu Tyr Lys Cys Asp Ser
        195                 200                 205

Glu Ile Leu Tyr Asn Asn His Lys Phe Thr Asn Ala Ser Lys Ile Ile
    210                 215                 220

Lys Thr Asp Phe Gly Ser Pro Gly Glu Pro Gln Ile Ile Phe Cys Arg
225                 230                 235                 240

Ser Glu Ala Ala His Gln Gly Val Ile Thr Trp Asn Pro Pro Gln Arg
                245                 250                 255

Ser Phe His Asn Phe Thr Leu Cys Tyr Ile Lys Glu Thr Glu Lys Asp
            260                 265                 270

Cys Leu Asn Leu Asp Lys Asn Leu Ile Lys Tyr Asp Leu Gln Asn Leu
        275                 280                 285

Lys Pro Tyr Thr Lys Tyr Val Leu Ser Leu His Ala Tyr Ile Ile Ala
    290                 295                 300

Lys Val Gln Arg Asn Gly Ser Ala Ala Met Cys His Phe Thr Thr Lys
305                 310                 315                 320

Ser Ala Pro Pro Ser Gln Val Trp Asn Met Thr Val Ser Met Thr Ser
                325                 330                 335

Asp Asn Ser Met His Val Lys Cys Arg Pro Pro Arg Asp Arg Asn Gly
            340                 345                 350

Pro His Glu Arg Tyr His Leu Glu Val Glu Ala Gly Asn Thr Leu Val
        355                 360                 365

Arg Asn Glu Ser His Lys Asn Cys Asp Phe Arg Val Lys Asp Leu Gln
    370                 375                 380

Tyr Ser Thr Asp Tyr Thr Phe Lys Ala Tyr Phe His Asn Gly Asp Tyr
385                 390                 395                 400

Pro Gly Glu Pro Phe Ile Leu His His Ser Thr Ser Tyr Asn Ser Lys
                405                 410                 415

Ala Leu Ile Ala Phe Leu Ala Phe Leu Ile Ile Val Thr Ser Ile Ala
            420                 425                 430

Leu Leu Val Val Leu Tyr Lys Ile Tyr Asp Leu His Lys Lys Arg Ser
        435                 440                 445

Cys Asn Leu Asp Glu Gln Gln Glu Leu Val Glu Arg Asp Asp Glu Lys
    450                 455                 460

Gln Leu Met Asn Val Glu Pro Ile His Ala Asp Ile Leu Leu Glu Thr
465                 470                 475                 480

Tyr Lys Arg Lys Ile Ala Asp Glu Gly Arg Leu Phe Leu Ala Glu Phe
                485                 490                 495

Gln Ser Ile Pro Arg Val Phe Ser Lys Phe Pro Ile Lys Glu Ala Arg
            500                 505                 510

Lys Pro Phe Asn Gln Asn Lys Asn Arg Tyr Val Asp Ile Leu Pro Tyr
        515                 520                 525

Asp Tyr Asn Arg Val Glu Leu Ser Glu Ile Asn Gly Asp Ala Gly Ser
    530                 535                 540
```

```
Asn Tyr Ile Asn Ala Ser Tyr Ile Asp Gly Phe Lys Glu Pro Arg Lys
545                 550                 555                 560

Tyr Ile Ala Ala Gln Gly Pro Arg Asp Glu Thr Val Asp Asp Phe Trp
                565                 570                 575

Arg Met Ile Trp Glu Gln Lys Ala Thr Val Ile Val Met Val Thr Arg
            580                 585                 590

Cys Glu Glu Gly Asn Arg Asn Lys Cys Ala Glu Tyr Trp Pro Ser Met
        595                 600                 605

Glu Glu Gly Thr Arg Ala Phe Gly Asp Val Val Val Lys Ile Asn Gln
    610                 615                 620

His Lys Arg Cys Pro Asp Tyr Ile Ile Gln Lys Leu Asn Ile Val Asn
625                 630                 635                 640

Lys Lys Glu Lys Ala Thr Gly Arg Glu Val Thr His Ile Gln Phe Thr
                645                 650                 655

Ser Trp Pro Asp His Gly Val Pro Glu Asp Pro His Leu Leu Leu Lys
            660                 665                 670

Leu Arg Arg Arg Val Asn Ala Phe Ser Asn Phe Phe Ser Gly Pro Ile
        675                 680                 685

Val Val His Cys Ser Ala Gly Val Gly Arg Thr Gly Thr Tyr Ile Gly
    690                 695                 700

Ile Asp Ala Met Leu Glu Gly Leu Glu Ala Glu Asn Lys Val Asp Val
705                 710                 715                 720

Tyr Gly Tyr Val Val Lys Leu Arg Arg Gln Arg Cys Leu Met Val Gln
                725                 730                 735

Val Glu Ala Gln Tyr Ile Leu Ile His Gln Ala Leu Val Glu Tyr Asn
            740                 745                 750

Gln Phe Gly Glu Thr Glu Val Asn Leu Ser Glu Leu His Pro Tyr Leu
        755                 760                 765

His Asn Met Lys Lys Arg Asp Pro Pro Ser Glu Pro Ser Pro Leu Glu
    770                 775                 780

Ala Glu Phe Gln Arg Leu Pro Ser Tyr Arg Ser Trp Arg Thr Gln His
785                 790                 795                 800

Ile Gly Asn Gln Glu Glu Asn Lys Ser Lys Asn Arg Asn Ser Asn Val
                805                 810                 815

Ile Pro Tyr Asp Tyr Asn Arg Val Pro Leu Lys His Glu Leu Glu Met
            820                 825                 830

Ser Lys Glu Ser Glu His Asp Ser Asp Glu Ser Ser Asp Asp Asp Ser
        835                 840                 845

Asp Ser Glu Glu Pro Ser Lys Tyr Ile Asn Ala Ser Phe Ile Met Ser
    850                 855                 860

Tyr Trp Lys Pro Glu Val Met Ile Ala Ala Gln Gly Pro Leu Lys Glu
865                 870                 875                 880

Thr Ile Gly Asp Phe Trp Gln Met Ile Phe Gln Arg Lys Val Lys Val
                885                 890                 895

Ile Val Met Leu Thr Glu Leu Lys His Gly Asp Gln Glu Ile Cys Ala
            900                 905                 910

Gln Tyr Trp Gly Glu Gly Lys Gln Thr Tyr Gly Asp Ile Glu Val Asp
        915                 920                 925

Leu Lys Asp Thr Asp Lys Ser Ser Thr Tyr Thr Leu Arg Val Phe Glu
    930                 935                 940

Leu Arg His Ser Lys Arg Lys Asp Ser Arg Thr Val Tyr Gln Tyr Gln
945                 950                 955                 960

Tyr Thr Asn Trp Ser Val Glu Gln Leu Pro Ala Glu Pro Lys Glu Leu
```

```
                965                 970                 975

Ile Ser Met Ile Gln Val Val Lys Gln Lys Leu Pro Gln Lys Asn Ser
            980                 985                 990

Ser Glu Gly Asn Lys His His Lys  Ser Thr Pro Leu Leu  Ile His Cys
        995                 1000                 1005

Arg Asp  Gly Ser Gln Gln Thr  Gly Ile Phe Cys Ala  Leu Leu Asn
    1010                 1015                 1020

Leu Leu  Glu Ser Ala Glu Thr  Glu Glu Val Val Asp  Ile Phe Gln
    1025                 1030                 1035

Val Val  Lys Ala Leu Arg Lys  Ala Arg Pro Gly Met  Val Ser Thr
    1040                 1045                 1050

Phe Glu  Gln Tyr Gln Phe Leu  Tyr Asp Val Ile Ala  Ser Thr Tyr
    1055                 1060                 1065

Pro Ala  Gln Asn Gly Gln Val  Lys Lys Asn Asn His  Gln Glu Asp
    1070                 1075                 1080

Lys Ile  Glu Phe Asp Asn Glu  Val Asp Lys Val Lys  Gln Asp Ala
    1085                 1090                 1095

Asn Cys  Val Asn Pro Leu Gly  Ala Pro Glu Lys Leu  Pro Glu Ala
    1100                 1105                 1110

Lys Glu  Gln Ala Glu Gly Ser  Glu Pro Thr Ser Gly  Thr Glu Gly
    1115                 1120                 1125

Pro Glu  His Ser Val Asn Gly  Pro Ala Ser Pro Ala  Leu Asn Gln
    1130                 1135                 1140

Gly Ser
    1145
```

<210> SEQ ID NO 131
<211> LENGTH: 3740
<212> TYPE: DNA
<213> ORGANISM: Homo sapiens

<400> SEQUENCE: 131

```
gggacggcgg cggcgcagct cggaacccgc cagggtccag ggtccaggtt ccagcgcccg     60
gcggcccagg caccccccga gcccagctcc acacaccgtt cctggatctc ctctccccag    120
gcggagcgtg cccctgccca gtccagtgac cttcgcctgt tggagccctg gttaattttt    180
gcccagtctg cctgttgtgg ggctcctccc ctttggggat ataagcccgg cctggggctg    240
ctccgttctc tgcctggcct gaggctccct gagccgcctc cccaccatca ccatggccaa    300
gggcttctat atttccaagt ccctgggcat cctggggatc ctcctgggcg tggcagccgt    360
gtgcacaatc atcgcactgt cagtggtgta ctcccaggag aagaacaaga acgccaacag    420
ctcccccgtg gcctccacca ccccgtccgc ctcagccacc accaaccccg cctcggccac    480
caccttggac caaagtaaag cgtggaatcg ttaccgcctc cccaacacgc tgaaacccga    540
ttcctaccgg gtgacgctga gaccgtacct cacccccaat gacaggggcc tgtacgtttt    600
taagggctcc agcaccgtcc gtttcacctg caaggaggcc actgacgtca tcatcatcca    660
cagcaagaag ctcaactaca ccctcagcca ggggcacagg gtggtcctgc gtggtgtggg    720
aggctcccag ccccccgaca ttgacaagac tgagctggtg gagcccaccg agtacctggt    780
ggtgcacctc aagggctccc tggtgaagga cagccagtat gagatggaca gcgagttcga    840
gggggagttg gcagatgacc tggcgggctt ctaccgcagc gagtacatgg agggcaatgt    900
cagaaaggtg gtggccacta cacagatgca ggctgcagat gcccggaagt ccttcccatg    960
cttcgatgag ccggccatga aggccgagtt caacatcacg cttatccacc ccaaggacct   1020
```

-continued gacagccctg tccaacatgc ttcccaaagg tcccagcacc ccacttccag aagaccccaa 1080
ctggaatgtc actgagttcc acaccacgcc caagatgtcc acgtacttgc tggccttcat 1140
tgtcagtgag ttcgactacg tggagaagca ggcatccaat ggtgtcttga tccggatctg 1200
ggcccggccc agtgccattg cggcgggcca cggcgattat gccctgaacg tgacgggccc 1260
catccttaac ttctttgctg gtcattatga cacaccctac ccactcccaa aatcagacca 1320
gattggcctg ccagacttca acgccggcgc catggagaac tggggactgg tgacctaccg 1380
ggagaactcc ctgctgttcg accccctgtc ctcctccagc agcaacaagg agcgggtggt 1440
cactgtgatt gctcatgagc tggcccacca gtggttcggg aacctggtga ccatagagtg 1500
gtggaatgac ctgtggctga acgagggctt cgcctcctac gtggagtacc tgggtgctga 1560
ctatgcggag cccacctgga acttgaaaga cctcatggtg ctgaatgatg tgtaccgcgt 1620
gatggcagtg gatgcactgg cctcctccca cccgctgtcc acacccgcct cggagatcaa 1680
cacgccggcc cagatcagtg agctgtttga cgccatctcc tacagcaagg gcgcctcagt 1740
cctcaggatg ctctccagct tcctgtccga ggacgtattc aagcagggcc tggcgtccta 1800
cctccacacc tttgcctacc agaacaccat ctacctgaac ctgtgggacc acctgcagga 1860
ggctgtgaac aaccggtcca tccaactccc caccaccgtg cgggacatca tgaaccgctg 1920
gaccctgcag atgggcttcc cggtcatcac ggtggatacc agcacgggga ccctttccca 1980
ggagcacttc ctccttgacc ccgattccaa tgttacccgc ccctcagaat tcaactacgt 2040
gtggattgtg cccatcacat ccatcagaga tggcagacag cagcaggact actggctgat 2100
agatgtaaga gcccagaacg atctcttcag cacatcaggc aatgagtggg tcctgctgaa 2160
cctcaatgtg acgggctatt accgggtgaa ctacgacgaa gagaactgga ggaagattca 2220
gactcagctg cagagagacc actcggccat ccctgtcatc aatcgggcac agatcattaa 2280
tgacgccttc aacctggcca gtgcccataa ggtccctgtc actctggcgc tgaacaacac 2340
cctcttcctg attgaagaga gacagtacat gccctgggag gccgccctga gcagcctgag 2400
ctacttcaag ctcatgtttg accgctccga ggtctatggc cccatgaaga actacctgaa 2460
gaagcaggtc acacccctct tcattcactt cagaaataat accaacaact ggagggagat 2520
cccagaaaac ctgatggacc agtacagcga ggttaatgcc atcagcaccg cctgctccaa 2580
cggagttcca gagtgtgagg agatggtctc tggccttttc aagcagtgga tggagaaccc 2640
caataataac ccgatccacc ccaacctgcg gtccaccgtc tactgcaacg ctatcgccca 2700
gggcggggag gaggagtggg acttcgcctg ggagcagttc cgaaatgcca cactggtcaa 2760
tgaggctgac aagctccggg cagccctggc ctgcagcaaa gagttgtgga tcctgaacag 2820
gtacctgagc tacaccctga acccggactt aatccggaag caggacgcca cctctaccat 2880
catcagcatt accaacaacg tcattgggca aggtctggtc tgggactttg tccagagcaa 2940
ctggaagaag ctttttaacg attatggtgg tggctcgttc tccttctcca acctcatcca 3000
ggcagtgaca cgacgattct ccaccgagta tgagctgcag cagctggagc agttcaagaa 3060
ggacaacgag gaaacaggct tcggctcagg cacccgggcc ctggagcaag ccctggagaa 3120
gacgaaagcc aacatcaagt gggtgaagga gaacaaggag gtggtgctcc agtggttcac 3180
agaaaacagc aaatagtccc cagcccttga agtcacccgg cccccatgca aggtgcccac 3240
atgtgtccat cccagcggct ggtgcagggc ctccattcct ggagcccgag gcaccagtgt 3300
cctcccctca aggacaaagt ctccagccca cgttctctct gcctgtgagc cagtctagtt 3360

-continued

```
cctgatgacc caggctgcct gagcacctcc cagcccctgc ccctcatgcc aaccccgccc   3420

taggcctggc atggcacctg tcgcccagtg ccctggggct gatctcaggg aagcccagct   3480

ccagggccag atgagcagaa gctctcgatg gacaatgaac ggccttgctg ggggccgccc   3540

tgtaccctct ttcacctttc cctaaagacc ctaaatctga ggaatcaaca gggcagcaga   3600

tctgtatatt tttttctaag agaaaatgta aataaaggat ttctagatga aaaaaaaaaa   3660

aaaaaaaaaa aaaaaaaaaa aaaaaaaaaa aaaaaaaaaa aaaaaaaaaa aaaaaaaaaa   3720

aaaaaaaaaa aaaaaaaaaa                                               3740
```

```
<210> SEQ ID NO 132
<211> LENGTH: 967
<212> TYPE: PRT
<213> ORGANISM: Homo sapiens

<400> SEQUENCE: 132

Met Ala Lys Gly Phe Tyr Ile Ser Lys Ser Leu Gly Ile Leu Gly Ile
1               5                   10                  15

Leu Leu Gly Val Ala Ala Val Cys Thr Ile Ile Ala Leu Ser Val Val
            20                  25                  30

Tyr Ser Gln Glu Lys Asn Lys Asn Ala Asn Ser Ser Pro Val Ala Ser
        35                  40                  45

Thr Thr Pro Ser Ala Ser Ala Thr Thr Asn Pro Ala Ser Ala Thr Thr
    50                  55                  60

Leu Asp Gln Ser Lys Ala Trp Asn Arg Tyr Arg Leu Pro Asn Thr Leu
65                  70                  75                  80

Lys Pro Asp Ser Tyr Arg Val Thr Leu Arg Pro Tyr Leu Thr Pro Asn
                85                  90                  95

Asp Arg Gly Leu Tyr Val Phe Lys Gly Ser Ser Thr Val Arg Phe Thr
            100                 105                 110

Cys Lys Glu Ala Thr Asp Val Ile Ile Ile His Ser Lys Lys Leu Asn
        115                 120                 125

Tyr Thr Leu Ser Gln Gly His Arg Val Val Leu Arg Gly Val Gly Gly
    130                 135                 140

Ser Gln Pro Pro Asp Ile Asp Lys Thr Glu Leu Val Glu Pro Thr Glu
145                 150                 155                 160

Tyr Leu Val Val His Leu Lys Gly Ser Leu Val Lys Asp Ser Gln Tyr
                165                 170                 175

Glu Met Asp Ser Glu Phe Glu Gly Glu Leu Ala Asp Asp Leu Ala Gly
            180                 185                 190

Phe Tyr Arg Ser Glu Tyr Met Glu Gly Asn Val Arg Lys Val Val Ala
        195                 200                 205

Thr Thr Gln Met Gln Ala Ala Asp Ala Arg Lys Ser Phe Pro Cys Phe
    210                 215                 220

Asp Glu Pro Ala Met Lys Ala Glu Phe Asn Ile Thr Leu Ile His Pro
225                 230                 235                 240

Lys Asp Leu Thr Ala Leu Ser Asn Met Leu Pro Lys Gly Pro Ser Thr
                245                 250                 255

Pro Leu Pro Glu Asp Pro Asn Trp Asn Val Thr Glu Phe His Thr Thr
            260                 265                 270

Pro Lys Met Ser Thr Tyr Leu Leu Ala Phe Ile Val Ser Glu Phe Asp
        275                 280                 285

Tyr Val Glu Lys Gln Ala Ser Asn Gly Val Leu Ile Arg Ile Trp Ala
    290                 295                 300
```

-continued

```
Arg Pro Ser Ala Ile Ala Ala Gly His Gly Asp Tyr Ala Leu Asn Val
305                 310                 315                 320

Thr Gly Pro Ile Leu Asn Phe Phe Ala Gly His Tyr Asp Thr Pro Tyr
                325                 330                 335

Pro Leu Pro Lys Ser Asp Gln Ile Gly Leu Pro Asp Phe Asn Ala Gly
            340                 345                 350

Ala Met Glu Asn Trp Gly Leu Val Thr Tyr Arg Glu Asn Ser Leu Leu
        355                 360                 365

Phe Asp Pro Leu Ser Ser Ser Ser Ser Asn Lys Glu Arg Val Val Thr
    370                 375                 380

Val Ile Ala His Glu Leu Ala His Gln Trp Phe Gly Asn Leu Val Thr
385                 390                 395                 400

Ile Glu Trp Trp Asn Asp Leu Trp Leu Asn Glu Gly Phe Ala Ser Tyr
                405                 410                 415

Val Glu Tyr Leu Gly Ala Asp Tyr Ala Glu Pro Thr Trp Asn Leu Lys
            420                 425                 430

Asp Leu Met Val Leu Asn Asp Val Tyr Arg Val Met Ala Val Asp Ala
        435                 440                 445

Leu Ala Ser Ser His Pro Leu Ser Thr Pro Ala Ser Glu Ile Asn Thr
    450                 455                 460

Pro Ala Gln Ile Ser Glu Leu Phe Asp Ala Ile Ser Tyr Ser Lys Gly
465                 470                 475                 480

Ala Ser Val Leu Arg Met Leu Ser Ser Phe Leu Ser Glu Asp Val Phe
                485                 490                 495

Lys Gln Gly Leu Ala Ser Tyr Leu His Thr Phe Ala Tyr Gln Asn Thr
            500                 505                 510

Ile Tyr Leu Asn Leu Trp Asp His Leu Gln Glu Ala Val Asn Asn Arg
        515                 520                 525

Ser Ile Gln Leu Pro Thr Thr Val Arg Asp Ile Met Asn Arg Trp Thr
    530                 535                 540

Leu Gln Met Gly Phe Pro Val Ile Thr Val Asp Thr Ser Thr Gly Thr
545                 550                 555                 560

Leu Ser Gln Glu His Phe Leu Leu Asp Pro Asp Ser Asn Val Thr Arg
                565                 570                 575

Pro Ser Glu Phe Asn Tyr Val Trp Ile Val Pro Ile Thr Ser Ile Arg
            580                 585                 590

Asp Gly Arg Gln Gln Gln Asp Tyr Trp Leu Ile Asp Val Arg Ala Gln
        595                 600                 605

Asn Asp Leu Phe Ser Thr Ser Gly Asn Glu Trp Val Leu Leu Asn Leu
    610                 615                 620

Asn Val Thr Gly Tyr Tyr Arg Val Asn Tyr Asp Glu Glu Asn Trp Arg
625                 630                 635                 640

Lys Ile Gln Thr Gln Leu Gln Arg Asp His Ser Ala Ile Pro Val Ile
                645                 650                 655

Asn Arg Ala Gln Ile Ile Asn Asp Ala Phe Asn Leu Ala Ser Ala His
            660                 665                 670

Lys Val Pro Val Thr Leu Ala Leu Asn Asn Thr Leu Phe Leu Ile Glu
        675                 680                 685

Glu Arg Gln Tyr Met Pro Trp Glu Ala Ala Leu Ser Ser Leu Ser Tyr
    690                 695                 700

Phe Lys Leu Met Phe Asp Arg Ser Glu Val Tyr Gly Pro Met Lys Asn
705                 710                 715                 720

Tyr Leu Lys Lys Gln Val Thr Pro Leu Phe Ile His Phe Arg Asn Asn
```

```
                725                 730                 735

Thr Asn Asn Trp Arg Glu Ile Pro Glu Asn Leu Met Asp Gln Tyr Ser
            740                 745                 750

Glu Val Asn Ala Ile Ser Thr Ala Cys Ser Asn Gly Val Pro Glu Cys
        755                 760                 765

Glu Glu Met Val Ser Gly Leu Phe Lys Gln Trp Met Glu Asn Pro Asn
    770                 775                 780

Asn Asn Pro Ile His Pro Asn Leu Arg Ser Thr Val Tyr Cys Asn Ala
785                 790                 795                 800

Ile Ala Gln Gly Gly Glu Glu Glu Trp Asp Phe Ala Trp Glu Gln Phe
                805                 810                 815

Arg Asn Ala Thr Leu Val Asn Glu Ala Asp Lys Leu Arg Ala Ala Leu
            820                 825                 830

Ala Cys Ser Lys Glu Leu Trp Ile Leu Asn Arg Tyr Leu Ser Tyr Thr
        835                 840                 845

Leu Asn Pro Asp Leu Ile Arg Lys Gln Asp Ala Thr Ser Thr Ile Ile
    850                 855                 860

Ser Ile Thr Asn Asn Val Ile Gly Gln Gly Leu Val Trp Asp Phe Val
865                 870                 875                 880

Gln Ser Asn Trp Lys Lys Leu Phe Asn Asp Tyr Gly Gly Gly Ser Phe
                885                 890                 895

Ser Phe Ser Asn Leu Ile Gln Ala Val Thr Arg Arg Phe Ser Thr Glu
            900                 905                 910

Tyr Glu Leu Gln Gln Leu Glu Gln Phe Lys Lys Asp Asn Glu Glu Thr
        915                 920                 925

Gly Phe Gly Ser Gly Thr Arg Ala Leu Glu Gln Ala Leu Glu Lys Thr
    930                 935                 940

Lys Ala Asn Ile Lys Trp Val Lys Glu Asn Lys Glu Val Val Leu Gln
945                 950                 955                 960

Trp Phe Thr Glu Asn Ser Lys
                965
```

<210> SEQ ID NO 133
<211> LENGTH: 3962
<212> TYPE: DNA
<213> ORGANISM: Homo sapiens

<400> SEQUENCE: 133

```
acacacacac agacgtgctc acggagcctg tgcctgcctc tacttgtctg ctctgcgcag      60

atggttcctg gcttttgggt cacctcatcc tgcagcccag tccagttaga acctttcttc     120

cacagagact ggcaagctgt ggggtaagag ttttggtaag gctgcctgtc ttcagagcat     180

gaaggacact gcccggagag ggaagagggc aatatttagt gtttgggcct acttgttgtt     240

gggctcccca ctgcctctcc tttgcagagc tatcactggc ccctggttgc aaactctcgg     300

tggctttcaa gcctacaaaa caaaaactga gagggtgtcc aaaaagagaa gaagaaaacg     360

ttgttgttgg tcctggattc cactgttgga ttttggtggg gatgagaaga aggaattacc     420

aggtgtgatc aacacctgca cggtacctgc acggctttaa agaatgcgtt ccagaggcag     480

tgataccgag ggctcagccc aaaagaaatt tccaagacat actaaaggcc acagtttcca     540

agggcctaaa aacatgaagc atagacagca agacaaagac tcccccagtg agtcggatgt     600

aatacttccg tgtcccaagg cagagaagcc acacagtggt aatggccacc aagcagaaga     660

cctctcaaga gatgacctgt tatttctcct cagcattctg gagggagaac tgcaggctcg     720
```

-continued

```
agatgaggtc ataggcattt taaaggctga aaaaatggac ctggctttgc tggaagctca    780
gtatgggttt gtcactccaa aaaaggtgtt agaggctctc cagagagatg cttttcaagc    840
gaaatctacc ccttggcagg aggacatcta tgagaaacca atgaatgagt tggacaaagt    900
tgtggaaaaa cataaagaat cttacagacg aatcctggga cagcttttag tggcagaaaa    960
atcccgtagg caaaccatat tggagttgga ggaagaaaag agaaaacata aagaatacat   1020
ggagaagagt gatgaattca tatgcctact agaacaggaa tgtgaaagat taaagaagct   1080
aattgatcaa gaaatcaagt ctcaggagga gaaggagcaa gaaaaggaga aaagggtcac   1140
caccctgaaa gaggagctga ccaagctgaa gtcttttgct ttgatggtgg tggatgaaca   1200
gcaaaggctg acggcacagc tcacccttca aagacagaaa atccaagagc tgaccacaaa   1260
tgcaaaggaa acacatacca aactagccct tgctgaagcc agagttcagg aggaagagca   1320
gaaggcaacc agactagaga aggaactgca aacgcagacc acaaagtttc accaagacca   1380
agacacaatt atggcgaagc tcaccaatga ggacagtcaa aatcgccagc ttcaacaaaa   1440
gctggcagca ctcagccggc agattgatga gttagaagag acaaacaggt ctttacgaaa   1500
agcagaagag gagctgcaag atataaaaga aaaaatcagt aagggagaat atggaaacgc   1560
tggtatcatg gctgaagtgg aagagctcag gaaacgtgtg ctagatatgg aagggaaaga   1620
tgaagagctc ataaaaatgg aggagcagtg cagagatctc aataagaggc ttgaaaggga   1680
gacgttacag agtaaagact ttaaactaga ggttgaaaaa ctcagtaaaa gaattatggc   1740
tctggaaaag ttagaagacg ctttcaacaa aagcaaacaa gaatgctact ctctgaaatg   1800
caatttagaa aaagaaagga tgaccacaaa gcagttgtct caagaactgg agagtttaaa   1860
agtaaggatc aaagagctag aagccattga aagtcggcta gaaaagacag aattcactct   1920
aaaagaggat ttaactaaac tgaaaacatt aactgtgatg tttgtagatg aacggaaaac   1980
aatgagtgaa aaattaaaga aaactgaaga taaattacaa gctgcttctt ctcagcttca   2040
agtggagcaa aataaagtaa caacagttac tgagaagtta attgaggaaa ctaaaagggc   2100
gctcaagtcc aaaaccgatg tagaagaaaa gatgtacagc gtaaccaagg agagagatga   2160
tttaaaaaac aaattgaaag cggaagaaga gaaaggaaat gatctcctgt caagagttaa   2220
tatgttgaaa aataggcttc aatcattgga agcaattgag aaagatttcc taaaaaacaa   2280
attaaatcaa gactctggga aatccacaac agcattacac caagaaaaca ataagattaa   2340
ggagctctct caagaagtgg aaagactgaa actgaagcta aaggacatga aagccattga   2400
ggatgacctc atgaaaacag aagatgaata tgagactcta gaacgaaggt atgctaatga   2460
acgagacaaa gctcaatttt tatctaaaga gctagaacat gttaaaatgg aacttgctaa   2520
gtacaagtta gcagaaaaga cagagaccag ccatgaacaa tggcttttca aaaggcttca   2580
agaagaagaa gctaagtcag ggcacctctc aagagaagtg gatgcattaa aagagaaaat   2640
tcatgaatac atggcaactg aagacctaat atgtcacctc cagggagatc actcagtcct   2700
gcaaaaaaaa ctaaatcaac aagaaaacag gaacagagat ttaggaagag agattgaaaa   2760
cctcactaag gagttagaga ggtaccggca tttcagtaag agcctcaggc ctagtctcaa   2820
tggaagaaga atttccgatc ctcaagtatt ttctaaagaa gttcagacag aagcagtaga   2880
caatgaacca cctgattaca agagcctcat tcctctggaa cgtgcagtca tcaatggtca   2940
gttatatgag gagagtgaga atcaagacga ggaccctaat gatgagggat ctgtgctgtc   3000
cttcaaatgc agccagtcta ctccatgtcc tgttaacaga aagctatgga ttccctggat   3060
gaaatccaag gagggccatc ttcagaatgg aaaaatgcaa actaaaccca atgccaactt   3120
```

```
tgtgcaacct ggagatctag tcctaagcca cacacctggg cagccacttc atataaaggt   3180
tactccagac catgtacaaa acacagccac tcttgaaatc acaagtccaa ccacagagag   3240
tcctcactct tacacgagta ctgcagtgat accgaactgt ggcacgccaa agcaaaggat   3300
aaccatcctc caaaacgcct ccataacacc agtaaagtcc aaaacctcta ccgaagacct   3360
catgaattta gaacaaggca tgtccccaat taccatggca acctttgcca gagcacagac   3420
cccagagtct tgtggttctc taactccaga aaggacaatg tcccctattc aggttttggc   3480
tgtgactggt tcagctagct ctcctgagca gggacgctcc ccagaaccaa cagaaatcag   3540
tgccaagcat gcgatattca gagtctcccc agaccggcag tcatcatggc agtttcagcg   3600
ttcaaacagc aatagctcaa gtgtgataac tactgaggat aataaaatcc acattcactt   3660
aggaagtcct tacatgcaag ctgtagccag ccctgtgaga cctgccagcc cttcagcacc   3720
actgcaggat aaccgaactc aaggcttaat taacggggca ctaaacaaaa caaccaataa   3780
agtcaccagc agtattacta tcacaccaac agccacacct cttcctcgac aatcacaaat   3840
tacagtggaa ccacttcttc tgcctcattg aactcaacat ccttcagact tttaaggcat   3900
tccaaatccc agtcttcatg ttgaactggg ttaagcattt attaaaaaat cgttttcttc   3960
ta                                                                  3962
```

<210> SEQ ID NO 134
<211> LENGTH: 3274
<212> TYPE: DNA
<213> ORGANISM: Homo sapiens

<400> SEQUENCE: 134

```
ataggccggg cgcgctcagc gccccgctcg cattgttcgg gcgactctcg gagcgcgcac     60
agtcggctcg cagcgcggca ctacagcggc cccggcccgg cccccgcccg gccccggcgc    120
aggcagttca gattaaagaa gctaattgat caagaaatca agtctcagga ggagaaggag    180
caagaaaagg agaaaagggt caccaccctg aaagaggagc tgaccaagct gaagtctttt    240
gctttgatgg tggtggatga acagcaaagg ctgacggcac agctcaccct tcaaagacag    300
aaaatccaag agctgaccac aaatgcaaag gaaacacata ccaaactagc ccttgctgaa    360
gccagagttc aggaggaaga gcagaaggca accagactag agaaggaact gcaaacgcag    420
accacaaagt ttcaccaaga ccaagacaca attatggcga agctcaccaa tgaggacagt    480
caaaatcgcc agcttcaaca aaagctggca gcactcagcc ggcagattga tgagttagaa    540
gagacaaaca ggtctttacg aaaagcagaa gaggagctgc aagatataaa agaaaaaatc    600
agtaagggag aatatggaaa cgctggtatc atggctgaag tggaagagct caggaaacgt    660
gtgctagata tggaagggaa agatgaagag ctcataaaaa tggaggagca gtgcagagat    720
ctcaataaga ggcttgaaag ggagacgtta cagagtaaag actttaaact agaggttgaa    780
aaactcagta aaagaattat ggctctggaa aagttagaag acgctttcaa caaaagcaaa    840
caagaatgct actctctgaa atgcaattta gaaaaagaaa ggatgaccac aaagcagttg    900
tctcaagaac tggagagttt aaaagtaagg atcaaagagc tagaagccat tgaaagtcgg    960
ctagaaaaga cagaattcac tctaaaagag gatttaacta aactgaaaac attaactgtg   1020
atgtttgtag atgaacggaa aacaatgagt gaaaaattaa agaaaactga agataaatta   1080
caagctgctt cttctcagct tcaagtggag caaaataaag taacaacagt tactgagaag   1140
ttaattgagg aaactaaaag ggcgctcaag tccaaaaccg atgtagaaga aaagatgtac   1200
```

-continued

```
agcgtaacca aggagagaga tgatttaaaa aacaaattga aagcggaaga agagaaagga   1260
aatgatctcc tgtcaagagt taatatgttg aaaaataggc ttcaatcatt ggaagcaatt   1320
gagaaagatt tcctaaaaaa caaattaaat caagactctg ggaaatccac aacagcatta   1380
caccaagaaa acaataagat taaggagctc tctcaagaag tggaaagact gaaactgaag   1440
ctaaaggaca tgaaagccat tgaggatgac ctcatgaaaa cagaagatga atatgagact   1500
ctagaacgaa ggtatgctaa tgaacgagac aaagctcaat ttttatctaa agagctagaa   1560
catgttaaaa tggaacttgc taagtacaag ttagcagaaa agacagagac cagccatgaa   1620
caatggcttt tcaaaaggct tcaagaagaa gaagctaagt cagggcacct ctcaagagaa   1680
gtggatgcat taaaagagaa aattcatgaa tacatggcaa ctgaagacct aatatgtcac   1740
ctccagggag atcactcagt cctgcaaaaa aaactaaatc aacaagaaaa caggaacaga   1800
gatttaggaa gagagattga aaacctcact aaggagttag agaggtaccg gcatttcagt   1860
aagagcctca ggcctagtct caatggaaga agaatttccg atcctcaagt attttctaaa   1920
gaagttcaga cagaagcagt agacaatgaa ccacctgatt acaagagcct cattcctctg   1980
gaacgtgcag tcatcaatgg tcagttatat gaggagagtg agaatcaaga cgaggaccct   2040
aatgatgagg gatctgtgct gtccttcaaa tgcagccagt ctactccatg tcctgttaac   2100
agaaagctat ggattccctg gatgaaatcc aaggagggcc atcttcagaa tggaaaaatg   2160
caaactaaac ccaatgccaa ctttgtgcaa cctggagatc tagtcctaag ccacacacct   2220
gggcagccac ttcatataaa ggttactcca gaccatgtac aaaacacagc cactcttgaa   2280
atcacaagtc caaccacaga gagtcctcac tcttacacga gtactgcagt gataccgaac   2340
tgtggcacgc caaagcaaag gataaccatc ctccaaaacg cctccataac accagtaaag   2400
tccaaaacct ctaccgaaga cctcatgaat ttagaacaag gcatgtcccc aattaccatg   2460
gcaacctttg ccagagcaca gaccccagag tcttgtggtt ctctaactcc agaaaggaca   2520
atgtccccta ttcaggtttt ggctgtgact ggttcagcta gctctcctga gcagggacgc   2580
tccccagaac caacagaaat cagtgccaag catgcgatat tcagagtctc cccagaccgg   2640
cagtcatcat ggcagtttca gcgttcaaac agcaatagct caagtgtgat aactactgag   2700
gataataaaa tccacattca cttaggaagt ccttacatgc aagctgtagc cagccctgtg   2760
agacctgcca gcccttcagc accactgcag gataaccgaa ctcaaggctt aattaacggg   2820
gcactaaaca aaacaaccaa taaagtcacc agcagtatta ctatcacacc aacagccaca   2880
cctcttcctc gacaatcaca aattacagta agtaatatat ataactgacc acgctcaccc   2940
tcatccagtc catactgata tttttgcaag gaactcaatc ctttttttaat catccctcca   3000
tatcccccaa gactgactga actcgtactt tgggaaggtt tgtgcatgaa ctatacaaga   3060
gtatctgaaa ctaactgttg cctgcatagt catatcgagt gtgcacttac tgtatatctt   3120
ttcatttaca tacttgtatg gaaaatattt agtctgcact tgtataaata catctttatg   3180
tatttcattt tccataactc actttaattt gactgcaact tgtcttggtg aaatacttta   3240
acattataaa acagtaaata atttgttatt ttta                                3274
```

<210> SEQ ID NO 135
<211> LENGTH: 4211
<212> TYPE: DNA
<213> ORGANISM: Homo sapiens

<400> SEQUENCE: 135

```
acacacacac agacgtgctc acggagcctg tgcctgcctc tacttgtctg ctctgcgcag     60
```

-continued atggttcctg gcttttgggt cacctcatcc tgcagcccag tccagttaga acctttcttc 120
cacagagact ggcaagctgt ggggtaagag ttttggtaag gctgcctgtc ttcagagcat 180
gaaggacact gcccggagag ggaagagggc aatatttagt gtttgggcct acttgttgtt 240
gggctcccca ctgcctctcc tttgcagagc tatcactggc ccctggttgc aaactctcgg 300
tggctttcaa gcctacaaaa caaaaactga gagggtgtcc aaaaagagaa gaagaaaacg 360
ttgttgttgg tcctggattc cactgttgga ttttggtggg gatgagaaga aggaattacc 420
aggtgtgatc aacacctgca cggtacctgc acggctttaa agaatgcgtt ccagaggcag 480
tgataccgag ggctcagccc aaaagaaatt tccaagacat actaaaggcc acagtttcca 540
agggcctaaa aacatgaagc atagacagca agacaaagac tcccccagtg agtcggatgt 600
aatacttccg tgtcccaagg cagagaagcc acacagtggt aatggccacc aagcagaaga 660
cctctcaaga gatgacctgt tatttctcct cagcattctg gagggagaac tgcaggctcg 720
agatgaggtc ataggcattt taaaggctga aaaaatggac ctggctttgc tggaagctca 780
gtatgggttt gtcactccaa aaaaggtgtt agaggctctc cagagagatg cttttcaagc 840
gaaatctacc ccttggcagg aggacatcta tgagaaacca atgaatgagt tggacaaagt 900
tgtggaaaaa cataaagaat cttacagacg aatcctggga cagcttttag tggcagaaaa 960
atcccgtagg caaaccatat tggagttgga ggaagaaaag agaaaacata aagaatacat 1020
ggagaagagt gatgaattca tatgcctact agaacaggaa tgtgaaagat taaagaagct 1080
aattgatcaa gaaatcaagt ctcaggagga gaaggagcaa gaaaaggaga aaagggtcac 1140
caccctgaaa gaggagctga ccaagctgaa gtcttttgct ttgatggtgg tggatgaaca 1200
gcaaaggctg acggcacagc tcacccttca aagacagaaa atccaagagc tgaccacaaa 1260
tgcaaaggaa acacatacca aactagccct tgctgaagcc agagttcagg aggaagagca 1320
gaaggcaacc agactagaga aggaactgca aacgcagacc acaaagtttc accaagacca 1380
agacacaatt atggcgaagc tcaccaatga ggacagtcaa aatcgccagc ttcaacaaaa 1440
gctggcagca ctcagccggc agattgatga gttagaagag acaaacaggt ctttacgaaa 1500
agcagaagag gagctgcaag atataaaaga aaaaatcagt aagggagaat atggaaacgc 1560
tggtatcatg gctgaagtgg aagagctcag gaaacgtgtg ctagatatgg aagggaaaga 1620
tgaagagctc ataaaaatgg aggagcagtg cagagatctc aataagaggc ttgaaaggga 1680
gacgttacag agtaaagact ttaaactaga ggttgaaaaa ctcagtaaaa gaattatggc 1740
tctggaaaag ttagaagacg ctttcaacaa aagcaaacaa gaatgctact ctctgaaatg 1800
caatttagaa aaagaaagga tgaccacaaa gcagttgtct caagaactgg agagtttaaa 1860
agtaaggatc aaagagctag aagccattga aagtcggcta gaaaagacag aattcactct 1920
aaaagaggat ttaactaaac tgaaaacatt aactgtgatg tttgtagatg aacggaaaac 1980
aatgagtgaa aaattaaaga aaactgaaga taaattacaa gctgcttctt ctcagcttca 2040
agtggagcaa aataaagtaa caacagttac tgagaagtta attgaggaaa ctaaaagggc 2100
gctcaagtcc aaaaccgatg tagaagaaaa gatgtacagc gtaaccaagg agagagatga 2160
tttaaaaaac aaattgaaag cggaagaaga gaaaggaaat gatctcctgt caagagttaa 2220
tatgttgaaa aataggcttc aatcattgga agcaattgag aaagatttcc taaaaaacaa 2280
attaaatcaa gactctggga aatccacaac agcattacac caagaaaaca ataagattaa 2340
ggagctctct caagaagtgg aaagactgaa actgaagcta aaggacatga aagccattga 2400

```
ggatgacctc atgaaaacag aagatgaata tgagactcta gaacgaaggt atgctaatga   2460
acgagacaaa gctcaatttt tatctaaaga gctagaacat gttaaaatgg aacttgctaa   2520
gtacaagtta gcagaaaaga cagagaccag ccatgaacaa tggcttttca aaaggcttca   2580
agaagaagaa gctaagtcag ggcacctctc aagagaagtg gatgcattaa aagagaaaat   2640
tcatgaatac atggcaactg aagacctaat atgtcacctc cagggagatc actcagtcct   2700
gcaaaaaaaa ctaaatcaac aagaaaacag gaacagagat ttaggaagag agattgaaaa   2760
cctcactaag gagttagaga ggtaccggca tttcagtaag agcctcaggc ctagtctcaa   2820
tggaagaaga atttccgatc ctcaagtatt ttctaaagaa gttcagacag aagcagtaga   2880
caatgaacca cctgattaca agagcctcat tcctctggaa cgtgcagtca tcaatggtca   2940
gttatatgag gagagtgaga atcaagacga ggaccctaat gatgagggat ctgtgctgtc   3000
cttcaaatgc agccagtcta ctccatgtcc tgttaacaga aagctatgga ttccctggat   3060
gaaatccaag gagggccatc ttcagaatgg aaaaatgcaa actaaaccca atgccaactt   3120
tgtgcaacct ggagatctag tcctaagcca cacacctggg cagccacttc atataaaggt   3180
tactccagac catgtacaaa acacagccac tcttgaaatc acaagtccaa ccacagagag   3240
tcctcactct tacacgagta ctgcagtgat accgaactgt ggcacgccaa agcaaaggat   3300
aaccatcctc caaaacgcct ccataacacc agtaaagtcc aaaacctcta ccgaagacct   3360
catgaattta gaacaaggca tgtccccaat taccatggca acctttgcca gagcacagac   3420
cccagagtct tgtggttctc taactccaga aaggacaatg tcccctattc aggttttggc   3480
tgtgactggt tcagctagct ctcctgagca gggacgctcc ccagaaccaa cagaaatcag   3540
tgccaagcat gcgatattca gagtctcccc agaccggcag tcatcatggc agtttcagcg   3600
ttcaaacagc aatagctcaa gtgtgataac tactgaggat aataaaatcc acattcactt   3660
aggaagtcct tacatgcaag ctgtagccag ccctgtgaga cctgccagcc cttcagcacc   3720
actgcaggat aaccgaactc aaggcttaat taacggggca ctaaacaaaa caaccaataa   3780
agtcaccagc agtattacta tcacaccaac agccacacct cttcctcgac aatcacaaat   3840
tacagtaagt aatatatata actgaccacg ctcaccctca tccagtccat actgatattt   3900
ttgcaaggaa ctcaatcctt ttttaatcat ccctccatat cccccaagac tgactgaact   3960
cgtactttgg gaaggtttgt gcatgaacta tacaagagta tctgaaacta actgttgcct   4020
gcatagtcat atcgagtgtg cacttactgt atatcttttc atttacatac ttgtatggaa   4080
aatatttagt ctgcacttgt ataaatacat ctttatgtat ttcattttcc ataactcact   4140
ttaatttgac tgcaacttgt cttggtgaaa tactttaaca ttataaaaca gtaaataatt   4200
tgttattttt a                                                        4211
```

<210> SEQ ID NO 136
<211> LENGTH: 1135
<212> TYPE: PRT
<213> ORGANISM: Homo sapiens

<400> SEQUENCE: 136

```
Met Arg Ser Arg Gly Ser Asp Thr Glu Gly Ser Ala Gln Lys Lys Phe
1               5                   10                  15

Pro Arg His Thr Lys Gly His Ser Phe Gln Gly Pro Lys Asn Met Lys
            20                  25                  30

His Arg Gln Gln Asp Lys Asp Ser Pro Ser Glu Ser Asp Val Ile Leu
        35                  40                  45
```

-continued

```
Pro Cys Pro Lys Ala Glu Lys Pro His Ser Gly Asn Gly His Gln Ala
    50                  55                  60

Glu Asp Leu Ser Arg Asp Asp Leu Leu Phe Leu Leu Ser Ile Leu Glu
65                  70                  75                  80

Gly Glu Leu Gln Ala Arg Asp Glu Val Ile Gly Ile Leu Lys Ala Glu
                85                  90                  95

Lys Met Asp Leu Ala Leu Leu Glu Ala Gln Tyr Gly Phe Val Thr Pro
            100                 105                 110

Lys Lys Val Leu Glu Ala Leu Gln Arg Asp Ala Phe Gln Ala Lys Ser
        115                 120                 125

Thr Pro Trp Gln Glu Asp Ile Tyr Glu Lys Pro Met Asn Glu Leu Asp
    130                 135                 140

Lys Val Val Glu Lys His Lys Glu Ser Tyr Arg Arg Ile Leu Gly Gln
145                 150                 155                 160

Leu Leu Val Ala Glu Lys Ser Arg Arg Gln Thr Ile Leu Glu Leu Glu
                165                 170                 175

Glu Glu Lys Arg Lys His Lys Glu Tyr Met Glu Lys Ser Asp Glu Phe
            180                 185                 190

Ile Cys Leu Leu Glu Gln Glu Cys Glu Arg Leu Lys Lys Leu Ile Asp
        195                 200                 205

Gln Glu Ile Lys Ser Gln Glu Glu Lys Glu Gln Glu Lys Glu Lys Arg
    210                 215                 220

Val Thr Thr Leu Lys Glu Glu Leu Thr Lys Leu Lys Ser Phe Ala Leu
225                 230                 235                 240

Met Val Val Asp Glu Gln Gln Arg Leu Thr Ala Gln Leu Thr Leu Gln
                245                 250                 255

Arg Gln Lys Ile Gln Glu Leu Thr Thr Asn Ala Lys Glu Thr His Thr
            260                 265                 270

Lys Leu Ala Leu Ala Glu Ala Arg Val Gln Glu Glu Glu Gln Lys Ala
        275                 280                 285

Thr Arg Leu Glu Lys Glu Leu Gln Thr Gln Thr Thr Lys Phe His Gln
    290                 295                 300

Asp Gln Asp Thr Ile Met Ala Lys Leu Thr Asn Glu Asp Ser Gln Asn
305                 310                 315                 320

Arg Gln Leu Gln Gln Lys Leu Ala Ala Leu Ser Arg Gln Ile Asp Glu
                325                 330                 335

Leu Glu Glu Thr Asn Arg Ser Leu Arg Lys Ala Glu Glu Glu Leu Gln
            340                 345                 350

Asp Ile Lys Glu Lys Ile Ser Lys Gly Glu Tyr Gly Asn Ala Gly Ile
        355                 360                 365

Met Ala Glu Val Glu Glu Leu Arg Lys Arg Val Leu Asp Met Glu Gly
    370                 375                 380

Lys Asp Glu Glu Leu Ile Lys Met Glu Glu Gln Cys Arg Asp Leu Asn
385                 390                 395                 400

Lys Arg Leu Glu Arg Glu Thr Leu Gln Ser Lys Asp Phe Lys Leu Glu
                405                 410                 415

Val Glu Lys Leu Ser Lys Arg Ile Met Ala Leu Glu Lys Leu Glu Asp
            420                 425                 430

Ala Phe Asn Lys Ser Lys Gln Glu Cys Tyr Ser Leu Lys Cys Asn Leu
        435                 440                 445

Glu Lys Glu Arg Met Thr Thr Lys Gln Leu Ser Gln Glu Leu Glu Ser
    450                 455                 460

Leu Lys Val Arg Ile Lys Glu Leu Glu Ala Ile Glu Ser Arg Leu Glu
```

-continued

```
465                 470                 475                 480

Lys Thr Glu Phe Thr Leu Lys Glu Asp Leu Thr Lys Leu Lys Thr Leu
                485                 490                 495

Thr Val Met Phe Val Asp Glu Arg Lys Thr Met Ser Glu Lys Leu Lys
            500                 505                 510

Lys Thr Glu Asp Lys Leu Gln Ala Ala Ser Ser Gln Leu Gln Val Glu
        515                 520                 525

Gln Asn Lys Val Thr Thr Val Thr Glu Lys Leu Ile Glu Glu Thr Lys
    530                 535                 540

Arg Ala Leu Lys Ser Lys Thr Asp Val Glu Glu Lys Met Tyr Ser Val
545                 550                 555                 560

Thr Lys Glu Arg Asp Asp Leu Lys Asn Lys Leu Lys Ala Glu Glu Glu
                565                 570                 575

Lys Gly Asn Asp Leu Leu Ser Arg Val Asn Met Leu Lys Asn Arg Leu
            580                 585                 590

Gln Ser Leu Glu Ala Ile Glu Lys Asp Phe Leu Lys Asn Lys Leu Asn
        595                 600                 605

Gln Asp Ser Gly Lys Ser Thr Thr Ala Leu His Gln Glu Asn Asn Lys
    610                 615                 620

Ile Lys Glu Leu Ser Gln Glu Val Glu Arg Leu Lys Leu Lys Leu Lys
625                 630                 635                 640

Asp Met Lys Ala Ile Glu Asp Asp Leu Met Lys Thr Glu Asp Glu Tyr
                645                 650                 655

Glu Thr Leu Glu Arg Arg Tyr Ala Asn Glu Arg Asp Lys Ala Gln Phe
            660                 665                 670

Leu Ser Lys Glu Leu Glu His Val Lys Met Glu Leu Ala Lys Tyr Lys
        675                 680                 685

Leu Ala Glu Lys Thr Glu Thr Ser His Glu Gln Trp Leu Phe Lys Arg
    690                 695                 700

Leu Gln Glu Glu Glu Ala Lys Ser Gly His Leu Ser Arg Glu Val Asp
705                 710                 715                 720

Ala Leu Lys Glu Lys Ile His Glu Tyr Met Ala Thr Glu Asp Leu Ile
                725                 730                 735

Cys His Leu Gln Gly Asp His Ser Val Leu Gln Lys Lys Leu Asn Gln
            740                 745                 750

Gln Glu Asn Arg Asn Arg Asp Leu Gly Arg Glu Ile Glu Asn Leu Thr
        755                 760                 765

Lys Glu Leu Glu Arg Tyr Arg His Phe Ser Lys Ser Leu Arg Pro Ser
    770                 775                 780

Leu Asn Gly Arg Arg Ile Ser Asp Pro Gln Val Phe Ser Lys Glu Val
785                 790                 795                 800

Gln Thr Glu Ala Val Asp Asn Glu Pro Pro Asp Tyr Lys Ser Leu Ile
                805                 810                 815

Pro Leu Glu Arg Ala Val Ile Asn Gly Gln Leu Tyr Glu Glu Ser Glu
            820                 825                 830

Asn Gln Asp Glu Asp Pro Asn Asp Glu Gly Ser Val Leu Ser Phe Lys
        835                 840                 845

Cys Ser Gln Ser Thr Pro Cys Pro Val Asn Arg Lys Leu Trp Ile Pro
    850                 855                 860

Trp Met Lys Ser Lys Glu Gly His Leu Gln Asn Gly Lys Met Gln Thr
865                 870                 875                 880

Lys Pro Asn Ala Asn Phe Val Gln Pro Gly Asp Leu Val Leu Ser His
                885                 890                 895
```

Thr Pro Gly Gln Pro Leu His Ile Lys Val Thr Pro Asp His Val Gln
900 905 910

Asn Thr Ala Thr Leu Glu Ile Thr Ser Pro Thr Thr Glu Ser Pro His
915 920 925

Ser Tyr Thr Ser Thr Ala Val Ile Pro Asn Cys Gly Thr Pro Lys Gln
930 935 940

Arg Ile Thr Ile Leu Gln Asn Ala Ser Ile Thr Pro Val Lys Ser Lys
945 950 955 960

Thr Ser Thr Glu Asp Leu Met Asn Leu Glu Gln Gly Met Ser Pro Ile
965 970 975

Thr Met Ala Thr Phe Ala Arg Ala Gln Thr Pro Glu Ser Cys Gly Ser
980 985 990

Leu Thr Pro Glu Arg Thr Met Ser Pro Ile Gln Val Leu Ala Val Thr
995 1000 1005

Gly Ser Ala Ser Ser Pro Glu Gln Gly Arg Ser Pro Glu Pro Thr
1010 1015 1020

Glu Ile Ser Ala Lys His Ala Ile Phe Arg Val Ser Pro Asp Arg
1025 1030 1035

Gln Ser Ser Trp Gln Phe Gln Arg Ser Asn Ser Asn Ser Ser Ser
1040 1045 1050

Val Ile Thr Thr Glu Asp Asn Lys Ile His Ile His Leu Gly Ser
1055 1060 1065

Pro Tyr Met Gln Ala Val Ala Ser Pro Val Arg Pro Ala Ser Pro
1070 1075 1080

Ser Ala Pro Leu Gln Asp Asn Arg Thr Gln Gly Leu Ile Asn Gly
1085 1090 1095

Ala Leu Asn Lys Thr Thr Asn Lys Val Thr Ser Ser Ile Thr Ile
1100 1105 1110

Thr Pro Thr Ala Thr Pro Leu Pro Arg Gln Ser Gln Ile Thr Val
1115 1120 1125

Glu Pro Leu Leu Leu Pro His
1130 1135

<210> SEQ ID NO 137
<211> LENGTH: 893
<212> TYPE: PRT
<213> ORGANISM: Homo sapiens

<400> SEQUENCE: 137

Met Val Val Asp Glu Gln Gln Arg Leu Thr Ala Gln Leu Thr Leu Gln
1 5 10 15

Arg Gln Lys Ile Gln Glu Leu Thr Thr Asn Ala Lys Glu Thr His Thr
20 25 30

Lys Leu Ala Leu Ala Glu Ala Arg Val Gln Glu Glu Glu Gln Lys Ala
35 40 45

Thr Arg Leu Glu Lys Glu Leu Gln Thr Gln Thr Thr Lys Phe His Gln
50 55 60

Asp Gln Asp Thr Ile Met Ala Lys Leu Thr Asn Glu Asp Ser Gln Asn
65 70 75 80

Arg Gln Leu Gln Gln Lys Leu Ala Ala Leu Ser Arg Gln Ile Asp Glu
85 90 95

Leu Glu Glu Thr Asn Arg Ser Leu Arg Lys Ala Glu Glu Glu Leu Gln
100 105 110

Asp Ile Lys Glu Lys Ile Ser Lys Gly Glu Tyr Gly Asn Ala Gly Ile

```
        115                 120                 125

Met Ala Glu Val Glu Glu Leu Arg Lys Arg Val Leu Asp Met Glu Gly
    130                 135                 140

Lys Asp Glu Glu Leu Ile Lys Met Glu Glu Gln Cys Arg Asp Leu Asn
145                 150                 155                 160

Lys Arg Leu Glu Arg Glu Thr Leu Gln Ser Lys Asp Phe Lys Leu Glu
                165                 170                 175

Val Glu Lys Leu Ser Lys Arg Ile Met Ala Leu Glu Lys Leu Glu Asp
            180                 185                 190

Ala Phe Asn Lys Ser Lys Gln Glu Cys Tyr Ser Leu Lys Cys Asn Leu
        195                 200                 205

Glu Lys Glu Arg Met Thr Thr Lys Gln Leu Ser Gln Glu Leu Glu Ser
    210                 215                 220

Leu Lys Val Arg Ile Lys Glu Leu Glu Ala Ile Glu Ser Arg Leu Glu
225                 230                 235                 240

Lys Thr Glu Phe Thr Leu Lys Glu Asp Leu Thr Lys Leu Lys Thr Leu
                245                 250                 255

Thr Val Met Phe Val Asp Glu Arg Lys Thr Met Ser Glu Lys Leu Lys
            260                 265                 270

Lys Thr Glu Asp Lys Leu Gln Ala Ala Ser Ser Gln Leu Gln Val Glu
        275                 280                 285

Gln Asn Lys Val Thr Thr Val Thr Glu Lys Leu Ile Glu Glu Thr Lys
    290                 295                 300

Arg Ala Leu Lys Ser Lys Thr Asp Val Glu Glu Lys Met Tyr Ser Val
305                 310                 315                 320

Thr Lys Glu Arg Asp Asp Leu Lys Asn Lys Leu Lys Ala Glu Glu Glu
                325                 330                 335

Lys Gly Asn Asp Leu Leu Ser Arg Val Asn Met Leu Lys Asn Arg Leu
            340                 345                 350

Gln Ser Leu Glu Ala Ile Glu Lys Asp Phe Leu Lys Asn Lys Leu Asn
        355                 360                 365

Gln Asp Ser Gly Lys Ser Thr Thr Ala Leu His Gln Glu Asn Asn Lys
    370                 375                 380

Ile Lys Glu Leu Ser Gln Glu Val Glu Arg Leu Lys Leu Lys Leu Lys
385                 390                 395                 400

Asp Met Lys Ala Ile Glu Asp Asp Leu Met Lys Thr Glu Asp Glu Tyr
                405                 410                 415

Glu Thr Leu Glu Arg Arg Tyr Ala Asn Glu Arg Asp Lys Ala Gln Phe
            420                 425                 430

Leu Ser Lys Glu Leu Glu His Val Lys Met Glu Leu Ala Lys Tyr Lys
        435                 440                 445

Leu Ala Glu Lys Thr Glu Thr Ser His Glu Gln Trp Leu Phe Lys Arg
    450                 455                 460

Leu Gln Glu Glu Glu Ala Lys Ser Gly His Leu Ser Arg Glu Val Asp
465                 470                 475                 480

Ala Leu Lys Glu Lys Ile His Glu Tyr Met Ala Thr Glu Asp Leu Ile
                485                 490                 495

Cys His Leu Gln Gly Asp His Ser Val Leu Gln Lys Lys Leu Asn Gln
            500                 505                 510

Gln Glu Asn Arg Asn Arg Asp Leu Gly Arg Glu Ile Glu Asn Leu Thr
        515                 520                 525

Lys Glu Leu Glu Arg Tyr Arg His Phe Ser Lys Ser Leu Arg Pro Ser
    530                 535                 540
```

Leu Asn Gly Arg Arg Ile Ser Asp Pro Gln Val Phe Ser Lys Glu Val
545 550 555 560

Gln Thr Glu Ala Val Asp Asn Glu Pro Pro Asp Tyr Lys Ser Leu Ile
565 570 575

Pro Leu Glu Arg Ala Val Ile Asn Gly Gln Leu Tyr Glu Glu Ser Glu
580 585 590

Asn Gln Asp Glu Asp Pro Asn Asp Glu Gly Ser Val Leu Ser Phe Lys
595 600 605

Cys Ser Gln Ser Thr Pro Cys Pro Val Asn Arg Lys Leu Trp Ile Pro
610 615 620

Trp Met Lys Ser Lys Glu Gly His Leu Gln Asn Gly Lys Met Gln Thr
625 630 635 640

Lys Pro Asn Ala Asn Phe Val Gln Pro Gly Asp Leu Val Leu Ser His
645 650 655

Thr Pro Gly Gln Pro Leu His Ile Lys Val Thr Pro Asp His Val Gln
660 665 670

Asn Thr Ala Thr Leu Glu Ile Thr Ser Pro Thr Thr Glu Ser Pro His
675 680 685

Ser Tyr Thr Ser Thr Ala Val Ile Pro Asn Cys Gly Thr Pro Lys Gln
690 695 700

Arg Ile Thr Ile Leu Gln Asn Ala Ser Ile Thr Pro Val Lys Ser Lys
705 710 715 720

Thr Ser Thr Glu Asp Leu Met Asn Leu Glu Gln Gly Met Ser Pro Ile
725 730 735

Thr Met Ala Thr Phe Ala Arg Ala Gln Thr Pro Glu Ser Cys Gly Ser
740 745 750

Leu Thr Pro Glu Arg Thr Met Ser Pro Ile Gln Val Leu Ala Val Thr
755 760 765

Gly Ser Ala Ser Ser Pro Glu Gln Gly Arg Ser Pro Glu Pro Thr Glu
770 775 780

Ile Ser Ala Lys His Ala Ile Phe Arg Val Ser Pro Asp Arg Gln Ser
785 790 795 800

Ser Trp Gln Phe Gln Arg Ser Asn Ser Asn Ser Ser Ser Val Ile Thr
805 810 815

Thr Glu Asp Asn Lys Ile His Ile His Leu Gly Ser Pro Tyr Met Gln
820 825 830

Ala Val Ala Ser Pro Val Arg Pro Ala Ser Pro Ser Ala Pro Leu Gln
835 840 845

Asp Asn Arg Thr Gln Gly Leu Ile Asn Gly Ala Leu Asn Lys Thr Thr
850 855 860

Asn Lys Val Thr Ser Ser Ile Thr Ile Thr Pro Thr Ala Thr Pro Leu
865 870 875 880

Pro Arg Gln Ser Gln Ile Thr Val Ser Asn Ile Tyr Asn
885 890

<210> SEQ ID NO 138
<211> LENGTH: 1133
<212> TYPE: PRT
<213> ORGANISM: Homo sapiens

<400> SEQUENCE: 138

Met Arg Ser Arg Gly Ser Asp Thr Glu Gly Ser Ala Gln Lys Lys Phe
1 5 10 15

Pro Arg His Thr Lys Gly His Ser Phe Gln Gly Pro Lys Asn Met Lys

-continued

```
            20                  25                  30

His Arg Gln Gln Asp Lys Asp Ser Pro Ser Glu Ser Asp Val Ile Leu
        35                  40                  45

Pro Cys Pro Lys Ala Glu Lys Pro His Ser Gly Asn Gly His Gln Ala
    50                  55                  60

Glu Asp Leu Ser Arg Asp Asp Leu Leu Phe Leu Leu Ser Ile Leu Glu
65                  70                  75                  80

Gly Glu Leu Gln Ala Arg Asp Glu Val Ile Gly Ile Leu Lys Ala Glu
                85                  90                  95

Lys Met Asp Leu Ala Leu Leu Glu Ala Gln Tyr Gly Phe Val Thr Pro
            100                 105                 110

Lys Lys Val Leu Glu Ala Leu Gln Arg Asp Ala Phe Gln Ala Lys Ser
        115                 120                 125

Thr Pro Trp Gln Glu Asp Ile Tyr Glu Lys Pro Met Asn Glu Leu Asp
    130                 135                 140

Lys Val Val Glu Lys His Lys Glu Ser Tyr Arg Arg Ile Leu Gly Gln
145                 150                 155                 160

Leu Leu Val Ala Glu Lys Ser Arg Arg Gln Thr Ile Leu Glu Leu Glu
                165                 170                 175

Glu Glu Lys Arg Lys His Lys Glu Tyr Met Glu Lys Ser Asp Glu Phe
            180                 185                 190

Ile Cys Leu Leu Glu Gln Glu Cys Glu Arg Leu Lys Lys Leu Ile Asp
        195                 200                 205

Gln Glu Ile Lys Ser Gln Glu Glu Lys Glu Gln Glu Lys Glu Lys Arg
    210                 215                 220

Val Thr Thr Leu Lys Glu Glu Leu Thr Lys Leu Lys Ser Phe Ala Leu
225                 230                 235                 240

Met Val Val Asp Glu Gln Gln Arg Leu Thr Ala Gln Leu Thr Leu Gln
                245                 250                 255

Arg Gln Lys Ile Gln Glu Leu Thr Thr Asn Ala Lys Glu Thr His Thr
            260                 265                 270

Lys Leu Ala Leu Ala Glu Ala Arg Val Gln Glu Glu Glu Gln Lys Ala
        275                 280                 285

Thr Arg Leu Glu Lys Glu Leu Gln Thr Gln Thr Thr Lys Phe His Gln
    290                 295                 300

Asp Gln Asp Thr Ile Met Ala Lys Leu Thr Asn Glu Asp Ser Gln Asn
305                 310                 315                 320

Arg Gln Leu Gln Gln Lys Leu Ala Ala Leu Ser Arg Gln Ile Asp Glu
                325                 330                 335

Leu Glu Glu Thr Asn Arg Ser Leu Arg Lys Ala Glu Glu Glu Leu Gln
            340                 345                 350

Asp Ile Lys Glu Lys Ile Ser Lys Gly Glu Tyr Gly Asn Ala Gly Ile
        355                 360                 365

Met Ala Glu Val Glu Glu Leu Arg Lys Arg Val Leu Asp Met Glu Gly
    370                 375                 380

Lys Asp Glu Glu Leu Ile Lys Met Glu Glu Gln Cys Arg Asp Leu Asn
385                 390                 395                 400

Lys Arg Leu Glu Arg Glu Thr Leu Gln Ser Lys Asp Phe Lys Leu Glu
                405                 410                 415

Val Glu Lys Leu Ser Lys Arg Ile Met Ala Leu Glu Lys Leu Glu Asp
            420                 425                 430

Ala Phe Asn Lys Ser Lys Gln Glu Cys Tyr Ser Leu Lys Cys Asn Leu
        435                 440                 445
```

```
Glu Lys Glu Arg Met Thr Thr Lys Gln Leu Ser Gln Glu Leu Glu Ser
    450                 455                 460

Leu Lys Val Arg Ile Lys Glu Leu Glu Ala Ile Glu Ser Arg Leu Glu
465                 470                 475                 480

Lys Thr Glu Phe Thr Leu Lys Glu Asp Leu Thr Lys Leu Lys Thr Leu
                485                 490                 495

Thr Val Met Phe Val Asp Glu Arg Lys Thr Met Ser Glu Lys Leu Lys
            500                 505                 510

Lys Thr Glu Asp Lys Leu Gln Ala Ala Ser Ser Gln Leu Gln Val Glu
        515                 520                 525

Gln Asn Lys Val Thr Thr Val Thr Glu Lys Leu Ile Glu Glu Thr Lys
    530                 535                 540

Arg Ala Leu Lys Ser Lys Thr Asp Val Glu Glu Lys Met Tyr Ser Val
545                 550                 555                 560

Thr Lys Glu Arg Asp Asp Leu Lys Asn Lys Leu Lys Ala Glu Glu Glu
                565                 570                 575

Lys Gly Asn Asp Leu Leu Ser Arg Val Asn Met Leu Lys Asn Arg Leu
            580                 585                 590

Gln Ser Leu Glu Ala Ile Glu Lys Asp Phe Leu Lys Asn Lys Leu Asn
        595                 600                 605

Gln Asp Ser Gly Lys Ser Thr Thr Ala Leu His Gln Glu Asn Asn Lys
    610                 615                 620

Ile Lys Glu Leu Ser Gln Glu Val Glu Arg Leu Lys Leu Lys Leu Lys
625                 630                 635                 640

Asp Met Lys Ala Ile Glu Asp Asp Leu Met Lys Thr Glu Asp Glu Tyr
                645                 650                 655

Glu Thr Leu Glu Arg Arg Tyr Ala Asn Glu Arg Asp Lys Ala Gln Phe
            660                 665                 670

Leu Ser Lys Glu Leu Glu His Val Lys Met Glu Leu Ala Lys Tyr Lys
        675                 680                 685

Leu Ala Glu Lys Thr Glu Thr Ser His Glu Gln Trp Leu Phe Lys Arg
    690                 695                 700

Leu Gln Glu Glu Glu Ala Lys Ser Gly His Leu Ser Arg Glu Val Asp
705                 710                 715                 720

Ala Leu Lys Glu Lys Ile His Glu Tyr Met Ala Thr Glu Asp Leu Ile
                725                 730                 735

Cys His Leu Gln Gly Asp His Ser Val Leu Gln Lys Lys Leu Asn Gln
            740                 745                 750

Gln Glu Asn Arg Asn Arg Asp Leu Gly Arg Glu Ile Glu Asn Leu Thr
        755                 760                 765

Lys Glu Leu Glu Arg Tyr Arg His Phe Ser Lys Ser Leu Arg Pro Ser
    770                 775                 780

Leu Asn Gly Arg Arg Ile Ser Asp Pro Gln Val Phe Ser Lys Glu Val
785                 790                 795                 800

Gln Thr Glu Ala Val Asp Asn Glu Pro Pro Asp Tyr Lys Ser Leu Ile
                805                 810                 815

Pro Leu Glu Arg Ala Val Ile Asn Gly Gln Leu Tyr Glu Glu Ser Glu
            820                 825                 830

Asn Gln Asp Glu Asp Pro Asn Asp Glu Gly Ser Val Leu Ser Phe Lys
        835                 840                 845

Cys Ser Gln Ser Thr Pro Cys Pro Val Asn Arg Lys Leu Trp Ile Pro
    850                 855                 860
```

-continued

```
Trp Met Lys Ser Lys Glu Gly His Leu Gln Asn Gly Lys Met Gln Thr
865                 870                 875                 880

Lys Pro Asn Ala Asn Phe Val Gln Pro Gly Asp Leu Val Leu Ser His
                885                 890                 895

Thr Pro Gly Gln Pro Leu His Ile Lys Val Thr Pro Asp His Val Gln
            900                 905                 910

Asn Thr Ala Thr Leu Glu Ile Thr Ser Pro Thr Thr Glu Ser Pro His
        915                 920                 925

Ser Tyr Thr Ser Thr Ala Val Ile Pro Asn Cys Gly Thr Pro Lys Gln
    930                 935                 940

Arg Ile Thr Ile Leu Gln Asn Ala Ser Ile Thr Pro Val Lys Ser Lys
945                 950                 955                 960

Thr Ser Thr Glu Asp Leu Met Asn Leu Glu Gln Gly Met Ser Pro Ile
                965                 970                 975

Thr Met Ala Thr Phe Ala Arg Ala Gln Thr Pro Glu Ser Cys Gly Ser
            980                 985                 990

Leu Thr Pro Glu Arg Thr Met Ser  Pro Ile Gln Val Leu  Ala Val Thr
        995                 1000                1005

Gly Ser  Ala Ser Ser Pro Glu  Gln Gly Arg Ser Pro  Glu Pro Thr
    1010                1015                1020

Glu Ile  Ser Ala Lys His Ala  Ile Phe Arg Val Ser  Pro Asp Arg
    1025                1030                1035

Gln Ser  Ser Trp Gln Phe Gln  Arg Ser Asn Ser Asn  Ser Ser Ser
    1040                1045                1050

Val Ile  Thr Thr Glu Asp Asn  Lys Ile His Ile His  Leu Gly Ser
    1055                1060                1065

Pro Tyr  Met Gln Ala Val Ala  Ser Pro Val Arg Pro  Ala Ser Pro
    1070                1075                1080

Ser Ala  Pro Leu Gln Asp Asn  Arg Thr Gln Gly Leu  Ile Asn Gly
    1085                1090                1095

Ala Leu  Asn Lys Thr Thr Asn  Lys Val Thr Ser Ser  Ile Thr Ile
    1100                1105                1110

Thr Pro  Thr Ala Thr Pro Leu  Pro Arg Gln Ser Gln  Ile Thr Val
    1115                1120                1125

Ser Asn  Ile Tyr Asn
    1130
```

<210> SEQ ID NO 139
<211> LENGTH: 4653
<212> TYPE: DNA
<213> ORGANISM: Homo sapiens

<400> SEQUENCE: 139

```
cccaaaccaa cttgtcccca tcaactccat ctttctagtc cccaccttcc ccggtgcaga     60

cacccggcga agcccacccg gttttcccag cggcatttcc gatgacagct tcggggctac    120

gtgtcctgtg ctgtcggaga cgcacaggaa gcaaagtttg tgagaagcct tgggggcgac    180

tttgccttgg gcacccgcat ttgtgcgtct gcgaggtgcc tcggtgtgcg cggagctagt    240

ttcccagttt cccgggcccc tcccttctcc gagcccctct agcgatttgt ttaggaaaag    300

tgatgacatg aactagtagt ggagaatcgc agcgccgctc cccgccctgg ggagggaggg    360

gagccccgga gagcctgccg gtgggagctg gaagcaggct cccggctgag cgccccagcc    420

cgaaaggcag ggtctgggtg cgggaagagg gctcggagct gccttcctgc tgccttgggg    480

ccgcccagat gagggaacag cccgatttgc ctggttctga ttctccaggc tgtcgtggtt    540
```

-continued

```
gtggaatgca aacgccagca cataatggaa acaggacctg aagacccttc cagcatgcca    600
gaggaaagtt cccccaggcg gaccccgcag agcattccct accaggacct ccctcacctg    660
gtcaatgcag acggacagta cctcttctgc aggtactgga aacccacagg cacacccaag    720
gccctcatct ttgtgtccca tggagccgga gagcacagtg gccgctatga agagctggct    780
cggatgctga tggggctgga cctgctggtg ttcgcccacg accatgttgg ccacggacag    840
agcgaagggg agaggatggt agtgtctgac ttccacgttt tcgtcaggga tgtgttgcag    900
catgtggatt ccatgcagaa agactaccct gggcttcctg tcttccttct gggccactcc    960
atgggaggcg ccatcgccat cctcacggcc gcagagaggc cgggccactt cgccggcatg   1020
gtactcattt cgcctctggt tcttgccaat cctgaatctg caacaacttt caaggtcctt   1080
gctgcgaaag tgctcaacct tgtgctgcca aacttgtccc tcgggcccat cgactccagc   1140
gtgctctctc ggaataagac agaggtcgac atttataact cagacccccct gatctgccgg   1200
gcagggctga aggtgtgctt cggcatccaa ctgctgaatg ccgtctcacg ggtggagcgc   1260
gccctcccca agctgactgt gcccttcctg ctgctccagg gctctgccga tcgcctatgt   1320
gacagcaaag ggcctacct gctcatggag ttagccaaga gccaggacaa gactctcaag   1380
atttatgaag gtgcctacca tgttctccac aaggagcttc ctgaagtcac caactccgtc   1440
ttccatgaaa taaacatgtg ggtctctcaa aggacagcca cggcaggaac tgcgtcccca   1500
ccctgaatgc attggccggt gcccggctca tggtctgggg gatgcaggca ggggaagggc   1560
agagatggct tctcagatat ggcttgccaa aaaaaaaaaa aaaaaaaaat cagaaattgg   1620
agaaatcctt agcacaattt tctaaaaaat aacagacatt tttgttatac attagactat   1680
cagacactgg acctacctta atggttagac actttatgca aaaaaagaga aaggtcccag   1740
gtgattttcc acaaagaatg tgctaaaatg tccactgaaa acaaagccaa gcctctgccc   1800
tgcctctccc agctcccaca agggttccag gaattcctgg tgttcccagg acaccagact   1860
gcaataactg gaggcgcctc cttcctgccc acccttcgct cacgccccag cgccctctct   1920
gaccagcctc cgcttggtgg ccttcctctg gccgtgtgat gaggtggttg ctgtctccat   1980
aggggccagc tccccagggc agactcacgt gcccctctga ggctcagaaa atgcccagcc   2040
cttcctcaaa atgagcagcc acccatgact ttgtgggctc cttgttagcc tgagaccagg   2100
ctttgcagag gggcgggggg tgaggcttag cccagaagga gaactgagca ggaaaccaag   2160
gctcttctct gtcccctgcc cttcccctcc tgccaggggg aggctcaggt tggtccccga   2220
gtgccgcctg tactcacaaa ggctgccttt cctctagagt cactaatttt acctgatgct   2280
atgagagaat catattgaag atgaaatgtc taatatataa tgtatatttt aaagcagaga   2340
ctattttggt ggataggtgg gagggagcaa ggggagtttg agggaatcag agcttgatgc   2400
tactgtacag aactggacag gttgggccgg cagtggtggg gccagagggc tctgtgctct   2460
aggagctaag ccagcagccc ccgagagggg acttggctgg gcctttccta tgggcaaggc   2520
ccagtgctct tcctgcccac cagggaccat ggagcagtgg caccctatgg ggctatgatc   2580
cctaggcctg ggcctgggcc tgcctatggc ccagagctac cctgggagtg tcagtgctag   2640
cagcacagct acctctggtg gcaggagaag agaggcccag cacagcagca ggccaggcct   2700
tcctgtccag gtctgcatgg agcactcggt gacccagagc agggactgga ggcaccccca   2760
gccctgcccc aggccacagc aggacaggcc gggacaggcc tcacccaagg ccaaggctgg   2820
catcagccaa tcattcagag ctgaggccct gggcctagcc tgcccttctc aggtgccaat   2880
```

-continued

```
accaccccag ccctgccctt ggcctcactt tttcccagca ataagtgggg ttcaccaccc   2940

gcctcgggaa tactttcccc ttctaaatgg gacttgctgt tacctcagga ggctccttag   3000

tgcaaatatg accctggtca gggctttgcc accgttgaag ccctgcagaa ggtgcaatgt   3060

aggggttctg ggccacaga ggagaggcca cttcccacca ggacccccaa catgaagtct   3120

aggcctcagg ggctcccgcc cttcttcctc cagcagcggg aactgccact gctctcccag   3180

gccctgttct ggaggctaac cttggttcct ggagagtgtg cccctccacc ctccctccag   3240

cagccctgat cacaccatga gagccaggaa cgggtcaccc tgctgaagat cactctgtgc   3300

cctgggggag gagccaagcc ctcaccccac aaggggcagg tgggggcttg gttgctgacc   3360

cggcccaagt ccccacagag caccttctgt agctccagct tgtctccctg gcttctcttt   3420

gaaggagaaa aatgtaaaat atgcactgag aaagccagcc ccgcctgctt agtcagcccc   3480

ggcagcaggg cagccatggg aactcaggaa aagcaggaac cctttccaaa agcccagaga   3540

tgccctgggc tcagatctgt aattctccca ggagctgtga tagagcaggc cacacaaagt   3600

ccctacgcct ccctgctgcc tcccccagat gcatgtggtg gcatcaccat tccccaaatt   3660

gaatatcagc atgcggcctg accagggact ctttagatgc atgaatttat ttatatgaag   3720

gctctcacag agacacacac agcacttcag tagcatttgc attcctggtt aaagaatcac   3780

caatatttaa aataaaaact ttcctgaaat tgggactgtc atgttatcca gaagggctgg   3840

tacatccgcc caccatgtcc ccctgctggg tcaggagcca acacaggacc ctgcgtgtga   3900

gcgtgcctga catctcacgc acggccactc cagagccggt ccctgtcctt ggaaagctgt   3960

gaagccttgc gttgagttcc ttctcgatac tgacggctcc gtgctgacat tctgagctct   4020

ggagtcacac cagcgcaggg gcgtggagga actgaggttt ggaaggaatg ccaggtctcg   4080

cacagcttgg cctcgagaag gtgagaggaa ggcaaaggcc agggagggga cccagagagg   4140

cctggcacac aaggcccaag caccaccgtc aacacagccc agtccataca gaaatgggtt   4200

tcatgcctga aaagcttttt acagaaagat gccgcctgta gccagtgaca gccgcaaccc   4260

tacaggcctc agttccttgc agaggtgagg ggtagagagt cagcctccct cccttccagc   4320

agcgacccag cttccctcca cttccaggtg gtgctgggct caccgaggga gcactggtgg   4380

gtgctctgaa aacccacagg atcccacctc caggcccacc tgggtcccat ctcactctct   4440

tcttctttca ccaattgcta acatagacct tgttgggatc acgatggctt cacaagccag   4500

ctgttgggtt tgctatgtca ctgtggctca gtcacatccc tgcgtgtata ctgtctgcgg   4560

ggcacatatg tatccattta gagctaaagg aatcagtgta cactacagct aatcctaata   4620

aatccgatgt tttcggaatg gcaaaaaaaa aaa                                4653
```

<210> SEQ ID NO 140
<211> LENGTH: 4246
<212> TYPE: DNA
<213> ORGANISM: Homo sapiens

<400> SEQUENCE: 140

```
acctcgggcc gcccccgccg ccgagccggc ccagggataa agtggcggcg cagacgccgc     60

accctgtcgc cgcgaagccg gtcgcgcgca gctcgtcccg gccctggccc gccgcaaacg    120

aggatccgct gcgctcgggg aacgcgacag cggcgctcgt ggccccggac ctgaagaccc    180

ttccagcatg ccagaggaaa gttcccccag gcggaccccg cagagcattc cctaccagga    240

cctccctcac ctggtcaatg cagacggaca gtacctcttc tgcaggtact ggaaacccac    300

aggcacaccc aaggccctca tctttgtgtc ccatggagcc ggagagcaca gtggccgcta    360
```

-continued

```
tgaagagctg gctcggatgc tgatggggct ggacctgctg gtgttcgccc acgaccatgt    420
tggccacgga cagagcgaag gggagaggat ggtagtgtct gacttccacg ttttcgtcag    480
ggatgtgttg cagcatgtgg attccatgca gaaagactac cctgggcttc ctgtcttcct    540
tctgggccac tccatgggag gcgccatcgc catcctcacg gccgcagaga ggccgggcca    600
cttcgccggc atggtactca tttcgcctct ggttcttgcc aatcctgaat ctgcaacaac    660
tttcaaggtc cttgctgcga aagtgctcaa ccttgtgctg ccaaacttgt ccctcgggcc    720
catcgactcc agcgtgctct ctcggaataa gacagaggtc gacatttata actcagaccc    780
cctgatctgc cgggcagggc tgaaggtgtg cttcggcatc caactgctga atgccgtctc    840
acgggtggag cgcgccctcc ccaagctgac tgtgcccttc ctgctgctcc agggctctgc    900
cgatcgccta tgtgacagca aaggggccta cctgctcatg gagttagcca agagccagga    960
caagactctc aagatttatg aaggtgccta ccatgttctc cacaaggagc ttcctgaagt   1020
caccaactcc gtcttccatg aaataaacat gtgggtctct caaaggacag ccacggcagg   1080
aactgcgtcc ccaccctgaa tgcattggcc ggtgcccggc tcatggtctg ggggatgcag   1140
gcaggggaag ggcagagatg gcttctcaga tatggcttgc caaaaaaaaa aaaaaaaaaa   1200
aatcagaaat tggagaaatc cttagcacaa ttttctaaaa aataacagac atttttgtta   1260
tacattagac tatcagacac tggacctacc ttaatggtta gacactttat gcaaaaaaag   1320
agaaaggtcc caggtgattt tccacaaaga atgtgctaaa atgtccactg aaaacaaagc   1380
caagcctctg ccctgcctct cccagctccc acaagggttc caggaattcc tggtgttccc   1440
aggacaccag actgcaataa ctggaggcgc ctccttcctg cccacccttc gctcacgccc   1500
cagcgccctc tctgaccagc ctccgcttgg tggccttcct ctggccgtgt gatgaggtgg   1560
ttgctgtctc catagggggcc agctccccag ggcagactca cgtgcccctc tgaggctcag   1620
aaaatgccca gcccttcctc aaaatgagca gccacccatg actttgtggg ctccttgtta   1680
gcctgagacc aggctttgca gaggggcggg gggtgaggct tagcccagaa ggagaactga   1740
gcaggaaacc aaggctcttc tctgtcccct gcccttcccc tcctgccagg gggaggctca   1800
ggttggtccc cgagtgccgc ctgtactcac aaaggctgcc tttcctctag agtcactaat   1860
tttacctgat gctatgagag aatcatattg aagatgaaat gtctaatata taatgtatat   1920
tttaaagcag agactatttt ggtggatagg tgggagggag caaggggagt ttgagggaat   1980
cagagcttga tgctactgta cagaactgga caggttgggc cggcagtggt ggggccagag   2040
ggctctgtgc tctaggagct aagccagcag cccccgagag gggacttggc tgggcctttc   2100
ctatgggcaa ggcccagtgc tcttcctgcc caccagggac catggagcag tggcacccta   2160
tggggctatg atccctaggc ctgggcctgg gcctgcctat ggcccagagc taccctggga   2220
gtgtcagtgc tagcagcaca gctacctctg gtggcaggag aagagaggcc cagcacagca   2280
gcaggccagg ccttcctgtc caggtctgca tggagcactc ggtgacccag agcagggact   2340
ggaggcaccc ccagccctgc cccaggccac agcaggacag gccgggacag gcctcaccca   2400
aggccaaggc tggcatcagc caatcattca gagctgaggc cctgggccta gcctgccctt   2460
ctcaggtgcc aataccaccc cagccctgcc cttggcctca ctttttccca gcaataagtg   2520
gggttcacca cccgcctcgg gaatactttc cccttctaaa tgggacttgc tgttacctca   2580
ggaggctcct tagtgcaaat atgaccctgg tcagggcttt gccaccgttg aagccctgca   2640
gaaggtgcaa tgtaggggtt ctggggccac agaggagagg ccacttccca ccaggacccc   2700
```

caacatgaag tctaggcctc aggggctccc gcccttcttc ctccagcagc gggaactgcc 2760
actgctctcc caggccctgt tctggaggct aaccttggtt cctggagagt gtgcccctcc 2820
accctccctc cagcagccct gatcacacca tgagagccag gaacgggtca ccctgctgaa 2880
gatcactctg tgccctgggg gaggagccaa gccctcaccc cacaaggggc aggtgggggc 2940
ttggttgctg acccggccca agtccccaca gagcaccttc tgtagctcca gcttgtctcc 3000
ctggcttctc tttgaaggag aaaaatgtaa aatatgcact gagaaagcca gccccgcctg 3060
cttagtcagc cccggcagca gggcagccat gggaactcag gaaaagcagg aaccctttcc 3120
aaaagcccag agatgccctg ggctcagatc tgtaattctc ccaggagctg tgatagagca 3180
ggccacacaa agtccctacg cctccctgct gcctccccca gatgcatgtg gtggcatcac 3240
cattccccaa attgaatatc agcatgcggc ctgaccaggg actctttaga tgcatgaatt 3300
tatttatatg aaggctctca cagagacaca cacagcactt cagtagcatt tgcattcctg 3360
gttaaagaat caccaatatt taaaataaaa actttcctga aattgggact gtcatgttat 3420
ccagaagggc tggtacatcc gcccaccatg tccccctgct gggtcaggag ccaacacagg 3480
accctgcgtg tgagcgtgcc tgacatctca cgcacggcca ctccagagcc ggtccctgtc 3540
cttggaaagc tgtgaagcct tgcgttgagt tccttctcga tactgacggc tccgtgctga 3600
cattctgagc tctggagtca caccagcgca ggggcgtgga ggaactgagg tttggaagga 3660
atgccaggtc tcgcacagct tggcctcgag aaggtgagag gaaggcaaag gccagggagg 3720
ggacccagag aggcctggca cacaaggccc aagcaccacc gtcaacacag cccagtccat 3780
acagaaatgg gtttcatgcc tgaaaagctt tttacagaaa gatgccgcct gtagccagtg 3840
acagccgcaa ccctacaggc ctcagttcct tgcagaggtg aggggtagag agtcagcctc 3900
cctcccttcc agcagcgacc cagcttccct ccacttccag gtggtgctgg gctcaccgag 3960
ggagcactgg tgggtgctct gaaaacccac aggatcccac ctccaggccc acctgggtcc 4020
catctcactc tcttcttctt tcaccaattg ctaacataga ccttgttggg atcacgatgg 4080
cttcacaagc cagctgttgg gtttgctatg tcactgtggc tcagtcacat ccctgcgtgt 4140
atactgtctg cggggcacat atgtatccat ttagagctaa aggaatcagt gtacactaca 4200
gctaatccta ataaatccga tgttttcgga atggcaaaaa aaaaaa 4246

<210> SEQ ID NO 141
<211> LENGTH: 4563
<212> TYPE: DNA
<213> ORGANISM: Homo sapiens

<400> SEQUENCE: 141
cccaaaccaa cttgtcccca tcaactccat ctttctagtc cccaccttcc ccggtgcaga 60
cacccggcga agcccacccg gttttcccag cggcatttcc gatgacagct tcggggctac 120
gtgtcctgtg ctgtcggaga cgcacaggaa gcaaagtttg tgagaagcct tgggggcgac 180
tttgccttgg gcacccgcat ttgtgcgtct gcgaggtgcc tcggtgtgcg cggagctagt 240
ttcccagttt cccgggcccc tcccttctcc gagcccctct agcgatttgt ttaggaaaag 300
tgatgacatg aactagtagt ggagaatcgc agcgccgctc cccgccctgg ggagggaggg 360
gagccccgga gagcctgccg gtgggagctg gaagcaggct cccggctgag cgccccagcc 420
cgaaaggcag ggtctgggtg cgggaagagg gctcggagct gccttcctgc tgccttgggg 480
ccgcccagat gagggaacag cccgatttgc ctggttctga ttctccaggc tgtcgtggtt 540
gtggaatgca aacgccagca cataatggaa acaggacctg aagacccttc cagcatgcca 600

-continued

```
gaggaaagtt cccccaggcg gaccccgcag agcattccct accaggacct ccctcacctg    660
gtcaatgcag acggacagta cctcttctgc aggtactgga aacccacagg cacacccaag    720
gccctcatct ttgtgtccca tggagccgga gagcacagtg gccgctatga agagctggct    780
cggatgctga tggggctgga cctgctggtg ttcgcccacg accatgttgg ccacggacag    840
agcgaagggg agaggatggt agtgtctgac ttccacgttt tcgtcaggga tgtgttgcag    900
catgtggatt ccatgcagaa agactaccct gggcttcctg tcttccttct gggccactcc    960
atgggaggcg ccatcgccat cctcacggcc gcagagaggc cgggccactt cgccggcatg   1020
gtactcattt cgcctctggt tcttgccaat cctgaatctg caacaacttt caaggtcgac   1080
atttataact cagacccccct gatctgccgg gcagggctga aggtgtgctt cggcatccaa   1140
ctgctgaatg ccgtctcacg ggtggagcgc gccctcccca agctgactgt gcccttcctg   1200
ctgctccagg gctctgccga tcgcctatgt gacagcaaag ggcctacct gctcatggag   1260
ttagccaaga gccaggacaa gactctcaag atttatgaag gtgcctacca tgttctccac   1320
aaggagcttc ctgaagtcac caactccgtc ttccatgaaa taaacatgtg ggtctctcaa   1380
aggacagcca cggcaggaac tgcgtcccca ccctgaatgc attggccggt gcccggctca   1440
tggtctgggg gatgcaggca ggggaagggc agagatggct tctcagatat ggcttgccaa   1500
aaaaaaaaaa aaaaaaaaat cagaaattgg agaaatcctt agcacaattt tctaaaaaat   1560
aacagacatt tttgttatac attagactat cagacactgg acctaccttta atggttagac   1620
actttatgca aaaaaagaga aaggtcccag gtgattttcc acaaagaatg tgctaaaatg   1680
tccactgaaa acaaagccaa gcctctgccc tgcctctccc agctcccaca agggttccag   1740
gaattcctgg tgttcccagg acaccagact gcaataactg gaggcgcctc cttcctgccc   1800
acccttcgct cacgccccag cgccctctct gaccagcctc cgcttggtgg ccttcctctg   1860
gccgtgtgat gaggtggttg ctgtctccat aggggccagc tccccagggc agactcacgt   1920
gcccctctga ggctcagaaa atgcccagcc cttcctcaaa atgagcagcc acccatgact   1980
ttgtgggctc cttgttagcc tgagaccagg ctttgcagag gggcgggggg tgaggcttag   2040
cccagaagga gaactgagca ggaaaccaag gctcttctct gtcccctgcc cttcccctcc   2100
tgccaggggg aggctcaggt tggtccccga gtgccgcctg tactcacaaa ggctgccttt   2160
cctctagagt cactaatttt acctgatgct atgagagaat catattgaag atgaaatgtc   2220
taatatataa tgtatatttt aaagcagaga ctattttggt ggataggtgg gagggagcaa   2280
ggggagtttg agggaatcag agcttgatgc tactgtacag aactggacag gttgggccgg   2340
cagtggtggg gccagagggc tctgtgctct aggagctaag ccagcagccc ccgagagggg   2400
acttggctgg gcctttccta tgggcaaggc ccagtgctct tcctgcccac cagggaccat   2460
ggagcagtgg caccctatgg ggctatgatc cctaggcctg ggcctgggcc tgcctatggc   2520
ccagagctac cctgggagtg tcagtgctag cagcacagct acctctggtg gcaggagaag   2580
agaggcccag cacagcagca ggccaggcct tcctgtccag gtctgcatgg agcactcggt   2640
gacccagagc agggactgga ggcaccccca gccctgcccc aggccacagc aggacaggcc   2700
gggacaggcc tcacccaagg ccaaggctgg catcagccaa tcattcagag ctgaggccct   2760
gggcctagcc tgcccttctc aggtgccaat accaccccag ccctgccctt ggcctcactt   2820
tttcccagca ataagtgggg ttcaccaccc gcctcgggaa tactttcccc ttctaaatgg   2880
gacttgctgt tacctcagga ggctccttag tgcaaatatg accctggtca gggctttgcc   2940
```

```
accgttgaag ccctgcagaa ggtgcaatgt aggggttctg ggccacaga ggagaggcca   3000

cttcccacca ggacccccaa catgaagtct aggcctcagg ggctcccgcc cttcttcctc   3060

cagcagcggg aactgccact gctctcccag gccctgttct ggaggctaac cttggttcct   3120

ggagagtgtg cccctccacc ctccctccag cagccctgat cacaccatga gagccaggaa   3180

cgggtcaccc tgctgaagat cactctgtgc cctgggggag gagccaagcc ctcaccccac   3240

aaggggcagg tgggggcttg gttgctgacc cggcccaagt ccccacagag caccttctgt   3300

agctccagct tgtctccctg gcttctcttt gaaggagaaa aatgtaaaat atgcactgag   3360

aaagccagcc ccgcctgctt agtcagcccc ggcagcaggg cagccatggg aactcaggaa   3420

aagcaggaac cctttccaaa agcccagaga tgccctgggc tcagatctgt aattctccca   3480

ggagctgtga tagagcaggc cacacaaagt ccctacgcct ccctgctgcc tcccccagat   3540

gcatgtggtg gcatcaccat tccccaaatt gaatatcagc atgcggcctg accagggact   3600

ctttagatgc atgaatttat ttatatgaag gctctcacag agacacacac agcacttcag   3660

tagcatttgc attcctggtt aaagaatcac caatatttaa aataaaaact ttcctgaaat   3720

tgggactgtc atgttatcca gaagggctgg tacatccgcc caccatgtcc ccctgctggg   3780

tcaggagcca acacaggacc ctgcgtgtga gcgtgcctga catctcacgc acggccactc   3840

cagagccggt ccctgtcctt ggaaagctgt gaagccttgc gttgagttcc ttctcgatac   3900

tgacggctcc gtgctgacat tctgagctct ggagtcacac cagcgcaggg gcgtggagga   3960

actgaggttt ggaaggaatg ccaggtctcg cacagcttgg cctcgagaag gtgagaggaa   4020

ggcaaaggcc agggagggga cccagagagg cctggcacac aaggcccaag caccaccgtc   4080

aacacagccc agtccataca gaaatgggtt tcatgcctga aaagcttttt acagaaagat   4140

gccgcctgta gccagtgaca gccgcaaccc tacaggcctc agttccttgc agaggtgagg   4200

ggtagagagt cagcctccct cccttccagc agcgacccag cttccctcca cttccaggtg   4260

gtgctgggct caccgaggga gcactggtgg gtgctctgaa aacccacagg atcccacctc   4320

caggcccacc tgggtcccat ctcactctct tcttctttca ccaattgcta acatagacct   4380

tgttgggatc acgatggctt cacaagccag ctgttgggtt tgctatgtca ctgtggctca   4440

gtcacatccc tgcgtgtata ctgtctgcgg ggcacatatg tatccattta gagctaaagg   4500

aatcagtgta cactacagct aatcctaata aatccgatgt tttcggaatg gcaaaaaaaa   4560

aaa                                                                 4563
```

<210> SEQ ID NO 142
<211> LENGTH: 313
<212> TYPE: PRT
<213> ORGANISM: Homo sapiens

<400> SEQUENCE: 142

```
Met Glu Thr Gly Pro Glu Asp Pro Ser Ser Met Pro Glu Glu Ser Ser
1               5                   10                  15

Pro Arg Arg Thr Pro Gln Ser Ile Pro Tyr Gln Asp Leu Pro His Leu
            20                  25                  30

Val Asn Ala Asp Gly Gln Tyr Leu Phe Cys Arg Tyr Trp Lys Pro Thr
        35                  40                  45

Gly Thr Pro Lys Ala Leu Ile Phe Val Ser His Gly Ala Gly Glu His
    50                  55                  60

Ser Gly Arg Tyr Glu Glu Leu Ala Arg Met Leu Met Gly Leu Asp Leu
65                  70                  75                  80
```

```
Leu Val Phe Ala His Asp His Val Gly His Gly Gln Ser Glu Gly Glu
                85                  90                  95

Arg Met Val Val Ser Asp Phe His Val Phe Val Arg Asp Val Leu Gln
            100                 105                 110

His Val Asp Ser Met Gln Lys Asp Tyr Pro Gly Leu Pro Val Phe Leu
        115                 120                 125

Leu Gly His Ser Met Gly Gly Ala Ile Ala Ile Leu Thr Ala Ala Glu
    130                 135                 140

Arg Pro Gly His Phe Ala Gly Met Val Leu Ile Ser Pro Leu Val Leu
145                 150                 155                 160

Ala Asn Pro Glu Ser Ala Thr Thr Phe Lys Val Leu Ala Ala Lys Val
                165                 170                 175

Leu Asn Leu Val Leu Pro Asn Leu Ser Leu Gly Pro Ile Asp Ser Ser
            180                 185                 190

Val Leu Ser Arg Asn Lys Thr Glu Val Asp Ile Tyr Asn Ser Asp Pro
        195                 200                 205

Leu Ile Cys Arg Ala Gly Leu Lys Val Cys Phe Gly Ile Gln Leu Leu
    210                 215                 220

Asn Ala Val Ser Arg Val Glu Arg Ala Leu Pro Lys Leu Thr Val Pro
225                 230                 235                 240

Phe Leu Leu Leu Gln Gly Ser Ala Asp Arg Leu Cys Asp Ser Lys Gly
                245                 250                 255

Ala Tyr Leu Leu Met Glu Leu Ala Lys Ser Gln Asp Lys Thr Leu Lys
            260                 265                 270

Ile Tyr Glu Gly Ala Tyr His Val Leu His Lys Glu Leu Pro Glu Val
        275                 280                 285

Thr Asn Ser Val Phe His Glu Ile Asn Met Trp Val Ser Gln Arg Thr
    290                 295                 300

Ala Thr Ala Gly Thr Ala Ser Pro Pro
305                 310


<210> SEQ ID NO 143
<211> LENGTH: 303
<212> TYPE: PRT
<213> ORGANISM: Homo sapiens

<400> SEQUENCE: 143

Met Pro Glu Glu Ser Ser Pro Arg Arg Thr Pro Gln Ser Ile Pro Tyr
1               5                   10                  15

Gln Asp Leu Pro His Leu Val Asn Ala Asp Gly Gln Tyr Leu Phe Cys
            20                  25                  30

Arg Tyr Trp Lys Pro Thr Gly Thr Pro Lys Ala Leu Ile Phe Val Ser
        35                  40                  45

His Gly Ala Gly Glu His Ser Gly Arg Tyr Glu Glu Leu Ala Arg Met
    50                  55                  60

Leu Met Gly Leu Asp Leu Leu Val Phe Ala His Asp His Val Gly His
65                  70                  75                  80

Gly Gln Ser Glu Gly Glu Arg Met Val Val Ser Asp Phe His Val Phe
                85                  90                  95

Val Arg Asp Val Leu Gln His Val Asp Ser Met Gln Lys Asp Tyr Pro
            100                 105                 110

Gly Leu Pro Val Phe Leu Leu Gly His Ser Met Gly Gly Ala Ile Ala
        115                 120                 125

Ile Leu Thr Ala Ala Glu Arg Pro Gly His Phe Ala Gly Met Val Leu
    130                 135                 140
```

```
Ile Ser Pro Leu Val Leu Ala Asn Pro Glu Ser Ala Thr Thr Phe Lys
145                 150                 155                 160

Val Leu Ala Ala Lys Val Leu Asn Leu Val Leu Pro Asn Leu Ser Leu
                165                 170                 175

Gly Pro Ile Asp Ser Ser Val Leu Ser Arg Asn Lys Thr Glu Val Asp
            180                 185                 190

Ile Tyr Asn Ser Asp Pro Leu Ile Cys Arg Ala Gly Leu Lys Val Cys
        195                 200                 205

Phe Gly Ile Gln Leu Leu Asn Ala Val Ser Arg Val Glu Arg Ala Leu
    210                 215                 220

Pro Lys Leu Thr Val Pro Phe Leu Leu Leu Gln Gly Ser Ala Asp Arg
225                 230                 235                 240

Leu Cys Asp Ser Lys Gly Ala Tyr Leu Leu Met Glu Leu Ala Lys Ser
                245                 250                 255

Gln Asp Lys Thr Leu Lys Ile Tyr Glu Gly Ala Tyr His Val Leu His
            260                 265                 270

Lys Glu Leu Pro Glu Val Thr Asn Ser Val Phe His Glu Ile Asn Met
        275                 280                 285

Trp Val Ser Gln Arg Thr Ala Thr Ala Gly Thr Ala Ser Pro Pro
    290                 295                 300


<210> SEQ ID NO 144
<211> LENGTH: 283
<212> TYPE: PRT
<213> ORGANISM: Homo sapiens

<400> SEQUENCE: 144

Met Glu Thr Gly Pro Glu Asp Pro Ser Ser Met Pro Glu Glu Ser Ser
1               5                   10                  15

Pro Arg Arg Thr Pro Gln Ser Ile Pro Tyr Gln Asp Leu Pro His Leu
            20                  25                  30

Val Asn Ala Asp Gly Gln Tyr Leu Phe Cys Arg Tyr Trp Lys Pro Thr
        35                  40                  45

Gly Thr Pro Lys Ala Leu Ile Phe Val Ser His Gly Ala Gly Glu His
    50                  55                  60

Ser Gly Arg Tyr Glu Glu Leu Ala Arg Met Leu Met Gly Leu Asp Leu
65                  70                  75                  80

Leu Val Phe Ala His Asp His Val Gly His Gly Gln Ser Glu Gly Glu
                85                  90                  95

Arg Met Val Val Ser Asp Phe His Val Phe Val Arg Asp Val Leu Gln
            100                 105                 110

His Val Asp Ser Met Gln Lys Asp Tyr Pro Gly Leu Pro Val Phe Leu
        115                 120                 125

Leu Gly His Ser Met Gly Gly Ala Ile Ala Ile Leu Thr Ala Ala Glu
    130                 135                 140

Arg Pro Gly His Phe Ala Gly Met Val Leu Ile Ser Pro Leu Val Leu
145                 150                 155                 160

Ala Asn Pro Glu Ser Ala Thr Thr Phe Lys Val Asp Ile Tyr Asn Ser
                165                 170                 175

Asp Pro Leu Ile Cys Arg Ala Gly Leu Lys Val Cys Phe Gly Ile Gln
            180                 185                 190

Leu Leu Asn Ala Val Ser Arg Val Glu Arg Ala Leu Pro Lys Leu Thr
        195                 200                 205

Val Pro Phe Leu Leu Leu Gln Gly Ser Ala Asp Arg Leu Cys Asp Ser
```

```
    210                 215                 220

Lys Gly Ala Tyr Leu Leu Met Glu Leu Ala Lys Ser Gln Asp Lys Thr
225                 230                 235                 240

Leu Lys Ile Tyr Glu Gly Ala Tyr His Val Leu His Lys Glu Leu Pro
                245                 250                 255

Glu Val Thr Asn Ser Val Phe His Glu Ile Asn Met Trp Val Ser Gln
            260                 265                 270

Arg Thr Ala Thr Ala Gly Thr Ala Ser Pro Pro
        275                 280


<210> SEQ ID NO 145
<211> LENGTH: 5556
<212> TYPE: DNA
<213> ORGANISM: Homo sapiens

<400> SEQUENCE: 145

gcgcttgccc cgcagctgat tcatagcccc ggcccgggcc gcctctgcac gtccgccccg     60

gagcccgcac ccgcgcccca cgcgccgccg aggactcggc ccggctcgtg gagcccttcg    120

cccgcggcgt gagtaccccc gacccgcccg tccccgctct gctcgcgccc tgccgctgcg    180

ccgccctcgg tggcttttcc gacgggcgag ccccgtgctg tgcgggaaag aatccgacaa    240

cttcgcagcc catcccggct ggacgcgacc gggagtgcag cagcccgttc ccctcctcgg    300

tgccgcctct gcccagcgtt tgcttggctg ggctaccacc tgcgctcgga cggcgctcgg    360

agggtcctcg ccccggcct gcctacctga aaaccagaac tgatggctct atttgcagtc    420

tttcagacaa cattcttctt aacattgctg tccttgagga cttaccagag tgaagtcttg    480

gctgaacgtt taccattgac tcctgtatca cttaaagttt ccaccaattc tacgcgtcag    540

agtttgcact tacaatggac tgtccacaac cttccttatc atcaggaatt gaaaatggta    600

tttcagatcc agatcagtag gattgaaaca tccaatgtca tctgggtggg gaattacagc    660

accactgtga agtggaacca ggttctgcat tggagctggg aatctgagct ccctttggaa    720

tgtgccacac actttgtaag aataaagagt ttggtggacg atgccaagtt ccctgagcca    780

aatttctgga gcaactggag ttcctgggag gaagtcagtg tacaagattc tactggacag    840

gatatattgt tcgttttccc taaagataag ctggtggaag aaggcaccaa tgttaccatt    900

tgttacgttt ctaggaacat tcaaaataat gtatcctgtt atttggaagg gaaacagatt    960

catggagaac aacttgatcc acatgtaact gcattcaact tgaatagtgt gcctttcatt   1020

aggaataaag ggacaaatat ctattgtgag gcaagtcaag gaaatgtcag tgaaggcatg   1080

aaaggcatcg ttctttttgt ctcaaaagta cttgaggagc ccaaggactt ttcttgtgaa   1140

accgaggact tcaagacttt gcactgtact tgggatcctg ggacggacac tgccttgggg   1200

tggtctaaac aaccttccca aagctacact ttatttgaat cattttctgg ggaaaagaaa   1260

ctttgtacac acaaaaactg gtgtaattgg caaataactc aagactcaca agaaacctat   1320

aacttcacac tcatagctga aaattactta aggaagagaa gtgtcaatat ccttttttaac   1380

ctgactcatc gagtttattt aatgaatcct tttagtgtca actttgaaaa tgtaaatgcc   1440

acaaatgcca tcatgacctg gaaggtgcac tccataagga ataatttcac atatttgtgt   1500

cagattgaac tccatggtga aggaaaaatg atgcaataca atgtttccat caaggtgaac   1560

ggtgagtact tcttaagtga actggaacct gccacagagt acatggcgcg agtacggtgt   1620

gctgatgcca gccacttctg gaaatggagt gaatggagtg gtcagaactt caccacactt   1680

gaagctgctc cctcagaggc ccctgatgtc tggagaattg tgagcttgga gccaggaaat   1740
```

catactgtga ccttattctg gaagccatta tcaaaactgc atgccaatgg aaagatcctg 1800
ttctataatg tagttgtaga aaacctagac aaaccatcca gttcagagct ccattccatt 1860
ccagcaccag ccaacagcac aaaactaatc cttgacaggt gttcctacca aatctgcgtc 1920
atagccaaca acagtgtggg tgcttctcct gcttctgtaa tagtcatctc tgcagacccc 1980
gaaaacaaag aggttgagga agaaagaatt gcaggcacag agggtggatt ctctctgtct 2040
tggaaacccc aacctggaga tgttataggc tatgttgtgg actggtgtga ccatacccag 2100
gatgtgctcg gtgatttcca gtggaagaat gtaggtccca ataccacaag cacagtcatt 2160
agcacagatg cttttaggcc aggagttcga tatgacttca gaatttatgg gttatctaca 2220
aaaaggattg cttgtttatt agagaaaaaa acaggatact ctcaggaact tgctccttca 2280
gacaaccctc acgtgctggt ggatacattg acatcccact ccttcactct gagttggaaa 2340
gattactcta ctgaatctca acctggtttt atacaagggt accatgtcta tctgaaatcc 2400
aaggcgaggc agtgccaccc acgatttgaa aaggcagttc tttcagatgg ttcagaatgt 2460
tgcaaataca aaattgacaa cccggaagaa aaggcattga ttgtggacaa cctaaagcca 2520
gaatccttct atgagttttt catcactcca ttcactagtg ctggtgaagg ccccagtgct 2580
acgttcacga aggtcacgac tccggatgaa cactcctcga tgctgattca tatcctactg 2640
cccatggttt tctgcgtctt gctcatcatg gtcatgtgct acttgaaaag tcagtggatc 2700
aaggagacct gttatcctga catccctgac ccttacaaga gcagcatcct gtcattaata 2760
aaattcaagg agaaccctca cctaataata atgaatgtca gtgactgtat cccagatgct 2820
attgaagttg taagcaagcc agaagggaca aagatacagt tcctaggcac taggaagtca 2880
ctcacagaaa ccgagttgac taagcctaac tacctttatc tccttccaac agaaaagaat 2940
cactctggcc ctggcccctg catctgtttt gagaacttga cctataacca ggcagcttct 3000
gactctggct cttgtggcca tgttccagta tccccaaaag ccccaagtat gctgggacta 3060
atgacctcac ctgaaaatgt actaaaggca ctagaaaaaa actacatgaa ctccctggga 3120
gaaatcccag ctggagaaac aagtttgaat tatgtgtccc agttggcttc acccatgttt 3180
ggagacaagg acagtctccc aacaaaccca gtagaggcac cacactgttc agagtataaa 3240
atgcaaatgg cagtctccct gcgtcttgcc ttgcctcccc cgaccgagaa tagcagcctc 3300
tcctcaatta ccctttttaga tccaggtgaa cactactgct aaccagcatg ccgatttcat 3360
accttatgct acacagacat taagaagagc agagctggca ccctgtcatc accagtggcc 3420
ttggtcctta atcccagtac gatttgcagg tctggtttat ataagaccac tacagtctgg 3480
ctaggttaaa ggccagaggc tatggaactt aacactcccc attggagcaa gcttgcccta 3540
gagacggcag gatcatggga gcatgcttac cttctgctgt ttgttccagg ctcaccttta 3600
gaacaggaga cttgagcttg acctaaggat atgcattaac cactctacag actcccactc 3660
agtactgtac agggtggctg tggtcctaga agttcagttt ttactgagga aatatttcca 3720
ttaacagcaa ttattatatt gaaggcttta ataaaggcca caggagacat tactatagca 3780
tagattgtca aatgtaaatt tactgagcgt gttttataaa aaactcacag gtgtttgagg 3840
ccaaaacaga ttttagactt accttgaacg gataagaatc tatagttcac tgacacagta 3900
aaattaactc tgtgggtggg ggcggggggc atagctctaa tctaatatat aaaatgtgtg 3960
atgaatcaac aagatttcca caattcttct gtcaagctta ctacagtgaa agaatgggat 4020
tggcaagtaa cttctgactt actgtcagtt gtacttctgc tccatagaca tcagtattct 4080

```
gccatcattt ttgatgacta cctcagaaca taaaaaggaa cgtatatcac ataattccag   4140
tcacagtttt tggttcctct tttctttcaa gaactatata taaatgacct gttttcactt   4200
agcatccttt ggactctgca gtaggttgtc tgggtcaaga taactctcag tcacatttat   4260
attcatatta tgctaaaata gtaaaatgaa acctcattgt tggacataat ttagatataa   4320
ctaaaaagtt ctatgaagtg ggaaattccg tgttggctct ggagcagctt tgtctcctct   4380
gaaccaatat atcccaaacc aatatatgca aagcacctgg tacacaactg gtattttagt   4440
acatgttggt tcttttggtg caatctcagc tcactgcagc ttccgcctcc tagattcaaa   4500
caaacagttc tcctgcccca gcctccagag cacctaggac tccaggtgca tgctaccaca   4560
cctgactagt ttttatattt ttagtagaga ttgggtttta ccatattggc caggctggtc   4620
tcaaactcct gaccgcaggt gatccacctg cctcagcttc cccaagggct gggattacag   4680
gtgtgagcca ccatgcccag cctatttgtc acattatttg tcacatttat tttactttta   4740
tttatttttt gagatgaaat ttcgctcttg ttgcccaggc tggagtgcaa tggtgcagcc   4800
ttggctcact gcaacctccg cctcccaggg tcaagcaatt ctcctgcctc agcctcctga   4860
gtagctggga ttacaggcat gcaccaccac acccaggtaa ttttgtatct ttagtagaga   4920
tggggtttca ccatgttggt caggctgttc tcgaactcct gacctcaggt gatctgcctg   4980
ccttggcctc ccaaagtgct gggattacag gcgtgagcca ctgcgcctag ccgtcacatt   5040
tctaaacaag catgaaaggg gttcattttt gtcttcttct tgcctgccgt cagcatggtg   5100
gaaatggctc tgcctatgct catgcttctg gtgcccaatg ccttgcactg tgccattcaa   5160
cactatgaag agaaacaagt agccacacct caaaataatg tggctgtcaa caactggcct   5220
aaataaacct acacaaacca gtacttgcct tttgctggaa acattgatta tgtgctcctc   5280
acgtagtaga aagcggtatc ctgattagtc taacagttgt gttagacttt agggccagta   5340
ttgtcagcat ttatttattt atgtaccttt gttatgatgg gatatttttc atttgaaact   5400
tgttcataaa aatgtcaatg acattgatga ctgatttgta catatttttc atatagtttt   5460
gtttaaaaaa taattcacgc aaaatcttga agtcattttt gctattgaaa taaaccttaa   5520
ttaaaatatt tcatcatcaa aaaaaaaaaa aaaaaa                              5556
```

<210> SEQ ID NO 146
<211> LENGTH: 1765
<212> TYPE: DNA
<213> ORGANISM: Homo sapiens

<400> SEQUENCE: 146

```
gcggccgcct ccccccggga ctgaagggag ggaattcctg tgggtcccag gagtgccaag     60
agtgcgcagc aagacgggaa attgcaaaag acctcacccc tctgccctcc cccgcggttt    120
tccagtaact cccgcccctc cgcgcttgcc ccgcagctga ttcatagccc cggcccgggc    180
cgcctctgca cgtccgcccc ggagcccgca cccgcgcccc acgcgccgcc gaggactcgg    240
cccggctcgt ggagcccttc gcccgcggca aaaccagaac tgatggctct atttgcagtc    300
tttcagacaa cattcttctt aacattgctg tccttgagga cttaccagag tgaagtcttg    360
gctgaacgtt taccattgac tcctgtatca cttaaagttt ccaccaattc tacgcgtcag    420
agtttgcact tacaatggac tgtccacaac cttccttatc atcaggaatt gaaaatggta    480
tttcagatcc agatcagtag gattgaaaca tccaatgtca tctgggtggg gaattacagc    540
accactgtga agtggaacca ggttctgcat tggagctggg aatctgagct ccctttggaa    600
tgtgccacac actttgtaag aataaagagt ttggtggacg atgccaagtt ccctgagcca    660
```

```
aatttctgga gcaactggag ttcctgggag gaagtcagtg tacaagattc tactggacag    720

gatatattgt tcgttttccc taaagataag ctggtggaag aaggcaccaa tgttaccatt    780

tgttacgttt ctaggaacat tcaaaataat gtatcctgtt atttggaagg gaaacagatt    840

catggagaac aacttgatcc acatgtaact gcattcaact tgaatagtgt gcctttcatt    900

aggaataaag ggacaaatat ctattgtgag gcaagtcaag gaaatgtcag tgaaggcatg    960

aaaggcatcg ttctttttgt ctcaaaagta cttgaggagc ccaaggactt ttcttgtgaa   1020

accgaggact tcaagacttt gcactgtact tgggatcctg ggacggacac tgccttgggg   1080

tggtctaaac aaccttccca aagctacact ttatttgaat cattttctgg ggaaaagaaa   1140

ctttgtacac acaaaaactg gtgtaattgg caaataactc aagactcaca agaaacctat   1200

aacttcacac tcatagctga aaattactta aggaagagaa gtgtcaatat ccttttttaac  1260

ctgactcatc gaggtgagac tagagttgtc acagcccacc gtggccacta acgtgtcttt   1320

gtttcacaga ctgtgtgatc aagtaaatgt gctgtagatc tttgcctcat tcacagcgga   1380

ggtgagagtt agaatttata cctattgttc atgccacgtt tctcctcatg gatgcacgca   1440

tcccctatta tttgtttctt ttaataatgt cacgagcacc aatgagctta ctacccaact   1500

tcaaaactag gactctaaca ataacttctg tcatatctca tcctgtaacg cccccacctt   1560

cgctccttcc gccaagataa ttatcacttt aaattgtgtg cgtgtgtatt ctcatttctt   1620

atgtgatggt aaaaatgcct ttatttttgtt tggttttaat gcatagaaag gacatcaagc  1680

tgtatgtaat aattcagtaa ttatgtttat ataatattaa attgctaata tttgcccata   1740

aaaaaaaaaa aaaaaaaaaa aaaaa                                          1765


<210> SEQ ID NO 147
<211> LENGTH: 979
<212> TYPE: PRT
<213> ORGANISM: Homo sapiens

<400> SEQUENCE: 147

Met Ala Leu Phe Ala Val Phe Gln Thr Thr Phe Phe Leu Thr Leu Leu
1               5                   10                  15

Ser Leu Arg Thr Tyr Gln Ser Glu Val Leu Ala Glu Arg Leu Pro Leu
            20                  25                  30

Thr Pro Val Ser Leu Lys Val Ser Thr Asn Ser Thr Arg Gln Ser Leu
        35                  40                  45

His Leu Gln Trp Thr Val His Asn Leu Pro Tyr His Gln Glu Leu Lys
    50                  55                  60

Met Val Phe Gln Ile Gln Ile Ser Arg Ile Glu Thr Ser Asn Val Ile
65                  70                  75                  80

Trp Val Gly Asn Tyr Ser Thr Thr Val Lys Trp Asn Gln Val Leu His
                85                  90                  95

Trp Ser Trp Glu Ser Glu Leu Pro Leu Glu Cys Ala Thr His Phe Val
            100                 105                 110

Arg Ile Lys Ser Leu Val Asp Asp Ala Lys Phe Pro Glu Pro Asn Phe
        115                 120                 125

Trp Ser Asn Trp Ser Ser Trp Glu Glu Val Ser Val Gln Asp Ser Thr
    130                 135                 140

Gly Gln Asp Ile Leu Phe Val Phe Pro Lys Asp Lys Leu Val Glu Glu
145                 150                 155                 160

Gly Thr Asn Val Thr Ile Cys Tyr Val Ser Arg Asn Ile Gln Asn Asn
                165                 170                 175
```

-continued

```
Val Ser Cys Tyr Leu Glu Gly Lys Gln Ile His Gly Glu Gln Leu Asp
            180                 185                 190

Pro His Val Thr Ala Phe Asn Leu Asn Ser Val Pro Phe Ile Arg Asn
        195                 200                 205

Lys Gly Thr Asn Ile Tyr Cys Glu Ala Ser Gln Gly Asn Val Ser Glu
    210                 215                 220

Gly Met Lys Gly Ile Val Leu Phe Val Ser Lys Val Leu Glu Glu Pro
225                 230                 235                 240

Lys Asp Phe Ser Cys Glu Thr Glu Asp Phe Lys Thr Leu His Cys Thr
                245                 250                 255

Trp Asp Pro Gly Thr Asp Thr Ala Leu Gly Trp Ser Lys Gln Pro Ser
            260                 265                 270

Gln Ser Tyr Thr Leu Phe Glu Ser Phe Ser Gly Glu Lys Lys Leu Cys
        275                 280                 285

Thr His Lys Asn Trp Cys Asn Trp Gln Ile Thr Gln Asp Ser Gln Glu
    290                 295                 300

Thr Tyr Asn Phe Thr Leu Ile Ala Glu Asn Tyr Leu Arg Lys Arg Ser
305                 310                 315                 320

Val Asn Ile Leu Phe Asn Leu Thr His Arg Val Tyr Leu Met Asn Pro
                325                 330                 335

Phe Ser Val Asn Phe Glu Asn Val Asn Ala Thr Asn Ala Ile Met Thr
            340                 345                 350

Trp Lys Val His Ser Ile Arg Asn Asn Phe Thr Tyr Leu Cys Gln Ile
        355                 360                 365

Glu Leu His Gly Glu Gly Lys Met Met Gln Tyr Asn Val Ser Ile Lys
    370                 375                 380

Val Asn Gly Glu Tyr Phe Leu Ser Glu Leu Glu Pro Ala Thr Glu Tyr
385                 390                 395                 400

Met Ala Arg Val Arg Cys Ala Asp Ala Ser His Phe Trp Lys Trp Ser
                405                 410                 415

Glu Trp Ser Gly Gln Asn Phe Thr Thr Leu Glu Ala Ala Pro Ser Glu
            420                 425                 430

Ala Pro Asp Val Trp Arg Ile Val Ser Leu Glu Pro Gly Asn His Thr
        435                 440                 445

Val Thr Leu Phe Trp Lys Pro Leu Ser Lys Leu His Ala Asn Gly Lys
    450                 455                 460

Ile Leu Phe Tyr Asn Val Val Val Glu Asn Leu Asp Lys Pro Ser Ser
465                 470                 475                 480

Ser Glu Leu His Ser Ile Pro Ala Pro Ala Asn Ser Thr Lys Leu Ile
                485                 490                 495

Leu Asp Arg Cys Ser Tyr Gln Ile Cys Val Ile Ala Asn Asn Ser Val
            500                 505                 510

Gly Ala Ser Pro Ala Ser Val Ile Val Ile Ser Ala Asp Pro Glu Asn
        515                 520                 525

Lys Glu Val Glu Glu Glu Arg Ile Ala Gly Thr Glu Gly Gly Phe Ser
    530                 535                 540

Leu Ser Trp Lys Pro Gln Pro Gly Asp Val Ile Gly Tyr Val Val Asp
545                 550                 555                 560

Trp Cys Asp His Thr Gln Asp Val Leu Gly Asp Phe Gln Trp Lys Asn
                565                 570                 575

Val Gly Pro Asn Thr Thr Ser Thr Val Ile Ser Thr Asp Ala Phe Arg
            580                 585                 590
```

```
Pro Gly Val Arg Tyr Asp Phe Arg Ile Tyr Gly Leu Ser Thr Lys Arg
        595                 600                 605

Ile Ala Cys Leu Leu Glu Lys Lys Thr Gly Tyr Ser Gln Glu Leu Ala
    610                 615                 620

Pro Ser Asp Asn Pro His Val Leu Val Asp Thr Leu Thr Ser His Ser
625                 630                 635                 640

Phe Thr Leu Ser Trp Lys Asp Tyr Ser Thr Glu Ser Gln Pro Gly Phe
                645                 650                 655

Ile Gln Gly Tyr His Val Tyr Leu Lys Ser Lys Ala Arg Gln Cys His
            660                 665                 670

Pro Arg Phe Glu Lys Ala Val Leu Ser Asp Gly Ser Glu Cys Cys Lys
        675                 680                 685

Tyr Lys Ile Asp Asn Pro Glu Glu Lys Ala Leu Ile Val Asp Asn Leu
    690                 695                 700

Lys Pro Glu Ser Phe Tyr Glu Phe Phe Ile Thr Pro Phe Thr Ser Ala
705                 710                 715                 720

Gly Glu Gly Pro Ser Ala Thr Phe Thr Lys Val Thr Thr Pro Asp Glu
                725                 730                 735

His Ser Ser Met Leu Ile His Ile Leu Leu Pro Met Val Phe Cys Val
            740                 745                 750

Leu Leu Ile Met Val Met Cys Tyr Leu Lys Ser Gln Trp Ile Lys Glu
        755                 760                 765

Thr Cys Tyr Pro Asp Ile Pro Asp Pro Tyr Lys Ser Ser Ile Leu Ser
    770                 775                 780

Leu Ile Lys Phe Lys Glu Asn Pro His Leu Ile Ile Met Asn Val Ser
785                 790                 795                 800

Asp Cys Ile Pro Asp Ala Ile Glu Val Val Ser Lys Pro Glu Gly Thr
                805                 810                 815

Lys Ile Gln Phe Leu Gly Thr Arg Lys Ser Leu Thr Glu Thr Glu Leu
            820                 825                 830

Thr Lys Pro Asn Tyr Leu Tyr Leu Leu Pro Thr Glu Lys Asn His Ser
        835                 840                 845

Gly Pro Gly Pro Cys Ile Cys Phe Glu Asn Leu Thr Tyr Asn Gln Ala
    850                 855                 860

Ala Ser Asp Ser Gly Ser Cys Gly His Val Pro Val Ser Pro Lys Ala
865                 870                 875                 880

Pro Ser Met Leu Gly Leu Met Thr Ser Pro Glu Asn Val Leu Lys Ala
                885                 890                 895

Leu Glu Lys Asn Tyr Met Asn Ser Leu Gly Glu Ile Pro Ala Gly Glu
            900                 905                 910

Thr Ser Leu Asn Tyr Val Ser Gln Leu Ala Ser Pro Met Phe Gly Asp
        915                 920                 925

Lys Asp Ser Leu Pro Thr Asn Pro Val Glu Ala Pro His Cys Ser Glu
    930                 935                 940

Tyr Lys Met Gln Met Ala Val Ser Leu Arg Leu Ala Leu Pro Pro Pro
945                 950                 955                 960

Thr Glu Asn Ser Ser Leu Ser Ser Ile Thr Leu Leu Asp Pro Gly Glu
                965                 970                 975

His Tyr Cys
```

<210> SEQ ID NO 148
<211> LENGTH: 342
<212> TYPE: PRT
<213> ORGANISM: Homo sapiens

<400> SEQUENCE: 148

```
Met Ala Leu Phe Ala Val Phe Gln Thr Thr Phe Phe Leu Thr Leu Leu
1               5                   10                  15

Ser Leu Arg Thr Tyr Gln Ser Glu Val Leu Ala Glu Arg Leu Pro Leu
            20                  25                  30

Thr Pro Val Ser Leu Lys Val Ser Thr Asn Ser Thr Arg Gln Ser Leu
        35                  40                  45

His Leu Gln Trp Thr Val His Asn Leu Pro Tyr His Gln Glu Leu Lys
    50                  55                  60

Met Val Phe Gln Ile Gln Ile Ser Arg Ile Glu Thr Ser Asn Val Ile
65                  70                  75                  80

Trp Val Gly Asn Tyr Ser Thr Thr Val Lys Trp Asn Gln Val Leu His
                85                  90                  95

Trp Ser Trp Glu Ser Glu Leu Pro Leu Glu Cys Ala Thr His Phe Val
            100                 105                 110

Arg Ile Lys Ser Leu Val Asp Asp Ala Lys Phe Pro Glu Pro Asn Phe
        115                 120                 125

Trp Ser Asn Trp Ser Ser Trp Glu Glu Val Ser Val Gln Asp Ser Thr
    130                 135                 140

Gly Gln Asp Ile Leu Phe Val Phe Pro Lys Asp Lys Leu Val Glu Glu
145                 150                 155                 160

Gly Thr Asn Val Thr Ile Cys Tyr Val Ser Arg Asn Ile Gln Asn Asn
                165                 170                 175

Val Ser Cys Tyr Leu Glu Gly Lys Gln Ile His Gly Glu Gln Leu Asp
            180                 185                 190

Pro His Val Thr Ala Phe Asn Leu Asn Ser Val Pro Phe Ile Arg Asn
        195                 200                 205

Lys Gly Thr Asn Ile Tyr Cys Glu Ala Ser Gln Gly Asn Val Ser Glu
    210                 215                 220

Gly Met Lys Gly Ile Val Leu Phe Val Ser Lys Val Leu Glu Glu Pro
225                 230                 235                 240

Lys Asp Phe Ser Cys Glu Thr Glu Asp Phe Lys Thr Leu His Cys Thr
                245                 250                 255

Trp Asp Pro Gly Thr Asp Thr Ala Leu Gly Trp Ser Lys Gln Pro Ser
            260                 265                 270

Gln Ser Tyr Thr Leu Phe Glu Ser Phe Ser Gly Glu Lys Lys Leu Cys
        275                 280                 285

Thr His Lys Asn Trp Cys Asn Trp Gln Ile Thr Gln Asp Ser Gln Glu
    290                 295                 300

Thr Tyr Asn Phe Thr Leu Ile Ala Glu Asn Tyr Leu Arg Lys Arg Ser
305                 310                 315                 320

Val Asn Ile Leu Phe Asn Leu Thr His Arg Gly Glu Thr Arg Val Val
                325                 330                 335

Thr Ala His Arg Gly His
            340
```

<210> SEQ ID NO 149
<211> LENGTH: 2397
<212> TYPE: DNA
<213> ORGANISM: Homo sapiens

<400> SEQUENCE: 149

```
gcaagaactg aaacgaatgg ggattgaact gctttgcctg ttctttctat ttctaggaag     60
```

-continued

```
gaatgatcac gtacaaggtg gctgtgccct gggaggtgca gaaacctgtg aagactgcct    120
gcttattgga cctcagtgtg cctggtgtgc tcaggagaat tttactcatc catctggagt    180
tggcgaaagg tgtgataccc cagcaaacct tttagctaaa ggatgtcaat taaacttcat    240
cgaaaaccct gtctcccaag tagaaatact taaaaataag cctctcagtg taggcagaca    300
gaaaaatagt tctgacattg ttcagattgc gcctcaaagc ttgatcctta agttgagacc    360
aggtggtgcg cagactctgc aggtgcatgt ccgccagact gaggactacc cggtggattt    420
gtattacctc atggacctct ccgcctccat ggatgacgac ctcaacacaa taaaggagct    480
gggctcccgg ctttccaaag agatgtctaa attaaccagc aactttagac tgggcttcgg    540
atcttttgtg gaaaaacctg tatccccttt cgtgaaaaca acaccagaag aaattgccaa    600
cccttgcagt agtattccat acttctgttt acctacattt ggattcaagc acattttgcc    660
attgacaaat gatgctgaaa gattcaatga aattgtgaag aatcagaaaa tttctgctaa    720
tattgacaca cccgaaggtg gatttgatgc aattatgcaa gctgctgtgt gtaaggaaaa    780
aattggctgg cggaatgact ccctccacct cctggtcttt gtgagtgatg ctgattctca    840
ttttggaatg gacagcaaac tagcaggcat cgtcattcct aatgacgggc tctgtcactt    900
ggacagcaag aatgaatact ccatgtcaac tgtcttggaa tatccaacaa ttggacaact    960
cattgataaa ctggtacaaa acaacgtgtt attgatcttc gctgtaaccc aagaacaagt   1020
tcatttatat gagaattacg caaaacttat tcctggagct acagtaggtc tacttcagaa   1080
ggactccgga aacattctcc agctgatcat ctcagcttat gaagaactgc ggtctgaggt   1140
ggaactggaa gtattaggag acactgaagg actcaacttg tcatttacag ccatctgtaa   1200
caacggtacc ctcttccaac accaaaagaa atgctctcac atgaaagtgg gagacacagc   1260
ttccttcagc gtgactgtga atatcccaca ctgcgagaga agaagcaggc acattatcat   1320
aaagcctgtg gggctggggg atgccctgga attacttgtc agcccagaat gcaactgcga   1380
ctgtcagaaa gaagtggaag tgaacagctc caaatgtcac cacgggaacg gctctttcca   1440
gtgtggggtg tgtgcctgcc accctggcca catggggcct cgctgtgagt gtggcgagga   1500
catgctgagc acagattcct gcaaggaggc cccagatcat ccctcctgca gcggaagggg   1560
tgactgctac tgtgggcagt gtatctgcca cttgtctccc tatggaaaca tttatgggcc   1620
ttattgccag tgtgacaatt tctcctgcgt gagacacaaa gggctgctct gcggaggtaa   1680
cggcgactgt gactgtggtg aatgtgtgtg caggagcggc tggactggcg agtactgcaa   1740
ctgcaccacc agcacggact cctgcgtctc tgaagatgga gtgctctgca gcgggcgcgg   1800
ggactgtgtt tgtggcaagt gtgtttgcac aaaccctgga gcctcaggac caacctgtga   1860
acgatgtcct acctgtggtg acccctgtaa ctctaaacgg agctgcattg agtgccacct   1920
gtcagcagct ggccaagccc gagaagaatg tgtggacaag tgcaaactag ctggtgcgac   1980
catcagtgaa gaagaagatt tctcaaagga tggttctgtt tcctgctctc tgcaaggaga   2040
aaatgaatgt cttattacat tcctaataac tacagataat gaggggaaaa ccatcattca   2100
cagcatcaat gaaaaagatt gtccgaagcc tccaaacatt cccatgatca tgttaggggt   2160
ttccctggct attcttctca tcggggttgt cctactgtgc atctggaagc tactggtgtc   2220
atttcatgat cgtaaagaag ttgccaaatt tgaagcagaa cgatcaaaag ccaagtggca   2280
aacgggaacc aatccactct acagaggatc cacaagtact tttaaaaatg taacttataa   2340
acacagggaa aaacaaaagg tagacctttc cacagattgc tagaactact ttatgca      2397
```

```
<210> SEQ ID NO 150
<211> LENGTH: 788
<212> TYPE: PRT
<213> ORGANISM: Homo sapiens

<400> SEQUENCE: 150

Met Gly Ile Glu Leu Leu Cys Leu Phe Phe Leu Phe Leu Gly Arg Asn
1               5                   10                  15

Asp His Val Gln Gly Gly Cys Ala Leu Gly Gly Ala Glu Thr Cys Glu
            20                  25                  30

Asp Cys Leu Leu Ile Gly Pro Gln Cys Ala Trp Cys Ala Gln Glu Asn
        35                  40                  45

Phe Thr His Pro Ser Gly Val Gly Glu Arg Cys Asp Thr Pro Ala Asn
    50                  55                  60

Leu Leu Ala Lys Gly Cys Gln Leu Asn Phe Ile Glu Asn Pro Val Ser
65                  70                  75                  80

Gln Val Glu Ile Leu Lys Asn Lys Pro Leu Ser Val Gly Arg Gln Lys
                85                  90                  95

Asn Ser Ser Asp Ile Val Gln Ile Ala Pro Gln Ser Leu Ile Leu Lys
            100                 105                 110

Leu Arg Pro Gly Gly Ala Gln Thr Leu Gln Val His Val Arg Gln Thr
        115                 120                 125

Glu Asp Tyr Pro Val Asp Leu Tyr Tyr Leu Met Asp Leu Ser Ala Ser
    130                 135                 140

Met Asp Asp Asp Leu Asn Thr Ile Lys Glu Leu Gly Ser Arg Leu Ser
145                 150                 155                 160

Lys Glu Met Ser Lys Leu Thr Ser Asn Phe Arg Leu Gly Phe Gly Ser
                165                 170                 175

Phe Val Glu Lys Pro Val Ser Pro Phe Val Lys Thr Thr Pro Glu Glu
            180                 185                 190

Ile Ala Asn Pro Cys Ser Ser Ile Pro Tyr Phe Cys Leu Pro Thr Phe
        195                 200                 205

Gly Phe Lys His Ile Leu Pro Leu Thr Asn Asp Ala Glu Arg Phe Asn
    210                 215                 220

Glu Ile Val Lys Asn Gln Lys Ile Ser Ala Asn Ile Asp Thr Pro Glu
225                 230                 235                 240

Gly Gly Phe Asp Ala Ile Met Gln Ala Ala Val Cys Lys Glu Lys Ile
                245                 250                 255

Gly Trp Arg Asn Asp Ser Leu His Leu Leu Val Phe Val Ser Asp Ala
            260                 265                 270

Asp Ser His Phe Gly Met Asp Ser Lys Leu Ala Gly Ile Val Ile Pro
        275                 280                 285

Asn Asp Gly Leu Cys His Leu Asp Ser Lys Asn Glu Tyr Ser Met Ser
    290                 295                 300

Thr Val Leu Glu Tyr Pro Thr Ile Gly Gln Leu Ile Asp Lys Leu Val
305                 310                 315                 320

Gln Asn Asn Val Leu Leu Ile Phe Ala Val Thr Gln Glu Gln Val His
                325                 330                 335

Leu Tyr Glu Asn Tyr Ala Lys Leu Ile Pro Gly Ala Thr Val Gly Leu
            340                 345                 350

Leu Gln Lys Asp Ser Gly Asn Ile Leu Gln Leu Ile Ile Ser Ala Tyr
        355                 360                 365

Glu Glu Leu Arg Ser Glu Val Glu Leu Glu Val Leu Gly Asp Thr Glu
    370                 375                 380
```

-continued

```
Gly Leu Asn Leu Ser Phe Thr Ala Ile Cys Asn Asn Gly Thr Leu Phe
385                 390                 395                 400

Gln His Gln Lys Lys Cys Ser His Met Lys Val Gly Asp Thr Ala Ser
                405                 410                 415

Phe Ser Val Thr Val Asn Ile Pro His Cys Glu Arg Arg Ser Arg His
            420                 425                 430

Ile Ile Ile Lys Pro Val Gly Leu Gly Asp Ala Leu Glu Leu Leu Val
        435                 440                 445

Ser Pro Glu Cys Asn Cys Asp Cys Gln Lys Glu Val Glu Val Asn Ser
    450                 455                 460

Ser Lys Cys His His Gly Asn Gly Ser Phe Gln Cys Gly Val Cys Ala
465                 470                 475                 480

Cys His Pro Gly His Met Gly Pro Arg Cys Glu Cys Gly Glu Asp Met
                485                 490                 495

Leu Ser Thr Asp Ser Cys Lys Glu Ala Pro Asp His Pro Ser Cys Ser
            500                 505                 510

Gly Arg Gly Asp Cys Tyr Cys Gly Gln Cys Ile Cys His Leu Ser Pro
        515                 520                 525

Tyr Gly Asn Ile Tyr Gly Pro Tyr Cys Gln Cys Asp Asn Phe Ser Cys
    530                 535                 540

Val Arg His Lys Gly Leu Leu Cys Gly Gly Asn Gly Asp Cys Asp Cys
545                 550                 555                 560

Gly Glu Cys Val Cys Arg Ser Gly Trp Thr Gly Glu Tyr Cys Asn Cys
                565                 570                 575

Thr Thr Ser Thr Asp Ser Cys Val Ser Glu Asp Gly Val Leu Cys Ser
            580                 585                 590

Gly Arg Gly Asp Cys Val Cys Gly Lys Cys Val Cys Thr Asn Pro Gly
        595                 600                 605

Ala Ser Gly Pro Thr Cys Glu Arg Cys Pro Thr Cys Gly Asp Pro Cys
    610                 615                 620

Asn Ser Lys Arg Ser Cys Ile Glu Cys His Leu Ser Ala Ala Gly Gln
625                 630                 635                 640

Ala Arg Glu Glu Cys Val Asp Lys Cys Lys Leu Ala Gly Ala Thr Ile
                645                 650                 655

Ser Glu Glu Glu Asp Phe Ser Lys Asp Gly Ser Val Ser Cys Ser Leu
            660                 665                 670

Gln Gly Glu Asn Glu Cys Leu Ile Thr Phe Leu Ile Thr Thr Asp Asn
        675                 680                 685

Glu Gly Lys Thr Ile Ile His Ser Ile Asn Glu Lys Asp Cys Pro Lys
    690                 695                 700

Pro Pro Asn Ile Pro Met Ile Met Leu Gly Val Ser Leu Ala Ile Leu
705                 710                 715                 720

Leu Ile Gly Val Val Leu Leu Cys Ile Trp Lys Leu Leu Val Ser Phe
                725                 730                 735

His Asp Arg Lys Glu Val Ala Lys Phe Glu Ala Glu Arg Ser Lys Ala
            740                 745                 750

Lys Trp Gln Thr Gly Thr Asn Pro Leu Tyr Arg Gly Ser Thr Ser Thr
        755                 760                 765

Phe Lys Asn Val Thr Tyr Lys His Arg Glu Lys Gln Lys Val Asp Leu
    770                 775                 780

Ser Thr Asp Cys
785
```

<210> SEQ ID NO 151
<211> LENGTH: 7889
<212> TYPE: DNA
<213> ORGANISM: Homo sapiens

<400> SEQUENCE: 151
atgggtggag tctcgctttt tctttccagt gttggctgac ttacagctct tataaactag 60
tggcaatttc tgaacccagc cggctccatc tcagcttctg gtttctaagt ccatgtgcca 120
aaggctgcca ggaaggagac gccttcctga gtcctggatc tttcttcctt ctggaaatct 180
ttgactgtgg gtagttattt atttctgaat aagagcgtcc acgcatcatg gacctcgcgg 240
gactgctgaa gtctcagttc ctgtgccacc tggtcttctg ctacgtcttt attgcctcag 300
ggctaatcat caacaccatt cagctcttca ctctcctcct ctggcccatt aacaagcagc 360
tcttccggaa gatcaactgc agactgtcct attgcatctc aagccagctg gtgatgctgc 420
tggagtggtg gtcgggcacg gaatgcacca tcttcacgga cccgcgcgcc tacctcaagt 480
atgggaagga aaatgccatc gtggttctca accacaagtt tgaaattgac tttctgtgtg 540
gctggagcct gtccgaacgc tttgggctgt taggggggctc caaggtcctg gccaagaaag 600
agctggccta tgtcccaatt atcggctgga tgtggtactt caccgagatg gtcttctgtt 660
cgcgcaagtg ggagcaggat cgcaagacgg ttgccaccag tttgcagcac ctccgggact 720
accccgagaa gtattttttc ctgattcact gtgagggcac acggttcacg gagaagaagc 780
atgagatcag catgcaggtg gcccgggcca aggggctgcc tcgcctcaag catcacctgt 840
tgccacgaac caagggcttc gccatcaccg tgaggagctt gagaaatgta gtttcagctg 900
tatatgactg tacactcaat ttcagaaata atgaaaatcc aacactgctg ggagtcctaa 960
acggaaagaa ataccatgca gatttgtatg ttaggaggat cccactggaa gacatccctg 1020
aagacgatga cgagtgctcg gcctggctgc acaagctcta ccaggagaag gatgcctttc 1080
aggaggagta ctacaggacg ggcaccttcc cagagacgcc catggtgccc ccccggcggc 1140
cctggaccct cgtgaactgg ctgttttggg cctcgctggt gctctaccct ttcttccagt 1200
tcctggtcag catgatcagg agcgggtctt ccctgacgct ggccagcttc atcctcgtct 1260
tctttgtggc ctccgtggga gttcgatgga tgattggtgt gacggaaatt gacaagggct 1320
ctgcctacgg caactctgac agcaagcaga aactgaatga ctgactcagg gaggtgtcac 1380
catccgaagg gaaccttggg gaactggtgg cctctgcata tcctccttag tgggacacgg 1440
tgacaaaggc tgggtgagcc cctgctgggc acggcggaag tcacgacctc tccagccagg 1500
gagtctggtc tcaaggccgg atggggagga agatgttttg taatcttttt ttccccatgt 1560
gctttagtgg gctttggttt tctttttgtg cgagtgtgtg tgagaatggc tgtgtggtga 1620
gtgtgaactt tgttctgtga tcatagaaag ggtattttag gctgcagggg agggcagggc 1680
tggggaccga aggggacaag ttcccctttc atcctttggt gctgagtttt ctgtaaccct 1740
tggttgccag agataaagtg aaaagtgctt taggtgagat gactaaatta tgcctccaag 1800
aaaaaaaaat taaagtgctt ttctgggtca tctgtggtgt atgttgacat ggaccgctgc 1860
ccctccatcc tgcccttgcc cgtggctttg gtgtttcaga tcctactcac gggaggcagc 1920
tgccgcggag gtgtgggcag ctgagagggg tgggcaggcc agcacagctc ctggcaggag 1980
acacaggtcc aggagcccgt gagcatttgt gagagcagag atggcaagca cgtgcgtgga 2040
gaccaacgaa gcgtgtccct ggcacacagc aagggagagt ttcgctcggt ctctgcagtg 2100
cagtctcctg gcgtaagtct tgaagatgga cccaactccc tgaagaaatg gatcttgaaa 2160

-continued ttgaacacaa acatcatgaa cgtacagcct gggcattctg cagtgatttg tgagatgagc 2220
ttgcatcgac tgttcctctc agcagtgaca gccaaagtca cccctgataa aatgcagttt 2280
cactttataa aatgcctcgc cccttcccag catgtagagc ttgtctgcag ccctaaagga 2340
gccaggtcct gctctgatga gggtcaaatc agagccgaca tcccatgtac aaaaaacccc 2400
caggcttctg ccttccttcc gggctcctgt ctgctcccat tttactccac ggaatagttc 2460
tgccctgtag catctccagc ggcctttgca gactgctgtc agccaacagg tgccaaaaat 2520
gcaaaagaag aagaaactaa aagcagtgct atttttgcag aacaaatgct agctattaaa 2580
tcatcttagg ccaagacacc aatggcactt ggaccgatag gtatttggag catgagttag 2640
gaaggatatg tctttctcca ggtgcgcagc tgaaagttgc tgagaaaagc tgcctgtgtt 2700
gctgtggtaa catgagaagg aatgaacagc tctatacaaa aactggccac acattataag 2760
gcctattcta tgcagttatg tttttggcta tttgctcatt tagtcattgt ttatcaacca 2820
aactaggtaa gccaaggagt tacaagacag ctctagagaa gctccctctg cttacaggac 2880
aataatgcat tgtttgtttg ttgatacaaa tgaattattt gaatccacag aagtgaaaaa 2940
gggaaaaaat cctggctgac ttgtgggaag agcgtactgc agagcctagg gcctgagtta 3000
actcgctggc ggccctgcag gcaggcttga tgggagcgcc cagcacatct gcccaccctg 3060
cacagggcat gaagcaccgt gtgcagagat ctgtgggcaa aagcccagga cgtgacctta 3120
ggcaagaggg gtccttggag aagtggaggt gtgcatggtg tgtagccttg cgtgtctgtg 3180
agcacgccct agtggacctg cgcctggatt atcgggccag tctctcggag gggtccgtga 3240
tgctgagtta cgccattcac ctgaactctg cagctcatcg gctgtaggat ttgggtgaga 3300
cacttttcct tgctgactca tttccccatc tgcaaaatgg gggtgacgat atctacctct 3360
tggggtgtgt caagggtaaa agagcacact ttaagaatcc taaagcacta agccaaggat 3420
gaaagactag aaagctgcct ctatgttgct actctcaaaa atgctcagaa attttcttgt 3480
cgtactaaaa atgtgttatt tttctcattt tcattcttcc attcaacaca gaagtaatct 3540
aagtaagttc taaaaacata gatccggggg cccacagaca ttcaattttc ttctgaattg 3600
gctctggtat cacacaacac acaagcaagc aaacagcctg cctgctaggg ccttgggttc 3660
caggctggag gaatgcaggc agaaatctct taggaaataa ctaagtgagc gccaagtttt 3720
gaattgcctt agagccgaaa gagaatgtgg cgtgctgggg agagatctgg acctctttct 3780
catcagtcat ttgacctgtc cacgaagaac aattttgtta tgcagcctgg gaacctggtt 3840
tccttacacc ctgcgccctt aatgacacag acaaccacgg gtactcctgg acggaagctc 3900
atcacgcctc ctcaaatacc ttcacccatg ttcaggtcac acggaggtca ccatctcctc 3960
agcacacaac aactgctttg gttcccaggg ttattttttc tacgagttga aaacccacgg 4020
agcctaagcc atctttttgt cccctaagga gagccccata gactaagagc tacacttcct 4080
gtctgtcttt cccacctttc catctcattc tagcttaaag cttatcacgc tactgagagc 4140
ctgttctgta gttcaaggtg gcagagaaaa atacgaacct tgagtgaaat ctggagagca 4200
gtgcagggtc atccccagac gtgacgggcc atatcctagg cgactcctgc agcttataga 4260
agcagggaat ttaatggact tcttccagga aagccagccc acggggactc ttaaaaagac 4320
accaaccatt tggaagatgc agcttgaggt ctgggggact ggactgattc tgccaccata 4380
tagtgaacac gattaatcgg gaggaagaag taaggcactc tgtgagttag tctaccaccc 4440
tattgacttt gacagagaga aaaccaactt ttttcatatg atcacacagt agtactggaa 4500
tatctcgact gcaatatcct ctaaacaaat gcatgcaaag ctttgtaaaa gcagctgatg 4560

-continued

```
attaaaaaaa ttttaaaaca ttagggtttt tctaatatat ccatatgtgg gacagtgatt   4620
taaatgtcat taattgtcca gccacaactt gtaacagtga tgtgaaagac acaaaaaagg   4680
ccccactgga gtggaggagt ggtctggctg gtccccaagc aaaacagaat gggcttcgca   4740
taggctttag aacttattca taaatattga ccaaagtgtg aagcaaggta tccagtgaag   4800
attctctagg gtctctactt ctgctcaaga gatttaatcc agctttctct aaagcagtgg   4860
tccagacttg ccacatacta ggttaaagat aaagtgagaa aaacaaatac tttggtttgc   4920
acgtctcttg aggggcccta ggctgtatgg aggaatattt agaggaatat ttgtgagctg   4980
ccatttgtgt ttaaaagaac atgaaagcaa gacgggccct aacccgcctg tgtctgtagc   5040
tgaccaggag gccactgctt ccttccccca gagcttctag gagagccccc caaaatgcaa   5100
ctctccaagg tcctgtggag tagtcccctc ataatgcctc caccacacct gtgtctcacg   5160
atgccttaac tgacgtagct cctaagtgat gttcacagag aaggaaatac ttaggcaagc   5220
ccatgtgtaa catgctcaca gatgtgctgg ctttgccaat gctttcggac tccaccatgc   5280
tttctgattc ttctggtcct agtcacgcct tggcacgggg cagaagcggc cgagctatgc   5340
tgacaggtgc tgctgagagc caacagccat tcagccgaga aggcgtttct aggtgagggc   5400
atgagagctg gcattccagg ctgctgagtg cggcatctgc aggtgcacca cattgctcca   5460
cggtgtgttc agaagagacc agcatcttga atctcaggct ctgggctcat tctttgcctc   5520
tgccaaggga ccattcaggg gcttcaagcc agctgctgaa aatccccctt ttctggattt   5580
ttccccatct atataaggat atggtggctg tgtggacaag aaattggttt catctcagaa   5640
gggtgcttcc ctacaaagat cttcagaaat ttaattgaaa acaatttttt gaactttttt   5700
tgtttggcca ggatgaatga agctgaagtc acatcctgaa tgtgcatgcc agacaaaggg   5760
taagcaagca gtctttacaa atgccaatcc ctctgcactc caaaaccgga gcccgtaatg   5820
aaggcccagg ttccagtcat cacaggatcc cccaagccag cacagtgcct gatgcctccc   5880
taggcattag cacatcccag cactctaatt cacatcctca gcatccctgc ctcctgcatc   5940
cagggcttag gttgagtgtt tccagagtgt caagtacatt taaacacaaa ccaaatactc   6000
cagggttttg acctgtcaca atggcttttg aaaacaacag acgtacaatt tgagagaagg   6060
actcgatgga cttcttaggc tgaggactaa ggacatgttg ctgttcctct tggtccagga   6120
cattcaatac cattcacagc attcatcacc aactgacata gtatcgatca cgacattcaa   6180
ctgtttgaaa ttactgctat tttggtcaaa aactaagaaa tcagaaattg cacctacata   6240
gtgtgtctcc tcattggagt cccatctctc tgagcacagg gatgggctcc tgagctcaca   6300
gccctgccct gcccccccag cagggcctca ccctcatggc cctcagtgaa tagtgactac   6360
atgaaggggg cacttactag aggcctgagt aatggaattt caattagctt ctgcttccct   6420
tttctaaaaa agaaccacct ttcttaagaa taattaggcc aaaataaact tgagtaattt   6480
gtacagtcaa tattttgaag tttcggagtt accagtgaaa tagcaaagct gttctccagg   6540
aaaggacatc caggttccca cccaggcctt ccttcctcag ctcctgcagc ctcatcctag   6600
tttaatatga aggttgtgaa tgggttaaaa agcagttctt aagcacctac ttagatcttt   6660
tcagtatctg gaaatagcac ccagggctgt gttagtaaag cttttcactg ggtaagagtc   6720
atacaatttt tacatttaat ttgttttttt aaaacaaggc agtcttgttt tacatattgg   6780
aatgactaga tattttttga catttctggc acctctggtt ctgctgaatt ttaagggagg   6840
tgagtggtat gtacacaaag ttaagattgc tgcataataa ttcctttgca tttccaaaat   6900
```

-continued

```
aaattacaca aatgtcactt ttccttttct attccatagt actagtttta gccagatctt   6960
tgccaaacat tctaggacat tcagaaaagt catccatgga attttggaat gccattctct   7020
ctgtatcttt gcagatcatg aggaaggaaa gttgatgaac tagtacggga tggctcagac   7080
ttgtaaagtg tctaagtcac aacgctgcag agccagcttc cgggtagcaa tggcatggcc   7140
tcagctgtgc caaggctaca actggagctt ccttactcgc atctgaggca aacacagcaa   7200
ggctggccca ggccgcccac agtcaacaga tgttcacggg agatggatca gcccctcttt   7260
tgcttgttct atcaaggaaa gagatctaac catgggcaag ggtggaacac acccggttca   7320
ggtcagggaa tgagttgctc taagtgaaca gtgaattctt acttctcagc ctgtatcaat   7380
tgtacccagg gttcatgatt actgtgaccc actaagggat gatctttgag gaaacagacc   7440
tggagggagg taatttaagg agggaaagcg agtgggtttt acagactgct ttgtggcgac   7500
attcaggaac agaccattca atggatgact tttcagtaca taaaagcaag cagtaatggc   7560
caggagagag caaagatgcc ctaagaatga catcagactg accaaatgtg ccttttcaaa   7620
taagttatga gaacgaatga attggaatta gagcaaggta ttggacagaa ccatgctagt   7680
ctttgagaga acgtgtggat tgggtggatg tttggaccga atgaatggta actttttaat   7740
gtgaaacaga gaactgatat atgggctgtc atgtcaccct agggtactgt cgctctgtca   7800
tgtgtagcaa tctttccaaa tttttgttgg tgggctgaac aaagataaaa ctaataaagt   7860
atgtgtggat accactagaa aaaaaaaaa                                     7889
```

```
<210> SEQ ID NO 152
<211> LENGTH: 378
<212> TYPE: PRT
<213> ORGANISM: Homo sapiens

<400> SEQUENCE: 152

Met Asp Leu Ala Gly Leu Leu Lys Ser Gln Phe Leu Cys His Leu Val
1               5                   10                  15

Phe Cys Tyr Val Phe Ile Ala Ser Gly Leu Ile Ile Asn Thr Ile Gln
            20                  25                  30

Leu Phe Thr Leu Leu Leu Trp Pro Ile Asn Lys Gln Leu Phe Arg Lys
        35                  40                  45

Ile Asn Cys Arg Leu Ser Tyr Cys Ile Ser Ser Gln Leu Val Met Leu
    50                  55                  60

Leu Glu Trp Trp Ser Gly Thr Glu Cys Thr Ile Phe Thr Asp Pro Arg
65                  70                  75                  80

Ala Tyr Leu Lys Tyr Gly Lys Glu Asn Ala Ile Val Val Leu Asn His
                85                  90                  95

Lys Phe Glu Ile Asp Phe Leu Cys Gly Trp Ser Leu Ser Glu Arg Phe
            100                 105                 110

Gly Leu Leu Gly Gly Ser Lys Val Leu Ala Lys Lys Glu Leu Ala Tyr
        115                 120                 125

Val Pro Ile Ile Gly Trp Met Trp Tyr Phe Thr Glu Met Val Phe Cys
    130                 135                 140

Ser Arg Lys Trp Glu Gln Asp Arg Lys Thr Val Ala Thr Ser Leu Gln
145                 150                 155                 160

His Leu Arg Asp Tyr Pro Glu Lys Tyr Phe Phe Leu Ile His Cys Glu
                165                 170                 175

Gly Thr Arg Phe Thr Glu Lys Lys His Glu Ile Ser Met Gln Val Ala
            180                 185                 190

Arg Ala Lys Gly Leu Pro Arg Leu Lys His His Leu Leu Pro Arg Thr
```

```
        195                 200                 205

Lys Gly Phe Ala Ile Thr Val Arg Ser Leu Arg Asn Val Val Ser Ala
    210                 215                 220

Val Tyr Asp Cys Thr Leu Asn Phe Arg Asn Asn Glu Asn Pro Thr Leu
225                 230                 235                 240

Leu Gly Val Leu Asn Gly Lys Lys Tyr His Ala Asp Leu Tyr Val Arg
                245                 250                 255

Arg Ile Pro Leu Glu Asp Ile Pro Glu Asp Asp Asp Glu Cys Ser Ala
            260                 265                 270

Trp Leu His Lys Leu Tyr Gln Glu Lys Asp Ala Phe Gln Glu Glu Tyr
        275                 280                 285

Tyr Arg Thr Gly Thr Phe Pro Glu Thr Pro Met Val Pro Pro Arg Arg
    290                 295                 300

Pro Trp Thr Leu Val Asn Trp Leu Phe Trp Ala Ser Leu Val Leu Tyr
305                 310                 315                 320

Pro Phe Phe Gln Phe Leu Val Ser Met Ile Arg Ser Gly Ser Ser Leu
                325                 330                 335

Thr Leu Ala Ser Phe Ile Leu Val Phe Phe Val Ala Ser Val Gly Val
            340                 345                 350

Arg Trp Met Ile Gly Val Thr Glu Ile Asp Lys Gly Ser Ala Tyr Gly
        355                 360                 365

Asn Ser Asp Ser Lys Gln Lys Leu Asn Asp
    370                 375


<210> SEQ ID NO 153
<211> LENGTH: 1863
<212> TYPE: DNA
<213> ORGANISM: Homo sapiens

<400> SEQUENCE: 153

gccggcgcgc ccctgggagg gtgagccggc gccgggccca ggcccggacc tggtgggagg     60

cggggggagg tggggacgag gcctggggag gcgggccccg cccatctgca ggtggctgtg    120

aacgctgagc ggctccaggc gggggccggg cccgggggcg gggtctgtgg cgcgcgtccc    180

cgccacgtgt ccccggtcac cggccctgcc cccgggccct gtgcttataa cctgggatgg    240

gcacccctgc cagtcctgct ctgccgcctg ccaccgctgc ccgagcccga gtggttcact    300

gcactgtgaa aacagattcc agacgccggg aactcacgcc tccaatccca gacgctatgt    360

ccagcaaagg ctccgtggtt ctggcctaca gtggcggcct ggacacctcg tgcatcctcg    420

tgtggctgaa ggaacaaggc tatgacgtca ttgcctatct ggccaacatt ggccagaagg    480

aagacttcga ggaagccagg aagaaggcac tgaagcttgg ggccaaaaag gtgttcattg    540

aggatgtcag cagggagttt gtggaggagt tcatctggcc ggccatccag tccagcgcac    600

tgtatgagga ccgctacctc ctgggcacct ctcttgccag gccctgcatc gcccgcaaac    660

aagtggaaat cgcccagcgg gagggggcca agtatgtgtc ccacggcgcc acaggaaagg    720

ggaacgatca ggtccggttt gagctcagct gctactcact ggccccccag ataaaggtca    780

ttgctccctg gaggatgcct gaattctaca accggttcaa gggccgcaat gacctgatgg    840

agtacgcaaa gcaacacggg attcccatcc cggtcactcc caagaacccg tggagcatgg    900

atgagaacct catgcacatc agctacgagg ctggaatcct ggagaacccc aagaaccaag    960

cgcctccagg tctctacacg aagacccagg acccagccaa agcccccaac accccctgaca   1020

ttctcgagat cgagttcaaa aaaggggtcc ctgtgaaggt gaccaacgtc aaggatggca   1080
```

ccacccacca gacctccttg gagctcttca tgtacctgaa cgaagtcgcg ggcaagcatg 1140
gcgtgggccg tattgacatc gtggagaacc gcttcattgg aatgaagtcc cgaggtatct 1200
acgagacccc agcaggcacc atcctttacc atgctcattt agacatcgag gccttcacca 1260
tggaccggga agtgcgcaaa atcaaacaag gcctgggctt gaaatttgct gagctggtgt 1320
ataccggttt ctggcacagc cctgagtgtg aatttgtccg ccactgcatc gccaagtccc 1380
aggagcgagt ggaagggaaa gtgcaggtgt ccgtcctcaa gggccaggtg tacatcctcg 1440
gccgggagtc cccactgtct ctctacaatg aggagctggt gagcatgaac gtgcagggtg 1500
attatgagcc aactgatgcc accgggttca tcaacatcaa ttccctcagg ctgaaggaat 1560
atcatcgtct ccagagcaag gtcactgcca aatagacccg tgtacaatga ggagctgggg 1620
cctcctcaat ttgcagatcc cccaagtaca ggcgctaatt gttgtgataa tttgtaattg 1680
tgacttgttc tccccggctg gcagcgtagt ggggctgcca ggccccagct ttgttccctg 1740
gtccccctga agcctgcaaa cgttgtcatc gaagggaagg gtgggggca gctgcggtgg 1800 ggagctataa aaatgacaat taaaagagac actagtcttt tatttctaaa aaaaaaaaaa 1860
aaa 1863

<210> SEQ ID NO 154
<211> LENGTH: 1801
<212> TYPE: DNA
<213> ORGANISM: Homo sapiens

<400> SEQUENCE: 154
gccggcgcgc ccctgggagg gtgagccggc gccgggccca ggcccggacc tggtgggagg 60
cggggggagg tggggacgag gcctggggag gcgggccccg cccatctgca ggtggctgtg 120
aacgctgagc ggctccaggc gggggccggg cccgggggcg gggtctgtgg cgcgcgtccc 180
cgccacgtgt ccccggtcac cggccctgcc cccgggccct gtgcttataa cctgggatgg 240
gcacccctgc cagtcctgct ctgccgcctg ccaccgctgc ccgagcccga cgctatgtcc 300
agcaaaggct ccgtggttct ggcctacagt ggcggcctgg acacctcgtg catcctcgtg 360
tggctgaagg aacaaggcta tgacgtcatt gcctatctgg ccaacattgg ccagaaggaa 420
gacttcgagg aagccaggaa gaaggcactg aagcttgggg ccaaaaaggt gttcattgag 480
gatgtcagca gggagtttgt ggaggagttc atctggccgg ccatccagtc cagcgcactg 540
tatgaggacc gctacctcct gggcacctct cttgccaggc cctgcatcgc ccgcaaacaa 600
gtggaaatcg cccagcggga gggggccaag tatgtgtccc acggcgccac aggaaagggg 660
aacgatcagg tccggtttga gctcagctgc tactcactgg ccccccagat aaaggtcatt 720
gctccctgga ggatgcctga attctacaac cggttcaagg gccgcaatga cctgatggag 780
tacgcaaagc aacacgggat tcccatcccg gtcactccca agaacccgtg gagcatggat 840
gagaacctca tgcacatcag ctacgaggct ggaatcctgg agaaccccaa gaaccaagcg 900
cctccaggtc tctacacgaa gacccaggac ccagccaaag cccccaacac ccctgacatt 960
ctcgagatcg agttcaaaaa aggggtccct gtgaaggtga ccaacgtcaa ggatggcacc 1020
acccaccaga cctccttgga gctcttcatg tacctgaacg aagtcgcggg caagcatggc 1080
gtgggccgta ttgacatcgt ggagaaccgc ttcattggaa tgaagtcccg aggtatctac 1140
gagaccccag caggcaccat cctttaccat gctcatttag acatcgaggc cttcaccatg 1200
gaccgggaag tgcgcaaaat caaacaaggc ctgggcttga aatttgctga gctggtgtat 1260
accggtttct ggcacagccc tgagtgtgaa tttgtccgcc actgcatcgc caagtcccag 1320

```
gagcgagtgg aagggaaagt gcaggtgtcc gtcctcaagg gccaggtgta catcctcggc   1380

cgggagtccc cactgtctct ctacaatgag gagctggtga gcatgaacgt gcagggtgat   1440

tatgagccaa ctgatgccac cgggttcatc aacatcaatt ccctcaggct gaaggaatat   1500

catcgtctcc agagcaaggt cactgccaaa tagacccgtg tacaatgagg agctggggcc   1560

tcctcaattt gcagatcccc caagtacagg cgctaattgt tgtgataatt tgtaattgtg   1620

acttgttctc cccggctggc agcgtagtgg ggctgccagg ccccagcttt gttccctggt   1680

ccccctgaag cctgcaaacg ttgtcatcga agggaagggt ggggggcagc tgcggtgggg   1740

agctataaaa atgacaatta aaagagacac tagtctttta tttctaaaaa aaaaaaaaaa   1800

a                                                                   1801
```

```
<210> SEQ ID NO 155
<211> LENGTH: 412
<212> TYPE: PRT
<213> ORGANISM: Homo sapiens

<400> SEQUENCE: 155

Met Ser Ser Lys Gly Ser Val Val Leu Ala Tyr Ser Gly Gly Leu Asp
1               5                   10                  15

Thr Ser Cys Ile Leu Val Trp Leu Lys Glu Gln Gly Tyr Asp Val Ile
            20                  25                  30

Ala Tyr Leu Ala Asn Ile Gly Gln Lys Glu Asp Phe Glu Glu Ala Arg
        35                  40                  45

Lys Lys Ala Leu Lys Leu Gly Ala Lys Lys Val Phe Ile Glu Asp Val
    50                  55                  60

Ser Arg Glu Phe Val Glu Glu Phe Ile Trp Pro Ala Ile Gln Ser Ser
65                  70                  75                  80

Ala Leu Tyr Glu Asp Arg Tyr Leu Leu Gly Thr Ser Leu Ala Arg Pro
                85                  90                  95

Cys Ile Ala Arg Lys Gln Val Glu Ile Ala Gln Arg Glu Gly Ala Lys
            100                 105                 110

Tyr Val Ser His Gly Ala Thr Gly Lys Gly Asn Asp Gln Val Arg Phe
        115                 120                 125

Glu Leu Ser Cys Tyr Ser Leu Ala Pro Gln Ile Lys Val Ile Ala Pro
    130                 135                 140

Trp Arg Met Pro Glu Phe Tyr Asn Arg Phe Lys Gly Arg Asn Asp Leu
145                 150                 155                 160

Met Glu Tyr Ala Lys Gln His Gly Ile Pro Ile Pro Val Thr Pro Lys
                165                 170                 175

Asn Pro Trp Ser Met Asp Glu Asn Leu Met His Ile Ser Tyr Glu Ala
            180                 185                 190

Gly Ile Leu Glu Asn Pro Lys Asn Gln Ala Pro Pro Gly Leu Tyr Thr
        195                 200                 205

Lys Thr Gln Asp Pro Ala Lys Ala Pro Asn Thr Pro Asp Ile Leu Glu
    210                 215                 220

Ile Glu Phe Lys Lys Gly Val Pro Val Lys Val Thr Asn Val Lys Asp
225                 230                 235                 240

Gly Thr Thr His Gln Thr Ser Leu Glu Leu Phe Met Tyr Leu Asn Glu
                245                 250                 255

Val Ala Gly Lys His Gly Val Gly Arg Ile Asp Ile Val Glu Asn Arg
            260                 265                 270

Phe Ile Gly Met Lys Ser Arg Gly Ile Tyr Glu Thr Pro Ala Gly Thr
```

```
        275                 280                 285

Ile Leu Tyr His Ala His Leu Asp Ile Glu Ala Phe Thr Met Asp Arg
    290                 295                 300

Glu Val Arg Lys Ile Lys Gln Gly Leu Gly Leu Lys Phe Ala Glu Leu
305                 310                 315                 320

Val Tyr Thr Gly Phe Trp His Ser Pro Glu Cys Glu Phe Val Arg His
                325                 330                 335

Cys Ile Ala Lys Ser Gln Glu Arg Val Glu Gly Lys Val Gln Val Ser
            340                 345                 350

Val Leu Lys Gly Gln Val Tyr Ile Leu Gly Arg Glu Ser Pro Leu Ser
        355                 360                 365

Leu Tyr Asn Glu Glu Leu Val Ser Met Asn Val Gln Gly Asp Tyr Glu
    370                 375                 380

Pro Thr Asp Ala Thr Gly Phe Ile Asn Ile Asn Ser Leu Arg Leu Lys
385                 390                 395                 400

Glu Tyr His Arg Leu Gln Ser Lys Val Thr Ala Lys
                405                 410


<210> SEQ ID NO 156
<211> LENGTH: 8305
<212> TYPE: DNA
<213> ORGANISM: Homo sapiens

<400> SEQUENCE: 156

gcgcccagga gcagagccgc gctcgctcca ctcagctccc agctcccagg actccgctgg     60

ctcctcgcaa gtcctgccgc ccagcccgcc gggatgcagt ccgggccgcg gcccccactt    120

ccagcccccg gcctggcctt ggctttgacc ctgactatgt tggccagact tgcatccgcg    180

gcttccttct tcggtgagaa ccacctggag gtgcctgtgg ccacggctct gaccgacata    240

gacctgcagc tgcagttctc cacgtcccag cccgaagccc tccttctcct ggcagcaggc    300

ccagctgacc acctcctgct gcagctctac tctggacgcc tgcaggtcag acttgttctg    360

ggccaggagg agctgaggct gcagactcca gcagagacgc tgctgagtga ctccatcccc    420

cacactgtgg tgctgactgt cgtagagggc tgggccacgt tgtcagtcga tgggtttctg    480

aacgcctcct cagcagtccc aggagccccc ctagaggtcc cctatgggct ctttgttggg    540

ggcactggga cccttggcct gccctacctg aggggaacca gccgacccct gaggggttgc    600

ctccatgcag ccaccctcaa tggccgcagc ctcctccggc ctctgacccc cgatgtgcat    660

gagggctgtg ctgaagagtt ttctgccagt gatgatgtgg ccctgggctt ctctgggccc    720

cactctctgg ctgccttccc tgcctggggc actcaggacg aaggaaccct agagtttaca    780

ctcaccacac agagccggca ggcacccttg gccttccagg cagggggccg gcgtggggac    840

ttcatctatg tggacatatt tgagggccac ctgcgggccg tggtggagaa gggccagggt    900

accgtattgc tccacaacag tgtgcctgtg gccgatgggc agccccatga ggtcagtgtc    960

cacatcaatg ctcaccggct ggaaatctcc gtggaccagt accctacgca tacttcgaac   1020

cgaggagtcc tcagctacct ggagccacgg ggcagtctcc ttctcggggg gctggatgca   1080

gaggcctctc gtcacctcca ggaacaccgc ctgggcctga caccagaggc caccaatgcc   1140

tccctgctgg gctgcatgga agacctcagt gtcaatggcc agaggcgggg gctgcgggaa   1200

gctttgctga cgcgcaacat ggcagccggc tgcaggctgg aggaggagga gtatgaggac   1260

gatgcctatg gacattatga agctttctcc accctggccc ctgaggcttg gccagccatg   1320

gagctgcctg agccatgcgt gcctgagcca gggctgcctc ctgtctttgc caatttcacc   1380
```

-continued

```
cagctgctga ctatcagccc actggtggtg gccgaggggg gcacagcctg gcttgagtgg   1440
aggcatgtgc agcccacgct ggacctgatg gaggctgagc tgcgcaaatc ccaggtgctg   1500
ttcagcgtga cccgaggggc acgccatggc gagctcgagc tggacatccc gggagcccag   1560
gcacgaaaaa tgttcaccct cctggacgtg gtgaaccgca aggcccgctt catccacgat   1620
ggctctgagg acacctccga ccagctggtg ctggaggtgt cggtgacggc tcgggtgccc   1680
atgccctcat gccttcggag gggccaaaca tacctcctgc ccatccaggt caaccctgtc   1740
aatgacccac cccacatcat cttcccacat ggcagcctca tggtgatcct ggaacacacg   1800
cagaagccgc tggggcctga ggttttccag gcctatgacc cggactctgc ctgtgagggc   1860
ctcaccttcc aggtccttgg cacctcctct ggcctccccg tggagcgccg agaccagcct   1920
ggggagccgg cgaccgagtt ctcctgccgg gagttggagg ccggcagcct agtctatgtc   1980
caccgcggtg gtcctgcaca ggacttgacg ttccgggtca gcgatggact gcaggccagc   2040
cccccggcca cgctgaaggt ggtggccatc cggccggcca tacagatcca ccgcagcaca   2100
gggttgcgac tggcccaagg ctctgccatg cccatcttgc ccgccaacct gtcggtggag   2160
accaatgccg tggggcagga tgtgagcgtg ctgttccgcg tcactggggc cctgcagttt   2220
ggggagctgc agaagcaggg ggcaggtggg gtggagggtg ctgagtggtg ggccacacag   2280
gcgttccacc agcgggatgt ggagcagggc cgcgtgaggt acctgagcac tgacccacag   2340
caccacgctt acgacaccgt ggagaacctg gccctggagg tgcaggtggg ccaggagatc   2400
ctgagcaatc tgtccttccc agtgaccatc cagagagcca ctgtgtggat gctgcggctg   2460
gagccactgc acactcagaa cacccagcag gagaccctca ccacagccca cctggaggcc   2520
accctggagg aggcaggccc aagcccccca accttccatt atgaggtggt tcaggctccc   2580
aggaaaggca accttcaact acagggcaca aggctgtcag atggccaggg cttcacccag   2640
gatgacatac aggctggccg ggtgacctat ggggccacag cacgtgcctc agaggcagtc   2700
gaggacacct tccgtttccg tgtcacagct ccaccatatt tctccccact ctataccttc   2760
cccatccaca ttggtggtga cccagatgcg cctgtcctca ccaatgtcct cctcgtggtg   2820
cctgagggtg gtgagggtgt cctctctgct gaccacctct ttgtcaagag tctcaacagt   2880
gccagctacc tctatgaggt catggagcgg ccccgccatg ggaggttggc ttggcgtggg   2940
acacaggaca agaccactat ggtgacatcc ttcaccaatg aagacctgtt gcgtggccgg   3000
ctggtctacc agcatgatga ctccgagacc acagaagatg atatcccatt tgttgctacc   3060
cgccagggcg agagcagtgg tgacatggcc tgggaggagg tacggggtgt cttccgagtg   3120
gccatccagc ccgtgaatga ccacgcccct gtgcagacca tcagccggat cttccatgtg   3180
gcccggggtg ggcggcggct gctgactaca gacgacgtgg ccttcagcga tgctgactcg   3240
ggctttgctg acgcccagct ggtgcttacc cgcaaggacc tcctctttgg cagtatcgtg   3300
gccgtagatg agcccacgcg gcccatctac cgcttcaccc aggaggacct caggaagagg   3360
cgagtactgt tcgtgcactc aggggctgac cgtggctgga tccagctgca ggtgtccgac   3420
gggcaacacc aggccactgc gctgctggag gtgcaggcct cggaacccta cctccgtgtg   3480
gccaacggct ccagccttgt ggtccctcaa ggaggccagg gcaccatcga cacggccgtg   3540
ctccacctgg acaccaacct cgacatccgc agtggggatg aggtccacta ccacgtcaca   3600
gctggccctc gctggggaca gctagtccgg gctggtcagc cagccacagc cttctcccag   3660
caggacctgc tggatggggc cgttctctat agccacaatg gcagcctcag cccccgcgac   3720
```

-continued

```
accatggcct tctccgtgga agcagggcca gtgcacacgg atgccaccct acaagtgacc   3780
attgccctag agggcccact ggccccactg aagctggtcc ggcacaagaa gatctacgtc   3840
ttccagggag aggcagctga gatcagaagg gaccagctgg aggcagccca ggaggcagtg   3900
ccacctgcag acatcgtatt ctcagtgaag agcccaccga gtgccggcta cctggtgatg   3960
gtgtcgcgtg gcgccttggc agatgagcca cccagcctgg accctgtgca gagcttctcc   4020
caggaggcag tggacacagg cagggtcctg tacctgcact cccgccctga ggcctggagc   4080
gatgccttct cgctggatgt ggcctcaggc ctgggtgctc ccctcgaggg cgtccttgtg   4140
gagctggagg tgctgcccgc tgccatccca ctagaggcgc aaaacttcag cgtccctgag   4200
ggtggcagcc tcaccctggc ccctccactg ctccgtgtct ccgggcccta cttccccact   4260
ctcctgggcc tcagcctgca ggtgctggag ccaccccagc atggagccct gcagaaggag   4320
gacggacctc aagccaggac cctcagcgcc ttctcctgga gaatggtgga agagcagctg   4380
atccgctacg tgcatgacgg gagcgagaca ctgacagaca gttttgtcct gatggctaat   4440
gcctccgaga tggatcgcca gagccatcct gtggccttca ctgtcactgt cctgcctgtc   4500
aatgaccaac cccccatcct cactacaaac acaggcctgc agatgtggga gggggccact   4560
gcgcccatcc ctgcggaggc tctgaggagc acggacggcg actctgggtc tgaggatctg   4620
gtctacacca tcgagcagcc cagcaacggg cgggtagtgc tgcggggggc gccgggcact   4680
gaggtgcgca gcttcacgca ggcccagctg gacggcgggc tcgtgctgtt ctcacacaga   4740
ggaaccctgg atggaggctt ccgcttccgc ctctctgacg gcgagcacac ttcccccgga   4800
cacttcttcc gagtgacggc ccagaagcaa gtgctcctct cgctgaaggg cagccagaca   4860
ctgactgtct gcccagggtc cgtccagcca ctcagcagtc agaccctcag ggccagctcc   4920
agcgcaggca ctgaccccca gctcctgctc taccgtgtgg tgcggggccc ccagctaggc   4980
cggctgttcc acgcccagca ggacagcaca ggggaggccc tggtgaactt cactcaggca   5040
gaggtctacg ctgggaatat tctgtatgag catgagatgc cccccgagcc cttttgggag   5100
gcccatgata ccctagagct ccagctgtcc tcgccgcctg cccgggacgt ggccgccacc   5160
cttgctgtgg ctgtgtcttt tgaggctgcc tgtccccagc gccccagcca cctctggaag   5220
aacaaaggtc tctgggtccc cgagggccag cgggccagga tcaccgtggc tgctctggat   5280
gcctccaatc tcttggccag cgttccatca ccccagcgct cagagcatga tgtgctcttc   5340
caggtcacac agttccccag ccggggccag ctgttggtgt ccgaggagcc cctccatgct   5400
gggcagcccc acttcctgca gtcccagctg gctgcagggc agctagtgta tgcccacggc   5460
ggtgggggca cccagcagga tggcttccac tttcgtgccc acctccaggg gccagcaggg   5520
gcctccgtgg ctggacccca aacctcagag gcctttgcca tcacggtgag ggatgtaaat   5580
gagcggcccc ctcagccaca ggcctctgtc ccactccggc tcacccgagg ctctcgtgcc   5640
cccatctccc gggcccagct gagtgtggtg gacccagact cagctcctgg ggagattgag   5700
tacgaggtcc agcgggcacc ccacaacggc ttcctcagcc tggtgggtgg tggcctgggg   5760
cccgtgaccc gcttcacgca agccgatgtg gattcagggc ggctggcctt cgtggccaac   5820
gggagcagcg tggcaggcat cttccagctg agcatgtctg atggggccag cccacccctg   5880
cccatgtccc tggctgtgga catcctacca tccgccatcg aggtgcagct gcgggcaccc   5940
ctggaggtgc cccaagcttt ggggcgctcc tcactgagcc agcagcagct ccgggtggtt   6000
tcagatcggg aggagccaga ggcagcatac cgcctcatcc agggacccca gtatgggcat   6060
ctcctggtgg gcgggcggcc cacctcggcc ttcagccaat tccagataga ccagggcgag   6120
```

```
gtggtctttg ccttcaccaa cttctcctcc tctcatgacc acttcagagt cctggcactg   6180
gctaggggtg tcaatgcatc agccgtagtg aacgtcactg tgagggctct gctgcatgtg   6240
tgggcaggtg ggccatggcc ccagggtgcc accctgcgcc tggaccccac cgtcctagat   6300
gctggcgagc tggccaaccg cacaggcagt gtgccgcgct tccgcctcct ggagggaccc   6360
cggcatggcc gcgtggtccg cgtgccccga gccaggacgg agcccggggg cagccagctg   6420
gtggagcagt tcactcagca ggaccttgag gacgggaggc tggggctgga ggtgggcagg   6480
ccagagggga gggcccccgg ccccgcaggt gacagtctca ctctggagct gtgggcacag   6540
ggcgtcccgc ctgctgtggc ctccctggac tttgccactg agccttacaa tgctgcccgg   6600
ccctacagcg tggccctgct cagtgtcccc gaggccgccc ggacggaagc agggaagcca   6660
gagagcagca cccccacagg cgagccaggc cccatggcat ccagccctga gcccgctgtg   6720
gccaagggag gcttcctgag cttccttgag gccaacatgt tcagcgtcat catccccatg   6780
tgcctggtac ttctgctcct ggcgctcatc ctgcccctgc tcttctacct ccgaaaacgc   6840
aacaagacgg gcaagcatga cgtccaggtc ctgactgcca agccccgcaa cggcctggct   6900
ggtgacaccg agacctttcg caaggtggag ccaggccagg ccatcccgct cacagctgtg   6960
cctggccagg ggcccccctcc aggaggccag cctgacccag agctgctgca gttctgccgg   7020
acacccaacc ctgcccttaa gaatggccag tactgggtgt gaggcctggc ctgggcccag   7080
atgctgatcg ggccagggac aggcttgccc atgtcccggg ccccattgct tccatgcctg   7140
gtgctgtctg agtatcccca gagcaagaga gacctggaga caccaggggt ggagggtcct   7200
gggagatagt cccaggggtc cggacagag tggagtcaag agctggaacc tccctcagct   7260
cactccgagc ctggagaact gcaggggcca aggtggaggc aggcttaagt tcagtcctcc   7320
tgccctggag ctggtttggg ctgtcaaaac cagggtaacc tcctacatgg gtcatgactc   7380
tgggtcctgg gtctgtgacc ttgggtaagt cgcgcctgac ccaggctgct aagagggcaa   7440
ggagaaggaa gtaccctggg gagggaaggg acagaggaag ctattcctgg cttttccact   7500
ccaacccagg ccaccctttg tctctgcccc agagttgaga aaaaaacttc ctcccctggt   7560
tttttaggga gatggtatcc cctggagtag agggcaagag gagagagcgc ctccagtcta   7620
gaaggcataa gccaatagga taatatattc agggtgcagg gtgggtaggt tgctctgggg   7680
atgggtttat ttaagggaga ttgcaaggaa gctatttaac atggtgctga gctagccagg   7740
actgatggag cccctggggg tgtgggatgg aggagggtct gcagccagtt cattcccagg   7800
gccccatctt gatgggccaa gggctaaaca tgcatgtgtc agtggctttg gagcaggtta   7860
ggctggggct catcgagggt ctcaggccga ggccactgcg gtgccagtgc ccccctgagg   7920
actagggcag gcagctgggg gcacttggtt ccatggagcc tggataaaca gtgctttgga   7980
ggctctggac agctgtgtgg tgtttgtgtc ttaactatgc actgggccct tgtctgcgtc   8040
ggcttgcata cagagggccc ctggggtcgg ccctccggcc tggcctcagc cagtgggatg   8100
gacagggcca ggcaggcctc tgaacttcca cctcctgggg cctcccagac ctcctgtgcc   8160
cccacctgtg tgggcaggtg ggccagtctt cgggtgatgg gaccaaaccc cttcagttca   8220
gtagagaaag gctaggtcct ctacaaagag ctgcaagaca aaaattaaaa taaatgctcc   8280
ccaccctaga aaaaaaaaaa aaaaa                                         8305
```

<210> SEQ ID NO 157
<211> LENGTH: 2322
<212> TYPE: PRT

<213> ORGANISM: Homo sapiens

<400> SEQUENCE: 157

Met Gln Ser Gly Pro Arg Pro Pro Leu Pro Ala Pro Gly Leu Ala Leu
1               5                   10                  15

Ala Leu Thr Leu Thr Met Leu Ala Arg Leu Ala Ser Ala Ala Ser Phe
            20                  25                  30

Phe Gly Glu Asn His Leu Glu Val Pro Val Ala Thr Ala Leu Thr Asp
        35                  40                  45

Ile Asp Leu Gln Leu Gln Phe Ser Thr Ser Gln Pro Glu Ala Leu Leu
    50                  55                  60

Leu Leu Ala Ala Gly Pro Ala Asp His Leu Leu Leu Gln Leu Tyr Ser
65                  70                  75                  80

Gly Arg Leu Gln Val Arg Leu Val Leu Gly Gln Glu Glu Leu Arg Leu
                85                  90                  95

Gln Thr Pro Ala Glu Thr Leu Leu Ser Asp Ser Ile Pro His Thr Val
            100                 105                 110

Val Leu Thr Val Val Glu Gly Trp Ala Thr Leu Ser Val Asp Gly Phe
        115                 120                 125

Leu Asn Ala Ser Ser Ala Val Pro Gly Ala Pro Leu Glu Val Pro Tyr
    130                 135                 140

Gly Leu Phe Val Gly Gly Thr Gly Thr Leu Gly Leu Pro Tyr Leu Arg
145                 150                 155                 160

Gly Thr Ser Arg Pro Leu Arg Gly Cys Leu His Ala Ala Thr Leu Asn
                165                 170                 175

Gly Arg Ser Leu Leu Arg Pro Leu Thr Pro Asp Val His Glu Gly Cys
            180                 185                 190

Ala Glu Glu Phe Ser Ala Ser Asp Asp Val Ala Leu Gly Phe Ser Gly
        195                 200                 205

Pro His Ser Leu Ala Ala Phe Pro Ala Trp Gly Thr Gln Asp Glu Gly
    210                 215                 220

Thr Leu Glu Phe Thr Leu Thr Thr Gln Ser Arg Gln Ala Pro Leu Ala
225                 230                 235                 240

Phe Gln Ala Gly Gly Arg Arg Gly Asp Phe Ile Tyr Val Asp Ile Phe
                245                 250                 255

Glu Gly His Leu Arg Ala Val Val Glu Lys Gly Gln Gly Thr Val Leu
            260                 265                 270

Leu His Asn Ser Val Pro Val Ala Asp Gly Gln Pro His Glu Val Ser
        275                 280                 285

Val His Ile Asn Ala His Arg Leu Glu Ile Ser Val Asp Gln Tyr Pro
    290                 295                 300

Thr His Thr Ser Asn Arg Gly Val Leu Ser Tyr Leu Glu Pro Arg Gly
305                 310                 315                 320

Ser Leu Leu Leu Gly Gly Leu Asp Ala Glu Ala Ser Arg His Leu Gln
                325                 330                 335

Glu His Arg Leu Gly Leu Thr Pro Glu Ala Thr Asn Ala Ser Leu Leu
            340                 345                 350

Gly Cys Met Glu Asp Leu Ser Val Asn Gly Gln Arg Arg Gly Leu Arg
        355                 360                 365

Glu Ala Leu Leu Thr Arg Asn Met Ala Ala Gly Cys Arg Leu Glu Glu
    370                 375                 380

Glu Glu Tyr Glu Asp Asp Ala Tyr Gly His Tyr Glu Ala Phe Ser Thr
385                 390                 395                 400

```
Leu Ala Pro Glu Ala Trp Pro Ala Met Glu Leu Pro Glu Pro Cys Val
                405                 410                 415

Pro Glu Pro Gly Leu Pro Pro Val Phe Ala Asn Phe Thr Gln Leu Leu
            420                 425                 430

Thr Ile Ser Pro Leu Val Val Ala Glu Gly Gly Thr Ala Trp Leu Glu
        435                 440                 445

Trp Arg His Val Gln Pro Thr Leu Asp Leu Met Glu Ala Glu Leu Arg
    450                 455                 460

Lys Ser Gln Val Leu Phe Ser Val Thr Arg Gly Ala Arg His Gly Glu
465                 470                 475                 480

Leu Glu Leu Asp Ile Pro Gly Ala Gln Ala Arg Lys Met Phe Thr Leu
                485                 490                 495

Leu Asp Val Val Asn Arg Lys Ala Arg Phe Ile His Asp Gly Ser Glu
            500                 505                 510

Asp Thr Ser Asp Gln Leu Val Leu Glu Val Ser Val Thr Ala Arg Val
        515                 520                 525

Pro Met Pro Ser Cys Leu Arg Arg Gly Gln Thr Tyr Leu Leu Pro Ile
    530                 535                 540

Gln Val Asn Pro Val Asn Asp Pro Pro His Ile Ile Phe Pro His Gly
545                 550                 555                 560

Ser Leu Met Val Ile Leu Glu His Thr Gln Lys Pro Leu Gly Pro Glu
                565                 570                 575

Val Phe Gln Ala Tyr Asp Pro Asp Ser Ala Cys Glu Gly Leu Thr Phe
            580                 585                 590

Gln Val Leu Gly Thr Ser Ser Gly Leu Pro Val Glu Arg Arg Asp Gln
        595                 600                 605

Pro Gly Glu Pro Ala Thr Glu Phe Ser Cys Arg Glu Leu Glu Ala Gly
    610                 615                 620

Ser Leu Val Tyr Val His Arg Gly Gly Pro Ala Gln Asp Leu Thr Phe
625                 630                 635                 640

Arg Val Ser Asp Gly Leu Gln Ala Ser Pro Pro Ala Thr Leu Lys Val
                645                 650                 655

Val Ala Ile Arg Pro Ala Ile Gln Ile His Arg Ser Thr Gly Leu Arg
            660                 665                 670

Leu Ala Gln Gly Ser Ala Met Pro Ile Leu Pro Ala Asn Leu Ser Val
        675                 680                 685

Glu Thr Asn Ala Val Gly Gln Asp Val Ser Val Leu Phe Arg Val Thr
    690                 695                 700

Gly Ala Leu Gln Phe Gly Glu Leu Gln Lys Gln Gly Ala Gly Gly Val
705                 710                 715                 720

Glu Gly Ala Glu Trp Trp Ala Thr Gln Ala Phe His Gln Arg Asp Val
                725                 730                 735

Glu Gln Gly Arg Val Arg Tyr Leu Ser Thr Asp Pro Gln His His Ala
            740                 745                 750

Tyr Asp Thr Val Glu Asn Leu Ala Leu Glu Val Gln Val Gly Gln Glu
        755                 760                 765

Ile Leu Ser Asn Leu Ser Phe Pro Val Thr Ile Gln Arg Ala Thr Val
    770                 775                 780

Trp Met Leu Arg Leu Glu Pro Leu His Thr Gln Asn Thr Gln Gln Glu
785                 790                 795                 800

Thr Leu Thr Thr Ala His Leu Glu Ala Thr Leu Glu Glu Ala Gly Pro
                805                 810                 815

Ser Pro Pro Thr Phe His Tyr Glu Val Val Gln Ala Pro Arg Lys Gly
```

```
            820                 825                 830

Asn Leu Gln Leu Gln Gly Thr Arg Leu Ser Asp Gly Gln Gly Phe Thr
        835                 840                 845

Gln Asp Asp Ile Gln Ala Gly Arg Val Thr Tyr Gly Ala Thr Ala Arg
    850                 855                 860

Ala Ser Glu Ala Val Glu Asp Thr Phe Arg Phe Arg Val Thr Ala Pro
865                 870                 875                 880

Pro Tyr Phe Ser Pro Leu Tyr Thr Phe Pro Ile His Ile Gly Gly Asp
                885                 890                 895

Pro Asp Ala Pro Val Leu Thr Asn Val Leu Leu Val Val Pro Glu Gly
            900                 905                 910

Gly Glu Gly Val Leu Ser Ala Asp His Leu Phe Val Lys Ser Leu Asn
        915                 920                 925

Ser Ala Ser Tyr Leu Tyr Glu Val Met Glu Arg Pro Arg His Gly Arg
    930                 935                 940

Leu Ala Trp Arg Gly Thr Gln Asp Lys Thr Thr Met Val Thr Ser Phe
945                 950                 955                 960

Thr Asn Glu Asp Leu Leu Arg Gly Arg Leu Val Tyr Gln His Asp Asp
                965                 970                 975

Ser Glu Thr Thr Glu Asp Asp Ile Pro Phe Val Ala Thr Arg Gln Gly
            980                 985                 990

Glu Ser Ser Gly Asp Met Ala Trp  Glu Glu Val Arg Gly  Val Phe Arg
        995                 1000                 1005

Val Ala  Ile Gln Pro Val Asn  Asp His Ala Pro Val  Gln Thr Ile
    1010                 1015                 1020

Ser Arg  Ile Phe His Val Ala  Arg Gly Gly Arg Arg  Leu Leu Thr
    1025                 1030                 1035

Thr Asp  Asp Val Ala Phe Ser  Asp Ala Asp Ser Gly  Phe Ala Asp
    1040                 1045                 1050

Ala Gln  Leu Val Leu Thr Arg  Lys Asp Leu Leu Phe  Gly Ser Ile
    1055                 1060                 1065

Val Ala  Val Asp Glu Pro Thr  Arg Pro Ile Tyr Arg  Phe Thr Gln
    1070                 1075                 1080

Glu Asp  Leu Arg Lys Arg Arg  Val Leu Phe Val His  Ser Gly Ala
    1085                 1090                 1095

Asp Arg  Gly Trp Ile Gln Leu  Gln Val Ser Asp Gly  Gln His Gln
    1100                 1105                 1110

Ala Thr  Ala Leu Leu Glu Val  Gln Ala Ser Glu Pro  Tyr Leu Arg
    1115                 1120                 1125

Val Ala  Asn Gly Ser Ser Leu  Val Val Pro Gln Gly  Gly Gln Gly
    1130                 1135                 1140

Thr Ile  Asp Thr Ala Val Leu  His Leu Asp Thr Asn  Leu Asp Ile
    1145                 1150                 1155

Arg Ser  Gly Asp Glu Val His  Tyr His Val Thr Ala  Gly Pro Arg
    1160                 1165                 1170

Trp Gly  Gln Leu Val Arg Ala  Gly Gln Pro Ala Thr  Ala Phe Ser
    1175                 1180                 1185

Gln Gln  Asp Leu Leu Asp Gly  Ala Val Leu Tyr Ser  His Asn Gly
    1190                 1195                 1200

Ser Leu  Ser Pro Arg Asp Thr  Met Ala Phe Ser Val  Glu Ala Gly
    1205                 1210                 1215

Pro Val  His Thr Asp Ala Thr  Leu Gln Val Thr Ile  Ala Leu Glu
    1220                 1225                 1230
```

```
Gly Pro  Leu Ala Pro Leu Lys  Leu Val Arg His Lys  Lys Ile Tyr
    1235                 1240                 1245

Val Phe  Gln Gly Glu Ala Ala  Glu Ile Arg Arg Asp  Gln Leu Glu
    1250                 1255                 1260

Ala Ala  Gln Glu Ala Val Pro  Pro Ala Asp Ile Val  Phe Ser Val
    1265                 1270                 1275

Lys Ser  Pro Pro Ser Ala Gly  Tyr Leu Val Met Val  Ser Arg Gly
    1280                 1285                 1290

Ala Leu  Ala Asp Glu Pro Pro  Ser Leu Asp Pro Val  Gln Ser Phe
    1295                 1300                 1305

Ser Gln  Glu Ala Val Asp Thr  Gly Arg Val Leu Tyr  Leu His Ser
    1310                 1315                 1320

Arg Pro  Glu Ala Trp Ser Asp  Ala Phe Ser Leu Asp  Val Ala Ser
    1325                 1330                 1335

Gly Leu  Gly Ala Pro Leu Glu  Gly Val Leu Val Glu  Leu Glu Val
    1340                 1345                 1350

Leu Pro  Ala Ala Ile Pro Leu  Glu Ala Gln Asn Phe  Ser Val Pro
    1355                 1360                 1365

Glu Gly  Gly Ser Leu Thr Leu  Ala Pro Pro Leu Leu  Arg Val Ser
    1370                 1375                 1380

Gly Pro  Tyr Phe Pro Thr Leu  Leu Gly Leu Ser Leu  Gln Val Leu
    1385                 1390                 1395

Glu Pro  Pro Gln His Gly Ala  Leu Gln Lys Glu Asp  Gly Pro Gln
    1400                 1405                 1410

Ala Arg  Thr Leu Ser Ala Phe  Ser Trp Arg Met Val  Glu Glu Gln
    1415                 1420                 1425

Leu Ile  Arg Tyr Val His Asp  Gly Ser Glu Thr Leu  Thr Asp Ser
    1430                 1435                 1440

Phe Val  Leu Met Ala Asn Ala  Ser Glu Met Asp Arg  Gln Ser His
    1445                 1450                 1455

Pro Val  Ala Phe Thr Val Thr  Val Leu Pro Val Asn  Asp Gln Pro
    1460                 1465                 1470

Pro Ile  Leu Thr Thr Asn Thr  Gly Leu Gln Met Trp  Glu Gly Ala
    1475                 1480                 1485

Thr Ala  Pro Ile Pro Ala Glu  Ala Leu Arg Ser Thr  Asp Gly Asp
    1490                 1495                 1500

Ser Gly  Ser Glu Asp Leu Val  Tyr Thr Ile Glu Gln  Pro Ser Asn
    1505                 1510                 1515

Gly Arg  Val Val Leu Arg Gly  Ala Pro Gly Thr Glu  Val Arg Ser
    1520                 1525                 1530

Phe Thr  Gln Ala Gln Leu Asp  Gly Gly Leu Val Leu  Phe Ser His
    1535                 1540                 1545

Arg Gly  Thr Leu Asp Gly Gly  Phe Arg Phe Arg Leu  Ser Asp Gly
    1550                 1555                 1560

Glu His  Thr Ser Pro Gly His  Phe Phe Arg Val Thr  Ala Gln Lys
    1565                 1570                 1575

Gln Val  Leu Leu Ser Leu Lys  Gly Ser Gln Thr Leu  Thr Val Cys
    1580                 1585                 1590

Pro Gly  Ser Val Gln Pro Leu  Ser Ser Gln Thr Leu  Arg Ala Ser
    1595                 1600                 1605

Ser Ser  Ala Gly Thr Asp Pro  Gln Leu Leu Leu Tyr  Arg Val Val
    1610                 1615                 1620
```

```
Arg Gly  Pro Gln Leu Gly Arg  Leu Phe His Ala Gln  Gln Asp Ser
    1625                 1630                 1635

Thr Gly  Glu Ala Leu Val Asn  Phe Thr Gln Ala Glu  Val Tyr Ala
    1640                 1645                 1650

Gly Asn  Ile Leu Tyr Glu His  Glu Met Pro Pro Glu  Pro Phe Trp
    1655                 1660                 1665

Glu Ala  His Asp Thr Leu Glu  Leu Gln Leu Ser Ser  Pro Pro Ala
    1670                 1675                 1680

Arg Asp  Val Ala Ala Thr Leu  Ala Val Ala Val Ser  Phe Glu Ala
    1685                 1690                 1695

Ala Cys  Pro Gln Arg Pro Ser  His Leu Trp Lys Asn  Lys Gly Leu
    1700                 1705                 1710

Trp Val  Pro Glu Gly Gln Arg  Ala Arg Ile Thr Val  Ala Ala Leu
    1715                 1720                 1725

Asp Ala  Ser Asn Leu Leu Ala  Ser Val Pro Ser Pro  Gln Arg Ser
    1730                 1735                 1740

Glu His  Asp Val Leu Phe Gln  Val Thr Gln Phe Pro  Ser Arg Gly
    1745                 1750                 1755

Gln Leu  Leu Val Ser Glu Glu  Pro Leu His Ala Gly  Gln Pro His
    1760                 1765                 1770

Phe Leu  Gln Ser Gln Leu Ala  Ala Gly Gln Leu Val  Tyr Ala His
    1775                 1780                 1785

Gly Gly  Gly Gly Thr Gln Gln  Asp Gly Phe His Phe  Arg Ala His
    1790                 1795                 1800

Leu Gln  Gly Pro Ala Gly Ala  Ser Val Ala Gly Pro  Gln Thr Ser
    1805                 1810                 1815

Glu Ala  Phe Ala Ile Thr Val  Arg Asp Val Asn Glu  Arg Pro Pro
    1820                 1825                 1830

Gln Pro  Gln Ala Ser Val Pro  Leu Arg Leu Thr Arg  Gly Ser Arg
    1835                 1840                 1845

Ala Pro  Ile Ser Arg Ala Gln  Leu Ser Val Val Asp  Pro Asp Ser
    1850                 1855                 1860

Ala Pro  Gly Glu Ile Glu Tyr  Glu Val Gln Arg Ala  Pro His Asn
    1865                 1870                 1875

Gly Phe  Leu Ser Leu Val Gly  Gly Gly Leu Gly Pro  Val Thr Arg
    1880                 1885                 1890

Phe Thr  Gln Ala Asp Val Asp  Ser Gly Arg Leu Ala  Phe Val Ala
    1895                 1900                 1905

Asn Gly  Ser Ser Val Ala Gly  Ile Phe Gln Leu Ser  Met Ser Asp
    1910                 1915                 1920

Gly Ala  Ser Pro Pro Leu Pro  Met Ser Leu Ala Val  Asp Ile Leu
    1925                 1930                 1935

Pro Ser  Ala Ile Glu Val Gln  Leu Arg Ala Pro Leu  Glu Val Pro
    1940                 1945                 1950

Gln Ala  Leu Gly Arg Ser Ser  Leu Ser Gln Gln Gln  Leu Arg Val
    1955                 1960                 1965

Val Ser  Asp Arg Glu Glu Pro  Glu Ala Ala Tyr Arg  Leu Ile Gln
    1970                 1975                 1980

Gly Pro  Gln Tyr Gly His Leu  Leu Val Gly Gly Arg  Pro Thr Ser
    1985                 1990                 1995

Ala Phe  Ser Gln Phe Gln Ile  Asp Gln Gly Glu Val  Val Phe Ala
    2000                 2005                 2010

Phe Thr  Asn Phe Ser Ser Ser  His Asp His Phe Arg  Val Leu Ala
```

2015 2020 2025

Leu Ala Arg Gly Val Asn Ala Ser Ala Val Val Asn Val Thr Val
2030 2035 2040

Arg Ala Leu Leu His Val Trp Ala Gly Gly Pro Trp Pro Gln Gly
2045 2050 2055

Ala Thr Leu Arg Leu Asp Pro Thr Val Leu Asp Ala Gly Glu Leu
2060 2065 2070

Ala Asn Arg Thr Gly Ser Val Pro Arg Phe Arg Leu Leu Glu Gly
2075 2080 2085

Pro Arg His Gly Arg Val Val Arg Val Pro Arg Ala Arg Thr Glu
2090 2095 2100

Pro Gly Gly Ser Gln Leu Val Glu Gln Phe Thr Gln Gln Asp Leu
2105 2110 2115

Glu Asp Gly Arg Leu Gly Leu Glu Val Gly Arg Pro Glu Gly Arg
2120 2125 2130

Ala Pro Gly Pro Ala Gly Asp Ser Leu Thr Leu Glu Leu Trp Ala
2135 2140 2145

Gln Gly Val Pro Pro Ala Val Ala Ser Leu Asp Phe Ala Thr Glu
2150 2155 2160

Pro Tyr Asn Ala Ala Arg Pro Tyr Ser Val Ala Leu Leu Ser Val
2165 2170 2175

Pro Glu Ala Ala Arg Thr Glu Ala Gly Lys Pro Glu Ser Ser Thr
2180 2185 2190

Pro Thr Gly Glu Pro Gly Pro Met Ala Ser Ser Pro Glu Pro Ala
2195 2200 2205

Val Ala Lys Gly Gly Phe Leu Ser Phe Leu Glu Ala Asn Met Phe
2210 2215 2220

Ser Val Ile Ile Pro Met Cys Leu Val Leu Leu Leu Leu Ala Leu
2225 2230 2235

Ile Leu Pro Leu Leu Phe Tyr Leu Arg Lys Arg Asn Lys Thr Gly
2240 2245 2250

Lys His Asp Val Gln Val Leu Thr Ala Lys Pro Arg Asn Gly Leu
2255 2260 2265

Ala Gly Asp Thr Glu Thr Phe Arg Lys Val Glu Pro Gly Gln Ala
2270 2275 2280

Ile Pro Leu Thr Ala Val Pro Gly Gln Gly Pro Pro Pro Gly Gly
2285 2290 2295

Gln Pro Asp Pro Glu Leu Leu Gln Phe Cys Arg Thr Pro Asn Pro
2300 2305 2310

Ala Leu Lys Asn Gly Gln Tyr Trp Val
2315 2320

<210> SEQ ID NO 158
<211> LENGTH: 3654
<212> TYPE: DNA
<213> ORGANISM: Homo sapiens

<400> SEQUENCE: 158
agatgccgcg ggggccgctc gcagccgccg ctgacttgtg aatgggaccg ggactggggc 60
cgggactgac accgcagcgc ttgccctgcg ccagggactg gcggctcgga ggttgcgtcc 120
accctcaagg gccccagaaa tcactgtgtt ttcagctcag cggccctgtg acattccttc 180
gtgttgtcat ttgttgagtg accaatcaga tgggtggagt gtgttacaga aattggcagc 240
aagtatccaa tgggtgaaga agaagctaac tggggacgtg ggcagccctg acgtgatgag 300

```
ctcaaccagc agagacattc catcccaaga gaggtctgcg tgacgcgtcc gggaggccac    360
cctcagcaag accaccgtac agttggtgga aggggtgaca gctgcattct cctgtgccta    420
ccacgtaacc aaaaatgaag gagaactact gtttacaagc cgccctggtg tgcctgggca    480
tgctgtgcca cagccatgcc tttgccccag agcggcgggg gcacctgcgg ccctccttcc    540
atgggcacca tgagaagggc aaggaggggc aggtgctaca gcgctccaag cgtggctggg    600
tctggaacca gttcttcgtg atagaggagt acaccgggcc tgaccccgtg cttgtgggca    660
ggcttcattc agatattgac tctggtgatg ggaacattaa atacattctc tcaggggaag    720
gagctggaac catttttgtg attgatgaca aatcagggaa cattcatgcc accaagacgt    780
tggatcgaga agagagagcc cagtacacgt tgatggctca ggcggtggac agggacacca    840
atcggccact ggagccaccg tcggaattca ttgtcaaggt ccaggacatt aatgacaacc    900
ctccggagtt cctgcacgag acctatcatg ccaacgtgcc tgagaggtcc aatgtgggaa    960
cgtcagtaat ccaggtgaca gcttcagatg cagatgaccc cacttatgga aatagcgcca   1020
agttagtgta cagtatcctc gaaggacaac cctatttttc ggtggaagca cagacaggta   1080
tcatcagaac agccctaccc aacatggaca gggaggccaa ggaggagtac cacgtggtga   1140
tccaggccaa ggacatgggt ggacatatgg gcggactctc agggacaacc aaagtgacga   1200
tcacactgac cgatgtcaat gacaacccac caaagtttcc gcagagcgta taccagatgt   1260
ctgtgtcaga agcagccgtc cctggggagg aagtaggaag agtgaaagct aaagatccag   1320
acattggaga aaatggctta gtcacataca atattgttga tggagatggt atggaatcgt   1380
ttgaaatcac aacggactat gaaacacagg agggggtgat aaagctgaaa aagcctgtag   1440
attttgaaac caaaagagcc tatagcttga aggtagaggc agccaacgtg cacatcgacc   1500
cgaagtttat cagcaatggc cctttcaagg acactgtgac cgtcaagatc tcagtagaag   1560
atgctgatga gccccctatg ttcttggccc caagttacat ccacgaagtc caagaaaatg   1620
cagctgctgg caccgtggtt gggagagtgc atgccaaaga ccctgatgct gccaacagcc   1680
cgataaggta ttccatcgat cgtcacactg acctcgacag atttttcact attaatccag   1740
aggatggttt tattaaaact acaaaacctc tggatagaga ggaaacagcc tggctcaaca   1800
tcactgtctt tgcagcagaa atccacaatc ggcatcagga agccaaagtc ccagtggcca   1860
ttagggtcct tgatgtcaac gataatgctc ccaagtttgc tgccccttat gaaggtttca   1920
tctgtgagag tgatcagacc aagccacttt ccaaccagcc aattgttaca attagtgcag   1980
atgacaagga tgacacggcc aatggaccaa gatttatctt cagcctaccc cctgaaatca   2040
ttcacaatcc aaatttcaca gtcagagaca accgagataa cacagcaggc gtgtacgccc   2100
ggcgtggagg gttcagtcgg cagaagcagg acttgtacct tctgcccata gtgatcagcg   2160
atggcggcat cccgcccatg agtagcacca acaccctcac catcaaagtc tgcgggtgcg   2220
acgtgaacgg ggcactgctc tcctgcaacg cagaggccta cattctgaac gccggcctga   2280
gcacaggcgc cctgatcgcc atcctcgcct gcatcgtcat tctcctggtc attgtagtat   2340
tgtttgtgac cctgagaagg caaaagaaag aaccactcat tgtctttgag gaagaagatg   2400
tccgtgagaa catcattact tatgatgatg aagggggtgg ggaagaagac acagaagcct   2460
ttgatattgc caccctccag aatcctgatg gtatcaatgg atttatcccc cgcaaagaca   2520
tcaaacctga gtatcagtac atgcctagac ctgggctccg gccagcgccc aacagcgtgg   2580
atgtcgatga cttcatcaac acgagaatac aggaggcaga caatgacccc acggctcctc   2640
```

```
cttatgactc cattcaaatc tacggttatg aaggcagggg ctcagtggcc gggtccctga   2700

gctccctaga gtcggccacc acagattcag acttggacta tgattatcta cagaactggg   2760

gacctcgttt taagaaacta gcagatttgt atggttccaa agacactttt gatgacgatt   2820

cttaacaata acgatacaaa tttggcctta agaactgtgt ctggcgttct caagaatcta   2880

gaagatgtgt aaacaggtat ttttttaaat caaggaaagg ctcatttaaa acaggcaaag   2940

ttttacagag aggatacatt taataaaact gcgaggacat caaagtggta aatactgtga   3000

aatacctttt ctcacaaaaa ggcaaatatt gaagttgttt atcaacttcg ctagaaaaaa   3060

aaaacacttg gcatacaaaa tatttaagtg aaggagaagt ctaacgctga actgacaatg   3120

aagggaaatt gtttatgtgt tatgaacatc caagtctttc ttcttttttta agttgtcaaa   3180

gaagcttcca caaaattaga aaggacaaca gttctgagct gtaatttcgc cttaaactct   3240

ggacactcta tatgtagtgc atttttaaac ttgaaatata taatattcag ccagcttaaa   3300

cccatacaat gtatgtacaa tacaatgtac aattatgtct cttgagcatc aatcttgtta   3360

ctgctgattc ttgtaaatct ttttgcttct actttcatct taaactaata cgtgccagat   3420

ataactgtct tgtttcagtg agagacgccc tatttctatg tcatttttaa tgtatctatt   3480

tgtacaattt taaagttctt attttagtat acgtataaat atcagtattc tgacatgtaa   3540

gaaaatgtta cggcatcaca cttatatttt atgaacattg tactgttgct ttaatatgag   3600

cttcaatata agaagcaatc tttgaaataa aaaaagattt ttttttaaaa aaaa         3654
```

<210> SEQ ID NO 159
<211> LENGTH: 796
<212> TYPE: PRT
<213> ORGANISM: Homo sapiens

<400> SEQUENCE: 159

```
Met Lys Glu Asn Tyr Cys Leu Gln Ala Ala Leu Val Cys Leu Gly Met
1               5                   10                  15

Leu Cys His Ser His Ala Phe Ala Pro Glu Arg Arg Gly His Leu Arg
            20                  25                  30

Pro Ser Phe His Gly His His Glu Lys Gly Lys Glu Gly Gln Val Leu
        35                  40                  45

Gln Arg Ser Lys Arg Gly Trp Val Trp Asn Gln Phe Phe Val Ile Glu
    50                  55                  60

Glu Tyr Thr Gly Pro Asp Pro Val Leu Val Gly Arg Leu His Ser Asp
65                  70                  75                  80

Ile Asp Ser Gly Asp Gly Asn Ile Lys Tyr Ile Leu Ser Gly Glu Gly
                85                  90                  95

Ala Gly Thr Ile Phe Val Ile Asp Asp Lys Ser Gly Asn Ile His Ala
            100                 105                 110

Thr Lys Thr Leu Asp Arg Glu Glu Arg Ala Gln Tyr Thr Leu Met Ala
        115                 120                 125

Gln Ala Val Asp Arg Asp Thr Asn Arg Pro Leu Glu Pro Pro Ser Glu
    130                 135                 140

Phe Ile Val Lys Val Gln Asp Ile Asn Asp Asn Pro Pro Glu Phe Leu
145                 150                 155                 160

His Glu Thr Tyr His Ala Asn Val Pro Glu Arg Ser Asn Val Gly Thr
                165                 170                 175

Ser Val Ile Gln Val Thr Ala Ser Asp Ala Asp Asp Pro Thr Tyr Gly
            180                 185                 190

Asn Ser Ala Lys Leu Val Tyr Ser Ile Leu Glu Gly Gln Pro Tyr Phe
```

```
        195                 200                 205

Ser Val Glu Ala Gln Thr Gly Ile Ile Arg Thr Ala Leu Pro Asn Met
    210                 215                 220

Asp Arg Glu Ala Lys Glu Glu Tyr His Val Val Ile Gln Ala Lys Asp
225                 230                 235                 240

Met Gly Gly His Met Gly Gly Leu Ser Gly Thr Thr Lys Val Thr Ile
                245                 250                 255

Thr Leu Thr Asp Val Asn Asp Asn Pro Pro Lys Phe Pro Gln Ser Val
            260                 265                 270

Tyr Gln Met Ser Val Ser Glu Ala Ala Val Pro Gly Glu Glu Val Gly
        275                 280                 285

Arg Val Lys Ala Lys Asp Pro Asp Ile Gly Glu Asn Gly Leu Val Thr
    290                 295                 300

Tyr Asn Ile Val Asp Gly Asp Gly Met Glu Ser Phe Glu Ile Thr Thr
305                 310                 315                 320

Asp Tyr Glu Thr Gln Glu Gly Val Ile Lys Leu Lys Lys Pro Val Asp
                325                 330                 335

Phe Glu Thr Lys Arg Ala Tyr Ser Leu Lys Val Glu Ala Ala Asn Val
            340                 345                 350

His Ile Asp Pro Lys Phe Ile Ser Asn Gly Pro Phe Lys Asp Thr Val
        355                 360                 365

Thr Val Lys Ile Ser Val Glu Asp Ala Asp Glu Pro Pro Met Phe Leu
    370                 375                 380

Ala Pro Ser Tyr Ile His Glu Val Gln Glu Asn Ala Ala Ala Gly Thr
385                 390                 395                 400

Val Val Gly Arg Val His Ala Lys Asp Pro Asp Ala Ala Asn Ser Pro
                405                 410                 415

Ile Arg Tyr Ser Ile Asp Arg His Thr Asp Leu Asp Arg Phe Phe Thr
            420                 425                 430

Ile Asn Pro Glu Asp Gly Phe Ile Lys Thr Thr Lys Pro Leu Asp Arg
        435                 440                 445

Glu Glu Thr Ala Trp Leu Asn Ile Thr Val Phe Ala Ala Glu Ile His
    450                 455                 460

Asn Arg His Gln Glu Ala Lys Val Pro Val Ala Ile Arg Val Leu Asp
465                 470                 475                 480

Val Asn Asp Asn Ala Pro Lys Phe Ala Ala Pro Tyr Glu Gly Phe Ile
                485                 490                 495

Cys Glu Ser Asp Gln Thr Lys Pro Leu Ser Asn Gln Pro Ile Val Thr
            500                 505                 510

Ile Ser Ala Asp Asp Lys Asp Asp Thr Ala Asn Gly Pro Arg Phe Ile
        515                 520                 525

Phe Ser Leu Pro Pro Glu Ile Ile His Asn Pro Asn Phe Thr Val Arg
    530                 535                 540

Asp Asn Arg Asp Asn Thr Ala Gly Val Tyr Ala Arg Arg Gly Gly Phe
545                 550                 555                 560

Ser Arg Gln Lys Gln Asp Leu Tyr Leu Leu Pro Ile Val Ile Ser Asp
                565                 570                 575

Gly Gly Ile Pro Pro Met Ser Ser Thr Asn Thr Leu Thr Ile Lys Val
            580                 585                 590

Cys Gly Cys Asp Val Asn Gly Ala Leu Leu Ser Cys Asn Ala Glu Ala
        595                 600                 605

Tyr Ile Leu Asn Ala Gly Leu Ser Thr Gly Ala Leu Ile Ala Ile Leu
    610                 615                 620
```

Ala Cys Ile Val Ile Leu Leu Val Ile Val Val Leu Phe Val Thr Leu
625 630 635 640

Arg Arg Gln Lys Lys Glu Pro Leu Ile Val Phe Glu Glu Glu Asp Val
645 650 655

Arg Glu Asn Ile Ile Thr Tyr Asp Asp Glu Gly Gly Gly Glu Glu Asp
660 665 670

Thr Glu Ala Phe Asp Ile Ala Thr Leu Gln Asn Pro Asp Gly Ile Asn
675 680 685

Gly Phe Ile Pro Arg Lys Asp Ile Lys Pro Glu Tyr Gln Tyr Met Pro
690 695 700

Arg Pro Gly Leu Arg Pro Ala Pro Asn Ser Val Asp Val Asp Asp Phe
705 710 715 720

Ile Asn Thr Arg Ile Gln Glu Ala Asp Asn Asp Pro Thr Ala Pro Pro
725 730 735

Tyr Asp Ser Ile Gln Ile Tyr Gly Tyr Glu Gly Arg Gly Ser Val Ala
740 745 750

Gly Ser Leu Ser Ser Leu Glu Ser Ala Thr Thr Asp Ser Asp Leu Asp
755 760 765

Tyr Asp Tyr Leu Gln Asn Trp Gly Pro Arg Phe Lys Lys Leu Ala Asp
770 775 780

Leu Tyr Gly Ser Lys Asp Thr Phe Asp Asp Asp Ser
785 790 795

<210> SEQ ID NO 160
<211> LENGTH: 468
<212> TYPE: DNA
<213> ORGANISM: Mus musculus

<400> SEQUENCE: 160
ttcacctccg cacccagcag cttgtagaga gcagttccga cccacagccg gcacccttcg 60
gctagcgctg tttgtttagg gctcggtgag tccaatcaga gcgcaggctg cagttttccg 120
gcagagcagt aagaggcgcc ctctctcctt tttattcacc agcagcgact agcagacccc 180
ggactctcgc tctccgccgg cgccctccgc ctctctccgc gccccggagc accctcggtc 240
gcggccgtct tctcgccatc gctcgaggaa tcaaaagtca ggttggagta ggccggacag 300
tggatggcct tgactgacgg cggctggtgc ctgccaaagc gtttcggggc gctgctgcgg 360
acgccggcga ctccgggccc tttccagcgc gggagccctc ctcgccgctt cccccatctc 420
gtcttcgtcc tcctcctgct cccggggcgg ggatcgcggt ccctgcgg 468

<210> SEQ ID NO 161
<211> LENGTH: 319
<212> TYPE: DNA
<213> ORGANISM: Artificial sequence
<220> FEATURE:
<223> OTHER INFORMATION: Synthetic consensus sequence

<400> SEQUENCE: 161
ttatttaggg gttccgatga gcaacaagcc cgggaggcct ctctctcctt attctcgctc 60
tccgccggcg ccctcccctc tctcgcgccg caccctcgtc ggcctcctcg ccgctgagga 120
atcaaaagtc aggttggagt aggccggaca gtggatggcc ttgactgacg gcggctggtg 180
cctgccaaag cgtttcgggg cgctgctgcg gacgccggcg actccgggcc ctttccagcg 240
cgggagccct cctcgccgct tcccccatct cgtcttcgtc ctcctcctgc tcccggggcg 300
gggatcgcgg tccctgcgg 319

<210> SEQ ID NO 162
<211> LENGTH: 527
<212> TYPE: DNA
<213> ORGANISM: Mus musculus

<400> SEQUENCE: 162
tgggcattaa ttttagtgtg gttatctccg atgagcctaa gcgatttgga aaacagcccg 60
gtggaggcct gcctggttcc ccacccctcc aagtctccct gtcattcttc ctgctctccc 120
tttggggtgg cctcggctct ggggcggtct caccccctc ccctcctgcg ttttccctcc 180
ttttctctgc gctctgctcc accctactat gaccaattcc agaacgatct ggccttcccc 240
tgctggggtt gaccatgggg tgggccaggg gtggcccggc ccgcctgagt acgccgctgg 300
tggttgtaag gcggtttgtg tttaaggaat caaaagtcag gttggagtag gccggacagt 360
ggatggcctt gactgacggc ggctggtgcc tgccaaagcg tttcggggcg ctgctgcgga 420
cgccggcgac tccgggccct ttccagcgcg ggagccctcc tcgccgcttc ccccatctcg 480
tcttcgtcct cctcctgctc ccggggcggg gatcgcggtc cctgcgg 527

<210> SEQ ID NO 163
<211> LENGTH: 900
<212> TYPE: DNA
<213> ORGANISM: Homo sapiens

<400> SEQUENCE: 163
gacccacagc ctggcaccct tcggcgagcg ctgtttgttt agggctcggt gagtccaatc 60
aggagcccag gctgcagttt tccggcagag cagtaagagg cgcctcctct ctccttttta 120
ttcaccagca gcgcggcgca gaccccggac tcgcgctcgc ccgctggcgc cctcggcttc 180
tctccgcgcc tgggagcacc ctccgccgcg gccgttctcc atgcgcagcg cccgcccgag 240
gagctagacg tcagcttgga gcggcgccgg accgtggatg gccttgactg acggcggctg 300
gtgcttgccg aagcgcttcg gggccgcggg tgcggacgcc agcgactcca gagcctttcc 360
agcgcgggag ccctccacgc cgccttcccc catctcttcc tcgtcctcct cctgctcccg 420
gggcggagag cggggccccg gcggcgccag caactgcggg acgcctcagc tcgacacgga 480
ggcggcggcc ggacccccgg cccgctcgct gctgctcagt tcctacgctt cgcatccctt 540
cggggctccc cacggacctt cggcgcctgg ggtcgcgggc cccgggggca acctgtcgag 600
ctgggaggac ttgctgctgt tcactgacct cgaccaagcc gcgaccgcca gcaagctgct 660
gtggtccagc cgcggcgcca agctgagccc cttcgcaccc gagcagccgg aggagatgta 720
ccagaccctc gccgctctct ccagccaggg tccggccgcc tacgacggcg cgcccggcgg 780
cttcgtgcac tctgcggccg cggcggcagc agccgcggcg gcggccagct ccccggtcta 840
cgtgcccacc acccgcgtgg gttccatgct gcccggccta ccgtaccacc tgcaggggtc 900

<210> SEQ ID NO 164
<211> LENGTH: 737
<212> TYPE: DNA
<213> ORGANISM: Homo sapiens

<400> SEQUENCE: 164
gaccacccgg gcgttttgag ggtctgagtc caaaggagag gctgcagcct cctctttacc 60
cgtcgctccc cgttcccccc cccccagggc tagacgtcag cttggagcgg cgccggaccg 120
tggatggcct tgactgacgg cggctgggct tgccgaagcg cttcggggcc gcgggtgcgg 180

-continued

```
acgccagcga ctccagagcc tttccacgcg ggagccctcc acgccgcctt cccccatctc    240

ttcctcgtcc tcctcctgct cccgggcgga gagcggggcc ccggcggcgc cagcaactgc    300

gggacgcctc agctcgacac ggagcggcgg ccggaccccc ggcccgctcg ctgctgctca    360

gttcctacgc ttcgcatccc ttcgggctcc ccacggacct tcggcgcctg ggtcgcgggg    420

ccccgggggc aacctgtcga gcgggaggac ttgctgctgt tcactgacct cgaccaagcc    480

gcgaccgcca gcaagctgct gggtccagcc gcggcgccaa gctgagcccc ttcgcacccg    540

agcagccgga ggagatgtac agaccctcgc cgctctctcc agccagggtc cggccgccta    600

cgacggcgcg cccggcggct cgtgcactct gcggccgcgg cggcagcagc cgcggcggcg    660

gccagctccc cggtctactg cccaccaccc gcgtgggttc catgctgccc ggcctaccgt    720

accacctgca ggggtcg                                                   737
```

<210> SEQ ID NO 165
<211> LENGTH: 831
<212> TYPE: DNA
<213> ORGANISM: Homo sapiens

<400> SEQUENCE: 165

```
attgatctcc acgcccgggg cagaaatagg atctttgaga agtctcaatg ggatctttga     60

gaagtcagat cccatttgaa ctagaaaaag gagtggaggc gaggtgcgtg cagcctacgc    120

tcttgttaac ccgtcgatct cctaccatac ccgttccccc accccacctc agggctagac    180

gtcagcttgg agcggcgccg gaccgtggat ggccttgact gacggcggct ggtgcttgcc    240

gaagcgcttc ggggccgcgg gtgcggacgc cagcgactcc agagcctttc cagcgcggga    300

gccctccacg ccgccttccc ccatctcttc ctcgtcctcc tcctgctccc ggggcggaga    360

gcggggcccc ggcggcgcca gcaactgcgg gacgcctcag ctcgacacgg aggcggcggc    420

cggacccccg gcccgctcgc tgctgctcag ttcctacgct tcgcatccct tcggggctcc    480

ccacggacct tcggcgcctg ggtcgcgggg ccccgggggc aacctgtcga gctgggagga    540

cttgctgctg ttcactgacc tcgaccaagc cgcgaccgcc agcaagctgc tgtggtccag    600

ccgcggcgcc aagctgagcc ccttcgcacc cgagcagccg gaggagatgt accagaccct    660

cgccgctctc tccagccagg gtccggccgc ctacgacggc gcgcccggcg gcttcgtgca    720

ctctgcggcc gcggcggcag cagccgcggc ggcggccagc tccccggtct acgtgcccac    780

cacccgcgtg ggttccatgc tgcccggcct accgtaccac ctgcaggggt c             831
```

<210> SEQ ID NO 166
<211> LENGTH: 958
<212> TYPE: DNA
<213> ORGANISM: Mus musculus

<400> SEQUENCE: 166

```
ctggtaacag caatgaggct gacgcccccg ggcccgctag ggagcacagc ccacagctcc     60

cccttgccag gcgcccaagg accctcaagg cgcggggctc acacttgaag cctgggaacg    120

ctcagacagg aaacccactt cctcctaagc agtttcttcc tagccggatg agaggcgccc    180

aattgaagca gaatgatcct catctactaa tatccagcgt ggccacaaag cgaccggcca    240

tttacgccgc cactttagac aaagatattt ggttattccc ggggaagcaa gtgcactttt    300

gcatggctga gctccgggag gaggcgagcc tcagcccagc ctcccgcccg ctgggctgcg    360

ggcgtcgaga tattcgcctc ctcccggaca acgagttcca cccgggttca gactcagttc    420

cactctgcaa cggatctgcg ggcgctcacg cggctccccg cccgggcttt cactgaagca    480
```

tcggaaggga aaactgcggg gatctgagct ggggtgctgg gactgggatg tcctcggaaa 540
gacagcatca gcttctgaag ccgaagtatc caggccatgg gcaagggtca ggggcaccag 600
ccgacgccga atcatgtcga tgagtccaaa gcacacgact ccgttctcag tgtctgacat 660
cttgagtccc ctggaggaaa gctacaagaa agtgggcatg gagggcggcg gcctcggggc 720
tccgctcgca gcgtacagac agggccaggc ggccccaccg gccgcggcca tgcagcagca 780
cgccgtgggg caccacggcg ccgtcaccgc cgcctaccac atgacggcgg cgggggtgcc 840
ccagctctcg cactccgccg tgggggggcta ctgcaacggc aacctgggca acatgagcga 900
gctgccgcct taccaggaca ccatgcggaa cagcgcttcg ggccccggat ggtacggc 958

<210> SEQ ID NO 167
<211> LENGTH: 390
<212> TYPE: DNA
<213> ORGANISM: Mus musculus

<400> SEQUENCE: 167
tttttttttc ctcctcttcc ttcctcctcc agccgacgcc gaatcatgtc gatgagtcca 60
aagcacacga ctccgttctc agtgtctgac atcttgagtc ccctggagga aagctacaag 120
aaagtgggca tggagggcgg cggcctcggg gctccgctcg cagcgtacag acagggccag 180
gcggccccac cggccgcggc catgcagcag cacgccgtgg ggcaccacgg cgccgtcacc 240
gccgcctacc acatgacggc ggcgggggtg ccccagctct cgcactccgc cgtggggggc 300
tactgcaacg gcaacctggg caacatgagc gagctgccgc cttaccagga caccatgcgg 360
aacagcgctt cgggccccgg atggtacggc 390

<210> SEQ ID NO 168
<211> LENGTH: 391
<212> TYPE: DNA
<213> ORGANISM: Mus musculus

<400> SEQUENCE: 168
tttttttttt cctcctcttc cttcctcctc cagccgacgc cgaatcatgt cgatgagtcc 60
aaagcacacg actccgttct cagtgtctga catcttgagt cccctggagg aaagctacaa 120
gaaagtgggc atggagggcg gcggcctcgg ggctccgctc gcagcgtaca gacagggcca 180
ggcggcccca ccggccgcgg ccatgcagca gcacgccgtg gggcaccacg gcgccgtcac 240
cgccgcctac cacatgacgg cggcgggggt gccccagctc tcgcactccg ccgtgggggg 300
ctactgcaac ggcaacctgg gcaacatgag cgagctgccg ccttaccagg acaccatgcg 360
gaacagcgct tcgggccccg gatggtacgg c 391

<210> SEQ ID NO 169
<211> LENGTH: 517
<212> TYPE: DNA
<213> ORGANISM: Homo sapiens

<400> SEQUENCE: 169
ctgacagaca cgtagaccaa cagtgcggcc ccagggttcg tccccagact cgctcgctca 60
tttgttggcg actggggctc agcgcagcga agcccgatgt ggtccggagg cagtgggaag 120
gcgcggggct gggaggccgc ggcgggaggg aggagcagcc ccggcaggct cagccgccgc 180
cgaatcatgt cgatgagtcc aaagcacacg actccgttct cagtgtctga catcttgagt 240
cccctggagg aaagctacaa gaaagtgggc atggagggcg gcggcctcgg ggctccgctg 300
gcggcgtaca ggcagggcca ggcggcaccg ccaacagcgg ccatgcagca gcacgccgtg 360
gggcaccacg gcgccgtcac cgccgcctac cacatgacgg cggcgggggt gccccagctc 420
tcgcactccg ccgtgggggg ctactgcaac ggcaacctgg gcaacatgag cgagctgccg 480
ccgtaccagg acaccatgag gaacagcgcc tctggcc 517

<210> SEQ ID NO 170
<211> LENGTH: 430
<212> TYPE: DNA
<213> ORGANISM: Homo sapiens

<400> SEQUENCE: 170
gaactaaggt tgtccagatc tcgcattgtt gcttagcgcg cctcggggcg aaggcgcggg 60
ctggcgggag ggagcagcag gctcagccgc cgccgaatca tgtcgatgag tccaaagcac 120
acgactccgt tctcagtgtc tgacatcttg agtcccctgg aggaaagcta caagaaagtg 180
ggcatggagg gcggcggcct cggggctccg ctggcggcgt acaggcaggg ccaggcggca 240
ccgccaacag cggccatgca gcagcacgcc gtggggcacc acggcgccgt caccgccgcc 300
taccacatga cggcggcggg ggtgccccag ctctcgcact ccgccgtggg gggctactgc 360
aacggcaacc tgggcaacat gagcgagctg ccgccgtacc aggacaccat gaggaacagc 420
gcctctggcc 430

<210> SEQ ID NO 171
<211> LENGTH: 672
<212> TYPE: DNA
<213> ORGANISM: Homo sapiens

<400> SEQUENCE: 171
gaaacttaaa ggtgtttacc ttgtcatcag catgtaagct aattatctcg ggcaagatgt 60
aggcttctat tgtcttgttg ctttagcgct tacgccccgc ctctggtggc tgcctaaaac 120
ctggcgccgg gctaaaacaa acgcgaggca gcccccgagc ctccactcaa gccaattaag 180
gaggactcgg tccactccgt tacgtgtaca tccaacaaga tcggcgttaa ggtaacacca 240
gaatatttgg caaagggaga aaaaaaaagc agcgaggctt cgccttcccc ctctcccttt 300
tttttcctcc tcttccttcc tcctccagcc gccgccgaat catgtcgatg agtccaaagc 360
acacgactcc gttctcagtg tctgacatct tgagtcccct ggaggaaagc tacaagaaag 420
tgggcatgga gggcggcggc ctcggggctc cgctggcggc gtacaggcag ggccaggcgg 480
caccgccaac agcggccatg cagcagcacg ccgtggggca ccacggcgcc gtcaccgccg 540
cctaccacat gacggcggcg ggggtgcccc agctctcgca ctccgccgtg gggggctact 600
gcaacggcaa cctgggcaac atgagcgagc tgccgccgta ccaggacacc atgaggaaca 660
gcgcctctgg cc 672

<210> SEQ ID NO 172
<211> LENGTH: 820
<212> TYPE: DNA
<213> ORGANISM: Mus musculus

<400> SEQUENCE: 172
ggtcgtttgt tgtggctgtt aaattttaaa ccgccatgca ctcggcttcc agtatgctgg 60
gagccgtgaa gatggaaggg cacgagccat ccgactggag cagctactac gcggagcccg 120
agggctactc ttccgtgagc aacatgaacg ccggcctggg gatgaatggc atgaacacat 180
acatgagcat gtccgcggct gccatgggcg gcggttccgg caacatgagc gcgggctcca 240

```
tgaacatgtc atcctatgtg ggcgctggaa tgagcccgtc gctagctggc atgtccccgg    300

gcgccggcgc catggcgggc atgagcggct cagccggggc ggccggcgtg gcgggcatgg    360

gacctcacct gagtccgagt ctgagcccgc tcgggggaca ggcggccggg gccatgggtg    420

gccttgcccc ctacgccaac atgaactcga tgagccccat gtacgggcag gccggcctga    480

gccgcgctcg ggaccccaag acataccgac gcagctacac acacgccaaa cctccctact    540

cgtacatctc gctcatcacc atggccatcc agcagagccc caacaagatg ctgacgctga    600

gcgagatcta tcagtggatc atggacctct tccctttcta ccggcagaac cagcagcgct    660

ggcagaactc catccgccac tctctctcct tcaacgactg ctttctcaag gtgccccgct    720

cgccagacaa gcctggcaag ggctccttct ggaccctgca cccagactcg ggcaacatgt    780

tcgagaacgg ctgctacctg cgccgccaga agcgcttcaa                          820
```

<210> SEQ ID NO 173
<211> LENGTH: 751
<212> TYPE: DNA
<213> ORGANISM: Mus musculus

<400> SEQUENCE: 173

```
ctgttaatta acgagggctc cagtatgctg ggagccgtga agatggaagg gcacgagcca     60

tccgactgga gcagctacta cgcggagccc gagggctact cttccgtgag caacatgaac    120

gccggcctgg ggatgaatgg catgaacaca tacatgagca tgtccgcggc tgccatgggc    180

ggcggttccg gcaacatgag cgcgggctcc atgaacatgt catcctatgt gggcgctgga    240

atgagcccgt cgctagctgg catgtccccg ggcgccggcg ccatggcggg catgagcggc    300

tcagccgggg cggccggcgt ggcgggcatg ggacctcacc tgagtccgag tctgagcccg    360

ctcgggggac aggcggccgg ggccatgggt ggccttgccc cctacgccaa catgaactcg    420

atgagcccca tgtacgggca ggccggcctg agccgcgctc gggaccccaa gacataccga    480

cgcagctaca cacacgccaa acctccctac tcgtacatct cgctcatcac catggccatc    540

cagcagagcc ccaacaagat gctgacgctg agcgagatct atcagtggat catggacctc    600

ttccctttct accggcagaa ccagcagcgc tggcagaact ccatccgcca ctctctctcc    660

ttcaacgact gctttctcaa ggtgccccgc tcgccagaca agcctggcaa gggctccttc    720

tggaccctgc acccagactc gggcaacatg t                                   751
```

<210> SEQ ID NO 174
<211> LENGTH: 878
<212> TYPE: DNA
<213> ORGANISM: Mus musculus

<400> SEQUENCE: 174

```
ctgacgacca gggcggccag accacgcgag tcctacgcgc ctcctgaggc cgccccggga     60

cttaactgta acggggaggg gcctccggag cagcggccag cgagttaaag tatgctggga    120

gccgtgaaga tggaagggca cgagccatcc gactggagca gctactacgc ggagcccgag    180

ggctactctt ccgtgagcaa catgaacgcc ggcctgggga tgaatggcat gaacacatac    240

atgagcatgt ccgcggctgc catgggcggc ggttccggca acatgagcgc gggctccatg    300

aacatgtcat cctatgtggg cgctggaatg agcccgtcgc tagctggcat gtccccgggc    360

gccggcgcca tggcgggcat gagcggctca gccggggcgg ccggcgtggc gggcatggga    420

cctcacctga gtccgagtct gagcccgctc gggggacagg cggccggggc catgggtggc    480
```

```
cttgcccccct acgccaacat gaactcgatg agccccatgt acgggcaggc cggcctgagc    540

cgcgctcggg accccaagac ataccgacgc agctacacac acgccaaacc tccctactcg    600

tacatctcgc tcatcaccat ggccatccag cagagcccca acaagatgct gacgctgagc    660

gagatctatc agtggatcat ggacctcttc cctttctacc ggcagaacca gcagcgctgg    720

cagaactcca tccgccactc tctctccttc aacgactgct ttctcaaggt gccccgctcg    780

ccagacaagc ctggcaaggg ctccttctgg accctgcacc cagactcggg caacatgttc    840

gagaacggct gctacctgcg ccgccagaag cgcttcaa                            878
```

<210> SEQ ID NO 175
<211> LENGTH: 811
<212> TYPE: DNA
<213> ORGANISM: Homo sapiens

<400> SEQUENCE: 175

```
cccgcccact tccaactacc gcctccggcc tgcccaggga gagagaggga gtggagccca     60

gggagaggga gcgcgagaga gggagggagg aggggacggt gctttggctg actttttttt    120

aaaagagggt gggggtgggg ggtgattgct ggtcgtttgt tgtggctgtt aaattttaaa    180

ctgccatgca ctcggcttcc agtatgctgg gagcggtgaa gatggaaggg cacgagccgt    240

ccgactggag cagctactat gcagagcccg agggctactc ctccgtgagc aacatgaacg    300

ccggcctggg gatgaacggc atgaacacgt acatgagcat gtcggcggcc gccatgggca    360

gcggctcggg caacatgagc gcgggctcca tgaacatgtc gtcgtacgtg ggcgctggca    420

tgagcccgtc cctggcgggg atgtccccccg gcgcgggcgc catggcgggc atgggcggct    480

cggccggggc ggccggcgtg gcgggcatgg ggccgcactt gagtcccagc ctgagcccgc    540

tcggggggca ggcggccggg gccatgggcg gcctggcccc ctacgccaac atgaactcca    600

tgagccccat gtacgggcag gcgggcctga gccgcgcccg cgaccccaag acctacaggc    660

gcagctacac gcacgcaaag ccgccctact cgtacatctc gctcatcacc atggccatcc    720

agcagagccc caacaagatg ctgacgctga gcgagatcta ccagtggatc atggacctct    780

tcccccttcta ccggcagaac cagcagcgct g                                  811
```

<210> SEQ ID NO 176
<211> LENGTH: 687
<212> TYPE: DNA
<213> ORGANISM: Homo sapiens

<400> SEQUENCE: 176

```
cgccctccct cgccccggcc cccagggagg agggagagcc aggagaggcg cgagaaggga     60

gggagagggc ggttaaagta tgctgggagc ggtgaagatg gaagggcacg agccgtccga    120

ctggagcagc tactatgcag agcccgaggg ctactcctcc gtgagcaaca tgaacgccgg    180

cctggggatg aacggcatga acacgtacat gagcatgtcg gcggccgcca tgggcagcgg    240

ctcgggcaac atgagcgcgg gctccatgaa catgtcgtcg tacgtgggcg ctggcatgag    300

cccgtccctg gcggggatgt cccccggcgc gggcgccatg gcgggcatgg gcggctcggc    360

cggggcggcc ggcgtggcgg gcatggggcc gcacttgagt cccagcctga gcccgctcgg    420

ggggcaggcg gccggggcca tgggcggcct ggccccctac gccaacatga actccatgag    480

ccccatgtac gggcaggcgg gcctgagccg cgcccgcgac cccaagacct acaggcgcag    540

ctacacgcac gcaaagccgc cctactcgta catctcgctc atcaccatgg ccatccagca    600

gagccccaac aagatgctga cgctgagcga gatctaccag tggatcatgg acctcttccc    660
```

cttctaccgg cagaaccagc agcgctg 687

<210> SEQ ID NO 177
<211> LENGTH: 798
<212> TYPE: DNA
<213> ORGANISM: Homo sapiens

<400> SEQUENCE: 177
cggccgctgc tagaggggct gcttgcgcca ggcgccggcc gccccactgc gggtccctgg 60
cggccggtgt ctgaggagtc ggagagccga ggcggccaga ccgtgcgccc cgcgcttctc 120
ccgaggccgt tccgggtctg aactgtaaca gggaggggcc tcgcaggagc agcagcgggc 180
gagttaaagt atgctgggag cggtgaagat ggaagggcac gagccgtccg actggagcag 240
ctactatgca gagcccgagg gctactcctc cgtgagcaac atgaacgccg gcctggggat 300
gaacggcatg aacacgtaca tgagcatgtc ggcggccgcc atgggcagcg gctcgggcaa 360
catgagcgcg ggctccatga acatgtcgtc gtacgtgggc gctggcatga gcccgtccct 420
ggcggggatg tcccccggcg cgggcgccat ggcgggcatg ggcggctcgg ccggggcggc 480
cggcgtggcg ggcatggggc cgcacttgag tcccagcctg agcccgctcg gggggcaggc 540
ggccggggcc atgggcggcc tggcccccta cgccaacatg aactccatga gccccatgta 600
cgggcaggcg ggcctgagcc gcgcccgcga ccccaagacc tacaggcgca gctacacgca 660
cgcaaagccg ccctactcgt acatctcgct catcaccatg gccatccagc agagccccaa 720
caagatgctg acgctgagcg agatctacca gtggatcatg gacctcttcc ccttctaccg 780
gcagaaccag cagcgctg 798

<210> SEQ ID NO 178
<211> LENGTH: 1079
<212> TYPE: DNA
<213> ORGANISM: Mus musculus

<400> SEQUENCE: 178
agcaaaacaa gaattcagaa ttaaagcatt ggagtcaaga gctctaaact ttttcaaaat 60
gtggctgcat ctaggaaggg tgctgaaaga ttccaaacct cgtacgtaac agaattttct 120
tttaaaaaca gcgataagct gtcagtcaat agctaggacc acctacctga caaagagctt 180
cccaagagct ctaagtgttg gaatgtgaca ccagaaatca cgatttgtgc ataattaatc 240
gcatcacttt gccacctaca ctgaagggca cagaccaagg gcagtgtatg taaatgtagt 300
tccagtgtgc aaaccccact aatgaccttc gattaatgga gtcattatag taaccctgcc 360
tcattcttgg gggtgggggg agttccgaat gcaccgggtc cctcggggct cctctgcggt 420
ctgagggaga ccgcacagtg ttcctacaat tcgtgtcact gagtttccga gaaggcctcc 480
cgcgttgctc caagttgcaa agcttcacgc taaacctgtc gtggacgtgt atgtgggcat 540
tggctgcgaa cgcggaagaa ccgagagctc atactcacca atgggagaat tcgcctggta 600
tgatggacgg gagcccttcc accaatggca attcagggat gcccgattga gcggccaggg 660
cgagtgcaca taaaagacgc cccgcccggc tcgcgcttca ttctgaaccg agcctggtgc 720
cgcgcagtca gctcagcccc ctgtggcggc tccctcccgg tcttcctcct acgagcagca 780
tgaaagcctt cagtccggtg aggtccgtta ggaaaaacag cctgtcggac cacagcttgg 840
gcatctcccg gagcaaaacc ccggtggacg acccgatgag tctgctctac aacatgaacg 900
actgctactc caagctcaag gaactggtgc ccagcatccc ccagaacaag aaggtgacca 960

-continued

```
agatggaaat cctgcagcac gtcatcgatt acatcttgga cctgcagatc gccctggact   1020

cgcatcccac tatcgtcagc ctgcatcacc agagacctgg acagaaccag gcgtccagg    1079
```

<210> SEQ ID NO 179
<211> LENGTH: 385
<212> TYPE: DNA
<213> ORGANISM: Mus musculus

<400> SEQUENCE: 179

```
gcttcattct gaaccgagcc tggtgccgcg cagtcagctc agccccctgt ggcggctccc     60

tcccggtctt cctcctacga gcagcatgaa agccttcagt ccggtgaggt ccgttaggaa    120

aaacagcctg tcggaccaca gcttgggcat ctcccggagc aaaaccccgg tggacgaccc    180

gatgagtctg ctctacaaca tgaacgactg ctactccaag ctcaaggaac tggtgcccag    240

catcccccag aacaagaagg tgaccaagat ggaaatcctg cagcacgtca tcgattacat    300

cttggacctg cagatcgccc tggactcgca tcccactatc gtcagcctgc atcaccagag    360

acctggacag aaccaggcgt ccagg                                          385
```

<210> SEQ ID NO 180
<211> LENGTH: 117
<212> TYPE: PRT
<213> ORGANISM: Mus musculus

<400> SEQUENCE: 180

```
Met Lys Ala Phe Ser Pro Val Arg Ser Val Arg Lys Asn Ser Leu Ser
1               5                   10                  15

Asp His Ser Leu Gly Ile Ser Arg Ser Lys Thr Pro Val Asp Asp Pro
            20                  25                  30

Met Ser Leu Leu Tyr Asn Met Asn Asp Cys Tyr Ser Lys Leu Lys Glu
        35                  40                  45

Leu Val Pro Ser Ile Pro Gln Asn Lys Lys Val Thr Lys Met Glu Ile
    50                  55                  60

Leu Gln His Val Ile Asp Tyr Ile Leu Asp Leu Gln Ile Ala Leu Asp
65                  70                  75                  80

Ser His Pro Thr Ile Val Ser Leu His His Gln Arg Pro Gly Gln Asn
                85                  90                  95

Gln Ala Ser Arg Thr Pro Leu Thr Thr Leu Asn Thr Asp Ile Ser Ile
            100                 105                 110

Leu Ser Leu Gln Val
        115
```

<210> SEQ ID NO 181
<211> LENGTH: 479
<212> TYPE: DNA
<213> ORGANISM: Homo sapiens

<400> SEQUENCE: 181

```
ggggacgaag ggaagctcca gcgtgtggcc ccggcgagtg cggataaaag ccgcccgcc     60

gggctcgggc ttcattctga gccgagcccg gtgccaagcg cagctagctc agcaggcggc    120

agcggcggcc tgagcttcag ggcagccagc tccctcccgg tctcgccttc cctcgcggtc    180

agcatgaaag ccttcagtcc cgtgaggtcc gttaggaaaa acagcctgtc ggaccacagc    240

ctgggcatct cccggagcaa aacccctgtg gacgacccga tgagcctgct atacaacatg    300

aacgactgct actccaagct caaggagctg gtgcccagca tcccccagaa caagaaggtg    360

agcaagatgg aaatcctgca gcacgtcatc gactacatct tggacctgca gatcgccctg    420
```

gactcgcatc ccactattgt cagcctgcat caccagagac ccgggcagaa ccaggcgtc 479

<210> SEQ ID NO 182
<211> LENGTH: 409
<212> TYPE: DNA
<213> ORGANISM: Homo sapiens

<400> SEQUENCE: 182
ttcattctga gccgagcccg gtgccaagcg cagctagctc agcaggcggc agcggcggcc 60
tgagcttcag ggcagccagc tccctcccgg tctcgccttc cctcgcggtc agcatgaaag 120
ccttcagtcc cgtgaggtcc gttaggaaaa acagcctgtc ggaccacagc ctgggcatct 180
cccggagcaa aacccctgtg gacgacccga tgagcctgct atacaacatg aacgactgct 240
actccaagct caaggagctg gtgcccagca tcccccagaa caagaaggtg agcaagatgg 300
aaatcctgca gcacgtcatc gactacatct tggacctgca gatcgccctg gactcgcatc 360
ccactattgt cagcctgcat caccagagac ccgggcagaa ccaggcgtc 409

<210> SEQ ID NO 183
<211> LENGTH: 117
<212> TYPE: PRT
<213> ORGANISM: Homo sapiens

<400> SEQUENCE: 183

Met Lys Ala Phe Ser Pro Val Arg Ser Val Arg Lys Asn Ser Leu Ser
1 5 10 15

Asp His Ser Leu Gly Ile Ser Arg Ser Lys Thr Pro Val Asp Asp Pro
20 25 30

Met Ser Leu Leu Tyr Asn Met Asn Asp Cys Tyr Ser Lys Leu Lys Glu
35 40 45

Leu Val Pro Ser Ile Pro Gln Asn Lys Lys Val Ser Lys Met Glu Ile
50 55 60

Leu Gln His Val Ile Asp Tyr Ile Leu Asp Leu Gln Ile Ala Leu Asp
65 70 75 80

Ser His Pro Thr Ile Val Ser Leu His His Gln Arg Pro Gly Gln Asn
85 90 95

Gln Ala Ser Arg Thr Pro Leu Thr Thr Leu Asn Thr Asp Ile Ser Ile
100 105 110

Leu Ser Leu Gln Pro
115

<210> SEQ ID NO 184
<211> LENGTH: 90
<212> TYPE: DNA
<213> ORGANISM: Artificial sequence
<220> FEATURE:
<223> OTHER INFORMATION: Synthetic oligonucleotide

<400> SEQUENCE: 184
gtggatggcc ttgactgacg gcggctggtg cttgccgaag cgcttcgggg ccgcgggtgc 60
ggacgccagc gactccagag cctttccagc 90

<210> SEQ ID NO 185
<211> LENGTH: 89
<212> TYPE: DNA
<213> ORGANISM: Artificial sequence
<220> FEATURE:
<223> OTHER INFORMATION: Synthetic oligonucleotide

```
<400> SEQUENCE: 185

aggacccaga ctgctgcccc cgccctggcg tcccactttc cctgggccga gttgcatttc     60

tctctggggc tcgcgttcgg gctggtcag                                       89


<210> SEQ ID NO 186
<211> LENGTH: 79
<212> TYPE: DNA
<213> ORGANISM: Artificial sequence
<220> FEATURE:
<223> OTHER INFORMATION: Synthetic oligonucleotide

<400> SEQUENCE: 186

cagcgaggct tcgccttccc cctctccctt ttttttcctc ctcttccttc ctcctccagc     60

cgccgccgaa tcatgtcga                                                  79


<210> SEQ ID NO 187
<211> LENGTH: 89
<212> TYPE: DNA
<213> ORGANISM: Artificial sequence
<220> FEATURE:
<223> OTHER INFORMATION: Synthetic oligonucleotide

<400> SEQUENCE: 187

tccggaggca gtgggaaggc gcggggctgg gaggccgcgg cgggagggag gagcagcccc     60

ggcaggctca gccgccgccg aatcatgtc                                       89
```